(12) United States Patent
Luly et al.

(10) Patent No.: US 7,271,176 B2
(45) Date of Patent: Sep. 18, 2007

(54) CHEMOKINE RECEPTOR ANTAGONISTS AND METHODS OF USE THEREOF

(75) Inventors: Jay R. Luly, Wellesley, MA (US); Yoshisuke Nakasato, Shizuoka (JP); Etsuo Ohshima, Nagareyama (JP); Geraldine C. B. Harriman, Charlestown, RI (US); Kenneth G. Carson, Needham, MA (US); Shomir Ghosh, Brookline, MA (US); Amy M. Elder, Arlington, MA (US); Karen M. Mattia, Marlborough, MA (US)

(73) Assignees: Millennium Pharmaceuticals, Inc., Cambridge, MA (US); Kyowa Hakko Kogyo Co., Ltd., Tokyo (JP)

(*) Notice: Subject to any disclaimer, the term of this patent is extended or adjusted under 35 U.S.C. 154(b) by 0 days.

(21) Appl. No.: 10/487,168

(22) PCT Filed: Nov. 13, 2002

(86) PCT No.: PCT/US02/36953

§ 371 (c)(1),
(2), (4) Date: Oct. 7, 2004

(87) PCT Pub. No.: WO03/045942

PCT Pub. Date: Jun. 5, 2003

(65) Prior Publication Data

US 2005/0070549 A1    Mar. 31, 2005

Related U.S. Application Data

(63) Continuation-in-part of application No. 09/989,086, filed on Nov. 21, 2001, now abandoned.

(51) Int. Cl.
  A01N 43/42   (2006.01)
  A61K 31/44   (2006.01)
  C07D 401/00  (2006.01)
  C07D 451/00  (2006.01)
  C07D 453/00  (2006.01)

(52) U.S. Cl. .................... 514/291; 546/18; 546/20; 546/80; 546/81; 546/89; 546/93

(58) Field of Classification Search ............... 546/18, 546/20, 80, 81, 89, 93; 514/291
See application file for complete search history.

(56) References Cited

U.S. PATENT DOCUMENTS

| | | |
|---|---|---|
| 3,409,621 A | 11/1968 | Villani et al. |
| 3,770,729 A | 11/1973 | Nakanishi et al. |
| 4,042,695 A | 8/1977 | Buss |
| 4,250,176 A | 2/1981 | Vandenberk et al. |
| 4,335,122 A | 6/1982 | McFadden et al. |
| 4,547,496 A | 10/1985 | Kumazawa et al. |
| 4,567,178 A | 1/1986 | Eberlein et al. |
| 4,645,758 A | 2/1987 | Willman et al. |
| 4,994,463 A | 2/1991 | Oshima et al. |
| 4,999,363 A | 3/1991 | Oshima et al. |
| 5,010,087 A | 4/1991 | Oshima et al. |
| 5,010,104 A | 4/1991 | Oshima et al. |
| 5,011,836 A | 4/1991 | Eberlein et al. |
| 5,089,496 A | 2/1992 | Piwinski et al. |
| 5,116,863 A | 5/1992 | Ohshima et al. |
| 5,118,701 A | 6/1992 | Oshima et al. |
| 5,143,922 A | 9/1992 | Oshima et al. |
| 5,239,083 A | 8/1993 | Kumazawa et al. |
| 5,242,931 A | 9/1993 | Oshima et al. |
| 5,302,596 A | 4/1994 | Oshima et al. |
| 5,302,602 A | 4/1994 | Oshima et al. |
| 5,340,807 A | 8/1994 | Kumazawa et al. |
| 5,378,701 A | 1/1995 | Ohshima et al. |
| 5,478,835 A | 12/1995 | Kumazawa et al. |
| 5,478,840 A | 12/1995 | Oshima et al. |
| 5,538,986 A | 7/1996 | Ting et al. |

(Continued)

FOREIGN PATENT DOCUMENTS

CH    421 138    3/1967

(Continued)

OTHER PUBLICATIONS

Pesce et al., "preliminary Evidence for 'Aberrant' Expression of the Leukocyte Integrin LFA-1 (CD11a/CD18) on Conjunctival Epithelial Cells of Patients with Mite Allergy", Int Arch Allergy Immunol 2001, pp. 160-163.*

(Continued)

Primary Examiner—Margaret D. Seaman
Assistant Examiner—Niloofar Rahmani
(74) Attorney, Agent, or Firm—Hamilton Brook Smith & Reynolds, P.C.

(57) ABSTRACT

Disclosed are novel compounds and a method of treating a disease associated with aberrant leukocyte recruitment and/or activation. The method comprises administering to a subject in need an effective amount of a compound represented by: formula (1) or physiologically acceptable salt thereof

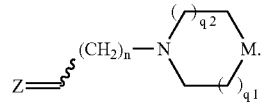
(1)

25 Claims, 72 Drawing Sheets

U.S. PATENT DOCUMENTS

| | | | |
|---|---|---|---|
| 5,607,955 | A | 3/1997 | Oshima et al. |
| 5,672,611 | A | 9/1997 | Doll et al. |
| 5,679,703 | A | 10/1997 | Yanase et al. |
| 5,688,788 | A | 11/1997 | Andersen et al. |
| 5,801,175 | A | 9/1998 | Afonso et al. |
| 5,874,428 | A | 2/1999 | Dorwald |
| 5,877,177 | A | 3/1999 | Taveras |
| 5,919,776 | A | 7/1999 | Hagmann |
| 6,040,318 | A | 3/2000 | Andersen et al. |
| 6,048,856 | A | 4/2000 | J.o slashed.rgensen et al. |
| 6,150,355 | A | 11/2000 | Kumazawa et al. |
| 6,281,212 | B1 | 8/2001 | Schwender et al. |
| 6,288,083 | B1 | 9/2001 | Luly et al. |
| 6,288,084 | B1 | 9/2001 | Luly et al. |
| 6,323,206 | B1 | 11/2001 | Schwender et al. |
| 6,329,385 | B1 | 12/2001 | Luly et al. |
| 6,433,165 | B1 | 8/2002 | Luly et al. |
| 6,503,926 | B2 | 1/2003 | Luly et al. |
| 6,509,346 | B2 | 1/2003 | Luly et al. |
| 6,613,905 | B1 | 9/2003 | Luly et al. |
| 2002/0169155 | A1 | 11/2002 | Luly et al. |
| 2003/0045516 | A1 | 3/2003 | Luly et al. |
| 2004/0016639 | A1 | 6/2004 | Carson et al. |
| 2005/0288319 | A1 | 12/2005 | Carson et al. |

FOREIGN PATENT DOCUMENTS

| | | |
|---|---|---|
| CZ | 240 698 | 6/1987 |
| DE | 80449 | 9/1969 |
| DE | 1 918 739 | 10/1969 |
| DE | 33 26 641 A1 | 2/1984 |
| EP | 0 235 796 A2 | 9/1987 |
| EP | 0 270 692 A1 | 6/1988 |
| EP | 0 309 422 A | 3/1989 |
| EP | 0 325 755 A1 | 8/1989 |
| EP | 0 341 860 A1 | 11/1989 |
| EP | 0 515 158 A1 | 11/1992 |
| EP | 0 524 784 A1 | 1/1993 |
| EP | 0 916 668 A1 | 5/1999 |
| GB | 1 003 292 | 9/1965 |
| GB | 1 003 950 | 9/1965 |
| GB | 1 013 574 | 12/1965 |
| GB | 1 085 406 | 10/1967 |
| GB | 1109847 | 4/1968 |
| GB | 1 206 216 | 9/1970 |
| GB | 1213172 | 11/1970 |
| GB | 1 330 966 | 9/1973 |
| GB | 1 347 935 | 2/1974 |
| JP | 61 167663 | 7/1986 |
| JP | 9040662 | 2/1997 |
| WO | WO89/10369 | 11/1989 |
| WO | WO92/16226 | 10/1992 |
| WO | WO92/20681 | 11/1992 |
| WO | WO93/02081 | 2/1993 |
| WO | WO96/31470 | 10/1996 |
| WO | WO96/31477 | 10/1996 |
| WO | WO96/31496 | 10/1996 |
| WO | WO96/31498 | 10/1996 |
| WO | WO97/24325 | 7/1997 |
| WO | WO97/44329 | 11/1997 |
| WO | WO98/02151 | 1/1998 |
| WO | WO98/04554 | 2/1998 |
| WO | WO98/11092 | 3/1998 |
| WO | WO98/11093 | 3/1998 |
| WO | WO98/11096 | 3/1998 |
| WO | WO98/11097 | 3/1998 |
| WO | WO98/11098 | 3/1998 |
| WO | WO98/11099 | 3/1998 |
| WO | WO98/11106 | 3/1998 |
| WO | WO98/15546 | 4/1998 |
| WO | WO98/25604 | 6/1998 |
| WO | WO98/25605 | 6/1998 |
| WO | WO98/25617 | 6/1998 |
| WO | WO98/27815 | 7/1998 |
| WO | WO98/43638 | 10/1998 |
| WO | WO98/46587 | 10/1998 |
| WO | WO99/37617 | 7/1999 |
| WO | WO99/37619 | 7/1999 |
| WO | WO99/37651 | 7/1999 |
| WO | WO 00/14086 | 3/2000 |
| WO | WO 00/14089 | 3/2000 |
| WO | WO 00/32193 A1 | 6/2000 |
| WO | WO 01/09094 A2 | 2/2001 |
| WO | WO 01/09119 A2 | 2/2001 |
| WO | WO 01/09137 | 2/2001 |
| WO | WO 01/09138 | 2/2001 |
| WO | 01/09137 * | 8/2001 |
| WO | WO 03/045942 | 6/2003 |

OTHER PUBLICATIONS

Kishimoto et al, "Leukocyte Adhesion Deficiency", The Journal of Biological Chemistry, vol. 264, pp. 3588-3595.*

Davis, M. A., et al., "New Psychotropic Agents. VIII Analogs of Amitriptyline Containing Normeperidine Group," *J. Med. Chem.*, 10:627-635 (1967).

Helwig, H., et al., "Helwig/Otto Arzneimittal, Ein Handbuch fur Arzte und Apotheker", pp. 4-1 through 4-24, 8th Ed., (1992).

Sindelar, Karel, et al., "Potential Antidiarrheal Agents:1-(11-Cyano-6,11-Dihydrodibenzo[b,e]Thiepin-11yl-Alklyl)- and 1-(10-cyano-10,11-Dihydrodibenzo[b,f]Thiepen-10-YL-Alkyl)-4-Substituted Piperidines," *Collection Czechoslovak Chem. Commun.* 50:1089-1096 (1985).

Sindelar, K., et al., Chemical Abstracts, 121:35275n (1994).

Sindelar, Karel, et al., "Antihistamine Substances: Tricyclic Analogues of N-(4,4-Diphenyl-3Butene-1YL)Nipecotic Acid and Some Related Compounds," *Collection Czechoslovak Chem. Commun.* 59:667-674 (1994).

Ali Fadia E., et al., "Orally Active and Potent Inhibitors of γ-Aminobutyric Acid Uptake," *J. Med. Chem.* 28:653-660 (1985).

Sindelar, Karel, et al., "Potential Antihistaminies: Tricyclic Carboxylic Acids Derived from 6,11-Dihydrodibenzo[b,e]Thiepine and 4,9-Dihydrothieno[2,3-c]-2-Benzothiepine," *Collection Czechoslovak Chem. Commun.* 56:2482-2493 (1991).

Polivka, Zdenek, et al., "Heterocyclic Ethers Derived from 6,11-Dihydrodibenzo-[b,e]Thiepin-11-ols and 4,9-Dihydrothieno[2,3-c]-2-Benzothiepin-4-ol; A New Series of Potential Antidepressants and Antihistamine Agents," *Collection Czechoslovak Chem. Commun.* 51:2034-2049 (1986).

Polivka, Zdenek, et al., "Antiaminic Agents Derived from Thieno[2,3-c]-2-Benzothiepin: 4-(1-Methyl-4-Piperidylidene)-4,9-Dihydrothieno[2,3-c]-2-Benzothiepin and some Related Compounds," *Collection Czechoslovak Chem. Commun.* 48:623-641 (1983).

Rajsner, M., et al., "Neurotropic and Psychotropic Compounds. XXXI Chemistry and Pharmacology of 11-(3-Dimethylaminopropylidene)-2-Mehtyl-6,11-Dihydrodibenzo[b,e]Thiepin and of Some Analogues," *Collection Czechoslovak Chem. Commun.* 34:1015-1024 (1969).

Rajsner, M., et al., "Neurotrope and Psychotrope Substanzen XV. 4,9-Dihydrothieno[2,3-b]Benzo[e]Thiepin-Derivate," *Collection Czechoslovak Chem. Commun.* 32:2854-2866 (1967).

Hesselgesser, Joseph, et al., "Identification and Characterization of Small Molecule Functional Antagonists of the CCR1 Chemokine Receptor", *The Journal of Biological Chemistry*, 273(25):15687-15692 (1998).

Masaru, E. et al., Chemical Abstracts, 93(19), 186323f (1980).

Tsujikawa, T. et al., Chemical Abstracts, 77(25), 164662h (1972).

Nakanishi, M. et al., Chemical Abstracts, 81, 25566Z (1974).

Ting, P.C. et al., Chemical Abstracts, 123:227838 (1995).

Kumazawa, T. et al., Chemical Abstracts, 126:212158 (1997).

Kato, K. et al., Chemical Abstracts, 130:237480 (1999).

Davis, M.A. et al., Chemical Abstracts, 67:99959 (1967).

Kukla, Michael, J., Chemical Abstracts, 92:198282 (1980).

Protiva, M. et al., Chemical Abstracts, 72:3387 (1970).
Protiva, M. et al., Chemical Abstracts, 109:92794 (1988).
Protiva, M. et al., Chemical Abstracts, 104:19527 (1986).
Protiva, M. et al., Chemical Abstracts, 107:134327 (1987).
Sindelar, K. et al., Chemical Abstracts, 104:33990 (1986).
Michaels, R.J. et al., Chemical Abstracts, 77:88537 (1972).
Foldeak, S. et al., Chemical Abstracts, 105:172012 (1986).
Iorio, L.C. et al., Chemical Abstracts, 115:126879 (1991).
Aftab, D.T. et al., Chemical Abstracts, 116:120373 (1992).
King, Frank D., "Bioisosteres, Conformational Restriction, and Pro-drugs-Case History: An Example of a Conformational Restriction Approach," *Medicinal Chemistry: Principles and Practice,* The Royal Society of Chemistry, London, 1995, Chapter 14, pp. 206-208.
Foldeak, S. et al., "The Mannich Reaction of 9-Acteyl- and 9, 10-Dihydro-9-Acetylanthracene. Reduction of the Mannich Bases, and Stereochemistry of the 9, 10-Dihydro Compounds," *Tetrahedron,* 41(24):5913-5918 (1985).

Iorio, L.C. et al., "Anticholinergic Drugs Potentiate Dopamine D1 but not D2 Antagonists on a Conditioned Avoidance Task in Rats," *J. Pharmacol. Exp. Ther.,* 258(1), 118-123 (1991).
Aftab, D.T. et al., "Structure-Activity Relationships of Phenothiazines and Related Drugs for Inhibiton of Protein Kinase C," *Mol. Pharmacol.* 40(5):798-805 (1991).
S.J. Rappaport, Ed., "Inflammation and Phagocytosis," In: *Physiological Basis of Medical Practice, Twelfth Edition,* J.B. West, Ed., Williams & Wilkins, Baltimore, pp. 362-368 (1990).
Schmelz, M. and Petersen, L.J., "Neurogenic Inflammation in Human and Rodent Skin," *News Physiol. Sci.,* 16:33-37 (2001).
Howard, O.M.Z. et al., "Chemokines: Progress Toward Identifying Molecular Targets for Therapeutic Agents," TIBTECH., 14:46-51 (1996).
Protiva, M. et al., Chemical Abstracts, 107:134326 (1987).
Oshima, E. et al., Chemical Abstracts, 115:256025 (1991).

* cited by examiner

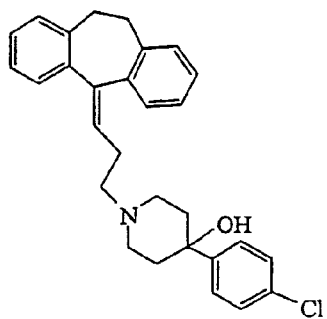 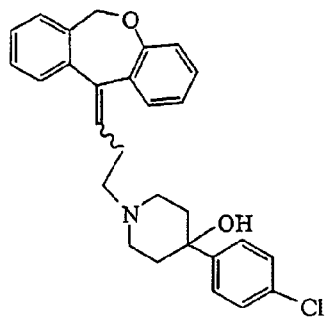
Example 1   Example 2
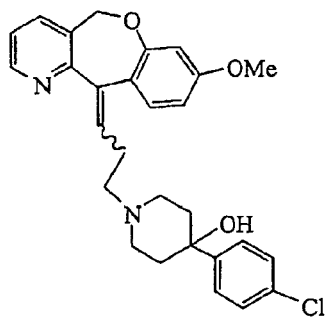 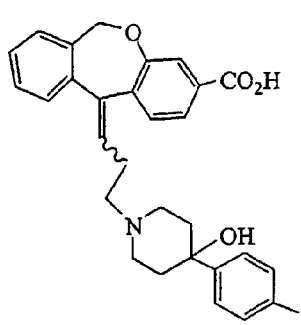 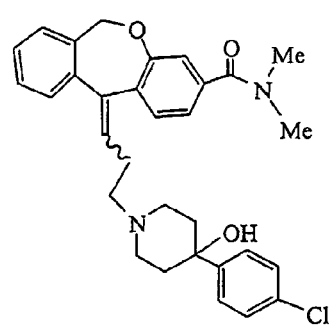
Example 4   Example 5   Example 6
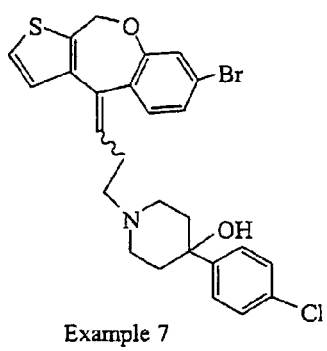 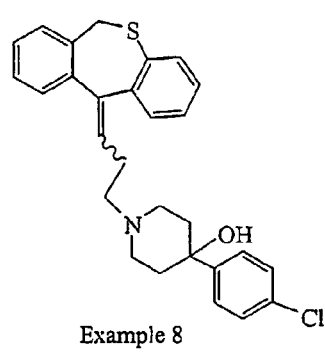 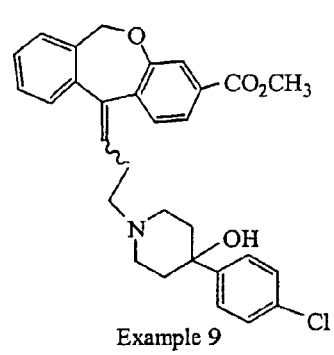
Example 7   Example 8   Example 9
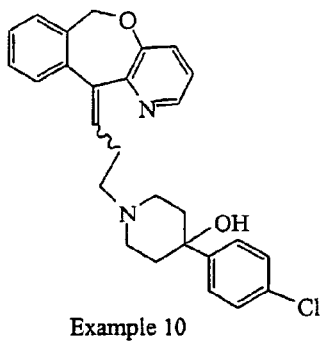 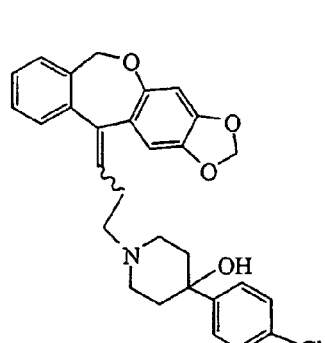 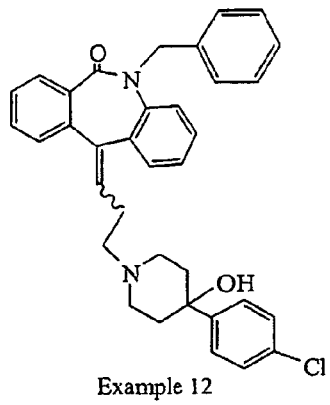
Example 10   Example 11   Example 12
Figure 6A

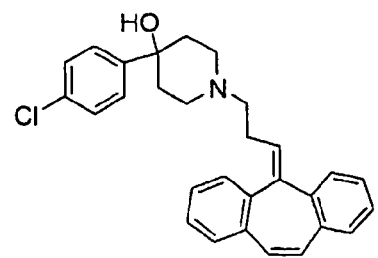
Example 21
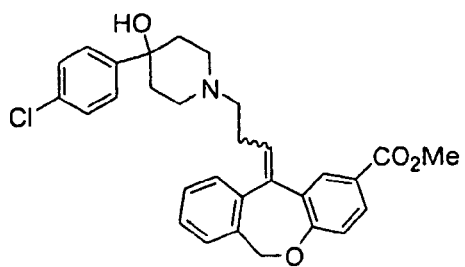
Example 22
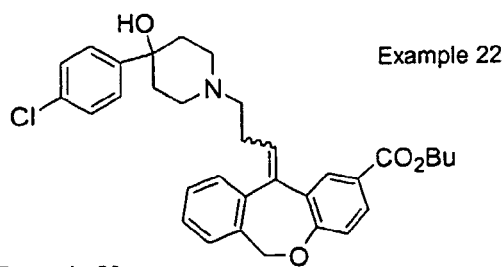
Example 23
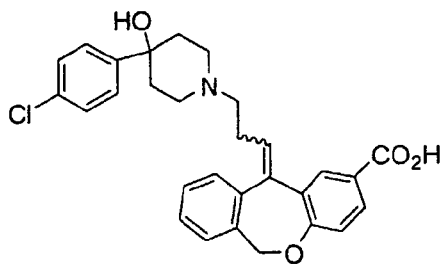
Example 24
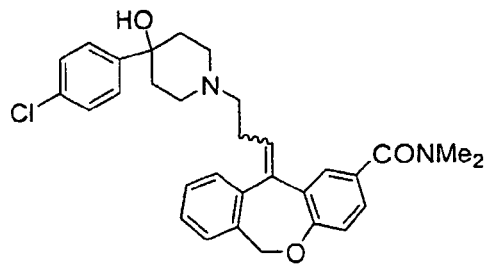
Example 25
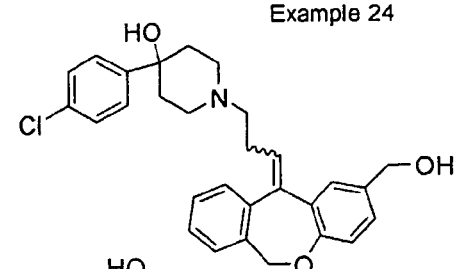
Example 26
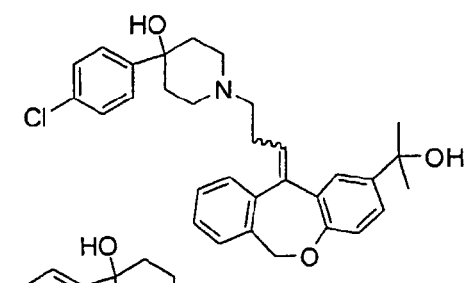
Example 27
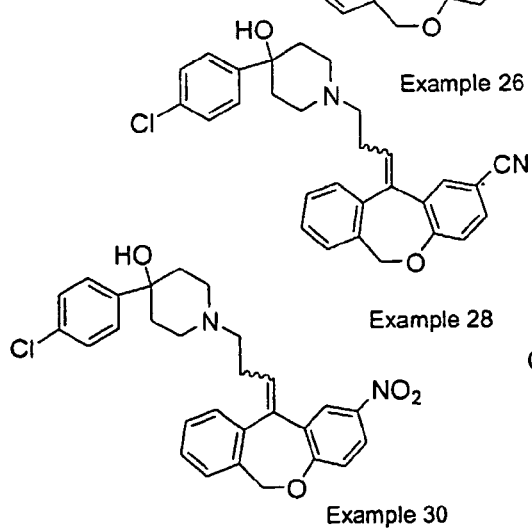
Example 28
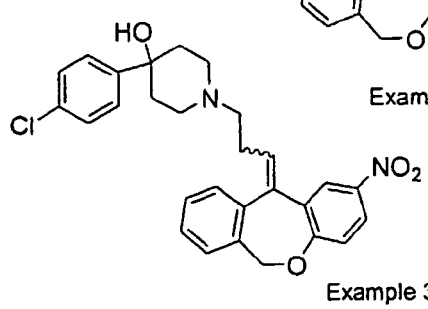
Example 30
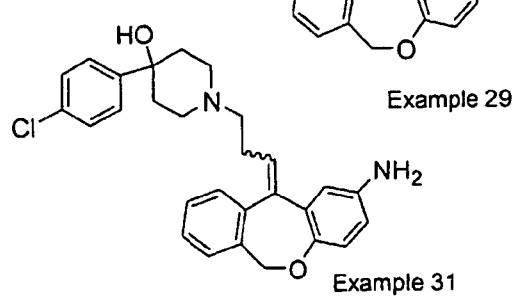
Example 29
Example 31
Figure 6C

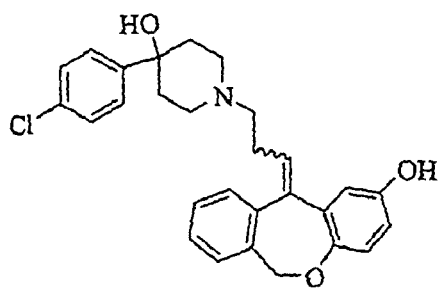
Example 32
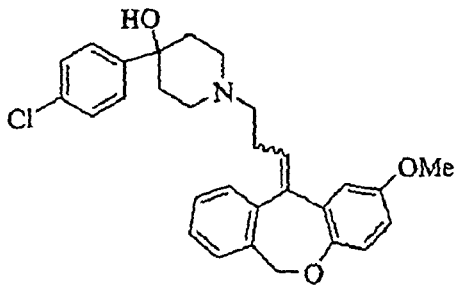
Example 33
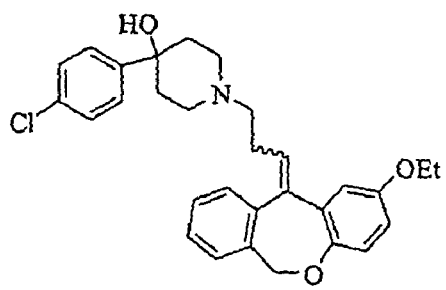
Example 34
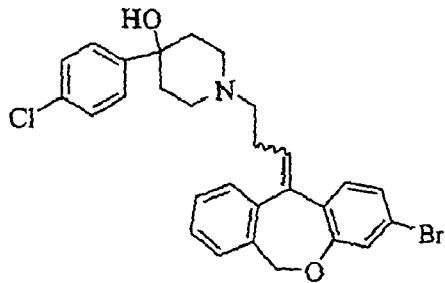
Example 35
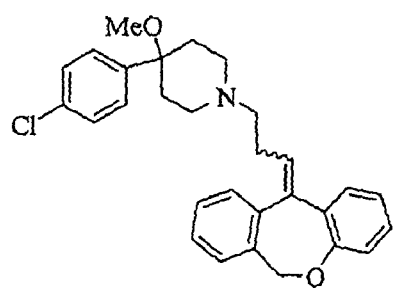
Example 36
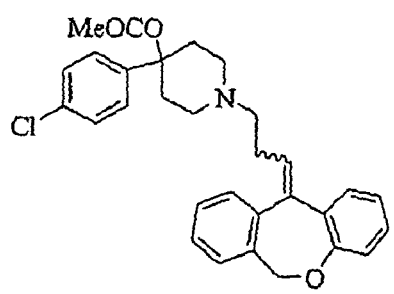
Example 37
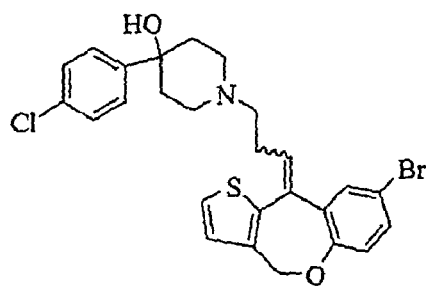
Example 38
Figure 6D

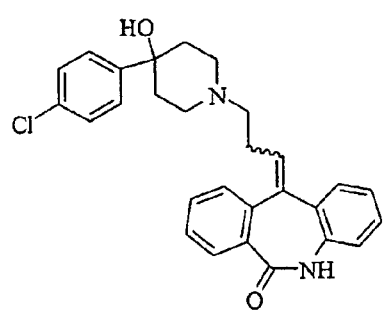
Example 39
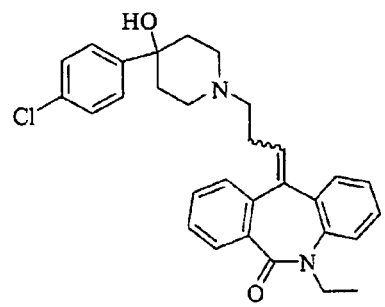
Example 40
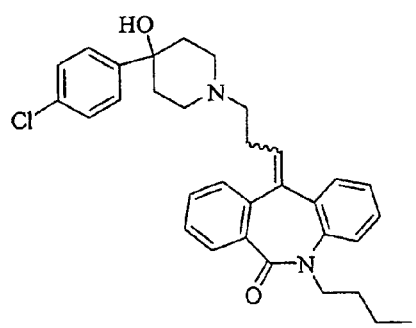
Example 41
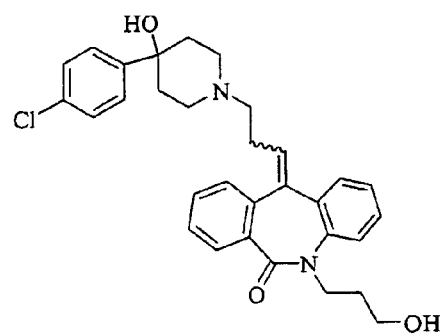
Example 42
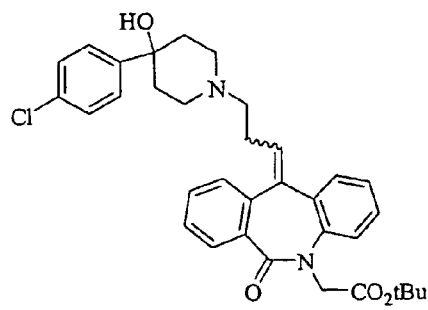
Example 43
Figure 6E

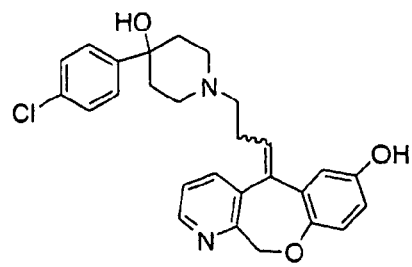
Example 44
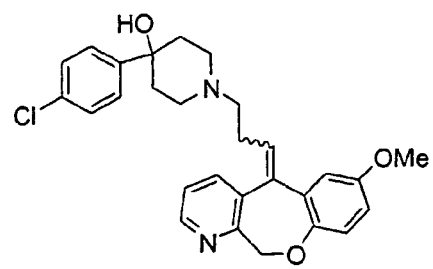
Example 45
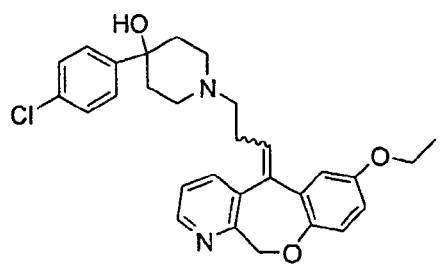
Example 46
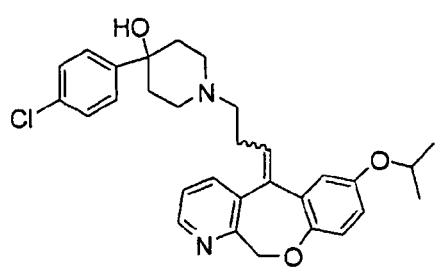
Example 47
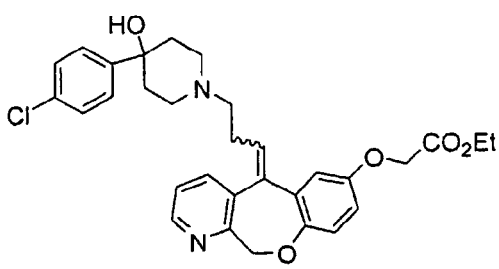
Example 48
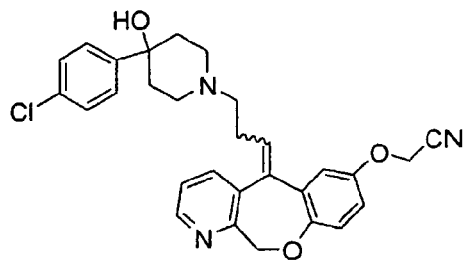
Example 49
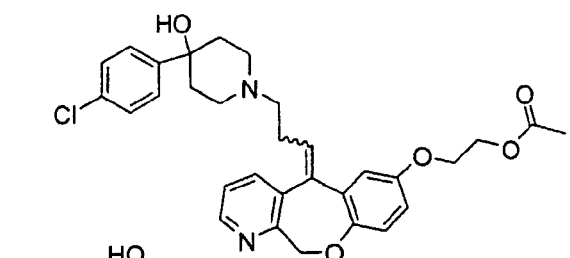
Example 50
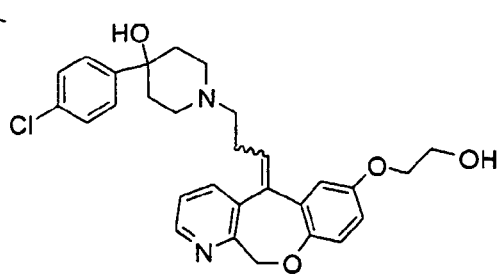
Example 51
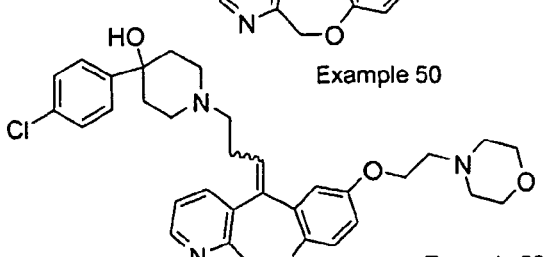
Example 52
Figure 6F

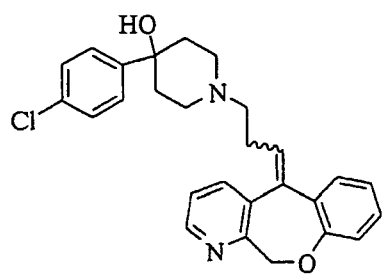
Example 53
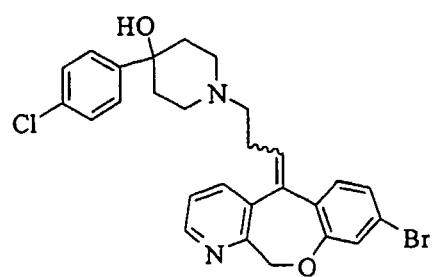
Example 54
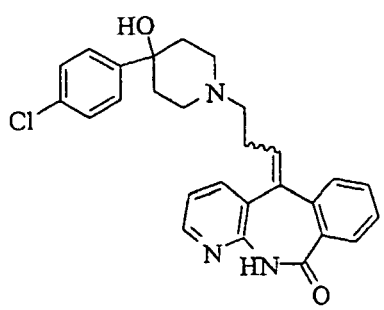
Example 55
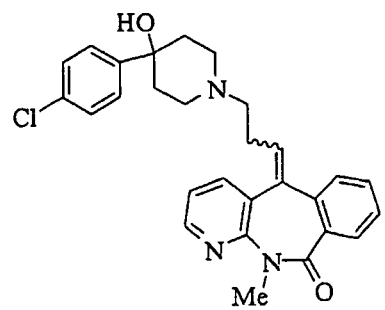
Example 56
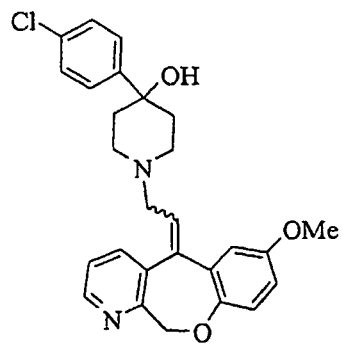
Example 57
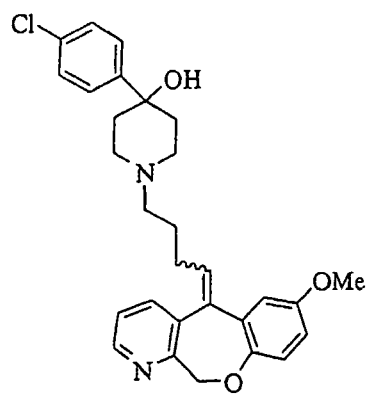
Example 58
Figure 6G

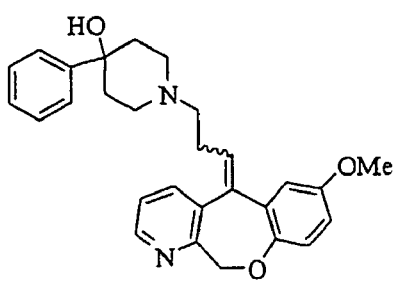
Example 59
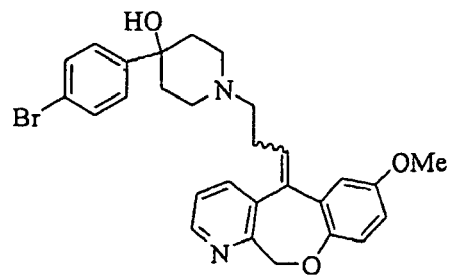
Example 60
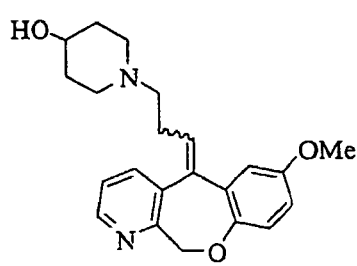
Example 61
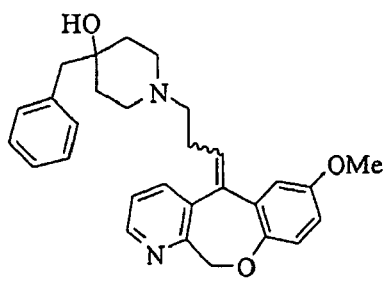
Example 62
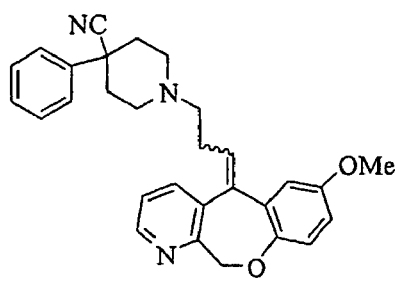
Example 63
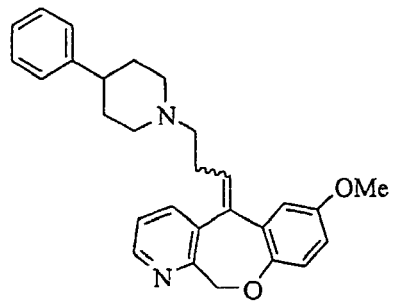
Example 64
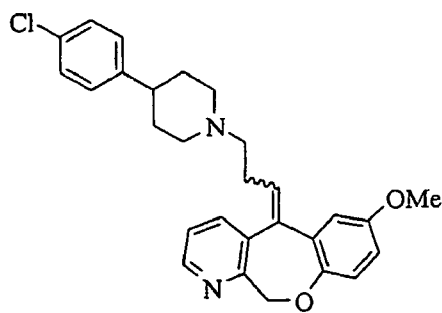
Example 65
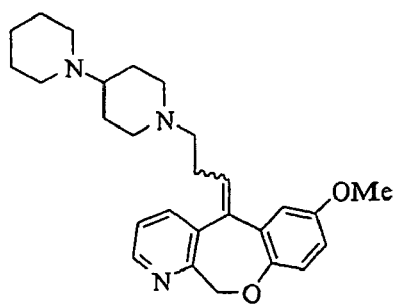
Example 66
Figure 6H

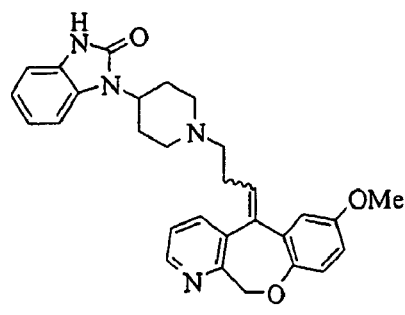
Example 67
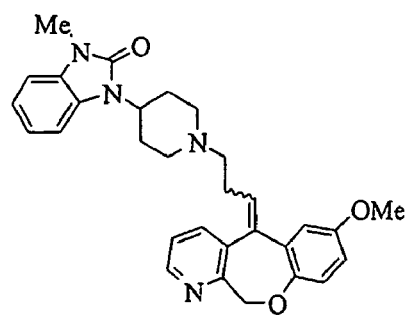
Example 68
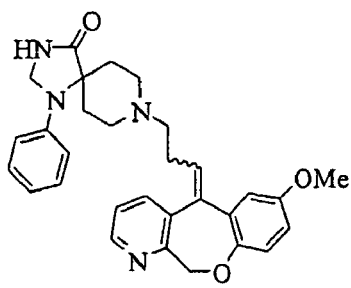
Example 69
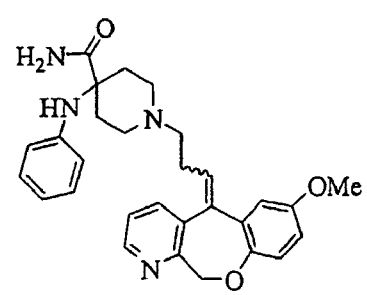
Example 70
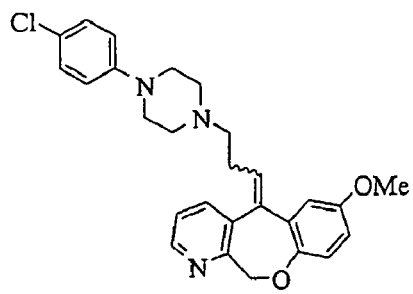
Example 71
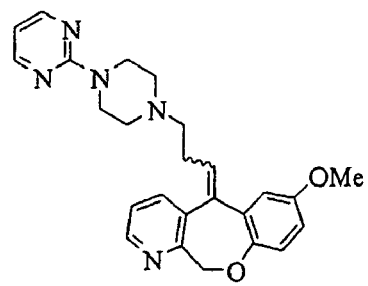
Example 72
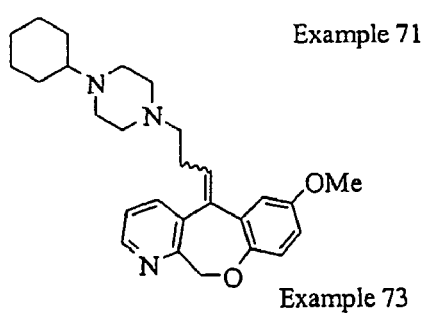
Example 73
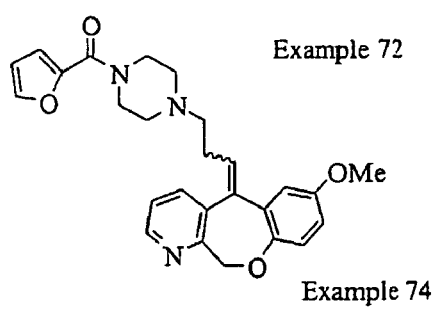
Example 74
Figure 6I

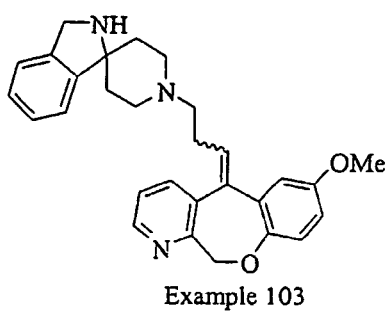
Example 103
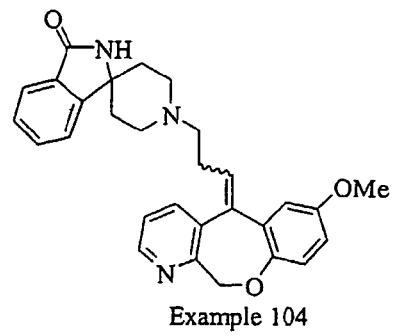
Example 104
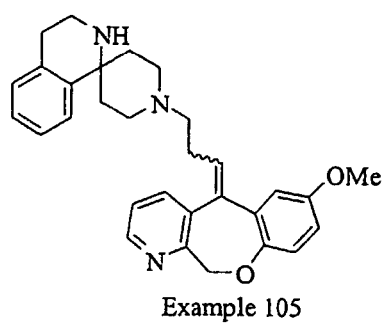
Example 105
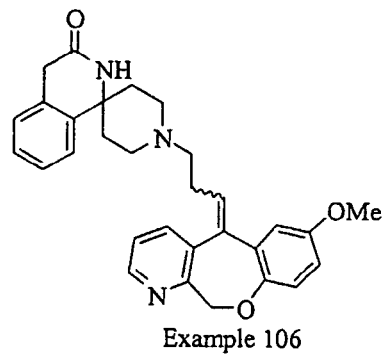
Example 106
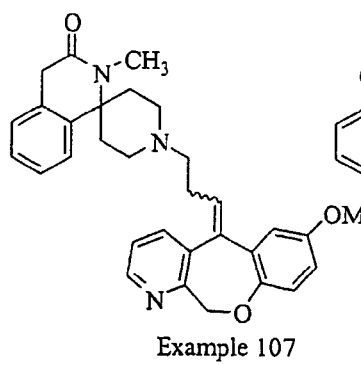
Example 107
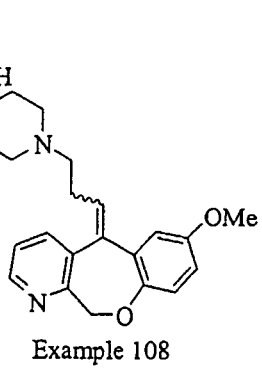
Example 108
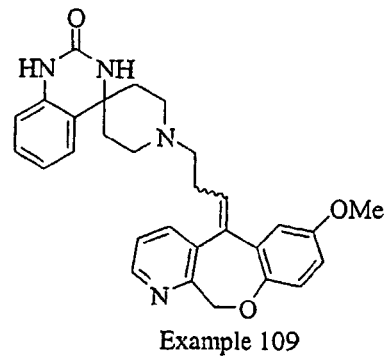
Example 109
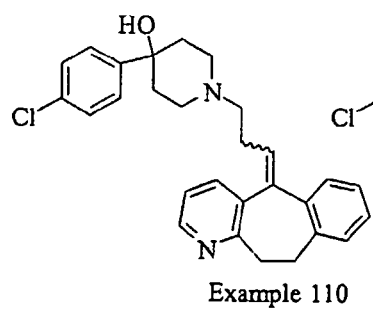
Example 110
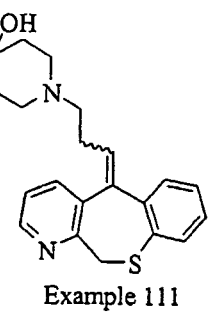
Example 111
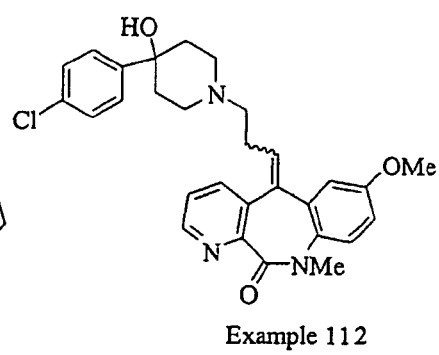
Example 112
Figure 6L

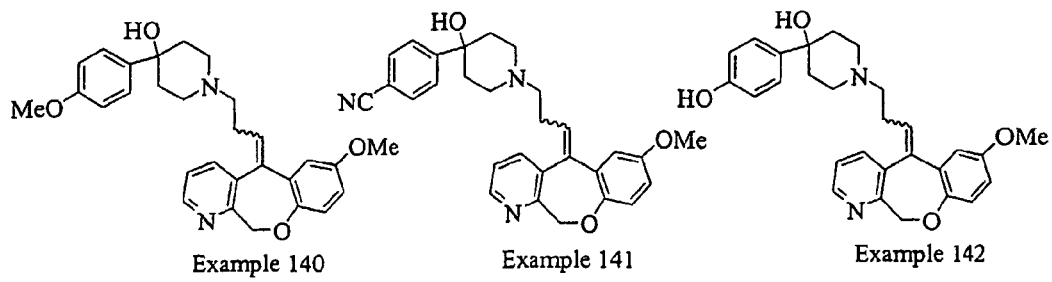
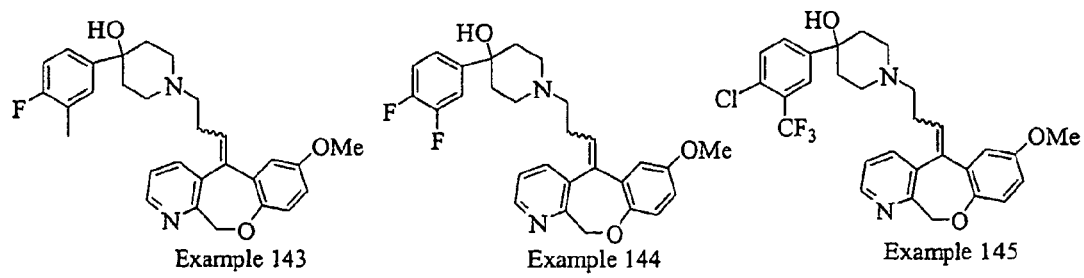
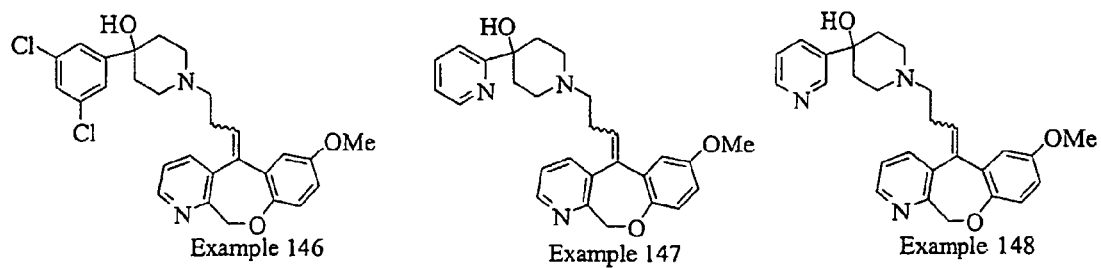
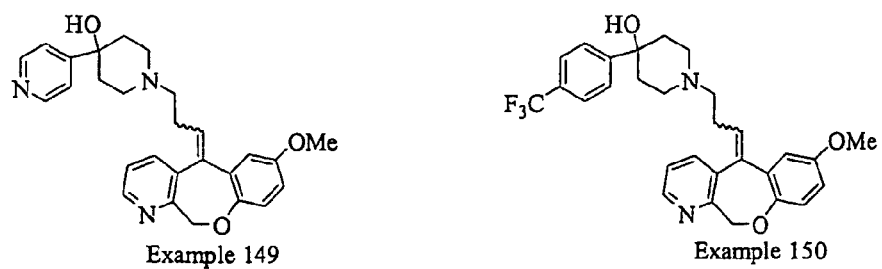
Figure 60

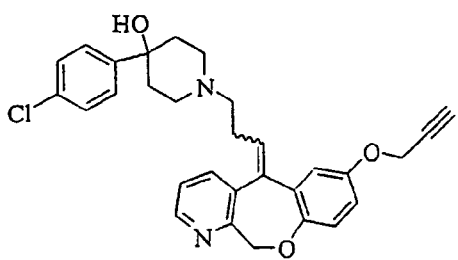
Example 173
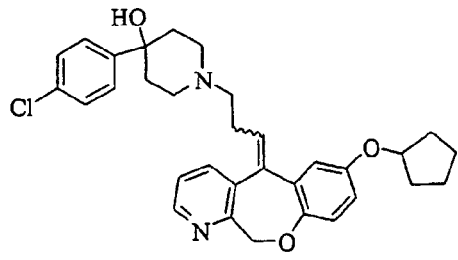
Example 174
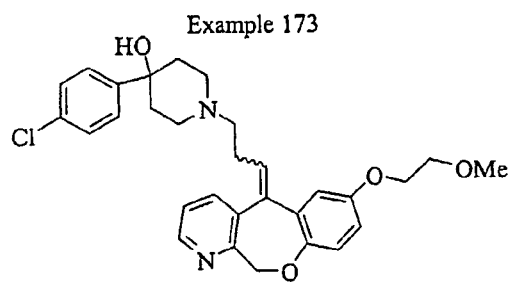
Example 175
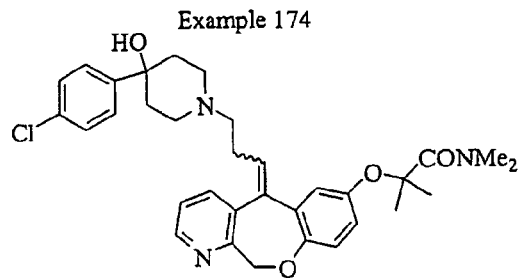
Example 176
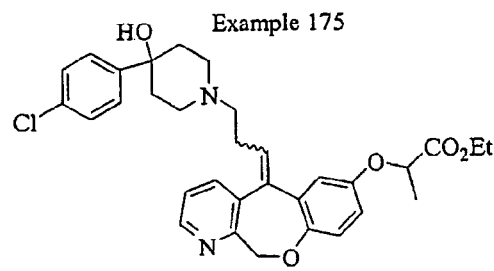
Example 177
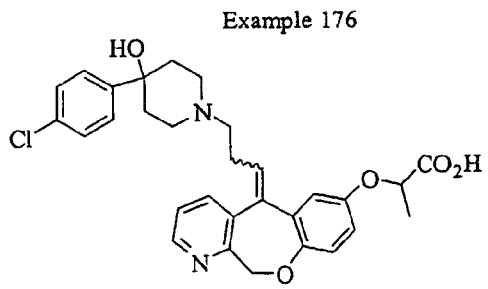
Example 178
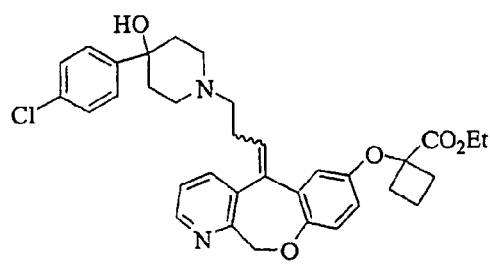
Example 179
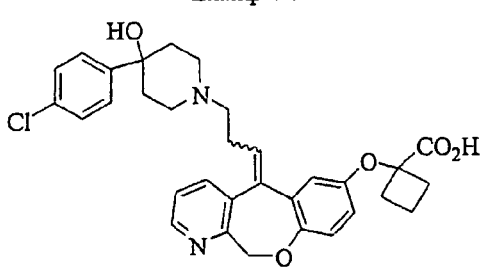
Example 180
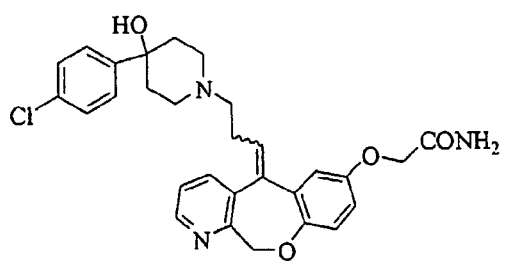
Example 181
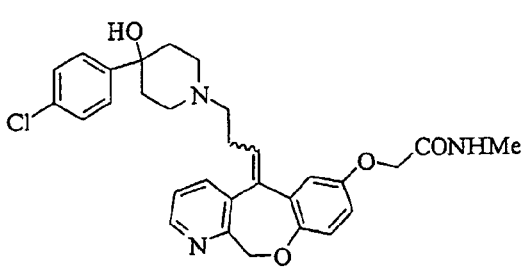
Example 182
Figure 6R

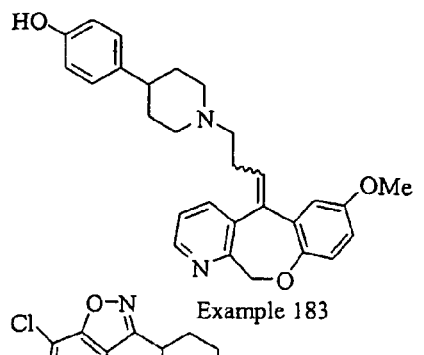
Example 183
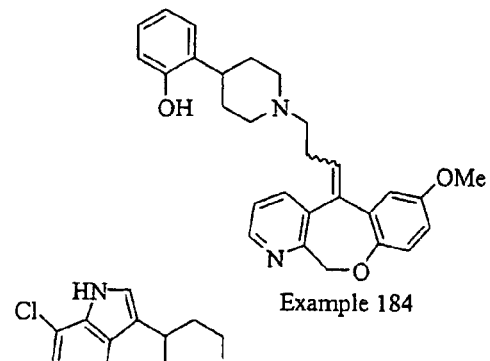
Example 184
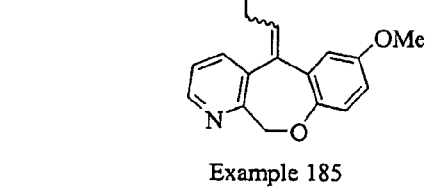
Example 185
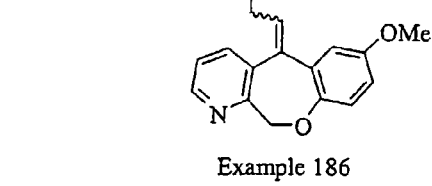
Example 186
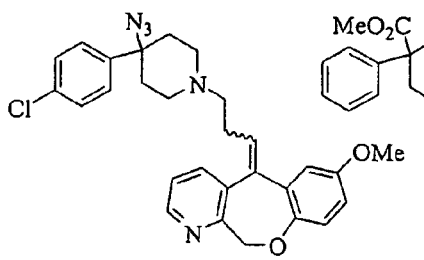
Example 187
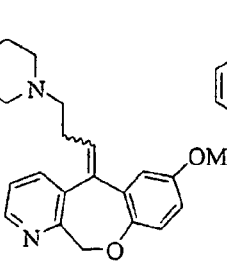
Example 188
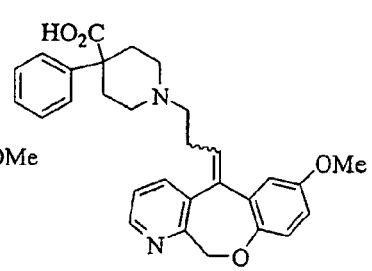
Example 189
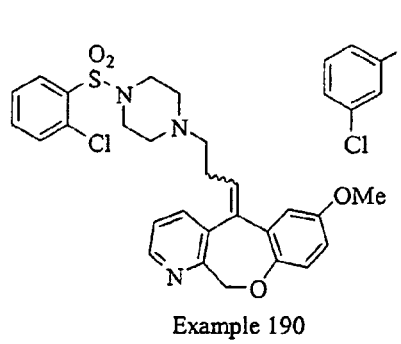
Example 190
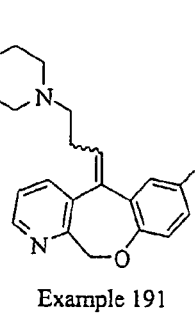
Example 191
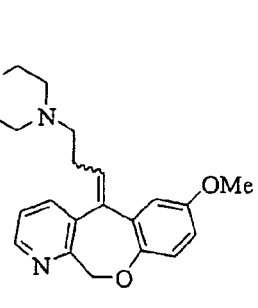
Example 192
Figure 6S

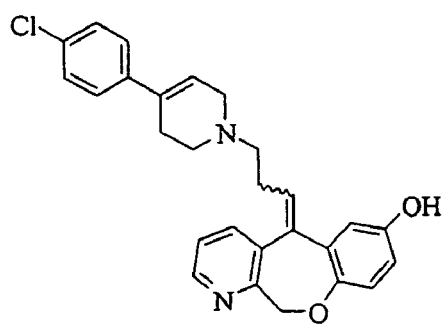
Example 193
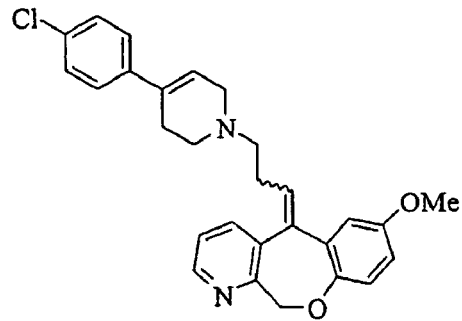
Example 194
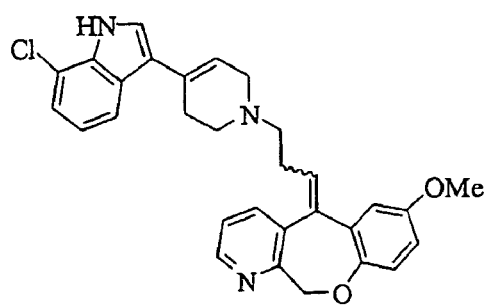
Example 195
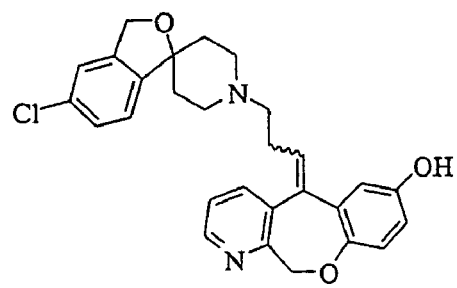
Example196
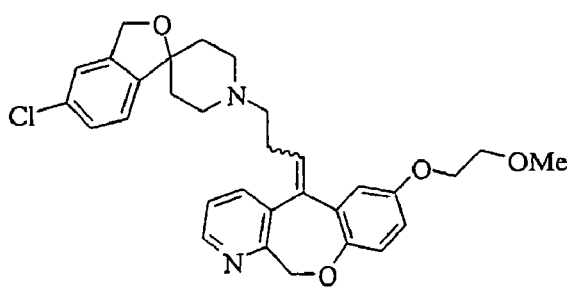
Example 197
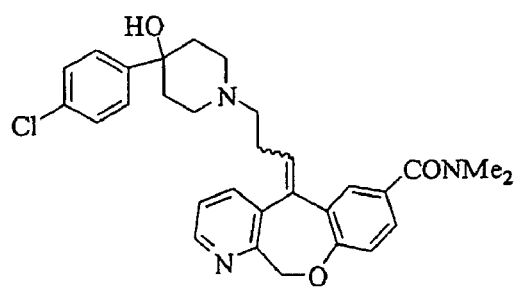
Example 198
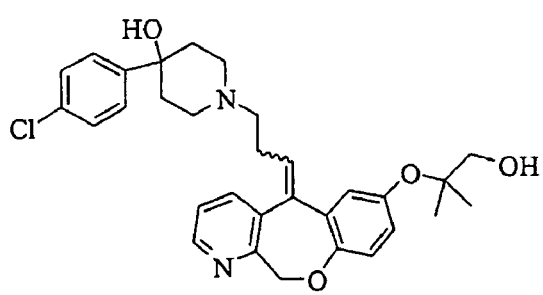
Example 199
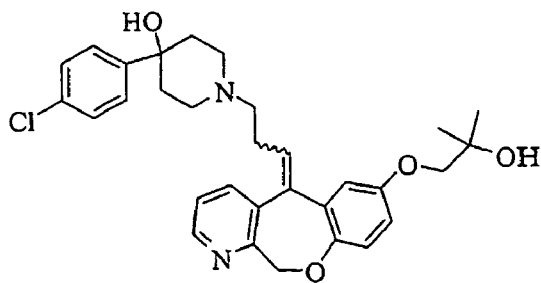
Example 200
Figure 6T

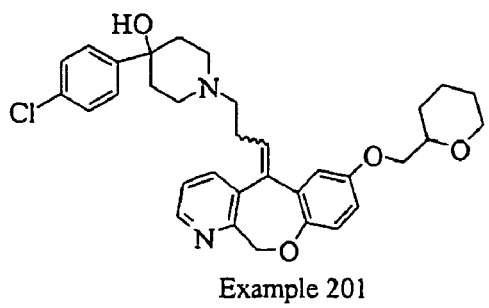
Example 201
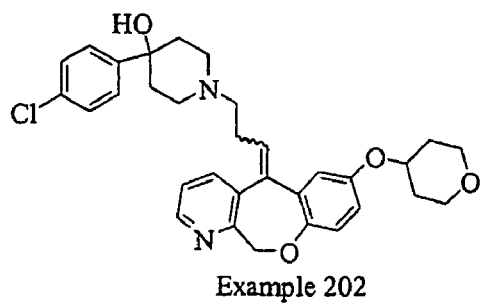
Example 202
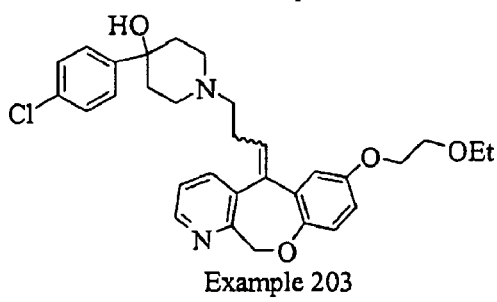
Example 203
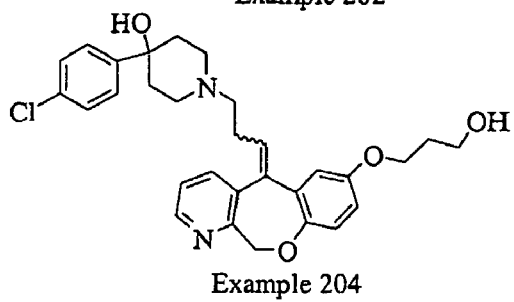
Example 204
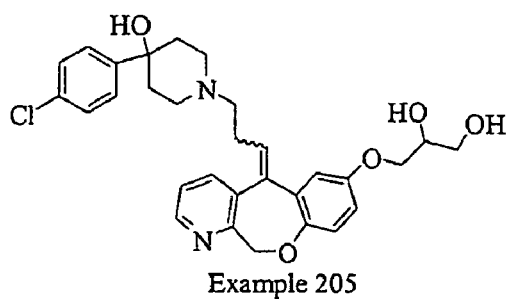
Example 205
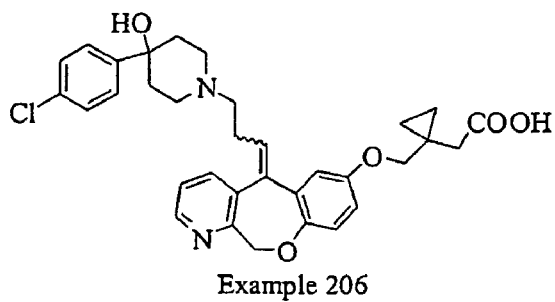
Example 206
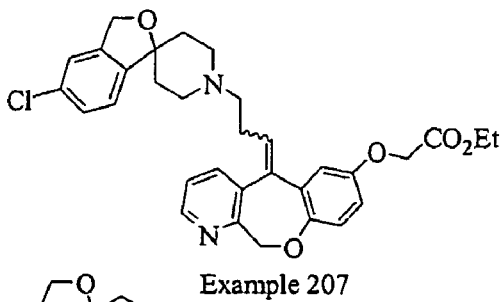
Example 207
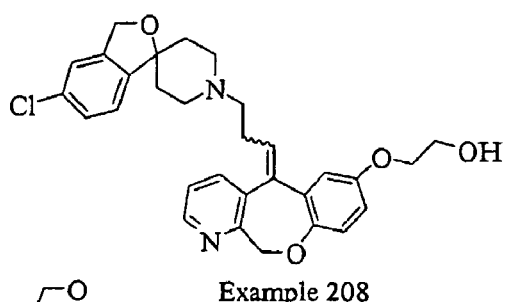
Example 208
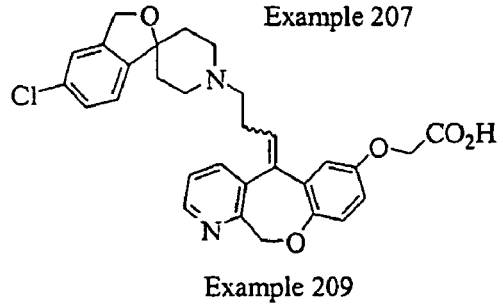
Example 209
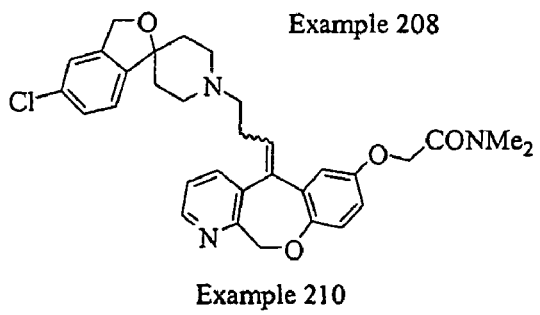
Example 210
Figure 6U

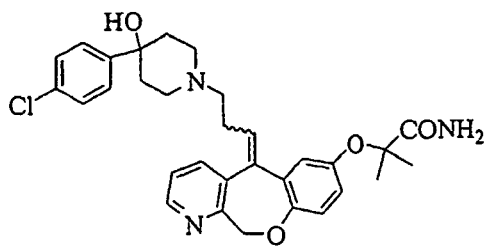
Example 211
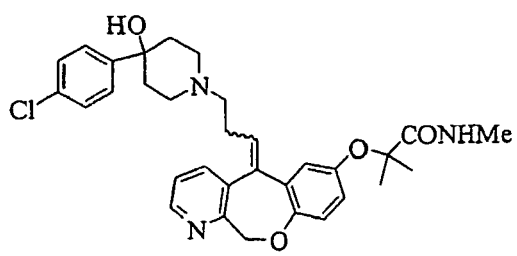
Example 212
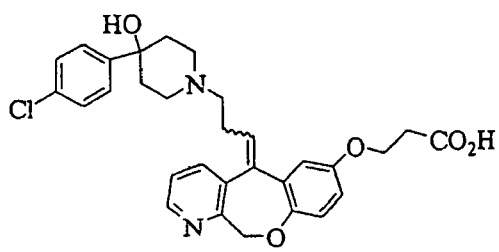
Example 213
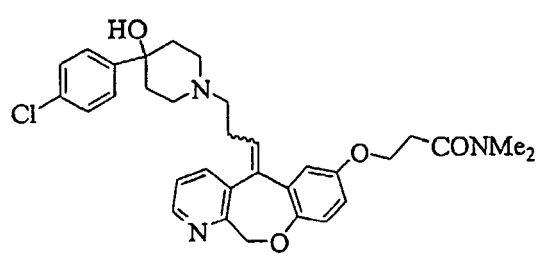
Example 214
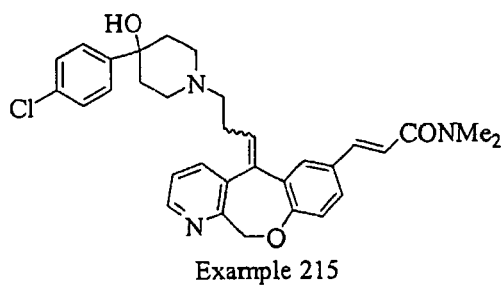
Example 215
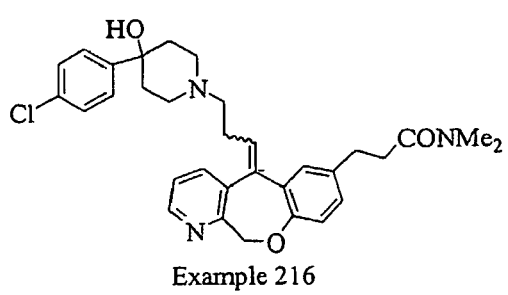
Example 216
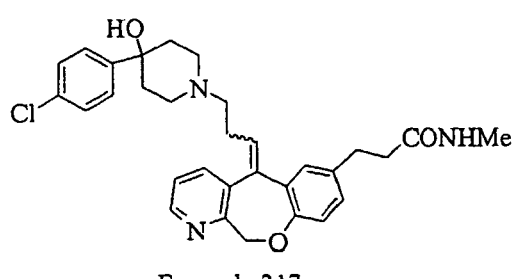
Example 217
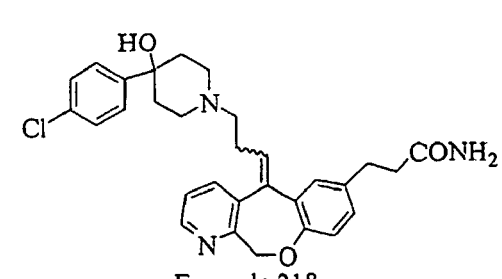
Example 218
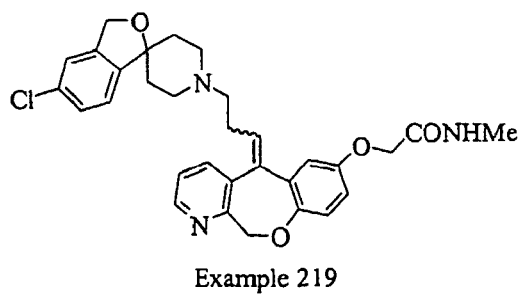
Example 219
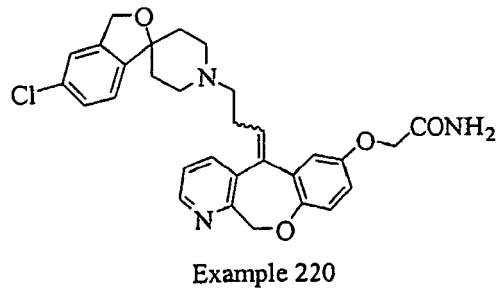
Example 220
Figure 6V

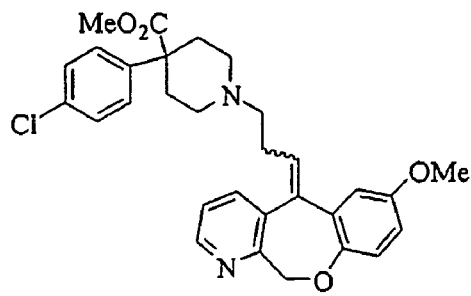
Example 232
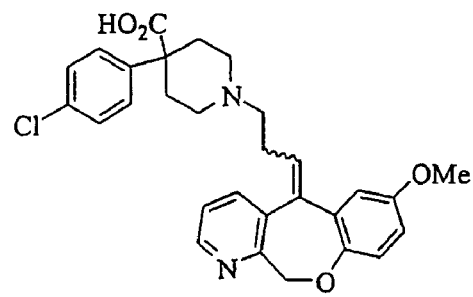
Example 233
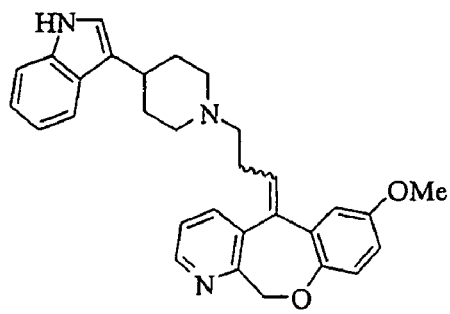
Example 234
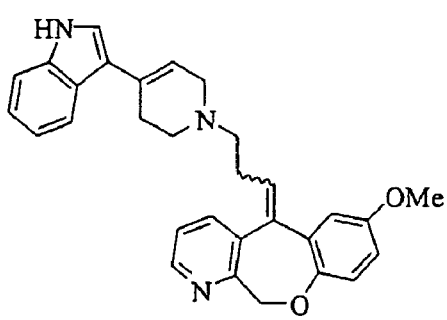
Example 235
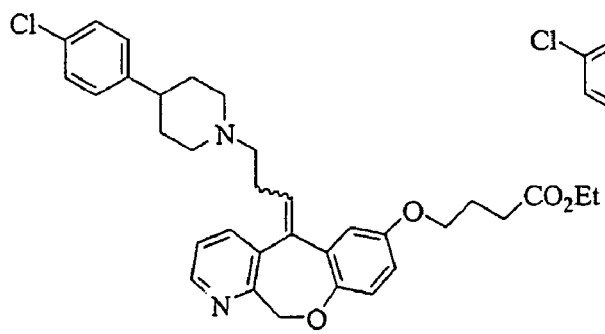
Example 236
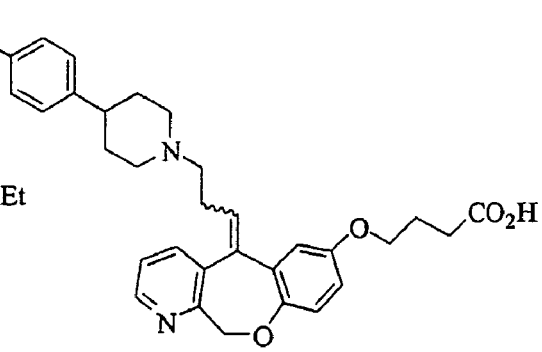
Example 237
Figure 6X

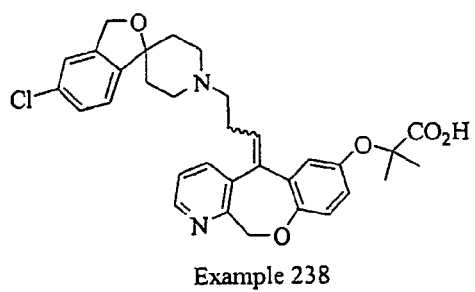
Example 238
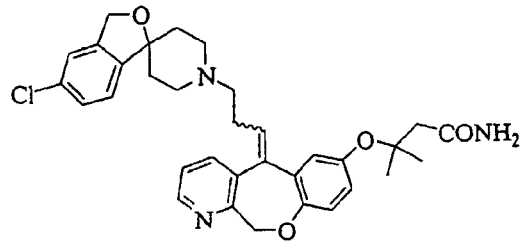
Example 239
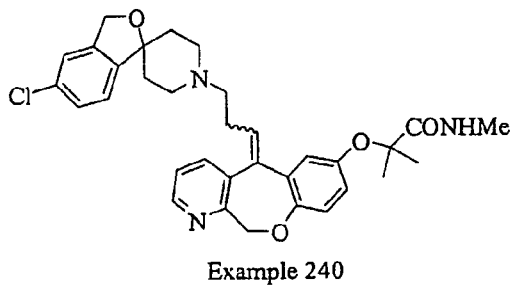
Example 240
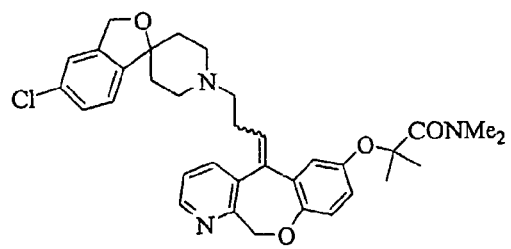
Example 241
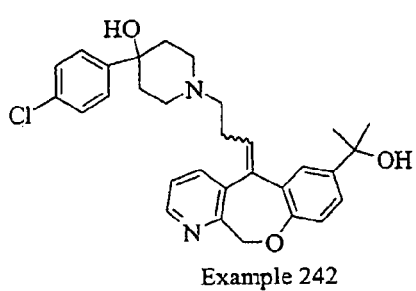
Example 242
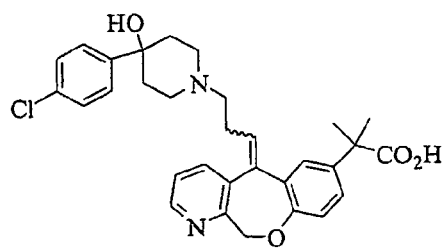
Example 243
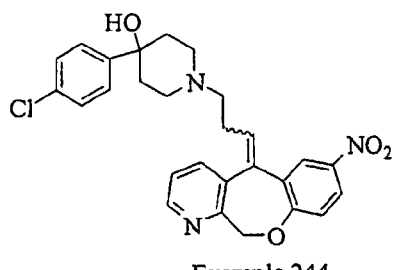
Example 244
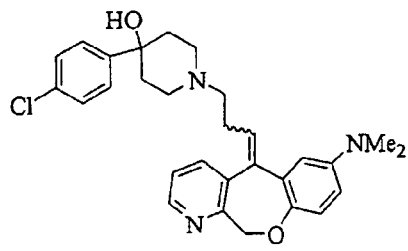
Example 245
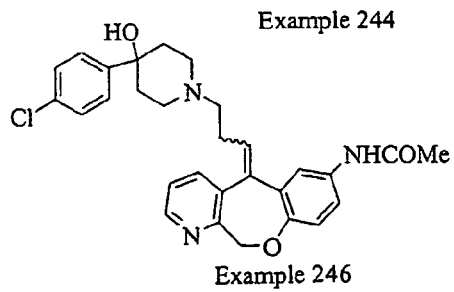
Example 246
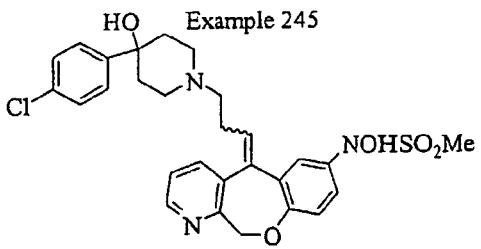
Example 247
Figure 6Y Example 248

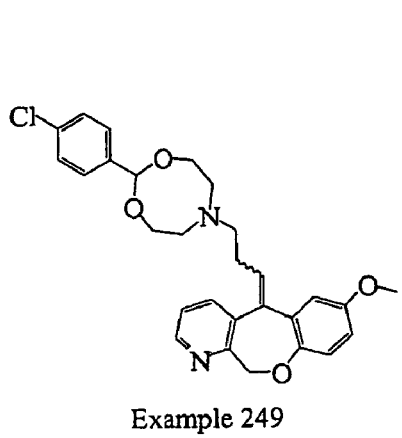
Example 249
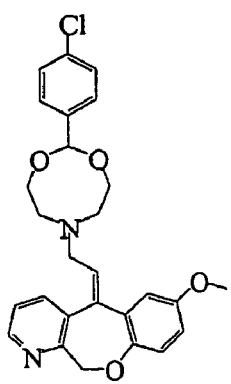
Example 250
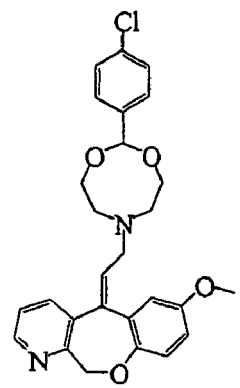
Example 251
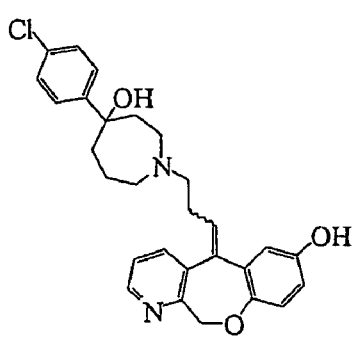
Example 252
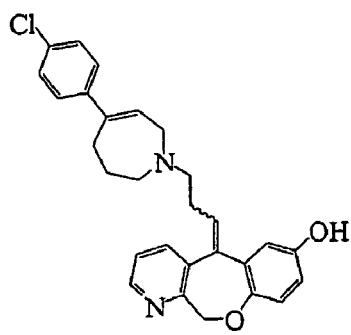
Example 253
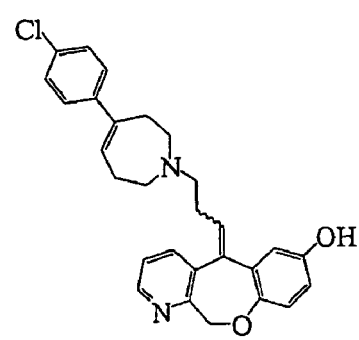
Example 254
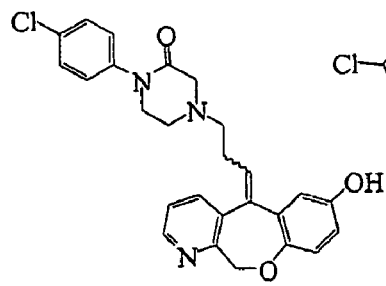
Example 255
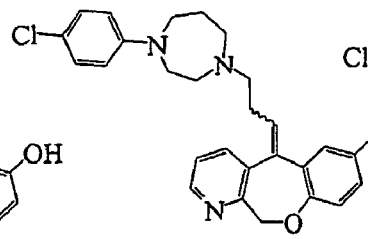
Example 256
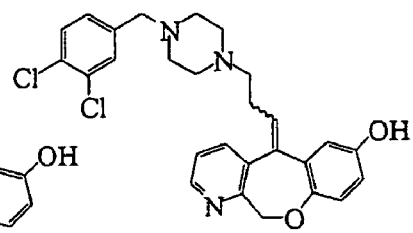
Example 257
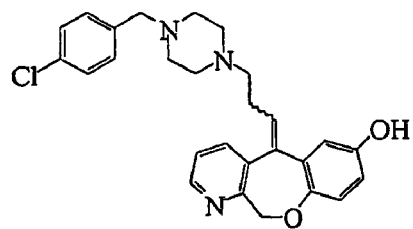
Example 258
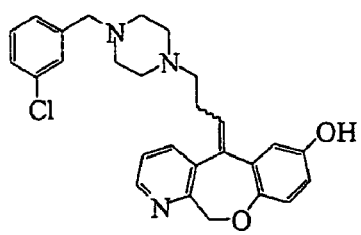
Example 259
Figure 11A

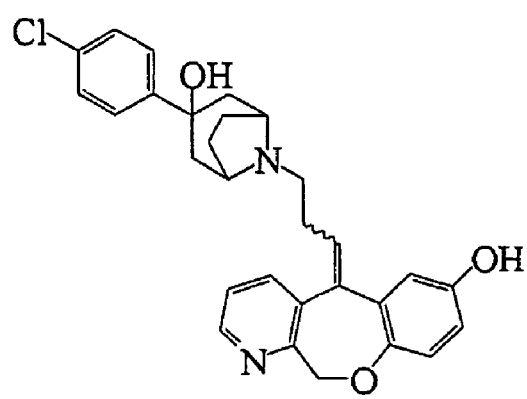
Example 260
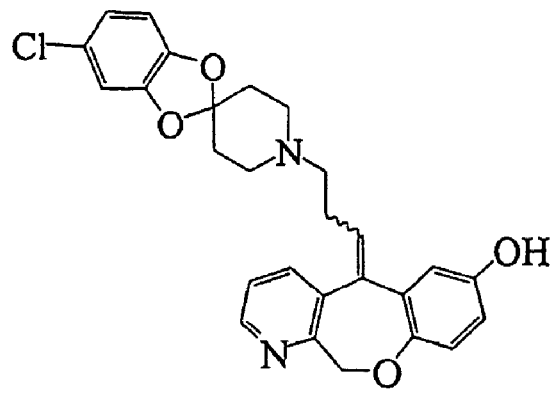
Example 261
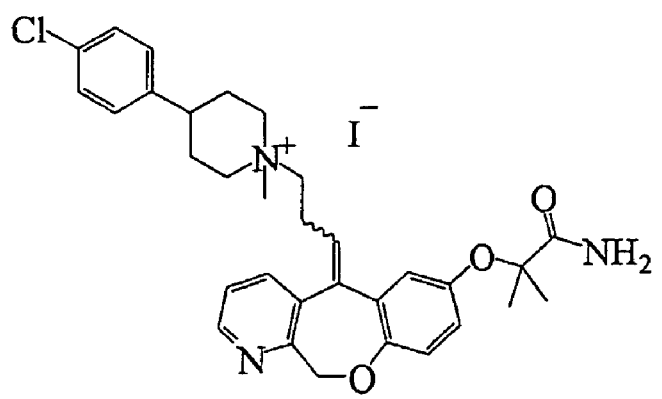
Example 262
Figure 11B

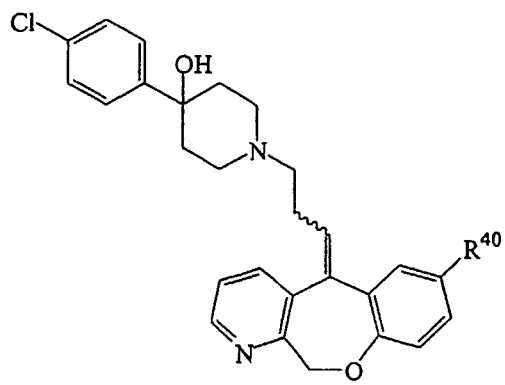
| | $R^{40}$ | | $R^{40}$ |
|---|---|---|---|
| Example 263 | 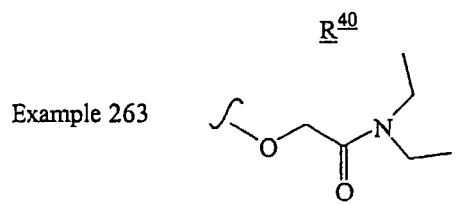 | Example 272 | 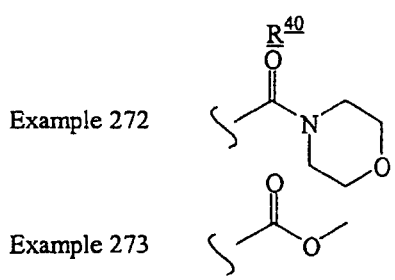 |
| Example 264 | 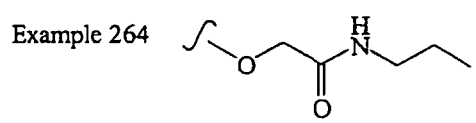 | Example 273 |  |
| Example 265 | 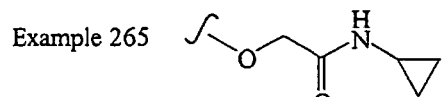 | Example 274 |  |
| Example 266 | 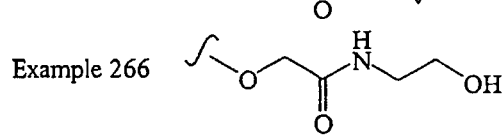 | Example 275 |  |
| Example 267 | 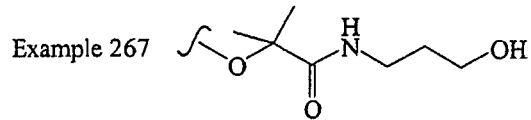 | Example 276 | 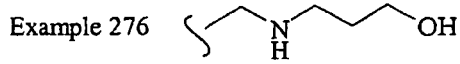 |
| Example 268 | 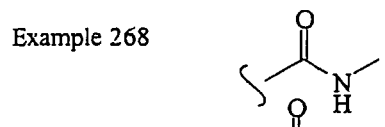 | Example 277 | 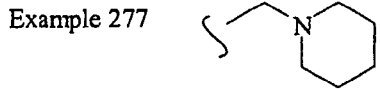 |
| Example 269 |  | Example 278 | 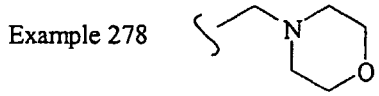 |
| Example 270 |  | Example 279 | 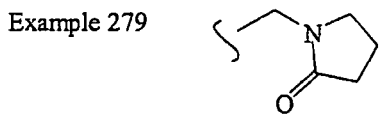 |
| Example 271 |  | Example 280 | 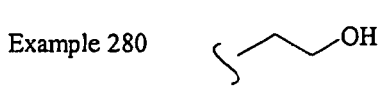 |
Figure 11C

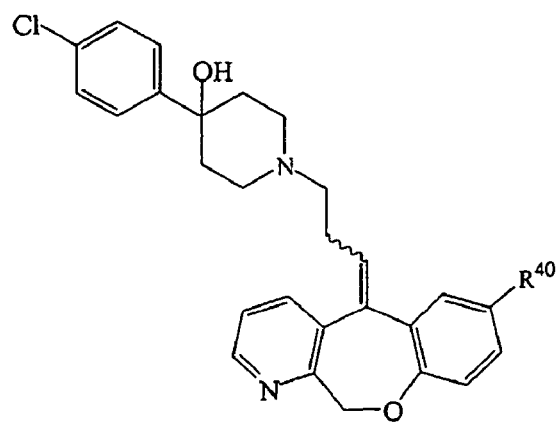
| | R40 |
|---|---|
| Example 316 | 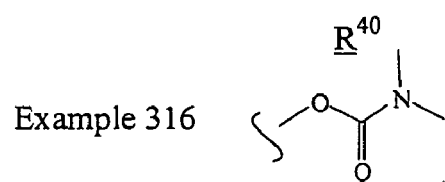 |
| Example 317 | 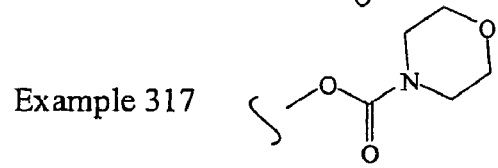 |
| Example 318 | 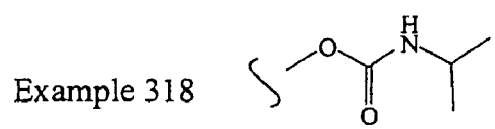 |
| Example 319 | 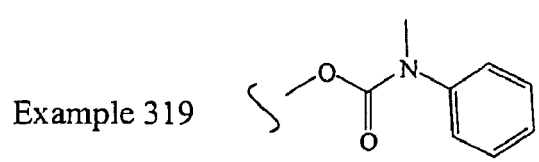 |
| Example 320 | 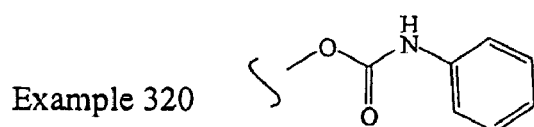 |
| Example 321 | 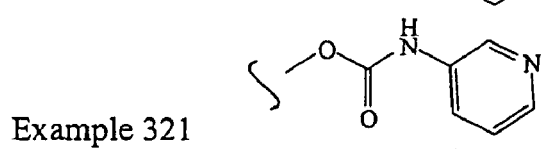 |
| Example 322 | 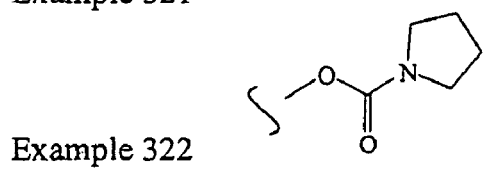 |
Figure 11F

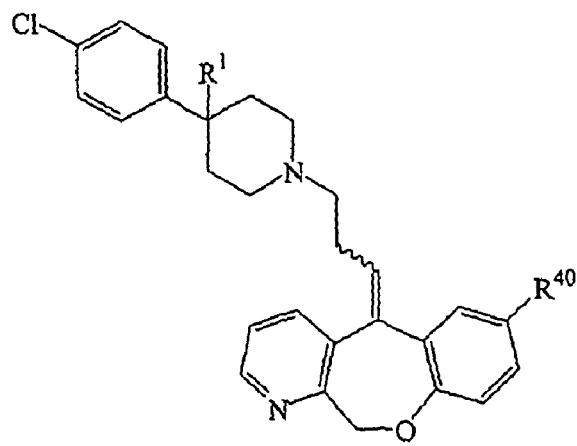
| | R¹ | R⁴⁰ |
|---|---|---|
| Example 323 | -CN | -OCH₃ |
| Example 324 | -CH₂NH₂ | -OCH₃ |
| Example 325 | -NH₂ | -OCH₃ |
| Example 326 | -CH₃ | -OCH₃ |
| Example 327 | -OCH₃ | -OCH₃ |
| Example 328 | -F | -OH |
| Example 329 | -CH₃ | -OH |
| Example 330 | -CH₃ | 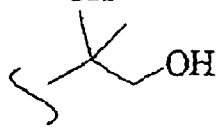 |
Figure 11G

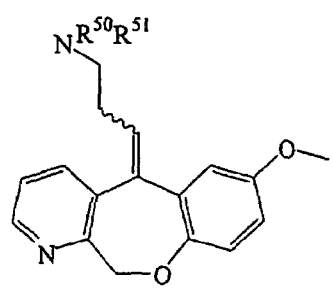
| | R[50] | R[51] |
|---|---|---|
| Example 331 | 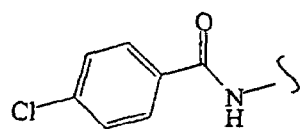 | -H |
| Example 332 | 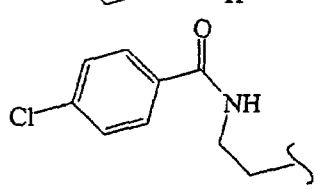 | -H |
| Example 333 | 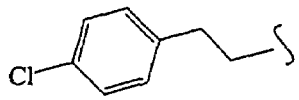 | -CH₃ |
| Example 334 | 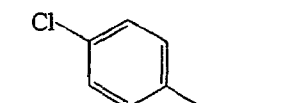 | -CH₃ |
| Example 335 | 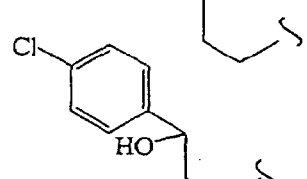 | -CH₃ |
| Example 336 | 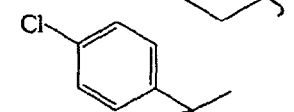 | -CH₃ |
| Example 337 | 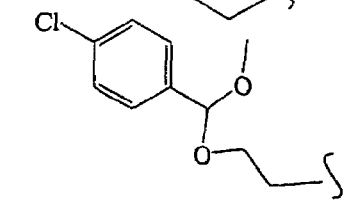 | 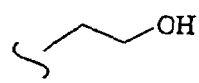 |
Figure 11H

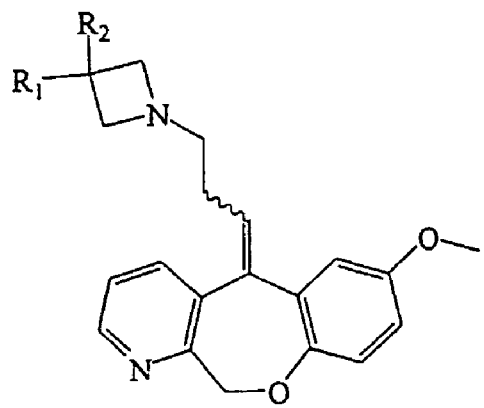
|  | R¹ | R² |
|---|---|---|
| Example 338 | -OH | 4-chlorophenyl (-CH-) |
| Example 339 | -H | 4-chlorophenoxy |
| Example 340 | -H | 4-chloroanilino (NH) |
| Example 341 | -OH | 4-chlorobenzyl |
| Example 342 |  | 6-chloro-1-oxo-2,3-dihydro-1H-indene (spiro at 2-position) |
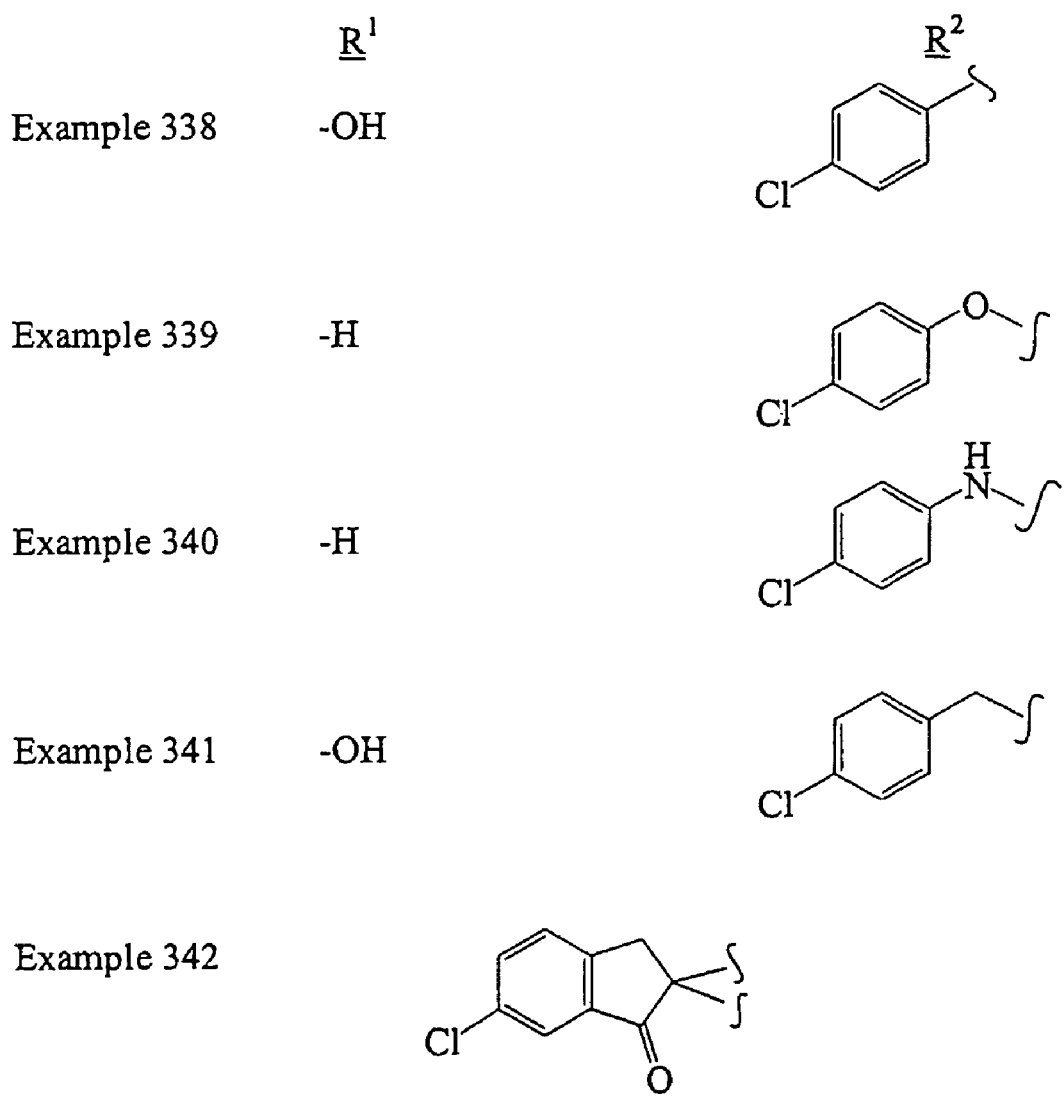
Figure 11I

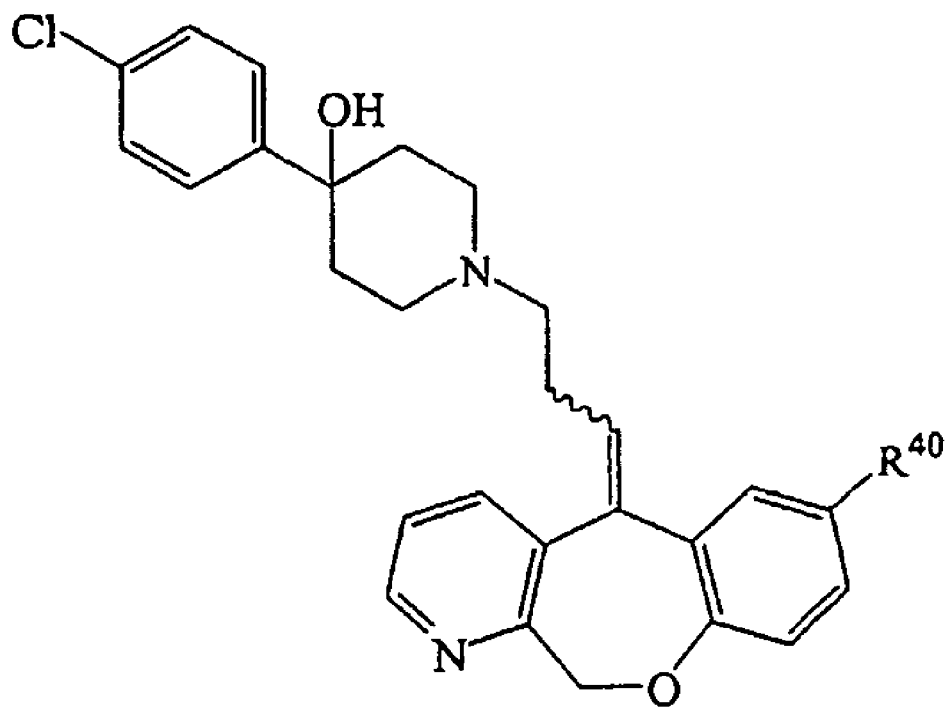
$\underline{R^{40}}$
Example 343 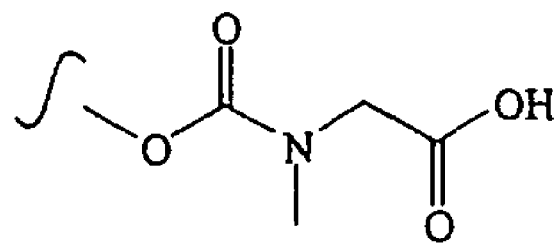
Example 344 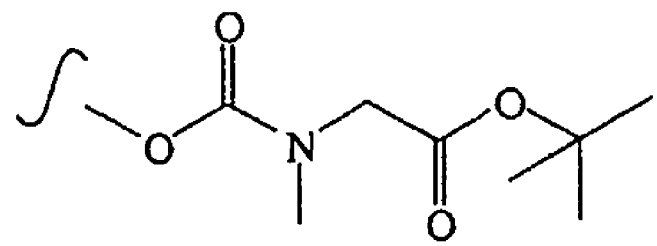
Figure 11J

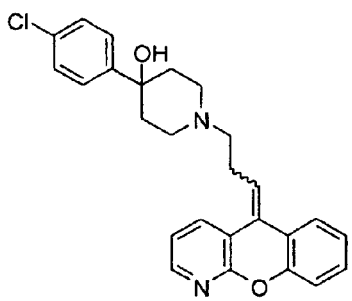
Example 345
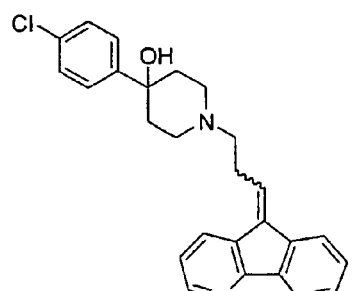
Example 346
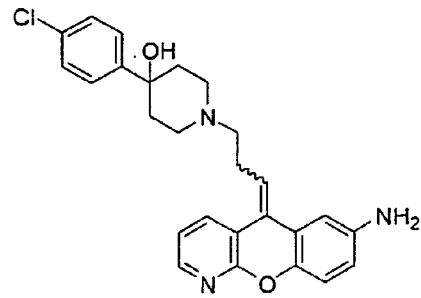
Example 347
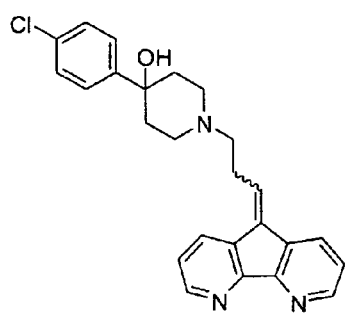
Example 348
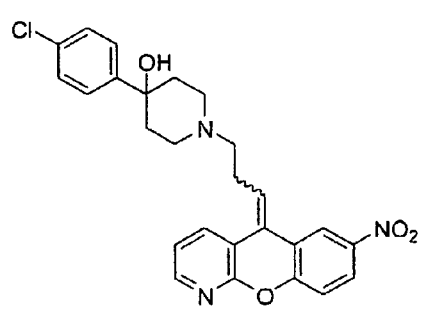
Example 349
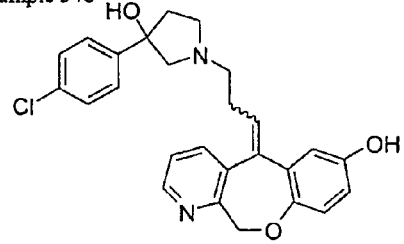
Example 350
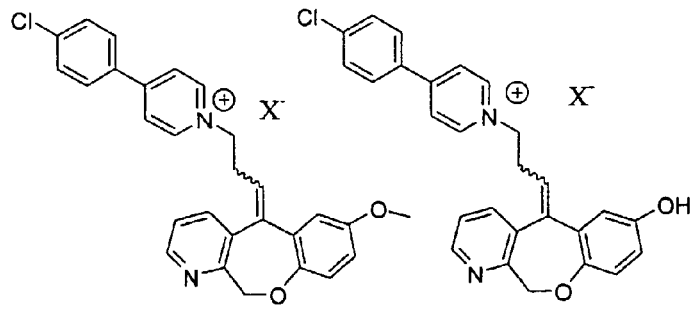
Example 351    Example 352
Figure 11K

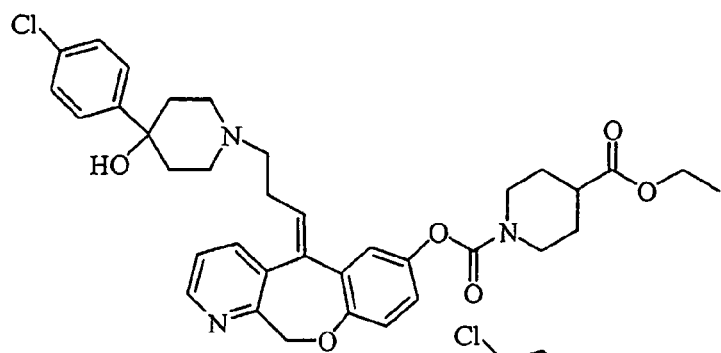
Example 420
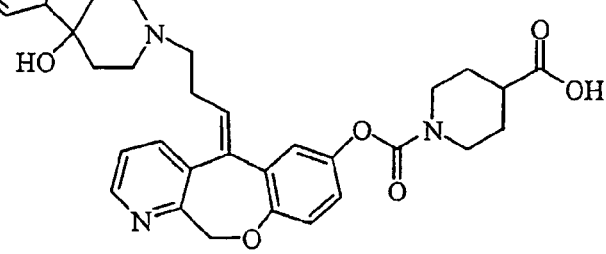
Example 421
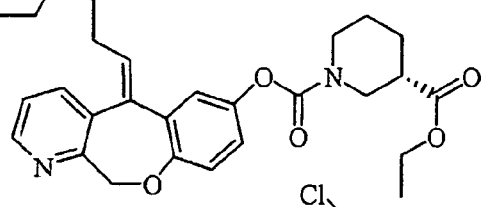
Example 422
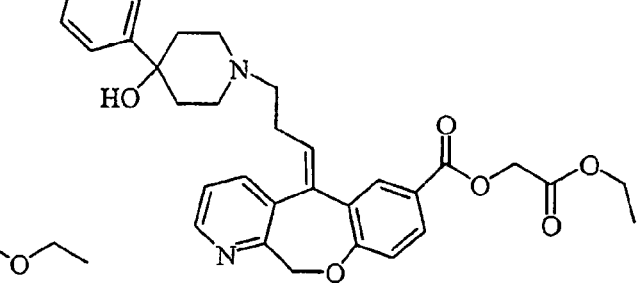
Example 424
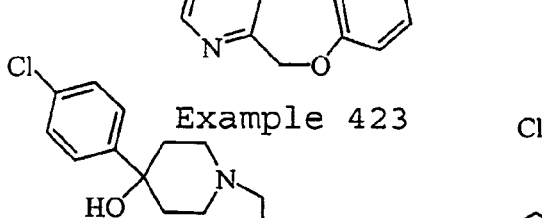
Example 423
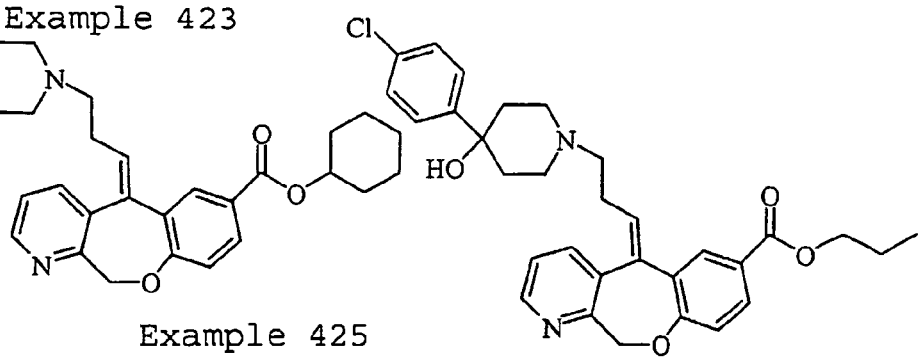
Example 425
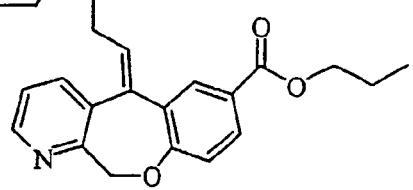
Example 426
Figure 11S

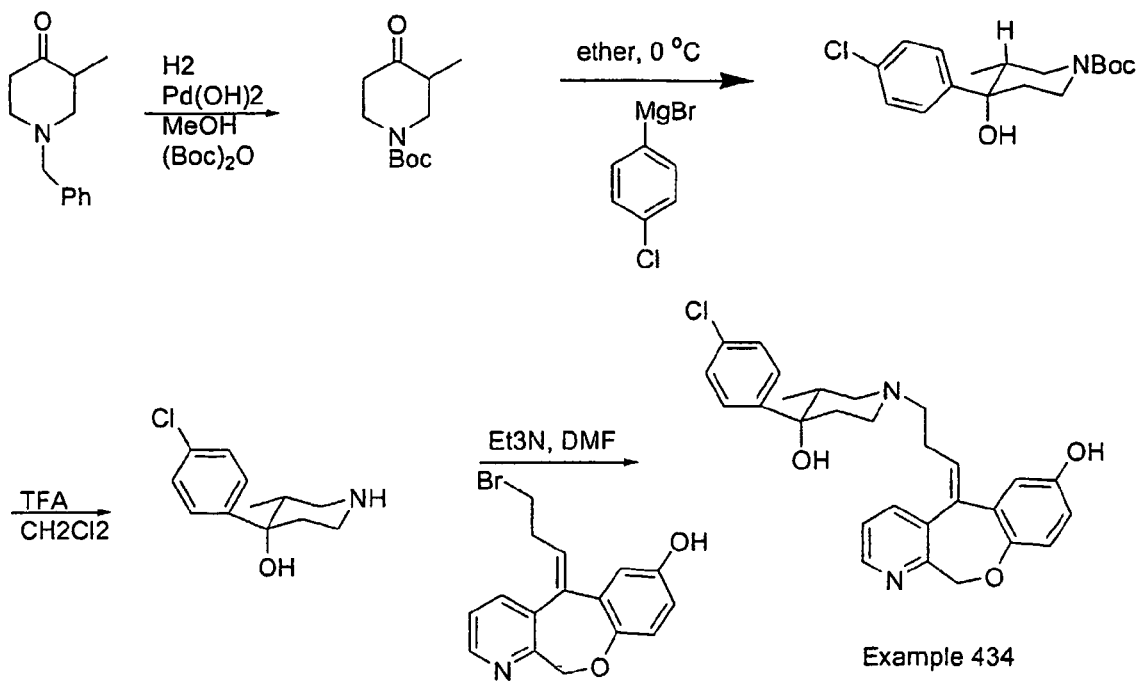
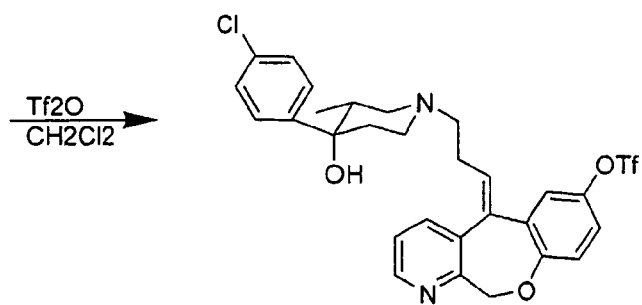
Figure 14

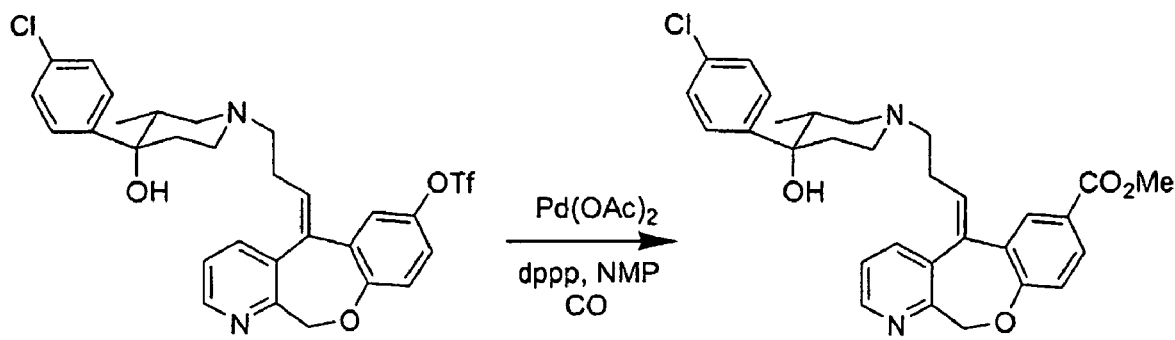
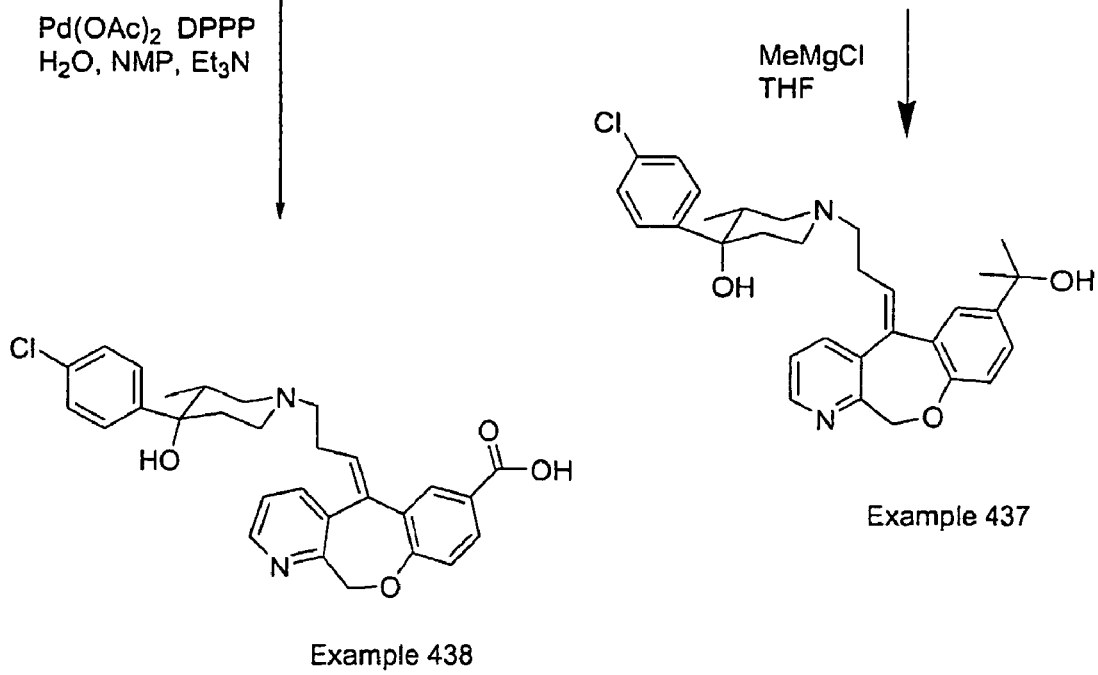
Figure 15

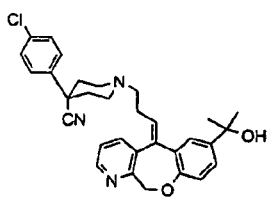
Example 456
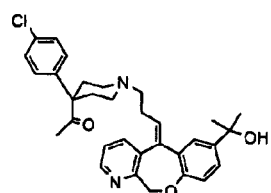
Example 457
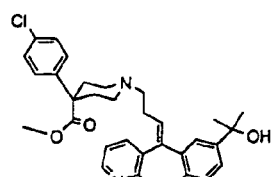
Example 458
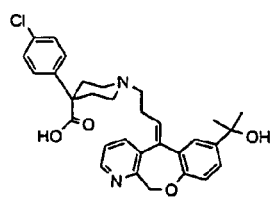
Example 459
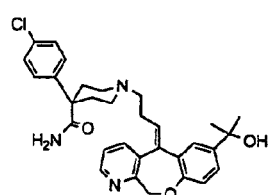
Example 460
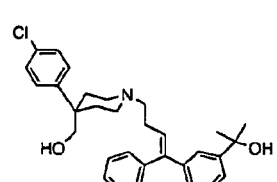
Example 561
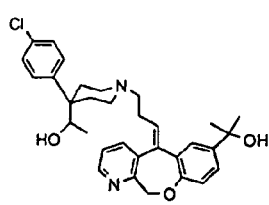
Example 462
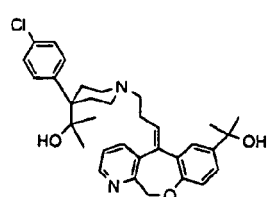
Example 463
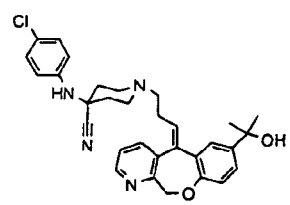
Example 464
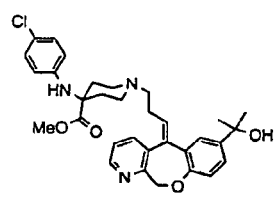
Example 465
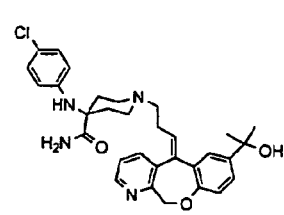
Example 466
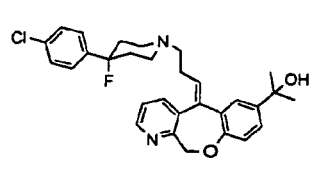
Example 467
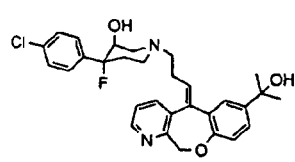
Example 468
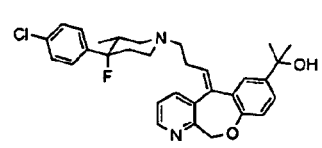
Example 469
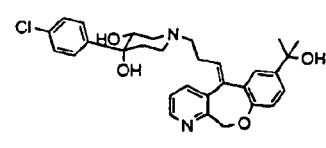
Example 470
Figure 21

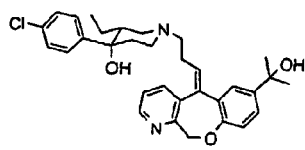 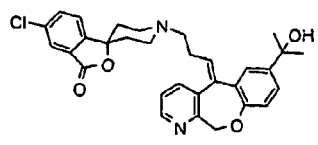 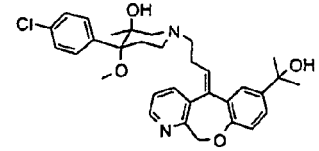
Example 471  Example 472  Example 473
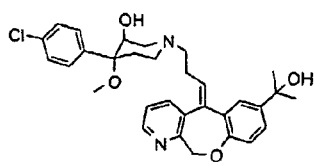 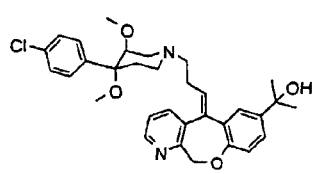 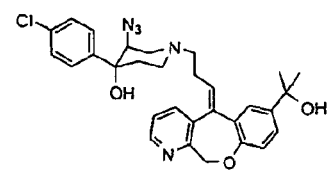
Example 474  Example 475  Example 476
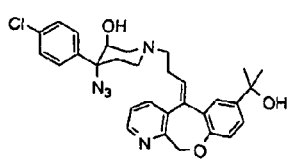 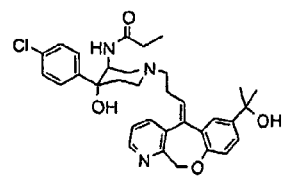 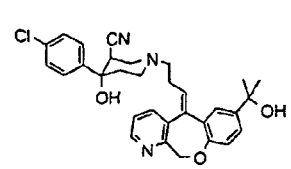
Example 477  Example 478  Example 479
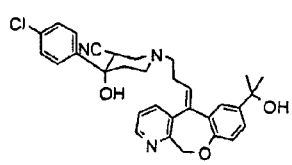 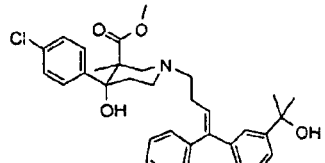 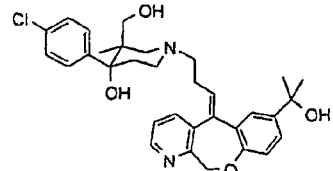
Example 480  Example 481  Example 482 (racemic)
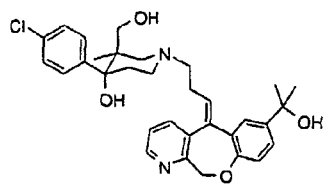 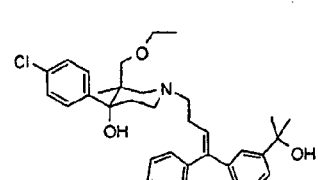 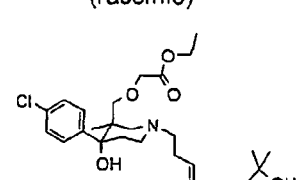
Example 483-1 (chiral)
Example 483-2 (chiral)  Example 484  Example 485
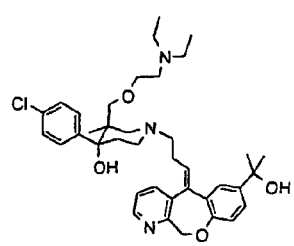 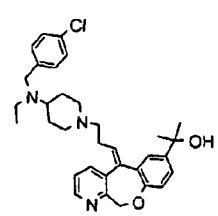 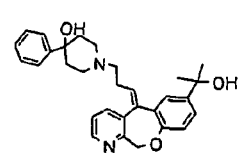
Example 486  Example 487  Example 488
Figure 22

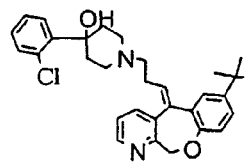 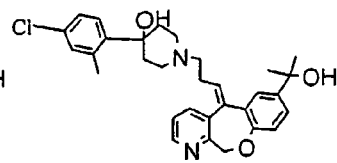 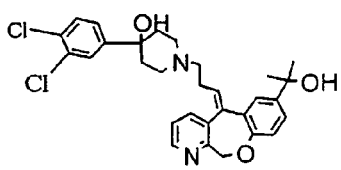
Example 489                Example 490                Example 491
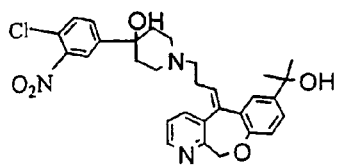 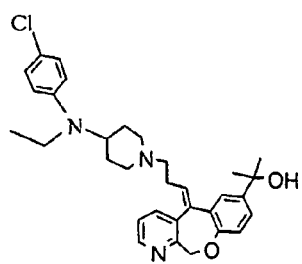 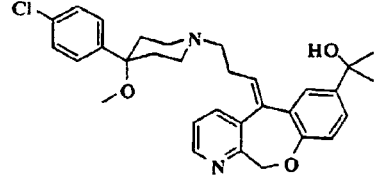
Example 492                Example 493                Example 494
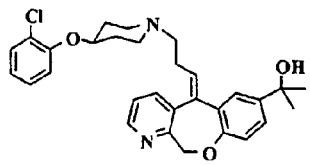 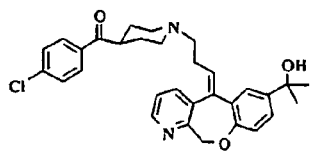 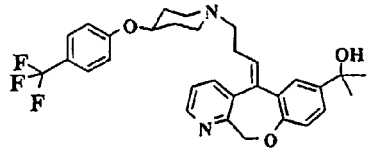
Example 495                Example 496                Example 497
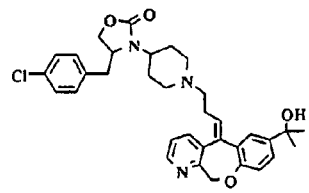 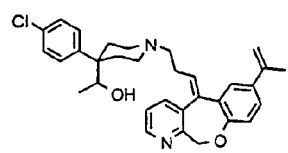 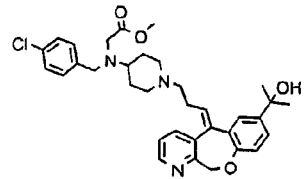
Example 498                Example 499                Example 500
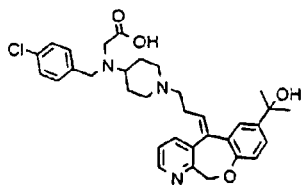 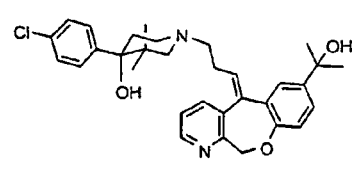 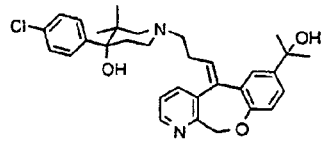
Example 501                Example 502                Example503
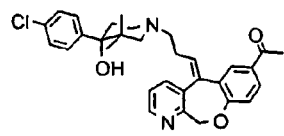 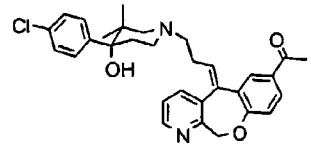 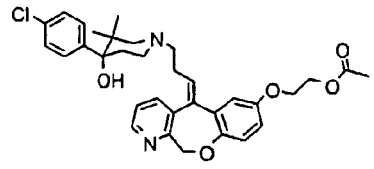
Example 504                Example 505                Example 506
Figure 23

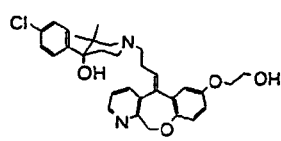
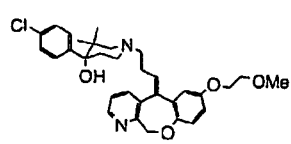
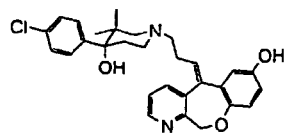
Example 507　　　　　　Example 508　　　　　　Example 509
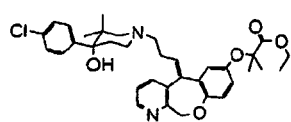
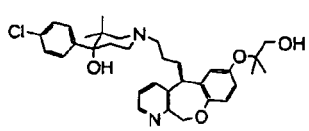
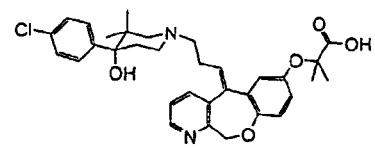
Example 510　　　　　　Example 511　　　　　　Example 512
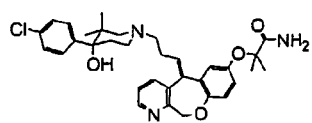
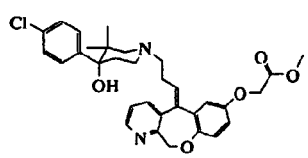
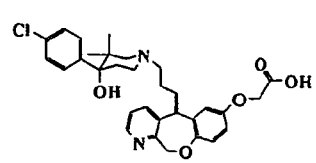
Example 513　　　　　　Example 514　　　　　　Example 515
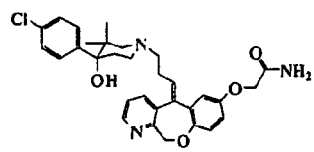
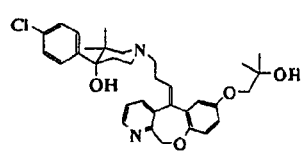
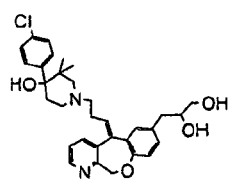
Example 516　　　　　　Example 517　　　　　　Example 518
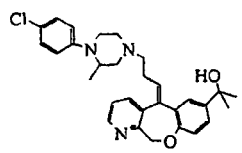
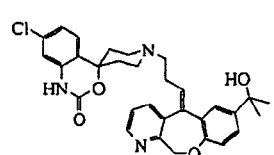
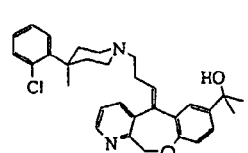
Example 519　　　　　　Example 520　　　　　　Example 521
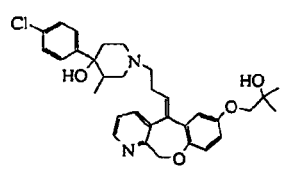
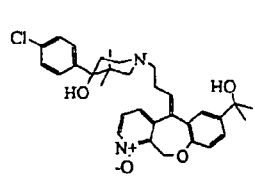
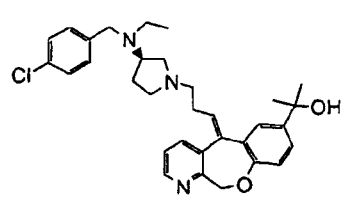
Example 522　　　　　　Example 523　　　　　　Example 524
Figure 24

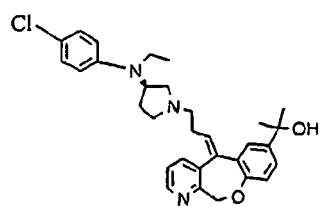
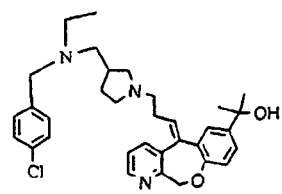
Example 525
Example 526
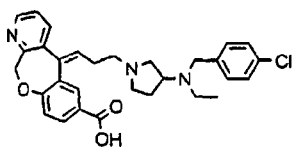
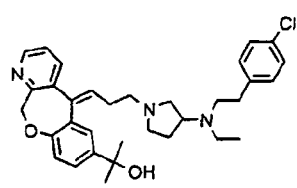
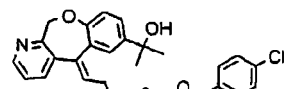
Example 527
Example 528
Example 529
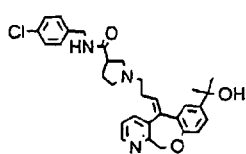
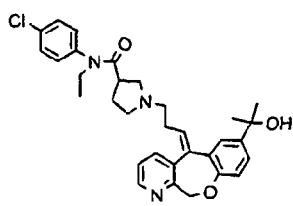
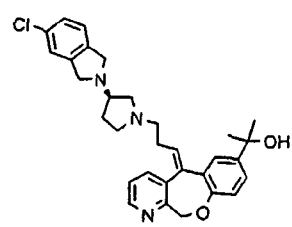
Example 530
Example 531
Example 532
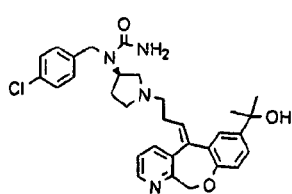
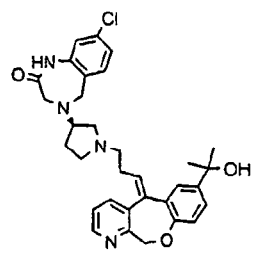
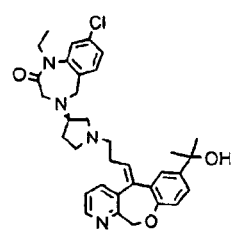
Example 533
Example 534
Example 535
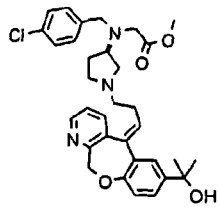
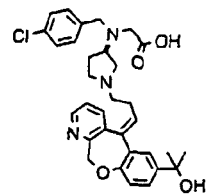
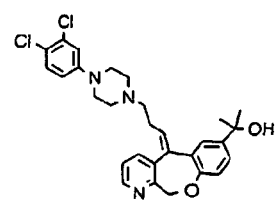
Example 536
Example 537
Example 538
Figure 25

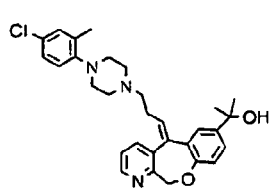
Example 539
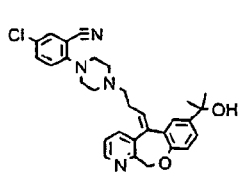
Example 540
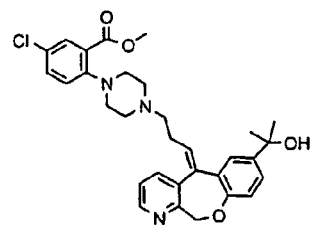
Example 541
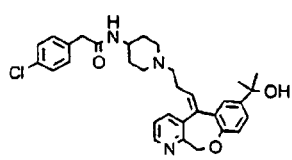
Example 542
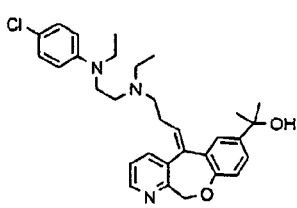
Example 543
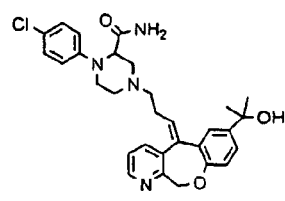
Example544
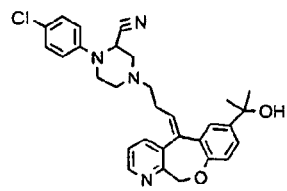
Example 545
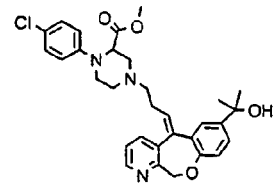
Example 546
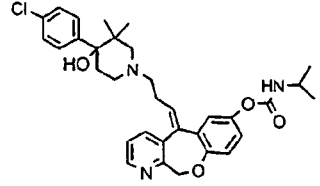
Example 547
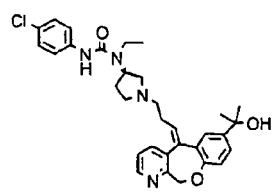
Example 548
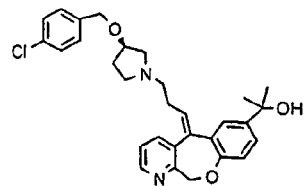
Example549
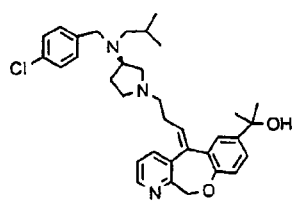
Example 550
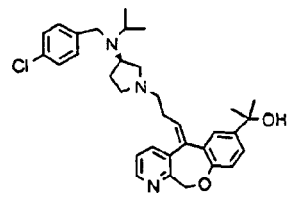
Example 551
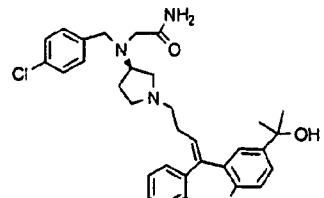
Example 552
Figure 26

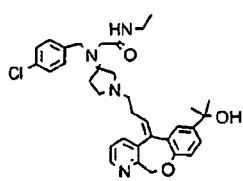 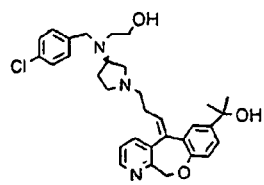 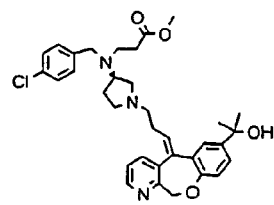
Example 553     Example 554     Example 555
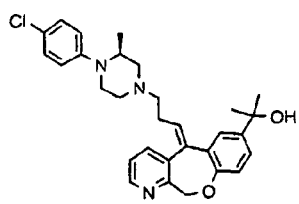 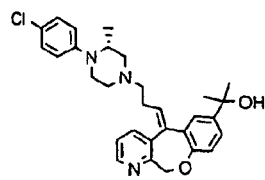 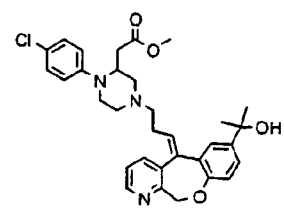
Example 556     Example 557     Example 558
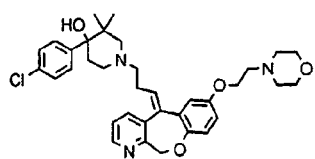 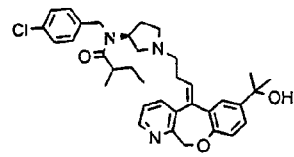 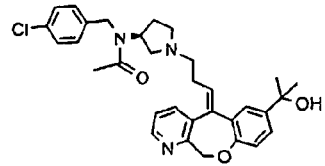
Example 559     Example560     Example 561
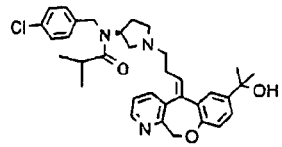 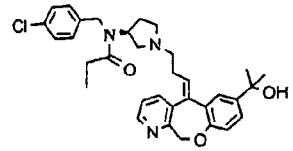 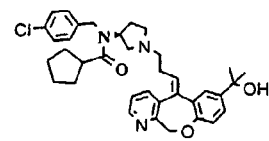
Example 562     Example 563     Example 564
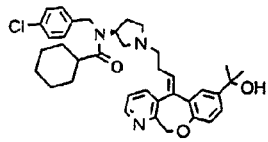 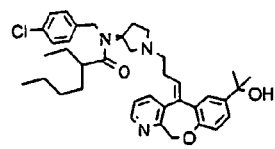 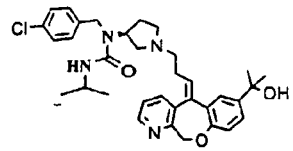
Example 565     Example 566     Example 567
Figure 27

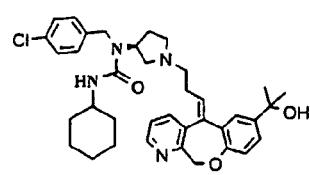
Example 568
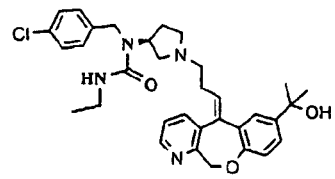
Example 569
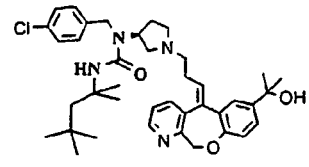
Example 570
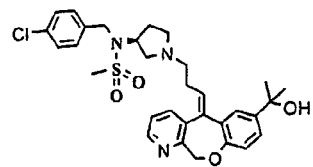
Example 571
Figure 28

CHEMOKINE RECEPTOR ANTAGONISTS AND METHODS OF USE THEREOF

RELATED APPLICATIONS

This application is the U.S. National Phase of International Application No. PCT/US02/36953, filed Nov. 13, 2002, published in English, which is a continuation-in-part of U.S. application Ser. No. 09/989,086, filed Nov. 21, 2001 (abandoned), the entire teachings of all above-referenced applications are incorporated herein by reference.

BACKGROUND OF THE INVENTION

Chemoattractant cytokines or chemokines are a family of proinflammatory mediators that promote recruitment and activation of multiple lineages of leukocytes and lymphocytes. They can be released by many kinds of tissue cells after activation. Continuous release of chemokines at sites of inflammation mediates the ongoing migration of effector cells in chronic inflammation. The chemokines characterized to date are related in primary structure. They share four conserved cysteines, which form disulfide bonds. Based upon this conserved cysteine motif, the family is divided into two main branches, designated as the C—X—C chemokines ($\alpha$-chemokines), and the C—C chemokines ($\beta$-chemokines), in which the first two conserved cysteines are separated by an intervening residue, or adjacent respectively (Baggiolini, M. and Dahinden, C. A., *Immunology Today*, 15:127–133 (1994)).

The C—X—C chemokines include a number of potent chemoattractants and activators of neutrophils, such as interleukin 8 (IL-8), PF4 and neutrophil-activating peptide-2 (NAP-2). The C—C chemokines include RANTES (Regulated on Activation, Normal T Expressed and Secreted), the macrophage inflammatory proteins 1$\alpha$ and 1$\beta$ (MIP-1$\alpha$ and MIP-1$\beta$), eotaxin and human monocyte chemotactic proteins 1–3 (MCP-1, MCP-2, MCP-3), which have been characterized as chemoattractants and activators of monocytes or lymphocytes but do not appear to be chemoattractants for neutrophils. Chemokines, such as RANTES and MIP-1$\alpha$, have been implicated in a wide range of human acute and chronic inflammatory diseases including respiratory diseases, such as asthma and allergic disorders.

The chemokine receptors are members of a superfamily of G protein-coupled receptors (GPCR) which share structural features that reflect a common mechanism of action of signal transduction (Gerard, C. and Gerard, N. P., *Annu Rev. Immunol.*, 12:775–808 (1994); Gerard, C. and Gerard, N. P., *Curr. Opin. Immunol.*, 6:140–145 (1994)). Conserved features include seven hydrophobic domains spanning the plasma membrane, which are connected by hydrophilic extracellular and intracellular loops. The majority of the primary sequence homology occurs in the hydrophobic transmembrane regions with the hydrophilic regions being more diverse. The first receptor for the C—C chemokines that was cloned and expressed binds the chemokines MIP-1$\alpha$ and RANTES. Accordingly, this MIP-1$\alpha$/RANTES receptor was designated C—C chemokine receptor 1 (also referred to as CCR-1; Neote, K., et al., *Cell*, 72:415–425 (1993); Horuk, R et al., WO 94/11504, May 26, 1994; Gao, J.-I. et al., *J. Exp. Med.*, 177:1421–1427 (1993)). Three receptors have been characterized which bind and/or signal in response to RANTES: CCR3 mediates binding and signaling of chemokines including eotaxin, RANTES, and MCP-3 (Ponath et al., *J. Exp. Med.*, 183:2437 (1996)), CCR4 binds chemokines including RANTES, MIP-1$\alpha$, and MCP-1 (Power, et al., *J. Biol. Chem.*, 270:19495 (1995)), and CCR5 binds chemokines including MIP-1$\alpha$, RANTES, and MIP-1$\beta$ (Samson, et al., *Biochem.* 35: 3362–3367 (1996)). RANTES is a chemotactic chemokine for a variety of cell types, including monocytes, eosinophils, and a subset of T-cells. The responses of these different cells may not all be mediated by the same receptor, and it is possible that the receptors CCR1, CCR4 and CCR5 will show some selectivity in receptor distribution and function between leukocyte types, as has already been shown for CCR3 (Ponath et al.). In particular, the ability of RANTES to induce the directed migration of monocytes and a memory population of circulating T-cells (Schall, T. et al., *Nature*, 347:669–71 (1990)) suggests this chemokine and its receptor(s) may play a critical role in chronic inflammatory diseases, since these diseases are characterized by destructive infiltrates of T cells and monocytes.

Many existing drugs have been developed as antagonists of the receptors for biogenic amines, for example, as antagonists of the dopamine and histamine receptors. No successful antagonists have yet been developed to the receptors for the larger proteins such as chemokines and C5a. Small molecule antagonists of the interaction between C—C chemokine receptors and their ligands, including RANTES and MIP-1$\alpha$, would provide compounds useful for inhibiting harmful inflammatory processes "triggered" by receptor ligand interaction, as well as valuable tools for the investigation of receptor-ligand interactions.

SUMMARY OF THE INVENTION

It has now been found that a class of small organic molecules are antagonists of chemokine receptor function and can inhibit leukocyte activation and/or recruitment. An antagonist of chemokine receptor function is a molecule which can inhibit the binding and/or activation of one or more chemokines, including C—C chemokines such as RANTES, MIP-1$\alpha$, MCP-2, MCP-3 and MCP-4 to one or more chemokine receptors on leukocytes and/or other cell types. As a consequence, processes and cellular responses mediated by chemokine receptors can be inhibited with these small organic molecules. Based on this discovery, a method of treating a disease associated with aberrant leukocyte recruitment and/or activation is disclosed as well as a method of treating a disease mediated by chemokine receptor function. The method comprises administering to a subject in need an effective amount of a compound or small organic molecule which is an antagonist of chemokine receptor function. Compounds or small organic molecules which have been identified as antagonists of chemokine receptor function are discussed in detail hereinbelow, and can be used for the manufacture of a medicament for treating or for preventing a disease associated with aberrant leukocyte recruitment and/or activation. In one aspect, the compound has the formula:

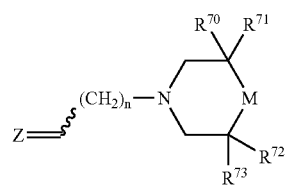

or a physiologically acceptable salt thereof, wherein Z, n, M, $R^{70}$, $R^{71}$, $R^{72}$ and $R^{73}$ are as described herein.

The invention also relates to the disclosed compounds and small organic molecules for use in treating or preventing a disease associated with aberrant leukocyte recruitment and/or activation. The invention also includes pharmaceutical compositions comprising one or more of the compounds or small organic molecules which have been identified herein as antagonists of chemokine function and a suitable pharmaceutical carrier. The invention further relates to novel compounds which can be used to treat an individual with a disease associated with aberrant leukocyte recruitment and/or activation and methods for their preparation.

BRIEF DESCRIPTION OF THE DRAWINGS

In FIG. 10C, $R^{40}$ is represented by $-(O)_u-(CH_2)_t-C(O)-NR^{21}R^{22}$, u is one, t is zero.

FIG. 14 is a schematic showing a procedure for the preparation of Examples 434 and 435.

FIG. 15 is a schematic showing a procedure for the preparation of Examples 436–438.

FIGS. 20–28 show the structures of exemplary compounds of the invention.

DETAILED DESCRIPTION OF THE INVENTION

Figure 1:
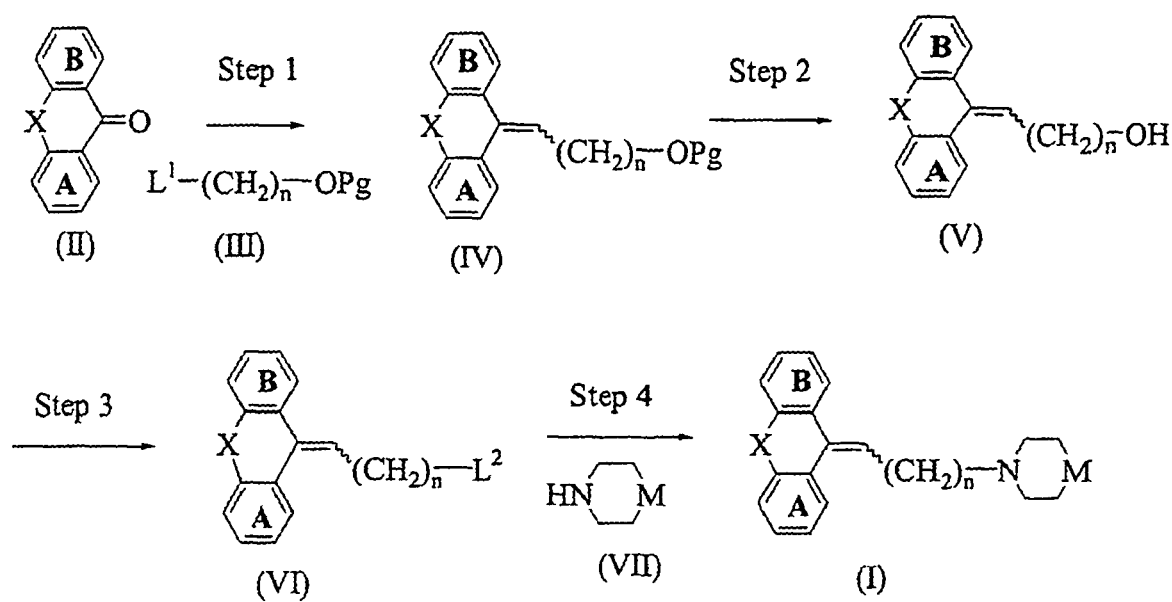
FIG. 1 is a schematic showing the preparation of the compounds represented by Structural Formula (I).

The present invention relates to small molecule compounds which are modulators of chemokine receptor function. In a preferred embodiment, the small molecule compounds are antagonists of chemokine receptor function. Accordingly, processes or cellular responses mediated by the binding of a chemokine to a receptor can be inhibited (reduced or prevented, in whole or in part), including leukocyte migration, integrin activation, transient increases in the concentration of intracellular free calcium $[Ca^{++}]_i$, and/or granule release of proinflammatory mediators.

The invention further relates to a method of treatment, including prophylactic and therapeutic treatments, of a disease associated with aberrant leukocyte recruitment and/or activation or mediated by chemokines or chemokine receptor function, including chronic inflammatory disorders characterized by the presence of RANTES, MIP-b 1α, MCP-2, MCP-3 and/or MCP-4 responsive T cells, monocytes and/or eosinophils, including but not limited to diseases such as arthritis (e.g., rheumatoid arthritis), atherosclerosis, arteriosclerosis, restenosis, ischemia/reperfusion injury, diabetes mellitus (e.g., type 1 diabetes mellitus), psoriasis, multiple sclerosis, inflammatory bowel diseases such as ulcerative colitis and Crohn's disease, rejection of transplanted organs and tissues (i.e., acute allograft rejection, chronic allograft rejection), graft versus host disease, as well as allergies and asthma. Other diseases associated with aberrant leukocyte recruitment and/or activation which can be treated (including prophylactic treatments) with the methods disclosed herein are inflammatory diseases associated with Human Immunodeficiency Virus (HIV) infection, e.g., AIDS associated encephalitis, AIDS related maculopapular skin eruption, AIDS related interstitial pneumonia, AIDS related enteropathy, AIDS related periportal hepatic inflammation and AIDS related glomerulo nephritis. The method comprises administering to the subject in need of treatment an effective amount of a compound (i.e., one or more compounds) which inhibits chemokine receptor function, inhibits the binding of a chemokine to leukocytes and/or other cell types, and/or which inhibits leukocyte migration to, and/or activation at, sites of inflammation.

The invention further relates to methods of antagonizing a chemokine receptor, such as CCR1, in a mammal comprising administering to the mammal a compound as described herein.

According to the method, chemokine-mediated chemotaxis and/or activation of pro-inflammatory cells bearing receptors for chemokines can be inhibited. As used herein, "pro-inflammatory cells" includes but is not limited to leukocytes, since chemokine receptors can be expressed on other cell types, such as neurons and epithelial cells.

While not wishing to be bound by any particular theory or mechanism, it is believed that compounds of the invention are antagonists of the chemokine receptor CCR1, and that therapeutic benefits derived from the method of the invention are the result of antagonism of CCR1 function. Thus, the method and compounds of the invention can be used to treat a medical condition involving cells which express CCR1 on their surface and which respond to signals transduced through CCR1, as well as the specific conditions recited above.

In one embodiment, the antagonist of chemokine receptor function is represented by Structural Formula (I):

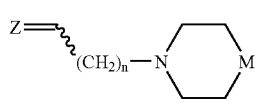

(I)

and physiologically acceptable salts thereof.

Z is a cycloalkyl or non-aromatic heterocyclic ring group fused to one, two or more aromatic rings, wherein each ring in Z is independently substituted or unsubstituted.

n is an integer, such as an integer from one to four. Preferably, n is one, two or three. More preferably n is two. In alternative embodiments, other aliphatic or aromatic spacer groups (L) can be employed for $(CH_2)_n$.

M is $>NR^2$ or $>CR^1R^2$. M is preferably $>C(OH)R^2$.

$R^1$ is —H, —OH, —$N_3$, a halogen, an aliphatic group, a substituted aliphatic group, an aminoalkyl group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —C(O)O-(aliphatic group), —C(O)O-(substituted aliphatic group), —COOH, —CN, —CO—$NR^3R^4$, —$NR^3R^4$; or $R^1$ can be a covalent bond between the ring atom at M and an adjacent carbon atom in the ring which contains M. $R^1$ is preferably —H or —OH.

$R^2$ is —H, —OH, a halogen, an acyl group, a substituted acyl group, —$NR^5R^6$, an aliphatic group, a substituted aliphatic group, an aromatic group, a substituted aromatic group, a benzyl group, a substituted benzyl group, a non-aromatic heterocyclic group, a substituted non-aromatic heterocyclic group, —O-(substituted or unsubstituted aromatic group), —O-(substituted or unsubstituted aliphatic group) or —C(O)-(substituted or unsubstituted aromatic group) or —C(O)-(substituted or unsubstituted aliphatic group). $R^2$ is preferably an aromatic group or a substituted aromatic group.

$R^3$, $R^4$, $R^5$ and $R^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group.

$R^1$ and $R^2$, $R^3$ and $R^4$, or $R^5$ and $R^6$ taken together with the atom to which they are bonded, can alternatively form a substituted or unsubstituted non-aromatic carbocyclic or heterocyclic ring.

In embodiments where M is $>CR^1R^2$ and $R^1$ is a covalent bond between the carbon atom at M and an adjacent carbon atom in the ring which contains M, the antagonist of chemokine function can be represented by Structural Formula (Ia).

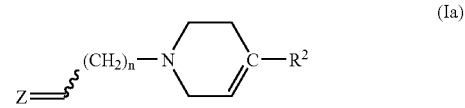

(Ia)

Z, n and $R^2$ are as described in Structural Formula (I).

In one embodiment, Z is a tricyclic ring system comprising two carbocyclic aromatic groups fused to a five, six, seven or eight membered cycloalkyl group or to a non-aromatic heterocyclic ring. In one example, Z is represented by Structural Formula (II):

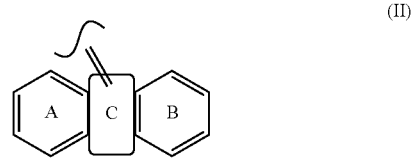

(II)

The phenyl rings in Structural Formula (II), labeled with an "A" and "B", are referred to herein as "Ring A" and "Ring B", respectively. The central ring, labeled with a "C", is referred to as "Ring C" and can be, for example, a five, six, seven or eight membered non-aromatic carbocyclic ring (e.g., a cycloheptane or cyclooctane ring) or a non-aromatic heterocyclic ring. When Ring C is a non-aromatic heterocyclic ring, it can contain one or two heteroatoms such as nitrogen, sulfur or oxygen. In particular embodiments, Ring c is When Z is represented by Structural Formula (II), the tricyclic ring system can be connected to the remainder of the molecule by a covalent double bond between a carbon atom in Ring C and the carbon atom which, as depicted in Structural Formula (I), is bonded to Z.

Ring A and/or Ring B in Structural Formula (II) can be unsubstituted. Alternatively, Ring A and/or Ring B can have one or more substituents. Suitable substituents are as described hereinbelow. In one example, Ring A or Ring B is substituted with —$(O)_u$—$(CH_2)_t$—$C(O)OR^{20}$, —$(O)_u$—$(CH_2)_t$—$OC(O)R^{20}$, —$(O)_u$—$(CH_2)_t$—$C(O)$—$NR^{21}R^{22}$ or —$(O)_u$—$(CH_2)_t$—$NHC(O)O$—$R^{20}$.

u is zero or one.

t is an integer, such as an integer from zero to three, and the methylene group —$(CH_2)_t$— can be substituted, as described herein for aliphatic groups, or unsubstituted.

$R^{20}$, $R^{21}$ or $R^{22}$ are independently —H, an aliphatic group, a substituted aliphatic group, an aromatic group, a substituted aromatic group or a non-aromatic heterocyclic group. Alternatively, $R^{21}$ and $R^{22}$, taken together with the nitrogen atom to which they are bonded, can form a non-aromatic heterocyclic ring.

Ring C optionally contains one or more substituents, as described hereinbelow. Examples of suitable tricyclic ring systems, Z, are provided by Structural Formula (III):

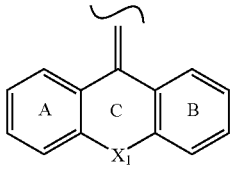

(III)

Ring A and Ring B in Structural Formula (III) are as described for Structural Formula (II).

$X_1$ is a bond, —O—, —S—, —$CH_2$—, —$CH_2$—$CH_2$—, —$CH_2$—S—, —S—$CH_2$—, —O—$CH_2$—, —$CH_2$—O—, —$NR_c$—$CH_2$—, —$CH_2$—$NR_c$—, —SO—$CH_2$—, —$CH_2$—SO—, —$S(O)_2$—$CH_2$—, —$CH_2$—$S(O)_2$—, —CH=CH—, —$NR_c$—CO— or —CO—$NR_c$—. Preferably $X_1$ is —$CH_2$—O—, —$CH_2$—$CH_2$—, —$CH_2$—S—, —$NR_c$—CO— or —CO—$NR_c$—.

$R_c$ is hydrogen, an aliphatic group, a substituted aliphatic group, an aromatic group, a substituted aromatic group, a benzyl group or a substituted benzyl group.

In one example, $R_c$ is —$(CH_2)_s$—$COOR^{30}$—, —$(CH_2)_s$—C(O)—$NR^{31}R^{32}$ or —$(CH_2)_s$—NHC(O)—O—$R^{30}$, wherein s is an integer, such as an integer from one to three;

$R^{30}$, $R^{31}$ and $R^{32}$ are independently —H, an aliphatic group, a substituted aliphatic group, an aromatic group, a substituted aromatic group or a non-aromatic heterocyclic group. Alternatively, $R^{31}$ and $R^{32}$, taken together with the nitrogen atom to which they are bonded, form a non-aromatic heterocyclic ring.

Other examples of suitable tricyclic ring systems for Z include benzodiazepines, benzooxazepines, benzooxazines, phenothiazines and groups represented by the following structural formulas:

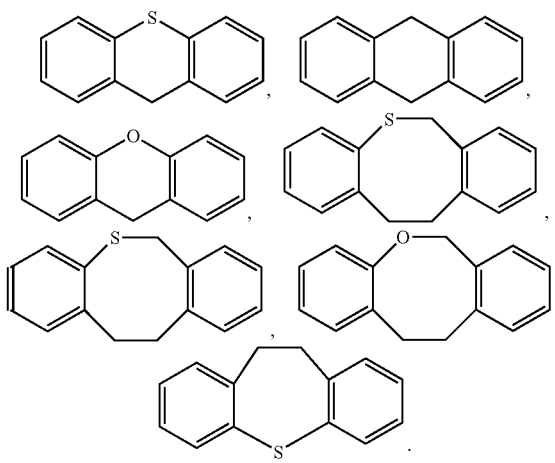

In other embodiments, Z is a tricyclic ring system comprising two aromatic groups fused to a seven or eight membered cycloalkyl group or to a non-aromatic heterocyclic ring, wherein at least one of the aromatic groups is a heteroaryl group. In one example, Z is represented by Structural Formula (IV):

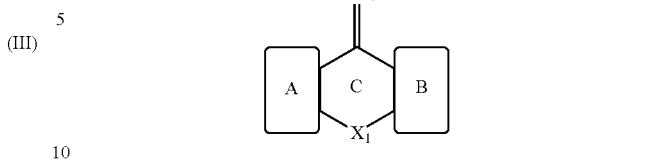

(IV)

Ring A in Structural Formula (IV) can be a substituted or unsubstituted heteroaryl group. Ring B in Structural Formula (IV) can be a substituted or unsubstituted aromatic group, e.g., a heteroaryl group or carbocyclic aryl group. Suitable substituents are as described hereinbelow. In one example, Ring A and/or Ring B is substituted with —$(O)_u$—$(CH_2)_t$—C(O)$OR^{20}$, —$(O)_u$—$(CH_2)_t$—OC(O)$R^{20}$, —$(O)_u$—$(CH_2)_t$—C(O)—$NR^{21}R^{22}$ or —$(O)_u$—$(CH_2)_t$—NHC(O)O—$R^{20}$ as described above. u, t, $R^{20}$, $R^{21}$, and $R^{22}$ are as described above. $X_1$ and $R_c$ can be as described above for Structural Formula (III).

In another embodiment of the present invention Z is represented by Structural Formula (IV), wherein Ring A is a pyridyl group and Ring B is an aromatic or heteroaromatic group. In one example, Z is represented by Structural Formula (IVa):

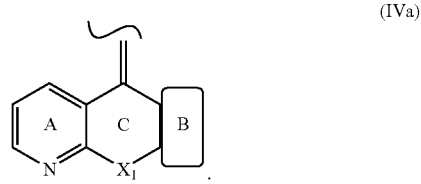

(IVa)

In this embodiment Ring A and Ring B are independently substituted or unsubstituted, and Ring B is preferably a phenyl group. $X_1$ and $R_c$ can be as described above for Structural Formula (III).

In another embodiment, both Ring A and Ring B are pyridyl groups, and Z is represented by Structural Formula (IVb):

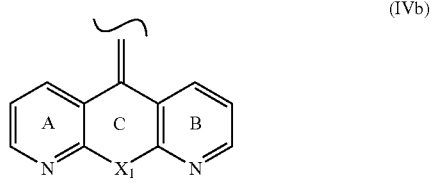

(IVb)

Ring A and Ring B can be independently substituted or unsubstituted as described above in Structural Formula (II), and $X_1$ can be as described above for Structural Formula (III).

In preferred embodiments, Z is represented by Structural Formula (V):

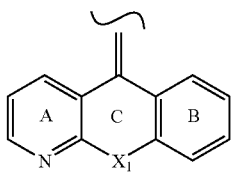

(V)

Ring A and Ring B can be independently substituted or unsubstituted as described above in Structural Formula (II), and $X_1$ can be as described above for Structural Formula (III).

In particularly preferred embodiments, Ring B in Structural Formula (V) is substituted para to the carbon atom of Ring B which is bonded to $X_1$ of Ring C, and Z is represented by Structural Formula (VI):

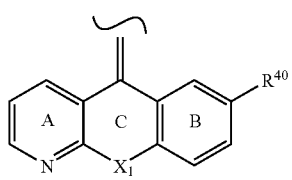

(VI)

$X_1$ can be as described above in Structural Formula (II). Preferably $X_1$ is —$CH_2$—O—, —$CH_2$—$CH_2$— or —$CH_2$—S—.

$R^{40}$ is a substituent as described herein for aromatic groups. In one embodiment, $R^{40}$ is —OH, —COOH, a halogen, —$NO_2$, an aliphatic group, a substituted aliphatic group, an aromatic group, a substituted aromatic group, —$NR^{24}R^{25}$, —$CONR^{24}R^{25}$, —$C(=NR^{60})NR^{21}R^{22}$, -Q-(aliphatic group), -Q-(substituted aliphatic group), —O-(aliphatic group), —O-(substituted aliphatic group), —O-(aromatic group), —O-(substituted aromatic group), an electron withdrawing group, —$(O)_u$—$(CH_2)_t$—$C(O)OR^{20}$, —$(O)_u$—$(CH_2)_t$—$OC(O)R^{20}$, —$(O)^u$—$(CH_2)_t$—$C(O)$—$NR^{21}R^{22}$ or —$(O)_u$—$(CH_2)_t$—$NHC(O)O$—$R^{20}$. Q, $R^{20}$, $R^{21}$, $R^{22}$, $R^{24}$, $R^{25}$, $R^{60}$, u and t are as described herein.

Preferably $R^{40}$ is an aliphatic group, substituted aliphatic group, —O-(aliphatic group) or —O-(substituted aliphatic group). In certain embodiments, $R^{40}$ is an —O-alkyl, such as —O—$CH_3$, —O—$C_2H_5$, —O—$C_3H_7$ or —O—$C_4H_9$.

In another embodiment, $R^{40}$ can be represented by —$(O)_u$—$(CH_2)_t$—$C(O)$—$NR^{21}R^{22}$, wherein u is one, t is zero, and $R^{21}$ and $R^{22}$ are as described herein. In this embodiment, $R^{21}$ and $R^{22}$ can each independently be —H, a substituted or unsubstituted aliphatic group, a substituted or unsubstituted aromatic group, or $R^{21}$ and $R^{22}$ taken together with the nitrogen atom to which they are bonded form a substituted or unsubstituted nonaromatic heterocyclic ring (e.g., pyrrolidine, piperidine, morpholine).

In another embodiment, $R^{40}$ can be represented by —$(O)_u$—$(CH_2)_t$—$C(O)$—$NR^{21}R^{22}$, wherein u is zero, t is one to about three, and $R^{21}$ and $R^{22}$ are as described herein.

In another embodiment, $R^{40}$ can be represented by —$(O)_u$—$(CH_2)_t$—$C(O)$—$NR^{21}R^{22}$, wherein both u and t are zero, and $R^{21}$ and $R^{22}$ are as described herein.

In another embodiment, $R^{40}$ is an aliphatic group (e.g., methyl, ethyl, propyl) that is substituted with —$NR^{24}R^{25}$ or —$CONR^{24}R^{25}$, wherein $R^{24}$ and $R^{25}$ are as described herein. For example, $R^{40}$ can be represented by

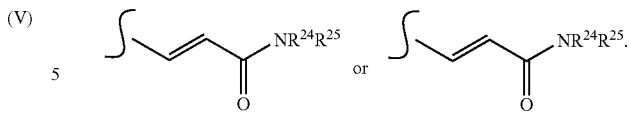

In another embodiment, $R^{40}$ is —O—C(O)—$NR^{21}R^{26}$, wherein $R^{21}$ is as described herein, $R^{26}$ can be —H, an aliphatic group, a substituted aliphatic group, an aromatic group, a substituted aromatic group, a non-aromatic heterocyclic group, —C(O)—O-(substituted or unsubstituted aliphatic group), —C(O)—O-(substituted or unsubstituted aromatic group), —$S(O)_2$-(substituted or unsubstituted aliphatic group), —$S(O)_2$-(substituted or unsubstituted aromatic group) or $R^{21}$ and $R^{26}$, taken together with the nitrogen atom to which they are bonded, can form a substituted or unsubstituted non-aromatic heterocyclic ring.

In additional embodiments, $R^{40}$ can be —$S(O)^2$—$NR^{21}R^{22}$ or —N—$C(O)$—$NR^{21}R^{22}$, wherein $R^{21}$ and $R^{22}$ are as described herein.

In a preferred embodiment, the chemokine receptor antagonist can be represented by Structural Formula I wherein n is three, M is $C(OH)R^2$, $R^2$ is a phenyl group or a halophenyl group (e.g., 4-chlorophenyl) and Z is represented by Structural Formula (VI) wherein $X_1$ is —$CH_2$—O—. In one example of this embodiment, $R^{40}$ can be —O-(substituted aliphatic group), such as

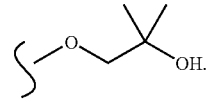

In particularly preferred embodiments, $R^{40}$ is

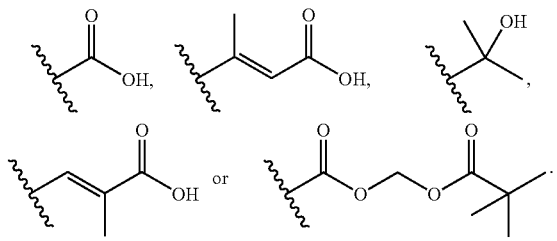

In other preferred embodiments, $R^{40}$ is a substituted aliphatic group, a substituted aromatic group, —O-substituted aliphatic group or —O-substituted aromatic group. Preferably the aliphatic or aromatic moiety of the substituted aliphatic group, substituted aromatic group, —O-substituted aliphatic group or —O-substituted aromatic group bears a substituent selected from the group consisting of —OH, —COOR -Q-aliphatic group or -Q-aromatic group substituent. Q is as described herein. Preferably, Q is —C(O)O—. For example, $R^{40}$ can be a linear, branched or cyclic aliphatic group that contains 1 to 6 carbon atoms, such as a $C_1$–$C_6$ alkyl group, a $C_2$–$C_6$ alkenyl, $C_2$–$C_6$ alkynyl, that is substituted with —OH, —COOH, —C(O)O—($C_1$–$C_6$ aliphatic) or —C(O)O-(aromatic).

In another embodiment, the antagonist of chemokine activity can be represented by Structural Formula (VII):

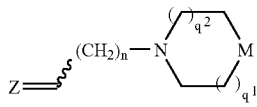
(VII)

and physiologically acceptable salts thereof.

n is as described in Structural Formula (I). Z is as described herein, preferably as described in Structural Formula (V) or (VI).

M is >NR², >CR¹R², —O—CR¹R²—O— or —CH₂—CR¹R²—O—.

R¹ and R² are as described in Structural Formula (I).

q¹ is an integer, such as an integer from zero to about three, and q² is an integer from zero to about one. The ring containing M can be substituted or unsubstituted.

Thus, the antagonist of chemokine function can be represent by, for example, Structural Formulas (VIIa)–(VIIk):

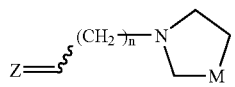
(VIIa)

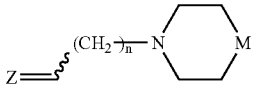
(VIIb)

(VIIc)

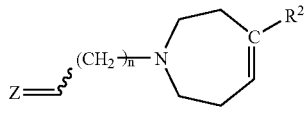
(VIId)

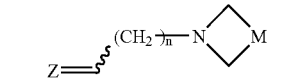
(VIIe)

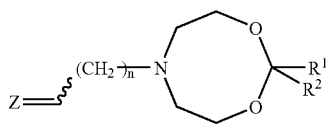
(VIIf)

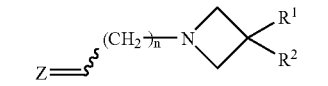
(VIIg)

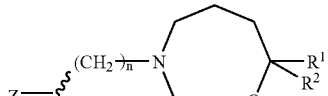
(VIIh)

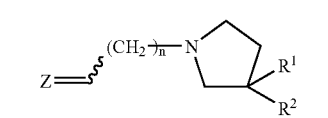
(VIIi)

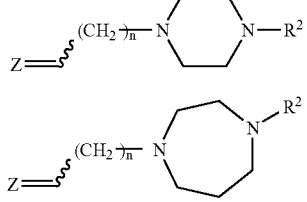
(VIIj)

(VIIk)

and physiologically acceptable salts thereof, wherein Z, n and M are as described in Structural Formula (VII), and the ring which contains M is substituted or unsubstituted. The ring containing M can have one or more suitable substituents which are the same or different. Suitable substituents for the ring which contains M and other nonaromatic heterocyclic rings are as described herein. For example, the ring containing M can be substituted with a methyl, ethyl, propyl, butyl or oxo group.

When the ring containing M is substituted, the compound can be represented by Structural Formula (VIII):

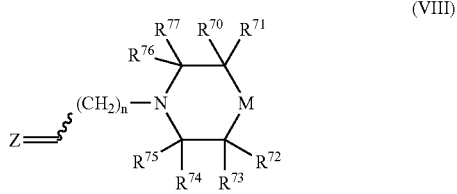
(VIII)

or physiologically acceptable salt thereof.

R⁷⁰, R⁷¹, R⁷², R⁷³, R⁷⁴, R⁷⁶ and R⁷⁷ are independently —H, —OH, —N₃, a halogen, an aliphatic group, a substituted aliphatic group, an aminoalkyl group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —C(O)O-(aliphatic group), —C(O)O-(substituted aliphatic group), —COOH, —CN, —CO—NR³R⁴, —NR³R⁴, an acyl group, a substituted acyl group, a benzyl group, a substituted benzyl group, a non-aromatic heterocyclic group, a substituted non-aromatic heterocyclic group, —O-(substituted or unsubstituted aromatic group), or any two of R⁷⁰, R⁷¹, R⁷², R⁷³, R⁷⁴, R⁷⁵, R⁷⁶ and R⁷⁷ taken together with the atoms to which they are bonded form a three to eight membered ring.

n is as described in Structural Formula (I). Z is as described herein, preferably as described in Structural Formula (V) or (VI). M is as described in Structural Formula (VII). Preferably, M is >NR² or >CR¹R².

In certain embodiments R⁷⁴, R⁷⁵, R⁷⁶ and R⁷⁷ are —H. In other embodiments, R⁷⁴, R⁷⁵, R⁷⁶ and R⁷⁷ are —H, and at least one of R⁷⁰, R⁷¹, R⁷² and R⁷³ is an aliphatic group or a substituted aliphatic group. Preferred aliphatic groups at R⁷⁰, R⁷¹, R⁷², R⁷³, R⁷⁴, R⁷⁵, R⁷⁶ and R⁷⁷ are C₁–C₆ alkyl, preferred substitituted aliphatic groups are are C₁–C₆ alkyl substituted with —OH, —(O)ᵤ—(CH₂)ₜ—C(O)OR₂₀ or —O-(aliphatic group) wherein t is zero to three, u is zero or one, and R²⁰ is C₁–C₆ alkyl. In more particular embodiments, the compound has the formula of Structural Formula VIII wherein R⁷⁰, R⁷³, R⁷⁴, R⁷⁵, R⁷⁶ and R⁷⁷ are —H, and at least one of R⁷¹ and R⁷² is —CH₃.

In a preferred embodiment, the chemokine receptor antagonist is represented by Structural Formula VIII wherein n is two; M is >C(OH)R$^2$; R$^2$ is a halophenyl group (e.g., 4-chlorophenyl);

R$^{72}$, R$^{73}$, R$^{74}$, R$^{75}$, R$^{76}$ and R$^{77}$ are —H and R$^{70}$ and R$^{71}$ are independently C$_1$–C$_6$ alkyl or substituted C$_1$–C$_6$ alkyl; or R$^{70}$, R$^{71}$, R$^{74}$, R$^{75}$, R$^{76}$ and R$^{77}$ are —H an R$^{72}$ and R$^{73}$ are independently C$_1$–C$_6$ alkyl or substituted C$_1$–C$_6$ alkyl; and Z is represented by Structural Formula (VI) wherein X$_1$ is —CH$_2$—O—.

When R$^{72}$ and R$^{73}$ are each —CH$_3$, the compounds of this preferred embodiment can have the formula:

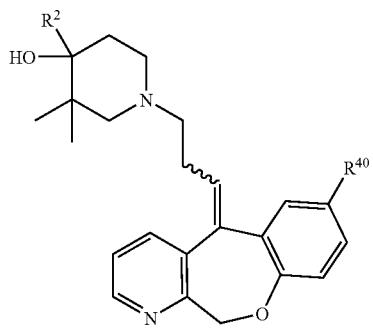

(XII)

or a physiologically acceptable salt thereof, wherein R$^2$ is 4-halophenyl. Preferably R$^2$ is selected from the group consisting of 4-chlorophenyl, 4-bromophenyl and 4-fluorophenyl. Preferred groups at R$^{40}$ are as described herein. Particularly preferred at R$^{40}$ are aliphatic groups (e.g., C$_1$–C$_6$ alkyl) and substituted aliphatic groups.

In a particularly preferred embodiment, the compound is the (S)-enantiomer of the compound of Formula (XII) and has the structure:

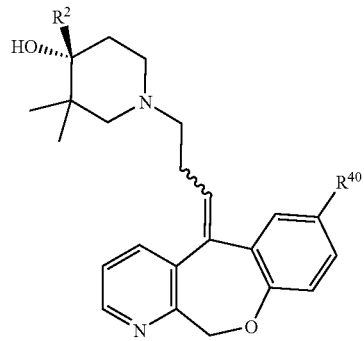

(XIII)

or a physiologically acceptable salt thereof, wherein R$^2$ is 4-halophenyl.

Particularly preferred compounds of the invention have the structure of Formula XIII wherein R$^2$ is 4-chlorophenyl and R$^{40}$ is selected from the group consisting of:

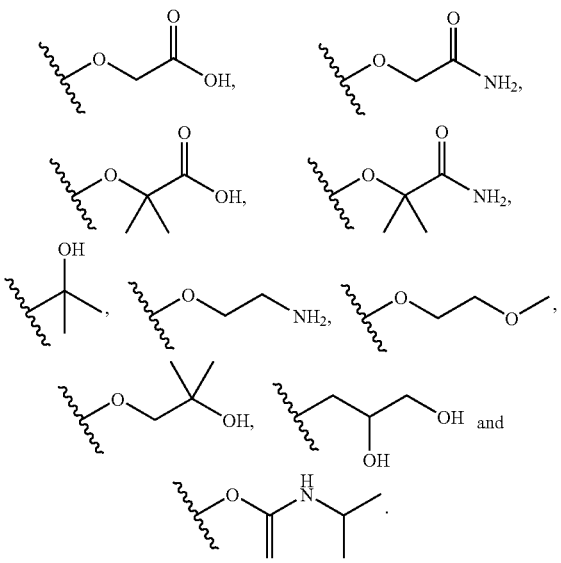

In another embodiment, the compound is represented by Structural Formula VIII:

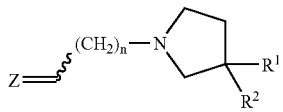

or a physiologically acceptable salt thereof, wherein n, R$^1$ and R$^2$ are as described in Structural Formula (I), and Z is as described in Structural Formula (V) or (VI).

In a certain embodiments, Z is represented by Structural Formula (VI) wherein X$_1$ is —CH$_2$—O—; n is two, R$^1$ is —H and R$^2$ is —NR$^5$R$^6$. Preferably, compounds of these embodiments have the structure:

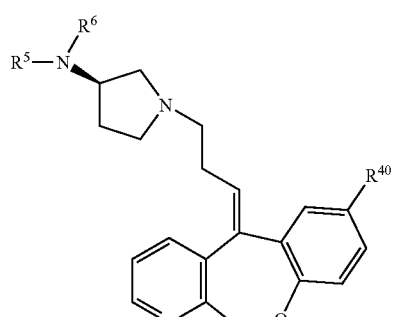

or a physiologically acceptable salt thereof, wherein R$^5$ and R$^6$ are as described in Structural Formula I, and preferred groups at R$^{40}$ are as described herein.

In particular embodiments, R$^5$ is aliphatic group (e.g., C$_1$–C$_6$ alkyl) or substituted aliphatic group, and R$^6$ is benzyl or substituted benzyl; or R$^5$ and R$^6$ taken together with the atom to which they are bonded, form a substituted or unsubstituted non-aromatic carbocyclic or heterocyclic ring. In more particular embodiments, $R^5$ is $C_1$–$C_6$ alkyl and $R^6$ is halo-substituted benzyl. In a preferred embodiment, $R^5$ is ethyl and $R^6$ is chloro-substituted benzyl (e.g., 4-chlorobenzyl).

The nitrogen atom in the ring containing M can be a tertiary nitrogen as depicted in Structural Formula (IV), or the nitrogen atom can be quaternized with a suitable substituent, such as a $C_1$ to about $C_6$ or a $C_1$ to about $C_3$ substituted or unsubstituted aliphatic group. Compounds which comprise a quaternary nitrogen atom can also contain a counteranion such as chloride, bromide, iodide, acetate, perchlorate and the like.

The antagonist of chemokine function can be represented by Structural Formula (VII) wherein the heterocyclic ring containing M is substituted with a suitable bivalent group which is bonded to two atoms that are in the ring, thereby forming a bicyclic moiety. Suitable bivalent groups include, for example, substituted or unsubstituted bivalent aliphatic groups, such as a $C_1$–$C_6$ alkylene group.

The antagonist of chemokine receptor function can comprise a variety of bicyclic moieties. In one embodiment, the antagonist of chemokine receptor function can be represented by Structural Formula (VIII):

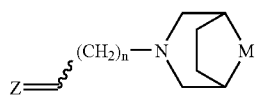

(VIII)

and physiologically acceptable salts thereof.

M is $>NR^2$, $>CR^1R^2$, —O—$CR^1R^2$—O— or —$CH_2$—$CR^1R^2$—O—. Preferably, M is $>NR^2$ or $>CR^1R^2$. $R^1$ and $R^2$ are as described in Structural Formula (I), and n and Z are as described in structural Formula (VII).

In another embodiment, the antagonist of chemokine receptor function is represented by Structural Formula (IX):

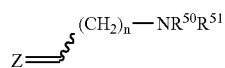

(IX)

and physiologically acceptable salts thereof.

Z is as described herein, preferably as described in Structural Formula (V) or (VI).

n is an integer, such as an integer from one to about four. Preferably, n is one, two or three. More preferably n is two. In alternative embodiments, other aliphatic or aromatic spacer groups (L) can be employed for $(CH_2)_n$.

$R^{50}$ and $R^{51}$ are each independently —H, an aliphatic group, a substituted aliphatic group, an aminoalkyl group, —$NR^3R^4$, an aromatic group, a substituted aromatic group, a benzyl group, a substituted benzyl group, a non-aromatic heterocyclic group, a substituted non-aromatic heterocyclic group or a covalent bond between the nitrogen atom an adjacent carbon atom.

$R^3$ and $R^4$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group.

$R^3$ and $R^4$ taken together with the atom to which they are bonded, can alternatively form a substituted or unsubstituted non-aromatic carbocyclic or heterocyclic ring.

In a preferred embodiment $R^{50}$ is a substituted aliphatic group, such as a substituted $C_1$ to about $C_{12}$ alkyl group, and $R^{51}$ is —H or a substituted or unsubstituted aliphatic group. More preferably, $R^{50}$ is a substituted linear or branched $C_2$ to about $C_7$ aliphatic group wherein one or more carbon atoms can be replaced by a heteroatom, such as nitrogen, oxygen or sulfur, and $R^{51}$ is —H or a linear or branched $C_1$ to about $C_6$ or a $C_1$ to about $C_3$ aliphatic group wherein one or more carbon atoms can be replaced by a heteroatom. $R^{50}$ and $R^{51}$ can be substituted with one or more suitable substituents, as described herein, preferably an aromatic group (e.g., phenyl, 4-halophenyl). For example, $R^{50}$ can be selected from the group consisting of:

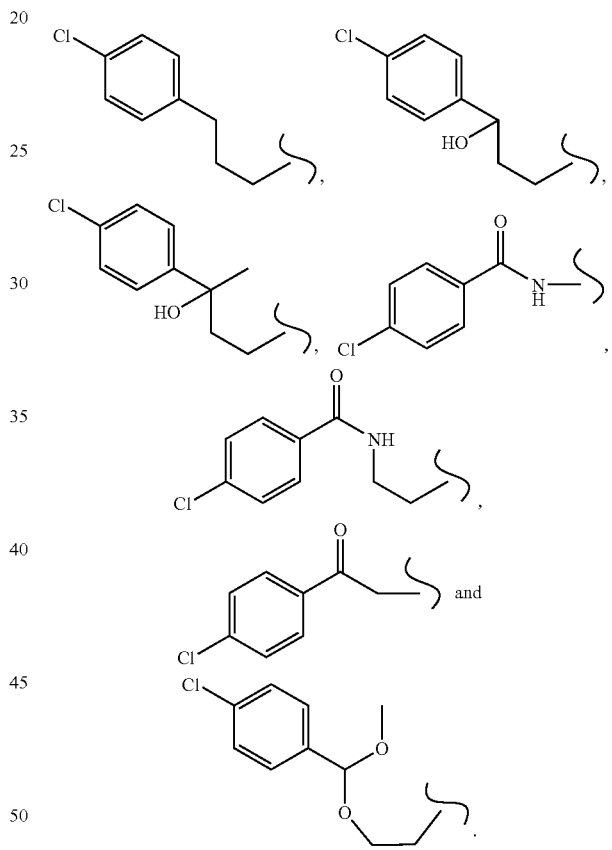

The activity of chemokine receptor antagonists represented by Structural Formula IX can be affected by the character of the nitrogen atom to which $R^{50}$ and $R^{51}$ are bonded. It is believed that compounds in which said nitrogen atom is basic can have potent chemokine receptor antagonist activity. It is known that the basicity of a nitrogen atom can be decreased when the nitrogen atom is bonded to a carbonyl group, sulfonyl group or a sulfinyl group. Therefore, it is preferred that neither $R^{50}$ nor $R^{51}$ comprise a carbonyl group, sulfonyl group or sulfinyl group that is directly bonded to the nitrogen atom.

In another aspect, the antagonist of chemokine receptor function is represented by Structural Formula (X):

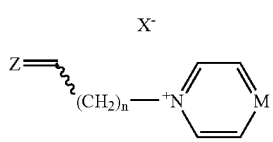

(X)

and physiologically acceptable salts thereof.

Z is a cycloalkyl or non-aromatic heterocyclic ring group fused to one, two or more aromatic rings, wherein each ring in Z is independently substituted or unsubstituted. Preferably, Z is as described in Structural Formula (VI).

n is an integer, such as an integer from one to about four. Preferably, n is one, two or three. More preferably n is two. In alternative embodiments, other aliphatic or aromatic spacer groups (L) can be employed for $(CH_2)_n$.

M is $>NR^2$ or $>CR^2$.

$R^2$ is —H, —OH, an acyl group, a substituted acyl group, —$NR^5R^6$, an aliphatic group, a substituted aliphatic group, an aromatic group, a substituted aromatic group, a benzyl group, a substituted benzyl group, a non-aromatic heterocyclic group, a substituted non-aromatic heterocyclic group, —O-(substituted or unsubstituted aromatic group) or —O-(substituted or unsubstituted aliphatic group). $R^2$ is preferably an aromatic group or a substituted aromatic group.

$R^5$ and $R^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group.

$R^5$ and $R^6$ taken together with the atom to which they are bonded, can alternatively form a substituted or unsubstituted non-aromatic carbocyclic or heterocyclic ring.

$X^-$ is a physiologically acceptable anion. Preferably, $X^-$ is $Cl^-$ or $Br^-$.

The chemokine receptor antagonist described herein can be prepared and administered as active compounds or as prodrugs. Generally, prodrugs are analogues of pharmaceutical agents which can undergo chemical conversion by metabolic processes to become fully active. For example, A prodrug of the invention can be prepared by selecting appropriate groups for $R^{40}$. In one embodiment, a prodrug can be represented by Structural Formula (XI):

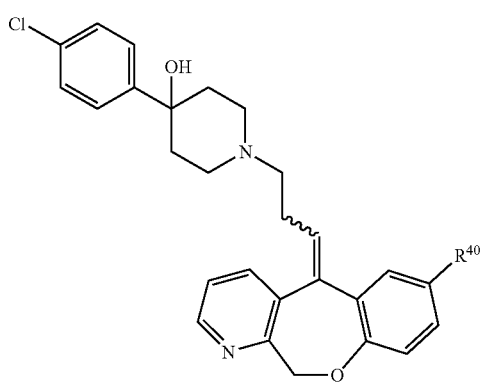

(XI)

wherein, $R^{40}$ is Q-substituted aliphatic group, and the aliphatic group is substituted with —$(O)_u$—$(CH_2)_t$—$C(O)$ $OR^{20}$, wherein Q is —C(O)O—, u is one, t is zero and $R^{20}$ is a cyclic aliphatic group. For example, when the substituted aliphatic group is a substituted ethyl group, $R^{40}$ can be represented by:

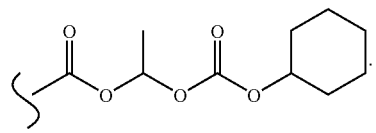

Such a prodrug can be converted to an active chemokine receptor antagonist represented by Structural Formula XI, wherein $R^{40}$ is —COOH.

Another embodiment of the present invention includes novel compounds employed in these methods.

The compounds disclosed herein can be obtained as E- and Z-configurational isomers. It is expressly pointed out that the invention includes compounds of the E-configuration and the Z-configuration around the double bond connecting Ring C of Z to the remainder of the molecule, and a method of treating a subject with compounds of the E-configuration, the Z-configuration, and mixtures thereof. Accordingly, in the structural formulas presented herein, the symbol:

is used to represent both the E-configuration and the Z-configuration. Preferably Ring A and the alkylene chain bonded to Ring C are in the cis configuration. For example, the compounds can have the configuration of:

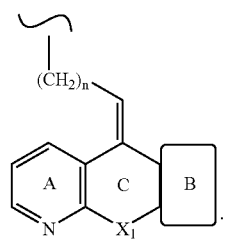

It is understood that one configuration can have greater activity than another. The desired configuration can be determined by screening for activity, employing the methods described herein.

Additionally, certain compounds of the invention may be obtained as different stereoisomers (e.g., diastereomers and enantiomers). The compounds of the invention can be prepared as racemates or as substantially pure stereoisomers. The stereoisomers of the invention (e.g., (S)- and (R)-enantiomers) can be prepared using any suitable method. For example, the enantiomers can be resolved from the racemate using chiral chromatography or recrystallization. Preferably, the stereoisomers (e.g., (S)- and/or (R)-enantiomers) are prepared by stereospecific synthesis as described herein.

The optical configuration of the stereoisomers of the invention are assigned using the (R),(S) method of Cahn- Ingold-Prelog. (See, J. March, "Advanced Organic Chemistry," 4th Edition, Wiley Interscience, New York, pp. 109–111 (1992).)

The invention includes all isomeric forms and racemic mixtures of the disclosed compounds and a method of treating a subject with both pure isomers and mixtures thereof, including racemic mixtures. Sterioisomers can be separated and isolated using any suitable method, such as chromatography. Again, it is understood that one sterioisomer may be more active than another. The desired isomer determined by screening.

Also included in the present invention are physiologically acceptable salts of the compounds represented by Structural Formulas (I) through (XIII). Salts of compounds containing an amine or other basic group can be obtained, for example, by reacting with a suitable organic or inorganic acid, such as hydrogen chloride, hydrogen bromide, acetic acid, citric acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a counteration such as sodium, potassium, ammonium, calcium and the like. (See, for example, Berge S. M. et al., "Pharmaceutical Salts," *J. Pharma. Sci.*, 66:1 (1977).)

As used herein, aliphatic groups include straight chained, branched or cyclic $C_1$–$C_{20}$ hydrocarbons which are completely saturated or which contain one or more units of unsaturation. Preferred aliphatic groups are $C_1$ to about $C_{10}$ hydrocarbons. More preferred are $C_1$ to about $C_6$ or $C_1$ to about $C_3$ hydrocarbons. One or more carbon atoms in an aliphatic group can be replaced with a heteroatom, such as nitrogen, oxygen or sulfur. For example, suitable aliphatic groups include substituted or unsubstituted linear, branched or cyclic $C_1$–$C_{20}$ alkyl, alkenyl or alkynyl groups.

An aminoalkyl group is an alkyl group substituted with —$NR^{24}R^{25}$, $R^{24}$ and $R^{25}$ are as described herein. Preferably the alkyl moiety comprises one to about twelve, more preferably one to about six carbon atoms. The alkyl moiety of an aminoalkyl group can be unsubstituted or substituted as described herein for aliphatic groups. Examples of suitable aminoalkyl groups include aminomethyl, 2-aminoethyl, 3-aminopropyl, 4-aminobutyl, dimethylaminoethyl, diethylaminomethyl, methylaminohexyl, aminoethylenyl and the like.

Aromatic groups include carbocyclic aromatic groups such as phenyl, 1-naphthyl, 2-naphthyl, 1-anthracyl and 2-anthracyl, and heterocyclic aromatic or heteroaryl groups such as N-imidazolyl, 2-imidazolyl, 4-imidazolyl, 5-imidazolyl, 2-thienyl, 3-thienyl, 2-furanyl, 3-furanyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 4-pyridazinyl, 3-pyrazolyl, 4-pyrazolyl, 5-pyrazolyl, 2-pyrazinyl, 2-thiazolyl, 4-thiazolyl, 5-thiazolyl, 5-tetrazolyl, 2-oxazolyl, 4-oxazolyl and 5-oxazolyl. Where these rings are fused, for example, to Ring C, the stated point of attachment can be either of the two fused bonds.

Aromatic groups also include fused polycyclic aromatic ring systems in which a carbocyclic aromatic ring or heteroaryl ring is fused to one or more other rings. Examples include tetrahydronaphthyl, 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzooxazolyl, 2-benzimidazolyl, 1-isoquinolinyl, 3-quinolinyl, 1-isoindolyl, 3-isoindolyl, acridinyl, 3-benzisoxazolyl, and the like. Also included within the scope of the term "aromatic group", as it is used herein, is a group in which one or more carbocyclic aromatic rings and/or heteroaryl rings are fused to a cycloalkyl or non-aromatic heterocyclic ring, for example, benzocyclopentane, benzocyclohexane.

Non-aromatic heterocyclic rings are non-aromatic carbocyclic rings which include one or more heteroatoms such as nitrogen, oxygen or sulfur in the ring. The ring can be five, six, seven or eight-membered and/or fused to another ring, such as a cycloalkyl on aromatic ring. Examples include 1,3-dioxolan-2-yl, 3-1H-benzimidazol-2-one, 3-1-alkyl-benzimidazol-2-one, 3-1-methyl-benzimidazol-2-one, 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidyl, 1-3-alkyl-phthalimidyl, benzoxane, benzopyrolidine, benzopiperidine, benzoxolane, benzothiolane, benzothiane, tetrahydrofuran-2-one-3-yl, 2,5-dihydro-5-oxo-4H-1,2,4-thiadiazol-3-yl, 2-oxo-3H-1,2,3,5-oxathiadiazol-4-yl,

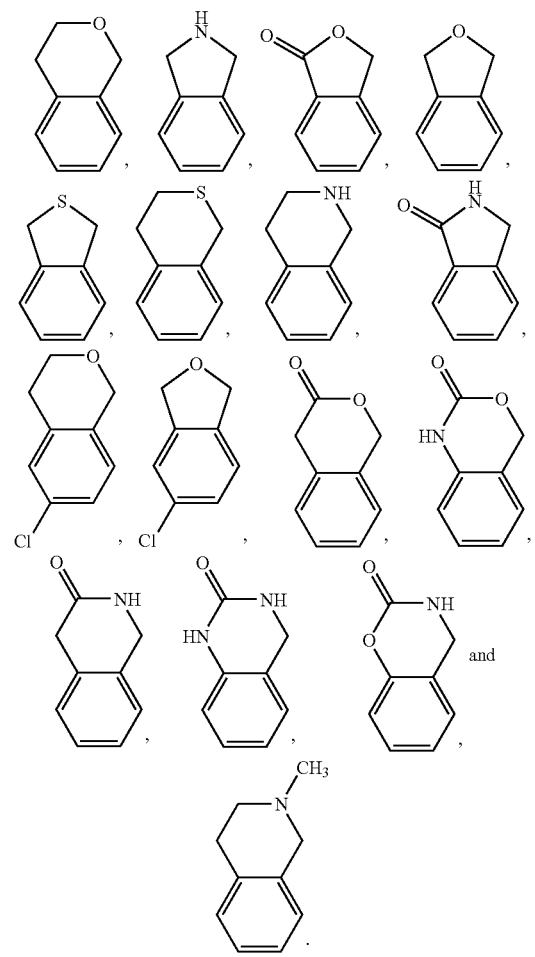

Suitable substituents on an aliphatic group, aromatic group (carbocyclic and heteroaryl), non-aromatic heterocyclic ring or benzyl group include, for example, an electron withdrawing group, a halogen (chloride, bromide, fluoride, iodide), azido, —CN, —COOH, —OH, —CONR$^{24}$R$^{25}$, —NR$^{24}$R$^{25}$, —OS(O)$_2$NR$^{24}$R$^{25}$, —S(O)$_2$NR$^{24}$R$^{25}$, —SO$_3$H, —S(O)$_2$NH$_2$, guanidino, ureido, oxalo, amidino, —C(=NR$^{60}$)NR$^{21}$R$^{22}$, =NR$^{60}$, —(O)$_u$—(CH$_2$)$_t$—C(O) OR$^{20}$, —(O)$_u$—(CH$_2$)$_t$—OC(O)R$^{20}$, —(O)$_u$—(CH$_2$)$_t$—C (O)—NR$^{21}$R$^{22}$, —(O)$_u$—(CH$_2$)$_t$—NHC(O)O—R$^{20}$, -Q-H, -Q-(aliphatic group), -Q-(substituted aliphatic group), -Q-(aryl), -Q-(aromatic group), -Q-(substituted aromatic group), -Q-(CH$_2$)$_p$-(substituted or unsubstituted aromatic group) p is an integer from 1–5), -Q-(non-aromatic heterocyclic group) or -Q-(CH$_2$)$_p$-(non-aromatic heterocyclic group).

R$^{20}$, R$^{21}$ and R$^{22}$ are independently —H, an aliphatic group, a substituted aliphatic group, an aromatic group, a substituted aromatic group, a non-aromatic heterocyclic group, —NHC(O)—O-(aliphatic group), —NHC(O)—O-(aromatic group) or —NHC(O)—O-(non-aromatic heterocyclic group) and wherein R$^{21}$ and R$^{22}$, taken together with the nitrogen atom to which they are bonded, can form a substituted or unsubstituted non-aromatic heterocyclic ring.

R$^{60}$ is a —H, —OH, —NH$_2$, an aromatic group or a substituted aromatic group.

t is an integer from zero to about three, and the methylene group, —(CH$_2$)$_t$—, can be substituted, as described herein for aliphatic groups, or unsubstituted.

u is zero or one.

Q is —O—, —S—, —S(O)—, —S(O)$_2$—, —OS(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N(R$^{23}$)—, —C(NR$^{23}$)NHNH—, —NHNHC(NR$^{23}$)—, —NR$^{24}$C(O) or —NR$^{24}$S(O)$_2$—.

R$^{23}$ is —H, an aliphatic group, a benzyl group, an aryl group or non-aromatic heterocyclic group.

R$^{24}$ and R$^{25}$ are independently —H, —OH, an aliphatic group, a substituted aliphatic group, a benzyl group, an aryl group, non-aromatic heterocyclic group or R$^{24}$ and R$^{25}$ taken together with the nitrogen atom to which they are bonded can form a substituted or unsubstituted non-aromatic heterocyclic ring.

A substituted non-aromatic heterocyclic ring, benzyl group or aromatic group can also have an aromatic group, an aliphatic or substituted aliphatic group, as a substituent. When a non-aromatic ring (carbocyclic or heterocyclic) or an aromatic ring (carbocyclic aromatic or heteroaryl) is substituted with another ring, the two rings can be fused. A substituted aliphatic group can also have an oxo group, epoxy group, non-aromatic heterocyclic ring, benzyl group, substituted benzyl group, aromatic group or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent, which can be the same or different.

Acyl groups include substituted and unsubstituted aliphatic carbonyl, aromatic carbonyl, aliphatic sulfonyl and aromatic sulfonyl.

Suitable electron withdrawing groups include, for example, alkylimines, alkylsulfonyl, carboxamido, carboxylic alkyl esters, —CH=NH, —CN, —NO$_2$ and halogens. In the structural formulas depicted herein, the single or double bond by which a chemical group or moiety is connected to the remainder of the molecule or compound is indicated by the following symbol:

$$" \overset{}{\underset{}{\text{S}}} ."$$

For example, the corresponding symbol in Structural Formulas (II), (III) and (IV) indicates the double bond by which the central ring of the tricyclic ring system is connected to the remainder of the molecule represented by Structural Formula (I).

A "subject" is preferably a bird or mammal, such as a human, but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

An "effective amount" of a compound is an amount which results in the inhibition of one or more processes mediated by the binding of a chemokine to a receptor in a subject with a disease associated with aberrant leukocyte recruitment and/or activation. Examples of such processes include leukocyte migration, integrin activation, transient increases in the concentration of intracellular free calcium [Ca$^{2+}$]$_i$ and granule release of proinflammatory mediators. Alternatively, an "effective amount" of a compound is a quantity sufficient to achieve a desired therapeutic and/or prophylactic effect, such as an amount which results in the prevention of or a decrease in the symptoms associated with a disease associated with aberrant leukocyte recruitment and/or activation.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compound can range from about 0.1 mg per day to about 100 mg per day for an adult. Preferably, the dosage ranges from about 1 mg per day to about 100 mg per day. An antagonist of chemokine receptor function can also be administered in combination with one or more additional therapeutic agents, e.g. theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1a, IFNβ-1b)) and the like.

The compound can be administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound can also be administered orally (e.g., dietary), transdermally, topically, by inhalation (e.g., intrabronchial, intranasal, oral inhalation or intranasal drops), or rectally, depending on the disease or condition to be treated. Oral or parenteral administration are preferred modes of administration.

The compound can be administered to the individual in conjunction with an acceptable pharmaceutical or physiological carrier as part of a pharmaceutical composition for treatment of HIV infection, inflammatory disease, or the other diseases discussed above. Formulation of a compound to be administered will vary according to the route of administration selected (e.g., solution, emulsion, capsule).

Suitable carriers may contain inert ingredients which do not interact with the compound. Standard pharmaceutical formulation techniques can be employed, such as those described in Remington's Pharmaceutical Sciences, Mack Publishing Company, Easton, Pa. Suitable carriers for parenteral administration include, for example, sterile water, physiological saline, bacteriostatic saline (saline containing about 0.9% benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The quantity of active ingredient (one or more compounds of the invention) in the composition can range from about 0.1% to about 99.9% by weight. Preferably the quantity of active ingredient is about 10% to about 90%, or about 20% to about 80% by weight. A unit dose preparation can contain from 1 mg to about 1000 mg active ingredient, preferably about 10 mg to about 100 mg active ingredient. The composition can, if desired, also contain other compatible therapeutic agents, such as theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1a, IFNβ-1b)) and the like.

In one embodiment, the pharmaceutical composition comprises the (S)-enantiomer of a compound of the invention (e.g., a compound of Structural Formula (XIII)) and a physiologically acceptable carrier or excipient. For example, in one embodiment, the composition comprises (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol and a physiologically acceptable carrier or excipient. In certain embodiments, the pharmaceutical composition comprises the (S)-enantiomer of a compound of the invention (e.g., a compound of Structural Formula (XIII)) and is substantially free of the corresponding (R)-enantiomer (contains at least about 98% or at least about 99% enantiomeric excess of (S)-enantiomer). In another embodiments, the composition comprises the (S)-enantiomer of a compound of the invention (e.g., a compound of Structural Formula (XII)), the corresponding (R)-enantiomer and a physiologically acceptable carrier or excipient. In a more particular embodiment, the composition comprises a racemic compound of Structural Formula (XII), for example, racemic-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol. In other embodiments, the ratio (S)-enantiomer:(R)-enantiomer (w/w) in the compositions is at least about 2:1 or about 5:1 or about 10:1 or about 20:1 or about 50:1.

The activity of compounds of the present invention can be assessed using suitable assays, such as receptor binding assays and chemotaxis assays. For example, as described in the Exemplification Section, small molecule antagonists of RANTES and MIP-1α binding have been identified utilizing THP-1 cells which bind RANTES and chemotax in response to RANTES and MIP-1α as a model for leukocyte chemotaxis. Specifically, a high through-put receptor binding assay, which monitors $^{125}$I-RANTES and $^{125}$I-MIP-1α binding to THP-1 cell membranes, was used to identify small molecule antagonists which block binding of RANTES and MIP-1α. Compounds of the present invention can also be identified by virtue of their ability to inhibit the activation steps triggered by binding of a chemokine to its receptor, such as chemotaxis, integrin activation and granule mediator release. They can also be identified by virtue of their ability to block RANTES and MIP-1α mediated HL-60, T-cell, peripheral blood mononuclear cell, and eosinophil chemotactic response.

The compounds disclosed herein can be prepared accordingly to the schemes shown in FIGS. 1–5 and 7. The schemes are described in greater detail below.

FIG. 1 shows the preparation of compounds represented by Structural Formula (I). $L^1$ is $PPh_3Cl$, $PPh_3Br$, $PPh_3I$ or $(EtO)_2P(O)$, $L^2$ is a suitable leaving group such as halogen, p-toluene sulfonate, mesylate, alkoxy, and phenoxy; Pg is a suitable protecting group such as tetrahydropyranyl; and the other symbols are as defined above.

In Step 1 of FIG. 1, a Wittig reaction is carried out in a solvent such as ether, or tetrahydrofuran (THF) in the presence of a base such as sodium hydride, n-butyl lithium or lithium diisopropylamide (LDA) at 0° C. up to the reflux temperature for the solvent used for 5 minutes to 72 h. Compounds represented by Formula II in FIG. 1 can be prepared by methods disclosed in JP 61/152673, U.S. Pat. No. 5,089,496, WO 89/10369, WO 92/20681 and WO 93/02081, the entire teachings of which are incorporated herein by reference.

In Step 2 of FIG. 1, deprotection is carried out with an acid in a solvent such as methanol at room temperature up to the reflux temperature for the solvent used for 5 minutes to 72 h. Alternatively, a compound of represented by Formula V in FIG. 1 can be prepared directly from step 1 without isolating an intermediate. The reaction mixture obtained after the work up of the reaction described in step 1 can be dissolved in the solvent and reacted with the acid.

In Step 3 of FIG. 1, the hydroxy group can be converted to a leaving group by known methods. Compounds represented by Formula VI in FIG. 1 can be prepared by methods disclosed in *J. Med. Chem.*, 1992 (35) 2074–2084 and JP 61/152673.

In Step 4 of FIG. 1, an alkylation reaction is carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide at room temperature up to the reflux temperature for the solvent used for 5 minutes to 72 h.

Figure 2:
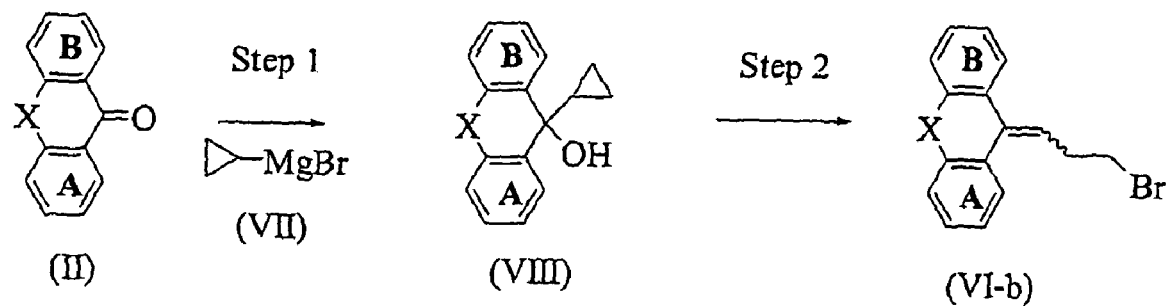
FIG. 2 is a schematic showing the preparation of the compounds represented by Compound (VI-b).

FIG. 2 shows the preparation of compounds represented by Compound (VI-b). In Step 1 of FIG. 2, a Grignard reaction may be carried out in a solvent such as ether, or tetrahydrofuran (THF) at 0° C. up to the reflux temperature for the solvent used for 5 minuets to 72 h. Compound VII is available commercially.

In Step 2 of FIG. 2, bromination may be carried out with brominate agents such as hydrobromic acid, bromotrimethylsilane or boron tribromide-methyl sulfide complex in a solvent such as acetic acid, dichloromethane or dichloroethane at room temperature up to the reflux temperature for the solvent used for 5 minutes to 72 h.

Figure 3:
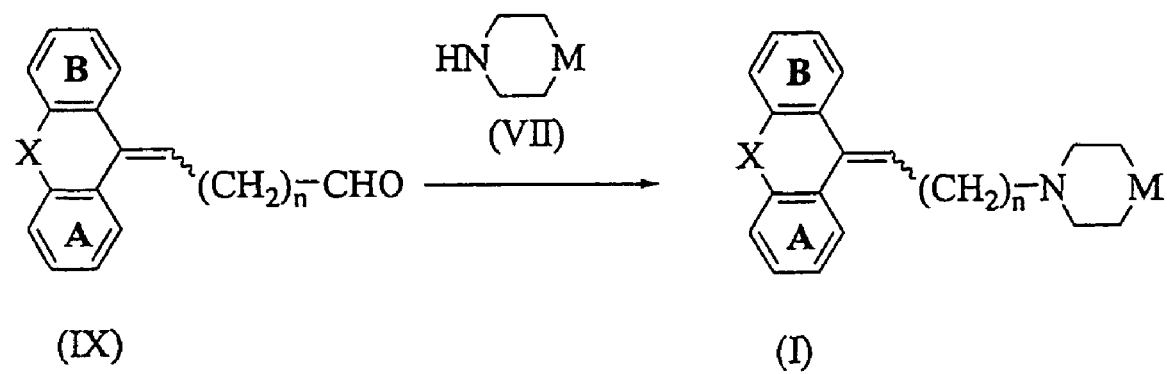
FIG. 3 is a schematic showing the preparation of the compounds represented by Structural Formula (I)

FIG. 3 shows the preparation of compounds represented by Structural Formula (I). In FIG. 3, a reductive amination may be carried out with reducing regents such as sodium cyanoborohydride, sodium acetoxyborohydride or sodium borohydride in a solvent such as methanol, ethanol, tetrahydrofuran (THF), dichloromethane or dichloroethane at room temperature up to the reflux temperature for the solvent used for 5 minutes to 72 h.

Figure 4:
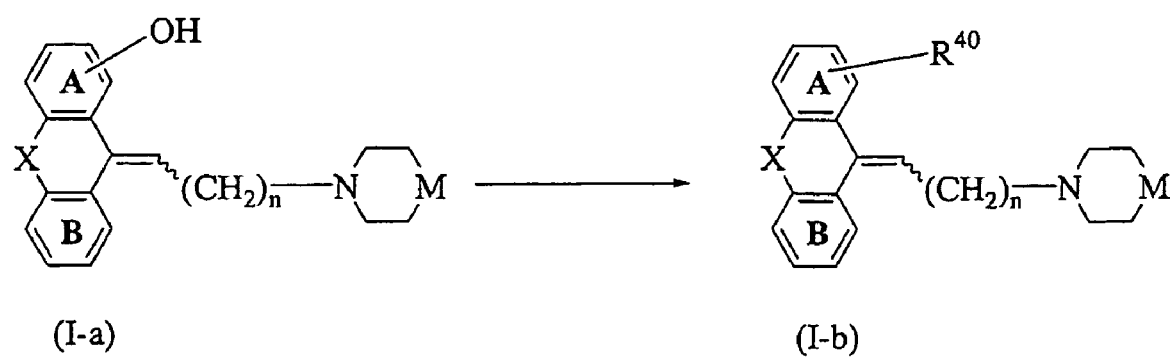
FIG. 4 is a schematic showing the preparation of the compounds represented by Structural Formula (I), wherein Z is represented by Structural Formula (III) and wherein Ring A and/or Ring B in Z is substituted with $R^{40}$.

FIG. 4 shows the preparation of compounds represented by Structural Formula (I), where in Z is represented by Structural Formulas (III) and wherein Ring A and/or Ring B in Z is substituted with $R^{40}$. In FIG. 4, the alkylation reaction can be carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide at room temperature up to the reflux temperature for the solvent used for 5 minutes to 72 h.

Figure 5:
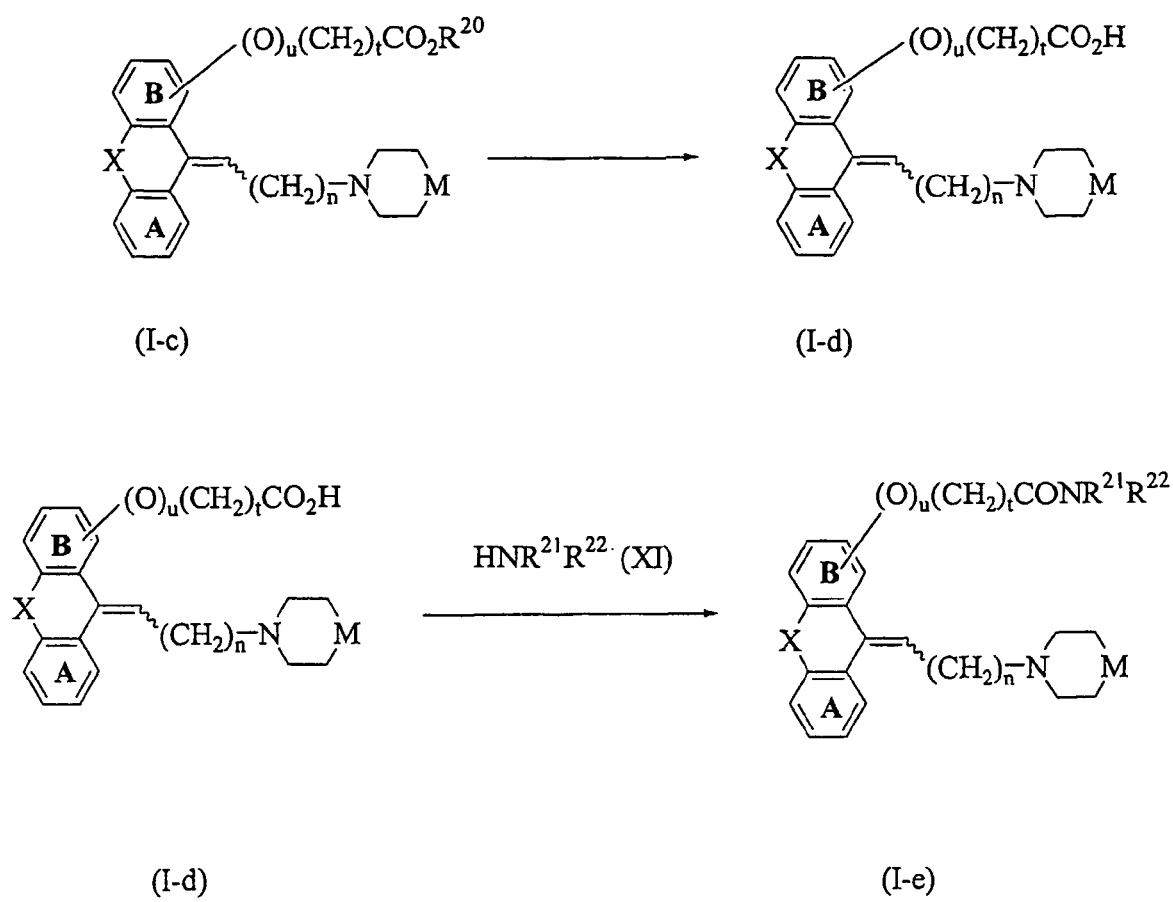
FIG. 5 is a schematic showing the preparation of the compounds represented by Structural Formula (I), wherein Z is represented by Structural Formula (III) and wherein Ring A and/or Ring B in Z is substituted with $-(O)_u-(CH_2)_t-COOR^{20}$, $-(O)_u-(CH_2)_t-OC(O)R^{20}$, $-(O)_u-(CH_2)_t-C(O)-NR^{21}R^{22}$ or $-(O)_u-(CH_2)_t-NHC(O)O-R^{20}$.
Figure 6B:
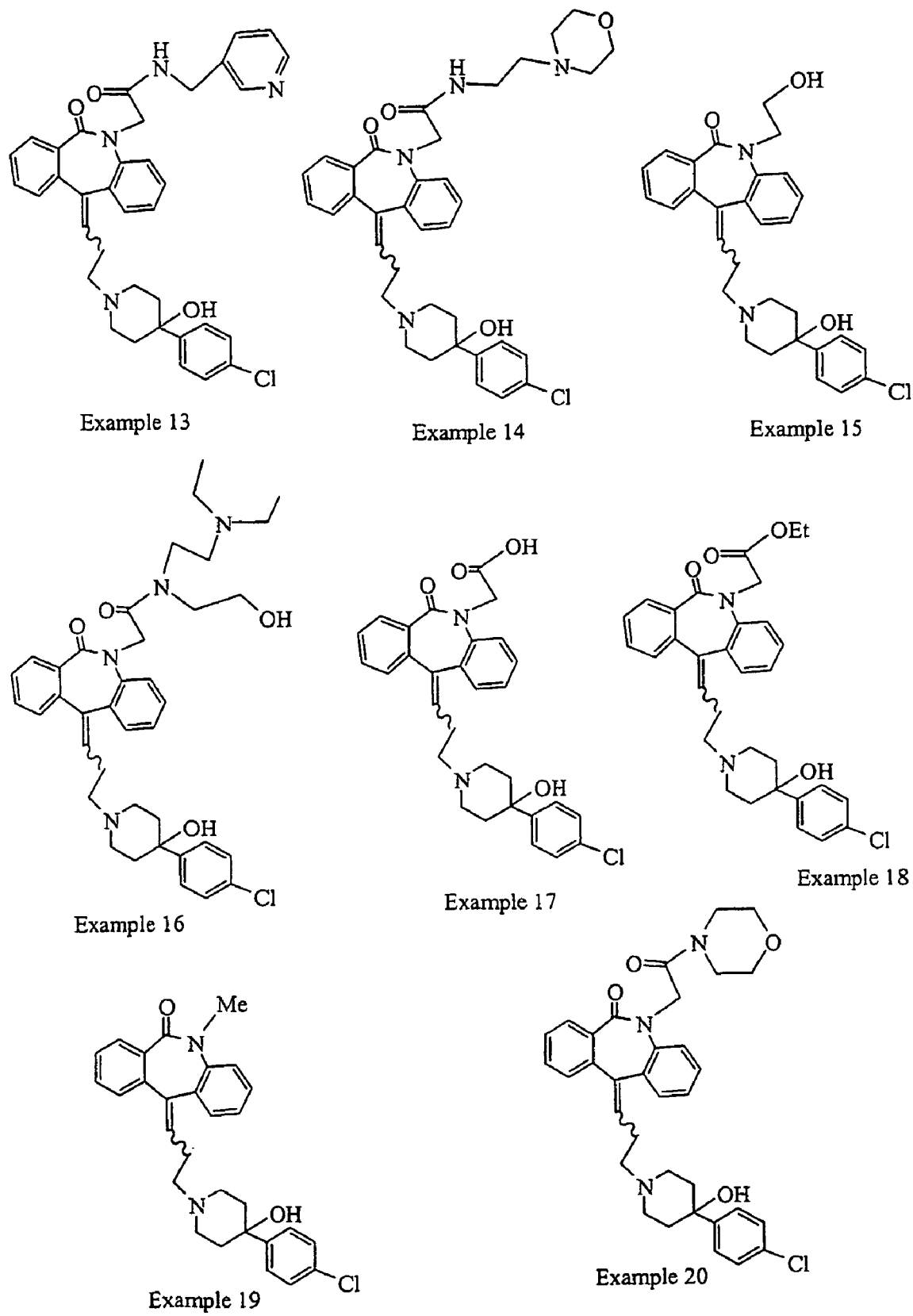
FIGS. 6A–6Z show the structures of exemplary compounds of the present invention.
Figure 6J:
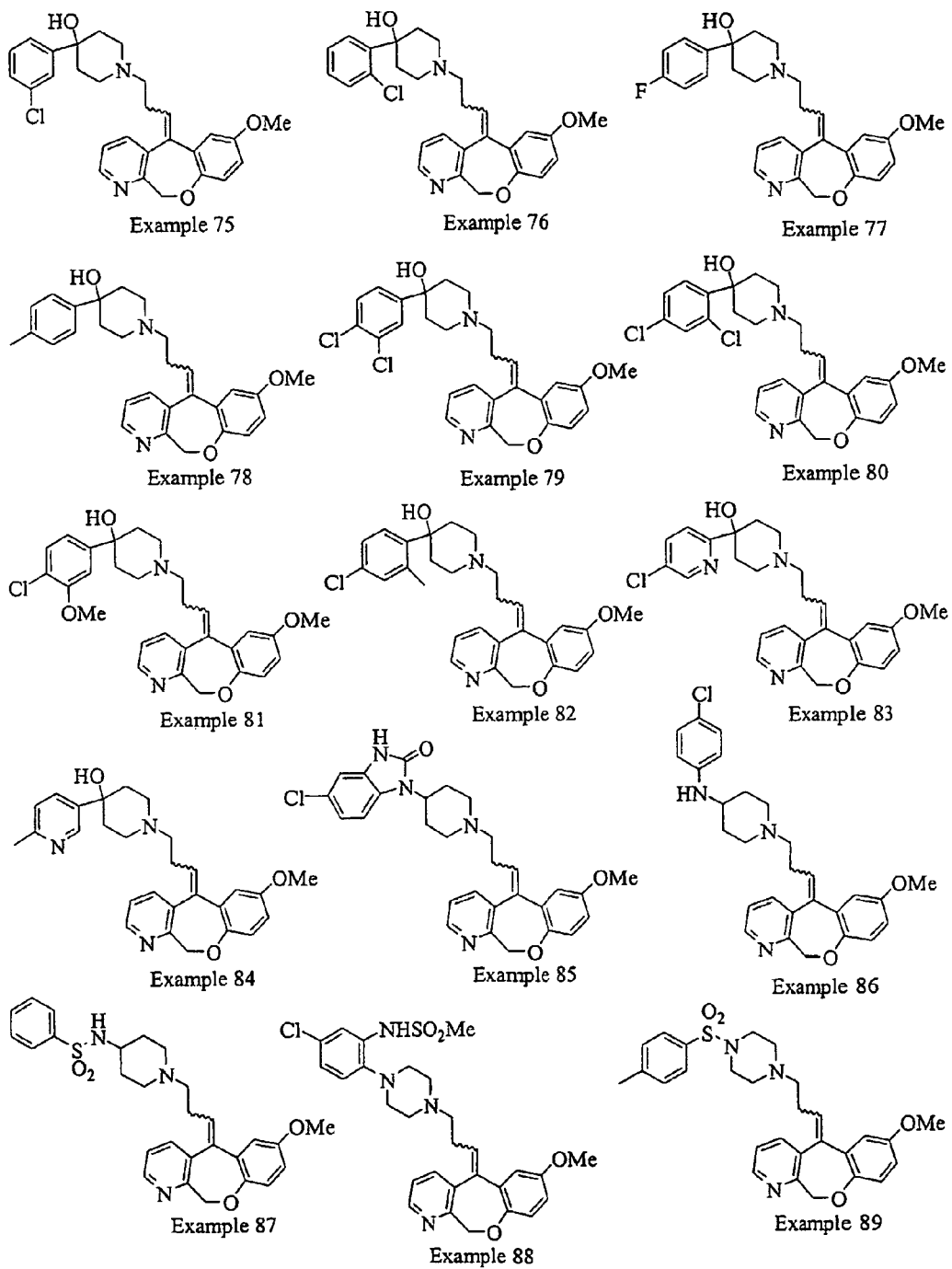
Figure 6K:
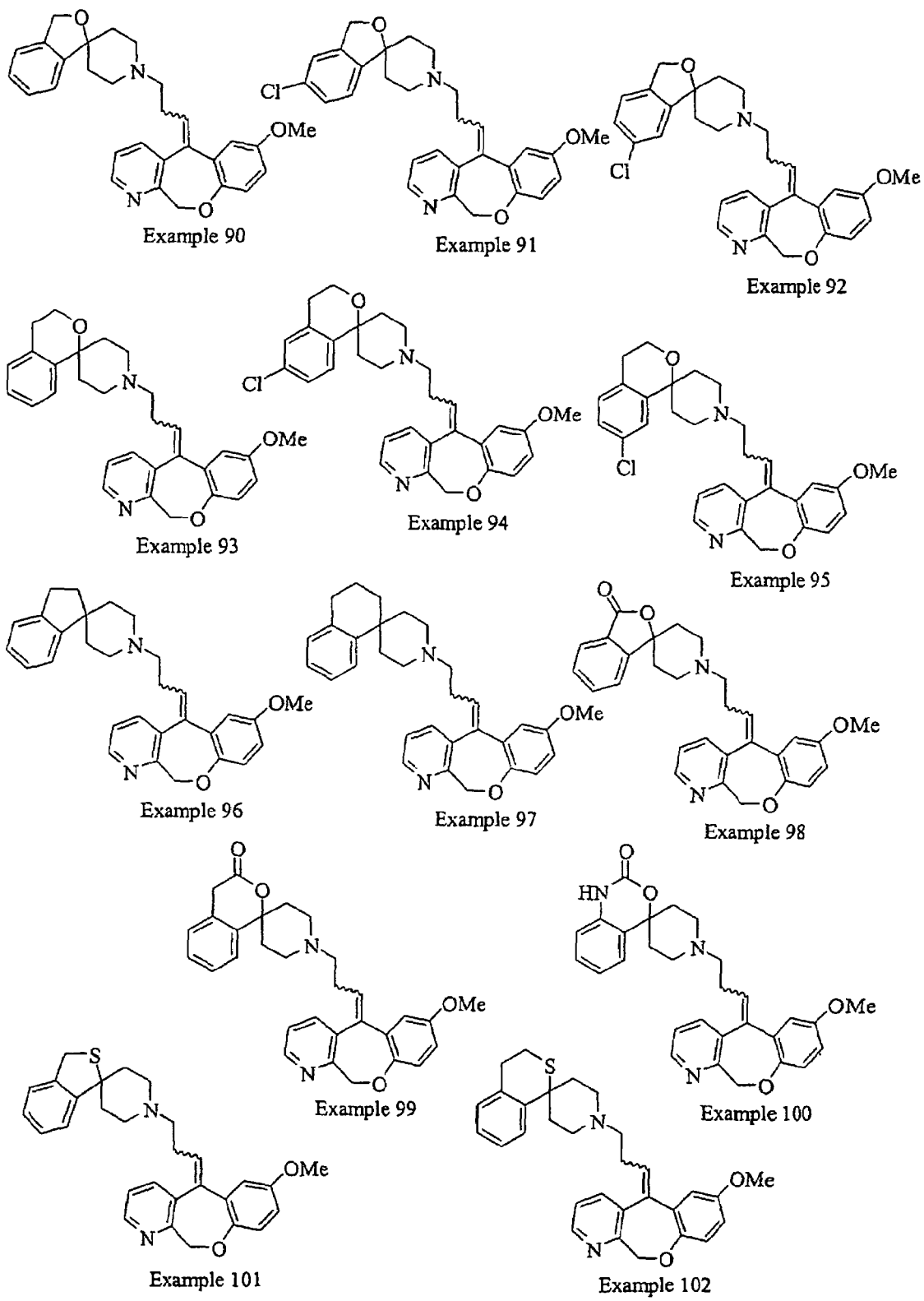
Figure 6M:
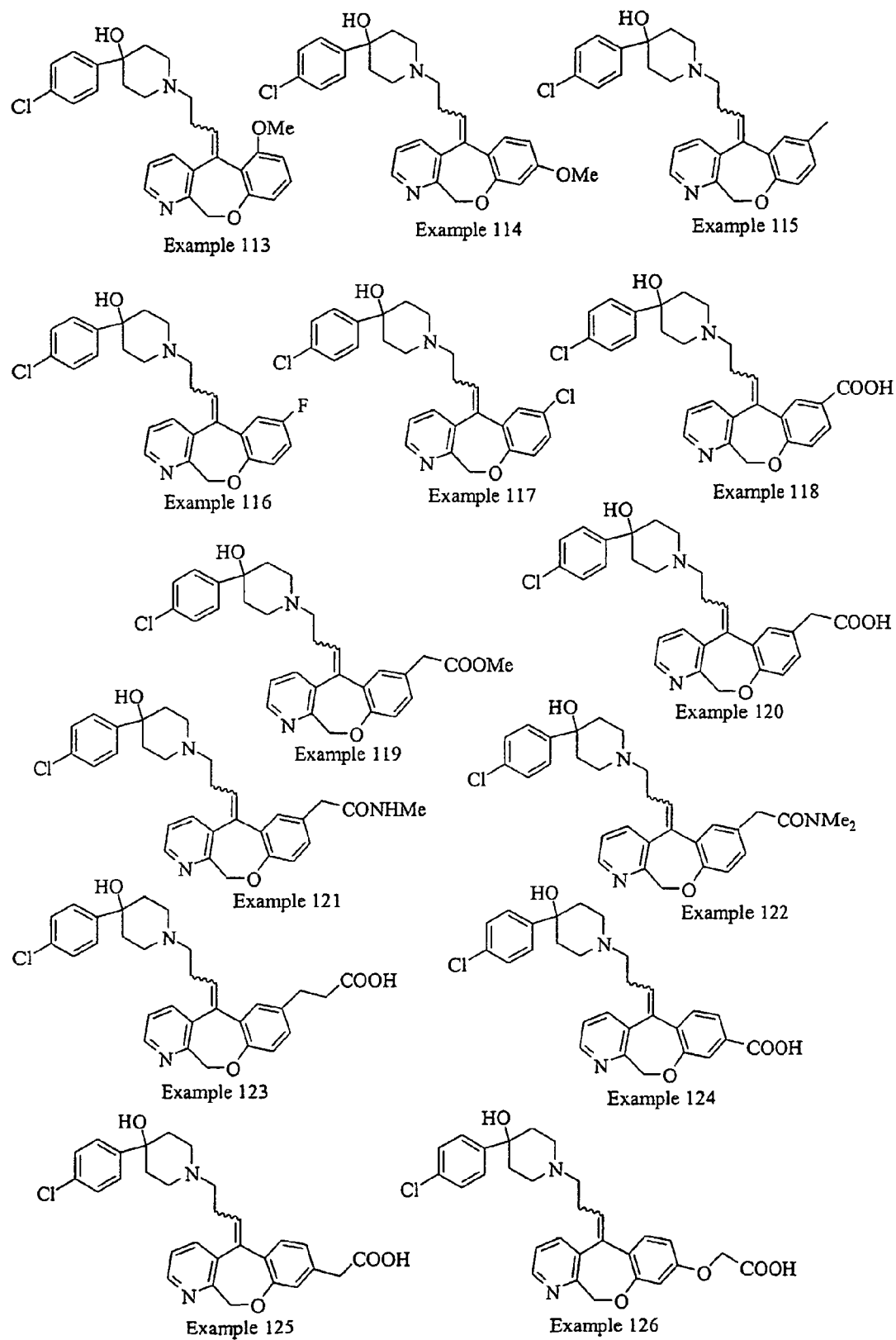
Figure 6N:
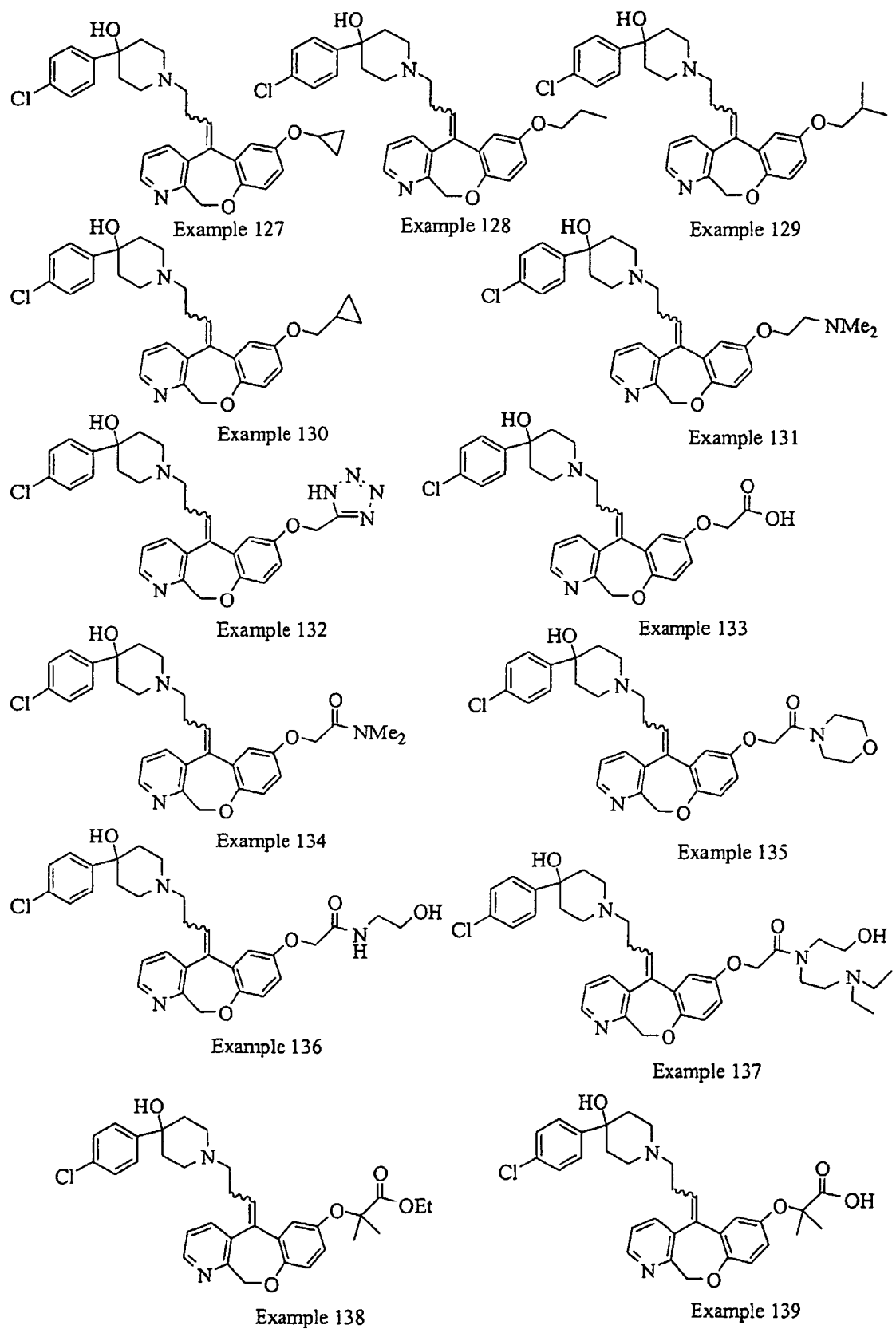
Figure 6P:
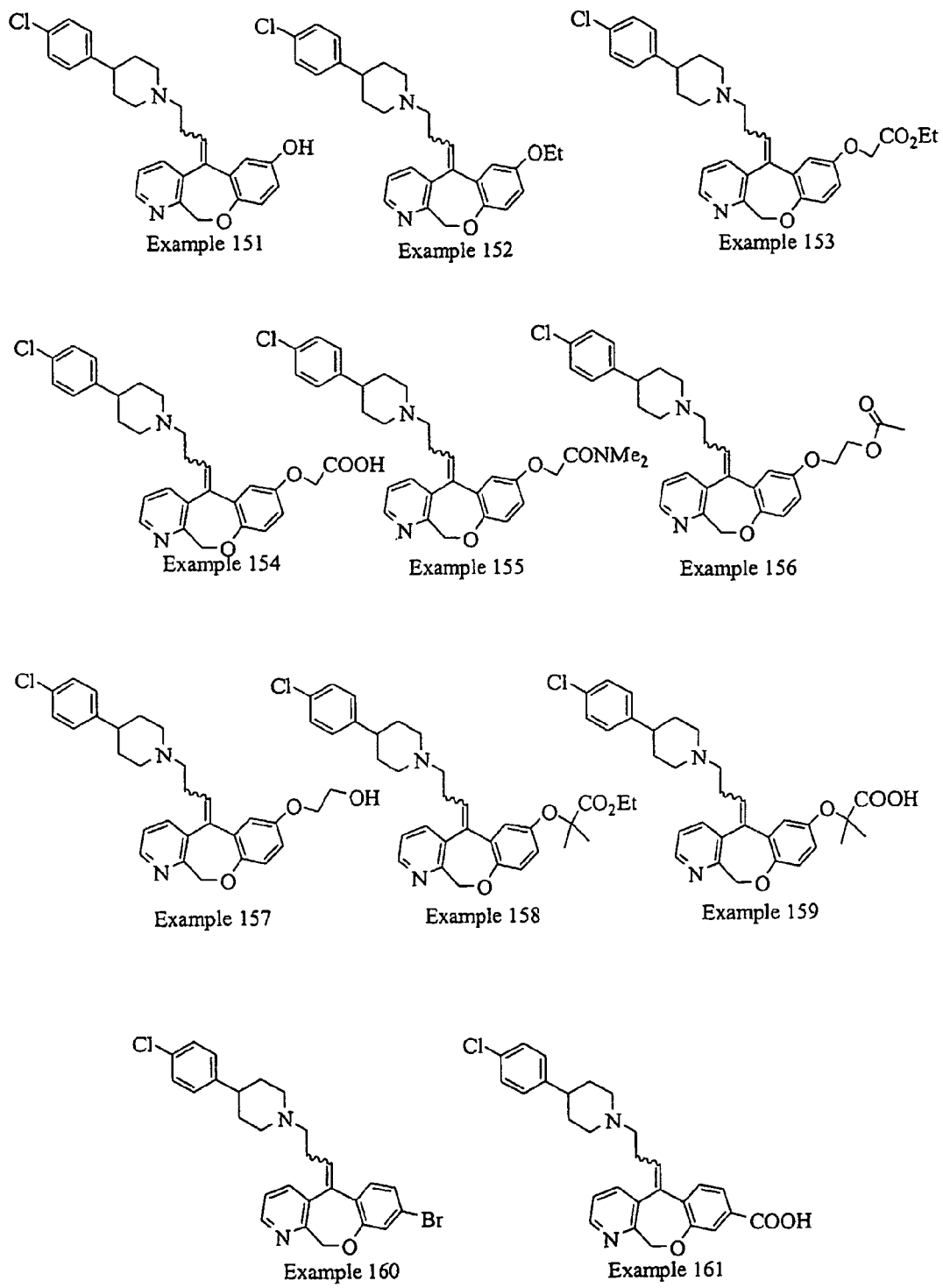
Figure 6Q:
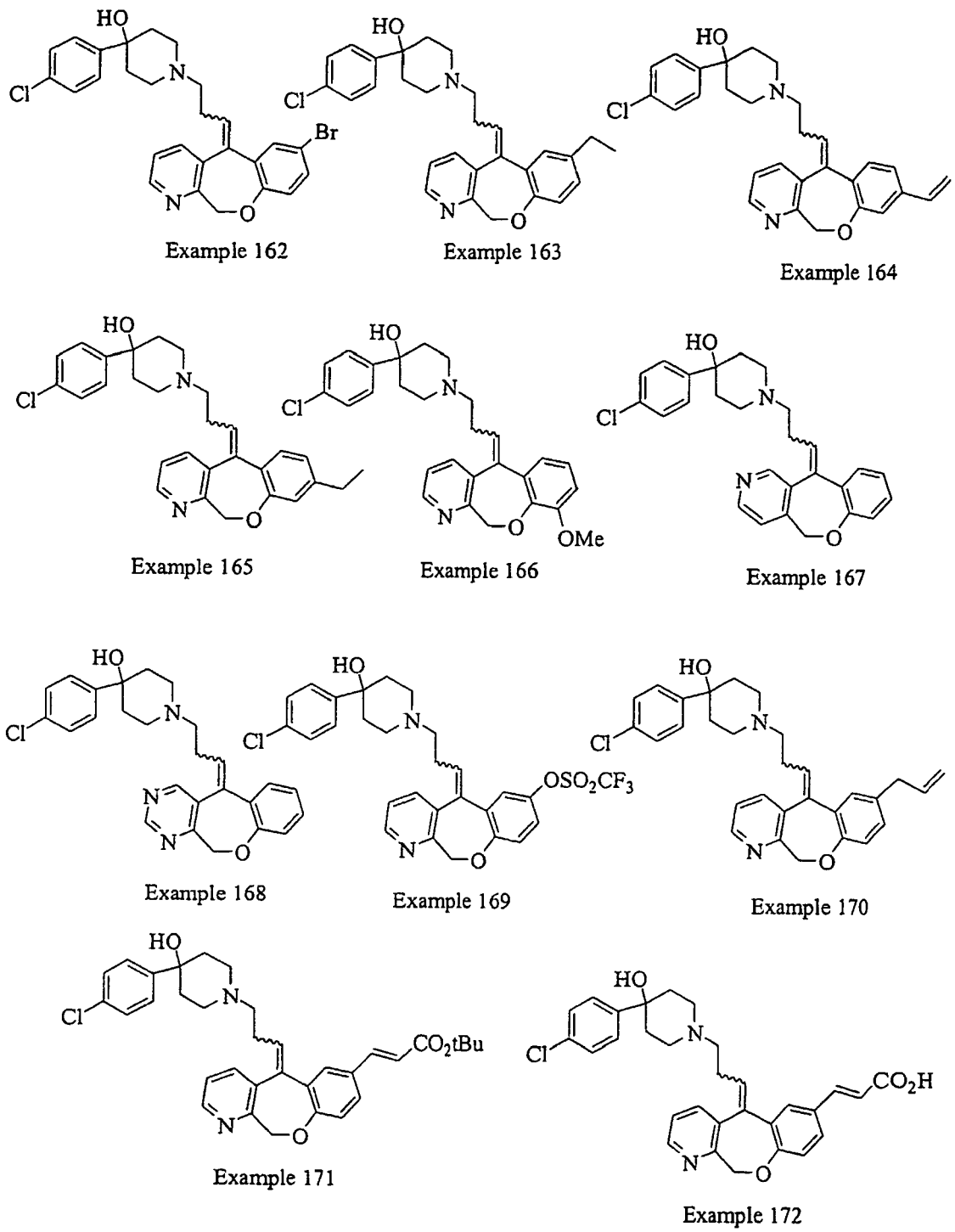
Figure 6W:
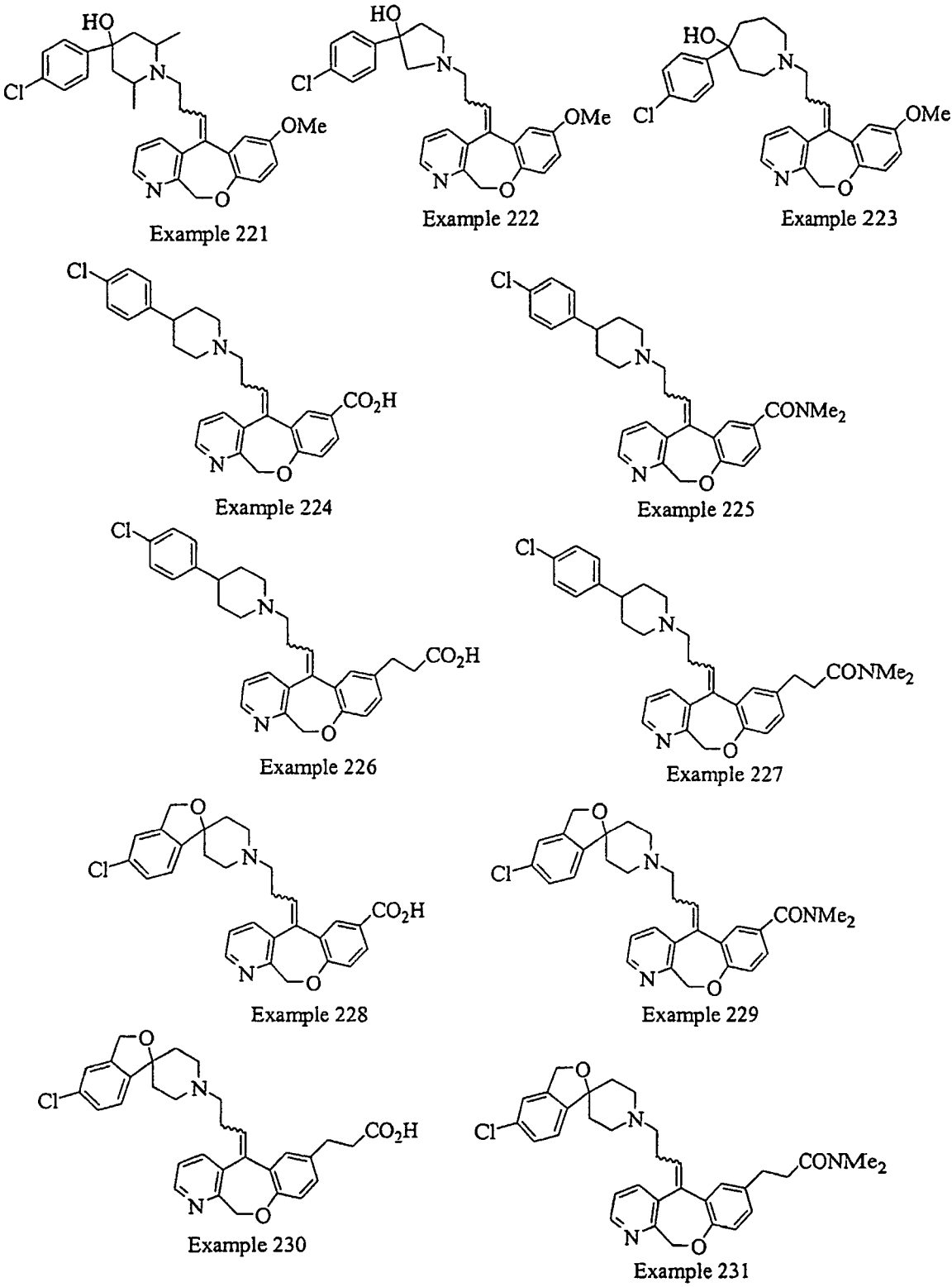
Figure 6Z:
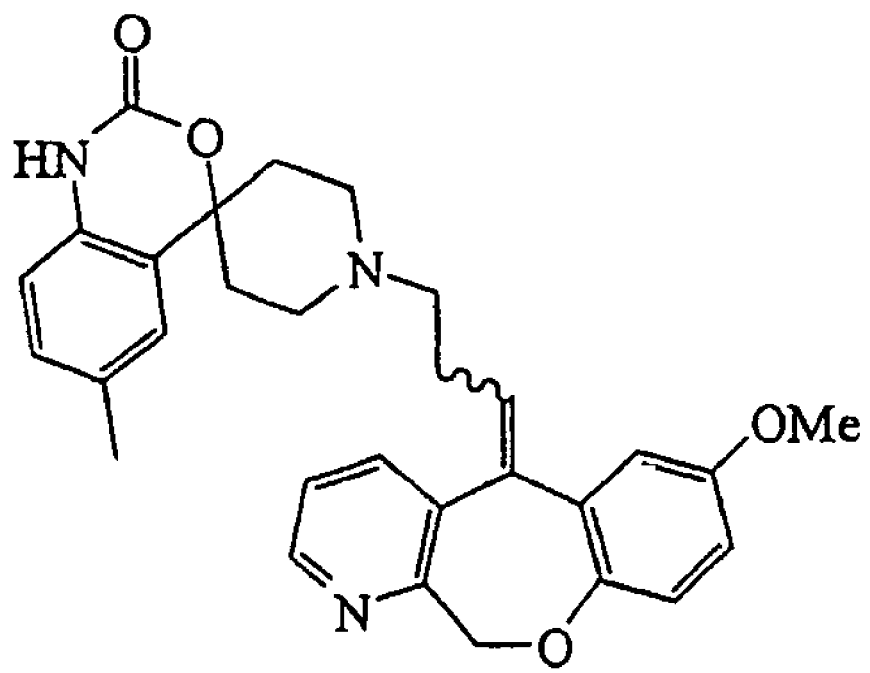

FIG. 5 is a schematic showing the preparation of the compounds represented by Structural Formula (I), wherein Z is represented by Structural Formulas (III) and wherein Ring A and/or Ring B in Z is substituted with —(O)$_u$—(CH$_2$)$_t$—COOR$^{20}$, —(O)$_u$—(CH$_2$)$_t$—OC(O)R$^{20}$, —(O)$_u$—(CH$_2$)$_t$—C(O)—NR$^{21}$R$^{22}$ or —(O)$_u$—(CH$_2$)$_t$—NHC(O)O—R$^{20}$. In FIG. 5, the hydrolysis reaction may be carried out in a mixture of aqueous alkali metal hydroxide solution and a solvent such as methanol, ethanol, tetrahydrofuran (THF) or dioxane at room temperature up to the reflux temperature for the solvent used for 5 minutes to 72 h. The acylation reaction can be carried out using dicyclohexylcarbodiimide (DCC) or (1-ethyl-3-(3-dimethylaminopropyl) carbodiimide (DEC) in a solvent such as tetrahydrofuran (THF), dimethylformamide (DMF) or methylene chloride in the presence of a base such as pyridine or triethylamine (when necessary) at temperatures of 0 to 100° C. for 5 minutes to 72 h.

Figure 7:
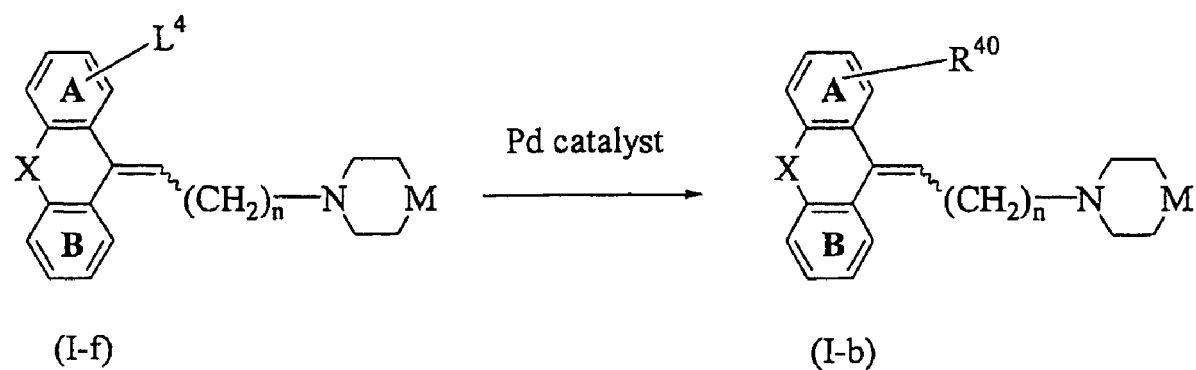
FIG. 7 shows the preparation of compounds represented by Structural Formula (I), where in Z is represented by Structural Formulas (III) and wherein Ring A or Ring B in Z is substituted with $R^{40}$.

FIG. 7 shows the preparation of compounds represented by Structural Formula (I), wherein Z is represented by Structural Formulas (III) and wherein Ring A or Ring B in Z is substituted with $R^{40}$. $L^4$ is a suitable leaving group such as halogen or trifluoromethylsulfonate. In FIG. 7, a palladium coupling reaction such as Stille coupling, Suzuki coupling, Heck reaction, or carboxylation using carbon monoxide may be carried out using a palladium catalyst such as tetrakis(triphenylphosphine)palladium, bis(triphenylphosphine)palladium chloride, and palladium acetate in a solvent such as tetrahydrofuran (THF), 1,4-dioxane, toluene, dimethylformamide (DMF), or dimethylsufoxide (DMSO) in the presence of additive (when necessary) such as triphenylphosphine, 1,1'-bis(diphenylphosphino)ferrocene, triethylamine, sodium bicarbonate, tetraethylammonium chloride, or lithium chloride at room temperature up to the reflux temperature for the solvent used for 5 minutes to 72 h.

Figure 10A:
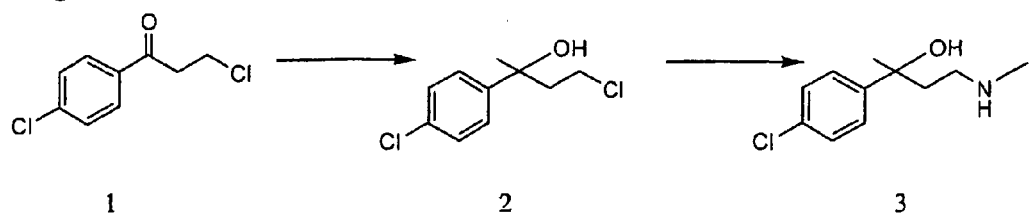
FIG. 10A is a schematic showing the preparation of 3-(4-chlorophenyl)-3-hydroxyl-3-methyl-1-N-methylaminopropane.
Figure 10B:
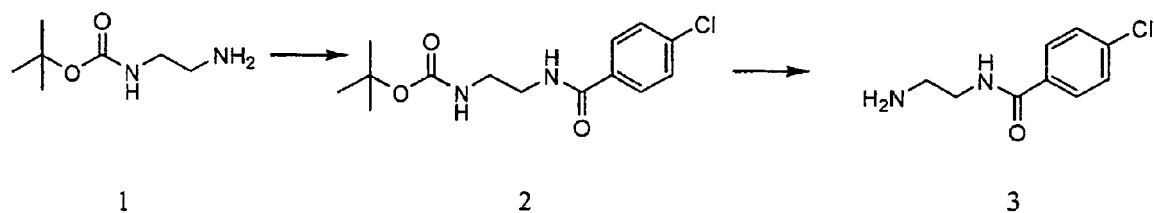
FIG. 10B is a schematic showing the preparation of 1-(4-chlorobenzoyl)-1,3-propylenediamine.
Figure 10C:
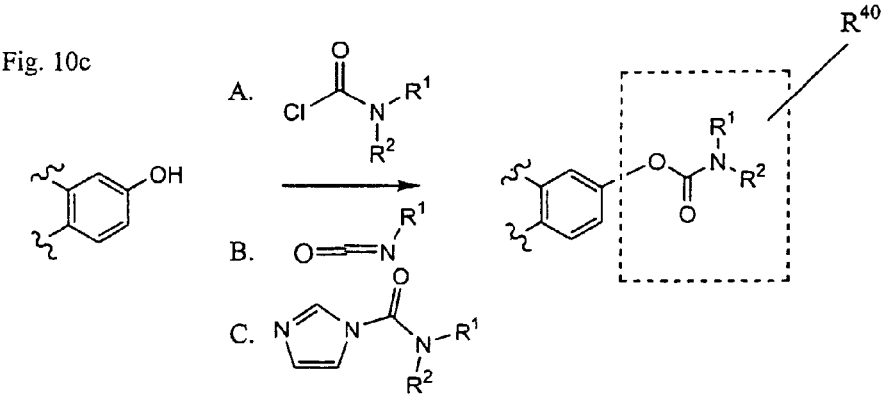
FIG. 10C is a schematic showing three procedures for the preparation of compounds represented by Structural Formulas (I), (VI), (VI), (IX) and (XI) wherein Z is represented by Structural Formula (III) and wherein Ring A or Ring B in Z is substituted with $R^{40}$.

FIG. 10C shows three procedures for the preparation of compounds represented by Structural Formulas (I), (VII), (VIII) and (IX), wherein Z is represented by Structural Formula (III) and wherein Ring A or Ring B in Z is substituted with $R^{40}$. In FIG. 10C, $R^{40}$ is represented by —(O)$_u$—(CH$_2$)$_t$—C(O)—NR$^{21}$R$^{22}$, u is one, t is zero. In FIG. 10C a compound containing a phenol can be reacted with a carbonate equivalent, such as a carbamoyl chloride (method A), an isocyanate (method B) or an acylimidazole (method C), in the presence of a base such as sodium hydroxide, potassium carbonate or sodium carbonate in a solvent such as dimethylformamide or tetrahydrofuran, at a temperature from 0° C. to reflux temperature for a period of about 5 minutes to about 72 hours.

Compounds represented by Structural Formula (I), wherein Z is represented by Structural Formulas (III) or (IV), X is —CO—NR$_c$— and R$_c$ is —(CH$_2$)$_s$—COOR$^{30}$, —(CH$^2$)$_s$—C(O)—NR$^{31}$R$^{32}$ or —(CH$_2$)$_s$—NHC(O)—O—R$^{30}$, can be prepared by suitable modification of the scheme shown in FIGS. 1–5 and 7. One modification utilizes the starting material shown in FIG. 1, wherein X is —CO—NH—. The amide is then alkylated with $L^3$-(CH$_2$)$_s$—COOR$^{30}$, wherein $L^3$ is a suitable leaving group, using the alkylation procedures described above. The remainder of the synthesis is as described in FIGS. 1–5 and 7.

Figure 12:
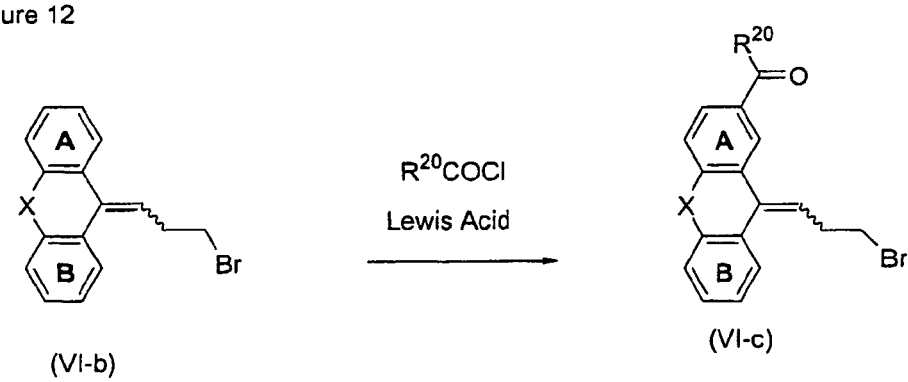
FIG. 12 is a schematic showing preparation of compounds of formula (VI-c).

FIG. 12 shows the preparation of compounds of formula (VI-c). The Friedel-Crafts acylation can be carried out using an acid chloride in the presence of a Lewis acid, such as aluminum trichloride or titanium tetrachloride, in a solvent such as dichloromethane, dichloroethane, nitrobenzene or carbon disulfide. The acylation reaction can be run at a temperature of about room temperature up to the reflux temperature of the chosen solvent, and for a period of about 5 minutes to about 72 hours.

Figure 13:
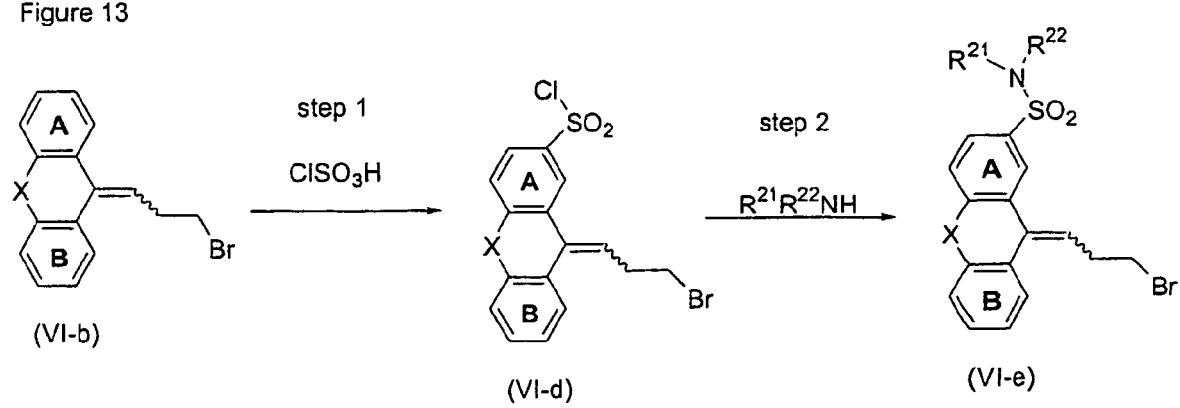
FIG. 13 is a schematic showing preparation of compounds of formula (VI-e).
Figure 16:
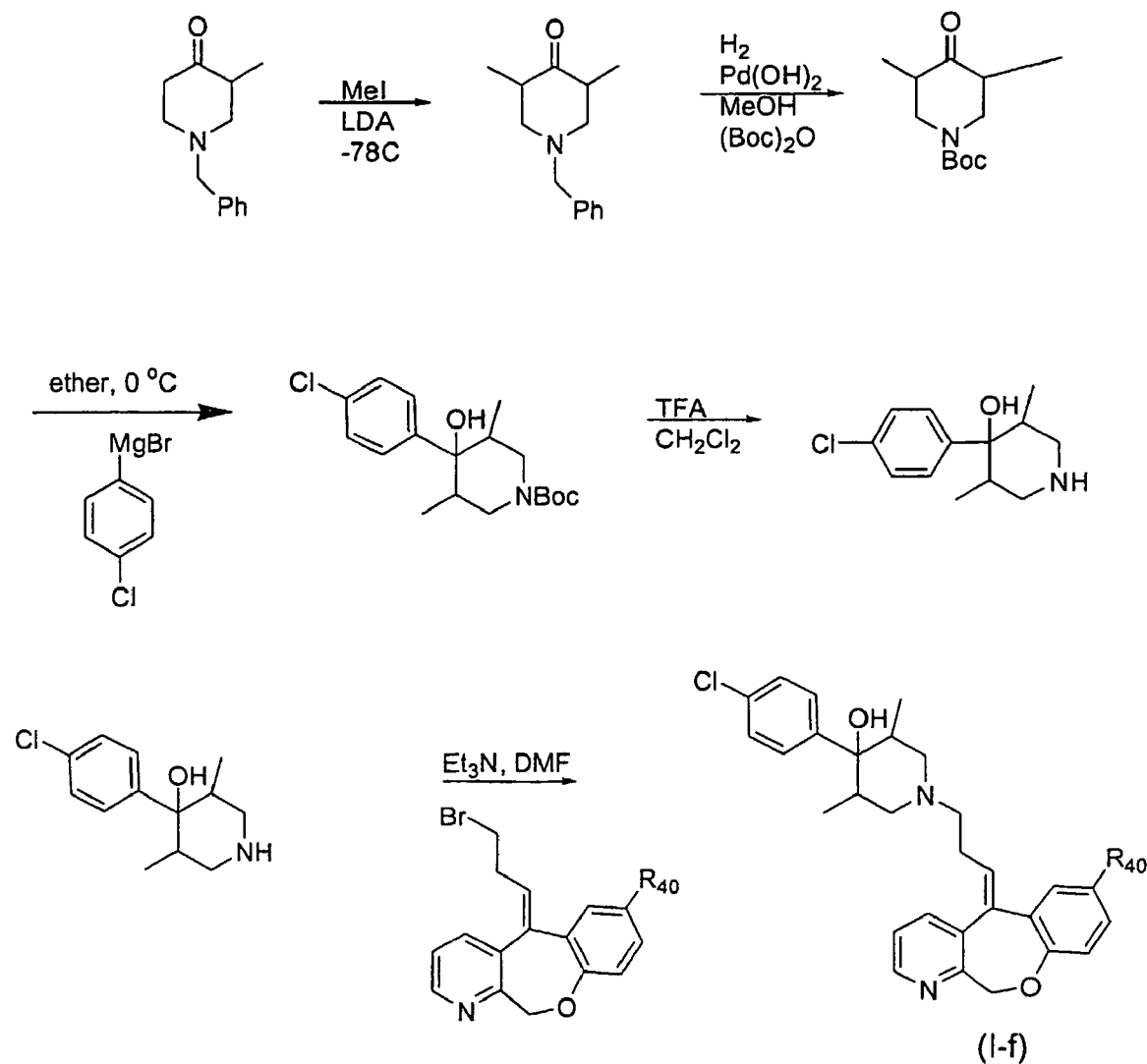
FIG. 16 is a schematic showing a procedure for the preparation of compounds of formula (I-f).
Figure 17:
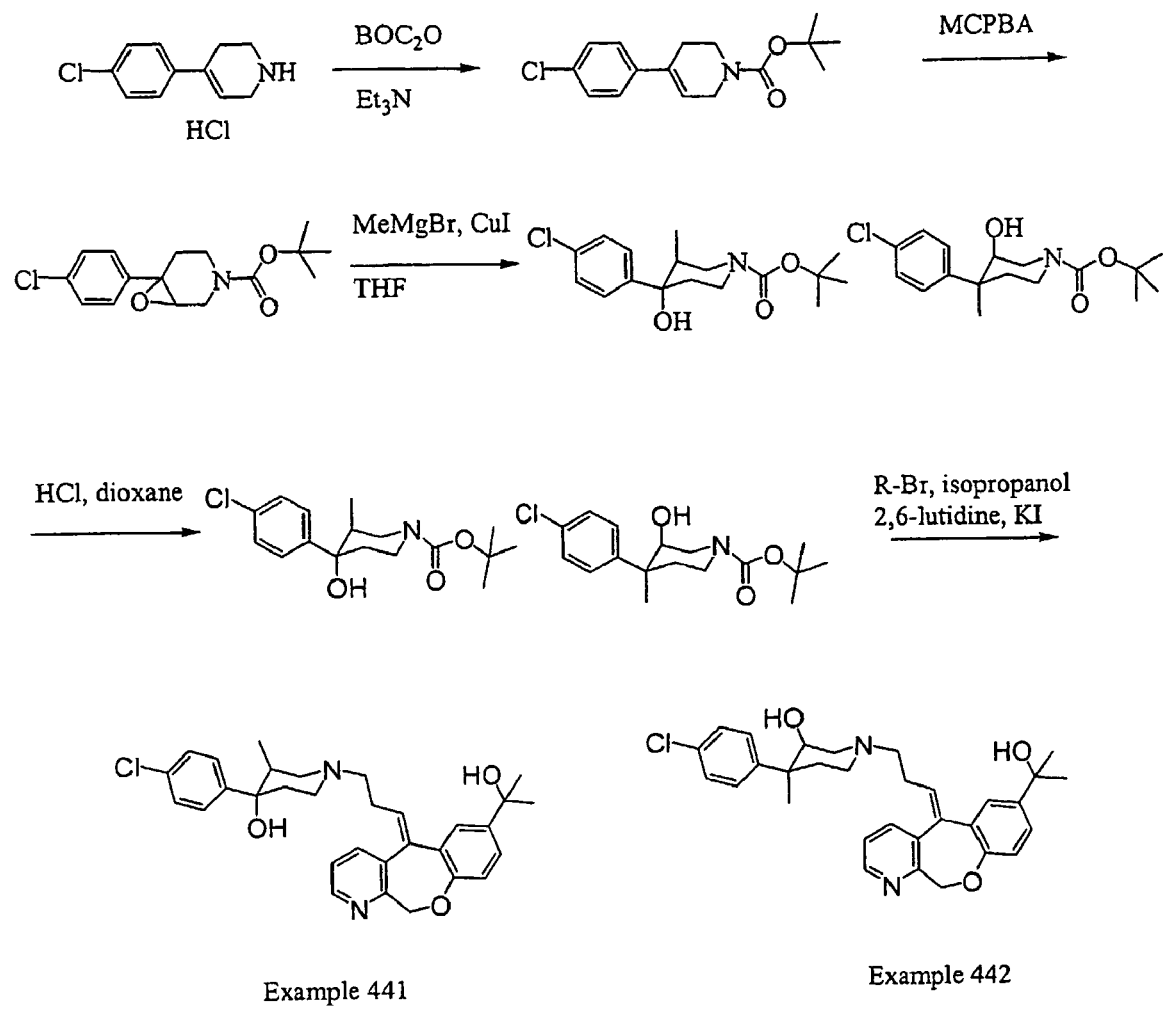
FIG. 17 is a schematic showing a procedure for the preparation of Examples 441 and 442.
Figure 18:
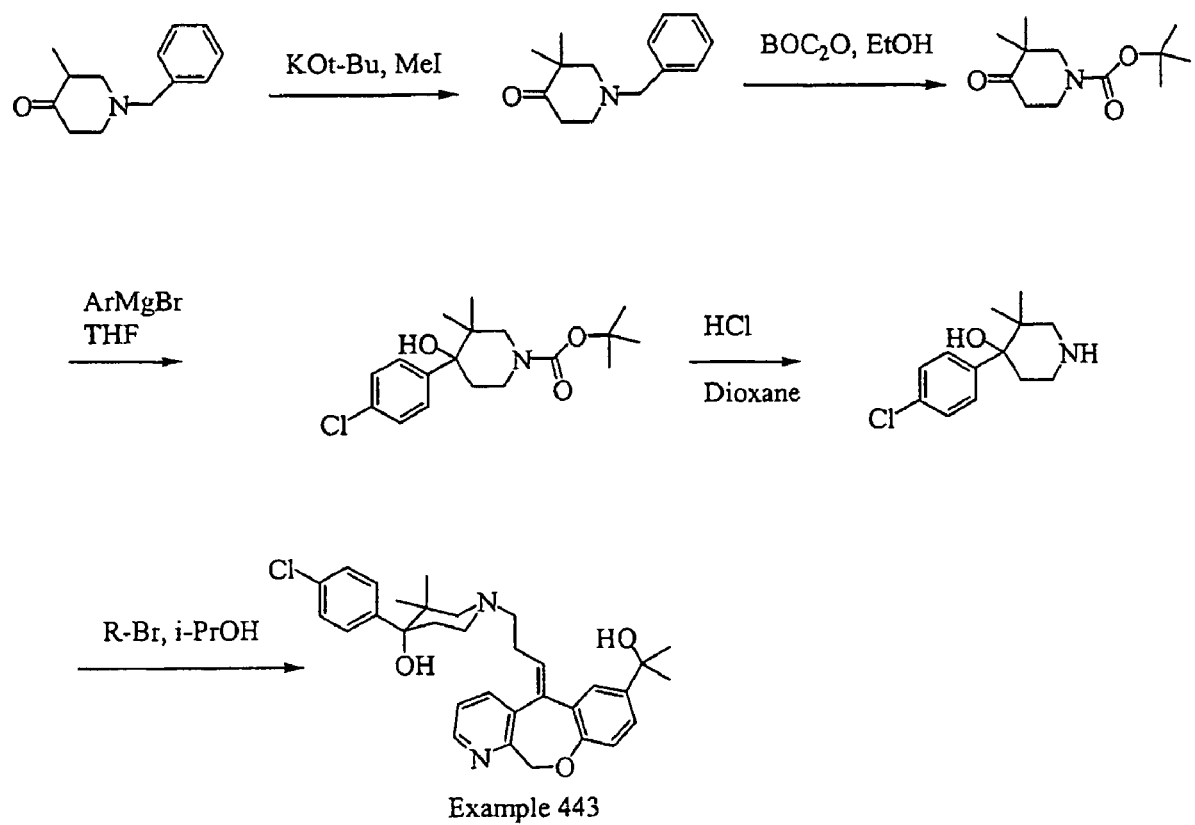
FIG. 18 is a schematic showing a procedure for the preparation of Example 443.
Figure 19:
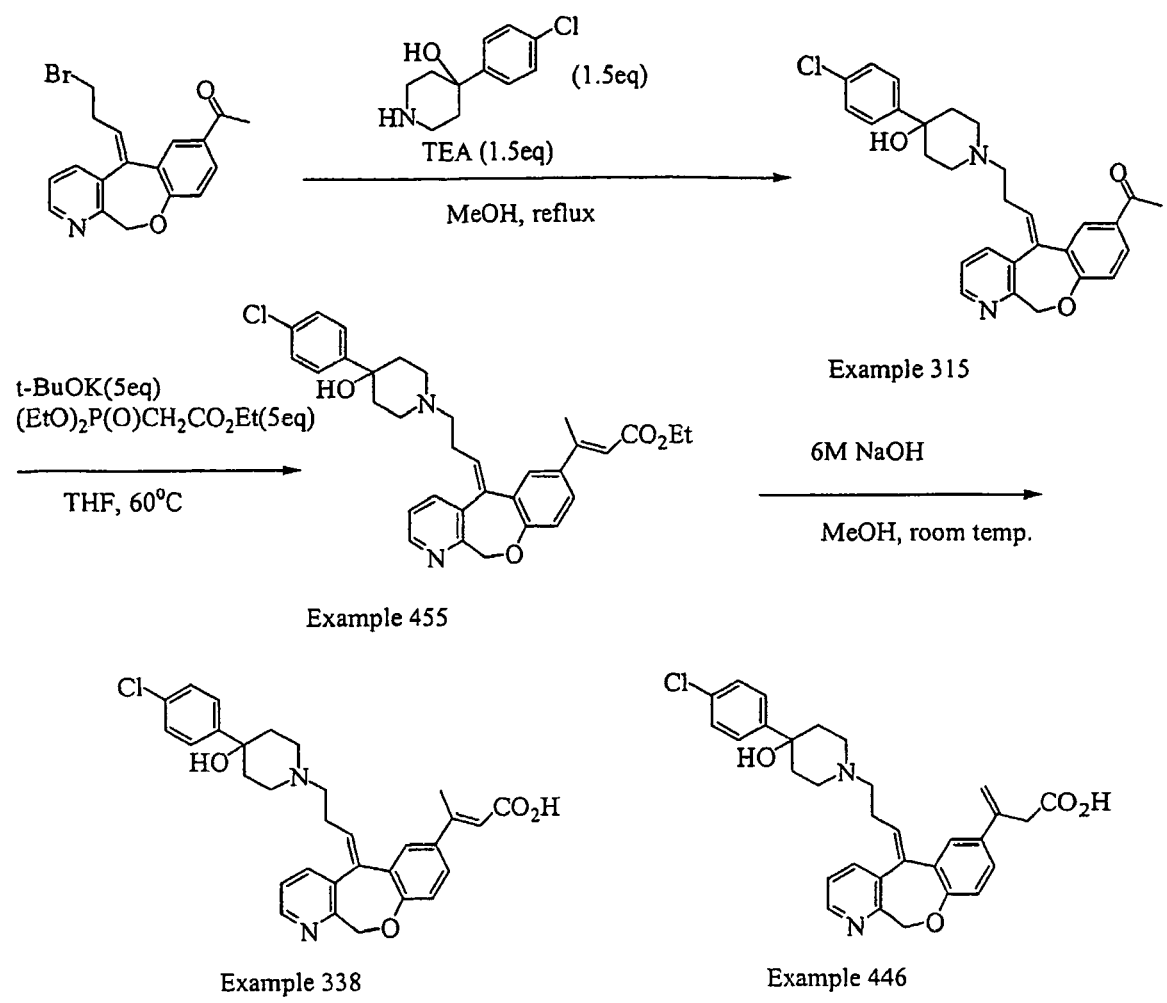
FIG. 19 is a schematic showing a procedure for the preparation of Examples 315, 455, 338 and 446.
Figure 20:
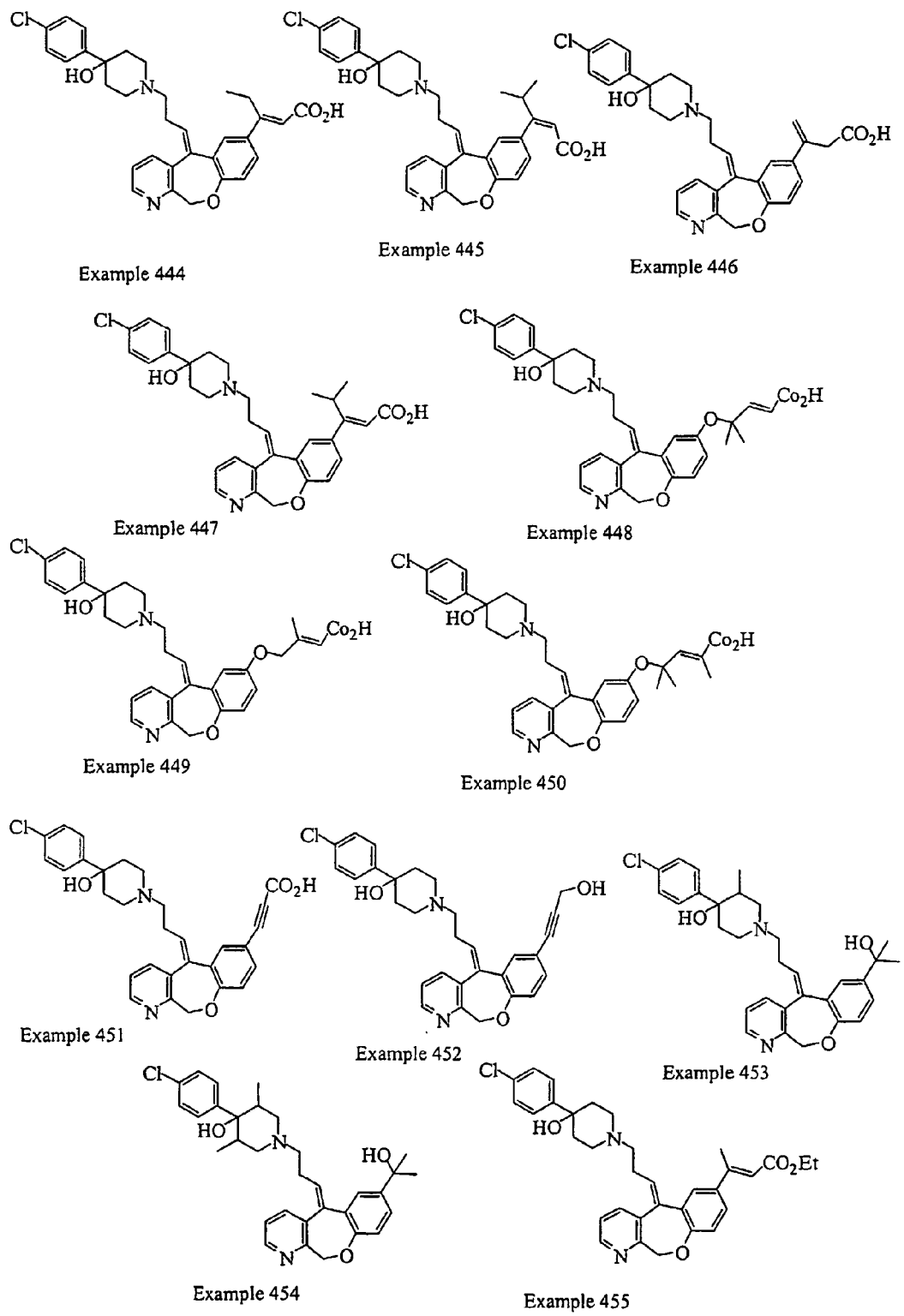

FIG. 13 shows the preparation of compounds of formula (VI-e). In Step 1 of FIG. 13, a chlorosulfonylation can be carried out using chlorosulfonic acid in a solvent, such as dichloromethane, or in the absence of a solvent at a temperature of about 0° C. to about 60° C. for a period of about 5 minutes to about 72 hours. In Step 2 of FIG. 12, a coupling reaction can be carried out using an amine in the presence of a base, such as triethylamine, in a solvent such as dichloromethane, acetone, ethanol, THF or DMF. The reaction can be carried out at a temperature of about room temperature up to the reflux temperature of the selected solvent, and for a period of about 5 minutes to about 72 hours.

Although FIGS. 1–5, 7, 12 and 13 show the preparation of compounds in which Rings A and B are phenyl rings, analogous compounds with heteroaryl groups for Rings A and B can be prepared by using starting materials with heteroaryl groups in the corresponding positions. These starting materials can be prepared according to methods disclosed in JP 61/152673, U.S. Pat. No. 5,089,496, WO 89/10369, WO 92/20681 and WO 93/02081.

The invention is illustrated by the following examples which are not intended to be limiting in any way.

EXEMPLIFICATION

Example 1

4-(4-Chlorophenyl)-1-[3-(10,11-dihydro-5H-dibenzo [a,d]cycloheptene-5-ylidene)propyl]piperidin-4-ol To a solution of 5-(3-bromopropylidene)-10,11-dihydro-5H-dibenzo[a,d]cycloheptene (described in JP 48-030064) (200 mg) in DMF (10 ml) were added 4-(4-chlorophenyl)-4-hydroxypiperidine (230 mg), potassium carbonate (360 mg), and potassium iodide (50 mg). The mixture was stirred at 70° C. for 24 hours. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:1) to give the titled compound (250 mg). $^1$H-NMR (CDCl$_3$) d: 1.65–2.11(5H,m), 2.32–3.10(8H,m), 3.22–3.67(4H,m), 5.87 (1H,t), 7.03–7.44(12H,m). MS m/z: 444(M+1).

Example 2

4-(4-Chlorophenyl)-1-[3-(6,11-dihydrodibenz[b,e] oxepin-11-ylidene)propyl]piperidin-4-ol The titled compound was prepared by following the procedure of Example 1, but replacing 5-(3-bromopropylidene)-10,11-dihydro-5H-dibenzo[a,d]cycloheptene with 11-(3-bromopropylidene)-6,11-dihydrodibenz[b,e]oxepine. $^1$H-NMR (CDCl$_3$) d: 1.61–2.16(5H,m), 2.37–2.80(8H,m), 5.22(2H,brs), 5.70(0.6×1H,t), 6.03(0.4×1H,t), 6.73–6.90(2H,m), 7.09–7.45(10H,m). MS m/z: 446(M+1).

Example 3

Membrane Preparations for Chemokine Binding and Binding Assays

Membranes were prepared from THP-1 cells (ATCC #TIB202). Cells were harvested by centrifugation, washed twice with PBS (phosphate-buffered saline), and the cell pellets were frozen at −70 to −85° C. The frozen pellet was thawed in ice-cold lysis buffer consisting of 5 mM HEPES (N-2-hydroxyethylpiperazine-N'-2-ethane-sulfonic acid) pH 7.5, 2 mM EDTA (ethylenediaminetetraacetic acid), 5 µg/ml each aprotinin, leupeptin, and chymostatin (protease inhibitors), and 100 µg/ml PMSF (phenyl methane sulfonyl fluoride—also a protease inhibitor), at a concentration of 1 to $5 \times 10^7$ cells/ml. This procedure results in cell lysis. The suspension was mixed well to resuspend all of the frozen cell pellet. Nuclei and cell debris were removed by centrifugation of 400×g for 10 minutes at 4° C. The supernatant was transferred to a fresh tube and the membrane fragments were collected by centrifugation at 25,000×g for 30 minutes at 4° C. The supernatant was aspirated and the pellet was resuspended in freezing buffer consisting of 10 mM HEPES pH 7.5, 300 mM sucrose, 1 µg/ml each aprotinin, leupeptin, and chymostatin, and 10 µg/ml PMSF (approximately 0.1 ml per each $10^8$ cells). All clumps were resolved using a minihomogenizer, and the total protein concentration was determined using a protein assay kit (Bio-Rad, Hercules, Calif., cat #500-0002). The membrane solution was then aliquoted and frozen at −70 to −85° C. until needed.

Binding Assays utilized the membranes described above. Membrane protein (2 to 20 µg total membrane protein) was incubated with 0.1 to 0.2 nM $^{125}$I-labeled RANTES or MIP-1α with or without unlabeled competitor (RANTES or MIP-1α) or various concentrations of compounds. The binding reactions were performed in 60 to 100 µl of a binding buffer consisting of 10 mM HEPES pH 7.2, 1 mM $CaCl_2$, 5 mM $MgCl_2$, and 0.5% BSA (bovine serum albumin), for 60 min at room temperature. The binding reactions were terminated by harvesting the membranes by rapid filtration through glass fiber filters (GF/B or GF/C, Packard) which were presoaked in 0.3% polyethyleneimine. The filters were rinsed with approximately 600 µl of binding buffer containing 0.5 M NaCl, dried, and the amount of bound radioactivity was determined by scintillation counting in a Topcount beta-plate counter.

The activities of test compounds are reported in the Table below as $IC_{50}$ values or the inhibitor concentration required for 50% inhibition of specific binding in receptor binding assays using $^{125}$I-RANTES or $^{125}$I-MIP-1α as ligand and THP-1 cell membranes. Specific binding is defined as the total binding minus the non-specific binding; non-specific binding is the amount of cpm still detected in the presence of excess unlabeled Rantes or MIP-1α.

TABLE

BIOLOGICAL DATA

| Example | IC50 (µM) |
|---|---|
| 1 | <1 |
| 2 | <1 |
| 8 | <1 |
| 12 | <1 |
| 17 | <10 |
| 18 | <1 |
| 19 | <1 |
| 21 | <1 |
| 22 | <1 |
| 23 | <1 |
| 24 | <10 |
| 25 | <1 |
| 26 | <1 |
| 27 | <1 |
| 28 | <1 |
| 29 | <1 |
| 30 | <1 |
| 31 | <1 |
| 32 | <1 |
| 33 | <1 |
| 34 | <1 |
| 35 | <1 |
| 36 | <1 |
| 38 | <1 |
| 39 | <10 |
| 40 | <1 |
| 41 | <1 |
| 42 | <1 |
| 43 | <10 |
| 44 | <1 |
| 45 | <1 |
| 46 | <1 |
| 47 | <1 |
| 48 | <1 |
| 49 | <1 |
| 51 | <1 |
| 52 | <1 |
| 53 | <1 |
| 54 | <1 |
| 55 | <1 |
| 56 | <1 |
| 57 | <10 |
| 59 | <1 |
| 60 | <1 |
| 61 | <10 |
| 62 | <10 |
| 63 | <10 |
| 64 | <1 |
| 65 | <1 |
| 66 | <1000 |
| 67 | <1 |
| 68 | <10 |
| 69 | <1 |
| 71 | <1 |
| 72 | <10 |
| 73 | <10 |
| 74 | <1000 |
| 75 | <10 |
| 76 | <10 |
| 77 | <1 |
| 78 | <1 |
| 79 | <1 |
| 83 | <1000 |
| 85 | <1 |
| 86 | >10 |
| 89 | >10 |
| 90 | <1 |
| 91 | <1 |
| 111 | <1 |
| 114 | <1 |
| 117 | <1 |
| 118 | <1 |
| 120 | <1 |
| 122 | <1 |
| 123 | <1 |
| 128 | <1 |

TABLE-continued

BIOLOGICAL DATA

| Example | IC50 (μM) |
|---|---|
| 130 | <1 |
| 131 | <1 |
| 132 | <1 |
| 133 | <1 |
| 134 | <1 |
| 135 | <1 |
| 138 | <1 |
| 139 | <1 |
| 140 | >10 |
| 141 | <1 |
| 142 | <10 |
| 143 | <1 |
| 144 | <1 |
| 145 | 10 |
| 146 | >10 |
| 147 | <10 |
| 148 | <10 |
| 149 | <1000 |
| 150 | <10 |
| 151 | <1 |
| 152 | <1 |
| 153 | <1 |
| 154 | <1 |
| 155 | <1 |
| 158 | <1 |
| 159 | <1 |
| 160 | <1 |
| 161 | <10 |
| 162 | <1 |
| 163 | <1 |
| 166 | <10 |
| 167 | >1 |
| 168 | 1 |
| 172 | <1 |
| 173 | <1 |
| 174 | <1 |
| 175 | <1 |
| 176 | <1 |
| 178 | <1 |
| 180 | <1 |
| 181 | <1 |
| 182 | <1 |
| 183 | <1 |
| 184 | <10 |
| 185 | <1000 |
| 186 | <1 |
| 187 | <1 |
| 188 | >10 |
| 190 | >10 |
| 191 | >10 |
| 192 | >10 |
| 193 | <1 |
| 194 | <1 |
| 195 | <10 |
| 197 | <1 |
| 198 | <1 |
| 199 | <1 |
| 200 | <1 |
| 201 | <1 |
| 203 | <1 |
| 204 | <1 |
| 205 | <1 |
| 211 | <1 |
| 212 | <1 |
| 215 | <1 |
| 216 | <1 |
| 218 | <1 |
| 242 | <1 |
| 248 | 10 |
| 249 | <1 |
| 262 | <1 |
| 263 | <1 |
| 264 | <1 |
| 265 | <1 |

TABLE-continued

BIOLOGICAL DATA

| Example | IC50 (μM) |
|---|---|
| 266 | <1 |
| 267 | <1 |
| 268 | <1 |
| 269 | <1 |
| 270 | <1 |
| 271 | <1 |
| 272 | <1 |
| 273 | <1 |
| 277 | <1 |
| 278 | <1 |
| 279 | <1 |
| 280 | <1 |
| 281 | <1 |
| 282 | <1 |
| 283 | <1 |
| 284 | <1 |
| 285 | <1 |
| 286 | <1 |
| 287 | <1 |
| 288 | <1 |
| 289 | <1 |
| 290 | <1 |
| 291 | <1 |
| 292 | <1 |
| 306 | <1 |
| 422 | <1 |
| 423 | <1 |
| 424 | <1 |
| 425 | <1 |
| 426 | <1 |
| 427 | <1 |
| 428 | <1 |
| 429 | <1 |
| 430 | <1 |
| 431 | <1 |
| 432 | <1 |
| 456 | <1 |
| 457 | <1 |
| 458 | <10 |
| 459 | <10 |
| 460 | <1 |
| 461 | <10 |
| 462 | <10 |
| 463 | <10 |
| 464 | <1 |
| 465 | <1 |
| 466 | <50 |
| 467 | <1 |
| 468 | <1 |
| 469 | <1 |
| 470 | <1 |
| 471 | <1 |
| 472 | <1 |
| 473 | <1 |
| 474 | <1 |
| 475 | <1 |
| 476 | <1 |
| 477 | <10 |
| 478 | <10 |
| 479 | <1 |
| 480 | <1 |
| 481 | <1 |
| 482 | <1 |
| 483-1 | <1 |
| 483-2 | <10 |
| 484 | <1 |
| 485 | <1 |
| 486 | <1 |
| 487 | <1 |
| 488 | <1 |
| 489 | <10 |
| 490 | <1 |
| 491 | <1 |
| 492 | <10 |

TABLE-continued

BIOLOGICAL DATA

| Example | IC50 (μM) |
|---|---|
| 493 | <10 |
| 494 | <1 |
| 495 | <1 |
| 496 | <10 |
| 497 | <10 |
| 498 | <10 |
| 499 | <10 |
| 500 | <10 |
| 501 | <10 |
| 502 | <1 |
| 503 | <1 |
| 504 | <1 |
| 505 | <1 |
| 506 | <1 |
| 507 | <1 |
| 508 | <1 |
| 509 | <1 |
| 510 | <1 |
| 511 | <1 |
| 512 | <1 |
| 513 | <1 |
| 514 | <1 |
| 515 | <1 |
| 516 | <1 |
| 517 | <1 |
| 518 | <1 |
| 519 | <1 |
| 520 | <1 |
| 521 | <1 |
| 522 | <1 |
| 523 | <1 |
| 524 | <1 |
| 525 | <20 |
| 526 | <1 |
| 527 | <1 |
| 528 | <10 |
| 529 | <20 |
| 530 | <20 |
| 531 | <1 |
| 532 | <2 |
| 533 | <10 |
| 534 | <1 |
| 535 | <10 |
| 536 | <1 |
| 537 | <1 |
| 538 | <10 |
| 539 | <10 |
| 540 | <10 |
| 541 | <10 |
| 542 | <10 |
| 543 | <10 |
| 544 | <10 |
| 545 | <10 |
| 546 | <1 |
| 547 | <1 |
| 548 | <10 |
| 549 | <1 |
| 550 | <1 |
| 551 | <1 |
| 552 | <1 |
| 553 | <1 |
| 554 | <1 |
| 555 | <1 |
| 556 | <1 |
| 557 | <1 |
| 558 | <10 |
| 559 | <1 |
| 560 | <10 |
| 561 | <10 |
| 562 | <10 |
| 563 | <10 |
| 564 | <10 |
| 565 | <10 |
| 566 | <20 |
| 567 | <1 |
| 568 | <1 |
| 569 | <1 |
| 570 | <10 |
| 571 | <10 |

Example 8

4-(4-Chlorophenyl) 1-[3-(6,11-dihydro-dibenz[b,e]thiepin-11-ylidene)propyl]piperidin-4-ol Step 1

11-(3-Bromopropylidene)-6,11-dihydrodibenz[b,e]thiepine was prepared by following the procedure of example 45, step 1 and 2, but replacing 5,11-dihydro-7-methoxypyrido[2,3-C][1]benzoxepin-5-one with 6,11-dihydrodibenz[b,e]thiepin-11-one.

$^1$H-NMR (CDCl$_3$) δ: 2.50–2.64(2H,m), 3.36–3.47(3H,m), 4.99(1H,d), 5.94(1H,t), 6.98–7.31(8H,m).

Step 2

The titled compound was prepared by following the procedure of example 45, step 3 but replacing 5-(3-bromopropylidene)-10,11-dihydro-5H-dibenzo[a,d]cycloheptene with the product of step 1.

$^1$H-NMR (CDCl$_3$) δ: 1.65–1.80(3H,m), 1.95–2.70(10H,m), 3.35(1H,d), 4.98(1H,d), 5.96(1H,t), 7.09–7.43(12H,m). MS m/z: 462(M+1)

Example 12

1-[3-(5-Benzyl-6,11-dihydro-6-oxo-5H-dibenz[b,e]azepin-11-ylidene)propyl]-4-(4-chlorophenyl)-piperidin-4-ol To a solution 4-(4-chlorophenyl)-1-[3-(6,11-dihydro-6-oxo-5H-dibenz[b,e]azepin-11-ylidene)propyl]piperidin-4-ol hydrochloride (Example 39) (300 mg) in DMF (5 ml) were added sodium hydride (60% in oil, 200 mg), benzyl bromide (0.15 ml) and the mixture was stirred at room temperature for 1 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate to give the titled compound (180 mg).

$^1$H-NMR (CDCl$_3$) δ: 1.62–1.67(2H,m), 1.99–2.20(3H,m), 2.33–2.65(8H,m), 5.10(1H,d), 5.75(1H,d), 5.94(1H,t), 7.11–7.42(16H,m), 7.91(1H,dd). MS m/z: 549(M+1)

Example 17

1-[3-(5-Carboxymethyl-6,11-dihydro-6-oxo-5H-dibenz[b,e]azepin-11-ylidene)propyl]-4-(4-chlorophenyl)-piperidin-4-ol 4-(4-Chlorophenyl)-1-[3-(6,11-dihydro-5-ethoxycarbonylmethyl-6-oxo-5H-dibenz[b,e]azepin-11-ylidene)propyl]piperidin-4-ol (Example 18) (1.0 g) was solved in 1M hydrogen chloride in diethyl ether and stirred at room temperature for 24 hours. Aqueous sodium hydroxide and ethyl acetate were added to the reaction mixture, the aqueous layer was separated and neutralized with dilute hydrochloric acid. The precipitation was filtered to give the titled compound (250 mg).

$^1$H-NMR (DMSO-$d_6$) δ: 1.44–1.61(2H,m), 2.07–2.17(1H,m), 2.35–3.01(9H,m), 4.28(1H,d), 4.59(1H,d), 5.83(1H,t), 7.18–7.71(12H,m). MS m/z: 517(M+1)

Example 18

4-(4-Chlorophenyl)-1-[3-(6,11-dihydro-5-ethoxycarbonylmethyl-6-oxo-5H-dibenz[b,e]azepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-5-ethoxycarbonylmethyl-6-oxo-5H-dibenz[b,e]azepine.

$^1$H-NMR (CDCl$_3$) δ: 1.30(3H,t), 1.64–1.69(2H,m), 1.97–2.10(3H,m), 2.38–2.71(8H,m), 4.27(2H,q), 4.32(1H,d), 4.84(1H,d), 5.88(1H,t), 7.16–7.45(11H,m), 7.88(1H,dd). MS m/z: 545(M+1)

Example 19

4-(4-Chlorophenyl)-1-[3-(6,11-dihydro-5-methyl-6-oxo-5H-dibenz[b,e]azepin-11-ylidene)propyl]piperidin-4-ol The titled compound was prepared by following the procedure of Example 1, but replacing 5-(3-bromopropylidene)-10,11-dihydro-5H-dibenzo[a,d]cycloheptene with 11-(3-bromopropylidene)-5-methyl-6-oxo-5H-dibenz[b,e]azepin.

$^1$H-NMR (CDCl$_3$) δ: 1.58–2.06(5H,m), 2.39–2.75(8H,m), 3.53(3H,s), 5.84(1H,t), 7.10–7.44(11H,m), 7.85–7.89(1H,m). MS m/z: 473(M+1).

Example 21

4-(4-Chlorophenyl)-1-[3-(5H-dibenzo[a,d]cyclohep-tene-5-ylidene)propyl]piperidin-4-ol The titled compound was prepared by following the procedure of example 1, but replacing 5-(3-bromopropylidene)-10,11-dihydro-5H-dibenzo[a,d]cycloheptene with 5-(3-bromopropylidene)-5H-dibenzo[a,d]cycloheptene.

$^1$H-NMR (CDCl$_3$) δ: 1.58–1.63(2H,m), 2.00–2.05(2H,m), 2.26–2.46(6H,m), 2.62–2.66 (2H,m), 5.55(1H,t), 6.85 (2H,s), 7.24–7.40(12H,m). MS m/z: 442 (M+1).

Example 22

4-(4-Chlorophenyl)-1-[3-(6,11-dihydro-2-methoxycarbonyldibenz[b,e]oxepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-6,11-dihydro-2-methoxy-carbonyldibenz[b,e]oxepine.

$^1$H-NMR (CDCl$_3$) δ: 1.65–1.70(2H,m), 2.01–2.13(3H,m), 2.41–2.80(7H,m), 3.85(3H, s), 5.40(2H,brs), 5.73(0.6×1H,t), 6.09(0.4×1H,t), 6.76(0.6×1H,d), 6.82(0.4×1H,d), 7.21–7.43(8H,m), 7.73(1H,dd), 7.87(0.6×1H,d), 7.97(0.4×1H,d). MS m/z: 504 (M+1).

Example 23

1-[3-(2-Butoxycarbonyl-6,11-dihydrodibenz[b,e]oxepin-11-ylidene)propyl]-4-(4-chlorophenyl)piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-2-butoxy-6,11-dihydrodibenz[b,e]oxepine.

$^1$H-NMR (CDCl$_3$) δ: 0.96(3H,t), 1.53(2H,q), 1.70–1.77(3H,m), 2.02–2.14(3H,m), 2.39–2.78(5H,m), 4.27(2H,t), 5.27(2H,brs), 5.75(0.8×1H,t), 6.10(0.2×1H,t), 6.78(1H,d), 7.27–7.43(8H,m), 7.76(1H,dd), 7.89(0.8×1H,d), 7.98(0.2×1H,d). MS m/z: 546 (M+1).

Example 24

1-[3-(2-Carboxyl-6,11-dihydrodibenz[b,e]oxepin-11-ylidene)propyl]-4-(4-chlorophenyl)piperidin-4-ol To a solution of 4-(4-Chlorophenyl)-1-[3-(6,11-dihydro-2-methoxycarbonyldibenz[b,e]oxepin-11-ylidene)propyl]piperidin-4-ol (Example 22) (100 mg) in ethanol (3 ml) were added 15% sodium hydroxide aqueous solution (0.6 ml) and the mixture was heated to reflux for 12 hours. The solvent was distilled off under reduced pressure. Water and ethyl acetate were added to the reaction mixture, the aqueous layer was separated and neutralized with dilute hydrochloric acid. The precipitation was filtered to give the titled compound (80 mg).

$^1$H-NMR (CD$_3$OD) δ: 1.73–1.79(2H,m), 2.14–2.19(2H,m), 2.80–2.93(3H,m), 3.02–3.11 (3H,m), 3.24–3.29(2H,m), 5.25(2H,brs), 5.61(0.7×1H,t), 6.05(0.3×1H,t), 6.72(1H,d), 7.22–7.40(8H,m), 7.52–7.65(1H,m), 7.75(0.7×1H,d), 7.80 (0.3×1H,d). MS m/z: 490 (M+1).

Example 25

4-(4-Chlorophenyl)-1-[3-(6,11-dihydro-2-dimethylaminocarbonyldibenz[b,e]oxepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-2-dimethylaminocarbonyl-6,11-dihydrodibenz[b,e]oxepine.

$^1$H-NMR (CDCl$_3$) δ: 1.62–1.67(2H,m), 2.00–2.12(2H,m), 2.37–2.47(8H,m), 2.89(6H, s), 5.25(2H,brs), 5.68(0.7×1H,t), 6.03 (0.3×1H,t), 6.71(0.3×1H,d), 6.78(0.7×1H,d), 7.13–7.40 (10H,m). MS m/z: 517 (M+1).

Example 26

4-(4-Chlorophenyl)-1-[3-(6,11-dihydro-2-hydroxymethyldibenz[b,e]oxepin-11-ylidene)propyl]piperidin-4-ol To a solution of (4-chlorophenyl)-1-[3-(6,11-dihydromethoxycarbonyldibenz[b,e]oxepin-11-ylidene)propyl]piperidin-4-ol (110 mg) in THF (8 ml) were added lithium aluminum hydride (1.0M, 0.42 ml) dropwise at 0° C., and the mixture was stirred at room temperature for 1 hour. Aqueous sodium hydroxide (1M) was added to the reaction mixture to stir for 30 minutes, then ethyl acetate and brine was added to the mixture. The organic layer was separated and washed with saturated aqueous sodium chloride, and dried with magnesium sulfate. The solvent was distilled off under reduced pressure. The residue was purified by silica gel chromatography eluting with dichloromethane-methanol (10:1) to give the titled compound (90 mg).

$^1$H-NMR (CDCl$_3$) δ: 1.61–1.66(2H,m), 1.98–2.03(2H, m), 2.39–2.48(3H,m), 2.57–2.79 (6H,m), 4.52(2H,s), 5.20 (2H,brs), 5.66(0.8×1H,t), 6.01(0.2×1H,t), 6.67(0.2×1H,d), 6.79(0.8×1H,d), 7.06(1H,dd), 7.15–7.37(9H,m). MS m/z: 476 (M+1).

Example 27

4-(4-Chlorophenyl)-1-[3-(6,11-dihydro-2-(1-hydroxy-1-methyl)ethyldibenz[b,e]oxepin-11-ylidene)propyl]piperidin-4-ol To a solution of 4-(4-chlorophenyl)-1-[3-(6,11-dihydro-2-methoxycarbonyldibenz[b,e]oxepin-11-ylidene)propyl]piperidin-4-ol (60 mg) in THF (6 ml) were added methylmagnesium chloride (3.0M, 0.16 ml) dropwise at 0° C., and the mixture was stirred at room temperature for 2 hour, the reaction mixture was quenched by saturated ammonium aqueous, then ethyl acetate and water was added to the mixture. The organic layer was separated and washed with saturated aqueous sodium chloride, and dried with magnesium sulfate. The solvent was distilled off under reduced pressure. The residue was purified by silica gel chromatography eluting with ethyl acetate-methanol (95:5) to give the titled compound (20 mg).

$^1$H-NMR (CDCl$_3$) δ: 1.54(0.7×6H,s), 1.62(0.3×6H,s), 1.63–1.70(2H,m), 2.03–2.10(3H,m), 2.38–2.49 (3H,m), 2.62–2.82(4H,m), 5.17(2H,brs), 5.68(0.7×1H,t), 6.05(0.3× 1H,t), 6.75(0.3×1H,d), 6.83(0.7×1H,d), 7.18–7.43(10H,m). MS m/z: 504 (M+1).

Example 28

4-(4-Chlorophenyl)-1-[3-(2-cyano-6,11-dihydrodibenz[b,e]oxepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-2-cyano-6,11-dihydrodibenz[b,e]oxepine.

$^1$H-NMR (CDCl$_3$) δ: 1.67–1.72(2H,m), 2.02–2.13(2H, m), 2.37–2.77 (8H,m), 5.35 (2H,brs), 5.75(0.7×1H,t), 6.07 (0.3×1H,t), 6.78(0.3×1H,d), 6.82(0.7×1H,d), 7.25–7.51(10H,m). MS m/z: 471 (M+1).

Example 29

1-[3-(2-Aminomethyl-6,11-dihydrodibenz[b,e]oxepin-11-ylidene)propyl]-4-(4-chlorophenyl)piperidin-4-ol To a solution of 4-(4-chlorophenyl)-1-[3-(2-cyano-6,11-dihydrodibenz[b,e]oxepin-11-ylidene)propyl]piperidin-4-ol (380 mg) in EtOH (20 ml) were added Raney nickel (50% slurry in water, 60 mg), and the mixture was hydrogenated at 15 psi for 2 hours. The mixture was filtered through the celite and distilled off under reduced pressure. The residue was purified by silica gel chromatography eluting with dichloromethane-methanol-aqueous ammonium (95:5:1) to give the titled compound (130 mg).

$^1$H-NMR (CDCl$_3$) δ: 1.76–1.94(3H,m), 2.18–2.34(2H, m), 2.85–3.10(8H,m), 3.88(2H,s), 5.30(2H,brs), 5.59(1H,t), 6.78(1H,d), 7.13–7.40(10H,m). MS m/z: 475 (M+1).

Example 30

4-(4-Chlorophenyl)-1-[3-(6,11-dihydro-2-nitrodibenz[b,e]oxepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-6,11-dihydro-2-nitorodibenz[b,e]oxepine.

$^1$H-NMR (CDCl$_3$) δ: 1.62–1.67(2H,m), 1.80–2.12(3H, m), 2.28–2.78(8H,m), 5.05(0.3×2H,brs), 5.40(0.7×2H,brs), 5.90(0.7×1H,t), 6.17(0.3×1H,t), 6.82(0.3×1H,d), 6.92(0.7× 1H), 7.28–7.41(8H,m), 7.82(1H,dd), 8.15(0.7×1H,d), 8.22 (0.3×1H,d). MS m/z: 491 (M+1).

Example 31

1-[3-(2-Amino-6,11-dihydrodibenz[b,e]oxepin-11-ylidene)propyl]-4-(4-chlorophenyl)piperidin-4-ol To a solution of 4-(4-chlorophenyl)-1-[3-(6,11-dihydro-2-nitrodibenz[b,e]oxepin-11-ylidene)propyl]piperidin-4-ol (120 mg) in EtOH (15 ml) were added tin (II) chloride (190 mg), and the mixture was heated to reflux for 1 hour. The solvent was distilled off under reduced pressure. To the residue was added ethyl acetate and sodium aqueous to neutralize. The organic layer was separated and washed with saturated aqueous sodium chloride, and dried with magnesium sulfate. The solvent was distilled off under reduced pressure. The residue was purified by silica gel chromatography eluting with dichloromethane-methanol (95:5) to give the titled compound (70 mg).

$^1$H-NMR (DMSO-d$_6$) δ: 1.54–1.60(2H,m), 1.85–2.00(2H,m), 2.30–2.80(8H,m), 3.88(2H,s), 5.07(2H, brs), 5.66(1H,t), 6.41–6.46(2H,m), 6.59(1H,d), 7.24–7.49 (8H,m). MS m/z: 461 (M+1).

Example 32

4-(4-Chlorophenyl)-1-[3-(6,11-dihydro-2-hydroxydibenz[b,e]oxepin-11-ylidene)propyl]piperidin-4-ol Step 1

11-(3-Bromopropylidene)-6,11-dihydro-2-hydroxydibenz[b,e]oxepine was prepared by following the procedure of example 45, step 1 and 2, but replacing 5,11-dihydro-7-methoxypyrido[2,3-c][1]benzoxepin-5-one with 6,11-dihydro-2-hydroxydibenz[b,e]oxepin-11-one.

$^1$H-NMR (CDCl$_3$) δ: 2.69(2H,q), 3.39 (2H,t), 5.20(2H, brs), 5.92(1H,t), 6.50–6.81(4H,m), 7.17–7.37(4H,m).

Step 2

The titled compound was prepared by following the procedure of example 45, step 3, but replacing 5-(3-bromopropylidene)-10,11-dihydro-5H-dibenzo[a,d]cycloheptene with the product of step 1.

¹H-NMR (CDCl₃) δ: 1.60–1.75(3H,m), 1.95–2.10(2H, m), 2.35–2.80(8H,m), 5.10(2H,brs), 5.93(1H,t), 6.56(2H, brs), 6.71(1H,brs), 7.11–7.35(8H,m). MS m/z: 462(M+1)

Example 33

4-(4-Chlorophenyl)-1-[3-(6,11-dihydro-2-methoxydibenz[b,e]oxepin-11-ylidene)propyl]piperidin-4-ol Step 1

11-(3-Bromopropylidene)-6,11-dihydro-2-methoxydibenz[b,e]oxepine was prepared by following the procedure of example 45, step 1 and 2, but replacing 5,11-dihydro-7-methoxypyrido[2,3-c][1]benzoxepin-5-one with 6,11-dihydro-2-methoxydibenz[b,e]oxepin-11-one.

¹H-NMR (CDCl₃) δ: 2.74(2H,q), 3.43 (2H,t), 3.77(3H,s), 5.10(2H,brs), 6.02(1H,t), 6.70–6.83(3H,m), 7.21–7.38(4H, m).

Step 2

The titled compound was prepared by following the procedure of example 45, step 3, but replacing 5-(3-bromopropylidene)-10,11-dihydro-5H-dibenzo[a,d]cycloheptene with the product of step 1.

¹H-NMR (CDCl₃) δ: 1.59–1.65(2H,m), 1.95–2.66(11H, m), 3.75(3H,s), 5.10(2H,brs), 6.03(1H,t), 6.69(2H,brs), 6.82 (1H,brs), 7.20–7.40(8H,m). MS m/z: 476(M+1)

Example 34

4-(4-Chlorophenyl)-1-[3-(6,11-dihydro-2-ethoxydibenz[b,e]oxepin-11-ylidene)propyl]piperidin-4-ol To a solution of 4-(4-chlorophenyl)-1-[3-(6,11-dihydro-2-hydroxydibenz[b,e]oxepin-11-ylidene)propyl]piperidin-4-ol (Example 32) (200 mg) in DMF (5 ml) were added sodium hydride (60% in oil, 25 mg), ethyl iodide (0.052 ml) and the mixture was stirred at room temperature for 1 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:1) to give the titled compound (170 mg).

¹H-NMR (CDCl₃) δ: 1.37(3H,t), 1.60–1.65(2H,m), 1.95–2.08(3H,m), 2.28–75(8H,m), 3.96(2H,q), 5.15(2H,brs), 6.02(1H,t), 6.68(2H,brs), 6.82(1H,brs), 7.19–7.42(8H,m). MS m/z: 490(M+1)

Example 35

1-[3-(3-Bromo-6,11-dihydrodibenz[b,e]oxepin-11-ylidene)propyl]-4-(4-chlorophenyl)piperidin-4-ol Step 1

3-Bromo-11-(3-bromopropylidene)-6,11-dihydrodibenz[b,e]oxepine was prepared by following the procedure of example 45, step 1 and 2, but replacing 5,11-dihydro-7-methoxypyrido[2,3-c][1]benzoxepin-5-one with 3-bromo-6,11-dihydrodibenz[b,e]oxepin-11-one.

¹H-NMR (CDCl₃) δ: 2.74(2H,q), 3.43 (2H,t), 3.77(3H,s), 5.10(2H,brs), 6.02(1H,t), 6.70–6.83(3H,m), 7.21–7.38(4H, m).

Step 2

The titled compound was prepared by following the procedure of example 45, step 3, but replacing 5-(3-bromopropylidene)-10,11-dihydro-5H-dibenzo[a,d]cycloheptene with the product of step 1.

¹H-NMR (CDCl₃) δ: 1.63–1.70(3H,m), 1.96–2.10(2H, m), 2.32–2.69(8H,m), 5.20(2H,brs), 6.00(1H,t), 6.92–7.00 (2H,m), 7.11–7.14(1H,m), 7.24–7.42(8H,m). MS m/z: 524, 526(M+1)

Example 36

4-(4-Chlorophenyl)-1-[3-(6,11-dihydrodibenz[b,e]oxepin-11-ylidene)propyl]-4-methoxypiperidine To a solution of 4-(4-chlorophenyl)-1-[3-(6,11-dihydro-2-methoxydibenz[b,e]oxepin-11-ylidene)propyl]piperidin-4-ol (Example 2) (400 mg) in DMF (5 ml) were added sodium hydride (60% in oil, 50 mg), methyl iodide (0.07 ml) and the mixture was stirred at room temperature for 1 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:1) to give the titled compound (100 mg).

¹H-NMR (CDCl₃) δ: 1.90–2.04(4H,m), 2.34–2.62(8H, m), 2.93(3H,s), 5.25(2H,brs), 6.04(1H,t), 6.75–6.91(3H,m), 7.09–7.37(9H,m). MS m/z: 460(M+1)

Example 37

4-Acetoxy-4-(4-chlorophenyl)-1-[3-(6,11-dihydrodibenz[b,e]oxepin-11-ylidene)propyl]piperidine To a solution of 4-(4-chlorophenyl)-1-[3-(6,11-dihydro-2-methoxydibenz[b,e]oxepin-11-ylidene)propyl]piperidin-4-ol (Example 2) (200 mg) in dichloromethane (5 ml) were added acetyl chloride (0.06 ml), triethylamine (0.19 ml) and the mixture was stirred at room temperature for 1 hour. Aqueous sodium bicarbonate and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:4) to give the titled compound (190 mg).

¹H-NMR (CDCl₃) δ: 1.98–2.85(12H,m), 2.02(3H,s), 2.93 (3H,s), 5.23(2H,brs), 6.01(1H,t), 6.73–6.90(3H,m), 7.11–7.40(9H,m). MS m/z: 488(M+1)

Example 38

1-[3-(8-Bromo-4,10-dihydrothieno[3,2-c][1]benzoxepin-10-ylidene)propyl]piperidin-4-(4-chlorophenyl)-4-ol Step 1

8-Bromo-10-(3-bromopropylidene)-4,10-dihydrothieno[3,2-c][1]benzoxepine was prepared by following the procedure of example 45, step 1 and 2, but replacing 5,11-dihydro-7-methoxypyrido[2,3-c][1]benzoxepin-5-one with 4,10-dihydrothieno[3,2-c][1]benzoxepin-10-one.

¹H-NMR (CDCl₃) δ: 2.84(2H,q), 3.45(2H,t), 5.10(2H,s), 6.11(1H,t), 6.65(1H,d), 7.03–7.08(2H,m), 7.38–7.43(2H,m).

Step 2

The titled compound was prepared by following the procedure of example 45, step 3, but replacing 5-(3-bromopropylidene)-10,11-dihydro-5H-dibenzo[a,d]cycloheptene with the product of step 1.

¹H-NMR (CDCl₃) δ: 1.66–1.75(3H,m), 2.03–2.16(2H, m), 2.40–2.86(8H,m), 5.09(0.7×2H,s), 5.14(0.3×2H,s), 5.90 (0.3×1H,t), 6.10(0.7×1H,t), 6.64(0.7×1H,d), 6.75(0.3×1H, d), 6.90(0.3×1H,d), 7.03–7.09(2H,m), 7.21–7.45(6H,m). MS m/z: 532(M+1)

Example 39

4-(4-Chlorophenyl)-1-[3-(6,11-dihydro-6-oxo-5H-dibenz[b,e]azepin-11-ylidene)propyl]piperidin-4-ol Step 1

11-(3-Bromopropylidene)-6,11-dihydro-6-oxo-5H-dibenz[b,e]azepine was prepared by following the procedure of example 45, step 1 and 2, but replacing 5,11-dihydro-7-methoxypyrido[2,3-c][1]benzoxepin-5-one with 6,11-dihydro-6-5H-dibenz[b,e]azepin-6,11-dione.

¹H-NMR (CDCl₃) δ: 2.70–2.92(2H,m), 3.45 (2H,t), 5.92 (1H,t), 7.08–7.58(7H,m), 8.05(1H,dd), 9.00(1H,brs).

Step 2

The titled compound was prepared by following the procedure of example 45, step 3, but replacing 5-(3-bromopropylidene)-10,11-dihydro-5H-dibenzo[a,d]cycloheptene with the product of step 1.

¹H-NMR (CDCl₃) δ: 1.61–1.66(2H,m), 1.97–2.20(3H, m), 2.35–2.68(8H,m), 5.80(1H,t), 7.03–7.53(11H,m), 8.02 (1H,dd), 9.27(1H,brs). MS m/z: 459(M+1)

Example 40

4-(4-Chlorophenyl)-1-[3-(6,11-dihydro-5-ethyl-6-oxo-5H-dibenz[b,e]azepin-11-ylidene)propyl]piperidin-4-ol The titled compound was prepared by following the procedure of example 12, but replacing benzyl bromide with ethyl iodide.

¹H-NMR (CDCl₃) δ: 1.19–1.28(3H,m), 1.63–1.69(2H, m), 1.99–2.16(3H,m), 2.37–2.70(8H,m), 3.77–3.85(1H,m), 4.40–4.48(1H,m), 5.85(1H,t), 7.12–7.45(11H,m), 7.85(1H, dd). MS m/z: 487(M+1)

Example 41

1-[3-(5-n-Butyl-6,11-dihydro-6-oxo-5H-dibenz[b,e] azepin-11-ylidene)propyl]-4-(4-chlorophenyl)-piperidin-4-ol The titled compound was prepared by following the procedure of example 12, but replacing benzyl bromide with n-butyl iodide.

¹H-NMR (CDCl₃) δ: 0.90–0.98(3H,m), 1.25–2.20(9H, m), 2.40–2.87(8H,m), 3.62–3.72(1H,m), 4.52–4.64(1H,m), 5.85(1H,t), 7.16–7.45(11H,m), 7.88(1H,dd). MS m/z: 515 (M+1)

Example 42

4-(4-Chlorophenyl)-1-[3-(6,11-dihydro-5-(3-hydroxypropyl)-6-oxo-5H-dibenz[b,e]azepin-11-ylidene) propyl]piperidin-4-ol To a solution 4-(4-chlorophenyl)-1-[3-(6,11-dihydro-6-oxo-5H-dibenz[b,e]azepin-11-ylidene)propyl]piperidin-4-ol hydrochloride (Example 39) (500 mg) in DMF (8 ml) were added sodium hydride (60% in oil, 200 mg), 2-(3-bromopropoxy)tetrahydro-2H-pyran (0.5 ml) and the mixture was stirred at room temperature for 6 hours. Water and ethyl acetate were added to the reaction mixture, the organic layer was separated and washed with saturated aqueous sodium chloride, and dried with magnesium sulfate. The solvent was distilled off under reduced pressure. The residue was solved in 1M hydrogen chloride in diehyl ether and stirred at room temperature for 1 hour. Aqueous sodium bicarbonate and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate to give the titled compound (250 mg).

¹H-NMR (CDCl₃) δ: 1.25–2.87(15H,m), 3.51–3.56(2H, m), 3.76–3.82(1H,m), 4.81–4.87(1H,m), 5.86(1H,t), 7.16–7.45(11H,m), 7.82(1H,dd). MS m/z: 517(M+1)

Example 43

1-[3-(5-tert-Butoxycarbonylmethyl-6,11-dihydro-6-oxo-5H-dibenz[b,e]azepin-11-ylidene)propyl]-4-(4-chlorophenyl)-piperidin-4-ol The titled compound was prepared by following the procedure of example 12, but replacing benzyl bromide with tert-butyl bromoacetate.

¹H-NMR (CDCl₃) δ: 1.50(9H,s), 1.65–1.70(2H,m), 1.95–2.10(3H,m), 2.42–2.75(8H,m), 4.24(1H,d), 4.75(1H, d), 5.88(1H,t), 7.16–7.46(11H,m), 7.90(1H,dd). MS m/z: 573(M+1)

Example 44

4-(4-Chlorophenyl)-1-[3-(5,11-dihydro-7-hydroxy[1] benzoxepino[2,3-b]pyridin-5-ylidene)propyl]piperidin-4-ol Step 1

To a solution of the product of example 45, step 1 (4.3 g) in dichloroethane (100 ml) was added boron tribromide-methyl sulfide complex (19.3 g) and the mixture was heated to reflux for 3 hour. Water and ethyl acetate were added to the reaction mixture and neutralized with dilute NaOH solution. The organic layer was separated and washed with saturated aqueous sodium chloride, and dried over magnesium sulfate. The solvent was distilled off under reduced pressure. The residue was purified by silica gel chromatography eluting with ethyl acetate-hexane (1:2) to give 5-(3-bromopropylidene)-5,11-dihydro-7-hydroxy[1]benzoxepino [2,3-b]pyridine (3.2 g).

¹H-NMR (CDCl₃) δ: 2.72(2H,q), 3.45(2H,t), 5.28(2H, brs), 6.03(1H,t), 6.66–6.80(3H,m), 7.26(1H,dd), 7.58(1H, dd), 8.51(1H,dd).

Step 2

The titled compound was prepared by following the procedure of example 45, step 3, but replacing 5-(3-bromopropylidene)-5,11-dihydro-7-methoxy[1]benzoxepino[2,3-b]pyridine with the product of step 1.

$^1$H-NMR (DMSO-d$_6$) δ: 1.46–1.51(2H,m), 1.74–1.85(2H,m), 2.29–2.51(8H,m), 5.15(2H,brs), 6.07(1H,t), 6.61–6.70(3H,m), 7.33–7.48(5H,m), 7.73(1H,dd), 8.47(1H,dd), 9.06(1H,s). MS m/z: 463(M+1)

Example 45

4-(4-Chlorophenyl)-1-[3-(5,11-dihydro-7-methoxy[1]benzoxepino[2,3-b]pyridin-5-ylidene)propyl]piperidin-4-ol Step 1

To a solution of 5,11-dihydro-7-methoxy[1]benzoxepino[2,3-b]pyridin-5-one (5.0 g) in THF (50 ml) was added 1.1M cyclopropylmagnesium bromide THF solution (25 ml) at 0° C. The reaction mixture was warmed to room temperature, and stirred for 30 minutes. Aqueous ammonium chloride and ethyl acetate were added to the reaction mixture, the organic layer was separated and washed with saturated aqueous sodium chloride, and dried with magnesium sulfate. The solvent was distilled off under reduced pressure. The residue was filtered and washed with ethyl acetate-hexane (1:2) to give 5-cyclopropyl-5,11-dihydro-7-methoxy[1]benzoxepino[2,3-b]pyridin-5-ol (5.0 g).

Step 2

To a solution of the product of step 1 (4.3 g) in acetic acid (30 ml) was added 48% aqueous HBr (25 ml) at 10° C. The reaction mixture was warmed to room temperature, and stirred for 12 hours. Water and ethyl acetate were added to the reaction mixture and neutralized with dilute NaOH solution. The organic layer was separated and washed with saturated aqueous sodium chloride, and dried over magnesium sulfate. The solvent was distilled off under reduced pressure. The residue was purified by silica gel chromatography eluting with ethyl acetate-hexane (1:4) to give 5-(3-bromopropylidene)-5,11-dihydro-7-methoxy[1]benzoxepino[2,3-b]pyridine (5.6 g).

$^1$H-NMR (CDCl$_3$) δ: 2.74(2H,q), 3.46(2H,t), 3.78(3H,s), 5.25(2H,brs), 6.07(1H,t), 6.72–6.82(3H,m), 7.21–7.42(5H,m), 7.56(1H,dd), 8.45(1H,dd).

Step 3

To a solution the product of step 2 (1.1 g) in DMF (15 ml) were added 4-(4-chlorophenyl)-4-hydroxypiperidine (0.81 g) and potassium carbonate (0.53 g) and the mixture was stirred at room temperature for 3 hours. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with methylene chloride-methanol (10:1) to give the titled compound as major regioisomer (0.86 g) and minor one (0.05 g). Major isomer $^1$H-NMR (CDCl$_3$) δ: 1.64–1.69(2H,m), 1.91–2.08(3H,m), 2.34–2.69(8H,m), 3.77(3H,s), 5.25(2H,brs), 6.07(1H,t), 6.72–6.82(3H,m), 7.21–7.42(5H,m), 7.56(1H,dd), 8.45(1H,dd). MS m/z: 477(M+1)

Minor Isomer $^1$H-NMR (CDCl$_3$) d: 1.65–1.79(3H,m), 2.01–2.13(2H,m), 2.35–2.76(8H,m), 3.76(3H,s), 5.22(2H,brs), 5.95(1H,t), 6.72–6.80(2H,m), 7.06(1H,d), 7.16(1H,dd), 7.28(2H,d), 7.42(2H,d), 7.66(1H,dd), 8.39(1H,dd). MS m/z: 477(M+1).

Example 46

4-(4-Chlorophenyl)-1-[3-(5,11-dihydro-7-ethoxy[1]benzoxepino[2,3-b]pyridin-5-ylidene)propyl]piperidin-4-ol The titled compound was prepared by following the procedure of example 34, but replacing 4-(4-chlorophenyl)-1-[3-(6,11-dihydro-2-hydroxydibenz[b,e]oxepin-11-ylidene)propyl]piperidin-4-ol with 4-(4-chlorophenyl)-1-[3-(5,11-dihydro-7-hydroxy[1]benzoxepino[2,3-b]pyridin-5-ylidene)propyl]piperidin-4-ol (example 44).

$^1$H-NMR (CDCl$_3$) δ: 1.38(3H,t), 1.67–1.72(3H,m), 2.05–2.16(2H,m), 2.40–2.80(8H,m), 3.99(2H,q), 5.26(2H,brs), 6.05(1H,t), 6.71–6.82(3H,m), 7.23–7.43(5H,m), 7.57(1H,dd), 8.47(1H,dd). MS m/z: 491(M+1)

Example 47

4-(4-Chlorophenyl)-1-[3-(5,11-dihydro-7-isopropoxy[1]benzoxepino[2,3-b]pyridin-5-ylidene)propyl]piperidin-4-ol The titled compound was prepared by following the procedure of example 46, but replacing ethyl iodide with isopropyl bromide.

$^1$H-NMR (CDCl$_3$) δ: 1.30(6H,d), 1.60–1.70(3H,m), 1.99–2.09(2H,m), 2.33–2.69(8H,m), 4.37–4.48(1H,m), 5.26(2H,brs), 6.06(1H,t), 6.73–6.82(3H,m), 7.21–7.43(5H,m), 7.55(1H,dd), 8.47(1H,dd). MS m/z: 505(M+1)

Example 48

4-(4-Chlorophenyl)-1-[3-(5,11-dihydro-7-ethoxycarbonylmethyloxy[1]benzoxepino[2,3-b]pyridin-5-ylidene)propyl]piperidin-4-ol The titled compound was prepared by following the procedure of example 46, but replacing ethyl iodide with ethyl bromoacetate.

$^1$H-NMR (CDCl$_3$) δ: 1.28(3H,t), 1.63–1.68(2H,m), 1.97–2.02(3H,m), 2.33–2.68(8H,m), 4.24(2H,q), 4.55(2H,s), 5.26(2H,brs), 6.06(1H,t), 6.73–6.88(3H,m), 7.21–7.42(5H,m), 7.55(1H,dd), 8.44(1H,dd). MS m/z: 549(M+1).

Example 49

4-(4-Chlorophenyl)-1-[3-(7-cyanomethyloxy-5,11-dihydro[1]benzoxepino[2,3-b]pyridin-5-ylidene)propyl]piperidin-4-ol The titled compound was prepared by following the procedure of example 46, but replacing ethyl iodide with bromoacetonitrile.

$^1$H-NMR (CDCl$_3$) δ: 1.62–1.67(2H,m), 1.94–2.06(2H,m), 2.21(1H,brs), 2.34–2.66(8H,m), 4.70(2H,s), 5.26(2H,brs), 6.10(1H,t), 6.80(2H,brs), 6.92(1H,brs), 7.22–7.41(5H,m), 7.56(1H,dd), 8.44(1H,dd). MS m/z: 502(M+1)

Example 50

1-[3-(7-(2-Acetoxyethyl)oxy-5,11-dihydro[1]benzoxepino[2,3-b]pyridin-5-ylidene)propyl]-4-(4-chlorophenyl)piperidin-4-ol The titled compound was prepared by following the procedure of example 46, but replacing ethyl iodide with 2-bromoethyl acetate.

$^1$H-NMR (CDCl$_3$) δ: 1.65–1.72(3H,m), 1.97–2.09(5H,m), 2.37–2.70(8H,m), 4.11–4.14(2H,m), 4.37–4.41(2H,m), 5.25(2H,brs), 6.07(1H,t), 6.75–6.84(3H,m), 7.23–7.43(5H,m), 7.56(1H,dd), 8.47(1H,dd). MS m/z: 549(M+1)

Example 51

4-(4-Chlorophenyl)-1-[3-(5,11-dihydro-7-(2-hydroxyethyl)oxy[1]benzoxepino[2,3-b]pyridin-5-ylidene)propyl]piperidin-4-ol To a solution of 1-[3-(7-(2-acetoxyethyl)oxy-5,11-dihydro[1]benzoxepino[2,3-b]pyridin-5-ylidene)propyl]-4-(4-chlorophenyl)piperidin-4-ol (Example 50) (140 mg) in ethanol (5 ml) were added 15% sodium hydroxide aqueous solution (2 ml) and the mixture was heated to reflux for 1 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with methylene chloride-methanol (10:1) to give the titled compound (120 mg).

$^1$H-NMR (CDCl$_3$) δ: 1.64–1.69(2H,m), 1.98–2.10(3H,m), 2.36–2.79(8H,m), 3.89–3.94(2H,m), 3.99–4.04(2H,m), 5.24(2H,brs), 6.04(1H,t), 6.71–6.84(3H,m), 7.23–7.41(5H,m), 7.54(1H,dd), 8.43(1H,dd). MS m/z: 507(M+1)

Example 52

4-(4-Chlorophenyl)-1-[3-(5,11-dihydro-7-(2-morpholinoethyl)oxy[1]benzoxepino[2,3-b]pyridin-5-ylidene)propyl]piperidin-4-ol The titled compound was prepared by following the procedure of example 46, but replacing ethyl iodide with 4-(2-chloroethyl)morpholine hydrochloride.

$^1$H-NMR (CDCl$_3$) δ: 1.62–1.67(2H,m), 1.95–2.08(2H,m), 2.20–2.67(13H,m), 2.74(2H,t), 3.67–3.71(4H,m), 4.04(2H,t), 5.23(2H,brs), 6.05(1H,t), 6.73–6.82(3H,m), 7.20–7.41(5H,m), 7.53(1H,dd), 8.42(1H,dd). MS m/z: 576(M+1)

Example 53

4-(4-Chlorophenyl)-1-[3-(5,11-dihydro[1]benzoxepino[2,3-b]pyridin-5-ylidene)propyl]piperidin-4-ol Step 1

5-(3-Bromopropylidene)-5,11-dihydro[1]benzoxepino[2,3-b]pyridine was prepared by following the procedure of example 45, step 1 and 2, but replacing 5,11-dihydro-7-methoxy[1]benzoxepino[2,3-b]pyridin-5-one with 5,11-dihydro[1]benzoxepino[2,3-b]pyridin-5-one.

$^1$H-NMR (CDCl$_3$) δ: 2.71(2H,q), 3.46(2H,t), 5.33(2H,brs), 6.04(1H,t), 7.01–7.17(3H,m), 7.29(1H,dd), 7.56(1H,dd), 8.53(1H,dd).

Step 2

The titled compound was prepared by following the procedure of example 45, step 3, but replacing 5-(3-bromopropylidene)-5,11-dihydro-7-methoxy[1]benzoxepino[2,3-b]pyridine with the product of step 1.

$^1$H-NMR (CDCl$_3$) δ: 1.66–1.71(2H,m), 2.00–2.20(3H,m), 2.36–2.69(8H,m); 5.34(2H,brs), 6.10(1H,t), 6.83–6.96(3H,m), 7.17–7.44(6H,m), 7.60(1H,dd), 8.46(1H,dd). MS m/z: 447(M+1)

Example 54

1-[3-(8-Bromo-5,11-dihydro[1]benzoxepino[2,3-b]pyridin-5-ylidene)propyl]-4-(4-chlorophenyl)piperidin-4-ol Step 1

8-Bromo-5-(3-bromopropylidene)-5,11-dihydro[1]benzoxepino[2,3-b]pyridine was prepared by following the procedure of example 45, step 1 and 2, but replacing 5,11-dihydro-7-methoxy[1]benzoxepino[2,3-b]pyridin-5-one with 8-bromo-5,11-dihydro[1]benzoxepino[2,3-b]pyridin-5-one.

$^1$H-NMR (CDCl$_3$) δ: 2.75(2H,q), 3.50(2H,t), 5.38(2H,brs), 6.08(1H,t), 6.85–6.98(2H,m), 7.18–7.35(3H,m), 7.59(1H,dd), 8.54(1H,dd).

Step 2

The titled compound was prepared by following the procedure of example 45, step 3, but replacing 5-(3-bromopropylidene)-5,11-dihydro-7-methoxy[1]benzoxepino[2,3-b]pyridine with the product of step 1.

$^1$H-NMR (CDCl$_3$) δ: 1.64–1.69(2H,m), 1.90–2.07(3H,m), 2.30–2.67(8H,m), 5.30(2H,brs), 6.08(1H,t), 7.00–7.07(2H,m), 7.13(1H,d), 7.25–7.42(5H,m), 7.56(1H,dd), 8.47(1H,dd). MS m/z: 525, 527(M+1)

Example 55

4-(4-Chlorophenyl)-1-[3-(10,11-dihydro-10-oxo-5H-pyrido[2,3-c][2]benzazepin-5-ylidene)propyl]piperidin-4-ol Step 1

5-(3-Bromopropylidene)-10,11-dihydro-10-oxo-5H-pyrido[2,3-c][2]benzazepine was prepared by following the procedure of example 45, step 1 and 2, but replacing 5,11-dihydro-7-methoxy[1]benzoxepino[2,3-b]pyridin-5-one with 10,11-dihydro-5H-pyrido[2,3-c][2]benzazepin-5,10-dione.

$^1$H-NMR (CDCl$_3$) δ: 2.75–2.90(2H,m), 3.45 (2H,t), 5.92 (1H,t), 7.04–7.70(5H,m), 8.10(1H,dd), 8.48(1H,dd), 10.00 (1H,brs).

Step 2

The titled compound was prepared by following the procedure of example 45, step 3, but replacing 5-(3-bromopropylidene)-10,11-dihydro-5H-dibenzo[a,d]cycloheptene with the product of step 1.

$^1$H-NMR (CDCl$_3$) δ: 1.64–1.69(3H,m), 2.00–2.12(2H,m), 2.35–2.70(8H,m), 5.82(1H,t), 7.08(1H,dd), 7.23–7.62(8H,m), 8.04(1H,dd), 8.32(1H,dd), 8.76(1H,brs). MS m/z: 460(M+1)

Example 56

4-(4-Chlorophenyl)-1-[3-(10,11-dihydro-11-methyl-10-oxo-5H-pyrido[2,3-c][2]benzazepin-5-ylidene)propyl]piperidin-4-ol

The titled compound was prepared by following the procedure of example 36, but replacing of 4-(4-chlorophenyl)-1-[3-(6,11-dihydro-2-methoxydibenz[b,e]oxepin-11-ylidene)propyl]piperidin-4-ol with 5-(3-bromopropylidene)-10,11-dihydro-10-oxo-5H-pyrido[2,3-c][2]benzazepine.

$^1$H-NMR (CDCl$_3$) δ: 1.64–1.70(3H,m), 2.00–2.10(2H,m), 2.41–2.69(8H,m), 3.62(3H,s), 5.82(1H,t), 7.07(1H,dd), 7.25–7.54(8H,m), 7.91(1H,dd), 8.34(1H,dd). MS m/z: 474 (M+1)

Example 57

4-(4-Chlorophenyl)-1-[3-(5,11-dihydro-7-methoxy[1]benzoxepino[2,3-b]pyridin-5-ylidene)ethyl]piperidin-4-ol

Step 1

To a solution of methyltriphenylphosphonium bromide (2.2 g) in THF (20 ml) was added 1.6M n-butyl lithium hexane solution (2.9 ml) at 0° C. for 30 minutes. To the reaction mixture cooled to 0° C. was added 5,11-dihydro-7-methoxy[1]benzoxepino[2,3-b]pyridin-5-one (1.0 g) dropwise as THF solution (5 ml), and the mixture was warmed to room temperature, and stirred for 3 hours. Aqueous ammonium chloride and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:4) to give 5,11-dihydro-7-methoxy-5-methylenepyrido[2,3-c][1]benzoxepine (0.14 g).

Step 2

To a solution of DMF (0.54 ml) was added phosphorus oxychloride (0.41 ml) at 0° C. for 10 minutes. To the reaction mixture was added the product of step 1 (210 mg) in carbontetrachloride (5 ml) and the mixture was heated to reflux for 5 hours. Aqueous sodium bicarbonate and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:4) to give 3-(5,11-dihydro-7-methoxy[1]benzoxepino[2,3-b]pyridin-5-ylidene)acetaldehyde (130 mg).

$^1$H-NMR (CDCl$_3$) δ: 3.77(0.7×3H,s), 3.79(0.3×3H, s), 5.31(2H,s), 6.46(0.7×1H,d), 6.52(0.3×1H,d), 6.78–7.40(4H,m), 7.68(0.3×1H,dd), 7.78(0.7×1H,dd), 8.55(0.7×1H,dd), 8.64(0.3×1H,dd), 9.62(0.3×1H,d), 9.79(0.7×1H,d).

Step 3

The titled compound was prepared by following the procedure of example 58, step 2, but replacing of 3-(5,11-dihydro-7-methoxy[1]benzoxepino[2,3-b]pyridin-5-ylidene)propanaldehyde with product of step 2.

$^1$H-NMR (CDCl$_3$) δ: 1.64–1.82(2H,m), 1.92–2.22(3H,m), 2.43–2.58(2H,m), 2.79–3.45(6H,m), 3.68(0.3×3H,s), 3.70(0.7×3H,s), 5.24(2H,brs), 6.18(0.7×1H,t), 6.21(0.3×1H,t), 6.72–7.42(8H,m), 7.78(0.3×1H,dd), 7.85(0.7×1H,dd), 8.42(0.7×1H,dd), 8.46(0.3×1H,dd). MS m/z: 463(M+1).

Example 58

4-(4-Chlorophenyl)-1-[4-(5,11-dihydro-7-methoxy[1]benzoxepino[2,3-b]pyridin-5-ylidene)butyl]piperidin-4-ol

Step 1

3-(5,11-Dihydro-7-methoxy[1]benzoxepino[2,3-b]pyridin-5-ylidene)propenaldehyde was prepared by following the procedure of example 57, step 2, but replacing 5,11-dihydro-7-methoxy-5-methylene[1]benzoxepino[2,3-b]pyridine with 5,11-dihydro-7-methoxy-5-(propyl-1-ene)[1]benzoxepino[2,3-b]pyridine (by-product of example 45, step 3).

$^1$H-NMR (CDCl$_3$) δ: 3.78(0.3×3H,s), 3.80(0.7×3H,s), –5.32(2H,brs), 6.34–6.39(1H,m), 6.72–7.38 (6H,m), 7.58 (0.7×1H,dd), 7.77(0.3×1H,dd), 8.49(0.3×1H,dd), 8.60(0.7×1H,dd), 9.51(0.7×1H,d), 9.54(0.3×1H,d).

Step 2

To a solution of the product of step 1 (90 mg) in dichloromethane (6 ml) were added sodium triacetoxyborohydride (170 mg), 4-(4-chlorophenyl)-4-hydroxypiperidine (70 mg) and acetic acid (0.02 ml) and the mixture stirred at room temperature for 24 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with dichloromethane-methanol (95:5) to give 4-(4-chlorophenyl)-1-[4-(5,11-dihydro-7-methoxy[1]benzoxepino[2,3-b]pyridin-5-ylidene)buten-2-yl]piperidin-4-ol (110 mg).

$^1$H-NMR (CDCl$_3$) δ: 1.68–1.73(2H,m), 2.04–2.16(2H, m), 2.43–2.72(3H,m), 2.77–2.81(2H,m), 3.08–3.13(2H,m), 3.73(0.3×3H,s), 3.77(0.7×3H,s), 5.20(2H,brs), 5.98–6.05(1H,m), 6.23–7.43(10H,m), 7.58(0.7×1H,dd), 7.65(0.3×1H,dd), 8.37(0.3×1H,dd), 8.45(0.7×1H,dd). MS m/z: 489(M+1).

Step 3

To a solution of the product of step 2 (8 mg) in ethanol (2 ml) were added 10% Pd—C (2 mg) was stirred under hydrogen (under a balloon) at room temperature for 1 hour. The mixture was filtered through the celite and distilled off under reduced pressure to give the titled compound (6 mg).

$^1$H-NMR (CDCl$_3$) δ: 1.68–3.00(15H,m), 3.77(3H,s), 5.18–5.35(2H,m), 5.94(0.4H,t, E isomer), 6.06(0.6H,t, Z isomer), 6.65–6.88(3H,m), 7.05–7.73(6H,m), 8.30–8.56(1H,m). MS m/z: 491(M+1)

Example 59

1-[3-(5,11-Dihydro-7-methoxy[1]benzoxepino[2,3-b]pyridin-5-ylidene)propyl]piperidin-4-phenyl-4-ol

The titled compound was prepared by following the procedure of example 45, step 3, but replacing 4-(4-chlorophenyl)-4-hydroxypiperidine with 4-phenyl-4-hydroxypiperidine.

$^1$H-NMR (CDCl$_3$) δ: 1.68–1.73(2H,m), 2.02–2.15(3H, m), 2.38–2.72(8H,m), 3.77(3H,s), 5.26(2H,brs), 6.08(1H,t), 6.72–6.83(3H,m), 7.21–7.36(4H,m), 7.46–7.49(2H,m), 7.58 (1H,dd), 8.46(1H,dd). MS m/z: 443 (M+1).

Example 60

4-(4-Bromophenyl)-1-[3-(5,11-dihydro-7-methoxy[1]benzoxepino[2,3-b]pyridin-5-ylidene)propyl]piperidin-4-ol

The titled compound was prepared by following the procedure of example 45, step 3, but replacing 4-(4-chlorophenyl)-4-hydroxypiperidine with 4-(4-bromophenyl)-4-hydroxypiperidine.

$^1$H-NMR (CDCl$_3$) δ: 1.65–1.69(2H,m), 2.00–2.10(3H, m), 2.37–2.71(8H,m), 3.76(3H,s), 5.24(2H,brs), 6.05(1H,t), 6.70–6.82(3H,m), 7.24(1H,dd), 7.38 (2H,d), 7.44(2H,s), 7.52(1H,dd), 8.44(1H,dd). MS m/z: 521,523 (M+1).

Example 61

1-[3-(5,11-Dihydro-7-methoxy[1]benzoxepino[2,3-b]pyridin-5-ylidene)propyl]piperidin-4-ol

The titled compound was prepared by following the procedure of example 45, step 3, but replacing 4-(4-chlorophenyl)-4-hydroxypiperidine with 4-hydroxypiperidine.

$^1$H-NMR (CDCl$_3$) δ: 1.43–1.60(2H,m), 1.80–1.98(2H, m), 2.00–2.18(3H,m), 2.34–2.48 (4H,m), 2.63–2.76(2H,m), 3.64–3.73(1H,m), 3.70(3H,s), 5.35(2H,brs), 6.06(1H,t), 6.74–6.84(3H,m), 7.25(1H,dd), 7.60(1H,dd), 8.50(1H,dd). MS m/z: 367 (M+1).

Example 62

4-Benzyl-1-[3-(5,11-dihydro-7-methoxy[1]benzoxepino[2,3-b]pyridin-5-ylidene)propyl]piperidin-4-ol

The titled compound was prepared by following the procedure of example 45, step 3, but replacing 4-(4-chlorophenyl)-4-hydroxypiperidine with 4-benzyl-4-hydroxypiperidine.

$^1$H-NMR (CDCl$_3$) δ: 1.42–1.57(3H,m), 1.62–1.75(2H, m), 2.22–2.70(8H,m), 2.79(2H,s), 3.80(3H,s), 5.25(2H,brs), 6.08(1H,t), 6.73–6.84(3H,m), 7.18–7.24(6H,m), 7.57(1H, dd), 8.50(1H,dd). MS m/z: 457 (M+1).

Example 63

4-Cyano-1-[3-(5,11-dihydro-7-methoxy[1]benzoxepino[2,3-b]pyridin-5-ylidene)propyl]-4-phenylpiperidine

The titled compound was prepared by following the procedure of example 45, step 3, but replacing 4-(4-chlorophenyl)-4-hydroxypiperidine with 4-cyano-4-phenylpiperidine.

$^1$H-NMR (CDCl$_3$) δ: 1.97–2.06(4H,m), 2.37–2.60(6H, m), 2.85–2.90(2H,m), 3.79(3H,s), 5.27(2H,brs), 6.08(1H,t), 6.72–6.84(3H,m), 7.24–7.58(7H,m), 8.49(1H,dd). MS m/z: 452 (M+1).

Example 64

1-[3-(5,11-Dihydro-7-methoxy[1]benzoxepino[2,3-b]pyridin-5-ylidene)propyl]-4-phenylpiperidine

The titled compound was prepared by following the procedure of example 45, step 3, but replacing 4-(4-chlorophenyl)-4-hydroxypiperidine with 4-phenylpiperidine.

$^1$H-NMR (CDCl$_3$) δ: 1.73–1.79(4H,m), 1.96–2.03(2H, m), 2.37–2.52(5H,m), 2.86–2.94(2H,m), 3.77(3H,s), 5.26 (2H,brs). 6.08(1H,t), 6.72–6.83(3H,m), 7.17–7.31(6H,m), 7.56 (1H,dd), 8.49(1H,dd). MS m/z 426 (M+1).

Example 65

4-(4-Chlorophenyl)-1-[3-(5,11-dihydro-7-methoxy[1]benzoxepino[2,3-b]pyridin-5-ylidene)propyl]piperidine

The titled compound was prepared by following the procedure of example 45, step 3, but replacing 4-(4-chlorophenyl)-4-hydroxypiperidine with 4-(4-chlorophenyl)piperidine.

$^1$H-NMR (CDCl$_3$) δ: 1.68–1.74(4H,m), 1.96–2.03(2H, m), 2.36–2.48(5H,m), 2.89–2.94(2H,m), 3.77(3H,s), 5.27 (2H,brs), 6.07(1H,t), 6.73–6.83(3H,m), 7.10–7.27(5H,m), 7.57(1H,dd), 8.48(1H,dd). MS m/z: 461 (M+1).

Example 66

1-[3-(5,11-Dihydro-7-methoxy[1]benzoxepino[2,3-b]pyridin-5-ylidene)propyl]-4-piperidinopiperidine

The titled compound was prepared by following the procedure of example 45, step 3, but replacing 4-(4-chlorophenyl)-4-hydroxypiperidine with 4-piperidinopiperidine.

$^1$H-NMR (CDCl$_3$) δ: 1.40–2.00(12H,m), 2.15–2.60(9H, m), 2.80–2.92(2H,m), 3.80(3H,s), 5.28(2H,brs), 6.05(1H,t), 6.75–6.86(3H,m), 7.30(1H,dd), 7.55(1H,dd), 8.46(1H,dd). MS m/z 434 (M+1).

Example 67

1-[3-(5,11-Dihydro-7-methoxy[1]benzoxepino[2,3-b]pyridin-5-ylidene)propyl]-4-(2-keto-1-benzimidazolinyl)piperidine

The titled compound was prepared by following the procedure of example 45, step 3, but replacing 4-(4-chlorophenyl)-4-hydroxypiperidine with 4-(2-keto-1-benzimidazolinyl)piperidine.

$^1$H-NMR (CDCl$_3$) δ: 1.75–1.79(2H,m), 2.03–2.15(2H, m), 2.38–2.52(6H,m), 2.93–2.98 (2H,m), 3.78(3H,s), 4.30–4.38(1H,m), 5.30(2H,brs), 6.10(1H,t), 6.73–6.84(3H, m), 7.01–7.03(3H,m), 7.21–7.28(2H,m), 7.59(1H,dd), 8.48 (1H,dd). MS m/z: 483 (M+1).

Example 68

1-[3-(5,1-Dihydro-7-methoxy[1]benzoxepino[2,3-b]pyridin-5-ylidene)propyl]-4-(2-keto-3-methyl-1-benzimidazolinyl)piperidine

The titled compound was prepared by following the procedure of example 36, but replacing of 4-(4-chlorophenyl)-1-[3-(6,11-dihydro-2-methoxydibenz[b,e]oxepin-11-ylidene)propyl]piperidin-4-ol with 1-[3-(5,11-dihydro-7-methoxy[1]benzoxepino[2,3-b]pyridin-5-ylidene)propyl]-4-(2-keto-1-benzimidazolinyl)piperidine.

$^1$H-NMR (CDCl$_3$) δ: 1.72–1.76(2H,m), 2.09–2.14(2H, m), 2.23–2.54(6H,m), 2.91–2.96 (2H,m), 3.38(3H,s), 3.77 (3H,s), 4.30–4.37(1H,m), 5.27(2H,brs), 6.08(1H,t), 6.71–6.83(3H,m), 6.93–7.06(3H,m), 7.23–7.60(2H,m), 8.08 (1H,dd), 8.48(1H,dd). MS m/z: 497 (M+1).

Example 69

8-[3-(5,11-Dihydro-7-methoxy[1]benzoxepino[2,3-b]pyridin-5-ylidene)propyl]-1-phenyl-1,3,8-triazaspiro[4,5]decan-4-one The titled compound was prepared by following the procedure of example 45, step 3, but replacing 4-(4-chlorophenyl)-4-hydroxypiperidine with 1-phenyl-1,3,8-triazaspiro[4,5]decan-4-one.

$^1$H-NMR (CDCl$_3$) δ: 1.65–1.70(2H,m), 2.36–2.41(2H, m), 2.53–2.79(8H,m), 3.76(3H, s), 4.70(2H,s), 5.25(2H,brs), 6.10(1H,t), 6.71–6.88(6H,m), 7.21–7.27(3H,m), 7.58–7.61 (2H,m), 8.48(1H,dd). MS m/z: 497 (M+1).

Example 70

4-Anilino-4-carbamyl-1-[3-(5,11-dihydro-7-methoxy[1]benzoxepino[2,3-b]pyridin-5-ylidene)propyl]piperidine The titled compound was prepared by following the procedure of example 45, step 3, but replacing 4-(4-chlorophenyl)-4-hydroxypiperidine with 4-anilino-4-carbamylpiperidine.

$^1$H-NMR (CDCl$_3$) d: 1.85–1.90(2H,m), 2.03–2.08(2H, m), 2.19–2.46(6H,m), 2.62–2.67(2H,m), 3.75(3H,s), 3.97 (1H,brs), 5.27(2H,brs), 5.53(1H,brs), 6.03(1H,t), 6.60(2H, d), 6.70–6.85(4H,m), 7.12–7.25(4H,m), 7.53(1H,dd), 8.46 (1H,dd). MS m/z 485 (M+1).

Example 71

1-(4-Chlorophenyl)-4-[3-(5,11-dihydro-7-methoxy[1]benzoxepino[2,3-b]pyridin-5-ylidene)propyl]piperazine The titled compound was prepared by following the procedure of example 45, step 3, but replacing 4-(4-chlorophenyl)-4-hydroxypiperidine with 1-(4-chlorophenyl)piperazine.

$^1$H-NMR (CDCl$_3$) δ: 2.36–2.53(8H,m), 3.07–3.09(4H, m), 3.76(3H,s), 5.26(2H,brs), 6.08(1H,t), 6.72–6.81(5H,m), 7.16–7.28(3H,m), 7.56(1H,dd), 8.49(1H,dd). MS m/z: 462 (M+1).

Example 72

1-[3-(5,11-Dihydro-7-methoxy[1]benzoxepino[2,3-b]pyridin-5-ylidene)propyl]-4-(2-pyrimidyl)piperazine The titled compound was prepared by following the procedure of example 45, step 3, but replacing 4-(4-chlorophenyl)-4-hydroxypiperidine with 1-(2-pyrimidyl)piperazine.

$^1$H-NMR (CDCl$_3$) δ: 2.37–2.53(8H,m), 3.74–3.83(7H, m), 5.27(2H, brs), 6.08(1H,t), 6.45(1H,t), 6.72–6.83(3H,m), 7.25(1H,dd), 7.56(1H,dd), 8.27(2H,d), 8.49(1H,dd). MS m/z: 430 (M+1).

Example 73

1-Cyclohexyl-4-[3-(5,11-dihydro-7-methoxy[1]benzoxepino[2,3-b]pyridin-5-ylidene)propyl]piperazine The titled compound was prepared by following the procedure of example 45, step 3, but replacing 4-(4-chlorophenyl)-4-hydroxypiperidine with 1-cyclohexylpiperazine.

$^1$H-NMR (CDCl$_3$) δ: 1.12–1.27(6H,m), 1.74–1.86(6H, m), 2.18–2.52 (11H,m), 3.76(3H,s), 5.26(2H,brs), 6.04(1H, t), 6.74–6.81(3H,m), 7.23 (1H,dd), 7.55(1H,dd), 8.48(1H, dd). MS m/z: 434 (M+1).

Example 74

1-[3-(5,11-Dihydro-7-methoxy[1]benzoxepino[2,3-b]pyridin-5-ylidene)propyl]-4-(2-furoyl)piperazine The titled compound was prepared by following the procedure of example 45, step 3, but replacing 4-(4-chlorophenyl)-4-hydroxypiperidine with 1-(2-furoyl)piperazine.

$^1$H-NMR (CDCl$_3$) δ: 2.34–2.48(8H,m), 3.71–3.74(7H,s), 5.24(2H,brs), 6.05(1H,t), 6.42(1H,dd), 6.70–6.80(3H,m), 6.93(1H,d), 7.23(1H,dd), 7.42(1H,d), 7.53(1H,dd), 8.46(1H, dd). MS m/z: 446 (M+1).

Example 75

4-(3-Chlorophenyl)-1-[3-(5,11-dihydro-7-methoxy[1]benzoxepino[2,3-b]pyridin-5-ylidene)propyl]piperidin-4-ol The titled compound was prepared by following the procedure of example 45, step 3, but replacing 4-(4-chlorophenyl)-4-hydroxypiperidine with 4-(3-chlorophenyl)-4-hydroxypiperidine.

$^1$H-NMR (CDCl$_3$) δ: 1.61–1.75(2H,m), 1.98(1H,brs), 1.99(2H,dt), 2.25(3H,s), 2.30–2.76(8H,m), 3.73(3H,s), 5.22 (2H,brs), 5.95(0.1H,t, E isomer), 6.04(0.9H,t, Z isomer), 6.71–6.89(3H,m), 6.95(1H,dd), 7.15–7.20(0.3H,m, E isomer), 7.21–7.35(2.7H,m, Z isomer), 7.53(0.9H,dd, Z isomer), 7.65(0.1H,dd, E isomer), 8.35(0.1H,dd, E isomer), 8.45(0.9H,dd, Z isomer). MS m/z: 477(M+1)

Example 76

4-(2-Chlorophenyl)-1-[3-(5,11-dihydro-7-methoxy[1]benzoxepino[2,3-b]pyridin-5-ylidene)propyl]piperidin-4-ol The titled compound was prepared by following the procedure of example 45, step 3, but replacing 4-(4-chlorophenyl)-4-hydroxypiperidine with 4-(2-chlorophenyl)-4-hydroxypiperidine.

$^1$H-NMR (CDCl$_3$) δ: 1.98–2.08(2H,m), 2.24(2H,dt), 2.38–2.78(9H,m), 3.77(3H,s), 5.27(2H,brs), 6.08(1H,t), 6.82–6.75(3H,m), 7.28–7.19(3H,m), 7.33(1H,dd), 7.49(1H, dd), 7.58(1H,dd), 8.40(0.1H,dd, Z isomer), 8.47(0.9H,dd, E isomer). MS m/z: 477(M+1)

Example 77

1-[3-(5,11-Dihydro-7-methoxy[1]benzoxepino[2,3-b]pyridin-5-ylidene)propyl]-4-(4-fluorophenyl)piperidin-4-ol The titled compound was prepared by following the procedure of example 45, step 3, but replacing 4-(4-chlorophenyl)-4-hydroxypiperidine with 4-(4-fluorophenyl)-4-hydroxypiperidine.

$^1$H-NMR (CDCl$_3$) δ: 1.58–1.72(2H,m), 2.04(2H,dt), 2.22–2.78(9H,m), 3.75(3H,s), 5.26(2H,brs), 6.09(1H,t), 6.70–6.88(3H,m), 7.00(2H,dd), 7.23(1H,dd), 7.42(2H,dd), 7.56(1H,dd), 8.41(1H,dd). MS m/z: 461(M+1)

Example 78

1-[3-(5,11-Dihydro-7-methoxy[1]benzoxepino[2,3-b]pyridin-5-ylidene)propyl]-4-(p-tolyl)piperidin-4-ol The titled compound was prepared by following the procedure of example 45, step 3, but replacing 4-(4-chlorophenyl)-4-hydroxypiperidine with 4-(p-tolyl)-4-hydroxypiperidine.

$^1$H-NMR (CDCl$_3$) δ: 1.65–1.78(2H,m), 2.02(2H,dt), 2.31 (3H,s), 2.24–2.75(9H,m), 3.75(3H,s), 5.25(2H,brs), 6.07(1H,t), 6.72–6.84(3H,m), 7.13(2H,d), 7.23(1H,dd), 7.34 (1H,d), 7.56(1H,dd), 8.43(1H,dd). MS m/z: 457(M+1).

Example 79

4-(3,4-Dichlorophenyl)-1-[3-(5,11-dihydro-7-methoxy[1]benzoxepino[2,3-b]pyridin-5-ylidene)propyl]piperidin-4-ol The titled compound was prepared by following the procedure of example 45, step 3, but replacing 4-(4-chlorophenyl)-4-hydroxypiperidine with 4-(3,4-dichlorophenyl)-4-hydroxypiperidine.

$^1$HNMR (CDCl$_3$) d: 1.58–1.72(2H,m), 1.84(1H,brs), 2.02 (2H,td), 2.32–2.72 (8H,m), 3.76(3H,s), 5.27(2H,brs), 5.95 (0.1H,t, E isomer), 6.07(0.9H,t, Z isomer), 6.72–6.85 (3H, M), 7.12–7.20(0.2H,m, E isomer), 7.21–7.32(0.18H,m, Z isomer), 7.32–7.45(1H,m), 7.52–7.56(2H,m), 8.37(0.9H,dd, E siomer), 8.45(0.1H,dd, Z isomer). MS m/z: 512(M+1)

Example 83

4-(5-Chloropyridin-2-yl)-1-[3-(5,11-dihydro-7-methoxy[1]benzoxepino[2,3-b]pyridin-5-ylidene)propyl]piperidin-4-ol The titled compound was prepared by following the procedure of example 45, step 3, but replacing 4-(4-chlorophenyl)-4-hydroxypiperidine with 4-(5-chloropyridin-2-yl)-4-hydroxypiperidine.

$^1$H-NMR (CDCl$_3$) δ: 1.77–1.82(2H,m), 2.36–2.94(11H, m), 3.77(3H,brs), 5.26(2H,brs), 6.07(1H,t), 6.76–6.84(3H, m), 7.26(1H,dd), 7.57(1H,dd), 8.49–7.48(1H,dd), 8.42–8.53 (3H,m). MS m/z: 478(M+1)

Example 85

4-(5-Chloro-2-keto-1-benzimidazolinyl)-1-[3-(5,11-dihydro-7-methoxy[1]benzoxepino[2,3-b]pyridin-5-ylidene)propyl]piperidine The titled compound was prepared by following the procedure of example 45, step 3, but replacing 4-(4-chlorophenyl)-4-hydroxypiperidine with 4-(5-chloro-2-keto-1-benzimidazolinyl)piperidine.

$^1$H-NMR (CDCl$_3$) δ: 1.68–1.72(2H,m), 2.03–2.60(8H, m), 2.90–3.02(2H,m), 3.78(3H,s), 4.32–4.21(1H,m), 5.29 (2H,brs), 5.95(0.1H,t, E siomer), 6.08(0.9H,t,Z isomer), 6.70–6.92(3H,m), 7.02(1H,dd), 7.08–7.20(1H,m), 7.26(1H, dd), 7.58(0.9H,dd, Z isomer), 7.70(0.1H,dd, E isomer), 8.42(0.1H,dd, E isomer), 8.48(0.9H,dd, Z isomer), 10.5(1H, s). (NH is not observed in the spectrum) MS m/z: 517(M+1)

Example 86

4-(p-Chloroanilino)-1-[3-(5,11-dihydro-7-methoxy[1]benzoxepino[2,3-b]pyridin-5-ylidene)propyl]piperidine The titled compound was prepared by following the procedure of example 45, step 3, but replacing 4-(4-chlorophenyl)-4-hydroxypiperidine with 4-(p-chloroanilino)piperidine.

$^1$H-NMR (CDCl$_3$) δ: 1.20–1.54(2H,m), 1.85–2.20(4H, m), 2.24–2.60(4H,m), 2.73(2H,m), 3.18(1H,m), 3.77(3H,s), 5.27(2H,brs), 6.06(1H,t), 6.47(2H,m), 6.68–6.90(3H,m), 7.07(2H,m), 7.24(1H,dd), 7.57(1H,dd), 8.48(1Hdd). NH signal was not observed. MS m/z: 476(M+1)

Example 89

1-[3-(5,11-Dihydro-7-methoxy[1]benzoxepino[2,3-b]pyridin-5-ylidene)propyl]-4-(p-tosyl)piperazine The titled compound was prepared by following the procedure of example 45, step 3, but replacing 4-(4-chlorophenyl)-4-hydroxypiperidine with 1-(p-tosyl)piperazine.

$^1$H-NMR (CDCl$_3$) δ: 2.20–2.54(11H,m), 2.82–3.10(4H, m), 3.73(3H,s), 5.16(2H,brs), 6.00(1H,t), 6.66–6.85(3H,m), 7.21(1H,dd), 7.31(2H,m), 7.51(1H,dd), 7.61(2H,m), 8.45 (1H,dd). MS m/z: 506(M+1)

Example 90

1'-[3-(5,11-Dihydro-7-methoxy[1]benzoxepino[2,3-b]pyridin-5-ylidene)propyl]spiro[isobenzofuran-1(3H),4'-piperidine]

The titled compound was prepared by following the procedure of example 45, step 3, but replacing 4-(4-chlorophenyl)-4-hydroxypiperidine with spiro[isobenzofuran-1(3H),4'-piperidine].

$^1$H-NMR (CDCl$_3$) δ: 1.62–1.82(2H,m), 1.92(2H,dt), 2.25–2.85(8H,m), 3.76(3H,s), 5.03(2H,s), 5.30(2H,brs), 6.11(1H,t), 6.68–6.90(3H,m), 7.02–7.34(5H,m), 7.58(1H, dd), 8.48(1H,dd). MS m/z: 455(M+1)

Example 91

5-Chloro-1'-[3-(5,11-dihydro-7-methoxy[1]benzoxepino[2,3-b]pyridin-5-ylidene)propyl]spiro[isobenzofuran-1(3H),4'-piperidine]

The titled compound was prepared by following the procedure of example 45, step 3, but replacing 4-(4-chlorophenyl)-4-hydroxypiperidine with 5-chlorospiro[isobenzofuran-1(3H),4'-piperidine].

$^1$H-NMR (CDCl$_3$) δ: 1.69–1.74(2H,m), 1.81–1.93(2H,m), 2.30–2.44(4H,m), 2.52–2.63(2H,m), 2.71–2.75(2H,m), 3.79(3H,s), 5.00(2H,s), 5.28(2H,brs), 6.09(1H,t), 6.73–6.84 (3H,m), 7.03(1H,d), 7.17–7.28(3H,m), 7.58(1H,dd), 8.49 (1H,dd). MS m/z: 489(M+1)

Example 111

4-(4-Chlorophenyl)-1-[3-(5,11-dihydro[1]benzothiepino[2,3-b]pyridin-5-ylidene)propyl]piperidin-4-ol The titled compound was prepared by following the procedure of example 45, but replacing 5,11-dihydro-7-methoxy[1]benzoxepino[2,3-b]pyridin-5-one with 5,11-dihydro[1]benzothiepino[2,3-b]pyridin-5-one.

$^1$H-NMR (CDCl$_3$) d: 1.66–1.78(3H,m), 2.04–2.65(10H, m), 3.66(1H,brd), 5.05(1H,brd), 6.03(1H,t), 7.04–7.46(10H, m), 8.44(1H,dd). MS m/z: 463(M+1)

Example 114

4-(4-Chlorophenyl)-1-[3-(5,11-dihydro-8-methoxy[1]benzoxepino[2,3-b]pyridin-5-ylidene)propyl]piperidin-4-ol The titled compound was prepared by following the procedure of example 45, but replacing 5,11-dihydro-7-methoxy[1]benzoxepino[2,3-b]pyridin-5-one with 5,11-dihydro-8-methoxy[1]benzoxepino[2,3-b]pyridin-5-one.

$^1$H-NMR (CDCl$_3$) d: 1.66–1.70(3H,m), 1.98–2.09(2H,m), 2.34–2.70(8H,m), 3.75(3H,s), 5.32(2H,brs), 6.02(1H,t), 6.39(1H,d), 6.51(1H,dd), 7.19–7.44(6H,m), 7.57(1H,dd), 8.49(1H,dd). MS m/z: 477(M+1)

Example 115

4-(4-Chlorophenyl)-1-[3-(5,11-dihydro-7-methyl[1]benzoxepino[2,3-b]pyridin-5-ylidene)propyl]piperidin-4-ol The titled compound was prepared by following the procedure of example 45, but replacing 5,11-dihydro-7-methoxy[1]benzoxepino[2,3-b]pyridin-5-one with 5,11-dihydro-7-methyl[1]benzoxepino[2,3-b]pyridin-5-one.

$^1$H-NMR (CDCl$_3$) δ: 1.50(1H,brs), 1.66–1.70(2H,m), 1.98–2.10(2H,m), 2.28(3H,s), 2.34–2.42(4H,m), 2.52–2.57 (2H,m), 2.66–2.70(2H,m), 5.30(2H,brs), 6.08(1H,t), 6.76 (1H,d), 6.97(1H,dd), 7.09(1H,d), 7.24–7.44(5H,m), 7.57(1H,dd), 8.49(1H,dd). MS m/z: 461(M+1)

Example 117

1-[3-(7-Chloro-5,11-dihydro[1]benzoxepino[2,3-b]pyridin-5-ylidene)propyl]-4-(4-chlorophenyl)piperidin-4-ol The titled compound was prepared by following the procedure of example 45, but replacing 5,11-dihydro-7-methoxy[1]benzoxepino[2,3-b]pyridin-5-one with 7-chloro-5,11-dihydro[1]benzoxepino[2,3-b]pyridin-5-one.

$^1$H-NMR (CDCl$_3$) δ: 1.66–1.71(3H,m), 2.00–2.10(2H, m), 2.36–2.44(4H,m), 2.52–2.57(2H,m), 2.66–2.70(2H,m), 5.32(2H,brs), 6.13(1H,t), 6.78(1H,d), 7.11(1H,dd), 7.26–7.44(5H,m), 7.58(1H,dd), 8.51(1H,dd). MS m/z: 481 (M+1)

Example 118

1-[3-(7-Carboxy-5,11-dihydro[1]benzoxepino[2,3-b]pyridin-5-ylidene)propyl]-4-(4-chlorophenyl)piperidin-4-ol A mixture of the product of example 169 (500 mg), potassium acetate (330 mg), palladium(II) diacetate (10 mg), 1,1'-bis(diphenylphosphino)ferrocene (93 mg), in dimethylsulfoxide (10 ml) was purged with carbon monoxide for 5 minutes and stirred under a carbon monoxide balloon at 60° C. for 3 hours. Water was added to the reaction mixture, the precipitation was filtered. The solid were dissolved with ethyl acetate and dilute sodium hydroxide solution. The aqueous layer was separated and neutralized with dilute hydrochloric acid. The precipitation was filtered to give the titled compound (250 mg).

$^1$H-NMR (DMSO-d$_6$) δ: 1.45–1.55(2H,m), 1.75–1.85(2H,m), 2.36–2.62(8H,m), 5.42(2H,brs), 6.21(1H, t), 6.90(1H,d), 7.40–7.52(5H,m), 7.75(1H,dd), 7.83(1H,dd), 7.95(1H,d), 8.56(1H,dd). MS m/z: 491(M+1)

Example 120

4-(4-Chlorophenyl)-1-[3-(7-carboxymethyl-5,11-dihydro[1]benzoxepino[2,3-b]pyridin-5-ylidene)propyl]piperidin-4-ol To a solution of product of Example 290 (3.7 g) in methanol (74 ml), acetic acid (6 ml), and water (37 ml) were added sodium periodate (1.7 g) in water (15 ml) at 0° C., and the mixture was stirred at room temperature for 1 hour. To the reaction mixture were added amidosulfuric acid (1.2 g) and sodium chlorite (0.89 g) in water (10 ml), and the mixture was stirred at room temperature for 15 minutes. The reaction mixture was distilled off under reduced pressure into half volume. The residue was neutralized with 1N sodium hydroxide. The precipitation was filtered and washed with water to give the titled compound (2.6 g).

$^1$H-NMR (DMSO-d$_6$) δ: 1.45–1.50(2H,m), 1.73–1.82(2H,m), 2.24–2.50(8H,m), 3.50(2H,s), 4.84(1H, brs), 5.24(2H,brs), 6.13(1H,t), 6.74(1H,d), 7.06(1H,dd), 7.21(1H,d), 7.33–7.48(5H,m), 7.74(1H,dd), 8.50(1H,dd).

Example 122

4-(4-Chlorophenyl)-1-[3-(7-dimethylaminocarbonyl-methyl-5,11-dihydro[1]benzoxepino[2,3-b]pyridin-5-ylidene)propyl]piperidin-4-ol The titled compound was prepared by following the procedure of example 134, but replacing the product of example 133 with the product of example 120.

$^{1}$H-NMR (CDCl$_{3}$) δ: 1.65–1.70(2H,m), 1.95–2.06(2H, m), 2.31–2.66(9H,m), 2.93(3H,s), 3.00(3H,s), 3.61(2H,s), 5.29(2H,brs), 6.09(1H,t), 6.78(1H,d), 7.00(1H,dd), 7.20–7.43(6H,m), 7.56(1H,dd), 8.42(1H,dd). MS m/z: 532 (M+1)

Example 123

1-[3-(7-(2-Carboxy)ethyl-5,11-dihydro[1]benzoxepino[2,3-b]pyridin-5-ylidene)propyl]-4-(4-chlorophenyl)-piperidin-4-ol The titled compound was prepared by following the procedure of example 133, but replacing the product of example 48 with the product of example 288.

$^{1}$H-NMR (DMSO-d$_{6}$) δ: 1.44–1.49(2H,m), 1.70–1.82(2H,m), 2.22–2.48(10H,m), 2.75(2H,t), 4.82(1H, brs), 5.23(2H,brs), 6.14(1H,t), 6.71(1H,d), 7.04(1H,dd), 7.17(1H,d), 7.33–7.48(5H,m), 7.72(1H,dd), 8.49(1H,dd). MS m/z: 519(M+1)

Example 128

4-(4-Chlorophenyl)-1-[3-(5,11-dihydro-7-propoxy[1]benzoxepino[2,3-b]pyridin-5-ylidene)propyl]piperidin-4-ol The titled compound was prepared by following the procedure of example 46, but replacing ethyl iodide with propyl iodide.

$^{1}$H-NMR (CDCl$_{3}$) δ: 1.03(3H,t), 1.65–1.70(2H,m), 1.78 (2H,q), 1.98–2.09(2H,m), 2.37–2.45(4H,m), 2.51–2.56(2H, m), 2.66–2.70(2H,m), 3.88(2H,t), 5.26(2H,brs), 6.08(1H,t), 6.72–6.84(3H,m), 7.23–7.43(5H,m), 7.58(1H,dd), 8.43(1H, dd). MS m/z: 505(M+1)

Example 130

4-(4-Chlorophenyl)-1-[3-(7-cyclopropylmethyloxy-5,11-dihydro[1]benzoxepino[2,3-b]pyridin-5-ylidene)propyl]piperidin-4-ol The titled compound was prepared by following the procedure of example 46, but replacing ethyl iodide with cyclopropylmethyl bromide.

$^{1}$H-NMR (CDCl$_{3}$) δ: 0.31–0.37(2H,m), 0.60–0.67(2H, m), 1.21–1.28(1H,m), 1.66–1.72(3H,m), 2.01–2.11(2H,m), 2.37–2.71(8H,m), 3.77(2H,d), 5.27(2H,brs), 6.08(1H,t), 6.73–6.86(3H,m), 7.23–7.44(5H,m), 7.58(1H,dd), 8.47(1H, dd). MS m/z: 517(M+1)

Example 131

4-(4-Chlorophenyl)-1-[3-(5,11-dihydro-7-(2-dimetylaminoethyl)oxy)[1]benzoxepino[2,3-b]pyridin-5-ylidene)propyl]piperidin-4-ol The titled compound was prepared by following the procedure of example 46, but replacing ethyl iodide with 2-(dimethylamino)ethyl chloride hydrochloride.

$^{1}$H-NMR (CDCl$_{3}$) δ: 1.71–1.76(2H,m), 2.12–2.21(2H, m), 2.38(6H,s), 2.40–2.79(11H,m), 4.07(2H,t), 5.28(2H,brs), 6.07(1H,t), 6.74–6.86(3H,m), 7.27–7.46(5H, m), 7.59(1H,dd), 8.49(1H,dd). MS m/z: 534(M+1)

Example 132

4-(4-Chlorophenyl)-1-[3-(5,11-dihydro-7-(tetrazol-5-yl)methyloxy)[1]benzoxepino[2,3-b]pyridin-5-ylidene)propyl]piperidin-4-ol Step 1

4-(4-Chlorophenyl)-1-[3-(5,11-dihydro-7-(2-triphenylmethyltetrazol-5-yl)methyloxy)[1]benzoxepino[2,3-b]pyridin-5-ylidene)propyl]piperidin-4-ol was prepared by following the procedure of example 46, but replacing ethyl iodide with (2-triphenylmethyltetrazol-5-yl)methyl chloride.

$^{1}$H-NMR (CDCl$_{3}$) δ: 1.64–1.70(3H,m), 2.02–2.15(2H, m), 2.35–2.71(8H,m), 5.29(2H,brs), 5.33(2H,s), 6.03(1H,t), 6.77(1H,d), 6.83(1H,dd), 6.96(1H,d), 7.04–7.08(6H,m), 7.23–7.45(14H,m), 7.54(1H,dd), 8.50(1H,dd).

Step 2

A solution of the product of step 1 (530 mg) in acetone (2.5 ml), acetic acid (2.5 ml) and water (2.5 ml) was stirred at 55° C. for 30 minutes. The reaction mixture was distilled off under reduced pressure. The residue was washed with methanol to give the titled compound (280 mg).

$^{1}$H-NMR(DMSO-d$_{6}$) δ: 1.69–1.74(2H,m), 1.99–2.09(2H, m), 2.95–3.14(8H,m), 5.18(2H,brs), 5.20(2H,s), 6.14(1H,t), 6.76(1H,d), 6.93(1H,dd), 7.04(1H,d), 7.39–7.48(5H,m), 7.78(1H,dd), 8.52(1H,dd). MS m/z: 545(M+1)

Example 133

1-[3-(7-Carboxymethyloxy-5,11-dihydro[1]benzoxepino[2,3-b]pyridin-5-ylidene)propyl]-4-(4-chlorophenyl)piperidin-4-ol To a solution of product of example 48 (3.0 g) in methanol (50 ml) was added 1N sodium hydroxide solution (8 ml) and the mixture stirred at room temperature for 1 hour. The reaction mixture was distilled off under reduced pressure. The residue was dissolved with water and neutralized with 1N hydrochloric acid. The precipitation was filtered and washed with water to give the titled compound (2.6 g).

$^{1}$H-NMR (DMSO-d$_{6}$) δ: 1.48–1.53(2H,m), 1.76–1.88(2H,m), 2.32–2.60(8H,m), 4.60(2H,s), 5.18(2H, brs), 6.16(1H,t), 6.72–6.84(3H,m), 7.34–7.48(5H,m), 7.73 (1H,dd), 8.50(1H,dd). MS m/z: 521(M+1)

Example 134

4-(4-Chlorophenyl)-1-[3-(5,11-dihydro-7-dimethylaminocarbonylmethyloxy[1]benzoxepino[2,3-b]pyridin-5-ylidene)propyl]piperidin-4-ol To a solution of product of example 133 (420 mg) in dimethylformamide (17 ml) were added 1-hydroxybenzotriazol hydrate (250 mg), 1-(3-dimethylaminopropyl)-3-ethylcarbodiimide hydrochloride (310 mg), dimethylamine hydrochloride (270 mg) and triethylamine (0.45 ml), and the mixture stirred at room temperature for 12 hours. Water and chloroform were added to the reaction mixture, the organic layer was separated and washed with saturated aqueous sodium chloride, and dried with magnesium sulfate. The solvent was distilled off under reduced pressure to give the titled compound (380 mg).

$^1$H-NMR (CDCl$_3$) δ: 1.67–1.71(2H,m), 1.95–2.11(3H,m), 2.37–2.71(8H,m), 2.97(3H,s), 3.08(3H,s), 4.64(2H,s), 5.27 (2H,brs), 6.09(1H,t), 6.74–6.82(2H,m), 6.93(1H,d), 7.24–7.44(5H,m), 7.58(1H,dd), 8.47(1H,dd). MS m/z: 548 (M+1)

Example 135

4-(4-Chlorophenyl)-1-[3-(5,11-dihydro-7-morpholinocarbonylmethyloxy[1]benzoxepino[2,3-b]pyridin-5-ylidene)propyl]piperidin-4-ol The titled compound was prepared by following the procedure of example 134, but replacing dimethylamine hydrochloride with morpholine.

$^1$H-NMR (CDCl$_3$) δ: 1.67–1.71(2H,m), 1.87(1H,brs), 2.00–2.11(2H,m), 2.38–2.71(8H,m), 3.61–3.68(8H,m), 4.65 (2H,s), 5.27(2H,brs), 6.09(1H,t), 6.74–6.83(2H,m), 6.90(1H,d), 7.25–7.44(5H,m), 7.58(1H,dd), 8.48(1H,dd). MS m/z: 590(M+1)

Example 138

4-(4-Chlorophenyl)-1-[3-(5,11-dihydro-7-(1-ethoxycarbonyl-1-methylethyl)oxy[1]benzoxepino[2,3-b]pyridin-5-ylidene)propyl]piperidin-4-ol The titled compound was prepared by following the procedure of example 46, but replacing ethyl iodide with ethyl 2-bromoisobutylate.

$^1$H-NMR (CDCl$_3$) δ: 1.27(3H,t), 1.56(6H,s), 1.63–1.71 (3H,m), 2.01–2.10(2H,m), 2.35–2.70(8H,m), 4.24(2H,q), 5.28(2H,brs), 6.05(1H,t), 6.67–6.75(2H,m), 6.87(1H,d), 7.24–7.44(5H,m), 7.56(1H,dd), 8.49(1H,dd). MS m/z: 577 (M+1)

Example 139

1-[3-(7-(1-Carboxy-1-methylethyl)oxy-5,11-dihydro[1]benzoxepino[2,3-b]pyridin-5-ylidene)propyl]-4-(4-chlorophenyl)piperidin-4-ol The titled compound was prepared by following the procedure of example 133, but replacing product of example 48 with product of example 138.

$^1$H-NMR (DMSO-d$_6$) δ: 1.45–1.52(8H,m), 1.79–1.85(2H,m), 2.28–2.53(8H,m), 5.19(2H,brs), 6.07(1H, t), 6.69–6.73(2H,m), 6.85(1H,d), 7.33–7.47(5H,m), 7.71(1H,dd), 8.48(1H,dd). MS m/z: 549(M+1)

Example 140

1-[3-(5,11-Dihydro-7-methoxy[1]benzoxepino[2,3-b]pyridin-5-ylidene)propyl]-4-(4-methoxyphenyl)piperidin-4-ol The titled compound was prepared by following the procedure of example 45, step 3, but replacing 4-(4-chlorophenyl)-4-hydroxypiperidine with 4-(4-methoxyphenyl)-4-hydroxypiperidine.

$^1$H-NMR (CDCl$_3$) δ: 1.62–1.75(2H,m), 2.08(2H,dt), 2.41–2.76(9H,m), 3.77(3H,s), 3.78(3H,s), 5.26(2H,brs), 6.06(1H,t), 6.75–6.871(5H,m), 7.23(1H,dd), 7.38(2H,d), 7.57(1H,dd), 8.45(1H,dd). MS m/z: 473(M+1)

Example 141

4-(4-Cyanophenyl)-1-[3-(5,11-dihydro-7-methoxy[1]benzoxepino[2,3-b]pyridin-5-ylidene)propyl]piperidin-4-ol The titled compound was prepared by following the procedure of example 45, step 3, but replacing 4-(4-chlorophenyl)-4-hydroxypiperidine with 4-(4-cyanophenyl)-4-hydroxypiperidine.

$^1$H-NMR (CDCl$_3$) δ: 1.58–1.70(2H,m), 2.03(2H,t), 2.31–2.64(7H,m), 2.65–2.78(2H,m), 3.75(3H,s), 5.26(2H, brs), 5.95(0.1H,t, E isomer), 6.05(0.9H,t, Z isomer), 6.70–6.80(3H,m), 7.22(1H,dd), 7.54–7.68(5H,m), 8.31(0.1H,dd, E iosmer), 8.39(0.9H,dd, Z isomer). MS m/z: 468(M+1)

Example 142

1-[3-(5,11-Dihydro-7-methoxy[1]benzoxepino[2,3-b]pyridin-5-ylidene)propyl]-4-(4-hydroxyphenyl)piperidin-4-ol The titled compound was prepared by following the procedure of example 45, step 3, but replacing 4-(4-chlorophenyl)-4-hydroxypiperidine with 4-(4-hydroxyphenyl)-4-hydroxypiperidine.

$^1$HNMR (CDCl$_3$) δ: 1.76–1.88(2H,m). 2.08–2.22(2H,m), 2.45–2.95(9H,m), 3.76(3H,s), 5.28(2H,brs), 5.95(0.3H,t, E isomer), 6.04(0.7H,t, Z iosmer), 6.69–6.72(3H,m), 6.90(2H, d), 7.20–7.30(3H,m), 7.56(0.7H,dd, Z isomer), 7.67(0.3H, dd, E isomer), 8.46(0.7H,dd, Z isomer), 8.47(0.3H,dd, E isomer). OH signal was not observed. MS m/z: 473(M+1)

Example 143

1-[3-(5,11-Dihydro-7-methoxy[1]benzoxepino[2,3-b]pyridin-5-ylidene)propyl]-4-(4-fluoro-3-methylphenyl)piperidin-4-ol The titled compound was prepared by following the procedure of example 45, step 3, but replacing 4-(4-chlorophenyl)-4-hydroxypiperidine with 4-(4-fluoro-3-methylphenyl)-4-hydroxypiperidine.

$^1$H-NMR (CDCl$_3$) δ: 1.62–1.75(2H,m), 2.05(1H,brs), 2.09(2H,dt), 2.25(3H,s), 2.30–2.76(8H,m), 3.76(3H,s), 5.26 (2H, brs), 5.96(0.1H,t, E isomer), 6.07(0.9H,t, Z isomer), 6.75–6.89(3H,m), 6.93(1H,t), 7.11–7.20(0.3H,m, E isomer), 7.21–7.35(0.24H,m, Z isomer), 7.56(0.9H,dd, E isomer), 7.67(0.1H, dd, E isomer), 8.38(0.1H,dd, E isomer), 8.45 (0.9H,dd, Z isomer). MS m/z: 475(M+1)

Example 144

4-(3,4-difluorophenyl)-1-[3-(5,11-dihydro-7-methoxy[1]benzoxepino[2,3-b]pyridin-5-ylidene)propyl]piperidin-4-ol The titled compound was prepared by following the procedure of example 45, step 3, but replacing 4-(4-chlorophenyl)-4-hydroxypiperidine with 4-(3,4-difluorophenyl)-4-hydroxypiperidine.

$^1$H-NMR (CDCl$_3$) δ: 1.58–1.72(2H,m), 1.96(2H,dt), 2.33–2.71(8H,m), 3.73(3H,s), 5.23(2H,brs), 5.94(0.1H,t, E isomer), 6.04(0.9H,t, Z isomer), 8.38–8.36(0.9H,m, Z isomer), 6.68–6.79(3H,m), 6.98–7.38(4H,m), 7.50–7.62(0.9H, m, Z isomer), 7.63–7.68(0.1H,m, E isomer), 8.29–8.32

(0.1H,m, E isomer), 8.32–8.44(0.9H,m, Z isomer). OH signal was not observed. MS m/z: 479(M+1)

Example 145

4-(4-Chloro-3-trifuluoromethylphenyl)-1-[3-(5,11-dihydro-7-methoxy[1]benzoxepino [2,3-b]pyridin-5-ylidene)propyl]piperidin-4-ol The titled compound was prepared by following the procedure of example 45, step 3, but replacing 4-(4-chlorophenyl)-4-hydroxypiperidine with 4-(4-chloro-3-trifluoromethylphenyl)-4-hydroxypiperidine.

$^1$H-NMR (CDCl$_3$) δ: 1.62–1.74(2H,m), 2.10(2H,dt), 2.35–2.80(8H,m), 2.42(1H, brs), 3.76(3H,s), 5.26(2H,brs), 6.07(0.9H,t, Z isomer), 6.03(0.1H,t, E isomer), 6.82–6.71 (3H,m), 7.24(1H,dd), 7.43(1H,d), 7.56(1.8H,dd, Z isomer), 7.65(0.2H,dd, E isomer) 7.83(1H,d), 8.36(0.1H,dd, E isomer), 8.44(0.9H,dd, Z iosmer), MS m/z: 545(M+1)

Example 146

4-(3,5-dichlorophenyl)-1-[3-(5,11-dihydro-7-methoxy[1]benzoxepino[2,3-b]pyridin-5-ylidene)propyl]piperidin-4-ol The titled compound was prepared by following the procedure of example 45, step 3, but replacing 4-(4-chlorophenyl)-4-hydroxypiperidine with 4-(3,5-dichlorophenyl)-4-hydroxypiperidine.

$^1$H-NMR (CDCl$_3$) δ: 1.58–2.22(5H,m), 2.38–2.77(8H,m), 3.76(3H,s), 5.26(2H,brs), 5.92(0.1H,t, E isomer), 6.07 (0.9H,t, Z isomer), 6.83–6.71(3H,m), 7.19–7.42(4H,m), 7.56(0.9H,dd, Z isomer), 7.68(0.1H,dd, E isomer), 8.38 (0.1H,dd, E isomer), 8.45(0.9H,dd, Z isomer). MS m/z: 512(M+1)

Example 147

1-[3-(5,11-Dihydro-7-methoxy[1]benzoxepino[2,3-b]pyridin-5-ylidene)propyl]-4-(2-pyridyl)piperidin-4-ol The titled compound was prepared by following the procedure of example 45, step 3, but replacing 4-(4-chlorophenyl)-4-hydroxypiperidine with 4-(2-pyridyl)-4-hydroxypiperidine $^1$H-NMR (CDCl$_3$) d: 1.54–1.65(2H,m), 2.06(2H,dt), 2.07 (1H,brs), 2.35–2.62(7H,m), 2.73–2.87(2H,m), 3.78(3H,s), 5.28(2H, brs), 6.08(1H,t), 6.72–6.85(3H,m), 7.14–7.29(2H, m), 7.57(1H,d), 7.70(1H,dd), 8.48(2H,dd). MS m/z: 444(M+1)

Example 148

1-[3-(5,11-Dihydro-7-methoxy[1]benzoxepino[2,3-b]pyridin-5-ylidene)propyl]-4-(3-pyridyl)piperidin-4-ol The titled compound was prepared by following the procedure of example 45, step 3, but replacing 4-(4-chlorophenyl)-4-hydroxypiperidine with 4-(3-pyridyl)-4-hydroxypiperidine.

$^1$H-NMR (CDCl$_3$) δ: 1.65–1.78(2H,m), 2.08(2H,dt), 2.37–2.88(7H,m), 2.63–2.79(2-H,m), 3.78(3H,s), 5.28(2H, brs), 6.02(0.1H,t, E isomer), 6.07(0.9H,t, Z isomer), 6.70–6.84(3H,m), 7.22–7.32(3H,m), 7.56(1H,dd), 7.77(1H, dd), 8.46(0.9H,d), 8.57(0.1H,dd, E isomer), 8.73(1H,dd). MS m/z: 444(M+1)

Example 149

1-[3-(5,11-Dihydro-7-methoxy[1]benzoxepino[2,3-b]pyridin-5-ylidene)propyl]-4-(4-pyridyl)piperidin-4-ol The titled compound was prepared by following the procedure of example 45, step 3, but replacing 4-(4-chlorophenyl)-4-hydroxypiperidine with 4-(4-pyridyl)-4-hydroxypiperidine.

$^1$H-NMR (CDCl$_3$) δ: 1.58–1.72(2H,m), 2.03(2H,dt), 2.34–2.89(8H,m), 2.96(1H,brs), 3.76(3H,s), 5.25(2H, brs), 6.06(1H,t), 6.72–6.83(3H,m), 7.24(1H,dd), 7.37(2H,dd), 7.56(1H,dd), 8.45(1H,dd), 8.48(2H,dd). MS m/z: 444(M+1)

Example 150

1-[3-(5,11-Dihydro-7-methoxy[1]benzoxepino[2,3-b]pyridin-5-ylidene)propyl]-4-(4-trifluoromethylphenyl)piperidin-4-ol The titled compound was prepared by following the procedure of example 45, step 3, but replacing 4-(4-chlorophenyl)-4-hydroxypiperidine with 4-(4-trifluoromethylphenyl)-4-hydroxypiperidine.

$^1$H-NMR (CDCl$_3$) δ: 1.64–1.75(2H,m), 2.01(1H, brs), 2.16(2H,dt), 2.38–2.86(8H,m), 3.76(3H,s), 5.26(2H,brs), 6.04(1H,t), 6.72–6.84(3H,m), 7.23(1H,dd), 7.56(5H,m), 8.42(1H,dd). MS m/z: 511(M+1)

Example 151

4-(4-Chlorophenyl)-1-[3-(5,11-dihydro-7-hydroxy[1]benzoxepino[2,3-b]pyridin-5-ylidene)propyl]piperidine The titled compound was prepared by following the procedure of example 44, step 2, but replacing 4-(4-chlorophenyl)-4-hydroxypiperidine with 4-(4-chlorophenyl)piperidine.

$^1$H-NMR (CDCl$_3$) δ: 1.62–1.92(4H,m), 1.94–2.18(2H, m), 2.28–2.64(5H,m), 2.99(2H,m), 5.25(2H,brs), 6.00(1H, t), 6.60–6.82(3H,m), 7.02–7.36(5H,m), 7.50(1H,dd), 8.47 (1H,dd). OH signal was not observed. MS m/z: 447(M+1)

Example 152

4-(4-Chlorophenyl)-1-[3-(5,11-dihydro-7-ethoxy[1]benzoxepino[2,3-b]pyridin-5-ylidene)propyl]piperidine The titled compound was prepared by following the procedure of example 46, but replacing the product of example 44 with the product of example 151.

$^1$H-NMR (CDCl$_3$) δ: 1.40(3H,t), 1.52–2.14(6H,m), 2.30–2.57(5H,m), 2.94(2H,m), 4.00(2H,q), 5.28(2H,brs), 6.07(1H,t), 6.68–6.86(3H,m), 7.05–7.36(5H,m), 7.58(1H, m), 8.49(1H,m). MS m/z: 475(M+1)

Example 153

4-(4-Chlorophenyl)-1-[3-(5,11-dihydro-7-ethoxycarbonylmethyloxy[1]benzoxepino[2,3-b]pyridin-5-ylidene)propyl]piperidine The titled compound was prepared by following the procedure of example 48, but replacing the product of example 44 with the product of example 151.
$^1$H-NMR (CDCl$_3$) δ: 1.29(3H,t), 1.56–1.85(4H,m), 1.99 (2H,dt), 2.28–2.55(5H,m), 2.91(2H,m), 4.27(2H,q), 4.58 (2H,s), 5.28(2H,brs), 6.09(1H,t), 6.68–6.95(3H,m), 7.07–7.32(5H,m), 7.58(1H,dd), 8.49(1H,dd). MS m/z: 533 (M+1)

Example 154

1-[3-(7-(Carboxymethyloxy-5,11-dihydro[1]benzoxepino[2,3-b]pyridin-5-ylidene)propyl]-4-(4-chlorophenyl)piperidine The titled compound was prepared by following the procedure of example 133, but replacing the product of example 48 with the product of example 153.
$^1$H-NMR (CD$_3$OD) δ: 1.82–2.17(4H,m), 2.69(2H,m), 2.86(1H,m), 3.07(2H,m), 3.30(2H,m), 3.57(2H,m), 4.57(2H,s), 5.21(2H,brs), 6.10(1H,t), 6.70–7.04(3H,m), 7.16–7.38(4H,m), 7.44(1H,m), 7.77(1H,m), 8.47(1H,m). COOH signal was not observed. MS m/z: 505(M+1)

Example 155

4-(4-Chlorophenyl)-1-[3-(5,11-dihydro-7-dimethylaminocarbonylmethyloxy[1]benzoxepino[2,3-b]pyridin-5-ylidene)propyl]piperidine The titled compound was prepared by following the procedure of example 134, but replacing the product of example 133 with the product of example 154.
$^1$H-NMR (CDCl$_3$) δ: 1.58–1.92(4H,m), 2.04(2H,m), 2.30–2.68(5H,m), 2.93(2H,m), 2.98(3H,s), 3.08(3H,s), 4.65 (2H,s), 5.28(2H,brs), 6.07(1H,t), 6.70–6.98(3H,m), 7.08–7.36(5H,m), 7.60(1H,m), 8.50(1H,m). MS m/z: 532 (M+1)

Example 156

1-[3-(7-(2-Acetoxyethyl)oxy-5,11-dihydro[1]benzoxepino[2,3-b]pyridin-5-ylidene)propyl]piperidine The titled compound was prepared by following the procedure of example 50, but replacing the product of example 44 with the product of example 151.
$^1$H-NMR (CDCl$_3$) δ: 1.55–1.88(4H,m), 1.90–2.32(2H, m), 2.10(3H,s), 2.28–2.60(5H,m), 2.82–3.02(2H,m), 4.14 (2H,dd), 4.41(2H,dd), 5.29(2H,brs), 6.08(1H,t), 6.72–6.90 (3H,m), 7.18–7.34(5H,m), 7.57(1H,m), 8.50(1H,m). MS m/z: 533(M+1)

Example 157

4-(4-Chlorophenyl)-1-[3-(5,11-dihydro-7-(2-hydroxyethyl)oxy[1]benzoxepino[2,3-b]pyridin-5-ylidene)propyl]piperidine The titled compound was prepared by following the procedure of example 51, but replacing the product of example 50 with the product of example 156.

$^1$H-NMR (CD$_3$OD) δ: 1.66–1.98(4H,m), 2.40–2.73(5H, m), 2.82–2.94(2H,m), 3.22(2H,m), 3.84(2H,dd), 4.01(2H, dd), 5.23(2H,brs), 6.13(1H,t), 6.64–6.98(3H,m), 7.13–7.34 (4H,m), 7.45(1H,m), 7.77(1H,m), 8.47(1H,m). OH signal was not observed. MS m/z: 491(M+1)

Example 158

4-(4-Chlorophenyl)-1-[3-(5,11-dihydro-7-(1-ethoxycarbonyl-1-methylethyl)oxy[1]benzoxepino[2,3-b]pyridin-5-ylidene)propyl]piperidine The titled compound was prepared by following the procedure of example 138, but replacing the product of example 44 with the product of example 151.
$^1$H-NMR (CDCl$_3$) d: 1.28(3H,t), 1.56(6H,s), 1.56–1.85 (4H,m), 1.97(2H,dt), 2.28–2.55(5H,m), 2.93(2H,m), 4.24 (2H,q), 5.28(2H,brs), 6.04(1H,t), 6.62–6.95(3H,m), 7.07–7.32(5H,m), 7.57(1H,dd), 8.50(1H,dd). MS m/z: 561 (M+1)

Example 159

1-[3-(7-(1-Carboxy-1-methylethyl)oxy-5,11-dihydro[1]benzoxepino[2,3-b]pyridin-5-ylidene)propyl]-4-(4-chlorophenyl)piperidine The titled compound was prepared by following the procedure of example 133, but replacing the product of example 48 with the product of example 158.
$^1$H-NMR (CD$_3$OD) d: 1.50(6H,s), 1.82–2.18(4H,m), 2.70 (2H,m), 2.87(1H,m), 3.12(2H,m), 3.30(2H,m), 3.60(2H,m), 5.25(2H,brs), 6.07(1H,t), 6.67–7.04(3H,m), 7.16–7.38(4H, m), 7.58(1H,m), 7.96(1H,m), 8.52(1H,m). COOH signal was not observed. MS m/z: 533(M+1)

Example 160

1-[3-(8-Bromo-5,11-dihydro[1]benzoxepino[2,3-b]pyridin-5-ylidene)propyl]-4-(4-chlorophenyl)piperidine The titled compound was prepared by following the procedure of example 65, but replacing the product of example 45, step 2 with the product of example 54, step 1.
$^1$H-NMR (CDCl$_3$) d: 1.50–1.86(4H,m), 1.98(2H,m), 2.26–2.60(5H,m), 2.88(2H,m), 5.30(2H,brs), 6.09(1H,t), 6.96–7.36(8H,m), 7.57(1H,dd), 8.51(1H,dd). MS m/z: 509, 511(M+1)

Example 161

1-[3-(8-Carboxy-5,11-dihydro[1]benzoxepino[2,3-b]pyridin-5-ylidene)propyl]-4-(4-chlorophenyl)piperidine To a solution of 1-[3-(8-Bromo-5,11-dihydro[1]benzoxepino[2,3-b]pyridin-5-ylidene)propyl]-4-(4-chlorophenyl) piperidine (Example 160) (130 mg) in THF (1.0 ml) was added 1.6M n-butyllithium hexane solution (0.17 ml) at −78° C. After stirring 10 minutes at the same temperature, CO$_2$ (dry-ice) was added to the mixture. After being warned to ambient temperature, the mixture was stirred for 30 minutes at the same temperature. The mixture was concentrated in vacuo. The resulting oil was purified by silica gel chromatography eluted with dichloromethane-methanol (5:1) to give the titled compound ¹H-NMR (CD₃OD) δ: 1.55–1.95(4H,m), 2.17(2H,dt), 2.32–2.78(5H,m), 3.00(2H,m), 5.30(2H,brs), 6.19(1H,t), 7.08–7.54(8H,m), 7.76(1H,dd), 8.45(1H,dd). COOH signal was not observed. MS m/z: 475(M+1)

Example 162

1-[3-(7-Bromo-5,11-dihydro[1]benzoxepino[2,3-b]pyridin-5-ylidene)propyl]-4-(4-chlorophenyl)piperidin-4-ol The titled compound was prepared by following the procedure of example 45, but replacing 5,11-dihydro-7-methoxy[1]benzoxepino[2,3-b]pyridin-5-one with 8-bromo-5,11-dihydro[1]benzoxepino[2,3-b]pyridin-5-one.

¹H-NMR (CDCl₃) δ: 1.60–1.71(3H,m), 1.98–2.09(2H,m), 2.34–2.69(8H,m), 5.32(2H,brs), 6.13(1H,t), 6.73(1H,d), 7.22–7.44(7H,m), 7.57(1H,dd), 8.52(1H,dd). MS m/z: 525, 527(M+1)

Example 163

4-(4-Chlorophenyl)-1-[3-(5,11-dihydro-7-ethyl[1]benzoxepino[2,3-b]pyridin-5-ylidene)propyl]piperidin-4-ol The titled compound was prepared by following the procedure of example 45, but replacing 5,11-dihydro-7-methoxy[1]benzoxepino[2,3-b]pyridin-5-one with 5,11-dihydro-7-ethyl[1]benzoxepino[2,3-b]pyridin-5-one.

¹H-NMR (CDCl₃) d: 1.23(3H,t), 1.52(1H,brs), 1.66–1.71(2H,m), 1.98–2.06(2H,m), 2.35–2.70(11H,m), 5.31(2H,brs), 6.09(1H,t), 6.79(1H,d), 7.01(1H,dd), 7.11(1H,d), 7.25–7.44(5H,m), 7.58(1H,dd), 8.49(1H,dd). MS m/z: 475(M+1)

Example 164

4-(4-Chlorophenyl)-1-[3-(5,11-dihydro-8-vinyl[1]benzoxepino[2,3-b]pyridin-5-ylidene)propyl]piperidin-4-ol The titled compound was prepared by following the procedure of example 45, but replacing 5,11-dihydro-7-methoxy[1]benzoxepino[2,3-b]pyridin-5-one with 5,11-dihydro-8-vinyl[1]benzoxepino[2,3-b]pyridin-5-one.

¹H-NMR (CDCl₃) d: 1.66–1.71(3H,m), 2.00–2.10(2H,m), 2.36–2.70(8H,m), 5.22(2H,d), 5.34(2H,brs), 5.70(1H,d), 6.11(1H,t), 6.61(1H,dd), 6.89(1H,d), 6.99(1H,dd), 7.24–7.44(6H,m), 7.58(1H,dd), 8.49(1H,dd). MS m/z: 473(M+1)

Example 165

4-(4-Chlorophenyl)-1-[3-(5,11-dihydro-8-ethyl[1]benzoxepino[2,3-b]pyridin-5-ylidene)propyl]piperidin-4-ol A mixture of the product of example 164 (100 mg) and Pd—C (20 mg) in ethanol (2 ml) stirred under a hydrogen balloon at room temperature for 1 hour. The mixture was filtered through the celite and distilled off under reduced pressure. The residue was purified by preparative thin layer chromatography eluting with chloroform-methanol (15:1) to give the titled compound (50 mg).

¹H-NMR (CDCl₃) δ: 1.22(3H,t), 1.55–1.77(3H,m), 2.00–2.13(2H,m), 2.33–2.74(10H,m), 5.32(2H,brs), 6.07(1H,t), 6.70(1H,d), 6.78(1H,dd), 7.19–7.44(6H,m), 7.57(1H,dd), 8.49(1H,dd). MS m/z: 475(M+1)

Example 166

4-(4-Chlorophenyl)-1-[3-(5,11-dihydro-9-methoxy[1]benzoxepino[2,3-b]pyridin-5-ylidene)propyl]piperidin-4-ol The titled compound was prepared by following the procedure of example 45, but replacing 5,11-dihydro-7-methoxy[1]benzoxepino[2,3-b]pyridin-5-one with 5,11-dihydro-9-methoxy[1]benzoxepino[2,3-b]pyridin-5-one.

¹H-NMR (CDCl₃) δ: 1.65–1.70(2H,m), 1.95–2.06(2H,m), 2.15(1H,brs), 2.37–2.67(8H,m), 3.83(3H,s), 5.43(2H,brs), 6.09(1H,t), 6.79–6.91(3H,m), 7.22–7.43(5H,m), 7.57(1H,dd), 8.44(1H,dd). MS m/z: 477(M+1)

Example 167

4-(4-Chlorophenyl)-1-[3-(5,11-dihydro[1]benzoxepino[4,3-c]pyridin-5-ylidene)propyl]piperidin-4-ol The titled compound was prepared by following the procedure of example 45, but replacing 5,11-dihydro-7-methoxy[1]benzoxepino[2,3-b]pyridin-5-one with 5,11-dihydro[1]benzoxepino[4,3-c]pyridin-5-one.

¹H-NMR (CDCl₃) δ: 1.67–1.71(2H,m), 1.97–2.08(2H,m), 2.16(1H,s), 2.40–2.69(8H,m), 5.16(2H,brs), 6.14(1H,t), 6.80(1H,dd), 6.91–6.97(1H,m), 7.13–7.19(1H,m), 7.26–7.44(6H,m), 7.50–8.54(2H,m). MS m/z: 447(M+1)

Example 168

4-(4-Chlorophenyl)-1-[3-(5,11-dihydro[1]benzoxepino[4,3-d]pyrimidin-5-ylidene)propyl]piperidin-4-ol The titled compound was prepared by following the procedure of example 45, but replacing 5,11-dihydro-7-methoxy[1]benzoxepino[2,3-b]pyridin-5-one with 5,11-dihydro[1]benzoxepino[4,3-d]pyrimidin-5-one.

¹H-NMR (CDCl₃) δ: 1.68–1.72(2H,m), 1.90(1H,brs), 2.06–2.19(2H,m), 2.41–2.78(8H,m), 5.20(2H,s), 6.12(1H,t), 7.14–7.45(8H,m), 8.72(1H,s), 8.97(1H,s). MS m/z: 448(M+1)

Example 169

4-(4-Chlorophenyl)-1-[3-(5,11-dihydro-7-trifluoromethanesulfonyloxy[1]benzoxepino[2,3-b]pyridin-5-ylidene)propyl]piperidin-4-ol To a solution of product of example 44 (1.0 g) in pyridine (10 ml) was added trifluoromethanesulfonic acid anhydride (0.55 ml) at 0° C., and the mixture was stirred at room temperature for 1 hour. Water and diethyl ether were added to the reaction mixture, the organic layer was separated and washed with saturated aqueous sodium chloride, and dried with magnesium sulfate. The solvent was distilled off under reduced pressure, and the residue was purified by silica gel chromatography eluting with ethyl acetate-methanol (10:1) to give the titled compound (1.1 g).

¹H-NMR (CDCl₃) δ: 1.56(1H,brs), 1.66–1.71(2H,m), 1.97–2.09(2H,m), 2.35–2.69(8H,m), 5.35(2H,brs) 6.15(1H,t), 6.88(1H,d), 7.05(1H,dd), 7.21–7.44(6H,m), 7.60(1H,dd), 8.54(1H,dd). MS m/z: 595(M+1)

Example 170

1-[3-(7-Allyl-5,11-dihydro[1]benzoxepino[2,3-b]pyridin-5-ylidene)propyl]-4-(4-chlorophenyl)piperidin-4-ol A mixture of the product of example 169 (240 mg), allyltributyltin (0.19 ml), dichlorobis(triphenylphosphine)palladium(II) (30 mg) and lithium chloride (76 mg), in dimethylformamide (3 ml) was heated under argon at 120° C. for 2 hours. Aqueous ammonium fluoride solution and ethyl acetate were added to the reaction mixture, the organic layer was separated and washed with saturated aqueous sodium chloride, and dried with magnesium sulfate. The solvent was distilled off under reduced pressure, and the residue was purified by silica gel chromatography eluting with chloroform-methanol (10:1) to give the titled compound (180 mg).

$^1$H-NMR (CDCl$_3$) δ: 1.62–1.72(3H,m), 2.03–2.11 (2H,m), 2.39–2.73(8H,m), 3.31(2H,d), 5.04–5.11(2H,m), 5.29(2H,brs), 5.87–6.02(1H,m), 6.06(1H,t), 6.77(1H,d), 6.99(1H,dd), 7.10(1H,d), 7.23–7.43(5H,m), 7.57(1H,dd), 8.40(1H,dd).

Example 171

1-[3-(7-(2-t-Butoxycarboxy)ethenyl-5,11-dihydro[1]benzoxepino[2,3-b]pyridin-5-ylidene)propyl]-4-(4-chlorophenyl)piperidin-4-ol A mixture of the product of example 169 (1.7 g), t-butyl acrylate (0.85 ml), triethylamine (2.5 ml), 1,1'-bis(diphenylphosphino)ferrocene (250 mg) and palladium(II) diacetate (33 mg) in dimethylformamide (3 ml) was heated under argon at 90° C. for 24 hours. Water ethyl acetate were added to the reaction mixture, the organic layer was separated and washed with saturated aqueous sodium chloride, and dried with magnesium sulfate. The solvent was distilled off under reduced pressure, and the residue was purified by silica gel chromatography eluting with ethyl acetate-methanol (30:1) to give the titled compound (780 mg).

$^1$H-NMR (CDCl$_3$) δ: 1.45(9H,s), 1.63–1.71(3H,m), 1.98–2.10(2H,m), 2.35–2.72(8H,m), 5.35(2H,brs), 6.15(1H,t), 6.26(1H,d), 6.83(1H,d), 7.22–7.44(7H,m), 7.53(1H,d), 7.58(1H,dd), 8.52(1H,dd).

Example 172

1-[3-(7-(2-Carboxy)ethenyl-5,11-dihydro[1]benzoxepino[2,3-b]pyridin-5-ylidene)propyl]-4-(4-chlorophenyl)piperidin-4-ol The product of example 171 (330 mg) was dissolved with 4N hydrochloric acid 1,4-dioxane solution (4 ml), and stirred at room temperature for 1 hour. The solvent was distilled off under reduced pressure. Water was added to the residue, and neutralized with sodium hydroxide solution. The precipitation was filtered to give the titled compound (190 mg).

$^1$H-NMR (DMSO-d$_6$) δ: 1.45–1.52(2H,m), 1.72–1.84(2H,m), 2.25–2.58(8H,m), 5.25(2H,brs), 6.28(1H,t), 6.43(1H,d), 6.82(1H,d), 7.34–7.60(8H,m), 7.75(1H,dd), 8.52(1H,dd).

Example 173

4-(4-Chlorophenyl)-1-[3-(5,11-dihydro-7-propargyloxy[1]benzoxepino[2,3-b]pyridin-5-ylidene)propyl]piperidin-4-ol The titled compound was prepared by following the procedure of example 46, but replacing ethyl iodide with propargyl chloride.

$^1$H-NMR (CDCl$_3$) δ: 1.66–1.71 (2H,m), 1.79(1H,brs), 1.99–2.10(2H,m), 2.35–2.71(9H,m), 4.66(2H,d), 5.28(2H,brs), 6.10(1H,t), 6.80–6.93(3H,m), 7.24–7.46(5H,m), 7.59(1H,dd), 8.48(1H,dd). MS m/z: 501(M+1)

Example 174

4-(4-Chlorophenyl)-1-[3-(7-cyclopentoxy-5,11-dihydro[1]benzoxepino[2,3-b]pyridin-5-ylidene)propyl]piperidin-4-ol The titled compound was prepared by following the procedure of example 46, but replacing ethyl iodide with cyclopentyl bromide.

$^1$H-NMR (CDCl$_3$) δ: 1.54–2.18(13H,m), 2.41–2.72(8H,m), 4.66–4.73(1H,m), 5.27(2H,brs), 6.08(1H,t), 6.70–6.87(3H,m), 7.23–7.44(5H,m), 7.58(1H,dd), 8.49(1H,dd). MS m/z: 531(M+1)

Example 175

4-(4-Chlorophenyl)-1-[3-(5,11-dihydro-7-(2-methoxyethyl)oxy)[1]benzoxepino[2,3-b]pyridin-5-ylidene)propyl]piperidin-4-ol The titled compound was prepared by following the procedure of example 46, but replacing ethyl iodide with 2-methoxyethyl chloride.

$^1$H-NMR (CDCl$_3$) δ: 1.66–1.75(3H,m), 2.00–2.11(2H,m), 2.36–2.71(8H,m), 3.45(3H,s), 3.71–3.75(2H,m), 4.07–4.11(2H,m), 5.27(2H,brs), 6.09(1H,t), 6.75–6.91(3H,m), 7.23–7.44(5H,m), 7.57(1H,dd), 8.48(1H,dd). MS m/z: 521(M+1)

Example 176

4-(4-Chlorophenyl)-1-[3-(7-(1-dimethyaminocarbonyl-1-methyl)ethyloxy-5,11-dihydro[1]benzoxepino[2,3-b]pyridin-5-ylidene)propyl]piperidin-4-ol The titled compound was prepared by following the procedure of example 134, but replacing the product of example 133 with the product of example 139.

$^1$H-NMR (CDCl$_3$) δ: 1.59(6H,s), 1.67–1.72(2H,m), 1.99–2.09(2H,m), 2.36–2.70(9H,m), 2.96(3H,s), 3.21(3H,s), 5.25(2H,brs), 6.02(1H,t), 6.60–6.77(3H,m), 7.24–7.44(5H,m), 7.58(1H,dd), 8.44(1H,dd). MS m/z: 576(M+1)

Example 177

4-(4-Chlorophenyl)-1-[3-(5,11-dihydro-7-(1-ethoxycarbonylethyl)oxy[1]benzoxepino[2,3-b]pyridin-5-ylidene)propyl]piperidin-4-ol The titled compound was prepared by following the procedure of example 46, but replacing ethyl iodide with ethyl 2-bromopropionate.

1H-NMR (CDCl₃) δ: 1.25(3H,t), 1.59(3H,d), 1.65–1.70 (2H,m), 1.98–2.08(2H,m), 2.35–2.68(8H,m), 2.80(1H,brs), 4.21(2H,q), 4.68(1H,q), 5.24(2H,brs), 6.07(1H,t), 6.68–6.79 (2H,m), 6.88(1H,d), 7.22–7.44(5H,m), 7.56(1H,dd), 8.40 (1H,dd).

Example 178

1-[3-(7-(1-Carboxyethyl)oxy-5,111-dihydro[1]benzoxepino[2,3-b]pyridin-5-ylidene)propyl]-4-(4-chlorophenyl)piperidin-4-ol The titled compound was prepared by following the procedure of example 133, but replacing product of example 48 with product of example 177.

1H-NMR (DMSO-d₆) δ: 1.46(3H,d), 1.58–1.63(2H,m), 1.98–2.06(2H,m), 2.41–2.45(2H,m), 2.72–2.86(6H,m), 4.74 (1H,q), 5.18(2H,brs), 6.11(1H,t), 6.73(2H,s), 6.84(1H,s), 7.36–7.47(5H,m), 7.73(1H,dd), 8.50(1H,dd). MS m/z: 535 (M+1)

Example 179

4-(4-Chlorophenyl)-1-[3-(5,11-dihydro-7-(1-ethoxycarbonyl)cyclobutoxy[1]benzoxepino[2,3-b]pyridin-5-ylidene)propyl]piperidin-4-ol The titled compound was prepared by following the procedure of example 46, but replacing ethyl iodide with ethyl 2-bromocyclobutanecarboxylate.

1H-NMR (CDCl₃) δ: 1.19(3H,t), 1.67–1.71(2H,m), 1.92–2.11(5H,m), 2.33–2.77(12H,m), 4.21(2H,q), 5.25(2H, brs), 6.05(1H,t), 6.47(1H,dd), 6.70(1H,d), 6.73(1H,d), 7.23–7.44(5H,m), 7.55(1H,dd), 8.44(1H,dd).

Example 180

1-[3-(7-(1-Carboxy)cyclbutoxy-5,11-dihydro[1]benzoxepino[2,3-b]pyridin-5-ylidene)propyl]-4-(4-chlorophenyl)piperidin-4-ol The titled compound was prepared by following the procedure of example 133, but replacing product of example 48 with product of example 179.

1H-NMR (DMSO-d₆) δ: 1.60–1.65(2H,m), 1.86–2.08(4H,m), 2.24–2.90(12H,m), 5.17(2H,brs), 6.05(1H,t), 6.50(1H,dd), 6.66(1H,d), 6.73(1H,d), 7.37–7.48 (5H,m), 7.74(1H,dd), 8.51(1H,dd). MS m/z: 561(M+1)

Example 181

1-[3-(7-Carbamoylmethyloxy-5,11-dihydro[1]benzoxepino[2,3-b]pyridin-5-ylidene) propyl]-4-(4-chlorophenyl)piperidin-4-ol The titled compound was prepared by following the procedure of example 134, but replacing dimethylamine hydrochloride with ammonium hydroxide.

1H-NMR (CDCl₃) δ: 1.66–1.71(2H,m), 1.98–2.09(2H, m), 2.21(1H,brs), 2.38–2.70(8H,m), 4.45(2H,s), 5.28(2H, brs), 6.09(1H,t), 6.11(1H,brs), 6.58(1H,brs), 6.74–6.85(3H, m), 7.24–7.44(5H,m), 7.58(1H,dd), 8.47(1H,dd). MS m/z: 520(M+1)

Example 182

4-(4-Chlorophenyl)-1-[3-(5,11-dihydro-7-methylaminocarbonylmethyloxy[1]benzoxepino[2,3-b]pyridin-5-ylidene)propyl]piperidin-4-ol The titled compound was prepared by following the procedure of example 134, but replacing dimethylamine hydrochloride with methylamine.

1H-NMR (CDCl₃) δ: 1.67–1.72(2H,m), 1.99–2.10(2H, m), 2.36–2.70(9H,m), 2.89(3H,d), 4.45(2H,s), 5.28(2H,brs), 6.08(1H,t), 6.66(1H,brs), 6.73–6.84(3H,m), 7.25–7.45(5H, m), 7.58(1H,dd), 8.47(1H,dd). MS m/z: 534(M+1)

Example 183

1-[3-(5,11-Dihydro-7-methoxy[1]benzoxepino[2,3-b]pyridin-5-ylidene)propyl]-4-(4-hydroxyphenyl) piperidine The titled compound was prepared by following the procedure of example 45, step 3, but replacing 4-(4-chlorophenyl)-4-hydroxypiperidine with 4-(4-hydroxyphenyl) piperidine.

1H-NMR (CDCL3) δ: 1.52–1.88(4H,m), 2.01(2H,dt), 2.28–2.60(5H,m), 2.93(2H,m), 3.79(3H,s), 5.28(2H,brs), 6.08(1H,t), 6.68–6.88(3H,m), 7.05–7.36(5H,m), 7.58(1H, dd), 8.50(1H,dd). MS m/z: 461(M+1)

Example 184

1-[3-(5,11-Dihydro-7-methoxy[1]benzoxepino[2,3-b]pyridin-5-ylidene)propyl]-4-(2-hydroxyphenyl) piperidine The titled compound was prepared by following the procedure of example 45, step 3, but replacing 4-(4-chlorophenyl)-4-hydroxypiperidine with 4-(2-hydroxyphenyl) piperidine.

¹H-NMR (CDCl₃) δ: 1.78–1.92(4H,m), 2.12–2.25(2H, m), 2.32–2.70(4H,m), 2.80–2.97(1H,m), 3.01–3.15(2H,m), 3.77(3H,s), 3.78(1H,brs), 5.28(2H,brs), 6.03(1H,t), 6.74–6.86(4H,m), 7.05(1H,dd), 7.11(1H,dd), 7.23–7.28(2H, m), 7.56(1H,dd), 8.48(1H,dd), OH signal was not observed. MS m/z: 443(M+1)

Example 185

4-(7-Chloro-1,2-benzisoxazol-3-yl)-1-[3-(5,11-dihydro-7-methoxy[1]benzoxepino[2,3-b]pyridin-5-ylidene)propyl]piperidine The titled compound was prepared by following the procedure of example 45, step 3, but replacing 4-(4-chlorophenyl)-4-hydroxypiperidine with 4-(7-chloro-1,2-benzisoxazol-3-yl)piperidine. This tetrahydropyridine was prepared by the same method described in J. Med. Chem. 28:761–769 (1985).

¹H-NMR (CDCl₃) δ: 1.94–2.20(6H,m), 2.30–2.60(4H, m), 2.86–3.14(3H,m), 3.79(3H,s), 5.29(2H,brs), 6.10(1H,t), 6.70–6.88(3H,m), 7.22(1H,t), 7.27(1H,dd), 7.50(1H,dd), 7.57–7.68(2H,m), 8.49(1H,dd).

Example 186

4-(7-Chloroindol-3-yl)-1-[3-(5,11-dihydro-7-methoxy[1]benzoxepino[2,3-b]pyridin-5-ylidene)propyl]piperidine The titled compound was prepared by following the procedure of example 45, step 3, but replacing 4-(4-chlorophenyl)-4-hydroxypiperidine with 4-(7-chloroindol-3-yl)piperidine. This piperidine was prepared by the same method described in *J. Med. Chem.* 36:4006–4014 (1993) and following hydrogenation described in Example 58, step 3.

$^1$H-NMR(CDCl$_3$) δ: 1.66–1.88(2H,m), 1.92–2.22(4H,m), 2.32–2.63(4H,m), 2.78(1H,m), 2.97(2H,m), 3.79(3H,s), 5.29(2H,brs), 6.09(1H,t), 6.70–6.87(3H,m), 6.97–7.07(2H,m), 7.12–7.30(2H,m), 7.52(1H,m), 7.59(1H,dd), 8.45(1H,brs), 8.50(1H,dd).

Example 187

Figure 8A:
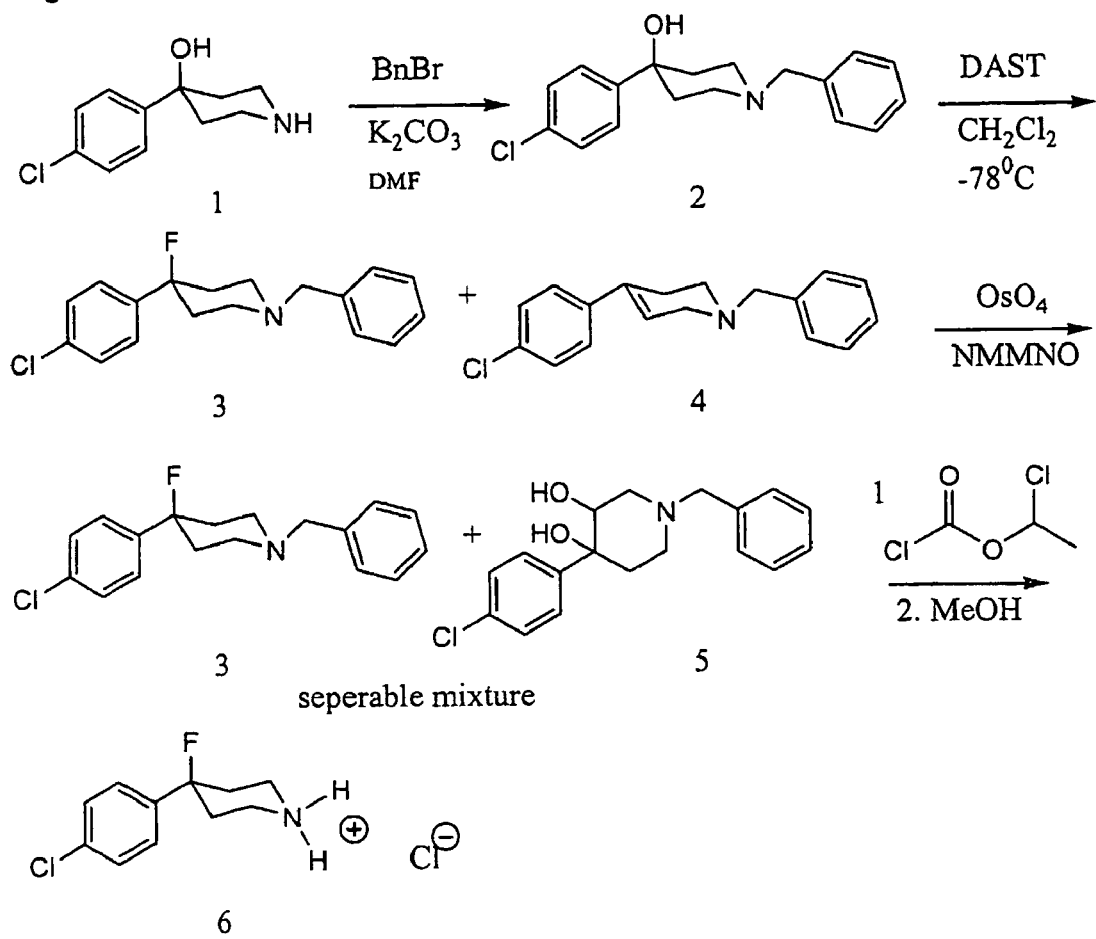
FIG. 8A is a schematic showing the preparation of 4-(4-chlorophenyl)-4-fluoropiperidine.
Figure 8B:
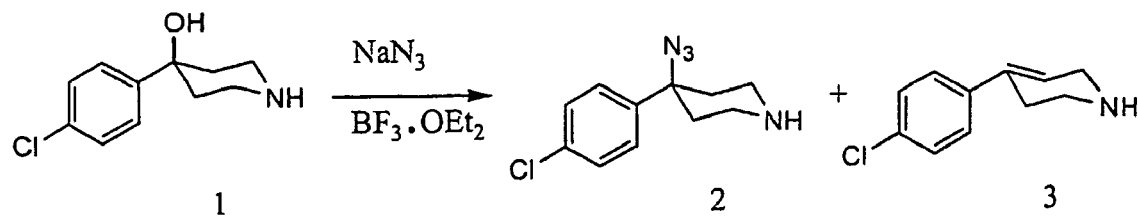
FIG. 8B is a schematic showing the preparation of 4-4-azido-4-(4-chlorophenyl)piperidine.

4-Azido-4-(4-chlorophenyl)-1-[3-(5,11-dihydro-7-methoxy[1]benzoxepino[2,3-b]pyridin-5-ylidene)propyl]piperidine Step 1 4-azido-4-(4-chlorophenyl)piperidine (15): FIG. 8b

To a cold (0° C.) solution of 1 (3.0 g, 14 mmol) in anhydrous dioxane (15 mL) under an inert atmosphere was added NaN$_3$ (1.0 g, 15.4 mmol) followed by the slow dropwise addition of and BF$_3$.OEt (4.4 mL, 35 mmol). The reaction was stirred at 0° C. for 3 hrs and was quenched at 0° C. by the slow careful addition of saturated aqueous NaHCO$_3$ to basicity. The organic layer was separated and dried over Na$_2$SO$_4$. The reaction mixture was purified via silica gel flash chromatography eluting a 2 g 1:3 mixture of azidopiperidine 2 and olefin 3 with 2% MeOH/CH$_2$Cl$_2$. The mixture was taken directly on to the next reaction.

Step 2

The titled compound was prepared by then following the procedure of example 45, step 3, with the above reaction mixture (thereby replacing 4-(4-chlorophenyl)-4-hydroxypiperidine with 4-azido-4-(4-chlorophenyl)piperidine)), but limiting the amount of bromide to 0.25 equivalents.

$^1$H-NMR (CDCL$_3$) δ: 1.88(2H,m), 2.55–2.85(4H,m), 3.00–3.30(6H,m). 3.75(3H,s), 5.19(2H,brs), 5.97(1H,t), 6.68–6.65(3H,m), 7.20–7.46(5H,m), 7.63(1H,dd), 8.35(1H,dd). MS m/z: 477(M+1–N$_2$+H$_2$)

Example 188

Methyl 1-[3-(5,11-dihydro-7-methoxy[1]benzoxepino[2,3-b]pyridin-5-ylidene)propyl]-4-phenylpiperidin-4-carboxylate The titled compound was prepared by following the procedure of example 45, step 3, but replacing 4-(4-chlorophenyl)-4-hydroxypiperidine with methyl 4-phenylpiperidin-4-carboxylate.

$^1$H-NMR (CDCl$_3$) δ: 1.82–2.15(4H,m), 2.28–2.60(6H,m), 2.78–2.82(2H,m), 3.62(3H,s), 3.68(3H,s), 5.26(2H,brs), 5.95(0.1H,t, E isomer), 6.05(0.9H,t, Z isomer), 6.82–6.70(3H,m), 7.33–7.22(6H,m), 7.65(0.1H,dd, Z isomer), 7.55(0.9H,dd, Z isomer), 8.39(0.1H,dd, E isomer), 8.48(0.9H,dd, Z isomer). MS m/z: 485(M+1)

Example 189

1-[3-(5,11-Dihydro-7-methoxy[1]benzoxepino[2,3-b]pyridin-5-ylidene)propyl]-4-phenylpiperidin-4-carboxylic acid The titled compound was prepared by following the procedure of example 133, but replacing product of example 48 with product of example 188.

$^1$H-NMR (CD$_3$OD) δ: 2.16–2.23(2H,m), 2.69–2.91(4H,m), 3.00–3.16(2H,m), 3.37–3.25(2H,m), 3.68–3.73(2H,m), 3.76(3H,s), 5.34(2H,brs), 6.24(1H,t), 6.70–7.04(3H,m), 7.26–7.55(5H,m), 7.79–7.89(1H,m), 8.21–8.34(1H,m), 8.56–8.62(0.1H,m), 8.63–8.77(0.9H,m), MS m/z: 471(M+1)

Example 190

1-(2-Chlorophenylsulfonyl)-4-[3-(5,11-Dihydro-7-methoxy[1]benzoxepino[2,3-b]pyridin-5-ylidene)propyl]piperazine The titled compound was prepared by following the procedure of example 45, step 3, but replacing 4-(4-chlorophenyl)-4-hydroxypiperidine with 1-(2-chlorophenylsulfonyl)piperazine.

$^1$H-NMR (CDCl$_3$) δ: 2.20–2.58(8H,m), 3.12–3.38(4H,m), 3.76(3H,s), 5.22(2H,brs), 6.03(1H,t), 6.64–6.90(3H,m), 7.23(1H,dd), 7.32–7.60(4H,m), 8.01(1H,dd), 8.48(1H,dd). MS m/z: 526(M+1)

Example 191

1-(3-Chlorophenylsulfonyl)-4-[3-(5,11-Dihydro-7-methoxy[1]benzoxepino[2,3-b]pyridin-5-ylidene)propyl]piperazine The titled compound was prepared by following the procedure of example 45, step 3, but replacing 4-(4-chlorophenyl)-4-hydroxypiperidine with 1-(3-chlorophenylsulfonyl)piperazine.

$^1$H-NMR (CDCl$_3$) δ: 2.20–2.60(8H,m), 2.82–3.12(4H,m), 3.76(3H,s), 5.18(2H,brs), 6.00(1H,t), 6.64–6.90(3H,m), 7.23(1H,dd), 7.42–7.78(5H,m), 8.48(1H,dd). MS m/z: 526(M+1)

Example 192

1-(4-Chlorophenylsulfonyl)-4-[3-(5,11-Dihydro-7-methoxy[1]benzoxepino[2,3-b]pyridin-5-ylidene)propyl]piperazine The titled compound was prepared by following the procedure of example 45, step 3, but replacing 4-(4-chlorophenyl)-4-hydroxypiperidine with 1-(4-chlorophenylsulfonyl)piperazine.

$^1$H-NMR (CDCl$_3$) δ: 2.20–2.56(8H,m), 2.82–3.10(4H,m), 3.76(3H,s), 5.18(2H,brs), 5.99(1H,t), 6.62–6.92(3H,m), 7.23(1H,dd), 7.42–7.78(5H,m), 8.48(1H,dd). MS m/z: 526(M+1)

Example 193

4-(4-Chlorophenyl)-1-[3-(5,11-dihydro-7-hydroxy[1]benzoxepino[2,3-b]pyridin-5-ylidene)propyl]-1,2,3,6-tetrahydropyridine The titled compound was prepared by following the procedure of example 44, step 2, but replacing 4-(4-chlorophenyl)-4-hydroxypiperidine with 4-(4-chlorophenyl)-1,2,3,6-tetrahydropyridine.

$^1$H-NMR (CDCl$_3$) d: 2.37–2.72(8H,m), 3.07(2H,m), 5.25 (2H,brs), 6.00(1H,m), 6.07(1H,t), 6.60–6.78(3H,m), 7.18–7.47(5H,m), 7.56(1H,dd), 8.50(1H,dd). OH signal was not observed. MS m/z: 445(M+1)

Example 194

4-(4-Chlorophenyl)-1-[3-(5,11-dihydro-7-methoxy[1]benzoxepino[2,3-b]pyridin-5-ylidene)propyl]-1,2,3,6-tetrahydropyridine The titled compound was prepared by following the procedure of example 45, step 3, but replacing 4-(4-chlorophenyl)-4-hydroxypiperidine with 4-(4-chlorophenyl)-1,2,3,6-tetrahydropyridine.

$^1$H-NMR (CDCl$_3$) δ: 2.37–2.72(8H,m), 3.06(2H,m), 3.78 (3H,s), 5.27(2H,brs), 5.99(1H,m), 6.10(1H,t), 6.72–6.90(3H,m), 7.20–7.44(5H,m), 7.60(1H,dd), 8.50(1H,dd). MS m/z: 459(M+1)

Example 195

4-(7-Chloroindol-3-yl)-1-[3-(5,11-dihydro-7-methoxy[1]benzoxepino[2,3-b]pyridin-5-ylidene)propyl]-1,2,3,6-tetrahydropyridine The titled compound was prepared by following the procedure of example 45, step 3, but replacing 4-(4-chlorophenyl)-4-hydroxypiperidine with 4-(7-chloroindol-3-yl)-1,2,3,6-tetrahydropyridine. This piperidine was prepared by the same method described in *J. Med. Chem.* 36:4006–4014 (1993).

$^1$H-NMR (CDCl$_3$) δ: 2.37–2.76(8H,m), 3.14(2H,m), 3.78 (3H,s), 5.29(2H,brs), 6.02–6.23(2H,m), 6.67–6.90(3H,m), 7.05(1H,dd), 7.12–7.33(3H,m), 7.60(1H,dd), 7.77(1H,m), 8.50(1H,dd), 9.06(1H,br s).

Example 196

5-Chloro-1'-[3-(5,11-dihydro-7-hydroxy[1]benzoxepino[2,3-b]pyridin-5-ylidene)propyl]spiro[isobenzofuran-1(3H),4'-piperidine]

The titled compound was prepared by following the procedure of example 44, step 2, but replacing 4-(4-chlorophenyl)-4-hydroxypiperidine with 5-chlorospiro[isobenzofuran-1(3H),4'-piperidine].

1H-NMR (CDCl$_3$) δ: 1.66–1.71(2H,m), 1.79–1.91(2H, m), 2.26–2.73(8H,m), 4.99(2H,s), 5.22(2H,brs), 6.07(1H,t), 6.63–6.70(2H,m), 6.76(1H,d), 7.06(1H,d), 7.19–7.32(3H, m), 7.60(1H,dd), 8.47(1H,dd), 8.63(1H,s). MS m/z: 475(M+1)

Example 197

5-Chloro-1'-[3-(5,11-dihydro-7-(2-methoxyethyl)oxy[1]benzoxepino[2,3-b]pyridin-5-ylidene)propyl]spiro[isobenzofuran-1(3H),4'-piperidine]

The titled compound was prepared by following the procedure of example 175, but replacing the product of example 44 with the product of example 196.

1H-NMR (CDCl$_3$) δ: 1.69–1.74(2H,m), 1.83–1.94(2H, m), 2.31–2.76(8H,m), 3.45(3H,s), 3.72–3.75(2H,m), 4.08–4.11(2H,m), 5.00(2H,s), 5.28(2H,brs), 6.09(1H,t), 6.74–6.82(2H,m), 6.89(1H,d), 7.04(1H,d), 7.17–7.28(3H, m), 7.57(1H,dd), 8.49(1H,dd). MS m/z: 531 (M+1)

Example 198

4-(4-Chlorophenyl)-1-[3-(7-dimethylaminocarbonyl-5,11-dihydro[1]benzoxepino[2,3-b]pyridin-5-ylidene)propyl]piperidin-4-ol The titled compound was prepared by following the procedure of example 134, but replacing the product of example 133 with the product of example 118.

1H-NMR (CDCl$_3$) δ: 1.65–1.70(2H,m), 1.99–2.09(3H, m), 2.32–2.69(8H,m), 2.17(3H,s), 5.35(2H,brs), 6.15(1H,t), 6.82(1H,d), 7.19(1H,dd), 7.28–7.46(6H,m), 7.58(1H,dd), 8.49(1H,dd).

Example 199

4-(4-Chlorophenyl)-1-[3-(7-(2-(1-hydroxy-2-methyl)propyl)oxy-5,11-dihydro[1]benzoxepino[2,3-b]pyridin-5-ylidene)propyl]piperidin-4-ol To a solution of product of example 138 (500 mg) in methanol (5 ml) was added sodium borohydride (330 mg), and the mixture was heated to reflux for 1 hour. The mixture was distilled off under reduced pressure. Water and ethyl acetate were added to the residue, the organic layer was separated and washed with saturated aqueous sodium chloride, and dried with magnesium sulfate. The solvent was distilled off under reduced pressure, and the residue was purified by silica gel chromatography eluting with chloroform-methanol (10:1) to give the titled compound (440 mg).

1H-NMR (CDCl$_3$) δ: 1.26(6H,s), 1.66–1.70(2H,m), 1.79 (1H.brs), 2.00–2.08(2H,m), 2.37–2.70(9H,m), 3.58(2H,s), 5.30(2H,brs), 6.05(1H,t), 6.75–6.84(2H,m), 6.91(1H,d), 7.26–7.44(5H,m), 7.58(1H,dd), 8.49(1H,dd). MS m/z: 535 (M+1)

Example 200

4-(4-Chlorophenyl)-1-[3-(7-(1-(2-methyl-2-hydroxy)propyl)oxy-5,11-dihydro[1]benzoxepino[2,3-b]pyridin-5-ylidene)propyl]piperidin-4-ol To a solution of product of example 48 (500 mg) in tetrahydrofuran (5 ml) was added 0.95M methylmagnesium bromide tetrahydrofuran solution (3.8 ml) at 0° C., and the mixture was stirred at room temperature for 20 minutes. Aqueous ammonium chloride solution and ethyl acetate were added to the mixture, the organic layer was separated and washed with saturated aqueous sodium chloride, and dried with magnesium sulfate. The solvent was distilled off under reduced pressure, and the residue was purified by silica gel chromatography eluting with chloroform-methanol (10:1) to give the titled compound (360 mg).

1H-NMR (CDCl$_3$) δ: 1.34(6H,s), 1.58(1H,brs), 1.66–1.71 (2H,m), 1.99–2.10(2H,m), 2.25(1H,brs), 2.36–2.71(8H,m), 3.77(2H,s), 5.28(2H,brs), 6.09(1H,t), 6.74–6.86(3H,m), 7.24–7.44(5H,m), 7.57(1H,dd), 8.49(1H,dd). MS m/z: 535 (M+1)

Example 203

4-(4-Chlorophenyl)-1-[3-(7-(2-ethoxy)ethyloxy)-5,11-dihydro[1]benzoxepino[2,3-b]pyridin-5-ylidene)propyl]piperidin-4-ol The titled compound was prepared by following the procedure of example 46, but replacing ethyl iodide with 2-ethoxyethyl bromide.

$^1$H-NMR (CDCl$_3$) δ: 1.24(3H,t), 1.66–1.75(3H,m), 2.00–2.11(2H,m), 2.36–2.71(8H,m), 3.59(2H,q), 3.71–0.75 (2H,m), 4.07–4.11(2H,m), 5.27(2H,brs), 6.09(1H,t), 6.75–6.91(3H,m), 7.23–7.44(5H,m), 7.57(1H,dd), 8.48(1H, dd). MS m/z: 535(M+1)

Example 205

4-(4-Chlorophenyl)-1-[3-(5,11-dihydro-7-(1-(2,3-dihydroxy)propyloxy)[1]benzoxepino[2,3-b]pyridin-5-ylidene)propyl]piperidin-4-ol The titled compound was prepared by following the procedure of example 46, but replacing ethyl iodide with glycidol.

$^1$H-NMR (CDCl$_3$) δ: 1.66–1.75(2H,m), 2.00–2.11 (2H, m), 2.36–2.71(8H,m), 3.62–3.76(2H,m), 3.94–4.02(4H,m), 4.21(2H,brs), 5.27(2H,brs), 6.09(1H,t), 6.76–6.86(3H,m), 7.23–7.44(5H,m), 7.57(1H,dd), 8.48(1H,dd). MS m/z: 537 (M+1)

Example 211

1-[3-(7-(1-Carbamoyl-1-methyl)ethyloxy-5,11-dihydro[1]benzoxepino[2,3-b]pyridin-5-ylidene)propyl]-4-(4-chlorophenyl)piperidin-4-ol The titled compound was prepared by following the procedure of example 176, but replacing dimethylamine hydrochloride with ammonium hydroxide.

$^1$H-NMR (CDCl$_3$) δ: 1.50(6H,s), 1.67–1.72(2H,m), 1.96–2.09(3H,m), 2.36–2.70(8H,m), 5.30(2H,brs), 5.70(1H, brs), 6.05(1H,t), 6.75–6.90(4H,m), 7.25–7.44(5H,m), 7.58 (1H,dd), 8.49(1H,dd). MS m/z: 548(M+1)

Example 212

4-(4-Chlorophenyl)-1-[3-(5,11-dihydro-7-(1-methylaminocarbonyl-1-methyl)ethyloxy[1]benzoxepino[2,3-b]pyridin-5-ylidene)propyl]piperidin-4-ol The titled compound was prepared by following the procedure of example 176, but replacing dimethylamine hydrochloride with methylamine.

$^1$H-NMR (CDCl$_3$) δ: 1.47(6H,s), 1.67–1.72(2H,m), 1.96–2.09(2H,m), 2.20(1H,brs), 2.36–2.70(8H,m), 2.87(3H, d), 5.29(2H,brs), 6.04(1H,t), 6.72–6.86(4H,m), 7.27–7.44 (5H,m), 7.58(1H,dd), 8.47(1H,dd). MS m/z: 562(M+1)

Example 215

4-(4-Chlorophenyl)-1-[3-(7-(2-dimethylaminocarboxy)ethenyl-5,11-dihydro[1]benzoxepino[2,3-b]pyridin-5-ylidene)propyl]piperidin-4-ol The titled compound was prepared by following the procedure of example 134, but replacing the product of example 133 with the product of example 172.

$^1$H-NMR (CDCl3) δ: 1.63–1.71(3H,m), 1.98–2.10(2H, m), 2.35–2.72(8H,m), 3.07(3H,s), 3.17(3H,s), 5.36(2H,brs), 6.16(1H,t), 6.76(1H,d), 6.84(1H,d), 7.28–7.45(7H,m), 7.59–7.65(2H,m), 8.52(1H,dd). MS m/z: 544(M+1)

Example 218

1-[3-(7-(2-Carbamoyl)ethyl-5,11-dihydro[1]benzoxepino[2,3-b]pyridin-5-ylidene)propyl]-4-(4-chlorophenyl)-piperidin-4-ol The titled compound was prepared by following the procedure of example 181, but replacing the product of example 133 with the product of example 123.

$^1$H-NMR (CDCl$_3$) δ: 1.65–1.90(3H,m), 2.10–2.22(2H, m), 2.40–2.80(10H,m), 2.91(2H,t), 5.31–5.46(4H,m), 6.11 (1H,t), 6.78(1H,d), 7.01(1H,dd), 7.16(1H,d), 7.28–7.46(5H, m), 7.57(1H,dd), 8.49(1H,dd). MS m/z: 518(M+1)

Example 234

1-[3-(5,11-Dihydro-7-methoxy[1]benzoxepino[2,3-b]pyridin-5-ylidine)propyl]-4-(indol-3-yl)-piperidine The titled compound was prepared by following the procedure of example 45, step 3, but replacing 4-(4-chlorophenyl)-4-hydroxypiperidine with 4-(indol-3-yl)-piperidine. This piperidine was prepared by the same method described in *J. Med. Chem.* 36:4006–4014 (1993) and follow hydrogenation described in Example 58, step 3.

$^1$H-NMR(CDCl$_3$) d: 1.65–1.93(2H,m), 1.94–2.28(4H,m), 2.34–2.70(4H,m), 2.81(1H,m), 2.96(2H,m), 3.78(3H,s), 5.28(2H,brs), 6.09(1H,t), 6.70–7.42(8H,m), 7.53–7.72(2H, m), 8.28(1H,brs), 8.49(1H,m).

Example 235

1-[3-(5,11-Dihydro-7-methoxy[1]benzoxepino[2,3-b]pyridin-5-ylidine)propyl]-4-(indol-3-yl)-1,2,3,6-tetrahydropyridine The titled compound was prepared by following the procedure of example 45, step 3, but replacing 4-(4-chlorophenyl)-4-hydroxypiperidine with 4-(indol-3-yl)-1,2,3,6-tetrahydropyridine. This piperidine was prepared by the same method described in *J. Med. Chem.* 36:4006–4014 (1993).

$^1$H-NMR (CDCl$_3$) d: 2.35–2.77(8H,m), 3.06–3.26(2H, m), 3.78(3H,s), 5.29(2H,brs), 6.05–6.22(2H,m), 6.70–6.88 (3H,m), 7.07–7.38(5H,m), 7.60(1H,dd), 7.87(1H,m), 8.42 (1H,brs), 8.50(1H,m).

Example 236

4-(4-Chlorophenyl)-1-[3-(5,11-dihydro-7-(3-(ethoxycarbonyl)propyloxy[1]benzoxipino[2,3-b]pyridin-5-ylidine)propyl]piperidine

The titled compound was prepared by following the procedure of example 153, but replacing ethyl bromoacetate with ethyl 4-bromobutyrate.

$^1$H-NMR (CDCL$_3$) δ: 1.26(3H,t), 1.56–1.85(4H,m), 2.01(2H,dt), 2.09(2H,quint), 2.30–2.60(7H,m), 2.93(2H,m), 3.98(2H,t), 4.15(2H,q), 5.28(2H,brs), 6.07(1H,t), 6.68–6.86(3H, m), 7.07–7.33(5H,m), 7.58(1H,dd), 8.50(1H,dd). MS m/z: 561(M+1)

Example 237

1-[3-(7-(3-Carboxypropyl)oxy-5,11-dihydro-[1]benzoxepino[2,3-b]pyridin-5-ylidine)propyl]-4-(4-chlorophenyl)-piperidine

The titled compound was prepared by following the procedure of example 133, but replacing the product of example 48 with the product of example 236.

$^1$H-NMR (CD$_3$OD) δ: 1.92–2.20(6H,m), 2.48(2H,t), 2.70–3.02(3H,m), 3.06–3.45(4H,m), 3.66(2H,m), 4.01(2H, t), 5.48(2H,brs), 6.36(1H,t), 6.85(2H,s), 7.00(1H,s), 7.20–7.40(4H,m), 8.11(1H,dd), 8.64(1H,d), 8.81(1H,d). COOH signal was not observed. MS m/z: 533(M+1)

Example 242

4-(4-Chlorophenyl)-1-[3-(5,11-dihydro-7-(1-hydroxy-1-methyl)ethyl[1]benzoxepino[2,3-b]pyridin-5-ylidene)propyl]piperidin-4-ol

The titled compound was prepared by following the procedure of example 200, but replacing the product of example 48 with the product of example 273.

$^1$H-NMR (CDCl$_3$) δ: 1.58(6H,s), 1.65–1.70(3H,m), 1.93–2.21(2H,m), 2.28–2.73(8H,m), 5.32(2H,brs), 6.13(1H, t), 6.82(1H,d), 7.20–7.50(7H,m), 7.59(1H,dd), 8.50(1H,dd) MS m/z: 505(M+1)

Example 243

1-[3-(7-(1-Carboxy-1-methyl)ethyl-5,11-dihydro[1]benzoxepino[2,3-b]pyridin-5-ylidine)propyl]-4(4-chlorophenyl)piperidin-4-ol

Step 1

To a solution of Example 363, step 2 (2.4 g) in toluene (30 ml) was added DIBAL (1 mol/L toluene solution, 9.2 ml) at −78° C., and the mixture stirred at 0° C. for 1 hour, and at room temperature for 30 minutes. The reaction mixture was added saturated aqueous ammonium chloride. 1 N aqueous hydrochloric acid, saturated sodium chloride and ethyl acetate were added to the mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:4) to give 5-(3-bromopropylidene)-5,11-dihydro-7-(1-hydroxy-1-methyl)ethyl[1]benzoxepino[2 m30b] pyridine (2.0 g).

$^1$H-NMR (CDCl$_3$) δ: 1.45(H,s), 2.75(2H,q), 3.47(1H,t), 5.33(2H, brs), 6.04(1H,t), 6.87(1H, d), 7.09–7.14(2H, m), 7.30(1H, dd), 7.57(1H, dd), 8.53(1H, dd), 9.46(1H,s).

Step 2

5-(3-bromopropylidene)-7-(1-carboxy-1-methyl)ethyl-5,11-dihydro[1]benzoxepino [2,3-b]pyridine was prepared by following the procedure of Example 382, step 2, but replacing the product of Example 382, step 1 with the product of step 1 above.

Step 3

The titled compound was prepared by following the procedure of example 44, step 2, but replacing the product of example 44, step 1 with the product of step 2.

$^1$H-NMR (DMSO-d6) δ: 1.46(6H, s), 1.63–1.84(2H, m), 2.17–2.37(4H, m), 2.37–2.53(4H, m), 3.20–3.43(2H, m), 4.83(1H, s), 5.23(2H, brs), 6.13(1H, t), 6.76(1H, d), 7.16 (1H, dd), 7.25(1H, d), 7.35(2H, d), 7.42–7.48(3H, m), 7.76(1H, dd), 8.50(1H, dd). MS m/z: 533(M+1)

Example 248

1'-[3-(5,11-Dihydro-7-methoxy[1]benzoxepino[2,3-b]pyridin-5-ylidine)propyl]-6-methylspiro[4H-3,1-benzoxazine-4,4'-piperidine]-2(1H)-one

The titled compound was prepared by following the procedure of example 45, step 3, but replacing 4-(4-chlorophenyl)-4-hydroxypiperidine with 6-methylspiro[4H-3,1-benzoxazine-4,4'-piperidin]-2(1H)-one.

$^1$H-NMR (CDCl$_3$) δ: 1.99–2.06(2H,m), 2.29(3H,s), 2.32–2.69(10H,m), 3.77(3H,s), 5.27(2H,brs), 6.08(1H,t), 6.69–6.83(4H,m), 6.94(1H,s), 7.02(1H,d), 7.25(1H,dd), 7.55(1H,dd), 8.48(1H,dd), 8.56(1H,s). MS m/z: 498(M+1)

Example 249

5-(4-Chlorophenyl)-1-[3-(5,11-dihydro-7-methoxy [1]benzoxepino[2,3-b]pyridin-5-ylidine)propyl]-4,6-dioxazacane

5-(4-Chlorophenyl)-1-[3-(5,11-dihydro-7-methoxy[1]benzoxepino[2,3-b]pyridin-5-ylidine)propyl]-4,6-diazacyclooctylamine Step 1

5-(3-(N,N'-Bis(2-hydroxyethyl)amino)propylidene)-5,11-dihydro-7-methoxy[1]benzoxepino[2,3-b]pyridine was prepared by following the procedure of example 45, step 3, but replacing 4-(4-chlorophenyl)-4-hydroxypiperidine with diethanolamine.

$^1$H-NMR (CD$_3$OD) δ: 2.46(2H,m), 2.84(4H,t), 2.98(2H, m), 3.67(4H,t), 3.75(3H,s), 5.20(2H,brs), 6.16(1H,t), 6.68–6.80(2H,m), 6.87(1H,d), 7.46(1H,dd), 7.81(1H,dd), 8.45(1H,dd).

Step 2

To a mixture of product of step 1 (78 mg) and 4-chlorobenzaldehyde dimethyl acetal (0.1 ml) in 1,2-dichloroethane (60 ml) was added p-toluenesulfonic acid monohydrate (5 mg) at room temperature, and the mixture was stirred at reflux for 12 hours. Dichloromethane and saturated aqueous sodium bicarbonate was added to the cooled reaction mixture, the organic layer was separated and washed with saturated aqueous sodium chloride, and dried with magnesium sulfate. The solvent was distilled off under reduced pressure, and the residue was purified by silica gel chromatography eluting with dichloromethane-methanol (20:1) to give the titled compound (40 mg).

¹H-NMR (CDCl₃) δ: 2.35(2H,m), 2.64–2.94(6H, m), 3.52–3.68(2H, m), 3.78(3H,s), 3.72–3.90(2H,m), 5.27(2H, brs), 5.66(1H,s), 6.08(1H,t), 6.68–6.88(3H,m), 7.18–7.46 (5H,m), 7.58(11,dd), 8.50(1H,dd).

Example 252

Step 1

To a cold (0° C.) stirred solution of 4-oxohomopiperidine-.HCl (0.6 g, 4.05 mmol), K₂CO₃ (0.615 g, 4.46 mmol) in anhydrous THF (10 mL) will be ethyl chloroformate (0.44 mL, 4.05 mmol) dropwise. The reaction was warmed to RT for 2 hrs then quenched with H₂O, extracted with EtOAc, and the organic layer dried over Na₂SO₄. Pure 1-ethylcarbonyl-4-oxohomopiperidine will be isolated via silica gel flash chromatography.

Step 2

To a cold (0° C.) stirred solution of 1-ethylcarbonyl-4-oxohomopiperidine (1.42 g, 6.07 mmol) in anhydrous THF (50 mL) under argon can be added dropwise 1.o mM 4-chlorophenylmagnesium bromide in diethyl ether (10 mL, 10 mmol). The reaction can be warmed to RT for 2 hrs then quenched with saturated aqueous NH₄Cl 95 mL). The reaction mixture can then be extracted with EtOAc (2×50 mL), the organic layers combined and dried over Na₂SO₄. Pure 1-ethoxycarbonyl-4-(4-chlorophenyl)-4-hydroxyhomopeperidine (2.1 g, 96%) can be isolated via silica gel flash chromatography eluting with 50% ETOAc/hexane.

4-(4-chlorophenyl)-4-hydroxyhomopiperidine can be prepared by reacting 1-ethoxycarbonyl-4-(4-chlorophenyl)-4-hydroxyhomopeperidine with a nucleophilic hydroxide equivalent such as LiOH in a solvent such as THF, methanol or ethanol. Removal of the solvent can afford 4-(4-chlorophenyl)-4-hydroxyhomopeperidine.

Step 4

The compound was prepared by following the procedure for Example 44, but replacing 4-(4-chlorophenyl)-4-hydroxypeperidine with 4-(4-chlorophenyl)-4-hydroxyhomopeperidine.

Examples 253 and 254

Step 1

To a stirred solution of 4-oxohomopiperidine.HCl (1.2 g, 8.05 mmol), NaOH (0.68 g, 16.9 mmol) in t-BuOH/H₂O (1:1, 10 mL) was added t-butyldicarbonate (1.93 mL, 8.9 mmol) drop-wise. The reaction was stirred at RT overnight, extracted with EtOAc (2×10 mL) and the organic layer separated. The organic layer was dried over Na₂SO₄ and concentrated under vacuo. Pure 1-t-butoxycarbonyl-4-oxohomopiperidine (1.42 g, 84%) was isolated via silica gel flash chromatography eluting with 50% EtOAc/hexane. ¹H NMR CDCl₃ δ: 44 (9H, s), 1.72–1.84 (2H, m), 2.60–2.65 (4H, m), 3.55–3.61 (4H, m).

Step 2

To a cold (0° C.) stirred solution of 1-t-butoxycarbonyl-4-oxohomopiperidine (1.42 g, 6.07 mmol) in anhydrous THF (50 mL) under argon was added dropwise 1.0 M 4-chlorophenylmagnesium bromide in diethyl ether (10 mL, 10 mmol). The reaction was warmed to RT for 2 hrs then quenched with sat'd aqueous NH₄Cl (5 mL). The reaction mixture was extracted with EtOAc (2×50 mL), the organic layers combined and dried over Na₂SO₄. Pure 1-t-butoxycarbonyl-4-(4-chlorophenyl)-4-hydroxyhomopiperidine (2.1 g, 96%) was isolated via silica gel flash chromatography eluting with 50% EtOAc/hexane. ¹H NMR CDCl₃ δ 1.43 (9H,s), 1.61–2.22 (6H, m), 3.21–3031 (2H, m), 3.48–3.82 (2H, m).

Step 3

To a stirred solution of 1-t-butoxycarbonyl-4-(4-chlorophenyl)-4-hydroxyhomopiperidine (2.1 g) at RT in CH₂Cl₂ (48 mL) was added TFA (2.0 mL). The reaction was stirred at RT for 2 hrs. Excess solvent and TFA was removed affording 2.0 g (92% yield) 1:1 mixture of 3-(4-chlorophenyl)-2,3-dehydrohomopiperidine and 3-(4-chlorophenyl)-3,4-dehydrohomopiperidine. ¹H NMR (MeOD, isomer A) δ 2.01–2.11 (2H, m, 4), 2.60–2.71 (2H, m, 5), 2.81–2.92 (2H, m, 4), 2.83–3.05 (2H, m, 5), 3.66–3.92 (4H, m, 5), 6.16–6.21 (1H, t, 5). ¹H NMR (MeOD, isomer B) 3.44–3.56 (2H, m, 4), 3.88–3.97 (2H, m, 4), 6.01–6.12 (1H, t, 4), 7.32–7.44 (1H, t, 4).

Step 4

The compounds can be prepared by following the procedure for Example 44 but replacing 4-(4-chlorophenyl)-4-hydroxypiperidine with 3-(4-chlorophenyl)-3,4-dehydrohomopiperidine and 3-(4-chlorophenyl)-4,5-dehydrohomopiperidine.

Example 255

1-(4-Chlorophenyl)-4-[3-(5,1-dihydro-7-hydroxy[1] benzoxepino[2,3-b]pyridin-5-ylidene)propyl]piperazinone The titled compound was prepared by following the procedure of example 44, step 2, but replacing 4-(4-chlorophenyl)-4-hydroxypiperidine with 1-(4-chlorophenyl)piperazinone.

¹H-NMR (DMSO-d₆) δ: 2.30–2.34(2H,m), 2,49–2.57(2H,m), 2.68(2H,t), 3.06(2H,s), 3.58(2H,t), 5.12 (2H,brs), 6.06(2H,t), 6.57–6.69(3H,m), 7.35–7.71(5H,m), 7.72(1H,dd), 8.48(1H,dd).

Example 256

1-(4-Chlorophenyl)-4-[3-(5,11-dihydro-7-hydroxy[1] benzoxepino[2,3-b]pyridin-5-ylidene)propyl]homopiperazdine The titled compound was prepared by following the procedure of example 44, step 2, but replacing 4-(4-chlorophenyl)-4-hydroxypiperidine with 1-(4-chlorophenyl)homopiperazdine.

¹H-NMR (CDCl₃) δ: 1.89(2H,brs), 2.27–2.35(2H,m), 2.51–2.70(6H,m), 3.37–3.53(4H,m), 5.23(2H,brs), 5.98(1H, t), 6.48–6.74(6H,m), 7.05–7.26(2H,m), 7.52(1H,dd), 8.45 (1H,dd). MS m/z: 462(M+1)

Example 260

3-(4-Chlorophenyl)-8-[3-(5,11-dihydro-7-hydroxy[1] benzoxepino[2,3-b]pyridin-5-ylidene)propyl]-8-azabicyclo[3.2.1]octan-3-ol The titled compound was prepared by following the procedure of example 44, step 2, but replacing 4-(4-chlorophenyl)-4-hydroxypiperidine with 3-(4-chlorophenyl)-8-azabicyclo[3.2.1]octan-3-ol ¹H-NMR(CDCl₃) δ:1.65–2.10(4H,m), 2.1–2.7(8H,m), 3.32(2H,bs), 3.78(3H,s), 5.24(2H,bs), 6.10(1H,dd), 6.70–6.90(3H,m), 7.15–7.31(3H,m), 7.45(bd,2H), 7.64(dd, 1H) 8.46(dd, 1H) MS m/z: 503(M+1)

Example 261

1'-(4-Chlorophenyl)-1-[3-(5,11-dihydro-7-hydroxy [1]benzoxepino[2,3-b]pyridin-5-ylidene)propyl]spiro [5-chloro-1,3-benzodioxole-2,4'-piperidine]

The titled compound was prepared by following the procedure of example 44, step 2, but replacing 4-(4-chlorophenyl)-4-hydroxypiperidine with spiro[5-chloro-1,3-benzodioxole-2,4'-piperidine] (*Journal of Medicinal Chemistry.* 1995, 38, 2009–2017).
¹H-NMR(DMSO-d₆) δ: 1.78–2.02(4H, m), 2.18–2.63(8H, m), 4.97–5.27(2H, brs), 6.06(1H, t), 6.58–6.67(3H, m), 6.79–6.87(2H, m), 6.99(1H, d), 7.42(1H, dd), 7.72(1H, dd), 8.49(1H, dd), 9.07(1H, s).

Example 262

1-[3-(7-(1-Carbamoyl-1-methyl)ethyloxy-5,11-dihydro[1]benzoxepino[2,3-b]pyridin-5-ylidene)propyl]-4-(4-chlorophenyl)-4-hydroxy-1-methylpiperidinium iodide To a solution of the product of example 211 (330 mg) and in acetonitrile (1.2 ml) was added iodomethane (0.07 ml), and the reaction mixture was stirred at room temperature for 2 hours. The precipitation was filtered and washed with acetonitrile to give the titled compound (250 mg).
¹H-NMR (DMSO-d₆) δ: 1.39(6H,s), 1.65–1.85(2H,m), 2.20–2.64(4H,m), 3.09(3H,s), 3.30–3.65(6H,m), 5.20(2H, m), 5.61(1H,s), 6.01(1H,t), 6.75–6.92(3H,m), 7.27(1H,s), 7.38–7.64(6H,m), 7.83(1H,dd), 8.56(1H,dd) MS m/z: 562 [(M−1)+].

Example 263

4-(4-Chlorophenyl)-1-[3-(7-diethylaminocarbonylmethyloxy-5,11-dihydro[1]benzoxepino[2,3-b]pyridin-5-ylidene)propyl]piperidin-4-ol The titled compound was prepared by following the procedure of example 134, but replacing dimethylamine hydrochloride with diethylamine.
¹H-NMR(CDCl₃) δ: 1.67–1.72(2H,m), 1.99–2.10(2H,m), 2.36–2.70(9H,m), 2.89(3H,d), 4.45(2H,s), 5.28(2H,brs), 6.08(1H,t), 6.66(1H,brs), 6.73–6.84(3H,m), 7.25–7.45(5H, m), 7.58(1H,dd), 8.47(1H,dd). MS m/z: 534(M+1)

Example 268

4-(4-Chlorophenyl)-1-[3-(5,11-dihydro-7methylaminocarbonyl[1]benzoxepino[2,3-b]pyridin-5-ylidene) propyl]piperidin-4-ol The titled compound was prepared by following the procedure of example 198, but replacing dimethylamine hydrochloride with methylamine.
¹H-NMR (DMSO-d6) δ: 1.75–1.80(2H, m), 2.38–2.50 (2H, m), 2.63–2.73(2H, m), 2.78(3H,d), 3.17–3.50(6H, m), 5.38(2H, brs), 6.36(1H, t), 6.87(1H, d), 7.41–7.50(4H, m), 7.55–7.99(4H, m), 8.48–8.50(1H, m), 8.61(1H, dd). MS m/z: 504(M+1)

Example 269

1-[3-(7-Carbamoyl-5,11-dihydro[1]benzoxepino[2,3-b]pyridin-5-ylidene)propyl]-4-(4-chlorophenyl)piperidin-4-ol The titled compound was prepared by following the procedure of example 198, but replacing dimethylamine hydrochloride with ammonium hydroxide.
¹H-NMR (CDCl₃) δ: 1.67–1.79(2H,m), 2.01–2.10(2H, m), 2.17–2.71(8H,m), 5.38(2H,brs), 6.21(1H,t), 6.85(1H,d), 7.27–7.57(9H,m), 7.90(1H,dd), 8.50(1H,dd). MS m/z: 490 (M+1)

Example 270

4-(4-Chlorophenyl)-1-[3-(7-diethylaminocarbonyl-5, 11-dihydro[1]benzoxepino[2,3-b]pyridin-5-ylidene) propyl]piperidin-4-ol The titled compound was prepared by following the procedure of example 198, but replacing dimethylamine hydrochloride with diethylamine.
MS m/z: 546(M+1)

Example 273

4-(4-Chlorophenyl)-1-[3-(5,11-dihydro-7-(methoxycarbonyl[1]benzoxepino[2,3-b]pyridin-5-ylidene) propyl]piperidin-4-ol A mixture of the product of example 169 (15.0 g), palladium(II) diacetate (170 mg), 1,3-bis(diphenylphosphino)propane (310 mg), and triethylamine (7.0 ml) in methanol (100 ml) and dimethylformamide (150 ml) was purged with carbon monoxide for 5 minutes and stirred under a carbon monoxide balloon at 70° C. for 8 hours. The reaction mixture was evaporated under reduced pressure. The residue was added water and extracted with ethyl acetate. The extract was dried over magnesium sulfate, and the solvent was evaporated under reduced pressure. The residue was purified by silica gel column chromatography (ethyl acetate:methanol=10:1) to give the titled compound (13.1 g).
¹H-NMR(CDCl₃) δ: 1.45–1.80 (3H,m), 1.90–2.15 (2H, m), 2.28–2.48 (4H,m), 2.50–2.75 (4H,m), 3.89(3H,s), 5.25–5.50(2H,m), 6.20(1H,dd), 6.85(1H,d), 7.20–7.37(3H, m), 7.42(2H,d), 7.58(1H,d), 7.80(1H,dd), 8.01(1H,dd), 8.52 (1H,dd) MS m/z: 505(M+1)

Example 274

4-(4-Chlorophenyl)-1-[3-(5,11-dihydro-7-hydroxymethyl[1]benzoxepino[2,3-b]pyridin-5-ylidene)propyl] piperidin-4-ol To an ice-cooled solution of the product of example 273 (2.0 g) in tetrahydrofuran (100 ml) was added lithium aluminum hydride (300 mg), and the reaction mixture was stirred at room temperature for 12 hours. After the reaction mixture was cooled to 0° C., water (0.3 ml), 15% sodium hydroxide aqueous solution (0.3 ml), and water (0.9 ml) were added. The reaction mixture was filtered, and the filtrate was dried over magnesium sulfate. The solvent was evaporated under reduced pressure and the residue was purified by silica gel column chromatography (chloroform: methanol: 28% ammonia in water=100:5:1) to give the titled compound (1.6 g).

$^1$H-NMR (CDCl$_3$) δ: 1.55–1.71(3H,m), 1.95–2.25(2H,m), 2.34–2.70(8H,m), 4.62(2H,s), 5.20–5.45(2H,brs), 6.13 (1H,t), 6.84(1H,d), 7.16(1H,dd), 7.23–7.43(6H,m), 7.58(1H,dd), 8.51(1H,dd) MS m/z: 477(M+1)

Example 275

4-(4-Chlorophenyl)-1-[3-(5,11-dihydro-7-(1-propylamino)methyl[1]benzoxepino[2,3-b]pyridin-5-ylidene)propyl]piperidin-4-ol To a solution of the product of example 314 (300 mg) and 1-propylamine (0.26 ml) in tetrahydrofuran (6 ml) was added acetic acid (0.36 ml), and the reaction mixture was stirred at 60° C. for 30 minutes. Then the reaction mixture was added sodium triacetoxyborohydride (670 mg) at 0° C., and stirred for 1.5 hours at room temperature. Sodium bicarbonate, water, and chloroform were added to the reaction mixture. The organic layer was extracted, and dried over potassium carbonate, and evaporated under reduced pressure. The residue was recrystallized with ethyl acetate to give titled compound (130 mg).

$^1$H-NMR (CDCl$_3$) δ: 0.92(3H,t), 1.49–1.70(6H,m), 1.98(2H,m), 2.34–2.42(4H,m), 2.51–2.70(6H,m), 3.71(2H,s), 5.32(2H,brs), 6.12(1H,t), 6.81(1H,d), 7.11(1H,dd), 7.25–7.45(6H,m), 7.57(1H,dd), 8.49(1H,dd). MS m/z: 518 (M+1)

Example 276

4-(4-Chlorophenyl) 1-[3-(5,11-dihydro-7-(3-hydroxy-1-propylamino)methyl[1]benzoxepino[2,3-b]pyridin-5-ylidene)propyl]piperidin-4-ol The titled compound was prepared by following the procedure of Example 275, but replacing 1-propylamine with 3-amino-1-propanol.

MS m/z: 534(M+1)

Example 277

4-(4-Chlorophenyl)-1-[3-(5,11-dihydro-7-(1-piperidino)methyl[1]benzoxepino[2,3-b]pyridin-5-ylidene)propyl]piperidin-4-ol The titled compound was prepared by following the procedure of example 275, but replacing 1-propylamine with piperidine.

MS m/z: 544(M+1)

Example 278

4-(4-Chlorophenyl)-1-[3-(5,11-dihydro-7-(4-morpholino)methyl[1]benzoxepino[2,3-b]pyridin-5-ylidene)propyl]piperidin-4-ol The titled compound was prepared by following the procedure of example 275, but replacing 1-propylamine with morpholine.

MS m/z: 546(M+1)

Example 279

4-(4-Chlorophenyl)-1-[3-(5,11-dihydro-7-(1-pyrrolidino)methyl [1]benzoxepino[2,3-b]pyridin-5-ylidene)propyl]piperidin-4-ol The titled compound was prepared by following the procedure of Example 275, but replacing 1-propylamine with 4-aminobutyric acid.

$^1$H-NMR (CDCl$_3$) δ: 1.70–1.75(2H,m), 1.98(2H,m), 2.12–2.23(2H,m), 2.40–2.86(10H,m), 3.27(2H,t), 4.36(2H,s), 5.29(2H,brs), 6.07(1H,t), 6.80(1H,d), 7.04(1H,dd), 7.19 (1H,d), 7.28–7.32(3H,m), 7.50(1H,t), 7.61(1H,dd), 8.51(1H,dd). MS m/z: 544(M+1)

Example 280

4-(4-Chlorophenyl)-1-[3-(5,11-dihydro-7-(2-hydroxy)ethyl[1]benzoxepino[2,3-b]pyridin-5-ylidene)propyl]piperidin-4-ol The titled compound was prepared by following the procedure of example 273, but replacing the product of example with the product of example 274.

$^1$H-NMR (CDCl$_3$) δ: 1.60–1.70(4H,m), 2.01–2.12(2H, m), 2.37–2.70(8H,m), 2.81(2H,t), 3.84(2H,t), 5.31(2H,brs), 6.09(1H,t), 6.81(1H,d), 7.03(1H,dd), 7.15(1H,d), 7.26–7.43 (5H,m), 7.57(1H,dd), 8.49(1H,dd). MS m/z: 491(M+1)

Example 281

1-[3-(7-Carbamoylmethyl-5,11-dihydro[1]benzoxepino[2,3-b]pyridin-5-ylidene)propyl]-4-(4-chlorophenyl)-piperidin-4-ol The titled compound was prepared by following the procedure of example 122, but replacing dimethylamine hydrochloride with ammonium hydroxide.

$^1$H-NMR (CDCl$_3$) δ: 1.65–1.70(2H,m), 1.98–2.06(2H, m), 2.27–2.70(9H,m), 3.46(2H,s), 5.30(2H,brs), 5.74(1H, brs), 6.04(1H,brs), 6.09(1H,t), 6.79(1H,d), 7.02(1H,dd), 7.18–7.41(6H,m), 7.54(1H,dd), 8.43(1H,dd). MS m/z: 504 (M+1)

Example 288

4-(4-Chlorophenyl)-1-[3-(7-(2-ethoxycarboxy)ethyl-5,11-dihydro[1]benzoxepino[2,3-b]pyridin-5-ylidene)propyl]piperidin-4-ol The titled compound was prepared by following the procedure of example 165, but replacing the product of example 164 with the product of example 310.

$^1$H-NMR (CDCl$_3$) δ: 1.23(3H,t), 1.63–1.71(3H,m), 1.98–2.10(2H,m), 2.35–2.71(10H,m), 2.89(2H,t), 4.13(2H, q), 5.31(2H,brs), 6.08(1H,t), 6.78(1H,d), 7.00(1H,dd), 7.12 (1H,d), 7.26–7.44(5H,m), 7.57(1H,dd), 8.49(1H,dd). MS m/z: 548(M+1)

Example 289

4-(4-Chlorophenyl)-1-[3-(7-(1-(3-hydroxy)propyl)-5,11-dihydro[1]benzoxepino[2,3-b]pyridin-5-ylidene)propyl]piperidin-4-ol The titled compound was prepared by following the procedure of example 133, but replacing the product of example 48 with the product of example 288.

$^1$H-NMR (DMSO-$d_6$) δ: 1.45–1.50(2H,m), 1.66–1.80(4H,m), 2.26–2.57(10H,m), 3.41(2H,q), 4.46(1H, t), 4.83(1H,s), 5.23(2H,brs), 6.14(1H,t), 6.71(1H,d), 7.01 (1H,dd), 7.13(1H,d), 7.34–7.48(5H,m), 7.72(1H,dd), 8.49 (1H,dd). MS m/z: 505(M+1)

Example 290

4-(4-Chlorophenyl)-1-[3-(5,11-dihydro-7-(2,3-dihydroxy)propyl[1]benzoxepino[2,3-b]pyridin-5-ylidene)propyl]piperidin-4-ol To a solution of product of example 170 (6.9 g) in tetrahydrofuran (70 ml) and water (14 ml) were added N-methylmorpholine oxide (1.7 g) and osmium tetraoxide at 0° C., and the mixture was stirred at room temperature for 3 hours. Ethyl acetate was added to the mixture, the aqueous layer was separated. Chloroform-isopropanol (4:1) was added to the aqueous layer, the organic layer was extracted, and dried with magnesium sulfate. The solvent was distilled off under reduced pressure to give the titled compound (7.0 g).

$^1$H-NMR (CDCl$_3$) δ: 1.65–1.73(2H,m), 1.95–2.10(2H, m), 2.30–2.75(13H,m), 3.45–3.50(1H,m), 3.60–3.65(1H,m), 3.83–3.90(1H,m), 5.28(2H,brs), 6.06(1H,t), 6.84(1H,d), 7.03(1H,dd), 7.15(1H,d), 7.26–7.43(5H,m), 7.57(1H,dd), 8.49(1H,dd). MS m/z: 521(M+1)

Example 291

4-(4-Chlorophenyl)-1-[3-(5,11-dihydro-7-phenyl[1]benzoxepino[2,3-b]pyridin-5-ylidene)propyl]piperidin-4-ol The titled compound was prepared by following the procedure of example 170, but replacing allyltributyltin with phenyltributyltin.

$^1$H-NMR (CDCl$_3$) δ: 1.84–1.92(2H, m), 2.85–3.40(10H, m), 5.33(2H, brs), 6.05(1H,t), 6.95(1H, d), 7.30–7.58(12H, m), 7.63–7.66(1H, m), 8.56–8.58(1H, m) MS m/z: 523(M+1)

Example 292

4-(4-Chlorophenyl)-1-[3-(7-(2-furyl)-5,11-dihydro[1]benzoxepino[2,3-b]pyridin-5-ylidene)propyl]piperidin-4-ol The titled compound was prepared by following the procedure of example 170, but replacing allyltributyltin with ethyl (2-furyl)tributyltin.

$^1$H-NMR (CDCl$_3$) δ: 1.70–1.80(3H,m), 1.97–2.16(2H, m), 2.3–2.8(8H,m), 5.36(2H,m), 6.19(1H,t), 6.45(1H,dd), 6.55(1H,d), 6.87(1H,d), 7.20–7.50(7H,m), 7.60–7.65(2H, m), 8.52(1H,dd) MS m/z: 513(M+1)

Example 293

4-(4-Chlorophenyl)-1-[3-(7-ethoxycarbonylamino-5,11-dihydro[1]benzoxepino[2,3-b]pyridin-5-ylidine)propyl]piperidin-4-ol A mixture of product of example 118 (490 mg) and diphenylphosphonic azide (0.28 ml) was stirred at 110° C. for 30 minutes. After the mixture was cooled, and triethylamine (0.14 ml) and ethanol (5 ml) were added, and the mixture was heated to reflux for 8 hours. The reaction mixture was diluted with ethyl acetate and filterd through Celite. The filtrate was washed with saturated aqueous sodium bicarbonate, and dried over magnesium sulfate. The solvent was removed under reduced pressure and the residue was purified by silica gel column chromatography (chloroform:methanol=10:1) to give the titled compound (210 mg).

1H-NMR (CDCl$_3$) δ 1.31(3H,t), 1.65–1.70(2H,m), 2.01–2.09(2H,m), 2.36–2.70(8H,m), 4.21(2H,q), 5.30(2H, brs), 6.13(1H,t), 6.46(1H,brs), 6.80(1H,d), 7.02(1H,dd), 7.28–7.50(6H,m), 7.57(1H,dd), 8.50(1H,dd). MS m/z: 534 (M+H).

Example 294

1-[Bis(ethoxycarbonylmetyl)methoxy-5,11-dihydro[1]benzoxepino[2,3-b]pyridin-5-ylidene)propyl]-4-(4-chlorophenyl)-piperidin-4-ol The titled compound was prepared by following the procedure of example 46, but replacing ethyl iodide with diethyl bromomalonate.

$^1$H-NMR (CDCl$_3$) δ: 1.30(3H,t), 1.66–1.71(2H,m), 1.98–2.09(2H,m), 2.35–2.69(9H,m), 4.30(2H,q), 5.14(1H, s), 5.26(2H,brs), 6.10(1H,t), 6.78(2H,d), 7.00(1H,t), 7.26–7.45(5H,m), 7.57(1H,dd), 8.43(1H,dd). MS m/z: 621 (M+1)

Example 295

1-[1-Bis(ethoxycarbonylmetyl)ethyloxy-5,1-dihydro[1]benzoxepino[2,3-b]pyridin-5-ylidene)propyl]-4-(4-chlorophenyl)-piperidin-4-ol The titled compound was prepared by following the procedure of example 46, but replacing ethyl iodide with diethyl 2-bromo-2-methylmalonate.

$^1$H-NMR (CDCl$_3$) δ: 1.27(6H,t), 1.65–1.70(5H,m), 1.99–2.08(3H,m), 2.31–2.69(8H,m), 4.28(4H,q), 5.27(2H, brs), 6.06(1H,t), 6.72(1H,d), 6.80(1H,dd), 7.00(1H,d), 7.27–7.45(5H,m), 7.56(1H,dd), 8.46(1H,dd).

Example 296

4-(4-Chlorophenyl)-1-[3-(5,11-dihydro-7-(2-hydroxy-1-hydroxymethyl)ethyloxy[1]benzoxepino[2,3-b]pyridin-5-ylidene)propyl]piperidin-4-ol The titled compound was prepared by following the procedure of example 199, but replacing the product of example 138 with the product of example 294.

$^1$H-NMR (CDCl$_3$) δ: 1.70–1.75(2H,m), 2.10–2.80(11H, m), 3.90(4H,d), 4.36(1H,quint), 5.28(2H,brs), 6.13(1H,t), 6.71–6.87(2H,m), 7.00(1H,d), 7.29–7.45(5H,m), 7.58(1H, dd), 8.51(1H,dd). MS m/z: 537(M+1)

Example 297

1-[1,1-Bis(hydroxymethyl)ethyloxy-5,11-dihydro[1]
benzoxepino[2,3-b]pyridin-5-ylidene)propyl]-4-(4-
chlorophenyl)-piperidin-4-ol The titled compound was prepared by following the procedure of example 199, but replacing the product of example 138 with the product of example 295.

$^1$H-NMR (CDCl$_3$) δ: 1.09(3H,s), 1.66–1.71(2H,m), 1.90–2.10(3H,m), 2.37–2.75(8H,m), 3.72–3.82(4H,m), 5.29 (2H,brs), 6.05(1H,t), 6.77(1H,d), 6.88(1H,dd), 7.03(1H,d), 7.26–7.43(5H,m), 7.56(1H,dd), 8.48(1H,dd). MS m/z: 551 (M+1)

Example 299

4-(4-Chlorophenyl)-1-[3-(5,11-dihydro-7-(5-ethoxy-
carbonylpropyl)oxy[1]benzoxepino[2,3-b]pyridin-5-
ylidene)propyl]piperidin-4-ol The titled compound was prepared by following the procedure of example 46, but replacing ethyl iodide with ethyl 4-bromobutyrate.

$^1$H-NMR (CDCl$_3$) δ: 1.24(3H, t), 1.65–1.69(2H, m), 1.96–2.12(4H, m), 2.26–2.67(10H,m), 3.96(2H, t), 4.12(2H, q), 5.24(2H, brs), 6.08(1H, t), 6.70–6.83(3H, m), 7.21–7.59 (6H,m), 8.39(1H, dd).

Example 300

1-[3-(7-(3-Carboxy-1-propyl)oxy-5,11-dihydro[1]
benzoxepino[2,3-b]pyridin-5-ylidene)propyl]piperi-
din-4-ol The titled compound was prepared by following the procedure of example 133, but replacing the product of example 48 with the product of example 299.

$^1$H-NM (DMSO-d6) δ: 1.41–1.95(2H, m), 1.41–1.95(4H, m), 2.20–2.72(10H, m), 3.95(2H,t), 5.18(2H, brs), 6.17(1H, t), 6.72–6.84(3H, m), 7.36–7.48(5H, m), 7.77(1H, dd), 8.50 (1H, dd). MS m/z: 549(M+1)

Example 301

4-(4-Chlorophenyl)-1-[3-(5,11-dihydro-7-(4-meth-
oxycarbonylphenyl)methoxy[1]benzoxepino[2,3-b]
pyridin-5-ylidene)propyl]piperidin-4-ol The titled compound was prepared by following the procedure of example 46, but replacing ethyl iodide with methyl 4-bromomethylbenzoate.

$^1$H-NMR (CDCl$_3$) δ: 1.66–1.70(2H, m), 1.93–2.09(3H, m), 2.37–2.70(8H, m), 3.91(3H,s), 5.09(2H, s), 5.27(2H, brs), 6.06(1H, t), 6.80–6.91(3H, m), 7.24–7.60(8H, m), 8.01–8.07(2H, m), 8.47(1H, dd).

Example 302

1-[3-(7-(4-Carboxypheny)methoxy-5,11-dihydro[1]
benzoxepino[2,3-b]pyridin-5-ylidene)propyl]-4-(4-
chlorophenyl)piperidin-4-ol The titled compound was prepared by following the procedure of example 133, but replacing the product of example 48 with the product of example 301.

$^1$H-NMR (DMSO-d6) δ: 1.44–1.49(2H, m), 1.67–1.87 (2H, m), 2.26–2.56(8H, m), 4.85(1H,brs), 5.15–5.25(4H, m), 6.17(1H, t), 6.72–6.95(3H, m), 7.30–7.75(8H, m), 7.92–7.99(2H, m), 8.48(1H, dd). MS m/z: 597(M+1)

Example 303

4-(4-Chlorophenyl)-1-[3-(5,11-dihydro-7-((1-hy-
droxymethyl)cyclopropyl)methoxy[1]benzoxepino
[2,3-b]pyridin-5-ylidene)propyl]piperidin-4-ol Step 1

1-[3-(7-((1-Benzoyloxymethyl)cyclopropyl)methoxy-5, 11-dihydro[1]benzoxepino [2,3-b]pyridin-5-ylidene)propyl]-4-(4-chlorophenyl)piperidin-4-ol was prepared by following the procedure of example 46, but replacing ethyl iodide with (1-benzoyloxymethyl)cyclopropylmethyl methanesulfonate.

$^1$H-NMR (CDCl$_3$) δ: 0.70–0.81(4H, m), 1.65–1.70(3H, m), 1.98–2.07(2H, m), 2.35–2.70(8H,m), 3.91(2H, s), 4.39 (2H, s), 5.25(2H, brs), 6.06(1H, t), 6.72–6.84(3H, m), 7.23–7.59(9H, m), 8.02–8.06(2H, m), 8.48(1H, dd).

Step 2

The titled compound was prepared by following the procedure of example 133, but replacing the product of example 48 with the product of step 1.

$^1$H-NMR (CDCl$_3$) δ:0.62(4H,s), 1.67–1.72(2H,m), 1.96–2.06(2H,m), 2.34–2.69(8H,m), 3.39(1H,brs), 3.91(2H, s), 3.91(2H,s), 5.26(2H,brs), 6.09(1H,t), 6.72–6.86(3H,M), 7.27–7.60(6H,m), 8.48(1H,dd). MS m/z: 547(M+1)

Example 305

1-[3-(5,11-dihydro-7-(2-hydroxyethyl)aminocarbo-
nyl[1]benzoxepino[2,3-b]pyridin-5-ylidene)propyl]-
4-(4-chlorophenyl)piperidin-4-ol The titled compound was prepared by following the procedure of example 198, but replacing dimethylamine hydrochloride with 2-hydroxyehylamine.

$^1$H-NMR (CDCl$_3$) δ: 1.65–1.70(2H,m), 2.03–2.06(2H, m), 2.21(1H,d), 2.32–2.68(8H,m), 3.63(2H,dt), 3.83(2H,t), 5.37(2H,brs), 6.18(1H,t), 6.67(1H,brs), 7.25–7.54(7H,m), 7.86(1H,dd), 8,50(1H,dd). MS m/z: 534(M+1)

Example 306

4-(4-Chlorophenyl)-1-[3-(5,11-dihydro-7-(1-cyclo-
hexyloxycarbonyloxy)ethyloxycarbonyl[1]benzox-
epino[2,3-b]pyridin-5-ylidene)propyl]piperidin-4-ol
dihydrochloride To a solution of product of example 118 (1.1 g) in dimethylformamide (15 ml) were added sodium iodide (0.17 g), potassium carbonate (0.38 g) and cyclohexyl 1-chloroethyl carbonate (*J. Antibiotics,* 1987, 40, 81.) (0.57 g) at room temperature. The mixture was stirred at 70° C. for 1 hour. Water and ethyl acetate were added to the reaction mixture, the organic layer was separated and washed with saturated aqueous sodium chloride, and dried with magnesium sulfate. The solvent was distilled off under reduced pressure and the residue was purified by silica gel column chromatography (ethyl acetate:methanol=100:3). The obtained oil was dissolved with ethyl acetate, and 4 N hydrochloric acid ethyl acetate solution (0.8 ml) was added. The precipitation was filtered to give the titled compound (0.96 g).

¹H-NMR (DMSO-d₆) δ: 1.22–1.47(6H,m), 1.58(3H,d), 1.63–1.81(6H,m), 2.38–3.30(10H,m), 4.07–4.59(1H,m), 5.80(2H,brs), 6.28(1H,t), 6.87(1H, q), 6.97(1H,d), 7.40–7.49(4H,m), 7.64(1H,dd), 7.79(1H,dd), 7.96(1H,d), 8.03(1H,dd), 8.65(1H,dd), 11.07(1H,brs). MS m/z: 661[(M−2HCl)+1]

Example 307

4-(4-Chlorophenyl)-1-[3-(5,11-dihydro-7(1-ethoxycarbonyloxy)ethyloxycarbonyl[1]benzoxepino[2,3-b]pyridin-5-ylidene)propyl]piperidin-4-ol The titled compound was prepared by following the procedure of Example 307, but replacing cyclohexyl 1-chloroethyl carbonate with ethyl 1-chloroethyl carbonate.
MS m/z: 607(M+1)

Example 308

4-(4-Chlorophenyl)-1-[3-(5,11-dihydro-7-(5-hydroxyfuran-2-yl)[1]benzoxepino[2,3-b]pyridin-5-ylidene)propyl]piperidin-4-ol Step 1
4-(4-Chlorophenyl)-1-[3-(5,11-dihydro-7-(5-formylfuran-2-yl)[1]benzoxepino[2,3-b]pyridin-5-ylidene)propyl]piperidin-4-ol was prepared by following the procedure of example 170, but replacing allyltributyltin with (5-formylfuran-2-yl)tributyltin.
1H-NMR (CDCl3) δ: 1.40–1.80(2H,m), 1.89–2.12(2H, m), 2.20–2.75(8H,m), 5.28(2H,brs), 6.16(1H,t), 6.69(1H,d), 6.84(1H,d), 7.22–7.55(8H,m), 7.76(1H,d), 8.42(1H,dd), 9.52(1H,s).
Step 2
The titled compound was prepared by following the procedure of example 199, but replacing the product of example 138 with the product of step 1.
MS m/z: 543(M+1)

Example 309

1-[3-(7-(5-Carboxyfuran-2-yl)-5,11-dihydro[1]benzoxepino[2,3-b]pyridin-5-ylidene)propyl]-4-(4-chlorophenyl)piperidin-4-ol The titled compound was prepared by following the procedure of Example 382, step 2, but replacing the product of Example 382, step 1 with the product of example 307, step 1.
MS m/z: 557(M+1)

Example 310

4-(4-Chlorophenyl)-1-[3-(7-(2-ethoxycarboxy)ethenyl-5,11-dihydro[1]benzoxepino[2,3-b]pyridin-5-ylidene)propyl]piperidin-4-ol The titled compound was prepared by following the procedure of example 171, but replacing t-butyl acrylate with ethyl acrylate.
¹H-NMR (CDCl₃) δ: 1.33(3H,t), 1.63–1.71(3H,m), 1.98–2.10(2H,m), 2.35–2.72(8H,m), 4.25(2H,q), 5.36(2H, brs), 6.10(1H,t), 6.33(1H,d), 6.85(1H,d), 7.22–7.44(7H,m), 7.58–7.65(2H,m), 8.53(1H,dd).

Example 311

4-(4-Chlorophenyl)-1-[3-(7-(1-(2-ethyl-2-hydroxy)butyl)oxy-5,11-dihydro[1]benzoxepino[2,3-b]pyridin-5-ylidene)propyl]piperidin-4-ol The titled compound was prepared by following the procedure of example 200, but replacing ethylmagnesium bromide with methylmagnesium bromide.
¹H-NMR (CDCl₃) δ: 0.93(6H,t), 1.60–1.70(6H,m), 1.95–2.10(3H,m), 2.36–2.70(8H,m), 3.79(2H,s), 5.28(2H, brs), 6.09(1H,t), 6.77–6.86(3H,m), 7.24–7.43(5H,m), 7.57(1H,dd), 8.47(1H,dd). MS m/z: 563(M+1)

Example 312

4-(4-Chlorophenyl)-1-[3-(7-(2-(2,3-dimethyl-3-hydroxy)butyl)oxy-5,11-dihydro[1]benzoxepino[2,3-b]pyridin-5-ylidene)propyl]piperidin-4-ol The titled compound was prepared by following the procedure of example 200, but replacing the product of example 48 with the product of example 138.
¹H-NMR (CDCl₃) δ: 1.22(6H,s), 1.32(6H,s), 1.66–1.71(2H,m), 1.99–2.10(2H,m), 2.35–2.85(9H,m), 3.77(2H,s), 5.28(2H,brs), 6.04(1H,t), 6.74–6.89(3H,m), 7.26–7.43(5H, m), 7.57(1H,dd), 8.44(1H,dd). MS m/z: 563(M+1)

Example 313

4-(4-Chlorophenyl)-1-[3-(5,11-dihydro-7-(2-oxopropyl)oxy[1]benzoxepino[2,3-b]pyridin-5-ylidene)propl]piperidin-4-ol The titled compound was prepared by following the procedure of example 146, but replacing ethyl iodide with chloracetone.
1H-NMR (CDCl₃) δ: 1.62–1.71(3H,m), 1.99–2.10(2H, m), 2.27(3H,s), 2.35–2.70(8H,m), 4.51(2H,s), 5.28(2H,brs), 6.08(1H,t), 6.70–6.84(3H,m), 7.25–7.32(3H,m), 7.41–7.44(2H,m), 7.58(1H,dd), 8.50(1H,dd). MS m/z: 519(M+1)

Example 314

4-(4-Chlorophenyl)-1-[3-(7-formyl-5,11-dihydro[1]benzoxepino[2,3-b]pyridin-5-ylidene)propyl]piperidin-4-ol To a solution of the product of example 274(1.0 g) in methylene chloride (200 ml) was added manganese(IV) oxide (3.0 g), and the suspension was stirred at ambient temperature for 12 hours. The reaction mixture was diluted with ethyl acetate and filtered through Celite. The solvent was evaporated under reduced pressure to give the titled compound (930 mg).
¹H-NMR (CDCl₃) δ: 1.71–1.80(3H,m), 1.98–2.09(2H, m), 2.35–2.43(4H,m), 2.53–2.69(4H,m), 5.30(2H,brs), 6.24(1H,t), 6.95(1H,d), 7.27–7.44(5H,m), 7.61(1H,dd), 7.67(1H, dd), 7.85(1H,d), 8.54(1H,dd), 9.88(1H,s).

Example 315

1-[3-(7-Acetyl-5,11-dihydro[1]benzoxepino[2,3-b]pyridin-5-ylidene)propyl]-4-(4-chlorophenyl)piperidin-4-ol Step 1

To a solution of example 53, step 1 (7.2 g) in dichloromethane (70 ml) was added aluminum chloride (9.1 g) and acetyl chloride (3.2 ml), and the mixture stirred at 0° C. for 10 minutes. The reaction mixture was poured into ice. The aqueous layer was extracted with ethyl acetate, and the organic layer was washed with saturated aqueous sodium chloride, and dried with magnesium sulfate. The solvent was distilled off under reduced pressure. The Residue was purified by silica gel chromatography, eluting with ethyl acetate-hexane (1:2) to give 7-acetyl-5-(3-bromopropylidene)-5,11-dihydro[1]benzoxepino[2,3-b]pyridine (7.9 g).

$^1$H-NMR (CDCl$_3$) δ:2.57(3H,s), 2.77(2H,m), 3.49(2H,t), 5.40(2H, brs), 6.16(1H,t), 6.88(1H,d), 8.33(1H,dd), 7.58 (1H,dd), 7.77(1H,dd), 7.96(1H,d), 8.56(1H,dd).

Step 2

The titled compound was prepared by following the procedure of example 44, step 2, but replacing the product of example 44, step 1 with the product of step 1.

$^1$H-NMR (CDCl$_3$) δ:1.52–1.79(2H,m), 1.93–2.11(2H,m), 2.27–2.49(4H,m), 2.49–2.60(5H,m), 2.60–2.73(2H,m), 5.40 (2H,brs), 6.22(1H,t), 6.87(1H,d), 7.29–7.34(3H,m), 7.42(2H,d), 7.59(1H,dd), 7.75(1H,dd), 7.96(1H,d), 8.53(1H, dd). MS m/z: 489(M+1)

Example 316

To a stirred solution of phenol containing the product of Example 44 (1.0 mmol) and K$_2$CO$_3$ (1.5 mmol) in THF (10 mL) at RT was added N,N-dimethylcarbamoylchloride (1.2 mmol). The reaction was stirred at reflux for 24 hrs. Excess solvent was removed and pure compound was isolated via silica gel chromatography eluting with 5% MeOH/CH$_2$Cl$_2$. MS m/z: (M+535)

Example 317

To a stirred solution of phenol containing the product of Example 44 (1.0 mmol) and K$_2$CO$_3$ (1.5 mmol) in THF (10 mL) at RT was added morpholinocarbamoylchloride (1.2 mmol). The reaction was stirred at reflux for 24 hrs. Excess solvent was removed and pure compound was isolated via silica gel chromatography eluting with 5% MeOH/CH$_2$Cl$_2$. MS m/z: (M+577)

Example 318

To a stirred solution of phenol containing the product of Example 44 (1.0 mmol) in DMF at RT was added NaH (1.5 mmol) followed by the addition of N-isopropylisocyanate (1.5 mmol). The reaction was heated to 60° C. for 6 hrs. The reaction was quenched with 1.5 equivalents of H$_2$O and excess DMF was removed under reduced pressure. Residue was charged on a silica gel column and eluted off with 5% MeOH/CH$_2$Cl$_2$. MS m/z: (M+548)

Example 319

To a stirred solution of phenol containing the product of Example 44 (1.0 mmol) and K$_2$CO$_3$ (1.5 mmol) in THF (10 mL) at RT was added N-methyl-N-phenylcarbamoylchloride (1.2 mmol). The reaction was stirred at reflux for 24 hrs. Excess solvent was removed and pure compound was isolated via silica gel chromatography eluting with 5% MeOH/CH$_2$Cl$_2$. MS m/z: (M+597)

Example 320

To a stirred solution of phenol containing the product of Example 44 (1.0 mmol) in DMF at RT was added NaH (1.5 mmol) followed by the addition of N-phenylisocyanate (1.5 mmol). The reaction was heated to 60° C. for 6 hrs. The reaction was quenched with 1.5 equivalents of H$_2$O and excess DMF was removed under reduced pressure. Residue was charged on a silica gel column and eluted off with 5% MeOH/CH$_2$Cl$_2$. MS m/z: (M+583)

Example 321

To a stirred solution of phenol containing the product of Example 44 (1.0 mmol) in DMF at RT was added NaH (1.5 mmol) followed by the addition of N-(3-pyridyl)isocyanate (1.5 mmol). The reaction was heated to 60° C. for 6 hrs. The reaction was quenched with 1.5 equivalents of H$_2$O and excess DMF was removed under reduced pressure. Residue was charged on a silica gel column and eluted off with 5% MeOH/CH$_2$Cl$_2$. MS m/z: (M+584)

Example 322

To a stirred solution of phenol containing the product of Example 44 (1.0 mmol) and K$_2$CO$_3$ (1.5 mmol) in THF (10 mL) at RT was added pyrolidinylcarbamoylchloride (1.2 mmol). The reaction was stirred at reflux for 24 hrs. Excess solvent was removed and pure compound was isolated via silica gel chromatography eluting with 5% MeOH/CH$_2$Cl$_2$. MS m/z: (M+560)

Example 323

The compound was prepared by following the procedure for example 45, step 3, but replacing 4-(4-chlorophenyl)-4-hydroxypiperidine with 4-(4-chlorophenyl)-4-cyanopiperidine. MS m/z: (M+486).

Example 324

To a cold (0° C.) stirred solution of Example 323 (0.50 g, 0.104 mmol) in anhydrous THF (5 mL) was added lithium aluminum hydride (8 mg, 0.21 mmol). The reaction was stirred at RT for 2 hrs. The reaction was then quenched by the careful addition of H$_2$O (0.21 mL), 15% aqueous KOH (0.21 mL), then H$_2$O (0.21 mL). The organic layer was separated and dried over Na$_2$SO$_4$. The compound was purified via silica gel flash chromatography eluting with 10% methanol/methylene chloride. MS m/z: (M+490)

Example 325

The compound can be obtained by the reduction of the azido functionality of Example 187 with a reducing agent, such as triphenyl phoshine, lithium aluminum hydride, sodium borohydride, in a solvent such as tetrahydrofuran or diethyl ether in reaction temperature ranges from 0° C. to reflux with a reaction time between 5 minutes and 72 hours.

Example 326

The compound was prepared by following the procedure for example 45, step 3, but replacing 4-(4-chlorophenyl)-4-hydroxypiperidine with 4-(4-chlorophenyl)-4-methylpiperidine provide in Example 329, steps 1–3. MS m/z: (M+475)

Example 328

Step 1.

N-benzyl-4-(4-chlorophenyl)-4-hydroxypiperidine: FIG. 8a

To a stirred solution of commercially available 4-(4-chlorophenyl)-4-hydroxypiperidine (10 g, 47 mmol., 1) in anhydrous DMF (10 mL) was added benzyl bromide (5.6 mL, 47 mmol) and $K_2CO_3$ (7.4 g, 94 mmol.) and stirred at RT overnight. Excess solvent was removed under reduced pressure, brought up into $CH_2Cl_2$ (100 mL) washed with $H_2O$ (2×50 mL). Organic layer separated, dried over $Na_2SO_4$ and charged on a silica gel flash column. Eluting off with 2% MeOH/$CH_2Cl_2Cl_2$ 10 g 2 (80% yield) was obtained as a viscous liquid. MS m/z: (M+303)

Step 2

N-benzyl-4-(4-chlorophenyl)-4-fluoropiperidine: FIG. 8a

To a cold (−78° C.) solution of 2 (10 g, 33 mmol) in $CH_2Cl_2$ (20 mL) was slowly added DAST (diethylaminosulfur trifluoride, 5.3 mL, 39.8 mmol) under an inert atmosphere. The reaction was stirred at −78° C. for an additional 45 min. The reaction was quenched at −78° C. by the slow addition of enough saturated aqueous sodium bicarbonate solution to afford a pH>8. This reaction resulted a quantitative conversion of the starting material to a 1:1 mixture of fluoropiperidine 3 and 4-(4-chlorophenyl)tetrahydropyridine 4. The mixture of 3 and 4 (3.5 g, mixture, 35% yield) was purified via silica gel flash chromatography, eluting with 2% MeOH/$CH_2Cl_2$. This mixture proved to be inseparable by silica gel flash chromatography. In order to separate out the desired product, the mixture of 3 and 4 were subjected to osmium tetroxide oxidation.

To a stirred solution of the mixture of 3 and 4 (1.8 g) in acetone/$H_2O$ (5:1, 10 mL) was added a catalytic amount of $OsO_4$ in isopropanol (2.5 mol %, 1 mL) and N-methylmorpholine-N-oxide (0.69 g, 6.56 mmol). The reaction was stirred at RT overnight. The reaction was then evaporated to dryness, brought up into $CH_2Cl_2$ and washed with NaHSO3. This reaction resulted in the dihydroxylation of the undesired 4 to 5 and the clean separation of the desired fluoropiperidine 3 (1.0 g, 55% yield) from the byproduct by silica gel flash chromatography eluting with 2% MeOH/$CH_2Cl_2$. MS m/z: (M+306)

Step 3

4-(4-chlorophenyl)-4-fluoropiperidine: FIG. 8a

To a cold (0° C.) solution of 3 (1.07 g, 3.5 mmol) in 1,2-dichloroethane was added 1,1-chloroethylchloroformate (0.45 mL, 4.2 mmol). The reaction was then heated to reflux for 2 hrs. Excess solvent was removed and the residue was brought up into 5 mL methanol. The mixture was refluxed for 2 hrs and excess methanol was removed under reduced pressure. Precipitation of the hydrochloride salt of 6 by the addition of $CH_2Cl_2$/hexane (1:1) followed by filtration resulted in the quantitative isolation of the desired crystalline product 6 (80%, 0.70 g). MS m/z: (M+215)

Step 4

The compound was prepared by following the procedure for example 44, but replacing 4-(4-chlorophenyl)-4-hydroxypiperidine with 4-(4-chlorophenyl)-4-fluoropiperidine. MS m/z: (M+466)

Example 329

Step 1

Figure 8C:
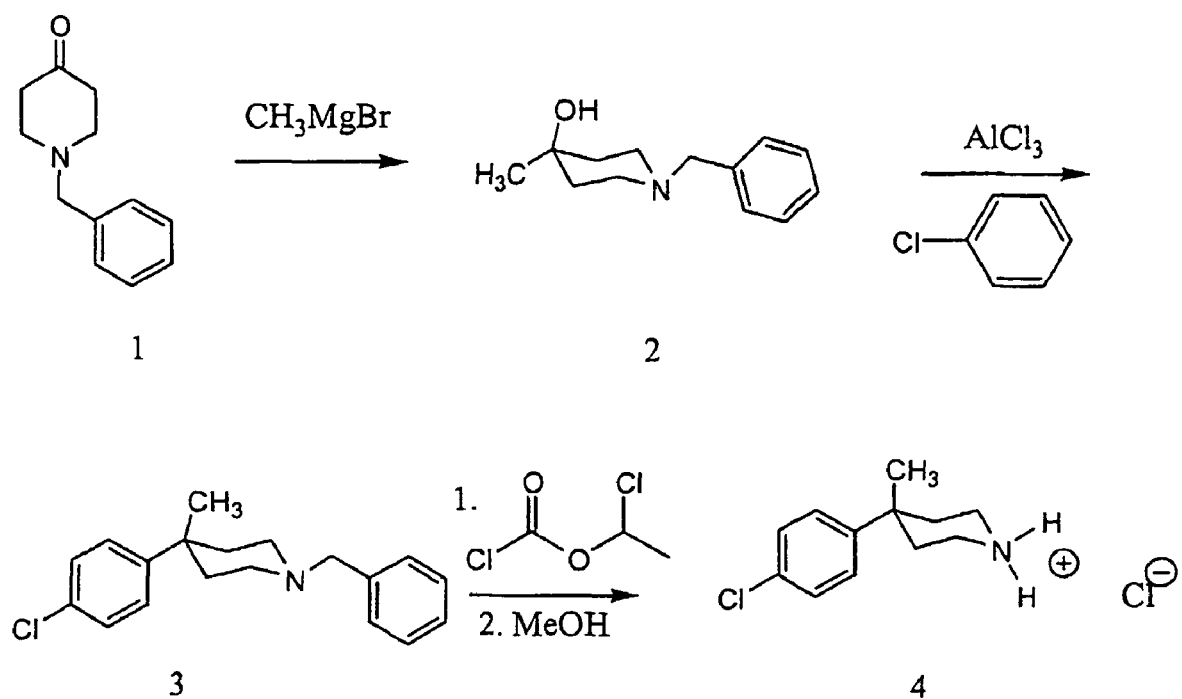
FIG. 8C is a schematic showing the preparation of 4-(4-chlorophenyl)-4-methylpiperidine.

N-benzyl-4-methylpiperidine: FIG. 8c

To a cold (−78° C.) stirred solution of 1.4 M methyllithium in THF (39 mL, 54 mmol) under an inert atmosphere was added N-benzyl-4-oxopiperidine (1, 5.1 g, 27 mmol). The reaction was stirred at −78° C. for 2 hrs. The reaction was quenched by the slow addition of saturated aqueous $NH_4Cl$, the organic layer was separated and dried over $Na_2SO_4$. Pure methylpiperidine (2) was isolated via silica gel flash chromatography eluting with 5% MeOH/$CH_2Cl_2$. MS m/z: (M+206)

Step 2

N-benzyl-4-(4-chlorophenyl)-4-methylpiperidine: FIG. 8c

To a flask containing chlorobenzene (10 mL, excess) and methylpiperidine (0.42 g, 2.06 mmol, 2) was added aluminum trichloride (1.65 mL, 12.4 mmol). The reaction was heated to reflux for 24 hrs. Excess chlorobenzene was removed under reduced pressure and pure 3 was obtained via silica gel flash chromatography eluting with % EtOAc/hexane. MS m/z: (M+300)

Step 3

4-(4-chlorophenyl)-4-methylpiperidine: FIG. 8c

To a cold (0° C.) solution of N-benzyl-4-(4-chlorophenyl)-4-methylpiperidine (3) (0.41 g, 1.4 mmol) in $CH_2Cl_2$ was 1.1 equivalent of 1-chloroethylchloroformate. The reaction was then heated to reflux for 2 hrs. Excess solvent was removed and the residue was brought up into methanol. The mixture was refluxed for 2 hrs and excess methanol was removed under reduced pressure. Precipitation of the hydrochloride salt 4 by the addition of $CH_2Cl_2$ followed by filtration resulted in the quantitative isolation of the desired crystalline product 4 (100%, 0.34 g). MS m/z: (M+210)

Step 4

The compound was prepared by following the procedure for example 44, step 2, but replacing 4-(4-chlorophenyl)-4-hydroxypiperidine with 4-(4-chlorophenyl)-4-methylpiperidine. MS m/z: (M+461)

Example 330

The compound was prepared by following the procedure for example 199, but replacing the resultant compound of example 44 with the resultant compound of Example 329. MS m/z: (M+533)

Example 331

Step 1

A mixture of epichlorohydrin (5.92 g, 64 mmol) and benzhydrylamine (11.7 g, 64 mmol) in MeOH (120 mL) was stirred under the protection of argon at room temperature for 48 hours. The mixture was then stirred at 50° C. for 72 hours. The reaction mixture was then stirred at room temperature for 72 hours. The reaction mixture was concentrated in vacuo and partitioned between EtOAc and $H_2O$. The aqueous layer was extracted with EtOAc (200 mL×3), dried over $MgSO_4$ and concentrated in vacuo. Chromatographic purification on silica gel ($CH_2Cl_2$/MeOH=95/5) provided 10.0 g (65%) of 1-benzhydril-3-hydroxyazetidine. m/z 240 (m+1)

Step 2

A mixture 1-benzhydril-3-hydroxyazetidine (2.6 g, 11 mmol) and palladium hydroxide on active carbon (0.26 g, w/w 20%) in EtOH (40 mL) was shaken in hydrogenation parr under 60 psi for 24 hours. The reaction mixture was filtered through celite and concentrated under vacuum. Concentration in vacuo provided 0.75 (95%) 3-hydroxyazetidine. $^1$H NMR (250 MHz, CD3OD) 3.81–3.92 (2H, m), 4.14–4.25 (2H, m), 4.61–4.69 (1H, m).

Step 3

The compound 1-[3-(5,11-dihydro-7-(methoxy[1]benzoxepino[2,3-b]pyridin-5-ylidene)propyl]azetidin-3-ol was prepared by following the procedure for example 45, step 3, but replacing 4-(4-chlorophenyl)-4-hydroxypiperidine with 3-hydroxyazetidine. m/z 339 (m+1)

Step 4

To a mixture of morpholine N-oxide (0.028 g, 0.244 mmol), crushed molecular sieves (0.066 g) and $Pr^4N^+RO_4$ (0.01 g, 0.024 mmol) in $CH_2Cl_2$ was added the 1-[3-(5,11-dihydro-7-(methoxy[1]benzoxepino[2,3-b]pyridin-5-ylidene)propyl]azetidin-3-ol (0.055 g, 0.16 mmol) under the protection of argon. The mixture was stirring over night at room temperature. The reaction mixture was filtered off through celite and concentrated under vacuum. Chromatographic purification on silica gel ($CH_2Cl_2$/MeOH=95/5 to 9/1) provided 0.033 g 1-[3-(5,11-dihydro-7-(methoxy[1]benzoxepino[2,3-b]pyridin-5-ylidene)propyl]azetidin-3-one (60%) of the desired product. m/z 337 (m+1)

Step 5

To a solution of 1-[3-(5,11-dihydro-7-(methoxy[1]benzoxepino[2,3-b]pyridin-5-ylidene)propyl]azetidin-3-one (0.06 g, 0.18 mmol) in THF (8 mL) was added dropwise a solution of 4-chlorophenyl magnesium bromide in diethyl ether (1.0 M, 0.27 mL) under the the protection of argon at 0° C. The reaction was stirred at room temperature for 1.5 hours and quenched by the addition of saturated aqueous $NH_4OH$ (4 mL). The aqueous layer was extracted with EtOAc (10 mL×2), dried over MgSO4 and concentrated in vacuo. Chromatographic purification on silica gel ($CH_2Cl_2$/MeOH=95/5) provided 0.048 g 3-(4-chlorophenyl)-1-[3-(5,11-dihydro-7-(methoxy[1]benzoxepino[2,3-b]pyridin-5-ylidene)propyl]azetidine (51%) m/z 449 (m+1)

Example 332

Step 1

Tert-Butyl 3-(4-chlorobenzoyl)-1-(2-aminoethyl) carbamate: FIG. 10b tert-Butyl N-(2-aminoethyl) carbamate (1, 0.50 g g, 3.12 mmol) was added to the mixture of 4-chlorobenzoic acid chloride (0.547 g, 3.12 mmol) and $Et_3N$ (1.74 mL, 12.5 mmol) in $CH_2Cl_2$ (20 mL) under the protection of argon. Stirring at room temperature for 2 hours. The reaction mixture was diluted with $H_2O$ (25 mL), extracted with $CH_2Cl_2$ (50 mL×2), dried over $MgSO_4$ and concentrated in vacuo. Chromatographic purification on silica gel ($CH_2Cl_2$/MeOH=95/5) to provide 0.86 g (2, 93%) of the desired product tert-Butyl 3-(4-chlorobenzoyl)-1-(2-aminoethyl) carbamate. MS m/z: (M+299)

Step 2

1-(4-chlorobenzoyl)-1,2-ethylenediamine: FIG. 10b

Trifluoroacetic acid (7.5 mL) was added to the solution of tert-Butyl 3-(4-chlorobenzoyl)-1-(2-aminoethyl)carbamate (2, 0.86 g, 2.89 mmol) in $CH_2Cl_2$ (35 mL) at 0° C. Stirring at room temperature for 30 minutes. Concentration in vacuo provided 0.88 g (95%) of the desired product 1-(4-chlorobenzoyl)-1,2-ethylenediamine (3). MS m/z: (M+199)

Step 3

The compound was prepared by following the procedure for example 45, step 3, but replacing 4-(4-chlorophenyl)-4-hydroxypiperidine with 1-(4-chlorobenzoyl)-1,3-propylenediamine. MS m/z: (M+465)

Example 333

Step 1

Figure 9A:
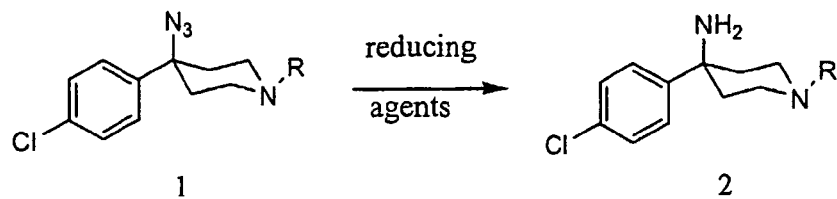
FIG. 9A is a schematic showing the preparation of compounds represented by Structural Formulas (I), (VIII) and (VIII) wherein $R^1$ is an amine.
Figure 9B:
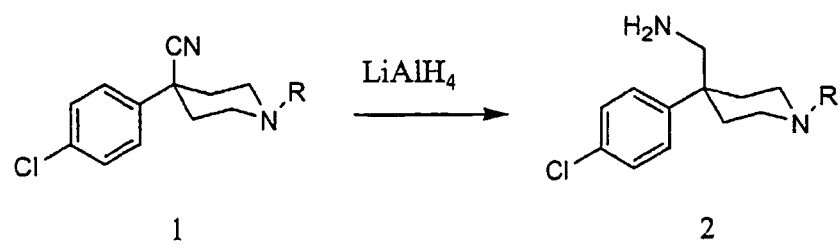
FIG. 9B is a schematic showing the preparation of compounds represented by Structural Formulas (I), (VIII) and (VIII) wherein $R^1$ is an alkylamine.
Figure 9C:
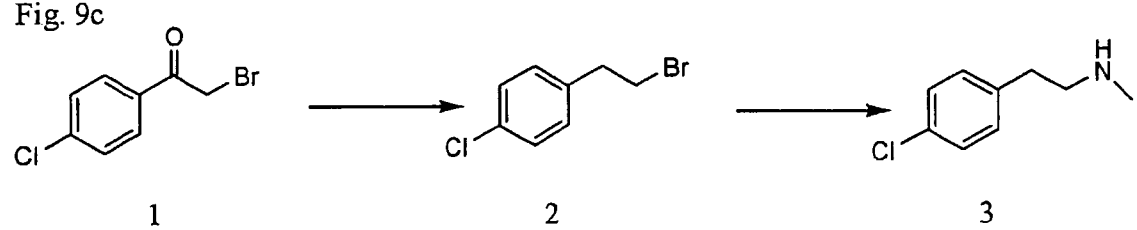
FIG. 9C is a schematic showing the preparation of 2-(4-chlorophenyl)-1-(N-methyl)ethylamine.

2-(4-Chlorophenyl)-1-bromoethylene: FIG. 9c

To a solution of $AlCl_3$ (1.96 g, 14.7 mmol) in anhydrous $CH_2Cl_2$ (50 mL), Borane-tert-butyl amine complex (2.57 g, 29.6 mmol) was added at 0° C. under argon protection, stirred for 10 minutes and clear solution was formed. 4-Chlorophenacyl bromide (1, 1.11 g, 4.91 mmol) in $CH_2Cl_2$ (5 mL) was added to the resulted mixture at 0° C. The reaction was stirred for 1.5 hours and then quenched by the addition of 0.1 N HCl (25 mL). The mixture was extracted with EtOAc (80 mL×3), dried over MgSO4 and concentrated in vacuo. Chromatographic purification on silica gel (Hexane/EtOAc=9:1) provided 0.85 g (84%) of 2-(4-chlorophenyl)-1-bromoethylene (2). MS m/z: (M+219)

Step 2

2-(4-chlorophenyl)-1-(N-methyl)ethylamine: FIG. 9c

A mixture of 2-(4-chlorophenyl) 1-bromoethylene (2, 1.02 g, 4.62 mmol), EtOH (3 mL) and $H_2NMe$ in $H_2O$ (6 mL, 40% w/w) was heated at 135 0° C. over night. The mixture was cooled down to room temperature. The mixture was extracted with $Et_2O$ (5 mL×2), dried over $MgSO_4$ and concentrated in vacuo. Chromatographic purification on silica gel ($CH_2Cl_2$/MeOH/$NH_4OH$=9/1/0.1) provided 0.61 g 2-(4-chlorophenyl)-1-(N-methyl)ethylamine (3, 79%). MS m/z: (M+170).

Step 3

The compound was prepared by following the procedure for example 45, step 3, but replacing 4-(4-chlorophenyl)-4-hydroxypiperidine with 2-(4-chlorophenyl)-1-(N-methyl) ethylamine. MS m/z: (M+451).

Example 334

Step 1

Figure 9D:
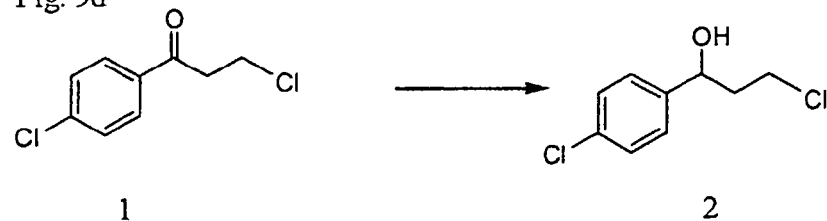
FIG. 9D is a schematic showing the preparation of 3-(4-chlorophenyl)-3-chloro-1-hydroxypropane.
Figure 9E:
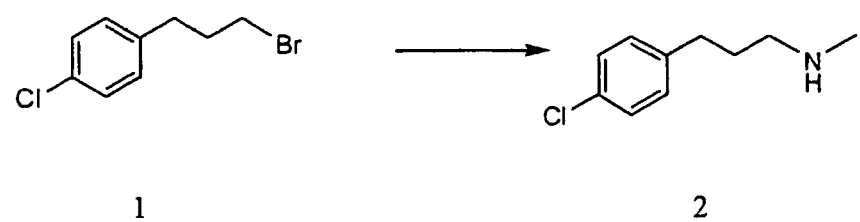
FIG. 9E is a schematic showing the preparation of 3-(4-chlorophenyl)-1-N-methylaminopropane.

3-(4-chlorophenyl)-1-N-methylaminopropane: FIG. 9e

A mixture of 3-(4-chlorophenyl)-1-bromoropane (1, 0.70 g, 3.73 mmol), EtOH (3 mL) and H$_2$NMe in H$_2$O (6 mL, 40% w/w) was heated at 135 0° C. overnight. The mixture was then cooled down to room temperature. The mixture was extracted with Et$_2$O (5 mL×2), dried over MgSO$_4$ and concentrated in vacuo. Chromatographic purification on silica gel (CH$_2$Cl$_2$/MeOH/NH$_4$OH=9/1/0.1) provided 0.5 g (76%) of 3-(4-chlorophenyl)-1-N-methylaminopropane (2). MS m/z: (M+189)

Step 2

The compound was prepared by following the procedure for example 45, step 3, but replacing 4-(4-chlorophenyl)-4-hydroxypiperidine with 3-(4-chlorophenyl)-1-N-methylaminopropane. MS m/z: (M+450)

Example 335

Step 1

3-(4-chlorophenyl)-3-chloro-1-hydroxypropane: FIG. 9d

To 3,4'-Dichloropropylphenone (0.52 g, 2.53 mmol) in anhydrous MeOH (10 mL) at 0° C. under the protection of argon, NaBH$_4$ (0.23 g, 3.03 mmol) was added to the solution by several portions. The reaction was stirred under the same condition for 15 minutes. The mixture was warmed up to room temperature, stirred an additional 30 minutes, then concentration in vacuo. The residue was partitioned between EtOAc and H$_2$O. The aqueous layer was re-extracted with EtOAc (30 mL×2), dried over MgSO$_4$ and concentrated in vacuo. Chromatographic purification on silica gel (Hexane/EtOAc=(1/1) provided 0.52 g (99%) of 3-(4-chlorophenyl)-3-chloro-1-hydroxypropane. MS m/z: (M+205).

Step 2

The compound was prepared by following the procedure for example 45, step 3, but replacing 4-(4-chlorophenyl)-4-hydroxypiperidine with 3-(4-chlorophenyl)-3-chloro-1-hydroxypropane. MS m/z: (M+481).

Example 336

Step 1

3-(4-chlorophenyl)-3-hydroxy-3-methyl-1-chloropropane: FIG. 10a

To 3,4'-Dichloropropylphenone (1, 1.10 g, 5.40 mmol) in anhydrous THF at 0° C. under the protection of argon, was added MeMgBr (2.50 mL, 7.35 mmol) dropwise at 0° C. The reaction was stirred at room temperature for an additional hour. The reaction was quenched by adding saturated aqueous NH$_4$Cl. The reaction was then extracted with Et$_2$O (60 mL×2), dried over MgSO$_4$ and concentrated in vacuo. Chromatographic purification on silica gel (Hexane/EtOAc=10/1) provided 1.0 g (85%) of 3-(4-chlorophenyl)-3-hydroxy-3-methyl-1-bromoropane (2). MS m/z: (M+219).

Step 2

3-(4-chlorophenyl)-3-hydroxyl-3-methyl-1-N-methylaminopropane: FIG. 10a

A mixture of 3,3,3-(4-Chlorophenyl)-hydroxylmethyl-1-bromoropane (2, 1.04 g, 4.74 mmol), EtOH (5 mL) and H$_2$NMe in H$_2$O (10 mL, 40% w/w) was heated at 135 0° C. for 3 hours. The mixture was cooled down to room temperature. The mixture was extracted with Et$_2$O (5 mL×2), dried over MgSO$_4$ and concentrated in vauco. Chromatographic purification on silica gel (CH$_2$Cl$_2$/MeOH/NH$_2$OH=9/1/0.1) provided 1.01 g 3-(4-chlorophenyl)-3-hydroxyl-3-methyl-1-N-methylaminopropane (3, 99%). MS m/z: (M+214).

Step 3

The compound was prepared by following the procedure for example 45, step 3, but replacing 4-(4-chlorophenyl)-4-hydroxypiperidine with 3-(4-chlorophenyl)-3-hydroxyl-3-methyl-1-N-methylaminopropane. MS m/z: (M+480).

Example 345

Using the procedure of Example 45, but replacing 5,11-dihydro-7-methoxy[1]benzoxepino[2,3-b]pyridin-5-one with 1-azaxanthone, gives the desired compound.

Example 346

Using the procedure of Example 45, but replacing 5,11-dihydro-7-methoxy[1]benzoxepino[2,3-b]pyridin-5-one with 1–4-azafluorene, gives the desired compound.

Example 347

Using the procedure of Example 45, but replacing 5,11-dihydro-7-methoxy[1]benzoxepino[2,3-b]pyridin-5-one with 7-amino-1-azaxanthone, gives the desired compound.

Example 348

Using the procedure of Example 45, but replacing 5,11-dihydro-7-methoxy[1]benzoxepino[2,3-b]pyridin-5-one with 4,5-diazafluorene, gives the desired compound.

Example 349

Using the procedure of Example 45, but replacing 5,11-dihydro-7-methoxy[1]benzoxepino[2,3-b]pyridin-5-one with 1-aza-7-nitroxanthone, gives the desired compound.

Example 350

3-(4-chlorophenyl)-1-[3-(5,11-dihydro-7-(methoxy[1]benzoxepino[2,3-b]pyridin-5-ylidene)propyl]pyrrolidine Step 1

A mixture of 1-benzyl-3-pyrrolidinone (10.0 g, 57 mmol), di-tert-butyl dicarbonate (13.7 g, 63 mmol) and palladium on active carbon (2.5 g, w/w 20%) in MeOH was shaken in a Parr hydrogenation vessel (50 psi H$_2$) for 48 hours. The reaction mixture was filtered through celite and concentrated in vacuo. Chromatographic purification on silica gel (Hexane/EtOAc=1/1) provided 6.21 g 1-t-butoxycarbonyl-3-pyrrolidinone (59%). $^1$H NMR (250 MHz, CDCl3) δ: 1.46 (9H, s), 2.57 (2H, t, J=7.8 Hz), 3.71–3.75 (4H, m).

Step 2

To a stirred solution of 1-t-butoxycarbonyl-3-pyrrolidinone (0.57 g, 3.23 mmol) in THF (10 mL) was added 4-chlorophenyl magnesium bromide (1.0 M, 5.2 mL) under the protection of argon at 0° C. The reaction was stirred at room temperature for 1 hour then quenched by the addition of saturated aqueous NH$_4$OH (8 mL). The aqueous layer was extracted with EtOAc (50 mL×2), dried over MgSO$_4$ and concentrated in vacuo. Chromatographic purification on silica gel (Hexane/EtOAc=3/1) provided 0.57 g 1-t-butoxycarbonyl-3-(4-chlorophenyl)-3-hydroxypyrrolidine (60%). m/z 298 (m+1)

Step 3

To a stirred solution of 1-t-butoxycarbonyl-3-(4-chlorophenyl)-3-hydroxypyrrolidine (0.335 g, 1.28 mmol) in CH$_2$Cl$_2$ (8 mL) was added trifluoroacetic acid (2 mL) at 0° C. slowly. The reaction was stirred at room temperature for 30 minutes and concentrated in vacuo. This provided 0.355 g 3-(4-chlorophenyl)-3-hydroxypyrrolidine (100%) the desired product. m/z 198 (m+1)

Step 4

The titled compound was prepared by following the procedure for example 44 but replacing 4-(4-chlorophenyl)-4-hydroxypiperidine with 3-(4-chlorophenyl)-3-hydroxypyrrolidine. m/z 432 (m+1).

Example 351

Step 1

Figure 10D:
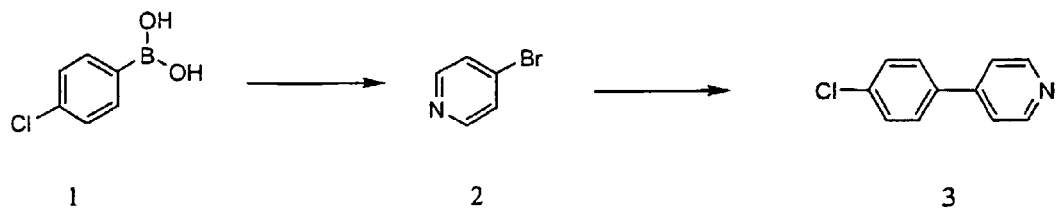
FIG. 10D is a schematic showing the preparation of 4-(4-chlorophenyl)-4-pyridine.
Figure 11D:
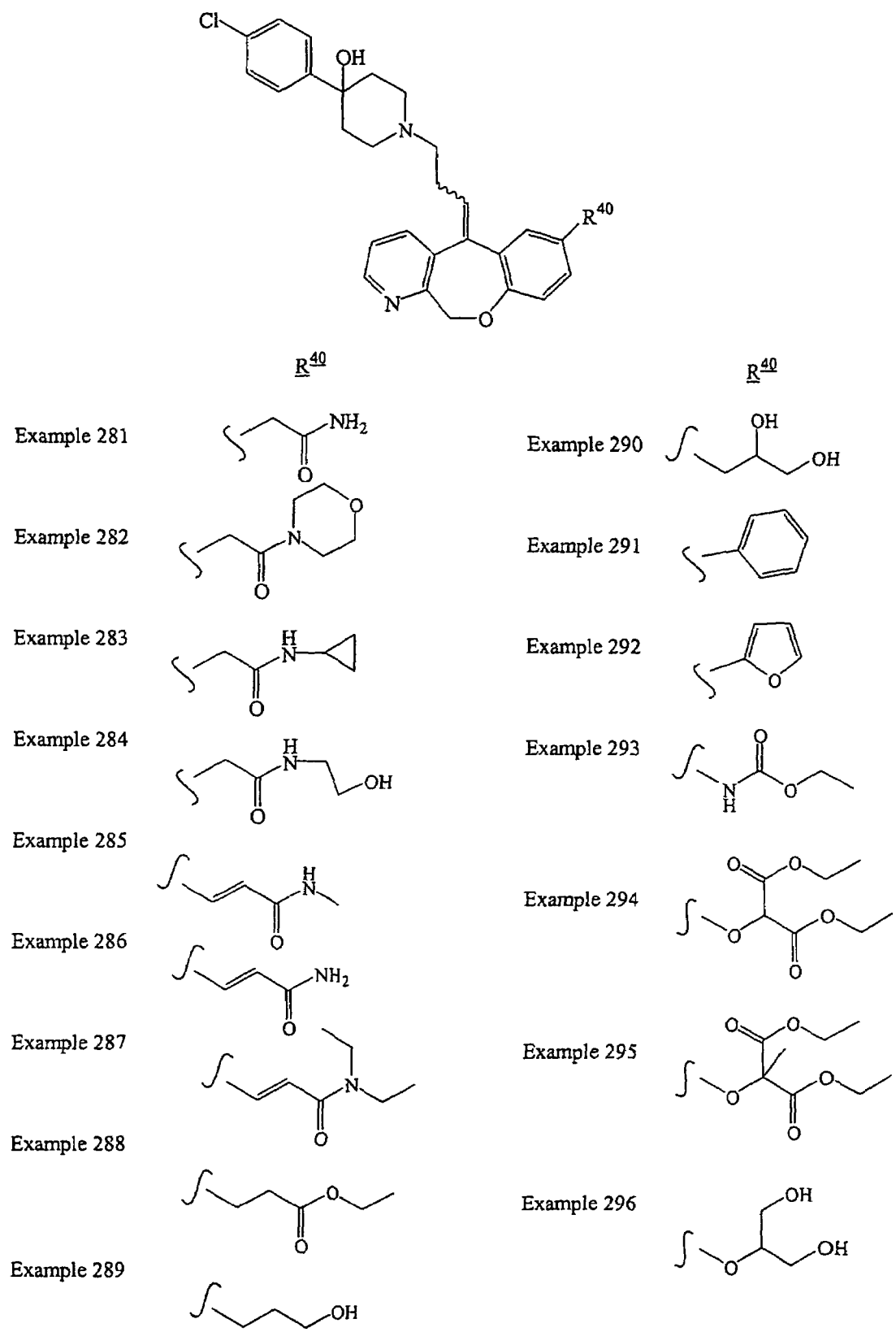
FIGS. 11A–11T show the structures of exemplary compounds of the present invention.
Figure 11E:
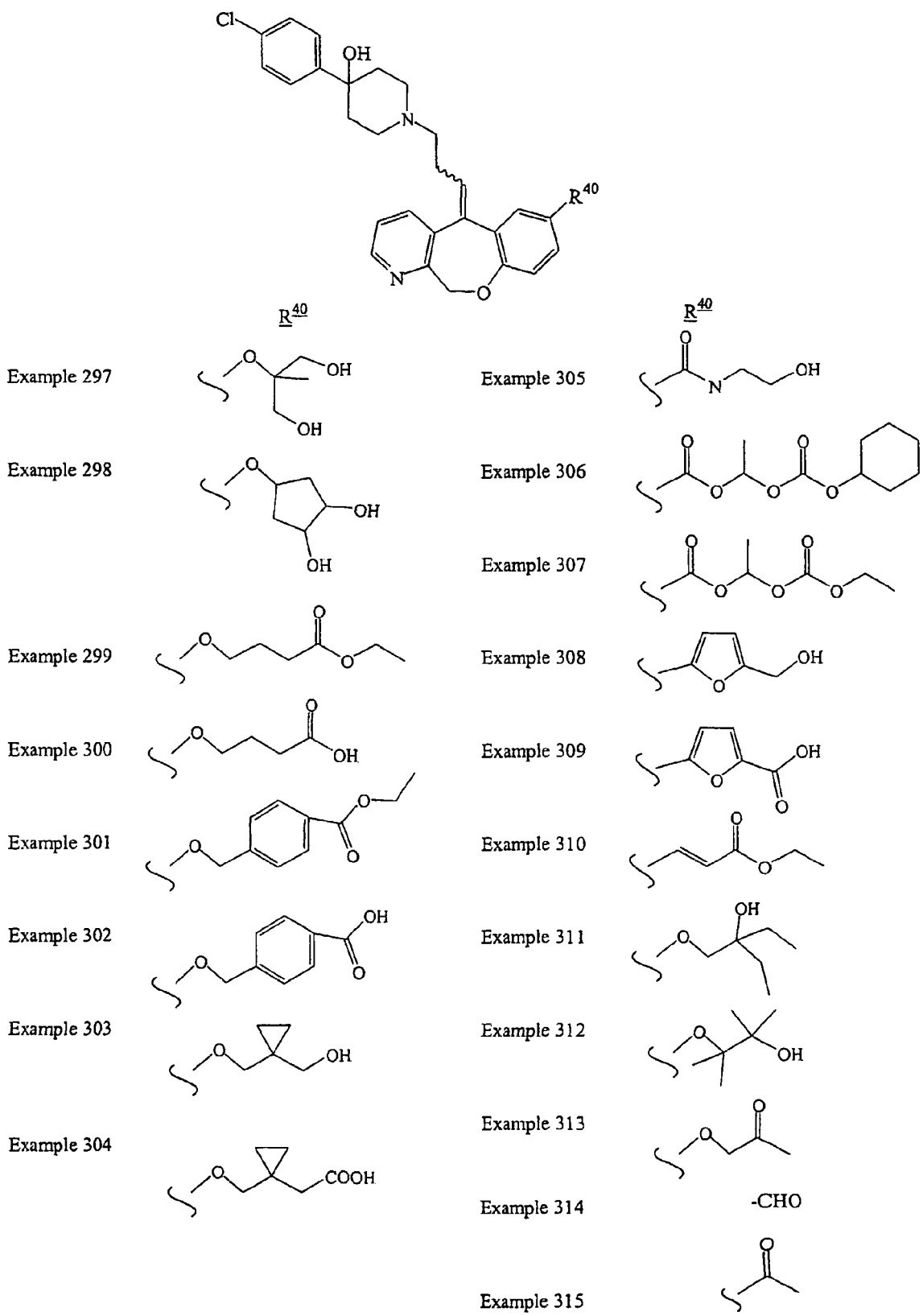
Figure 11L:
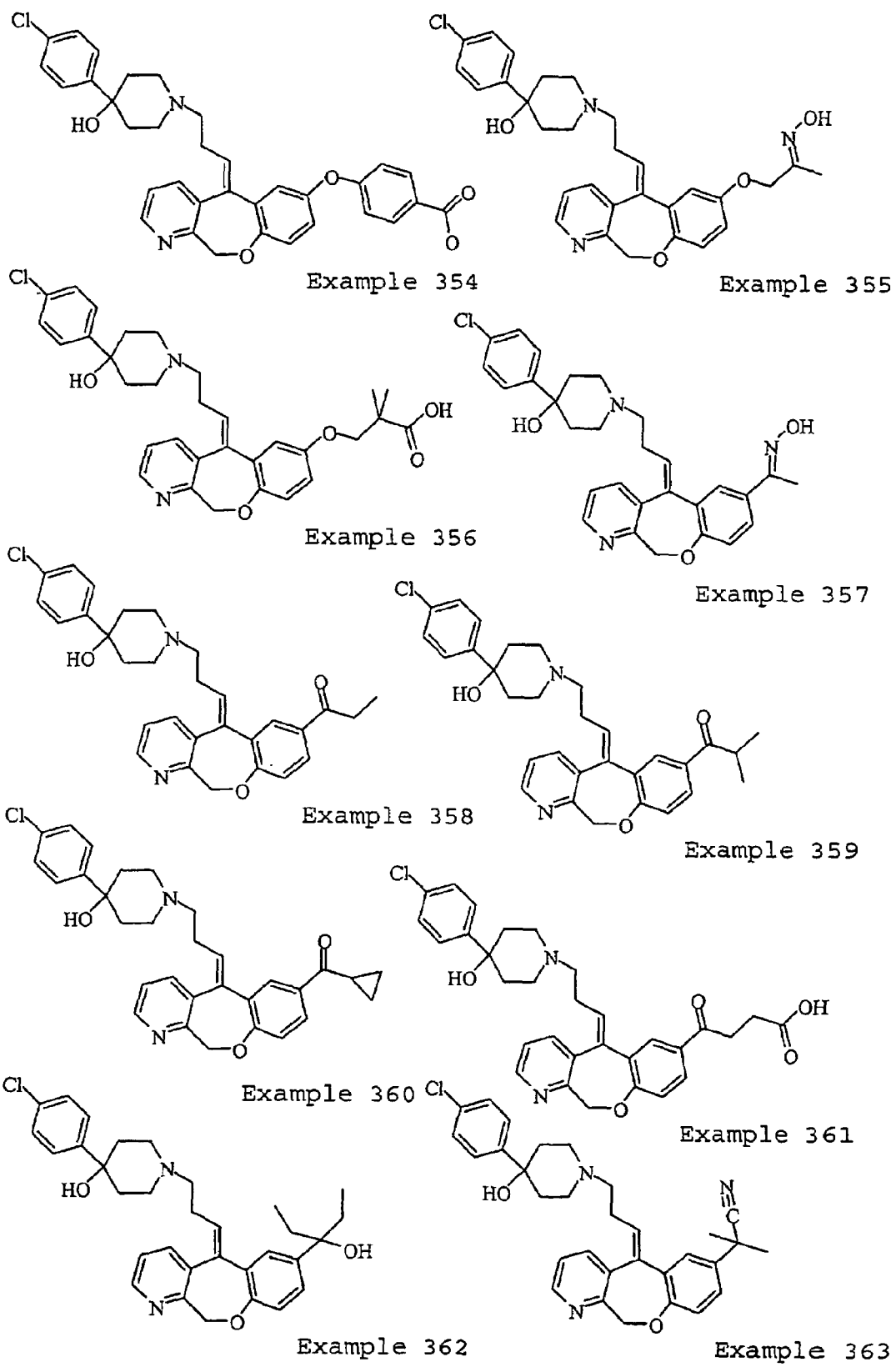
Figure 11M:
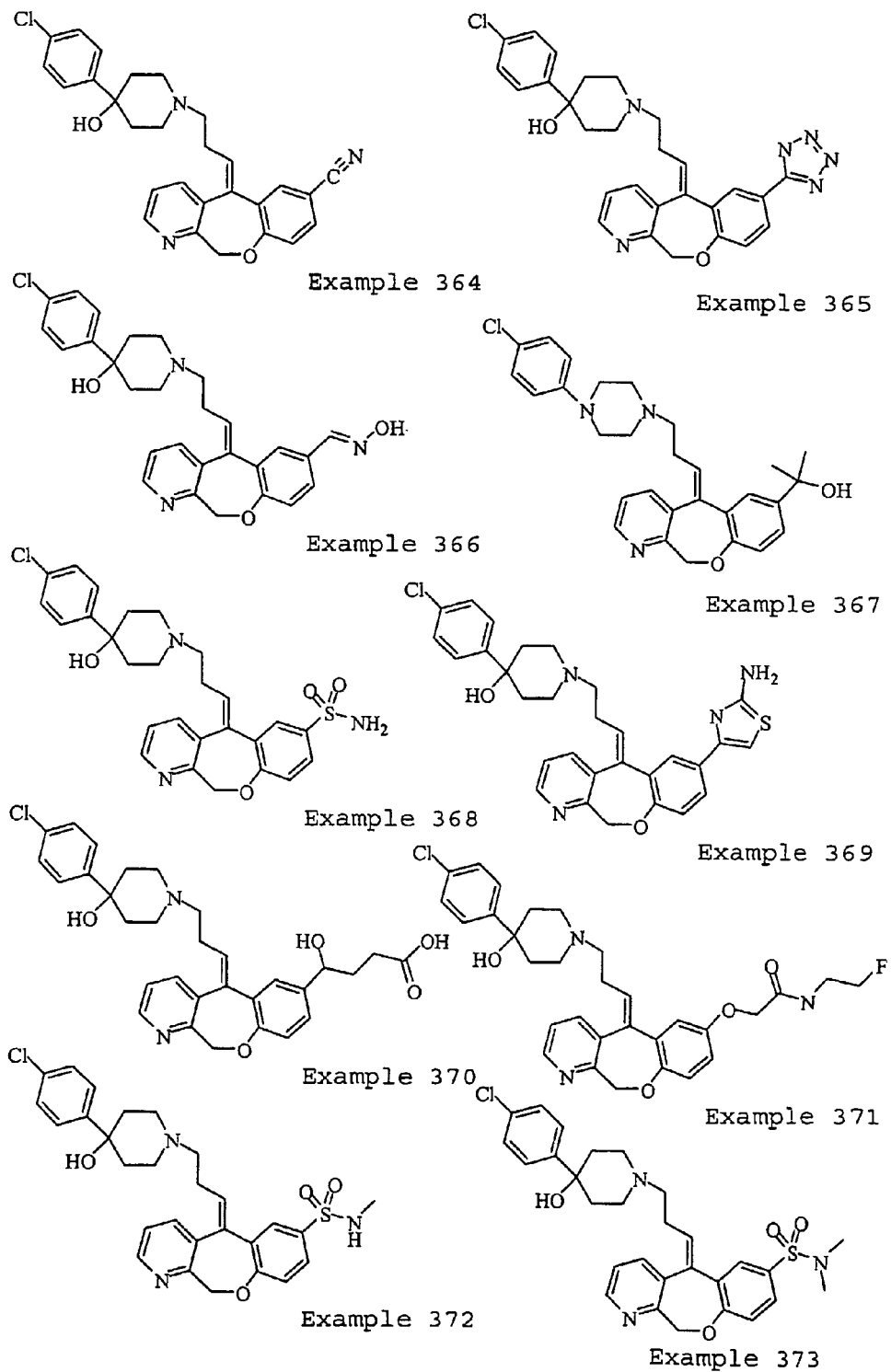
Figure 11N:
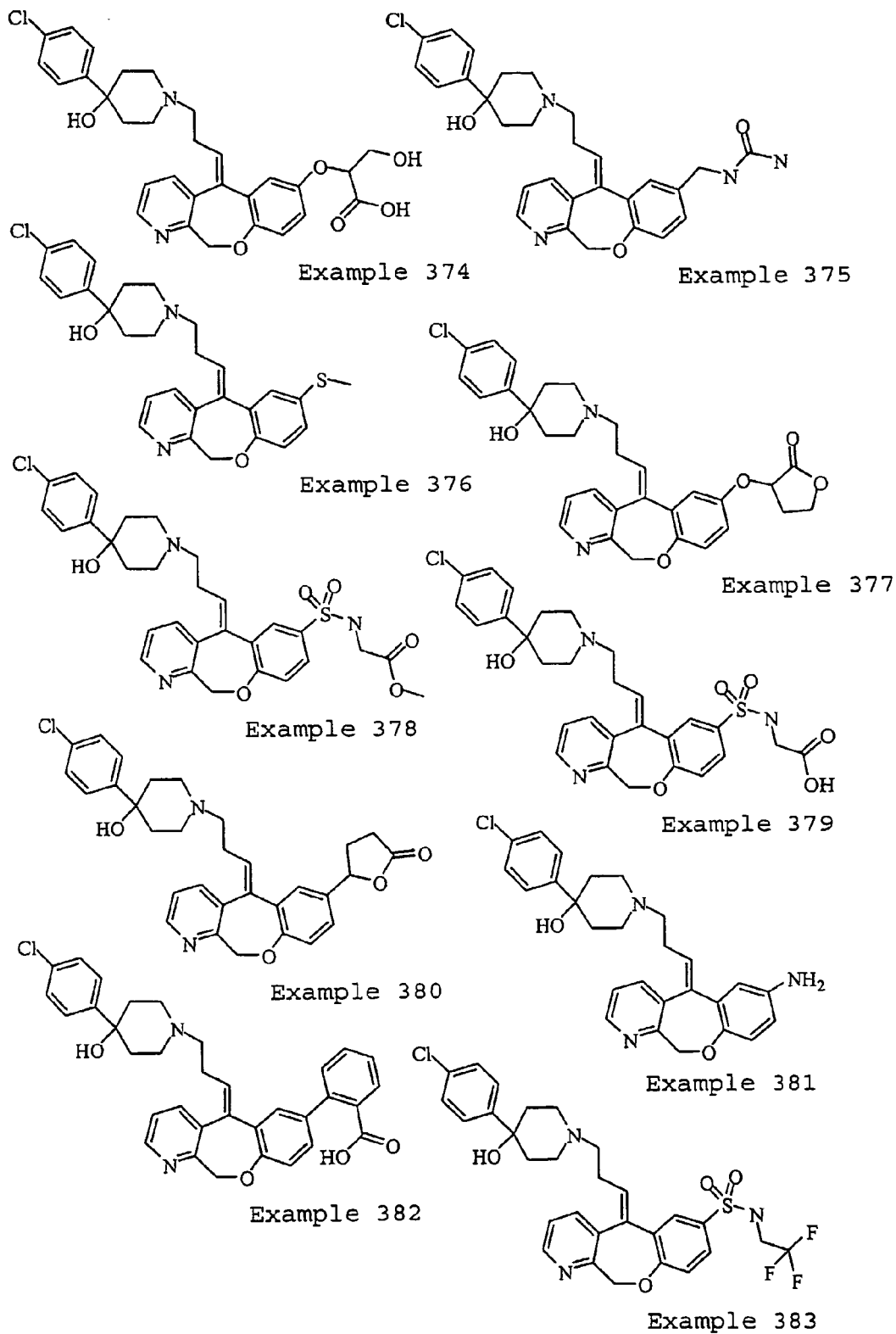
Figure 11O:
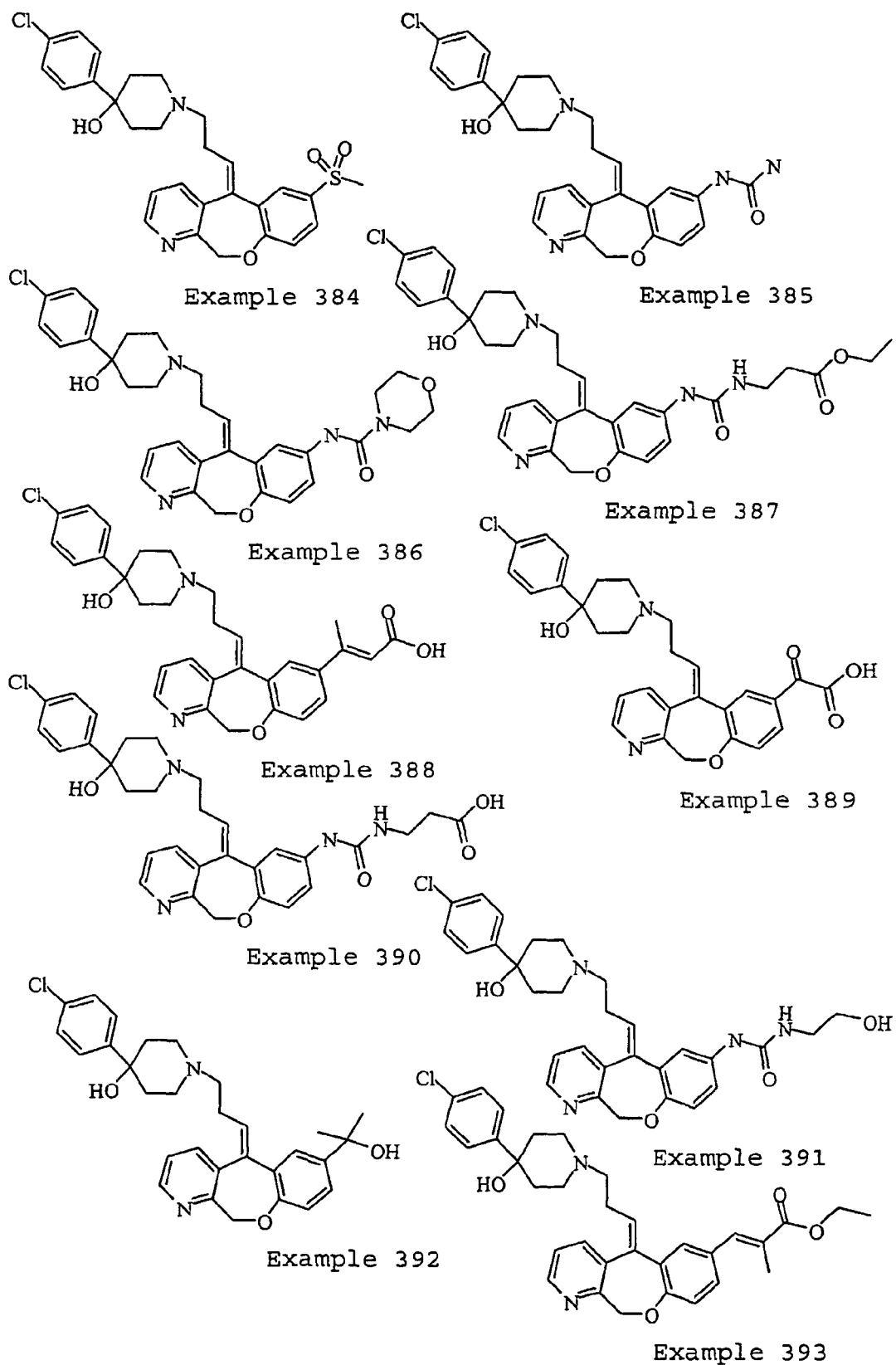
Figure 11P:
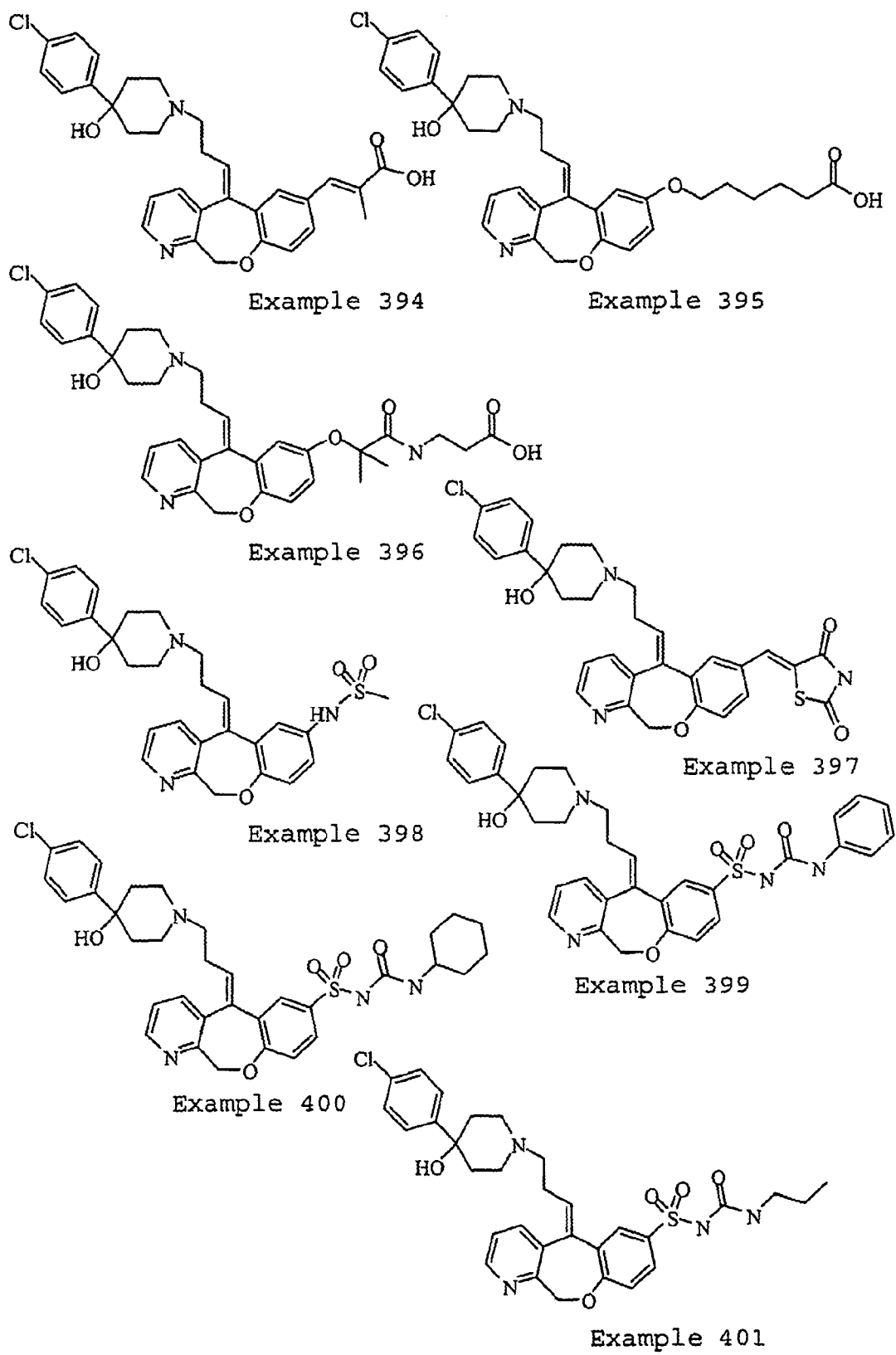
Figure 11Q:
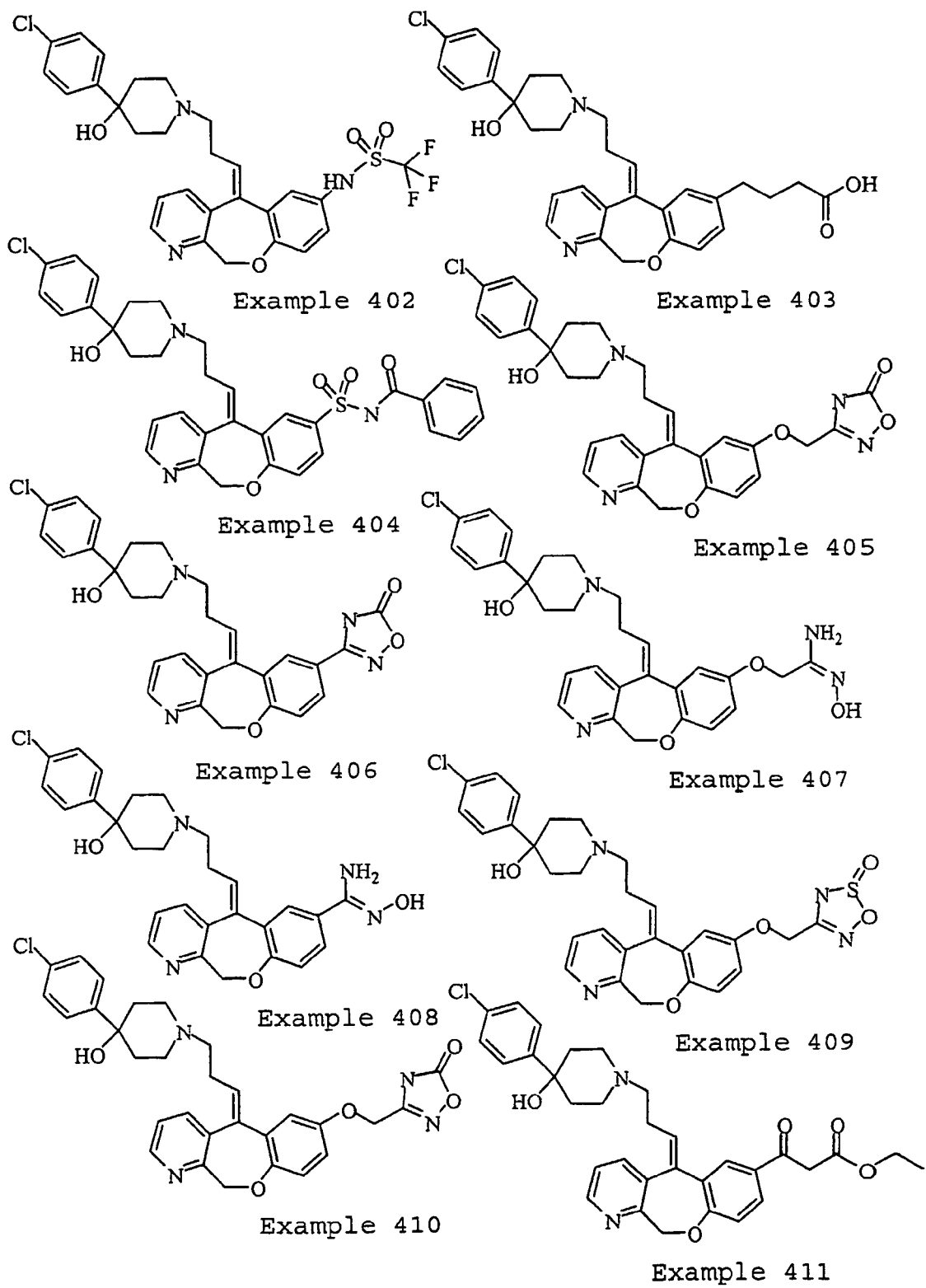
Figure 11R:
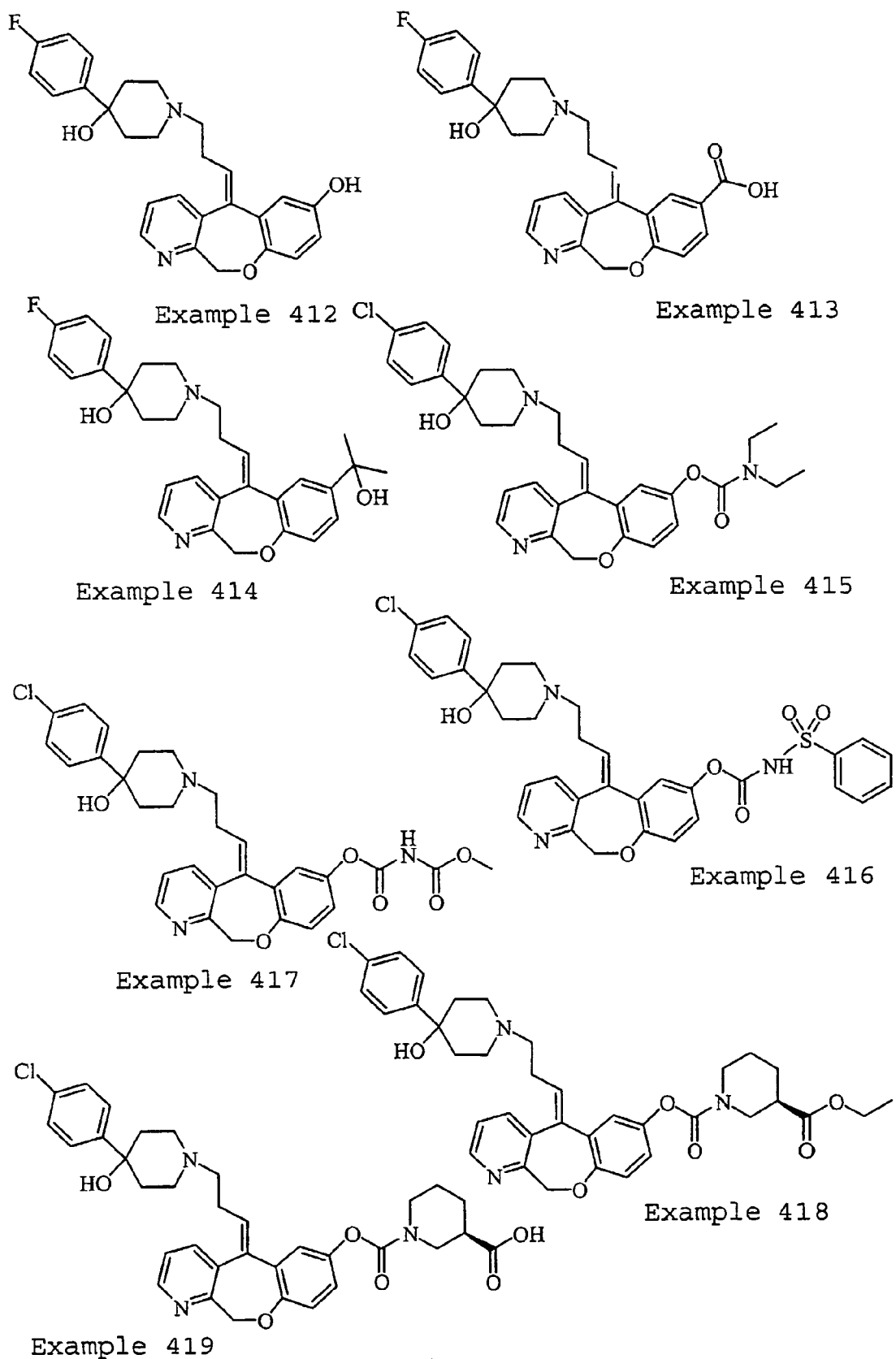
Figure 11T:
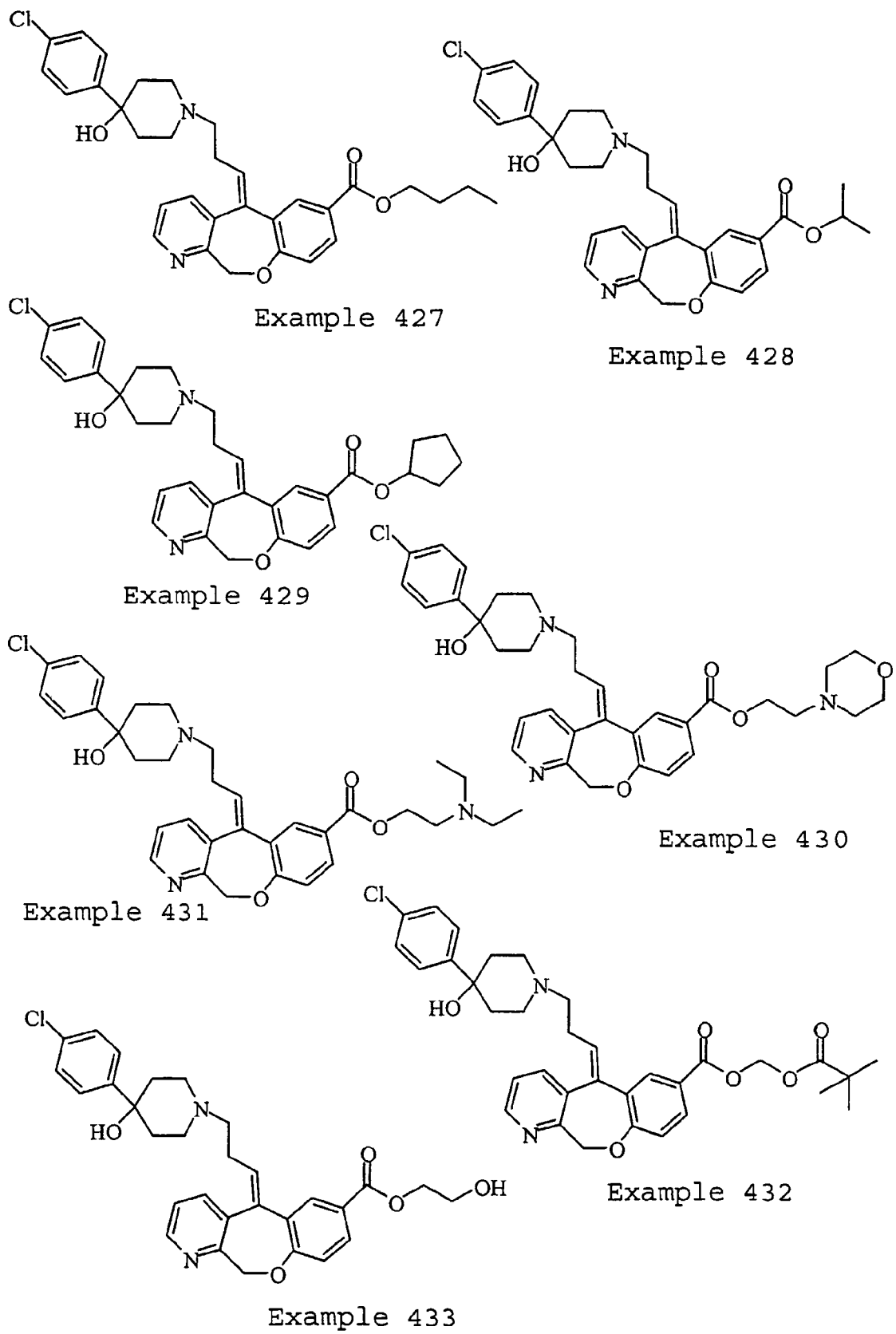

4-(4-chlorophenyl)-4-pyridine: FIG. 10d

To a solution of 4-bromopyridine (1, 1.94 g, mmol), 4-chlorophenylboronic acid (2, 1.56 g, mmol) and K$_2$CO$_3$ (2.76 g, 2.0 equiv) in ethanol/toluene (5 mL/100 mL) was added Pd(PPh$_3$)$_3$. The reaction was refluxed for 1 hr, cooled back down to RT and quenched with H$_2$O (15 mL). The reaction mixture was extracted with EtOAc and the organic layer was dried over Na$_2$SO$_4$. Pure 4-(4-chlorophenyl)-4-pyridine 2 (1.3 g, 68% yield) was isolated after silica gel flash column purification eluting with 50% EtOAc/hexane. MS m/z: (M+191).

Step 2

The titled compound was prepared by following the procedure for example 45, step 3, but replacing 4-(4-chlorophenyl)-4-hydroxypiperidine with 4-(4-chlorophenyl)-4-pyridine. MS m/z: (M+456).

Example 352

The compound was prepared by following the procedure for example 44, but replacing 4-(4-chlorophenyl)-4-hydroxypiperidine with 4-(4-chlorophenyl)-4-pyridine. MS m/z: (M+442).

Example 353

5-(2-(N-(4-(4-Chlorophenyl)-4-hydroxycyclohexyl)-N-methyl)ethylidene)-5,11-dihydro-7-methoxy[1]benzoxepino[2,3-b]pyridine The compound was prepared by the procedure of Example 57, step 3, but replacing 4-(4-chlorophenyl)-4-hydroxypiperidine with 4-(4-N-methyl-(4-chlorophenyl)-4-hydroxycyclohexylamin. The starting material can be prepared according to methods disclosed in Journal of Medicinal Chemistry, Vol. 15, No. 12, pp. 1239–1243 (1972).

Example 354

1-[3-(7-(4-Carboxyphenoxy)-5,11-dihydro[1]benzoxepino[2,3-b]pyridin-5-ylidene)propyl]-4-(4-chlorophenyl)piperidin-4-ol Step 1

4-(4-Chlorophenyl)-1-[3-(5,11-dihydro-7-(4-ethoxycarbonylphenoxy)[1]benzoxepino[2,3-b]pyridin-5-ylidene)propyl]piperidin-4-ol was prepared by following the procedure of example 46, but replacing ethyl iodide with ethyl 4-fluorobenzoate $^1$H-NMR (CDCl$_3$) δ: 1.36(3H,t), 1.65–2.07(4H,m), 2.32–2.63(8H,m), 4.34(2H,q), 5.33(2H,brs), 6.07(1H,t). 6.88–7.10(5H,m), 7.27–7.51(5H,m), 7.58(1H,dd), 7.97–8.00(2H,m), 8.49(1H, dd).

Step 2

The titled compound was prepared by following the procedure of example 133, but replacing the product of example 48 with the product of step 1.

$^1$H-NMR (DMSO-d6) δ: 1.44–1.49(2H, m), 1.67–1.87 (2H,m), 2.26–2.56(8H,m), 4.85(1H,brs), 5.29(2H,brs), 6.17 (1H,t), 6.88–7.09(5H,m), 7.33–7.48(5H,m), 7.75(1H,dd), 7.89–7.93(2H,m), 8.52(1H,dd). MS m/z: 582(M)

Example 355

4-(4-Chlorophenyl)-1-[3-(5,11-dihydro-7-(2-(hydroxyimino)propyl)oxy[1]benzoxepino[2,3-b]pyridin-5-ylidene)propyl]piperidin-4-ol To a solution of the product of example 313 (300 mg) in ethanol (3,ml) was added hydroxylammonium chloride (80 mg) at room temperature, and the mixture was stirred for 1 hour. The precipitation was filtered and washed with ethanol to give the titled compound (300 mg).

$^1$H-NMR (DMSO-d6) δ: 1.75–1.80(2H,m). 2.23–2.42(2H,m), 2.53(3H,s) 3.16–3.48(8H,m), 4.54(2H,s), 5.19(2H,brs), 5.57(1H,s), 6.14(1H,t), 6.76–6.98(3H,m), 7.41–7.48(5H,m), 7.79(1H,dd), 8.53(1H,dd), 10.93(1H,s). MS m/z: 515(M+1)

Example 356

1-[3-(7-(2-Carboxy-2-methyl-1-propyl)oxy-5,11-dihydro[1]benzoxepino[2,3-b]pyridin-5-ylidene)propyl]-4-(4-chlorophenyl)piperidin-4-ol Step 1

4-(4-Chlorophenyl)-1-[3-(5,11-dihydro-7-(2-ethoxycarbonyl-2-methylproyl)oxy)[1]benzoxepino[2,3-b]pyridin-5- ylidene)propyl]piperidin-4-ol was prepared by following the procedure of example 46, but replacing ethyl iodide with ethyl 2-bromo-1,1-dimethyl propionate.

$^1$H-NMR (CDCl$_3$) δ: 1.31(6H,s), 1.67–1.72(2H,m), 1.96–2.15(2H,m), 2.39–2.78(8H,m), 3.69(3H,s), 3.93(2H,s), 5.27(2H, brs), 6.09(1H,t), 6.70–6.83(3H,m), 7.23–7.59(6H, m), 8.46(1H,dd).

Step 2

The titled compound was prepared by following the procedure of example 133, but replacing the product of example 48 with the product of step 1.

$^1$H-NMR (DMSO-d6) δ: 1.46–1.50(2H,m), 1.74–1.85(2H,m), 2.22–2.38(8H,m), 3.92(2H,s), 4.58(1H, brs), 5.19(2H,brs), 6.18(1H,t), 6.71–6.83(3H,m), 7.33–7.48 (5H,m), 7.72(1H,dd), 8.49(1H,dd). MS m/z: 514(M+1)

Example 357

4-(4-Chlorophenyl)-1-[3-(5,11-dihydro-7-(2-(hydroxyimino)propyl)[1]benzoxepino[2,3-b]pyridin-5-ylidene)propyl]piperidin-4-ol The titled compound was prepared by following the procedure of Example 354, but replacing the product of example 313 with the product of example 315.

$^1$H-NMR (DMSO-d6) δ: 1.39–1.54(2H,m), 1.64–1.86(2H,m), 2.13(3H,s), 2.19–2.36(4H,m), 2.36–2.52 (4H,m), 4.83(1H,s), 5.28(2H,brs), 6.20(1H,t), 6.80(1H,d), 7.35(2H,d), 7.43–7.49(4H,m), 7.58(1H,d), 7.76(1H,d), 8.51 (1H,dd), 11.04(1H,s). MS m/z: 504(M+1)

Example 358

4-(4-Chlorophenyl)-1-[3-(5,11-dihydro-7-propionyl [1]benzoxepino[2,3-b]pyridin-5-ylidene)propyl]piperidin-4-ol The titled compound was prepared by following the procedure of example 315, but replacing acetyl chloride with propionyl chloride.

$^1$H-NMR (CDCl$_3$) δ:1.22(3H,t), 1.63–1.77(2H,m), 1.97–2.13(2H,m), 2.25–2.48(4H,m), 2.48–2.60(2H,m). 2.60–2.73(2H,m), 2.96(2H,q), 5.41(2H,brs), 6.21 (1H,t), 6.86(1H,d), 7.30–7.34(3H,m), 7.43(2H,d), 7.59(1H,d), 7.75 (1H,dd), 7.97(1H,d), 8.53(1H,d). MS m/z: 503(M+1)

Example 359

4-(4-Chlorophenyl)-1-[3-(5,11-dihydro-7-isobutyry [1]benzoxepino[2,3-b]pyridin-5-ylidene)propyl]piperidin-4-ol The titled compound was prepared by following the procedure of example 315, but replacing acetyl chloride with isobutyryl chloride.

1H-NMR (CDCL$_3$) δ: 1.21–1.33(2H,m), 1.76–2.00(2H, m), 2.46–3.47(8H, m), 3.53(1H,m), 5.47(2H,brs), 6.09(1H, t), 6.89(1H,d), 7.32–7.45(6H,m), 7.64(1H,d), 7.79(1H,dd), 7.94(1H,d), 8.57(1H,d). MS m/z: 517(M+1)

Example 360

4-(4-Chlorophenyl)-1-[3-(7-cyclopropylacetyl-5,11-dihydro[1]benzoxepino[2,3-b]pyridin-5-ylidene) propyl]piperidin-4-ol The titled compound was prepared by following the procedure of Example 315, but replacing acetyl chloride with cyclopropylacetyl chloride.

$^1$H-NMR (CDCl$_3$) δ: 0.98–1.05(2H,m), 1.20–1.24(2H, m), 1.58–1.70(2H,m), 1.99–2.09(2H,m), 2.34–2.55(4H,m), 2.58–2.68(5H,m), 5.40(2H,brs), 6.23(1H,t), 6.89(1H,d), 7.30–7.34(3H,m), 7.43(2H,d), 7.59(1H,dd), 7.86(1H,dd), 8.00(1H,d), 8.53(1H, dd). MS m/z: 515(M+1)

Example 361

1-[3-(7-(3-Carboxypropionyl)-5,11-dihydro[1]benzoxepino[2,3-b]pyridin-5-ylidene)propyl]-4-(4-chlorophenyl)piperidin-4-ol Step 1

4-(4-Chlorophenyl)-1-[3-(5,11-dihydro-7-(3-methoxycarbonylpropionyl)[1]benzoxepino[2,3-b]pyridin-5-ylidene)piperidin-4-ol was prepared by following the procedure of Example 315, but replacing acetyl chloride with methyl succinyl chloride.

$^1$H-NMR (CDCl$_3$) δ: 1.57–1.77(4H,m), 1.94–2.14(4H, m), 2.27–2.61(6H,m) 2.61–2.73(2H,m), 3.67(3H,s), 4.70 (1H,t), 5.30(2H,brs), 6.11(1H,t), 6.83(1H,d), 7.14(1H,d), 7.29–7.32(4H,m), 7.42(2H,d), 7.58(1H,d), 8.50(1H,d).

Step 2

The titled compound was prepared by following the procedure of Example 133, but replacing the product of example 48 with the product of step 1.

$^1$H-NMR (DMSO-d6) δ: 1.37–1.57(2H,m), 1.63–1.86(2H,m), 2.13–2.37(4H,m), 2.45–2.63(4H,m), 3.17–3.28(4H, m), 4.85(1H,brs), 5.36(2H,brs), 6.30(1H, t), 6.91(1H, d), 7.35(2H,d), 7.46–7.50(3H,m), 7.78–7.83(2H, m), 7.95(1H, d), 8.53(1H,dd). MS m/z: 547(M+1)

Example 362

4-(4-Chlorophenyl)-1-[3-(5,11-dihydro-7-(1-ethyl-1-hydroxy)propyl[1]benzoxepino[2,3-b]pyridin-5-ylidene)propyl]piperidin-4-ol The titled compound was prepared by flowing the procedure of example 242, but replacing methylmagnesium bromide with ethylmagnesium bromide.

$^1$H-NMR (CDCl$_3$) δ: 0.79(6H,t), 1.65–2.04(9H,m), 2.35–2.66(8H, m), 5.37(2H, brs), 6.09(1H,t), 6.81(1H,d), 7.10(1H, dd), 7.26–7.51(6H, m), 7.59(1H, dd), 8.49(1H, dd). MS m/z: 533(M+1)

Example 363

4-(4-Chlorophenyl)-1-[3-(7-(1-cyano-1 methyl) ethyl-5,11-dihydro[1]benzoxepino[2,3-b]pyridin-5-ylidene)propyl]piperidin-4-ol Step 1

5-(3-bromopropylidene)-7-(1-hydroxy-1-methyl)ethyl-5, 11-dihydro[1]benzoxepino[2,3-b]pyridine was prepared by following the procedure of Example 200, but replacing the product of example 48 with the product of example 315.

Step 1.

¹H-NMR (CDCl₃) δ: 1.58(6H, s), 2.74(2H, q), 3.47(2H,t), 5.34(2H, brs), 6.09(1H, t), 6.82(1H, d), 7.25–7.31(2H, m), 7.45(1H, d), 7.57(1H, dd), 8.52(1H, dd).

Step 2

To a solution of the product of step 1 (3.8 g) in dichloromethane (40 ml) was added trimethylsilyl cyanide (4.1 ml) and boron trifluoride diethyl etherate (2.5 ml) at 0° C., and the mixture stirred at room temperature for 10 minutes. The reaction mixture was poured into saturated aqueous sodium bicarbonate. The aqueous layer was extracted with ethyl acetate, and the organic layer was washed with saturated aqueous sodium chloride, and dried with magnesium sulfate. The solvent was distilled off under reduced pressure. The residue was purified by silica gel chromatography eluting with ethyl acetate-hexane (1:3) to give 5-(3-bromopropylidene)-7-(−1-cyano-1-methyl)ethyl-5,11-dihydro[1]benzoxepino[2,3-b]pyridine (3.4 g).

¹H-NMR (CDCl₃) δ: 1.58(6H,s), 2.76(2H,m), 3.48(2H,t), 5.34(2H,brs), 6.09(1H,t), 6.87(1H,d), 7.22(1H,dd), 7.32(1H, dd), 7.42(1H,d), 7.58(1H,dd), 8.55(1H,dd).

Step 3

The titled compound was prepared by following the procedure of example 44, step 2,but replacing the product of example 44, step 1 with the product of step 2.

¹H-NMR (CDCl₃) δ: 1.58(6H,s), 1.60–1.70(2H,m), 1.93–2.12(2H,m), 2.30–2.47(4H,m), 2.50–2.74(4H, m), 5.31(2H,brs), 6.15(1H,t), 6.86(1H, d), 7.19(1H,dd), 7.28–7.32(3H, m), 7.41–7.43(3H, m), 7.61(1H,d), 8.53(1H, dd). MS m/z: 514(M+1)

Example 364

4-(4-Chlorophenyl)-1-[3-(7-cyano-5,11-dihydro[1]benzoxepino[2,3-b]pyridin-5-ylidene)propyl]piperidin-4-ol The titled compound was prepared by following the procedure of example 44, step 2, but replacing the product of example 44, step 1 with 5-(3-bromopropylidene)-7-cyano-5,11-dihydro[1]benzoxepino[2,3-b]pyridine.

¹H-NMR (CDCL₃) δ: 1.62–1.75(2H, m), 1.98–2.09(2H, m), 2.36–2.69(8H, m), 5.36(2H,brs), 6.19(1H, t), 6.89(1H, d), 7.29–7.62(8H, m), 8.55(1H, d). MS m/z: 472(M+1)

Example 365

4-(4-Chlorophenyl)-1-[3-(5,11-dihydro-7-(tetrazol-5-yl)[1]benzoxepino[2,3-b]pyridin-5-ylidene)propyl]piperidin-4-ol To a solution of the product of Example 364 (1.0 g) in DMF (10 ml) were added sodium azide (0.69 g) and ammonium chloride (0.56 g) and the mixture stirred at 100° C. for 36 hour. Water was added to the reaction mixture, and the precipitate was filtered and washed with ethanol to give the titled compound (800 mg).

¹H-NMR (DMSO-d6) δ: 1.66–1.71(2H, m), 1.91–2.01 (2H, m), 2.86–3.09(8H, m), 5.33(2H, brs), 6.22(1H, t), 6.91(1H, d), 7.39–7.51(5H, m), 7.79–7.84(2H, m), 8.03(1H, d), 8.55(1H, dd). MS m/z: 515(M+1)

Example 366

4-(4-Chlorophenyl)-1-[3-(5,11-dihydro-7-(hydroxyiminomethyl)[1]benzoxepino[2,3-b]pyridin-5-ylidene)propyl]piperidin-4-ol The titled compound was prepared by following the procedure of Example 357, but replacing the product of example 315, step 2 with the product of example 314.

¹H-NMR (DMSO-d6) δ: 141–1.52(2H, m), 1.70–1.82 (2H, m), 2.27–2.46(8H, m), 4.83(1H, s), 5.37(2H, brs), 6.20(1H, t), 6.83(1H, d), 7.34–7.53(7H, m), 7.76(2H, dd), MS m/z: 490(M+1)

Example 367

1-(4-Chlorophenyl)-4-[3-(5,11-dihydro-7-(1-hydroxy-1-methyl)ethyl[1]benzoxepino[2,3-b]pyridin-5-ylidene)propyl]piperazine The titled compound was prepared by following the procedure of example 71, but replacing the product of example 45, step 2 with the product of Example 363, step 1.

¹H-NMR (CDCl₃) δ: 1.58(6H, s), 2.31–2.63(8H, m), 3.02–3.20(4H, m), 5.32(2H, brs), 6.12(1H, t), 6.79–6.83(3H, m), 7.17–7.31(6H, m), 7.45(1H, d), 7.58(1H, dd), 8.51(1H, dd). MS m/z: 490(M+1)

Example 368

4-(4-Chlorophenyl)-1-[3-(5,11-dihydro-7-sulfamoyl[1]benzoxepino[2,3-b]pyridin-5-ylidene)propyl]piperidin-4-ol Step 1

To the product of example 53, step 1 (5.4 g) was added chlorosulfonic acid (50 ml) and the mixture stirred at 0° C. for 1 hour. The reaction mixture was poured to ice, and ethyl acetate was added to the mixture, the organic layer was separated and washed with saturated aqueous sodium chloride, and dried with magnesium sulfate. The solvent was distilled off under reduced pressure. To the residue were added THF (250 ml) and ammonium hydroxide (30 ml) and the mixture stirred at room temperature for 10 minutes. Ethyl acetate and water were added to the mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:1) to give 5-(3-bromopropylidene)-5,11-dihydro-7-sulfamoyl[1]benzoxepino[2,3-b]pyridine (5.0 g).

¹H-NMR (CDCl₃) δ: 2.70–2.75(2H, m), 3.48(2H, t), 5.39–5.49(4H, m), 6.16(1H, t), 6.88(1H,d), 7.25–7.34(2H, m), 7.53(1H, dd), 7.68(1H, dd), 7.93(1H, d), 8.53(1H, dd).

Step 2

The titled compound was prepared by following the procedure of example 44, step 2, but replacing the product of example 44, step 1 with the product of step 1.

¹H-NMR (DMSO-d6) δ: 1.65–1.70(3H, m), 1.98–2.07 (2H, m), 2.35–2.64(8H, m), 4.98(2H, brs), 5.39(2H, brs), 6.22(1H, t), 6.92(1H, d) 7.26–7.43(5H, m), 7.55–7.69(2H, m), 7.91(1H, d), 8.53(1H, dd). MS m/z: 526(M+1)

Example 369

1-[-3-(7-(2-Aminothiazol-4-yl)-5,11-dihydro[1]benzoxepino[2,3-b]pyridin-5-ylidene)propyl]-4-(4-chlorophenyl)piperidin-4-ol Step 1

7-bromoacetyl-5-(3-bromopropylidene)-5,11-dihydro[1]benzoxepino[2,3-b]pyridine was prepared by following the procedure of example 315, step 1, but replacing acetyl chloride with bromoacetyl chloride.

¹H-NMR (CDCl₃) δ: 2.77(2H, m), 3.50(2H, m), 4.40(2H, s), 5.45(2H, brs), 6.17(1H, t), 6.90(1H, d), 7.35(1h, dd), 7.60(1H, dd), 7.79(1H, dd), 8.01(1H, d), 8.57(1H, dd).

Step 2

To a solution of the product of step 1 (1.1 g) in ethanol (11 ml) was added thiourea (193 mg) at room temperature, and the mixture stirred at 70° C. for 30 minutes. The reaction mixture was cooled to room temperature and poured into saturated aqueous sodiumbicarbonate. The aqueous layer was extracted with ethyl acetate, and the organic layer was washed with saturated aqueous sodium chloride, and dried with magnesium sulfate. The solvent was distilled off under reduced pressure. The residue was purified by silica gel chromatography eluting with ethyl acetate to give 7-(2-aminothiazol-4-yl)-5-(3-bromopropylidene)-5,11-dihydro[1]benzoxepino[2,3-b]pyridine (749 mg).

¹H-NMR (CDCl₃) δ: 2.74(2H, m), 3.47(2H, t), 5.02(2H, brs), 5.39(2H, brs), 6.16(1H, t), 6.62(1H, s), 6.85(1H, d), 7.30(1H, dd), 7.54–7.57(2H, m), 7.77(1H, d), 8.53(1H, dd).

Step 3

The titled compound was prepared by following the procedure of example 44, step 2, but replacing the product of example 44, step 1 with the product of step 2.

¹H-NMR (CDCl₃) δ: 1.57–1.70(2H, m), 1.83–2.13(2H, m), 2.30–2.46(4H, m), 2.46–2.60(2H, m), 2.60–2.73(2H, M), 5.02(2H, s), 5.37(2H, brs), 6.20(1H, t), 6.61(1H, s), 6.85(1H, d), 7.27–7.32(3H, m), 7.42(2H, d), 7.50–7.58(2H, m), 7.76(1H, d), 8.50(1H, dd). MS m/z: 545(M+1)

Example 370

1-[3-(7-(3-Carboxy-1-hydroxy)propyl-5,11-dihydro[1]benzoxepino[2,3-b]pyridin-5-ylidene)propyl]-4-(4-chlorophenyl)piperidin-4-ol Step 1

4-(4-Chlorophenyl)-1-[3-(5,11-dihydro-7-(3-methoxycarbony-1-hydroxy)propyl[1]benzoxepino[2,3-b]pyridin-5-ylidene)propyl]piperidin-4-ol was prepared by following the procedure of example 199, but replacing the product of example 138 with the product of Example 361, step 1.

¹H-NMR (CDCl₃) δ: 1.57–1.77(4H, m), 1.94–2.14(4H, m), 2.27–2.61(6H, m), 2.61–2.73(2H, m), 3.67(3H, s), 4.70(1H, t), 5.30(2H, brs), 6.11(1H, t), 6.83(1H, d), 7.14(1H,d), 7.29–7.32(4H, m), 7.42(2H,d), 7.58(1H, d), 8.50(1H, d).

Step 2

The titled compound was prepared by following the procedure of example 133, but replacing the product of example 48 with the product step 1.

¹H-NMR (DMSO-d6) δ: 1.44–1.63(2H, m), 1.69–1.90(2H, m), 2.17–2.29(2H, m), 2.29–2.82(6H, m), 3.24–3.53(4H, m), 4.49(1H, t), 5.03(1H, brs), 5.20(2H, brs), 6.13(1H, t), 6.76(1H, d), 7.12(1H, dd), 7.27(1H, d), 7.37(2H, d), 7.43–7.48(3H, m), 7.76(1H, d), 8.32(1H, s), 8.51(1H, dd). MS m/z: 549(M+1)

Example 371

4-(4-Chlorophenyl)-1-[3-(5,11-dihydro-7-(2-fluoroethylamino)carbonylmethyloxy[1]benzoxepino[2,3-b]pyridin-5-ylidene)propyl]piperidin-4-ol The titled compound was prepared by following the procedure of example 134, but replacing dimethylamine hydrochloride with 2-fluoroethylamine.

¹H-NMR (CDCl₃) δ: 1.62–1.71(3H, m), 1.98–2.10(2H, m), 2.36–2.71(8H, m), 3.63(1H, q), 3.73(1H, q), 4.46(1H, t), 4.49(2H, s), 4.63(1H, t), 5.29(2H, brs), 6.10(1H, t), 6.75–6.96(4H, m), 7.28–7.44(5H, m), 7.60(1H, dd), 8.51(1H, dd). MS m/z: 566(M+1)

Example 372

4-(4-Chlorophenyl)-1-[3-(5,11-dihydro-7-(N-methylsulfamoyl)[1]benzoxepino[2,3-b]pyridin-5-ylidene)propyl]piperidin-4-ol The titled compound was prepared by following the procedure of Example 368, but replacing ammonium hydroxide with methylamine.

¹H-NMR (CDCl₃) δ: 1.57–1.70(3H, m), 1.93–2.08(2H, m), 2.34–2.73(11H, m), 4.33(1H, q), 5.36(2H, brs), 6.21(1H, t), 6.91(1H, d), 7.29–7.45(6H, m), 7.58–7.65(2H, m), 7.83(1H, dd), 8.53(1H, dd). MS m/z: 540(M+1)

Example 373

4-(4-Chlorophenyl)-1-[3-(5,11-dihydro-7-(N,N-dimethylsulfamoyl)[1]benzoxepino[2,3-b]pyridin-5-ylidene)propyl]piperidin-4-ol The titled compound was prepared by following the procedure of Example 368, but replacing ammonium hydroxide with dimethylamine.

¹H-NMR (CDCl₃) δ: 1.55–1.75(3H, m), 1.96–2.07(2H, m), 2.35–2.67(8H, m), 2.71(6H, s), 5.51(2H, brs), 6.19(1H, t), 6.92(1H, d), 7.29–7.73(8H, m), 8.55(1H, dd). MS m/z: 554(M+1)

Example 374

1-[3-(7-(1-Carboxy-2-hydroxyethyl)oxy-5,11-dihydro[1]benzoxepino[2,3-b]pyridin-5-ylidene)propyl]-4-(4-chlorophenyl)piperidin-4-ol Step 1

4-(4-Chlorophenyl-1-[3-(5,11-dihydro-7-(1-ethoxycarboxy-2-hydroxyethyl)oxy[1]benzoxepino[2,3-b]pyridin-5-ylidene)propyl]piperidin-4-ol was prepared by following the procedure of example 199, but replacing the product of example 138 with the product of example 294.

¹H-NMR (CDCl₃) δ: 1.65–1.70(2H, m), 2.01–2.11(2H, m), 2.35–2.70(8H, m), 3.76(3H, s), 3.97–4.08(2H, m), 4.71(1H, t), 5.25(1H, brs) 6.02(1H, t) 6.70–6.91(3H, m), 7.23–7.56(6H, m), 8.44(1H, dd).

Step 2

The titled compound was prepared by following the procedure of example 133, but replacing the product of example 48 with the product of Step 1.

$^1$H-NMR (DMSO-d6) δ: 1.51–1.56(2H, m), 1.86–1.94 (2H, m), 2.33–2.67(8H, m), 3.65–3.82(2H, m), 4.58(1H, t), 5.17(2H, brs), 6.10(1H, t), 6.71–6.89(3H, m), 7.34–7.47(5H, m), 7.72(1H, dd), 8.48(1H, dd). MS m/z: 551(M+1)

Example 375

4-(4-Chlorophenyl)-1-[3-(5,11-dihydro-7-ureidomethy[1]benzoxepino[2,3-b]pyridin-5-ylidene)propyl]piperidin-4-ol To a solution of the product of example 314 (800 mg) in acetic acid (20 ml) were added urea (2 g) and trimethylsilyl chloride (0.24 ml) at room temperature, and the mixture stirred for 2 hours. Sodium borohydride was added to the reaction mixture at room temperature, and the mixture was stirred for 1 hour. The solvent was distilled off under reduced pressure, and, chloroform, 2-propanol and water were added. The organic layer was extracted, and the solvent was distilled off under reduced pressure. The residue was purified by silica gel chromatography eluting with chloroform-methanol-ammonium hydroxide (100:10:1) to give the titled compound (250 mg).

$^1$H-NMR (CDCl$_3$) δ: 1.62–2.04(5H, m), 2.35–2.69(8H, m), 4.26(2H, d), 4.40(2H, s), 4.48(1H, t), 5.32(2H, brs), 6.12(1H, t), 6.80(1H, d), 7.07(1H, dd), 7.23–7.58(7H, m), 8.49(1H, dd). MS m/z: 519(M+1)

Example 376

4-(4-Chlorophenyl)-1-[3-(5,11-dihydro-7-methylthio[1]benzoxepino[2,3-b]pyridin-5-ylidene)propyl]piperidin-4-ol The titled compound was prepared by following the procedure of example 44, step 2, but replacing the product of example 44, step 1 with 5-(3-bromopropylidene)-5,11-dihydro-7-methylthio[1]benzoxepino[2,3-b]pyridine.

$^1$H-NMR (CDCl$_3$) δ: 1.53–1.70(3H, m), 1.98–2.16(2H, m), 2.17(3H, s), 2.34–2.70(8H, m), 5.32(2H, brs), 6.12(1H, t), 6.81(1H, d), 7.11–7.44(7H, m), 7.57(1H, dd), 8.50(1H, dd). MS m/z: 493(M+1)

Example 377

4-(4-Chlorophenyl)-1-[3-(5,11-dihydro-7-(2-furanon-3-yl)oxy[1]benzoxepino[2,3]b]pyridin-5-ylidene)propyl]piperidin-4-ol The titled compound was prepared by following the procedure of example 46, but replacing ethyl iodide with 3-bromotetrahydro-2-franon.

$^1$H-NMR (CDCl$_3$) δ:1.65–1.70(2H, m), 1.97–2.13(2H, m), 2.25–2.73(10H, m), 4.25–4.53(2H, m), 4.82(1H, t), 5.27(2H, brs), 6.09(1H, t), 6.73–6.91(2H, m), 7.03(1H, d), 7.22–7.59(6H, m), 8.43(1H, dd). MS m/z: 547(M+1)

Example 378

4-(4-Chlorophenyl)-1-[3-(5,11-dihydro-7-(N-methoxycarbonylmethylsulfamoyl)[1]benzoxepino[2,3-b]pyridin-5-ylidene)propyl]piperidin-4-ol The titled compound was prepared by following the procedure of Example 368, but replacing ammonium hydroxide with glycine methyl ester hydrochloride.

$^1$H-NMR (CDCl$_3$) δ: 1.66–1.74(3H, m), 1.97–2.15(2H, m), 2.37–2.80(8H, m), 3.63(3H, s), 3.78(2H, s) 5.40(2H, brs), 6.22(1H, t), 6.92(1H, d), 7.28–7.45(5H, m), 7.62(2H, dd), 7.83(1H, d), 8.53(1H, dd). MS m/z: 598(M+1)

Example 379

1-[3-(7-(N-Carboxymethylsulfamoyl-5,11-dihydro[1]benzoxepino[2,3-b]pyridin-5-ylidene)propyl]-4-(4-chlorophenyl)piperidin-4-ol The titled compound was prepared by following the procedure of example 133, but replacing the product of example 48 with the product of Example 378.

$^1$H-NMR (DMSO-d6) δ: 1.60–1.65(2H, m), 2.16–2.25 (2H, m), 2.43–3.03(8H, m), 3.45(2H, s), 5.33(2H, brs), 6.39(1H, t), 6.94(1H, d), 7.41–7.57(6H, m), 7.83(1H, dd), 8.00(1H, d), 8.54(1H, dd).

Example 380

4-(4-Chlorophenyl)-1-[3-(5,11-dihydro-7-(2-furanon-5-yl)[1]benzoxepino[2,3-b]pyridin-5-ylidene)propyl]piperidin-4-ol The titled compound was prepared by following the procedure of example 249, step 2, but replacing the product of example 249, step 1 with the product of Example 370, step 1.

$^1$H-NMR (CDCl$_3$) δ: 1.45–1.78(4H, m), 1.93–2.12(2H, m), 2.30–2.50(4H, m), 2.50–2.78(6H, m), 5.33(2H, brs), 5.46(1H, t), 6.12(1H, t), 6.86(1H, d), 7.09(1H, dd), 7.27–7.32(4H, m), 7.42(2H, d), 7.58(1H, dd), 8.51(1H, dd). MS m/z: 531(M+1)

Example 381

1-[3-(7-Amino-5,11-dihydro[1]benzoxepino[2,3-b]pyridin-5-ylidene)propyl[-4-(4-chlorophenyl)piperidin-4-ol To a solution of the produce of example 293 (3.7 g) in ethanol (130 ml) was added 5N sodium hydroxide solution (100 ml) and the mixture stirred at 90° C. for 1 hour. The reaction mixture was distilled off under reduced pressure. The residue was dissolved with water and neutralized with 1N hydrochloric acid. Ethyl acetate was added to the mixture, the organic layer was separated and washed with saturated aqueous sodium chloride, and dried with magnesium sulfate to give the titled compound (3.0 g).

$^1$H-NMR (CDCl$_3$) δ: 1.62–1.72(2H, m), 1.96–2.08(2H, m), 2.27–2.72(8H, m), 3.48(2H, brs), 5.23(2H, brs), 6.01 (1H, t), 6.49–6.73(3H, m), 7.18–7.59(6H, m), 8.49(1H, dd). MS m/z: 462(M+1)

Example 382

1-[3-(7-(2-Carboxyphenyl)-5,11-dihydro[1]benzoxepino[2,3-b]pyridin-5-ylidene)propyl]-4-(4-chlorophenyl)piperidin-4-ol Step 1

4-(4-Chlorophenyl)-1-[3-(5,11-dihydro-7-(2-formylphenyl)[1]benzoxepino[2,3-b]pyridin-5-ylidene)propyl]piperidin-4-ol was prepared by following the similar procedure of example 170, but replacing allyltributyltin with 2-formylphenylboronic acid.

$^1$H-NMR (CDCl$_3$) δ: 1.65–1.91(3H, m), 1.99–2.04(2H, m), 2.37–2.65(8H, m), 5.39(2H, brs), 6.15(1H, t), 6.95(1H, d), 7.19–7.65(10H, m), 7.97–8.05(2H, m), 8.52(1H, dd), 10.03(1H, s).

Step 2

To a solution of the product of step 1 (270 mg) in acetic acid (2.2 ml) and water (0.5 ml) were added amidosulfuric acid (67 mg) and sodium chlorite (68 mg) in water (0.1 ml), and the mixture was stirred at room temperature for 15 minutes. The reaction mixture was distilled off under reduced pressure into half volume. The residue was neutralized with 1N sodium hydroxide. The precipitation was filtered and washed with water to give the titled compound (80 mg).

$^1$H-NMR (DMSO-d6) δ: 1.41–1.57(2H, m), 1.74–1.92 (2H, m), 2.21–2.58(8H, m), 5.32(2H, brs), 6.20(1H, t), 6.82(1H, d), 7.15(1H, dd), 7.31–7.78(11H, m), 8.52(1H, dd). MS m/z: 567(M+1)

Example 383

4-(4-Chlorophenyl)-1-[3-(5,11-dihydro-7-(N(2,2,2-trifluoroethyl)sulfamoyl)[1]benzoxepino[2,3-b]pyridin-5-ylidene)propyl]piperidin-4-ol The titled compound was prepared by following the procedure of Example 368, but replacing ammonium hydroxide with 2,2,2-trifluoroethylamine hydrochloride.

$^1$H-NMR (CDCl$_3$) δ: 1.64–1.77(2H, m), 1.97–2.18(2H, m), 2.35–2.80(8H, m), 3.63(2H, q), 5.41(2H, brs), 6.21(1H, t), 6.91(1H, d), 7.22–7.65(7H, m), 7.84(1H, d), 8.57(1H, dd). MS m/z: 608(M+1)

Example 384

4-(4-Chlorophenyl)-1-[3-(5,11-dihydro-7-methylsulfonyl[1]benzoxepino[2,3-b]pyridin-5-ylidene)propyl]piperidin-4-ol The titled compound was prepared by following the procedure of Example 44, step 2, but replacing the product of Example 44, step 1 with 5-(3-bromopropylidene)-5,11-dihydro-7-metylsulfonyl[1]benzoxepino[2,3-b]pyridine.

$^1$H-NMR (CDCl$_3$) δ: 1.54–1.71(3H, m), 1.99–2.08(2H, m), 2.34–2.68(8H, m), 3.04(3H, s), 5.43(2H, brs), 6.24(1H, t), 6.97(1H, d), 7.22–7.70(7H, m), 7.89(1H, d), 8.55(1H, dd). MS m/z: 525(M+1)

Example 385

4-(4-Chlorophenyl)-1-[3-(5,11-dihydro-7-ureido[1]benzoxepino[2,3-b]pyridin-5-ylidene)propyl]piperidin-4-ol Step 1

4-(4-Chlorophenyl)-1-[3-(5,11-dihydro-7-pheoxycarbonylamino[1]benzoxepino[2,3-b]pyridin-5-ylidene)propyl]piperidin-4-ol The titled compound was prepared by following the procedure of Example 293, but replacing ethanol with phenol.

$^1$H-NMR (CDCl$_3$) δ: 1.62–1.68(2H, m), 1.96–2.08(2H, m), 2.35–2.65(8H, m), 5.28(2H, brs), 6.10(1H, t), 6.78(1H, m), 7.08–7.40(6H, m), 7.52(1H, dd), 7.62(1H, s), 8.44(1H, dd). MS m/z: 582(M+1)

Step 2

To a solution of the product of Step 1 (300 mg) in DMF (3 ml) was added ammonium hydroxide (1.5 ml) and the mixture was stirred at room temperature for 2 hours. Ethyl acetate and water were added to the mixture, the organic layer was separated and washed with saturated aqueous sodium chloride, and dried with magnesium sulfate. The solvent was distilled off under reduced pressure. The residue was purified by silica gel chromatography eluting with (chloroform:methanol=10:1) to give the titled compound (140 mg).

$^1$H-NMR (DMSO-d6) δ: 1.45–1.50(2H, m), 1.72–1.88 (2H, m), 2.28–2.51(8H, m), 4.82(1H, s), 5.19(1H, brs), 5.74(2H, brs), 6.09(1H, t), 6.69(1H, d), 7.12(1H, dd), 7.32–7.48(6H, m), 7.74(1H, dd), 8.37(1H, s), 8.50(1H, dd). MS m/z: 505(M+1)

Example 386

4-(4-Chlorophenyl)-1-[3-(5,11-dihydro-7-(1-morpholinocarbonylamino[1]benzoxepino[2,3-b]pyridin-5-ylidene)propyl]piperidin-4-ol The titled compound was prepared by following the procedure of Example 385, step 2, but replacing ammonium hydroxide with morpholine.

$^1$H-NMR (CDCl$_3$) δ: 1.62–1.67(2H, m), 1.95–2.16(2H, m), 2.28–2.64(8H, m), 3.41(4H, t), 3.69(4H, t), 5.26(2H, brs), 6.08(1H, t), 6.69–6.76(2H, m), 6.98(1H, dd), 7.21–7.51 (7H, m), 8.42(1H, dd). MS m/z: 575(M+1)

Example 387

4-(4-Chlorophenyl)-1-[3-(5,11-dihydro-7-(3(2-ethoxy)carbonylethyl)ureido[1]benzoxepino[2,3-b]pyridin-5-ylidene)propyl]piperidin-4-ol The titled compound was prepared by following the procedure of Example 385, step 2, but replacing ammonium hydroxide with beta-alanine ethyl ester hydrochloride.

$^1$H-NMR (CDCl$_3$) δ: 1.18–1.39(3H, t), 1.62–1.66(2H, m), 1.92–2.01(2H, m), 2.21–2.62(10H, m), 3.47–3.50(2H, m), 4.08(2H, q), 5.22(2H, brs), 5.98–6.03(2H, m), 6.68–6.92 (2H, m), 7.15–7.42(7H, m), 7.62(1H, s), 8.36(1H, dd). MS m/z: 605(M+1)

Example 388

1-[3-(7-(E)-(2-Carboxy-1-methyl)ethenyl-5,11-dihydro[1]benzoxepino[2,3-b]pyridin-5-ylidene)propyl]-4-(4-chlorophenyl)piperidin-4-ol Step 1

4-(4-Chlorophenyl)-1-[3-(7-(E)-(2-ethoxycarboxy-1-methyl)ethenyl-5,11-dihydro[1]benzoxepino[2,3-b]pyridin-5-ylidene)propyl]piperidin-4-ol was prepared by following the procedure of Example 411, but replacing ethyl cyanoformate with ethyl(trimethylsilyl)acetate.

$^1$H-NMR (CDCl$_3$) δ: 1.30(3H, t), 1.67–1.72(3H, m), 1.98–2.05(2H, m), 2.42–2.67(11H, m), 4.23(2H, q), 5.36 (2H, brs), 6.14–6.19(2H, m), 6.85(1H, d), 7.20–7.61(8H, m), 8.52(1H, dd).

Step 2

The titled compound was prepared by following the procedure of Example 133, but replacing the product of Example 48 with the product of step 1.

¹H-NMR (DMSO-d6) δ: 1.50–1.55(2H, m), 1.87–1.99 (2H, m), 2.34–2.61(11H, m), 5.29(2H, brs), 6.12(1H, s), 6.31(1H, t), 6.83(1H, d), 7.35–7.49(7H, m), 7.76(1H, dd), 8.52(1H, dd). MS m/z: 530(M+1)

Example 389

4-(4-Chlorophenyl)-1-[3-(5,11-dihydro-7-oxalo[1]benzoxepino[2,3-b]pyridin-5-ylidene)propyl]piperidin-4-ol The titled compound was prepared by following the procedure of Example 361, but replacing methyl succinyl chloride with methyl oxalyl chloride.

¹H-NMR (DMSO-d6) δ: 1.66–1.86(2H, m), 2.08–2.34 (2H; m), 2.46–2.77(2H, m), 3.00–3.68(6H, m), 5.10(2H, brs), 5.53(1H, s), 6.15(1H, t), 6.89(1H, d), 7.34–7.49(5H, m), 7.68(1H, dd), 7.75(1H, dd), 7.87(1H, d), 8.53(1H, dd). MS m/z: 519(M+1)

Example 390

1-[3-(7-(3-(2-Carboxy)ethyl)ureido-5,11-dihydro[1]benzoxepino[2,3-b]pyridin-5-ylidene)propyl]-4-(4-chlorophenyl)piperidin-4-ol The titled compound was prepared by following the procedure of Example 133, but replacing the product of Example 48 with the product of Example 387.

¹H-NMR (DMSO-d6) δ: 1.45–1.55(2H, m), 1.72–1.85 (2H, m), 2.32–2.49(10H, m), 3.29(2H, q), 4.88(1H, s), 5.19(2H, brs), 6.06–6.14(2H, m), 6.69(1H, d), 7.07(1H, dd), 7.33–7.48(6H, m), 7.73(1H, dd), 8.43(1H, s), 8.49(1H, dd). MS m/z: 577(M+1)

Example 391

1-[3-(7-(3-(2-Hydroxy)ethyl)ureido-5,11-dihydro[1]benzoxepino[2,3-b]pyridin-5-ylidene)propyl]-4-(4-chlorophenyl)piperidin-4-ol The titled compound was prepared by following the procedure of Example 385, step 2, but replacing ammonium hydroxide with 2-aminoethanol.

¹H-NMR (DMSO-d6) δ: 1.45–1.51(2H, m), 1.72–1.84 (2H, m), 2.24–2.51(8H, m), 3.11–3.46(4H, m), 4.71(1H, t), 4.83(1H, s), 5.19(2H, brs), 6.08(1H, t), 6.69(1H, d), 7.08 (1H, dd), 7.33–7.48(6H, m), 7.73(1H, dd), 8.41(1H, s), 8.50(1H, dd). MS m/z: 549(M+1)

Example 392

1-[3-(5,11-Dihydro-7-(1-hydroxy-1-methyl)ethyl[1]benzoxepino[2,3-b]pyridin-5-ylidene)propyl]-4-(2-keto-1-imidazolinyl)piperidine The titled compound was prepared by following the procedure of Example 67, but replacing the product of Example 45, step 2 with the product of Example 363, step 1.

¹H-NMR (CDCl₃) δ: 1.59(6H, s), 1.71–1.87(2H, m), 2.01–2.18(2H, m), 2.28–2.61(6H, m), 2.86–3.00(2H, m), 4.32(1H, m), 5.36(2H, brs), 6.15(1H, t), 6.84(1H, d), 7.02–7.07(3H, m), 7.24–7.31(3H, m), 7.47(1H, d), 7.60(1H, dd), 8.51(1H, dd), 8.97(1H, s). MS m/z: 511(M+1)

Example 393

4-(4-Chlorophenyl)-1-[3-(7-(E)-(2-ethoxycarboxy-2-methyl)ethenyl-5,11-dihydro[1]benzoxepino[2,3-b]pyridin-5-ylidene)propyl]piperidin-4-ol To a solution of sodium hydride (60% in oil, 100 mg) in THF (6 ml) were added triethyl 2-phosphonopropionate (0.3 ml) and the product of Example 314 (300 mg) at 0° C., and the mixture was stirred at room temperature for 30 minutes. Water and ethyl acetate were added to the reaction mixture. The organic layer was extracted, and the solvent was distilled off under reduced pressure. The residue was purified by silica gel chromatography eluting with chloroform-methanol (30:1) to give the titled compound (310 mg).

¹H-NMR (CDCl₃) δ: 1.34(3H, t), 1.58–1.71(3H, m), 1.98–2.15(5H, m), 2.37–2.70(8H, m), 2.27(2H, q), 5.37(2H, brs), 6.14(1H, t), 6.86(1H, d), 7.25–7.44(7H, m) 7.58–7.63 (2H, m), 8.52(1H, dd). MS m/z: 559(M+1)

Example 394

1-[3-(7-(E)-(2-Carboxy-2-methyl)ethenyl-5,11-dihydro[1]benzoxepino[2,3-b]pyridin-5-ylidene)propyl]-4-(4-chlorophenyl)piperidin-4-ol The titled compound was prepared by following the procedure of Example 133, but replacing the product of Example 48 with the product of step 1.

¹H-NMR (DMSO-d6) δ: 1.62–1.67(2H, m), 1.91–2.05 (5H, m), 2.50–2.94(8H, m), 5.28(2H, brs), 6.23(1H, t), 6.87(1H, d), 7.34–7.55(8H, m), 7.79(1H, dd), 8.54(1H, dd). MS m/z: 531(M+1)

Example 395

1-[3-(7-(5-Carboxy-1-pentyl)oxy-5,11-dihydro[1]benzoxepino[2,3-b]pyridin-5-ylidene)propyl]-4-(4-chlorophenyl)piperidin-4-ol Step 1

4-(4-Chlorophenyl)-1-[3-(7-(5-ethoxycarbonyl-1-pentyl)oxy-5,11-dihydro[1]benzoxepino[2,3-b]pyridin-5-ylidene)propyl]piperidin-4-ol was prepared by following the procedure of Example 46, but replacing ethyl iodide with ethyl 6-bromohexanoate.

¹H-NMR (CDCl₃) δ: 1.21(3H, t), 1.42–1.79(8H, m), 1.98–2.03(2H, m), 2.26–2.67(10H, m), 3.87(2H, t), 4.16(2H, q), 5.23(2H, brs), 6.09(1H, t), 6.67–6.81(3H, m), 7.21–7.63 (6H, m), 8.16(1H, dd).

Step 2

The titled compound was prepared by following the procedure of Example 133, but replacing the product of Example 48 with the product of step 1.

¹H-NMR (DMSO-d6) δ: 1.41–1.95(10H, m), 2.20–2.72 (10H, m), 3.92(2H, t), 5.18(2H, brs), 6.17(1H, t), 6.72–6.84 (3H, m), 7.36–7.48(5H, m), 7.77(1H, dd), 8.50(1H, dd). MS m/z: 577(M+1)

Example 396

1-[3-(7-(1-(2-Carboxy)ethyl)aminocarbonyl-1-methyl)ethyloxy[1]benzoxepino[2,3-b]pyridin-5-ylidene)propyl]-4-(4-chlorophenyl)piperidin-4-ol Step 1

4-(4-Chlorophenyl)-1-[3-(7-(1-(2-ethoxycarbonyl)ethyl)aminocarbonyl-1-methyl)ethyloxy[1]benzoxepino[2,3-b]pyridin-5-ylidene)propyl]piperidin-4-ol was prepared by following the procedure of Example 176, but replacing dimethylamine hydrochloride with beta-alanine ethyl ester hydrochloride.

$^1$H-NMR (CDCl$_3$) δ: 1.42(3H, s), 1.62–1.67(2H, m), 1.95–2.10(3H, m), 2.35–2.59(10H, m), 3.51–3.53(2H, m), 4.00(2H, q), 5.23(2H, brs), 6.00(1H, t), 6.68–6.81(3H, m), 7.24–7.56(6H, m), 8.39(1H, dd).

Step 2

The title compound was prepared by following the procedure of Example 133, but replacing the product of Example 48 with the product of step 1.

$^1$H-NMR (DMSO-d6) δ: 1.37(6H, s), 1.41–1.52(2H, m), 1.79–1.87(2H, m), 2.28–2.41(10H, m), 3.33(2H, q), 5.21(2H, brs), 6.12(1H, t), 6.70–6.87(3H, m), 7.34–7.48(5H, m), 7.74(1H, dd), 8.08(1H, t), 8.50(1H, dd). MS m/z: 620(M+1)

Example 397

4-(4-Chlorophenyl)-1-[3-(5,11-dihydro-7-(thiazoline-2,4-dione-5-ylidene)methyl[1]benzoxepino[2,3-b]pyridin-5-ylidene)propyl]piperidin-4-ol To a solution of the product of Example 314 (590 mg) in ethanol (6 ml) were added 2,4-thiazolinedione (440 mg) and piperidine (0.36 ml), and the mixture was heated to reflux for 3 hours. The solvent was distilled off under reduced pressure, and, chloroform, 2-propanol and water were added. The organic layer was extracted, and the solvent was distilled off under reduced pressure. The residue was purified by silica gel chromatography eluting with chloroform-methanol (5:1) to give the titled compound (510 mg).

$^1$H-NMR (DMSO-d6) δ: 1.61–1.66(2H, m), 1.97–2.12(2H, m), 2.79–2.99(8H, m), 5.21(2H, brs), 6.25(1H, t), 6.90(1H, d), 7.34–7.52(7H, m), 7.81(1H, dd), 8.54(1H, dd). MS m/z: 574(M+1)

Example 398

4-(4-Chlorophenyl)-1-[3-(5,11-dihydro-7-methanesulfonamido[1]benzoxepino[2,3-b]pyridin-5-ylidene)propyl]piperidin-4-ol The titled compound was prepared by following the procedure of Example 402, but replacing trifluoromethanesulfonic acid anhydride with methanesulfony chloride.

$^1$H-NMR (CDCl$_3$) δ: 1.64–1.69(2H, m), 1.89–2.05(2H, m), 2.24–2.77(8H, m), 2.95(3H, s), 5.29(2H, brs), 6.10(1H, t), 6.84(1H, d), 7.06(1H, dd), 7.18–7.40(6H, m), 7.56(1H, dd), 8.42(1H, dd). MS m/z: 540(M+1)

Example 399

4-(4-Chlorophenyl)-1-[3-(5,11-dihydro-7-(3-phenylureido)sulfonyl[1]benzoxepino[2,3-b]pyridin-5-ylidene)propyl]piperidin-4-ol The titled compound was prepared by following the procedure of Example 320, but replacing compound of Example 44, step 2 with compound of Example 368, step 2.

$^1$H-NMR (DMSO-db) δ: 1.65–1.69(2H, m), 1.95–2.05(2H, m), 2.89–3.06(8H, m), 5.31(2H, brs), 6.14(1H, t), 6.74–6.85(2H, m), 7.08–7.12(2H, m), 7.37–7.64(8H, m), 7.80–7.84(2H, m), 8.44(1H, s), 8.54(1H, dd). MS m/z: 645(M+1)

Example 400

4-(4-Chlorophenyl)-1-[3-(7-(3-cyclohexylureido)sulfonyl-5,11-dihydro[1]benzoxepino[2,3-b]pyridin-5-ylidene)propyl]piperidin-4-ol The titled compound was prepared by following the procedure of Example 399, but replacing phenyl isocyanate with cyclohexyl isocyanate.

$^1$H-NMR (DMSO-d6) δ: 1.07–1.81(14H, m), 2.23–2.58(8H, m), 3.22–3.35(1H, m), 4.91(1H, s), 5.38(2H, brs), 6.17–6.29(2H, m), 6.96(1H, d), 7.34–7.51(5H, m), 7.62–7.84(3H, m), 8.53(1H, dd). MS m/z: 651(M+1)

Example 401

4-(4-Chlorophenyl)-1-[3-(5,11-dihydro-7-(3-propylureido)sulfonyl[1]benzoxepino[2,3-b]pyridin-5-ylidene)propyl]piperidin-4-ol The titled compound was prepared by following the procedure of Example 399, but replacing phenyl isocyanate with propyl isocyanate.

$^1$H-NMR (DMSIO-d6) δ: 0.74(3H, t), 1.25–1.53(4H, m), 1.81–1.91(2H, m), 2.33–2.59(10H, m), 2.89(2H, q), 4.92(1H, s), 5.35(2H, brs), 6.20(1H, t), 6.44(1H, brs), 6.96(1H, d), 7.34–7.51(5H, m), 7.64(1H, dd), 7.78–7.85(2H, m), 8.54(1H, dd). MS m/z: 611(M+1)

Example 402

4-(4-Chlorophenyl)-1-[3-(5,11-dihydro-7-trifluoromethanesulfonamido[1]benzoxepino[2,3-b]pyridin-5-ylidene)propyl]piperidin-4-ol The title compound was prepared by following the procedure of Example 169, but replacing the product of Example 44, step 2 with the product of Example 381.

$^1$H-NMR (DMSO-d6) δ: 1.75–1.80(2H, m), 2.02–2.07(2H, m), 2.49–2.54(2H, m), 3.10–3.40(6H, m), 5.15(2H, brs), 5.52(1H, s), 5.97(1H, t), 6.58(1H, d), 6.80(1H, dd), 6.96(1H, d), 7.43–7.47(5H, m), 7.78(1H, dd), 8.51(1H, dd). MS m/z: 593(M+1)

Example 403

1-[3-(7-(3-carboxy)propyl-5,11-dihydro[1]benzoxepino[2,3-b]pyridin-5-ylidene)propyl]-4-(4-chlorophenyl)piperidin-4-ol Step 1

To a solution of the product of Example 361, step 1 (820 mg) in TFA (8.0 ml) was added triethyl silane (0.92 ml) at 0° C., and the mixture stirred at room temperature for 4 hour. The solvent was distilled off under reduced pressure. The residue was poured into saturated aqueous sodium bicarbonate, and the aqueous layer was extracted with ethyl acetate. The organic layer was washed with saturated aqueous sodium chloride, and dried with magnesium sulfate. The solvent was distilled off under reduced pressure. The residue was purified by silica gel chromatography eluting with ethyl acetate-hexane (1:4) to give 4-(4-Chlorophenyl)-1-[3-(5,11-dihydro-7-(3-methoxycarbonyl)propyl[1]benzoxepino[2,3-b]pyridin-5-ylidene)propyl]piperidin-4-ol (636 mg).

$^1$H-NMR (CDCl$_3$) δ: 1.93(2H, m), 2.34(2H, t), 2.59(2H, t), 2.74(2H, q), 3.47(2H, t), 3.67(3H, s), 5.33(2H, brs), 6.05(1H, t), 6.78(1H, d), 7.00(1H, dd), 7.09(1H, d), 7.29(1H, dd), 7.57(1H, dd), 8.52(1H, dd).

Step 2

The titled compound was prepared by following the procedure of Example 133, but replacing the product of Example 48 with the product of step 1.

$^1$H-NMR (DMSO-d6) δ: 1.37–1.57(2H, m), 1.63–1.87 (4H, m), 2.10–2.36(6H, m), 2.36–2.61(6H, m), 4.83(1H, brs), 5.24(2H, brs), 6.14(1H, t), 6.72(1H, d), 7.00(1H, dd), 7.12(1H, d), 7.35(2H, d), 7.41–7.48(3H, m), 7.73(1H, dd), 8.49(1H, dd). MS m/z: 533(M+1)

Example 404

1-[3-(7-Benzoylsulfamoyl-5,11-dihydro[1]benzoxepino[2,3-b]pyridin-5-ylidene)propyl]-4-(4-chlorophenyl)piperidin-4-ol The titled compound was prepared by following the procedure of Example 399, but replacing phenyl isocyanate with benzoyl chloride. MS m/z: 630(M+1)

Example 405

4-(4-Chlorophenyl)-1-[3-(5,11-dihydro-7-(2,5-dihydro-5-oxo-4H-1,2,4-oxadiazol-3-yl)methyloxy[1]benzoxepino[2,3-b]pyridin-5-ylidene)propyl]piperidin-4-ol To a solution of the product of Example 407 (1.7 g) in DMF (20 ml) was added 2-ethylhexyl chloroformate (0.62 ml) and the mixture was stirred at 0° C. for 1 hour. Chloroform and water were added to the reaction mixture. The organic layer was extracted, and the solvent was distilled off under reduced pressure. The residue was purified by silica gel chromatography eluting with chloroform-methanol (30:1) and dissolved in xylene (50 ml). The solution was heated to reflux for 4 hours. The solvent was distilled off under reduced pressure. The residue was reslurried with ethanol to the titled compound (490 mg).

$^1$H-NMR (DMSO-d6) δ: 1.60–1.65(2H, m), 1.91–1.99 (2H, m), 2.41–2.52(2H, m), 2.70–2,89(6H, m), 4.90(2H, s), 5.19(2H, brs), 6.16(1H, t), 6.75–7.05(3H, m), 7.37–7.48(5H, m), 7.75(1H, dd), 8.52(1H, dd). MS m/z: 561(M+1)

Example 406

4-(4-Chlorophenyl)-1-[3-(5,11-dihydro-7-(2,5-dihydro-5-oxo-4H-1,2,4-oxadiazol-3-yl)[1]benzoxepino[2,3-b]pyridin-5-ylidene)propyl]piperidin-4-ol The titled compound was prepared by following the procedure of Example 405, but replacing the product of Example 407 with the product of Example 408.

$^1$H-NMR (DMSO-d6) δ: 1.58–1.63(2H, m), 1.87–1.96 (2H, m), 2.40–2.51(2H, m), 2.63–2.85(6H, m), 5.14(2H, brs), 6.23(1H, t), 6.92(1H, d), 7.36–7.62(6H, m), 7.77–7.81 (2H, m), 8.54(1H, dd). MS m/z: 531(M+1)

Example 407

4-(4-Chlorophenyl)-1-[3-(7-hydroxyamidinomethoxy-5,11-dihydro[1]benzoxepino[2,3-b]pyridin-5-ylidene)propyl]piperidin-4-ol The titled compound was prepared by following the procedure of Example 355, but replacing the product of Example 313 with the product of Example 49.

$^1$H-NMR (DMSO-d6) δ:1.45–1.50(2H, m), 1.70–1.82(2H, m), 2.27–2.51(8H, m), 4.37(2H, s), 4.83(1H, s), 5.20(1H, brs), 5.57(2H, brs), 6.17(1H, t), 6.72–6.94(3H, m), 7.33–7.48(5H, m), 7.72(1H, dd), 8.49(1H, dd), 9.26(1H, s). MS m/z: 535(M+1)

Example 408

4-(4-Chlorophenyl)-1-[3-(7-hydroxyamidino-5,11-dihydro[1]benzoxepino[2,3-b]pyridin-5-ylidene) propyl]piperidin-4-ol The titled compound was prepared by following the procedure of Example 355, but replacing the product of Example 313 with the product of Example 364.

$^1$H-NMR (DMSO-d6) δ: 1.45–1.50(2H, m), 1.73–1.81 (2H, m), 2.28–2.51(8H, m), 4.83(1H, s), 5.79(2H, brs), 6.25(1H, t), 6.81(1H, d), 7.33–7.49(6H, m), 7.63–7.76(2H, m), 8.51(1H, dd), 9.48(1H, s). MS m/z: 505(M+1)

Example 409

4-(4-Chlorophenyl)-1-[3-(5,11-dihydro-7-(2-oxo-3H-1,2,3,5-oxathiadiazol-4-yl)methyloxy[1]benzoxepino[2,3-b]pyridin-5-ylidene)propyl]piperidin-4-ol To a solution of the product of Example 407 (700 mg) in THF (20 ml) were added pyridine (0.21 ml) and thionyl chloride (0.1 ml) at 0° C., and the mixture was stirred at 0° C. for 1 hour and the mixture was stirred at room temperature for 30 minutes. Water, chloroform and 2-propanol were added to the reaction mixture. The organic layer was extracted and the solvent was distilled off under reduced pressure. The residue was purified by silica gel chromatography eluting with chloroform-methanol (5:1) to give the titled compound (170 mg). MS m/z: 581(M+1)

Example 410

4-(4-Chlorophenyl)-1-[3-(5,11-dihydro-7-(2,5-dihydro-5-oxo-4H-1,2,4-thiadiazol-3-yl)methyloxy[1]benzoxepino[2,3-b]pyridin-5-ylidene)propyl]piperidin-4-ol To a solution of the product of Example 407 (700 mg) in THF (20 ml) was added thiocarbonyldiimidazole (280 mg) and the mixture was stirred at room temperature for 30 minutes. Water and ethyl acetate were added to the reaction mixture. The organic layer was extracted, and the solvent was distilled off under reduced pressure. To the residue were added THF (50 ml) and boron trifluoride diethyl etherate (0.8 ml), and the mixture was stirred at room temperature for 1 hour. Chloroform, 2-propanol and water were added to the reaction mixture. The organic layer was extracted, and the solvent was distilled off under reduced pressure. The residue was reslurried with acetone to the titled compound (180 mg). MS m/z: 577(M+1)

Example 411

4-(4-Chlorophenyl)-1-[3-(5,11-dihydro-7-ethoxycarbonylacetyl[1]benzoxepino[2,3-b]pyridin-5-ylidene)propyl]piperidin-4-ol To a solution of the product of Example 315 (250 mg) in THF (3.0 ml) was added LDA (0.51 mol/L THF-hexane solution, 3.0 ml) at −78° C., and the mixture stirred at room temperature for 20 minutes. The reaction mixture was cooled to −78° C. again, and added ethyl cyanoformate (76 μl), stirred at room temperature for 1 hour. Saturated aqueous ammonium chloride and aqueous sodium chloride were added to the mixture, and the aqueous layer was extracted with ethyl acetate. The organic layer was washed with saturated aqueous sodium chloride, and dried with magnesium sulfate. The solvent was distilled off under reduced pressure. The residue was purified by silica gel chromatography eluting with chloroform-methanol (10:1) to give the titled compound (280 mg).

$^1$H-NMR (CDCl$_3$) δ: 1.26(3H, t), 1.67–1.85(2H, m), 1.93–2.13(2H, m), 2.28–2.47(4H, m), 2.47–2.60(2H, m), 2.60–2.76(2H, m), 3.94(2H, s), 4.21(2H, q), 5.60(2H, brs), 6.22(1H, t), 6.88(1H, d), 7.29–7.34(3H, m), 7.43(2H, d), 7.59(1H, d), 7.71(1H, dd), 7.97(1H, d), 8.53(1H, d). MS m/z: 561(M+1)

Example 412

4-(4-fluorophenyl)-1-[3-(5,11-dihydro-7-hydroxy[1]benzoxepino[2,3-b]pyridin-5-ylidene)propyl]piperidine-4-ol To a solution of 5-(3-bromopropylidene)-5,11-dihydro-7-hydroxy-[1]benzoxepino[2,3-b]pyridine (2.59 g) in DMF (10 ml) was added 4-(4-Fluorophenyl)-4-hydroxypiperidine (1.02 g) and triethylamine (835 μM). The solution was stirred at room temperature for 23 hours. The reaction was quenched with water, extracted with ethyl acetate, and evaporated in vacuo. The residue was purified by silica gel chromatography (87:10:3 ethyl acetate: methanol:triethylamine) to yield 0.9 g (39%) of the title compound. $^1$H-NMR (DMSO) d: 1.64–1.69 (2H, m), 1.74–1.85 (2H, m), 2.27–2.52 (8H, m), 4.81 (1H, s), 5.16 (2H, brs), 6.08 (1H, t), 6.62–6.71 (3H, m), 7.12 (2H, t), 7.40–7.51 (3H, m), 7.72 (1H, dd), 8.48 (1H, dd), 9.09 (1H, s). ESI-MS m/z: 447 (M+1).

Example 413

4-(4-fluorophenyl)-1-[3-(5,11-dihydro-7-carboxy[1]benzoxepino[2,3-b]pyridin-5-ylidene)propyl]piperidine-4-ol The titled compound was prepared by following the procedure of example 118, but replacing the compound of Example 169 with the triflate derived from compound 412.

$^1$H-NMR (MeOD) δ:1.78–1.85 (2H, m), 2.25–2.40 (2H, m), 2.57–2.70 (2H, m), 3.06–3.35 (7H, m), 5.06–5.81 (2H, brs), 6.23 (1H, t), 6.77 (1H, d), 7.00–7.11 (2H, m), 7.37–7.56 (3H, m), 7.65–7.80 (2H, m), 8.01 (1H, d), 8.48 (1H, dd). MS m/z: 475

Example 414

4-(4-fluorophenyl)-1-[3-(5,11-dihydro-7-(1-hydroxy-1-methylethyl)-[1]benzoxepino[2,3-b]pyridin-5-ylidene)propyl]piperidine-4-ol The titled compound was prepared by following the procedure of Example 27, but starting with the methyl ester of the compound of Example 413.

$^1$H-NMR (CDCl$_3$) δ: 1.57–2.14 (12H,m), 2.34–2.45 (4H, m), 2.50–2.61 (2H,m), 2.63–2.78 (2H,m), 5.22–5.43 (2H, brs), 6.14 (1H,t), 6.95–7.10 (2H,m), 7.25–7.35 92H,m), 7.40–7.60 (4H,m), 8.50 (1H,dd). MS m/z: 489

Example 415

4-(4-Chlorophenyl)-1-[3-(5,11-dihydro-7-diethylcarbamoyl-[1]benzoxepino[2,3-b]pyridin-5-ylidene)propyl]piperidine-4-ol The titled compound was prepared by following the procedure of Example 316, but replacing dimethylamine with diethylamine.

$^1$H-NMR (CDCl$_3$) δ: 1.18–1.30 (6H, m), 1.65 (2H, d), 1.80 (1H, s), 2.05 (2H, dt), 2.30–2.45 (4H, m), 2.50 (2H, t), 2.60–2.70 (2H, m), 3.35–3.50 (4H, m), 5.30 (2H, brs), 6.15 (1H, t), 6.83 (1H, d), 6.90 (1H, dd), 7.10 (1H, dd), 7.23–7.35 (3H, m), 7.40 (2H, d), 7.56 (1H, dd), 8.50 (1H, dd). MS m/z: 563

Example 416

4-(4-Chlorophenyl)-1-[3-(5,11-dihydro-7-phenylsulfonylcarbamoyl-[1]benzoxepino[2,3-b]pyridin-5-ylidene)propyl]piperidine-4-ol To a solution of the compound of Example 44 (0.511 g, 1.1 mmol) in dry THF (20 mL) was added sodium hydride (60% in mineral oil, 48 mg, 1.2 mmol), and the slurry heated at 40° C. under argon with stirring for 20 minutes. Phenylsulfonylisocyanate (160 μL, 1.2 mmol) was added and the mixture was stirred for 14 hours. The solvent was then removed by rotary evaporation to give the crude product. The solid material was washed twice with 20 mL CH$_2$Cl$_2$, and then twice with 20 mL MeoH: CH$_2$Cl$_2$ (1:1) to give the title compound (274 mg). MS m/z: 647

Example 417

4-(4-Chlorophenyl)-1-[3-(5,11-dihydro-7-methoxycarbonyl-carbamoyl-[1]benzoxepono[2,3-b]pyridin-5-ylidene)propyl]piperidine-4-ol To a solution of the compound of Example 44 (0.214 g, 0.46 mmol) in dry THF (5 mL) was added sodium hydride (60% in mineral oil, 28 mg, 0.7 mmol), and the slurry heated at 50° C. under argon with stirring for 20 minutes. Methyl isocyanatoformate (56 μl, 0.7 mmol) was added and the mixture was stirred for 14 hours. The solvent was then removed by rotary evaporation to give the crude product. The residue was purified by silica gel chromatography eluting with a dichloromethane/2.0 M ammonia in methanol gradient (0 to 4% MeOH over 1 hour) to give the title compound (102 mg).

$^1$H-NMR (CDCl$_3$) δ: 1.60–1.65 (2H, m), 1.80 (1H, s), 2.05 (2H, dt), 2.30–2.45 (4H, m), 2.50 (2H, t), 2.60–2.70 (2H, m), 3.35 (3H, s), 5.30 (2H, brs), 6.15 (1H, t), 6.83 (1H, d), 6.90 (1H, dd), 7.10 (1H, dd), 7.23–7.35 (3H, m), 7.40 (2H, d), 7.56 (1H, dd), 8.50 (1H, dd). MS m/z: 565

Example 418

4-(4-Chlorophenyl)-1-[3-(5,11-dihydro-7-(R-3-ethoxycarbonyl-piperidine-1-yl)-carbamoyl-[1]benzoxepino[2,3-b]pyridin-5-ylidene)propyl]piperidine-4-ol Step 1:

R-ethyl nipecotate-L-tartrate (1.53 g) was freebased with aqueous sodium hydroxide and ethyl acetate. The organic layers were evaporated, and the resulting amine was redissolved in THF (10 mL) and treated with carbonyl-diimidazole (0.81 g). The resulting solution was stirred at room temperature for 23 hours, concentrated in vacuo, and redissolved in acetonitrile (5 mL). This solution was treated with methyl iodide (0.347 mL) and stirred for 18 hours at room temperature.

Step 2:

The compound of Example 44 (0.7 g) was suspended in THF (25 mL) and treated with sodium hydride (0.036 g) and stirred at room temperature for one hour. The resulting anion was added to the imidazolium salt prepared in Step 1, and the solution was heated to reflux for 18 hr. The crude material was then loaded on silica gel and purified by silica gel chromatography (87:10:3 ethyl acetate:methanol:triethylamine) to yield 0.278 g (64%) of the title compound.

$^1$H-NMR (DMSO) δ: 1.11–1.21 (3H, m), 1.45–2.0 (8H, m), 2.15–2.40 (6H, m), 3.05–3.15 (2H, m), 3.31 (2H, m), 3.95–4.15 (3H, m), 5.31 (2H, brs), 6.14 (1H, t), 6.78 (1H, d), 6.92 (1H, dd), 7.05 (1H, d), 7.33 (2H, d), 7.42–7.47 (3H, m), 7.72 (1H, dd), 8.50 (1H, dd). ESI-MS m/z: 646 (M+1).

Example 419

4-(4-Chlorophenyl)-1-[3-(5,11-dihydro-7-(R-3-ethoxycarbonyl-piperidine-1-yl)-carbamoyl-[1]benzoxepino[2,3-b]pyridin-5-ylidene)propyl]piperidine-4-ol The compound of Example 418 (0.195 g) was dissolved in THF (1 mL) and treated with aqueous lithium hydroxide (0.0084 g) and stirred at room temperature for 18 hours. The resulting solution was concentrated in vacuo, and the residue was purified by chromatography on a reverse-phase solid-phase-extraction column, eluting with water-acetonitrile, 0.1% formic acid, to yield 0.153 g (77%) of the title compound.

$^1$H-NMR (DMSO) δ: 1.55–2.25 (8H, m), 2.30–2.80 (10H, m), 3.22 (1H, m), 4.15–4.35 (2H, m), 5.41 (2H, brs), 6.35 (1H, t), 6.98 (1H, d), 7.13 (1H, dd), 7.25 (1H, d), 7.54 (2H, d), 7.64 (3H, m), 7.90 (1H, dd), 8.50 (1H, s), 8.70 (1H, dd). ESI-MS m/z: 618 (M+1).

Example 420

4-(4-Chlorophenyl)-1-[3-(5,11-dihydro-7-(4-ethoxycarbonyl-piperidine-1-yl)-carbamoyl-[1]benzoxepino[2,3-b]pyridin-5-ylidene)propyl]piperidine-4-ol The titled compound was prepared by following the procedure of Example 418, but replacing R-ethyl nipecotate-L-tartrate with ethyl isonipecotate.

$^1$H-NMR (CDCl$_3$) δ: 1.25 (3H, t), 1.60–1.80 (4H, m), 1.90–2.05 (4H, m), 2.25–2.65 (10H, m), 2.90–3.15 (2H, m), 4.05–4.25 (4H, m), 5.30 (2H, brs), 6.15 (1H, t), 6.75–6.90 (2H, m), 7.05 (1H, d), 7.20–7.40 (3H, m), 7.40 (2H, d), 7.56 (1H, dd), 8.45 (1H, dd). MS m/z: 647

Example 421

4-(4-Chlorophenyl)-1-[3-(5,11-dihydro-7-(4-carboxy-piperidine-1-yl)-carbamoyl-[1]benzoxepino[2,3-b]pyridin-5-ylidene)propyl]piperidine-4-ol A solution of the compound of Example 420 (91 mg, 0.14 mmol) in MeOH (5 mL) was treated with a 0.4 M solution of lithium hydroxide (5 mL, 2 mmol) and stirred for 3 hours. After addition of 5 mL of 0.4 N HCl, the solvent was removed under reduced pressure to give the crude product. The residue was purified using silica gel chromatography eluting with a dichloromethane:methanol gradient (0 to 50% MeOH over 1 hour) to give the title compound (48 mg).

$^1$H-NMR (MeOD) δ: 1.60–1.65 (2H, m) 2.10–2.70 (10H, m), 5.30 (2H, brs), 6.15 (1H, t), 6.80–6.90 (2H, m), 7.20–7.50 (6H, m), 7.62 (1H, dd), 8.48 (1H, dd). MS m/z: 619

Example 422

4-(4-Chlorophenyl)-1-[3-(5,11-dihydro-7-(S-3-ethoxycarbonyl-piperidine-1-yl)-carbamoyl-[1]benzoxepino[2,3-b]pyridin-5-ylidene)propyl]piperidine-4-ol The titled compound was prepared by following the procedure of Example 418, but replacing R-ethyl nipecotate-L-tartrate with ethyl (S)-nipecotate-D-tartrate.

$^1$H-NMR (CDCl$_3$) δ: 1.25 (3H, t), 1.30–1.70 (5H, m), 1.94–2.05 (3H, m), 2.25–2.65 (11H, m), 3.05–3.15 (1H, m), 4.05–4.25 (4H, m), 5.30 (2H, brs), 6.15 (1H, t), 6.75–6.90 (2H, m), 7.05 (1H, d), 7.20–7.40 (3H, m), 7.40 (2H, d), 7.56 (1H, dd), 8.45 (1H, dd). MS m/z: 647

Example 423

4-(4-Chlorophenyl)-1-[3-(5,11-dihydro-7-ethoxycarbonyl-[1]benzoxepino[2,3-b]pyridin-5-ylidene)propyl]piperidine-4-ol The compound of Example 169 (0.166 g) was dissolved in DMF (1 mL) and treated with palladium (II) acetate (0.007 g), 1,3-bis-diphenylphosphinopropane (0.012 g), triethylamine (0.1 mL) and ethanol (1 mL), and stirred at 60° C. for 18 hours under a CO balloon. The resulting solution was quenched with water, extracted with ethyl acetate, concentrated in vacuo, and purified by silica gel chromatography (87:10:3 ethyl acetate:methanol:triethylamine). The residue was further purified by chromatography on a reverse-phase solid-phase-extraction column, eluting with water-acetonitrile, 0.1% formic acid, to yield 0.114 g (73%) of the title compound.

$^1$H-NMR (DMSO) δ: 1.28 (3H, t), 1.40–1.55 (2H, m), 1.71–1.85 (2H, m), 2.20–2.60 (6H, m), 3.22 (2H, m), 4.28 (2H, q), 5.00–5.60 (2H, brs), 6.21 (1H, t), 6.92 (1H, d), 7.40–7.80 (8H, m), 8.50 (1H, d). ESI-MS m/z: 519 (M+1).

Example 424

4-(4-Chlorophenyl)-1-[3-(5,11-dihydro-7-(ethoxy-carbonylmethyl)-oxycarbonyl-[1]benzoxepino[2,3-b]pyridin-5-ylidene)propyl]piperidine-4-ol The procedure of Example 423 was followed, but replacing ethanol with ethyl glyoxylate to yield 0.041 g (26%) of the title compound.

$^1$H-NMR (DMSO) δ: 1.10–1.30 (3H, m), 1.35–1.55 (2H, m), 1.60–1.85 (2H, m), 2.20–2.60 (6H, m), 3.32 (2H, m), 4.05–4.25 (2H, m), 4.87 (2H, s), 5.00–5.60 (2H, brs), 6.21 (1H, t), 6.92 (1H, d), 7.2–7.90 (8H, m), 8.50 (1H, d). ESI-MS m/z: 577 (M+1).

Example 425

4-(4-Chlorophenyl)-1-[3-(5,11-dihydro-7-cyclohexyloxycarbonyl-[1]benzoxepino[2,3-b]pyridin-5-ylidene)propyl]piperidine-4-ol The procedure of Example 423 was followed, but replacing ethanol with cyclohexanol to yield 0.050 g (32%) of the title compound.

$^1$H-NMR (MeOD) δ: 1.30–2.20 (14H, m), 2.53–2.60 (2H, m), 2.95–3.32 (6H, m), 5.00 (1H, m), 5.00–5.60 (2H, brs), 6.28 (1H, t), 6.92 (1H, d), 7.40–7.55 (8H, m), 7.95 (2H, m), 8.05 (1H, s), 8.50 (2H, m). ESI-MS m/z: 573 (M+1).

Example 426

4-(4-Chlorophenyl)-1-[3-(5,11-dihydro-7-(1-propoxy)carbonyl-[1]benzoxepino[2,3-b]pyridin-5-ylidene)propyl]piperidine-4-ol To a solution of the compound of Example 118 (109 mg, 0.22 mmol) in dry DMF (5 mL) was added potassium carbonate (91 mg) followed by propyl iodide (24 μL, 0.66 mmol). The mixture was heated to 55° C. for 14 hours. The mixture was diluted with ethyl acetate (200 mL), washed twice with water (200 mL) and then with brine (100 mL), and dried with sodium sulfate. The organic solvent was removed under reduced pressure and the residue subjected to silica gel chromatography using a dichloromethane: methanol gradient (0 to 5% MeOH over 1 hour) to give the title compound (103 mg).

$^1$H-NMR (CDCl$_3$) δ: 1.06 (3H, t), 1.50–2.10 (4H, m), 2.14–2.25 (2H, m), 2.31–2.75 (10H, m), 4.28 (2H, t), 6.15 (1H, t), 6.83 (1H, d), 7.24–7.38 (3H, m), 7.42 (2H, d), 7.59 (1H, dd), 7.78 (1H, dd), 8.00 (1H, d), 8.50 (1H, dd). MS m/z: 533

Example 427

4-(4-Chlorophenyl)-1-[3-(5,11-dihydro-7-(1-butoxy)carbonyl-[1]benzoxepino[2,3-b]pyridin-5-ylidene)propyl]piperidine-4-ol The procedure of Example 423 was followed, but replacing ethanol with n-butanol to yield 0.065 g (45%) of the title compound.

$^1$H-NMR (MeOD) δ: 0.85–0.91 (3H, m), 1.25–1.45 (2H, m), 1.55–1.70 (2H, m), 1.70–1.85 (2H, m), 2.10–2.28 (2H, m), 2.53–2.60 (2H, m), 3.15–3.38 (6H, m), 4.12–4.21 (2H, m), 5.00–5.60 (2H, brs), 6.10 (1H, t), 6.76 (1H, d), 7.22–7.40 (3H, m), 7.71 (1H, m), 7.95 (1H, m), 8.05 (1H, s), 8.30 (1H, s), 8.41 (1H, m). ESI-MS m/z: 547 (M+1).

Example 428

4-(4-Chlorophenyl)-1-[3-(5,11-dihydro-7-(2-propoxy)carbonyl-[1]benzoxepino[2,3-b]pyridin-5-ylidene)propyl]piperidine-4-ol The titled compound was prepared by following the procedure of Example 426, but replacing propyl iodide with 2-bromopropane.

$^1$H-NMR (CDCl$_3$) δ: 1.30–2.10 (8H, m), 2.14–2.25 (2H, m), 2.31–2.75 (10H, m), 5.15–5.60 (2H, m), 6.15 (1H, t), 6.83 (1H, d), 7.24–7.38 (3H, m), 7.44 (2H, d), 7.59 (1H, dd), 7.80 (1H, dd), 8.02 (1H,d), 8.50 (1H, dd). MS m/z: 533

Example 429

4-(4-Chlorophenyl)-1-[3-(5,11-dihydro-7-cyclopentyl-oxycarbonyl-[1]benzoxepino[2,3-b]pyridin-5-ylidene)propyl]piperidine-4-ol The titled compound was prepared by following the procedure of Example 426, but replacing propyl iodide with cyclopentyl bormide.

$^1$H-NMR (MeOD) δ: 1.23–1.33 (1H, m), 1.50–2.04 (10H, m), 2.27–2.41 (2H, m), 2.70–2.90 (2H, m), 3.30–3.62 (5H, m), 5.21–5.85 (3H, m), 6.15 (1H, t), 6.85 (1H, d), 7.38 (2H, d), 7.42 (2H, d), 7.60–7.82 (2H, m), 8.04 (1H, d), 8.61 (1H, dd). MS m/z: 559

Example 430

4-(4-Chlorophenyl)-1-[3-(5,11-dihydro-7-(2-morpholinoethyl-1-yl)-oxycarbonyl-[1]benzoxepino[2,3-b]pyridin-5-ylidene)propy]piperidine-4-ol The titled compound was prepared by following the procedure of Example 426, but replacing propyl iodide with 2-morpholinoethyl chloride.

$^1$H-NMR (CDCl$_3$) δ: 1.62–1.70 (2H, m) 1.90–2.13 (2H, m), 2.30–2.80 (14H, m), 3.62–3.75 (4H, m), 4.41 (2H, t), 5.11–5.62 (2H, brs), 6.19 (1H, t), 6.83 (1H, d), 7.23–7.38 (3H, m), 7.42 (2H, d), 7.59 (1H, dd), 7.78 (1H, dd), 8.00 (1H, d), 8.50 (1H, dd). MS m/z: 604

Example 431

4-(4-Chlorophenyl)-1-[3-(5,11-dihydro-7-(2,2-diethylaminoethyl-1-yl)-oxycarbonyl-[1]benzoxepino[2,3-b]pyridin-5-ylidene)propyl]piperidine-4-ol The titled compound was prepared by following the procedure of Example 426, but replacing propyl iodide with 2-(N,N-diethylamino)ethyl chloride.

$^1$H-NMR (CDCl$_3$) δ: 1.06 (6H, t), 1.62–1.71 (2H, m), 1.93–2.10 (2H, m), 2.30–2.75 (12H, m), 2.85 (2H, t), 4.38 (2H, t), 5.20–5.58 (2H, brs), 6.15 (1H, t), 6.83 (1H, d), 7.24–7.38 (3H, m), 7.42 (2H, d), 7.59 (1H, dd), 7.78 (1H, dd), 8.00 (1H, d), 8.50 (1H, dd). MS m/z: 590

Example 432

4-(4-Chlorophenyl)-1-[3-(5,11-dihydro-7-(1-2,2-dimethylpropionyl-oxymethyl)-oxycarbonyl-[1]benzoxepino[2,3-b]pyridin-5-ylidene)propyl]piperidine-4-ol The procedure of Example 426 was followed, but replacing with chloromethyl pivalate to yield 0.36 g (77%) of the title compound.

$^1$H-NMR (CDCl$_3$) δ: 1.18 (9H, s), 1.58–1.72 (2H, m), 1.85–2.85 (10H, m), 5.00–5.60 (2H, brs), 5.94 (2H, s), 6.17 (1H, t), 6.82 (1H, d), 7.22–7.42 (5H, m), 7.56 (1H, dd), 7.80 (1H, dd), 7.99 (1H, d), 8.05 (1H, d), 8.46 (1H, dd). ESI-MS m/z: 605 (M+1).

Example 433

4-(4-Chlorophenyl)-1-[3-(5,11-dihydro-7-(2-hydroxyethyl-1-yl)-oxycarbonyl-[1]benzoxepino[2,3-b]pyridin-5-ylidene)propyl]piperidine-4-ol The procedure of Example 423 was followed, but replacing ethanol with ethylene glycol to yield 0.076 g (42%) of the title compound.

$^1$H-NMR (MeOD) δ: 1.80–2.00 (4H, m), 2.25–2.35 (2H, m), 2.55–2.65 (2H, m), 3.15–3.45 (5H, m), 3.75 (2H, dd), 4.24 (2H, dd), 5.00–5.60 (2H, brs), 6.10 (1H, t), 6.76 (1H, d), 7.18–7.42 (5H, m), 7.71 (2H, m), 7.99 (1H, m), 8.05 (1H, s), 8.30 (1H, s), 8.41 (1H, m). ESI-MS m/z: 535 (M+1).

Example 434

5-{3-[4-(4-Chloro-phenyl)-4-hydroxy-3-methyl-piperidin-1-yl]-propylidene}-5,11-dihydro-10-oxa-1-aza-dibenzo[a,d]cyclohepten-7-ol Step 1: 3-Methyl-4-oxo-piperidine-1-carboxylic acid tert-butyl ester In a Parr shaker flask, 1-benzyl-3-methyl-4-piperidone (19 g, 93 mmol), di-tert-butyl dicarbonate (27 g, 121 mmol) and palladium hydroxide (2.6 g) were suspended in methanol (75 mL) and then purged with argon. The reaction mixture was then purged with hydrogen and placed on a Parr shaker apparatus for about 16 hours at about 44 psi of hydrogen. The catalyst was filtered over celite and washed with methanol. The crude product was chromatographed on silica gel, eluting with EtOAc/hexane (1:5) to give a white crystalline solid.

$^1$H-NMR (CDCl$_3$) δ: 0.97 (3H, d), 1.45 (9H, s), 2.37–2.53 (3H, m), 2.80 (1H, brs), 3.16–3.26 (1H, m), 4.11–4.18 (2H, m). ESI-MS m/z: 158 [M–CH=C(CH$_3$)$_2$+1].

Step 2: 4-(4-Chloro-phenyl)-4-hydroxy-3-methyl-piperidine-1-carboxylic acid tert-butyl ester To 4-chlorophenyl magnesium bromide (49 mL, 49 mmol, 1M in diethyl 25 ether) at about 0° C. under argon, was added 3-Methyl-4-oxo-piperidine-1-carboxylic acid tert-butyl ester (7 g, 32.8 mmol) in THF (50 mL) over a period of about 1 hour. The reaction was allowed to warm to room temperature and stirred overnight. The reaction was quenched with saturated ammonium chloride solution and extracted with ethyl acetate. The organic layer was washed with water, then brine and dried over sodium sulfate. The solvent was evaporated and the crude residue was recrystallized in EtOAc to give a white solid.

$^1$H-NMR (CDCl$_3$) δ: 0.58 (3H, d), 1.45 (9H, s), 1.50–1.69 (2H, m), 1.76–2.13 (2H, m), 2.80 (1H, t), 3.10 (1H, t), 3.96 (2H, brs), 7.29 (4H, m). ESI-MS m/z: 252 [M-CH=C(CH$_3$)$_2$—H$_2$O+1].

Step 3: 4-(4-Chloro-phenyl)-3-methyl-piperidin-4-ol

To a solution of 4-(4-Chloro-phenyl)-4-hydroxy-3-methyl-piperidine-1-carboxylic acid tert-butyl ester (1.5 g, 4.6 mmol) in dichloromethane (40 mL) at about 0° C. was added trifluoroacetic acid (10 mL). The solution was stirred for about 2 hours. The solvent was evaporated and the residue was dissolved in ethyl acetate. The solution was neutralized with saturated sodium bicarbonate, and washed with brine and dried over magnesium sulfate. The solvent was removed to give a yellow solid. No purification was needed.

$^1$H-NMR (CDCl$_3$) δ: 0.65 (3H, d), 1.85 (1H, d), 2.52 (2H, m), 3.05 (1H, t), 3.27 (1H, dd), 3.34 (2H, d), 7.40 (4H, m). ESI-MS m/z: 240 [M+1].

5-{3-[4-(4-Chloro-phenyl)-4-hydroxy-3-methyl-piperidin-1-yl]-propylidene}-5,11-dihydro-10-oxa-1-aza-dibenzo[a,d]cyclohepten-7-ol To a solution of 4-(4-Chloro-phenyl)-3-methyl-piperidin-4-ol (1.0 g, 4.6 mmol) in DMF (10 mL) with triethylamine (1.75 mL, 12.54 mmol), was added 5-(3-Bromo-propylidene)-5,11-dihydro-10-oxa-1-aza-dibenzo[a,d]cyclohepten-7-ol (1.38 g, 4.18 mmol) dropwise for over a period of about 1.5 hours at about 50° C. The reaction was stirred overnight at about 50° C. The reaction was quenched with water, extracted with ethyl acetate, and evaporated in vacuo. The residue was purified by silica gel chromatography (87:10:3 ethyl acetate:methanol:triethylamine) to yield a brown solid of the title compound.

$^1$H-NMR (CDCl$_3$) δ: 0.53 (3H, d), 1.60–1.69 (2H, m), 2.07–2.30 (3H, m), 2.34–2.51 (3H, m), 2.56–2.75 (3H, m), 2.76–2.87 (1H, m), 2.98–3.11 (1H, m), 5.25 (2H, brs), 6.12 (1H, t), 6.64–6.79 (3H, m), 7.20–7.40 (5H, m), 7.53 (1H, d), 8.50 (1H, d). ESI-MS m/z: 477 [M+1].

Example 435

Trifluoro-methanesulfonic Acid 5-{3-[4-(4-chloro-phenyl)-4-hydroxy-3-methyl-piperidin-1-yl]-propylidene}-5,11-dihydro-10-oxa-1-aza-dibenzo[a,d]cyclohepten-7-yl ester The title compound was prepared according to the procedure of Example 169 and obtained as a brown solid.

$^1$H-NMR (CDCl$_3$) δ: 0.55 (3H, d), 1.55–1.68 (2H, m), 1.92–2.18 (2H, m), 2.24–2.69 (7H, m), 5.36 (2H, brs), 6.15 (1H, t), 6.88 (1H, d), 7.05 (1H, dd), 7.19–7.43 (6H, m), 7.60 (1H, d), 8.54 (1H, d). ESI-MS m/z: 609 [M+1].

Example 436

5-{3-[4-(4-Chloro-phenyl)-4-hydroxy-3-methyl-piperidin-1-yl]-propylidene}-5,11-dihydro-10-oxa-1-aza-dibenzo[a,d]cycloheptene-7-carboxylic acid methyl ester The title compound was prepared according to the procedure of Example 423 and obtained as a brown solid (formate salt).

$^1$H-NMR (CDCl$_3$) δ: 0.62 (3H, d), 1.75 (1H, d), 2.41–2.71 (5H, m), 2.90–3.14 (4H, m), 3.27 (1H, d), 3.89 (3H, s), 5.00–5.70 (2H, brs), 6.08 (1H, t), 6.86 (1H, d), 7.26–7.39

(5H, m), 7.59 (1H, d), 7.83 (1H, d), 7.98 (1h, s), 8.34 (1H, s), 8.56 (1H, d). ESI-MS m/z: 519 [M+1].

Example 437

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3-methyl-piperidin-4-ol The title compound was prepared according to the procedure of Example 27. The racemic compound was resolved using preparative chiral HPLC (ChiralPak AD, 20 mm×250 mm, isocrati elution with 10% ethanol:90% hexane, 15 mL/min., 35 minute run time). The more active enantiomer eluted first, at 17 minutes. The less active enantiomer eluted second, at 23 minutes. white solid (formate salt).
$^1$H-NMR (CDCl$_3$) δ: 0.61 (3H, d), 1.57 (6H, s), 1.76 (1H, d), 2.43–2.72 (5H, m), 2.91–3.12 (4H, m), 3.25 (1H, d), 5.04–5.46 (2H, brs), 6.01 (1H, t), 6.82 (1H, d), 7.22–7.37 (5H, m), 7.46 (1H, s), 7.55 (1H, d), 8.30–8.40 (1H, brs), 8.52 (1H, d). ESI-MS m/z: 519 [M+1].

Example 438

5-{3-[4-(4-Chloro-phenyl)-4-hydroxy-3-methyl-piperidin-1-yl]-propylidene}-5,11-dihydro-10-oxa-1-aza-dibenzo[a,d]cycloheptene-7-carboxylic acid The title compound was prepared according to the procedure of Example 118 and obtained as a brown solid (formate salt).
$^1$H-NMR (CDCl$_3$) δ: 0.49 (3H, d), 1.63 (1H, d), 2.29–2.43 (2H, m), 2.45–2.63 (3H, m), 2.78–3.18 (5H, m), 4.82–5.85 (2H, brs), 6.13 (1H, t), 6.67 (1H, d), 7.19–7.31 (5H, m), 7.55 (1H, d), 7.67 (1H, d), 7.87 (1h, s), 8.19 (1H, s), 8.40 (1H, d). ESI-MS m/z: 505 [M+1].

Example 439

5-{3-[4-(4-Chloro-phenyl)-4-hydroxy-3,5-dimethyl-piperidin-1-yl]-propylidene}-5,11-dihydro-10-oxa-1-aza-dibenzo[a,d]cyclohepten-7-ol Step 1: 1-Benzyl-3,5-dimethyl-piperidin-4-one
To 1-benzyl-3-methyl-4-piperidone (2.0 g, 9.8 mmol) in THF at about −78° C. under argon, was added Lithium diisopropylamide (7.35 mL, 14.7 mmol, 2 M in heptane/THF/ethylbenzene). After stirring for about 1 hour at about −78° C., iodomethane (0.73 mL, 11.8 mmol) was added. The reaction mixture was stirred for about 1 hour at about −78° C., then warmed to room temperature. Stirring was continued overnight at room temperature. The reaction was quenched with saturated ammonium chloride solution, and extracted with ethyl acetate. The organic layer was washed with water, then brine and dried over magnesium sulfate. The crude product was chromatographed on silica gel, eluting with EtOAc/hexane (3:10) to give a yellow oil of the title compound.
$^1$H-NMR (CDCl$_3$) δ: 0.96 (6H, d), 2.04 (2H, t), 2.62–2.78 (2H, m), 3.12–3.17 (2H, m), 3.59 (2H, s), 7.23–7.38 (5H, m). ESI-MS m/z: 218 [M+1].

Step 2: 3,5-Dimethyl-4-oxo-piperidine-1-carboxylic acid tert-butyl ester
The title compound was prepared according to the procedure of Example 434, step 1 and obtained as a white crystalline solid.
$^1$H-NMR (CDCl$_3$) δ: 1.02 (6H, d), 1.5 (9H, s), 2.47–2.75 (4H, m), 4.25–4.54 (2H, brs). ESI-MS m/z: 172 [M-CH=C(CH$_3$)$_2$+1].

Step 3: 4-(4-Chloro-phenyl)-4-hydroxy-3,5-dimethyl-piperidine-1-carboxylic acid tert-butyl ester
The title compound was prepared according to the procedure of Example 434, step 2 and obtained as a white solid.
$^1$H-NMR (CDCl$_3$) δ: 0.57 (6H, d), 1.49 (9H, s), 1.98–2.08 (2H, m), 2.71–2.98 (2H, m), 3.79–4.10 (2H, m), 7.29–7.36 (4H, m). ESI-MS m/z: 266 [M-CH=C(CH$_3$)$_2$—H$_2$O+1].

Step 4: 4-(4-Chloro-phenyl)-3,5-dimethyl-piperidin-4-ol
The title compound was prepared according to the procedure of Example 434, step 3 and obtained as a light yellow solid.
$^1$H-NMR (CDCl$_3$) δ: 0.54 (6H, d), 1.97–2.11 (4H, m), 2.75 (2H, t), 2.88 (2H, d), 7.27–7.32 (4H, m). ESI-MS m/z: 240 [M+1].

5-{3-[4-(4-Chloro-phenyl)-4-hydroxy-3,5-dimethyl-piperidin-1-yl]-propylidene}-5,11-dihydro-10-oxa-1-aza-dibenzo[a,d]cyclohepten-7-ol The title compound was prepared according to the procedure of Example 434, and obtained as a yellow solid.
$^1$H-NMR (CDCl$_3$) δ: 0.58 (6H, d), 2.50–2.80 (6H, m), 2.94–3.06 (2H, m), 3.17 (2H, d), 5.14–5.29 (2H, brs), 5.87 (1H, t), 6.75–6.90 (2H, m), 7.10–7.45 (6H, m), 8.44 (1H, d), 8.52 (1H, s). ESI-MS m/z: 491 [M+1].

Example 440

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,5-dimethyl-piperidin-4-ol The title compound was prepared according to the procedure of Example 439 but using 2-[5-(3-Bromo-propylidene)-5,11-dihydro-10-oxa-1-aza-dibenzo[a,d]cyclohepten-7-yl]-propan-2-ol, and was obtained as a white solid (formate salt).
$^1$H-NMR (CDCl$_3$) δ: 0.59 (6H, d), 1.58 (6H, s), 2.49–2.74 (6H, m), 2.97–3.10 (2H, m), 3.16 (2H, d), 5.20–5.45 (2H, brs), 6.06 (1H, t), 6.83 (1H, d), 7.12–7.43 (6H, m), 7.49 (1H, s), 7.60 (1H, d), 8.38 (1H, s), 8.54 (1H, m). ESI-MS m/z: 533 [M+1].

Examples 441 and 442

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3-methyl-piperidin-4-ol and 4-(4-Chloro-phenyl)-1-{3-[7-(1-hydroxy-1-methyl-ethyl)-11H-10-oxa-1-azadibenzo[a,d]cyclohepten-5-ylidene]-propyl}-4-methyl-piperidin-3-ol Step 1: 4-(4-Chloro-phenyl)-3,6-dihydro-2H-pyridine-1-carboxylic acid tert-butyl ester
To a solution of di-tert-butyl-dicarbonate (3.27 g, 15.0 mmol) in CH$_2$Cl$_2$ (50 mL) was added 4-(4-chlorophenyl)-1,2,3,6-tetrahydropiperidine hydrochloride (3.02 g, 13.1 mmol) and triethylamine (3.6 mL, 20 mmol). The solution was stirred at about room temperature for about 15 hours.

Gas evolution was observed. The reaction was quenched with aqueous ammonium chloride, extracted with $CH_2Cl_2$, and the organic layers were evaporated in vacuo. The residue was purified by plug filtration through silica gel to yield the title compound as a colorless oil.

$^1$H-NMR ($CDCL_3$) d: 1.50 (9H, s), 2.46 (2H, br s), 3.62 (2H, br s), 4.05 (2H, br s), 6.01 (1H, br s), 7.25 (4H, s).

Step 2: 6-(4-Chloro-phenyl)-7-oxa-3-aza-bicyclo[4.1.0]heptane-3-carboxylic acid tert-butyl ester To a solution of 4-(4-Chloro-phenyl)-3,6-dihydro-2H-pyridine-1-carboxylic acid tert-butyl ester (3.8 g, 13 mmol) in $CH_2Cl_2$ (50 mL) was added 3-chloroperbenzoic acid (3.8 g, 17.0 mmol) and triethylamine (3.6 mL, 20 mmol). The solution was stirred at room temperature for about 4 hours. A white precipitate was observed. The reaction was quenched with aqueous sodium bicarbonate, extracted with $CH_2Cl_2$, and the organic layers were evaporated in vacuo. The residue was purified by flash chromatography on silica gel (35 g $SiO_2$, gradient elution from 100% hexane to 100% ethyl acetate) to yield the title compound as a colorless oil.

$^1$H-NMR ($CDCL_3$) $\partial$: 1.50 (9H, s), 2.15 (1H, m), 3.15 (2H, m), 3.6–4.2 (4H, m), 7.31 (4H, s).

Step 3: 4-(4-Chloro-phenyl)-4-hydroxy-3-methyl-piperidine-1-carboxylic acid tert-butyl ester and 4-(4-Chloro-phenyl)-3-hydroxy-4-methyl-piperidine-1-carboxylic acid tert-butyl ester A suspension of copper(I) iodide (0.38 g, 2 mmol) in THF (20 mL) was cooled to about 4° C., and treated with methylmagnesium bromide (6 mL of 3M solution in diethyl ether, 18 mmol). To the cooled suspension of cuprate was added 6-(4-Chloro-phenyl)-7-oxa-3-aza-bicyclo[4.1.0]heptane-3-carboxylic acid tert-butyl ester (1.9 g, 6.1 mmol) in THF (5 mL). The solution was stirred and allowed to warm to about room temperature for about 4 hours. The reaction was quenched with aqueous ammonium chloride, extracted with ethyl acetate, and the organic layers were evaporated in vacuo. The residue was purified by flash chromatography on silica gel (35 g $SiO_2$, gradient elution from 100% hexane to 50% ethyl acetate) to yield a mixture of the title compounds as a white foam. This mixture was carried on to the next step.

Step 4: Synthesis of 4-(4-Chloro-phenyl)-3-methyl-piperidin-4-ol and 4-(4-Chloro-phenyl)-4-methyl-piperidin-3-ol The BOC-protected amino-alcohol mixture (0.8 g, 2.5 mmol) was dissolved in 4M HCl/Dioxane (5 mL, 20 mmol). The solution was stirred at room temperature for about 1 hour. The solvent was removed in vacuo. The residue was quenched with aqueous sodium hydroxide, extracted with ethyl acetate, and the organic layers were dried over sodium sulfate and evaporated in vacuo to yield the title compound as a brown solid.

ESI-MS m/z: 226 (M+1), 208 (M+1–$H_2O$). The mixture was carried on to the next step without further purification.

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3-methyl-piperidin-4-ol and 4-(4-Chloro-phenyl)-1-{3-[7-(1-hydroxy-1-methyl-ethyl)-11H-10-oxa-1-azadibenzo[a,d]cyclohepten-5-ylidene]-propyl}-4-methyl-piperidin-3-ol To a solution of the amino alcohol mixture (0.53 g, 2.3 mmol) in isopropanol (10 mL) was added 2,6-lutidine (0.23 mL, 2.0 mmol) and catalytic potassium iodide. This mixture was heated to about 80° C., and treated with 2-[5-(3-Bromo-propylidene)-5,11-dihydro-10-oxa-1-aza-dibenzo[a,d]cyclohepten-7-yl]-propan-2-ol (0.37 g, 1.0 mmol), added in portions over about 2 hours. The solution was then stirred at about 80° C. for about an additional 2 hours. The reaction was concentrated in vacuo, then purified by flash chromatography on silica gel (35 g $SiO_2$, gradient elution from 100% ethyl acetate to 87% ethyl acetate:10% methanol:3% triethylamine) to yield the title compounds.

The faster eluting isomer: 4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3-methyl-piperidin-4-ol, a brown semisolid. $^1$H-NMR ($CDCL_3$) $\partial$: 0.70 (3H, d, J=7.2 Hz), 1.53 (6H, s), 1.92 (3H, m), 2.28–2.69 (8H, m), 5.30 (2H, br s), 6.15 (1H, t, J=1.4 Hz), 6.79 (2H, d, J=8.4 Hz), 7.18–7.45 (7H, m), 7.59 (1H, d, J=8 Hz), 8.45 (1H, m). ESI-MS m/z: 519(M+1).

The slower eluting isomer: 4-(4-Chloro-phenyl)-1-{3-[7-(1-hydroxy-1-methyl-ethyl)-, a brown semisolid. $^1$H-NMR ($CDCL_3$) $\partial$: 1.16 (3H, s), 1.55 (6H, s), 2.28–2.69 (5H, m), 3.86 (1H, br s), 5.30 (2H, br s), 6.07 (1H, t, J=1.4 Hz), 6.79 (2H, d, J=8.4 Hz), 7.18–7.45 (7H, m), 8.45 (1H, m). ESI-MS m/z: 519(M+1).

Example 443

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol Step 1:1-Benzyl-3,3-dimethyl-piperidin-4-one To a solution of 1-Benzyl-3-methyl-piperidin-4-one (2.03 g, 10 mmol) in THF (10 mL) was added potassium t-Butoxide (1.1 g, 10 mmol) and methyl iodide (0.62 mL, 10 mmol). The solution was then stirred at room temperature for about 72 hours. The reaction was quenched with brine and extracted with ethyl acetate. The combined organic layers were concentrated in vacuo, then purified by flash chromatography on silica gel (35 g $SiO_2$, gradient elution from 100% hexane to 100% ethyl acetate) to yield the title compound as a colorless oil.

$^1$H-NMR ($CDCL_3$) $\partial$: 1.12 (6H, s), 2.41 (2H, s), 2.52 (2H, m), 2.73 (2H, m), 3.56 (2H, s), 7.20–7.40 (5H, m). ESI-MS m/z: 218 (M+1).

Step 2: 3,3-Dimethyl-4-oxo-piperidine-1-carboxylic acid tert-butyl ester

To a solution of 1-Benzyl-3,3-dimethyl-piperidin-4-one (2.48 g, 11 mmol) in ethanol (100 mL) was added di-tert-butyl dicarbonate (2.18, 10 mmol) and palladium hydroxide (0.10 g), The suspension was then shaken under a hydrogen atmosphere (40 PSI) at room temperature for about an additional 12 hours. The reaction was filtered through celite and evaporated in vacuo to yield the title compound as a white solid.

$^1$H-NMR ($CDCL_3$) $\partial$: 1.12 (6H, br s), 1.48 (9H, s), 2.45–2.80 (3H, m), 3.12 (1H, m), 3.42 (1H, br s), 3.70 (1H, m).

Step 3: 4-(4-Chloro-phenyl)-4-hydroxy-3,3-dimethyl-piperidine-1-carboxylic acid tert-butyl ester To an ice-cooled solution 3,3-Dimethyl-4-oxo-piperidine-1-carboxylic acid tert-butyl ester (1.6 g, 7.2 mmol) in THF (20 mL) was added 4-chlorophenylmagnesium bromide (1 M in ether, 15 mL, 15 mmol). The solution was allowed to warm to about room temperature, then stirred at room temperature for about 22 hours. The reaction was quenched with aqueous ammonium chloride and extracted with ethyl acetate. The combined organic layers were concentrated in vacuo, then purified by flash chromatography on silica gel (35 g SiO$_2$, gradient elution from 100% hexane to 100% ethyl acetate) to yield the title compound as a colorless oil.

$^1$H-NMR (CDCL$_3$) ∂: 1.12 (6H, s), 1.50 (11H, m), 2.60 (1H, m), 3.20 (2H, m), 3.56 (1H, m), 4.20 (1H, m), 7.20–7.40 (4H, m). ESI-MS m/z: 218 (M+1).

Step 4: 4-(4-Chloro-phenyl)-3,3-dimethyl-piperidin-4-ol 4-(4-Chloro-phenyl)-4-hydroxy-3,3-dimethyl-piperidine-1-carboxylic acid tert-butyl ester (0.25 g, 0.73 mmol) was dissolved in 4M HCl/Dioxane (2 mL, 8 mmol). The solution was stirred at room temperature for about 4 hours. The solvent was removed in vacuo. The residue was quenched with aqueous sodium hydroxide, extracted with ethyl acetate, and the organic layers were dried over sodium sulfate and evaporated in vacuo to yield the title compound as a yellow solid. The mixture was carried on to the next step without further purification.

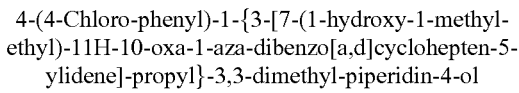

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol To a solution of the amino alcohol mixture (0.17 g, 0.7 mmol) in isopropanol (5 mL) was added 2,6-lutidine (0.23 mL, 2.0 mmol) and catalytic potassium iodide. This mixture was heated to about 80° C., and treated with 2-[5-(3-Bromo-propylidene)-5,11-dihydro-10-oxa-1-aza-dibenzo[a,d]cyclohepten-7-yl]-propan-2-ol (0.19 g, 0.5 mmol), added in portions over about 2 hours. The solution was then stirred at about 80° C. for an additional 2 hours. The reaction was concentrated in vacuo, then purified by flash chromatography on silica gel (10 g SiO$_2$, gradient elution from 100% ethyl acetate to 87% ethyl acetate:10% methanol:3% triethylamine) to yield the title compound as a brown semi-solid.

$^1$H-NMR (CDCL$_3$) ∂: 0.78 (3H, s), 0.90 (3H, s), 1.45 (2H, m), 1.53 (6H, s), 2.28–2.80 (9H, m), 5.30 (2H, br s), 6.15 (1H, t, J=1.4 Hz), 6.79 (2H, d, J=8.4 Hz), 7.18–7.45 (7H, m), 7.59 (1H, d, J=8 Hz), 8.45 (1H, m). ESI-MS m/z: 533 (M+1).

Example 456

4-(4-Chloro-phenyl)-1-{3-[7-(1-hydroxy-1-methyl-ethyl)-11H-10-oxa-1-aza-dibenzo-[a,d]cyclohepten-5-ylidene]-propyl}-piperidine-4-carbonitrile Step 1: Bis-(2-chloroethyl)-carbamic acid tert-butyl ester To a solution of bis-(2-chloroethyl)-amine hydrochloride (7.12 g, 40 mmol) in dichloromethane (65 ml) was added N,N-diisopropylethylamine (34.8 ml, 200 mmol) and catalytic amount of 4-dimethylaminopyridine, followed by portionwise addition of di-tert-butyl dicarbonate (8.72 g, 40 mmol). The solution was stirred at room temperature for 72 hours. The reaction mixture was concentrated and triturated with ether (70 ml). The solid was filtered and the filtrate was concentrated under vacuum. The residue was purified by silica gel chromatography eluting with hexane-ethyl acetate (9:1) to give the title compound (2.02 g, 21%).

$^1$H-NMR (CDCl$_3$) δ: 1.5 (9H, s), 3.5–3.6 (8H, m).

Step 2: 4-(4-Chloro-phenyl)-4-cyano-piperidine-1-carboxylic acid tert-butyl ester To 1.26 g (8.37 mmol) 4-chloro-benzylcyanide was added bis-(2-chloroethyl)-carbamic acid tert-butyl ester (2.02 g, 8.37 mmol) in 25 ml N,N-dimethylformamide. The resulting mixture was stirred and cooled in an ice bath, then sodium hydride (60% suspension in mineral oil) (1.1 g, 42 mmol) was added portionwise. The reaction was brought to room temperature and then heated in an oil bath at 60° C. for 16 hours. The reaction mixture was quenched by addition of ice water and the aqueous phase was extracted with ethyl acetate. The combined organic layers were washed twice with water, once with brine, dried with magnesium sulfate and concentrated in vacuo. The residual brown oil was purified by silica gel chromatography eluting with hexane-ethyl acetate (9:1) to give the title compound (1.44 g, 54%).

$^1$H-NMR (CDCl$_3$) δ: 1.5 (9H, s), 1.8–2.0 (2H, m), 2.1 (2H, d), 3.2 (2H, t), 4.3 (2H, brs), 7.4 (4H, m). MS m/z: 221 (M+1−100)

Step 3: 4-(4-Chloro-phenyl)-piperidine-4-carbonitrile

To a chilled solution of 4-(4-chloro-phenyl)-4-cyano-piperidine-1-carboxylic acid tert-butyl ester (315 mg, 1 mmol) in 5 ml dichloromethane was added 1 ml trifluoroacetic acid. The reaction was stirred at 0° C. for 3 hours, then concentrated under vacuum. The resulting oil was diluted with dichloromethane and washed twice with saturated aqueous sodium bicarbonate. The aqueous washings were extracted three times with dichloromethane. The combined organic layers were dried with magnesium sulfate and concentrated under vacuum to yield the title compound (180 mg, 82%).

$^1$H-NMR (CDCl$_3$) δ: 1.9–2.1 (4H, m), 3.0–3.2 (4H, m), 7.3–7.5 (4H, m). MS m/z: 221 (M+1)

Step 4

To a suspension of 4-(4-chloro-phenyl)-piperidine-4-carbonitrile (180 mg, 0.8 mmol) in acetonitrile/water (4/1) was added potassium carbonate (221 mg, 1.6 mmol), followed by 2-[5-(3-bromo-propylidene)-5,11-dihydro-10-oxa-1-aza-dibenzo[a,d]cyclohepten-7-yl]-propan-2-ol (150 mg, 0.4 mmol). The reaction mixture was stirred at room temperature for 48 hours and then concentrated in vacuo. The resulting residue was treated with water and extracted with ethyl acetate. Solvent was evaporated from the combined dried (MgSO$_4$) organic extracts, and the residue was purified by column chromatography on silica gel using hexane-ethyl acetate (6:4) to afford the title compound.

$^1$H-NMR (CDCl$_3$) δ: 1.5 (6H, s), 1.8–2.0 (4H, m), 2.4 (4H, m), 2.55 (2H, m), 2.8 (2H, d), 5.3 (2H, brs), 6.1 (1H, t), 6.8 (1H, d), 7.27–7.4 (7H, m), 7.5 (1H,d), 8.5 (1H, d) MS m/z: 514 (M+1)

Example 457

1-(4-(4-Chloro-phenyl)-1-{3-[7-(1-hydroxy-1-methyl-ethyl)-1 1H-10-oxa-1-aza-dibenzo[a,d]cyclohepten-5-ylidene]-propyl}-piperidin-4-yl)-ethanone

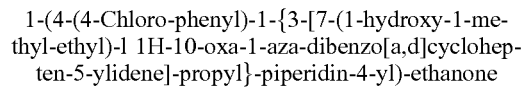

Step 1:1-[4-(4-Chloro-phenyl)-piperidin-4-yl]-ethanone

To a dry round bottom flask was added via syringe 10 ml methyl magnesium bromide in toluene/tetrahydrofuran (75:25, 1.4 M). The flask was cooled in an ice bath under a stream of nitrogen. A solution of 4-(4-Chloro-phenyl)-4-cyano-piperidine-1-carboxylic acid tert-butyl ester (357 mg, 1.11 mmol) in 4 ml tetrahydrofuran was added dropwise to the flask over 20 minutes and the resulting mixture was stirred at 0° C. for 8 hours. The reaction mixture was warmed to room temperature and stirred for 5 days. The reaction was quenched by slowly pouring 150 ml saturated aqueous ammonium chloride and extracted with ethyl acetate. The combined organic phases were dried over magnesium sulfate and concentrated under vacuum. The yellow residue was purified by reverse phase HPLC to get the formate salt of the title compound (106 mg, 40%).

MS m/z: 238 (M+1)

Step 2

To a suspension of 1-[4-(4-chloro-phenyl)-piperidin-4-yl]-ethanone in acetonitrile/water (4/1) was added potassium carbonate (221 mg, 1.6 mmol), followed by 2-[5-(3-bromo-propylidene)-5,11-dihydro-10-oxa-1-aza-dibenzo[a,d]cyclohepten-7-yl]-propan-2-ol (150 mg, 0.4 mmol). The reaction mixture was stirred at room temperature for 48 hours and then concentrated in vacuo. The resulting residue was treated with water and extracted with ethyl acetate. Solvent was evaporate from the combined dried ($MgSO_4$) organic extracts. Purification on silica gel chromatography using dichloromethane-methanol (9.5:0.5) afforded the title compound.

$^1$H-NMR ($CDCl_3$) δ: 1.3 (2H, m), 1.5 (6H, s), 1.9 (3H, s), 2.1–2.5 (10H, m), 5.3 (2H, brs), 5.9 (1H, t), 6.8 (1H, d), 7.3 (6H, m), 7.4 (1H, d), 7.6 (1H,d), 8.5 (1H, d) MS m/z: 531 (M+1)

Example 458

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-piperidine-4-carboxylic acid methyl ester Step 1: 4-(4-Chloro-phenyl)-piperidine-1,4-dicarboxylic acid mono-tert-butyl ester To a solution of 4-(4-chloro-phenyl)-4-cyano-piperidine-1-carboxylic acid tert-butyl ester (1.1 g, 3.44 mmol) in 40 ml ethanol was added 10 ml 10 N aqueous sodium hydroxide. The resulting solution was warmed to reflux for 48 hours, cooled to room temperature, poured into 1 N aqueous hydrochloric acid, and extracted into ethyl acetate. The organic extracts were washed with brine, dried over magnesium sulfate, and concentrated in vacuo. Recovered orange oil was purified by silica gel chromatography, eluting with dichloromethane-methanol (9.5:0.5) to give the title compound (1.0 g, 86%). MS m/z: 338 (M–1)

Step 2: 4-(4-Chloro-phenyl)-piperidine-1,4-dicarboxylic acid 1-tert-butyl ester 4-methyl ester To a stirred 4-(4-chloro-phenyl)-piperidine-1,4-dicarboxylic acid mono-tert-butyl ester (852 mg, 2.5 mmol) in methanol (5 ml)-benzene (17.5 ml) was added 15 ml (trimethylsilyl)diazomethane (2.0 M solution in hexanes) at room temperature. The mixture was stirred for 16 hours at room temperature and concentrated in vacuo. The residual yellow oil was purified by silica gel chromatography eluting with hexane-ethyl acetate (9:1) to give the corresponding ester (780 mg, 88%).

$^1$H-NMR ($CDCl_3$) δ: 1.5 (9H, s), 2.8–2.9 (2H, m), 2.5 (2H,d), 3.0 (2H, t). 3.7 (3H, s), 4.0 (2H, d), 7.4 (4H, m). MS m/z: 354 (M+1)

Step 3: 4-(4-Chloro-phenyl)-piperidine-4-carboxylic acid methyl ester

The title compound was prepared by following the procedure of Example 456, Step 3, but replacing 4-(4-chloro-phenyl)-4-cyano-piperidine-1-carboxylic acid tert-butyl ester with 4-(4-chloro-phenyl)-piperidine-1,4-dicarboxylic acid 1-tert-butyl ester 4-methyl ester.

$^1$H-NMR ($CDCl_3$) δ: 1.9 (2H, t), 2.55 (2H, d), 2.9 (2H, t), 3.25 (2H, d), 3.8 (3H, s), 7.2 (4H, m) MS m/z: 254 (M+1)

Step 4

To a suspension of 4-(4-chloro-phenyl)-piperidine-4-carboxylic acid methyl ester in acetonitrile/water (4/1) was added potassium carbonate (221 mg, 1.6 mmol), followed by 2-[5-(3-bromo-propylidene)-5,11-dihydro-10-oxa-1-aza-dibenzo[a,d]cyclohepten-7-yl]-propan-2-ol (150 mg, 0.4 mmol). The reaction mixture was stirred at room temperature for 48 hours and then concentrated in vacuo. The resulting residue was treated with water and extracted with ethyl acetate. Solvent was evaporate from the combined dried ($MgSO_4$) organic extracts. Purification on silica gel chromatography using dichloromethane-methanol (9.6:0.4) afforded the title compound.

$^1$H-NMR ($CDCl_3$) δ: 1.5 (6H, s), 1.8–2.0 (4H, m), 2.1 (2H, m), 2.4–2.5 (7H, m), 2.6 (2H, m), 5.3 (2H, brs), 6.1 (1H, t), 6.8 (1H, d), 7.3 (6H, m), 7.4 (1H, d), 7.6 (1H,d), 8.5 (1H, d) MS m/z: 547 (M+1)

Example 459

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-piperidine-4-carboxylic acid To a solution 4-(4-Chloro-phenyl)-1-{3-[7-(1-hydroxy-1-methyl-ethyl)-11H-10-oxa-1-aza-dibenzo[a,d]cyclohepten-5-ylidene]-propyl}-piperidine-4-carboxylic acid methyl ester (110 mg, 0.2 mmol) in methanol (5 ml) was added 1 ml 1 N aqueous sodium hydroxide. The resulting solution was warmed to 50° C. for 16 hours, cooled to room temperature, and concentrated under a stream of nitrogen. The residue was purified by reverse phase HPLC to get the formate salt of the title compound (96 mg. 90%).

$^1$H-NMR ($CDCl_3$) δ: 1.5 (6H, s), 1.8–1.9 (2H, m), 2.4 (4H, m), 2.55 (2H, m), 2.6–2.8 (4H, d), 5.3 (2H, brs), 5.9 (1H, t), 6.8 (1H, d), 7.27–7.4 (7H, m), 7.5 (1H,m), 8.5 (1H, d) MS m/z: 533 (M+1)

Example 460

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-piperidine-4-carboxylic acid amide Step 1: 4-Carbamoyl-4-(4-chloro-phenyl)-piperidine-1-carboxylic acid tert-butyl ester To a solution of 4-(4-chloro-phenyl)-4-cyano-piperidine-1-carboxylic acid tert-butyl ester (500 mg, 1.56 mmol) in ethanol (15 ml) was added 2 ml 10 N aqueous sodium hydroxide. The resulting solution was warmed to reflux for 2 hours, cooled to room temperature, poured into 1 N aqueous hydrochloric acid, and extracted into ethyl acetate. The organic extracts were washed with brine, dried over magnesium sulfate, and concentrated in vacuo. Recovered yellow oil was purified by silica gel chromatography, eluting with dichloromethane-methanol (9.6:0.4) to give the title compound (306 mg, 58%). MS m/z: 339 (M+1)

Step 2: 4-(4-Chloro-phenyl)-piperidine-4-carboxylic acid amide

The title compound was prepared by following the procedure of Example 456, step 3, but replacing 4-(4-chloro-phenyl)-4-cyano-piperidine-1-carboxylic acid tert-butyl ester with 4-carbamoyl-4-(4-chloro-phenyl)-piperidine-1-carboxylic acid tert-butyl ester.

MS m/z: 239 (M+1).

Step 3

The title compound was prepared by following the procedure of Example 456, step 4 but replacing 4-(4-chloro-phenyl)-piperidine-4-carbonitrile with 4-(4-chloro-phenyl)-piperidine-4-carboxylic acid amide. Purification on silica gel chromatography using dichloromethane-methanol (9:1) afforded the title compound.

$^1$H-NMR (CDCl$_3$) δ: 1.5 (6H, s), 1.8–2.0 (6H, m), 2.3–2.6 (6H, m), 5.3 (2H, brs), 6.1 (1H, t), 6.8 (1H, d), 7.3 (6H, m), 7.4 (1H, d), 7.5 (1H,d), 8.5 (1H, d) MS m/z: 532 (m+1)

Example 461

2-(5-{3-[4-(4-Chloro-phenyl)-4-hydroxymethyl-piperidin-1-yl]-propylidene}-5,11-dihydro-10-oxa-1-aza-dibenzo[a,d]cyclohepten-7-yl)-propan-2-ol Step 1: 4-(4-Chloro-phenyl)-4-hydroxymethyl-piperidine-1-carboxylic acid tert-butyl ester To a chilled solution of 4-(4-chloro-phenyl)-piperidine-1,4-dicarboxylic acid 1-tert-butyl ester 4-methyl ester (700 mg, 1.98 mmol) in 6 ml ether was added dropwise 2 ml lithium aluminium hydride 1M solution in ether. The reaction was stirred at 0° C. for 3 hours, then water (100 ml) was slowly added. The resulting gel was filtered and the aqueous filtrate was extracted three times with ether. The combined organic layers were dried with magnesium sulfate and concentrated under vacuum. Recovered oil was purified by silica gel chromatography, eluting with hexane-ethyl acetate (6:4) to give the title compound (297 mg, 46%).

$^1$H-NMR (CDCl$_3$) δ: 1.5 (9H,s), 1.7–1.8 (2H, m), 2.1 (2H,d), 3.0 (2H, m), 3.5 (2H, s), 3.7 (2H, d), 7.4 (4H, m) MS m/z: 324 (M−1)

Step 2: [4-(4-Chloro-phenyl)-piperidin-4-yl]-methanol

The title compound was prepared by following the procedure of Example 456, step 3, but replacing 4-(4-chloro-phenyl)-4-cyano-piperidine-1-carboxylic acid tert-butyl ester with 4-(4-chloro-phenyl)-4-hydroxymethyl-piperidine-1-carboxylic acid tert-butyl ester.

MS m/z: 224 (M−1)

Step 3

The title compound was prepared by following the procedure of Example 456, step 4, but replacing 4-(4-chloro-phenyl)-piperidine-4-carbonitrile with [4-(4-chloro-phenyl)-piperidin-4-yl]-methanol. Purification on silica gel chromatography using dichloromethane-methanol (9.5:0.5) afforded the title compound.

$^1$H-NMR (CDCl$_3$) δ: 1.5 (6H, s), 2.0 (2H, m), 2.2–2.3 (4H, m) 2.4 (2H, m), 2.55 (2H, m), 2.8 (2H, d), 3.5 (2H, s), 5.3 (2H, brs), 6.0 (1H, t), 6.8 (1H, d), 7.27–7.4 (7H, m), 7.5 (1H,d), 8.5 (1H, d) MS m/z: 517 (M−1)

Example 462

2-(5-{3-[4-(4-chloro-phenyl)-4-(1-hydroxy-ethyl)-piperidin-1-yl]-propylidene}-5,11-dihydro-10-oxa-1-aza-dibenzo[a,d]cyclohepten-7-yl)-propan-2-ol To a chilled solution of 1-(4-(4-Chloro-phenyl)-1-{3-[7-(1-hydroxy-1-methyl-ethyl)-11H-10-oxa-1-aza-dibenzo[a,d]cyclohepten-5-ylidene]-propyl}-piperidin-4-yl)-ethanone (70 mg, 0.13 mmol) in 5 ml methanol was added sodium borohydride (20 mg, 0.53 mmol). The reaction mixture was stirred at 0° C. for 4 hours, then concentrated down under a stream of nitrogen. The residue was purified by reverse phase HPLC to get the formate salt of the title compound (39 mg, 56%).

$^1$H-NMR (CDCl$_3$) δ: 0.8 (4H, d), 1.5 (6H, s), 2.1–2.7 (10H, m), 3.1 (2H, m), 5.3 (2H, brs), 5.95 (1H, t), 6.8 (1H, d), 7.27–7.4 (7H, m), 7.5 (1H,d), 8.5 (H, d) MS m/z: 533 (M+1)

Example 463

2-(5-{3-[4-(4-Chloro-phenyl)-4-(1-hydroxy-1-methyl-ethyl)-piperidin-1-yl]-propylidene}-5,11-dihydro-10-oxa-1-aza-dibenzo[a,d]cyclohepten-7-yl)-propan-2-ol Step 1: 4-Acetyl-4-(4-chloro-phenyl)-piperidine-1-carboxylic acid tert-butyl ester To a chilled solution of 1-[4-(4-chloro-phenyl)-piperidin-4-yl]-ethanone (540 mg, 1.98 mmol) in dichloromethane (10 ml) was added triethylamine (0.6 ml, 3.82 mmol), followed by portionwise addition of di-tert-butyl dicarbonate (470 mg, 1.98 mmol). The solution was stirred at room temperature for 16 hours. The reaction mixture was concentrated down, quenched with 1 N aqueous hydrochloric acid, and extracted into dichloromethane. The organic extracts were washed with saturated aqueous sodium bicarbonate solution, brine, dried over magnesium sulfate, and concentrated in vacuo. Recovered oil was purified by silica gel chromatography, eluting with hexane-ethyl acetate (8:2) to give the title compound (445 mg, 67%).

$^1$H-NMR (CDCl$_3$) δ: 1.5 (9H, s), 1.9 (5H, m), 2.3–2.4 (2H, m), 3.1 (2H, t), 3.7–3.8 (2H, m), 7.4 (4H, m) MS m/z: 338 (M+1)

Step 2: 4-(4-Chloro-phenyl)-4-(1-hydroxy-1-methyl-ethyl)-piperidine-1-carboxylic acid tert-butyl ester To a dry round bottom flask was added via syringe 16 ml methyl magnesium bromide in toluene/tetrahydrofuran (75:25, 1.4 M). The flask was cooled in an ice bath under a stream of nitrogen. A solution 4-acetyl-4-(4-chloro-phenyl)-piperidine-1-carboxylic acid tert-butyl ester (337 mg, 1.02 mmol) in 5 ml tetrahydrofuran was added dropwise to the flask over 20 minutes and the resulting mixture was stirred at 0° C. for 8 hours. The reaction mixture was warmed to room temperature and stirred for 5 days. The reaction was quenched by slow addition of 150 ml saturated aqueous ammonium chloride and extracted with ethyl acetate. The combined organic phases were washed with brine, dried over magnesium sulfate and concentrated under vacuum. The yellow residue was purified by silica gel chromatography, eluting with hexane-ethyl acetate (7.5:2.5) to give the title compound (242 mg, 67%).

$^1$H-NMR (CDCl$_3$) δ: 1.1 (6H, s), 1.4 (9H, s), 1.8–1.9 (2H, m), 2.3–2.4 (2H, d), 2.6 (2H, t), 3.9 (2H, d), 7.3 (4H, m) MS m/z: 354 (M+1)

Step 3: 2-[4-(4-Chloro-phenyl)-piperidin-4-yl]-propan-2-ol

The title compound was prepared by following the procedure of Example 456, step 3, but replacing 4-(4-chlorophenyl)-4-cyano-piperidine-1-carboxylic acid tert-butyl ester with: 4-(4-chloro-phenyl)-4-(1-hydroxy-1-methyl-ethyl)-piperidine-1-carboxylic acid tert-butyl ester.

MS m/z: 254 (+1)

Step 4

The title compound was prepared by following the procedure of Example 456, step 4, but replacing 4-(4-chlorophenyl)-piperidine-4-carbonitrile with 2-[4-(4-chloro-phenyl)-piperidin-4-yl]-propan-2-ol. Purification on silica gel chromatography using dichloromethane-methanol (9:1) afforded the title compound.

$^1$H-NMR (CDCl$_3$) δ: 1.1 (6H, s), 1.5 (6H, s), 1.8 (2H, m), 2.3–2.6 (10H, m), 5.3 (2H, brs), 5.95 (1H, t), 6.8 (1H, d), 7.27–7.4 (7H, m), 7.5 (1H,d), 8.5 (1H, d) MS m/z: 547 (M+1)

Example 464

4-(4-Chloro-phenylamino)-1-{3-[7-(1-hydroxy-1-methyl-ethyl)-11H-10-oxa-1-aza-dibenzo[a,d]cyclohepten-5-ylidene]-propyl}-piperidine-4-carbonitrile Step 1: 1-Benzyl-4-(4-chloro-phenylamino)-piperidine-4-carbonitrile To a solution of 1-Benzyl-piperidin-4-one (2.68 g, 14.20 mmol) in acetic acid (13 ml, glacial) was added 4-Chloro-phenylamine (1.99 g, 15.6 mmol). The reaction was cooled in a cool temperature water bath. Trimethylsilylcyanide (1.89 ml, 14.20 mmol) was added slowly. The reaction mixture was allowed to warm to room temperature and stir overnight under N$_2$. The reaction was cooled to 0° C. Concentrated ammonium hydroxide (15 ml) was added slowly. Next added was cold water. The pH of the mixture was ≈10. The mixture was extracted three times with methylene chloride, and the organic layers were dried over magnesium sulfate, filtered, and concentrated under reduced pressure. Ether was added to the residue, and the white solid was filtered off and dried under high vacuum to give the titled compound (3.73 g, 81%)

$^1$H-NMR (CDCl$_3$) δ: 1.90–2.01(2H,t), 2.3–2.4(2H,m), 2.45–2.55(2H,t), 2.81–2.93(2H,m), 3.61(2H,s), 3.68(1H,s) 6.87(1H,s), 6.90(1H,s) 7.2–7.38(7H, m). MS m/z: 326 (M+1).

Step 2: 4-(4-Chloro-phenylamino)-piperidine-4-carbonitrile

To 1-Benzyl-4-(4-chloro-phenylamino)-piperidine-4-carbonitrile (163 mg, 0.5002 mmol) in dichloroethane (5 ml) was added 1-chloroethyl chloroformate (65 μl, 0.600 mmol). The mixture was heated to reflux and stirred under N$_2$. After 1 hour 15 minutes, an additional 86 μl (0.800 mmol) of the chloroformate was added to the reaction and stirred for an additional 2 hours at reflux. After cooling to room temperature the reaction was concentrated under reduced pressure. To this residue was added methanol (5 ml) and the reaction was heated at reflux for 2 hours. Next, the reaction was allowed to cool to room temperature and concentrated under reduced pressure. The residue was diluted with ethyl acetate and water. The organic layer was removed and sodium hydroxide (1N) was added to the aqueous layer until pH≈9. The aqueous layer was extracted with ethyl acetate 2 times and dried over magnesium sulfate. The solvent was distilled off under reduced pressure to obtain the title compound (84 mg, 71%).

$^1$H-NMR (CDCl$_3$) δ: 1.66–1.68(1H,d), 1.70–1.75(2H,d), 2.22–2.28(2H,d), 2.87–3.12(4H,m), 3.61(1H,bs), 6.53–7.27 (4H,m) MS m/z: 236 (M+1)

Step 3

The title compound was prepared by dissolving 2-[5-(3-Bromo-propylidene)-5,11-dihydro-10-oxa-1-aza-dibenzo[a,d]cyclohepten-7-yl]-propan-2-ol (106.7 mg, 0.285 mmol) in water (4 ml) and acetonitrile (1 ml). To this was added potassium carbonate (82.7 mg, 0.599 mmol) and 4-(4-Chloro-phenylamino)-piperidine-4-carbonitrile (84.0 mg, 0.356 mmol). The reaction was heated to 50° C. and stirred overnight. The next day the reaction was allowed to cool to room temperature and diluted with ethyl acetate and water. The organic layer was washed twice with water, dried over magnesium sulfate, and concentrated under reduced pressure. The crude residue was purified by reverse phase HPLC to give the title compound (11.5 mg, 8% yield, 88% pure by LC/MS).

$^1$H-NMR(CDCl$_3$) δ: 1.52(6H,bs), 2.2–2.8(12H, m), 3.4 (1H,b), 5.16–5.36(2H,b), 6.00–6.10(1H,m), 6.75–6.80(2H, m), 6.95–7.55(7H,m), 8.45–8.76(1H,m) MS m/z: 529 (M+1).

Example 465

4-(4-Chloro-phenylamino)-1-{3-[7-(1-hydroxy-1-methyl-ethyl)-11H-10-oxa-1-aza-dibenzo[a,d]cyclohepten-5-ylidene]-propyl}-piperidine-4-carboxylic acid methyl ester Step 1: 1-Benzyl-4-(4-chloro-phenylamino)-piperidine-4-carboxylic acid amide To 1-Benzyl-4-(4-chloro-phenylamino)-piperidine-4-carbonitrile (1.97 g, 6.05 mmol) was added concentrated sulfuric acid (50 ml). The reaction stirred at room temperature as an orange homogeneous solution. After 24 hours the reaction was cooled to 0° C. and very slowly poured into concentrated ammonium hydroxide in ice. The precipitate was filtered and washed with water to give a white solid (202 mg, 71%).

$^1$H-NMR(CDCl$_3$) δ: 1.87–1.92(2H,bd), 2.06–2.14 (2H,t) 2.27–2.38(2H,m), 2.70–2.78(2H,bd), 3.50(2H,s), 3.05(1H, s), 5.42–5.44(1H,bs), 6.55–6.57(2H,d), 6.76–6.82(1H,bs), 7.10–7.15(2H,d), 7.24–7.31(5H,m) MS m/z: 344 (M+1).

Step 2: 1-Benzyl-4-(4-chloro-phenylamino)-piperidine-4-carboxylic acid methyl ester To a solution of 1-Benzyl-4-(4-chloro-phenylamino)-piperidine-4-carboxylic acid amide (1.19 g 3.46 mmol) in methanol (10 ml) in a sealed tube was added toluene sulfonic acid (2.33 g, 12.11 mmol). The reaction was heated to 120° C., and stirred at that temperature behind a blast shield for 5 days. The reaction was then allowed to cool to room temperature at which time it was worked up by diluting with water, then by adding concentrated ammonium hydroxide until the pH≈8. The mixture was extracted three times with ethyl acetate and dried over magnesium sulfate. The solvent was distilled off under reduced pressure. The yellow oil was used crude (744 mg, 60%).

$^1$H-NMR(CDCl$_3$) δ: 1.93–2.03(2H,bd), 2.19–2.28(2H,dt), 2.32–2.48(2H,m), 2.55–2.64(2H,m), 3.51 (2H,s), 3.68(3H,s), 3.85 (1H,s) 6.47–6.51(2H,bd), 7.07–7.10 (2H,bd), 7.21–7.35(5H,m) MS m/z: 359(M+1)

Step 3: 4-(4-Chloro-phenylamino)-piperidine-4-carboxylic acid methyl ester

The titled compound was prepared by following the procedure of Example 464, step 2, but replacing 1-Benzyl-4-(4-chloro-phenylamino)-piperidine-4-carbonitrile with 1-Benzyl-4-(4-chloro-phenyl amino)-piperidine-4-carboxylic acid methyl ester. This compound was also purified on a sep-pak silica column eluted with 2%–10% MeOH/CH$_2$Cl$_2$.

$^1$H-NMR(CDCl$_3$) δ: 1.92–1.99(2H,bd), 2.11–2.22(2H,m), 2.73–3.03(4H,m), 3.69(3H,s), 3.94(1H,s), 6.50–6.53(2H,bd), 7.09–7.12(2H,bd) MS m/z: 269(M+1)

Step 4

The titled compound was prepared by following the procedure of Example 464, step 3, but replacing 4-(4-chlorophenylamino)-piperidine-4-carbonitrile with 4-(4-Chloro-phenylamino)-piperidine-4-carboxylic acid methyl ester. The residue was purified by reverse phase HPLC to give the title compound (62 mg, 32%).

$^1$H-NMR(CDCl$_3$) δ: 1.58(6H,s) 2.09–2.20(2H,m), 2.36–2.47(2H,m), 2.51–2.60(2H,m), 2.85–3.02(6H, m), 3.69(3H,s), 5.19–5.41(3H,bs), 6.01–6.06(1H,t), 6.51–6.54 (2H,d), 6.82–6.84(1H,d), 7.10–7.13(2H,d), 7.24–7.34(2H, m), 7.43–7.44(1H,d), 7.55–7.58(1H,d), 8.26(1H,s), 8.53–8.55(1H,dd) MS m/z: 562 (M)

Example 466

4-(4-Chloro-phenylamino)-1-{3-[7-(1-hydroxy-1-methyl-ethyl)-11H-10-oxa-1-aza-dibenzo [a,d]cyclohepten-5-ylidene]-propyl}-piperidine-4-carboxylic acid amide Step 1: 4-(4-Chloro-phenylamino)-piperidine-4-carboxylic acid amide The titled compound was prepared by following the procedure of Example 464, step 2, but replacing 1-Benzyl-4-(4-chloro-phenylamino)-piperidine-4-carbonitrile with 1-Benzyl-4-(4-chloro-phenyl amino)-piperidine-4-carboxylic acid amide.

$^1$H-NMR(CDCl$_3$) δ: 1.82–1.92(2H,bd), 2.10–2.37(3H,m), 2.69–2.79(2H,m), 2.89–3.03(2H,m), 5.42–5.46(1H,bs), 6.47–6.59(2H,m), 6.76–6.82(1H,bs), 7.08–7.15(2H,bd). MS m/z: 254 (M+1)

Step 2

The titled compound was prepared by following the procedure of Example 464, step 3, but replacing 4-(4-chlorophenylamino)-piperidine-4-carbonitrile with 4-(4-Chloro-phenylamino)-piperidine-4-carboxylic acid amide. The sample was purified using reverse phase HPLC to give the title compound (25 mg, 25%).

$^1$H-NMR(CDCl$_3$) δ: 1.53–1.55(7H,s), 1.97–2.07(2H,m), 2.40–2.61(3H,m), 2.67–2.76(3H,m), 2.86–2.96(2H,m), 5.20–5.38(2H,bs), 6.04–6.09(1H,t), 6.51–6.54(2H,bd), 6.77–6.80(1H,bd), 7.08–7.11(2H,bd), 7.19–7.29(2H,m), 7.42–7.43(1H,bd), 7.51–7.55(1H,dd), 8.18(1H,bs), 8.48–8.50(1H,dd) MS m/z: 547 (M)

Example 467

2-(5-{3-[4-(4-Chloro-phenyl)-4-fluoro-piperidin-1-yl]-propylidene}-5,11-dihydro-10-oxa-1-aza-dibenzo [a,d]cyclohepten-7-yl)-propan-2-ol Step 1

To a cooled (0° C.) solution of hydrogen fluoride (65–70%) in pyridine (4 mL) was added 4-(4-chloro-phenyl)-piperidin-4-ol (500 mg, 2.36 mmol). The resulting solution was stirred at 0° C. for 15 min and then warmed to rt and stirred 1 h. The mixture was slowly poured into a saturated aqueous sodium bicarbonate solution (30 mL) and extracted with methylene chloride (100 mL; ADD SOLVENT AND EXTRACT SLOWLY AND WITH CAUTION).

Excess hydrogen fluoride was neutralized with solid sodium carbonate. The organic phase was washed with brine, dried over magnesium sulfate, filtered and concentrated. The crude residue was purified by silica gel chromatography, eluting with a methylene chloride to methylene chloride/methanol/ammonium hydroxide (8.5/1/0.5) gradient to give 4-(4-Chloro-phenyl)-4-fluoro-piperidine (260 mg, 52%).

$^1$H-NMR (CDCl$_3$, 300 MHz) δ: 2.98–3.14 (m, 4 H), 1.87–2.10 (m, 4 H), 7.33–7.36 (m, 4 H). $^{19}$F-NMR (CDCl$_3$, 282 MHz) d: −160.40–160.20 (m). MS m/z: 214 (M+1).

Step 2

To a solution of the product of Step 1 (252 mg, 1.18 mmol) in isopropyl alcohol (5 mL) was added 2,6-lutidine (197 mg, 214 uL, 1.84 mmol) and potassium iodide (few mg). The resulting suspension was warmed to 80° C. Solid 2-[5-(3-Bromo-propylidene)-5,11-dihydro-10-oxa-1-aza-dibenzo[a,d]cyclohepten-7-yl]-propan-2-ol (221 mg, 0.591 mmol) was added in approximately equal portions over 2 h. Stirring was continued an additional 20 h at 80° C. The mixture was concentrated and the resulting residue purified by silica gel chromatography (methylene chloride to methylene/methanol 95:5 gradient) to afford the title compound (160 mg, 54%).

$^1$H-NMR (CDCl$_3$, 300 MHz) δ: 1.57–1.66 (m, 8 H), 1.88–1.97 (m, 3 H), 2.31–2.46 (m, 4 H), 2.52–2.62 (m, 2 H), 2.67–2.76 (m, 2 H), 5.20–5.45 (br s, 2 H), 6.14, (t, 1 H), 6.83 (d, 1 H), 7.22–7.37 (m, 6 H), 7.45 (d, 1 H), 7.59 (dd, 1 H), 8.51 (dd, 1 H). $^{19}$F-NMR (CDCl$_3$, 282 MHz) δ: −160.30–160.50 (m). MS m/z: 507 (M+1).

Example 468

4-(4-Chloro-phenyl)-4-fluoro-1-{3-[7-(1-hydroxy-1-methyl-ethyl)-11H-10-oxa-1-aza-dibenzo[a,d]cyclohepten-5-ylidene]-propyl}-piperidin-3-ol Step 1

To a solution of 4-(4-chloro-phenyl)-3,4-dihydroxy-piperidine-1-carboxylic acid tert-butyl ester (1.213 g, 3.34 mmol) in methylene chloride (30 mL) at −78° C. was added diethylaminosulfur trifluoride (DAST, 3 mL). The resulting solution was stirred at −78° C. 4 h. Methanol (20 mL) was added to quench excess DAST and the mixture was allowed to remain at −78° C. 5 min before warming to rt. The mixture was concentrated and purified by silica gel chromatography (80% hexanes/20% ethyl acetate gradient) to afford 4-(4-chloro-phenyl)-4-fluoro-piperidin-3-ol (262 mg, 24%).

$^1$H-NMR (CDCl$_3$, 300 MHz) δ: 1.48 (s, 9 H), 1.84 (br dd, 1 H), 2.50 (dddd, 1 H), 3.15 (br dd, 1 H), 3.38 (d, 1 H), 3.76 (s, 1 H), 4.04–4.36 (m, 2 H), 7.33–7.44 (m, 4 H). $^{19}$F-NMR (CDCl$_3$, 282 MHz) δ: −159.90 (d).

Step 2

4-(4-Chloro-phenyl)-4-fluoro-piperidin-3-ol was prepared as in step 3 of Example 502, substituting 4-(4-chloro-phenyl)-4-fluoro-3-hydroxy-piperidine-1-carboxylic acid tert-butyl ester for 4-(4-chloro-phenyl)-4-hydroxy-3,3-dimethyl-piperidine-1-carboxylic acid tert-butyl ester. Following isolation from the crude mixture, the free amine was used immediately without further purification.

¹H-NMR (CDCl₃, 300 MHz). 4-(4-Chloro-phenyl)-4-fluoro-piperidin-3-ol appears as the major constituent of a mixture of compounds. MS m/z: 230 (M+1; major peak in chromatogram).

Step 3

The titled compound was prepared as in step 5 of Example 502, substituting 4-(4-chloro-phenyl)-4-fluoro-piperidin-3-ol for S-4-(4-chloro-phenyl)-3,3-dimethyl-piperidin-4-ol.

¹H-NMR (CDCl₃, 300 MHz) δ: 1.58 (s, 6 H), 1.74–1.96 (m, 2 H), 2.31–2.75 (m, 8 H), 2.80 (br d, 1 H), 3.06 (d, 1 H), 3.67 (br d, 1 H), 5.20–5.45 (br s, 2 H), 6.11 (t, 1 H), 6.84 (d, 1 H), 7.22–7.36 (m, 4 H), 7.39–7.47 (m, 3 H), 7.57 (d, 1 H), 8.56 (dd, 1 H). ¹⁹F-NMR (CDCl₃, 282 MHz) δ: −158.30 (d). MS m/z: 523 (M+1).

Example 469

2-(5-{3-[4-(4-Chloro-phenyl)-4-fluoro-3-methyl-piperidin-1-yl]-propylidene}-5,11-dihydro-10-oxa-1-aza-dibenzo[a,d]cyclohepten-7-yl)-propan-2-ol Step 1

4-(4-Chloro-phenyl)-4-fluoro-3-methyl-piperidine was prepared following the procedure in Step 1 in Example 467, replacing 4-(4-chloro-phenyl)-piperidin-4-ol with 4-(4-Chloro-phenyl)-3-methyl-piperidin-4-ol.

¹H-NMR (CDCl₃, 300 MHz) δ: 0.67 (d, 3 H), 1.91–2.26 (m, 2 H), 2.84 (t, 1 H), 3.02 (dd, 1 H), 3.06–3.21 (m, 2 H), 3.33 (br s, 2 H), 7.27 (d, 2 H), 7.34 (d, 2 H). ¹⁹F-NMR (CDCl₃, 282 MHz) δ: −180.60 (ddd). MS m/z: 228 (M+1).

Step 2

The titled compound was prepared following the procedure step 2 of Example 467, replacing 4-(4-chloro-phenyl)-4-fluoro-piperidine with 4-(4-chloro-phenyl)-4-fluoro-3-methyl-piperidine.

¹H-NMR (CDCl₃, 300 MHz) δ: 0.63 (d, 3 H), 1.58 (s, 6 H), 1.76–1.96 (m, 2 H), 2.09–2.52 (m, 6 H), 2.55–2.88 (m, 4 H), 5.18–5.50 (br s, 2 H), 6.12 (t, 1 H), 6.83 (d, 1 H), 7.22–7.36 (m, 6 H), 7.46 (dd, 1 H), 7.59 (d, 1 H), 8.51 (d, 1 H). MS m/z: 521 (M+1).

Example 470

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-piperidine-3,4-diol Step 1

To a suspension of 4-(4-Chloro-phenyl)-1,2,3,6-tetrahydro-pyridine hydrochloride (2 g, 8.73 mmol) in methylene chloride (50 mL) was added triethylamine (1.42 g, 1.95 mL, 14.0 mol). The resulting mixture was cooled to 0° C. and di-tert-butyl-dicarbonate (2.19 g, 10.0 mmol) was added in a single portion. After 10 min at 0° C., the mixture was warmed to rt and stirred 90 min. The contents of the flask were poured into 250 mL methylene chloride and washed with 1 N hydrochloric acid/brine (3:1), saturated aqueous sodium bicarbonate and brine. The organic phase was dried over magnesium sulfate, filtered, concentrated and the resulting oil filtered through a plug of silica with methylene chloride elution, to afford 2.88 g (>100%) of 4-(4-Chloro-phenyl)-3,6-dihydro-2H-pyridine-1-carboxylic acid tert-butyl ester.

¹H-NMR (CDCl₃, 300 MHz) δ: 1.49 (s, 9 H), 2.45–2.52 (m, 2 H), 3.63 (t, 2 H), 4.07 (q, 2 H), 6.02 (br s, 1 H), 7.29 (s, 4 H).

Step 2

The product of step 1 (2.88 g, approx. 8.7 mmol) was dissolved in 15 mL of a 5:1 acetone:water solution. Osmium tetroxide (2.5% in tert-butyl alcohol, 1 mL) was added followed by 4-methyl morpholine N-oxide (1.13 g, 9.65 mmol). The mixture was stirred at rt 16 h. Saturated aqueous sodium bisulfite (5 mL) was added and the acetone was removed under reduced pressure. The resulting aqueous phase was extracted with methylene chloride and the extracts washed with an aliquot of saturated aqueous sodium bisulfite, 1 N hydrochloric acid, saturated aqueous sodium bicarbonate and brine. The extracts were then dried over magnesium sulfate, filtered and concentrated to afford an oil which was purified by silica gel chromatography (100% methylene chloride to 90:10 methylene chloride:methanol gradient). 4-(4-Chloro-phenyl)-3,4-dihydroxy-piperidine-1-carboxylic acid tert-butyl ester was afforded as an oil (2.64 g, 83%, 2 steps).

¹H-NMR (CDCl₃, 300 MHz) δ: 1.44 (s, 9 H), 1.62 (br d, 1 H), 1.82 (br s, 2 H), 2.69 (br s, 1 H), 2.99 (br t, 1 H), 3.12 (br s, 1 H), 3.90–4.30 (m, 3 H), 7.33 (d, 2 H), 7.41 (d, 2 H).

Step 3

The product of step 2 (500 mg, 1.37 mmol) was dissolved in methylene chloride (10 mL) and the resulting solution cooled to 0° C. Trifluoroacetic acid (3 mL) was slowly added and the reaction was allowed to stir at 0° C. for 2 h, before concentration under reduced pressure. The trifluoroacetate salt was dissolved in tetrahydrofuran and excess triethylamine was added. Solids generated were removed by suction filtration and the supernatant solution was concentrated to afford 4-(4-chloro-phenyl)-piperidine-3,4-diol.

¹H-NMR (CD₃OD, 300 MHz) δ: 1.91 (ddd, 1 H), 2.13 (ddd, 1 H), 3.12–3.28 (m, 4 H), 4.08 (dd, 1 H), 7.37 (ddd, 2 H), 7.51 (ddd, 2 H).

Step 4

The titled compound was prepared following the procedure in step 2 of Example 467, but replacing 4-(4-Chloro-phenyl)-4-fluoro-piperidine with 4-(4-Chloro-phenyl)-piperidine-3,4-diol.

¹H-NMR (CD₃OD, 300 MHz) δ: 1.51 (s, 6 H), 1.80 (br d, 1 H), 2.03–2.11 (m, 1 H), 2.56 (q, 2 H), 2.68–3.12 (m, 6 H), 4.00 (dd, 1 H), 5.00–5.50 (br s, 2 H), 6.17 (t, 1 H), 6.76 (d, 2 H), 7.27 (dd, 1 H), 7.33 (ddd, 2 H), 7.44–7.49 (m, 4 H), 7.80 (dd, 1 H), 8.48 (dd, 1 H). MS m/z: 521 (M+1).

Example 471

4-(4-Chloro-phenyl)-3-ethyl-1-{3-[7-(1-hydroxy-1-methyl-ethyl)-11H-10-oxa-1-aza-dibenzo[a,d]cyclo-hepten-5-ylidene]-propyl}-piperidin-4-ol Step 1

A solution of 4-oxo-piperidine-1-carboxylic acid tert-butyl ester (5 g, 25.1 mmol), pyrollidine (5 mL) and p-toluenesulfonic acid (25 mg) in benzene (100 mL) was heated at reflux for 16 h with azeotropic distillation of water. The resulting enamine solution was cooled to rt and concentrated. The crude enamine was dissolved in acetonitrile (50 mL); iodoethane (4.67 g, 30.1 mmol.) was added and the mixture was heated at 100° C. for 0.5 h, cooled to rt and concentrated. The mixture was dissolved in ethyl acetate (200 mL), washed with 1 N hydrochloric acid, saturated aqueous sodium bicarbonate, and brine. The extract was dried over magnesium sulfate, filtered and concentrated. The crude compound was purified by silica gel chromatography (80% hexanes/20% ethyl acetate) to afford 3-ethyl-4-oxo-piperidine-1-carboxylic acid tert-butyl ester (680 mg).

$^1$H-NMR (CDCl$_3$, 300 MHz) δ: 0.95 (t, 3 H), 1.26–1.42 (m, 1 H), 1.50 (s, 9 H), 1.69–1.85 (m, 1 H), 2.30 (br s, 1 H), 2.43 (q, 2 H), 2.90–4.36 (m, 4 H).

Step 2

4-(4-Chloro-phenyl)-3-ethyl-4-hydroxy-piperidine-1-carboxylic acid tert-butyl ester was prepared following the procedure in step 2 of Example 502, substituting 3-ethyl-4-oxo-piperidine-1-carboxylic acid tert-butyl ester for 3,3-dimethyl-4-oxo-piperidine-1-carboxylic acid tert-butyl ester.

$^1$H-NMR (CDCl$_3$, 300 MHz) δ: 0.80 (t, 3 H), 0.91–1.13 (m, 2 H), 1.18–1.28 (m, 1 H), 1.48 (s, 9 H), 1.57–1.64 (br d, 1 H), 1.75–1.91 (m, 2 H), 2.79 (t, 1 H), 3.14 (ddd, 1 H), 4.02 (br d, 1 H), 4.19 (br d, 1 H), 7.28–7.37 (m, 4 H).

Step 3

4-(4-Chloro-phenyl)-3-ethyl-piperidin-4-ol was prepared according to the procedure of step 3 in Example 502, substituting 4-(4-chloro-phenyl)-3-ethyl-4-hydroxy-piperidine-1-carboxylic acid tert-butyl ester for 4-(4-chloro-phenyl)-4-hydroxy-3,3-dimethyl-piperidine-1-carboxylic acid tert-butyl ester.

$^1$H-NMR (CDCl$_3$, 300 MHz) δ: 0.75 (t, 3 H), 0.88–1.17 (m, 2 H), 1.26 (t, 1 H), 1.65 (br d, 2 H), 1.83–2.02 (m, 2 H), 2.75 (t, 1 H), 2.95–3.21 (m, 3 H), 7.32 (d, 2 H), 7.40 (d, 2 H). MS m/z: 240 (M+1).

Step 4

The titled compound was prepared following the procedure in step 5 of Example 502, substituting 4-(4-chloro-phenyl)-3-ethyl-piperidin-4-ol for 4-(4-chloro-phenyl)-3,3-dimethyl-piperidin-4-ol.

$^1$H-NMR (CDCl$_3$, 300 MHz) δ: 0.70 (t, 3 H), 0.81–1.11 (m, 3 H), 1.56–1.64 (m, 7 H), 1.77–2.09 (m, 4 H), 2.23–2.86 (m, 7 H), 5.00–5.60 (m, 2 H), 6.13 (t, 1 H), 6.83 (d, 1 H), 7.23–7.47 (m, 6 H), 7.46 (d, 1 H), 7.59 (dd, 1 H), 8.49 (dd, 1 H). MS m/z: 533 (M+1).

Example 472

5-Chloro-1-{3-[7-(1-hydroxy-1-methyl-ethyl)-11H-10-oxa-1-aza-dibenzo[a,d]-cyclohepten-5-ylidene]-propyl}-spiro[3-oxo-1,3-dihydroisobenzofuran-1,4'-piperidine]

Step 1

To a suspension of 2-bromo-5-chlorobenzoic acid (1.5 g, 6.4 mmol) in methylene chloride (15 mL) at room temperature was added oxalyl chloride (969 mg, 666 µL, 7.64 mmol) and 2 drops of dimethylformamide; bubbling commenced and the mixture ultimately became homogenous. The mixture was stirred at room temperature for 7 hours and concentrated. The resulting acid chloride residue was dissolved in methylene chloride (15 mL). Triethylamine (325 mg, 450 µL, 3.2 mmol) was added, followed by 2-amino-2-methyl-1-propanol (627 mg, 672 µL, 7.04 mmol) and the reaction was allowed to stir at rt 3 h. The mixture was poured into 1 N hydrochloric acid (50 mL), extracted with methylene chloride (2×75 mL). The combined extracts were washed with saturated aqueous sodium bicarbonate, brine and dried over magnesium sulfate, filtered and concentrated and dried in vacuo. The crude amide residue was dissolved in methylene chloride (15 mL) and thionyl chloride (1.29 g, 794 µL, 10.9 mmol) was added. Stirring at room temperature was carried out for 4 h after which the mixture was poured into saturated sodium bicarbonate (50 mL). The pH was adjusted to 9 by the addition of solid sodium bicarbonate and further basified by the addition of several milliliters of aqueous sodium hydroxide (5 N). The biphasic mixture was extracted with methylene chloride (150+50 mL). The combined extracts were washed with brine, dried over magnesium sulfate, filtered and concentrated to afford the crude residue which was purified by silica gel chromatography (80% hexanes/20% ethyl acetate gradient) to yield 2-(2-bromo-5-chloro-phenyl)-4,4-dimethyl-4,5-dihydro-oxazole (1.15 g, 62%).

$^1$H-NMR (CDCl$_3$, 300 MHz) δ: 1.42 (s, 6 H), 4.14 (s, 2 H), 7.25 (dd, 1 H), 7.55 m (d, 1 H), 7.67 (d, 1 H).

Step 2

To a cold (−78° C.) solution of the product of step 1 (1.09 g, 4.63 mmol) in anhydrous tetrahydrofuran (10 mL) was added a solution of n-butyllithium (1.6 M in hexanes, 2.89 mL, 4.63 mmol) and the contents of the reaction were allowed to react for 0.5 h. A solution of 4-oxo-piperidine-1-carboxylic acid tert-butyl ester (922 mg, 4.63 mmol) in tetrahydrofuran (10 mL) was added and the combined contents stirred for 2 h at −78° C. Reaction was quenched by the addition of saturated aqueous ammonium chloride (30 mL), followed by warming to rt. The biphasic mixture was extracted with ethyl acetate (150 mL); washed with water and brine; dried over magnesium sulfate; filtered and concentrated. 4-[4-Chloro-2-(4,4-dimethyl-4,5-dihydro-oxazol-2-yl)-phenyl]-4-hydroxy-piperidine-1-carboxylic acid tert-butyl ester was isolated (412 mg, 22%) following silica gel chromatography (80% hexanes/20% ethyl acetate).

$^1$H-NMR (CDCl$_3$, 300 MHz, mixture; spectrum of major component:) δ: 1.36 (s, 6 H), 1.50 (s, 9 H), 1.66 (d, 2 H), 1.96 (dd, 2 H), 3.19 (br d, 2 H), 3.42 (d, 2 H), 4.24 (br s, 2 H), 7.16 (d, 1 H), 7.45 (dd, 1 H), 7.71 (br s, 1 H). MS m/z: 409 (M+1).

Step 3

To a solution of the product of step 2 (200 mg, 0.49 mmol) in tetrahydrofuran (5 mL) was added water (5 mL) and oxalic acid (300 mg). Stir at rt for about 4 days. The solids were separated and dissolved in ethyl acetate (50 mL); the resulting solution was washed with saturated aqueous sodium bicarbonate and brine. The extracts were dried over magnesium sulfate; filtered and concentrated. The 5-chlorospiro[3-oxo-1,3-dihydroisobenzofuran-1,4'-piperidine]-1-carboxylic acid tert-butyl ester thus afforded (100 mg, 61%) was used without further purification.

$^1$H-NMR (CDCl$_3$, 300 MHz) δ: 1.49 (s, 9 H), 1.67 (d, 2 H), 2.04 (ddd, 2 H), 3.24 (dd, 2 H), 4.21 (br s, 2 H), 7.32 (d, 1 H), 7.64 (dd, 1 H), 7.85 (d, 1 H). MS m/z: 238 (M+1−100).

Step 4

5-Chlorospiro[3-oxo-1,3-dihydroisobenzofuran-1,4'-piperidine] was prepared according to the procedure in step 3 of Example 502, using 5-chlorospiro[3-oxo-1,3-dihydroisobenzofuran-1,4'-piperidine]-1-carboxylic acid tert-butyl ester instead of 4-(4-chloro-phenyl)-4-hydroxy-3,3-dimethyl-piperidine-1-carboxylic acid tert-butyl ester.

$^1$H-NMR (CDCl$_3$, 300 MHζ) δ: 1.71 (d, 2 H), 2.09–2.22 (m, 2 H), 3.13–3.28 (m, 4 H), 7.37 (d, 1 H), 7.64 (dd, 1 H), 7.84 (d, 1 H). MS m/z: 238 (M+1).

Step 5

The titled compound was prepared according to the procedure in step 2 of Example 467, substituting 5-chlorospiro[3-oxo-1,3-dihydroisobenzofuran-1,4'-piperidine] for 4-(4-chloro-phenyl)-4-fluoro-piperidine.

$^1$H-NMR (CDCl$_3$, 300 MHz) δ: 1.58 (s, 6 H), 1.64 (d, 2 H), 2.04–2.15 (m, 3 H), 2.33–2.50 (m, 3 H), 2.57 (t, 2 H), 2.76 (d, 2 H), 5.20–5.50 (br s, 2 H), 6.12 (t, 1 H), 6.81 (d, 1 H), 7.22–7.34 (m, 3 H), 7.45 (d, 2 H), 7.55–7.63 (m, 2 H), 7.81 (d, 1 H), 8.48 (dd, 1 H). MS m/z: 531 (M+1).

Example 473

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-4-methoxy-3-methyl-piperidin-3-ol Step 1

To a suspension of 4-(4-chloro-phenyl)-1,2,3,6-tetrahy-dro-pyridine hydrochloride (5 g, 21.8 mmol) in methylene chloride (100 mL) was added triethylamine (3.6 g, 4.9 mL, 35 mmol). The resulting solution was cooled to 0° C. in an ice-water bath. Di-tert-butyl-dicarbonate (5.4 g, 25 mmol) was added and the resulting reaction was allowed to warm to rt and stir over night. The mixture was poured into 100 mL of a 1:1 1 N HCl:brine solution and diluted with methylene chloride (300 mL). The organic phase was washed with saturated aqueous sodium bicarbonate and brine, dried over magnesium sulfate, filtered and concentrated to afford 4-(4-Chloro-phenyl)-3,6-dihydro-2H-pyridine-1-carboxylic acid tert-butyl ester (6.68 g, 93%) as a colorless oil, which was used without further purification.

$^1$H-NMR (CDCl$_3$, 300 MHz) δ: 1.48 (s, 9 H), 2.45–2.55 (m, 2 H), 3.63 (t, 2 H), 4.07 (q, 2 H), 6.03 (br s, 1 H), 7.29 (m, 4 H).

Step 2

To a cooled (0° C.) solution of 4-(4-chloro-phenyl)-3,6-dihydro-2H-pyridine-1-carboxylic acid tert-butyl ester (7.10 g, approx. 24.1 mmol) in methylene chloride (150 mL) was added a solution of 3-chloroperbenzoic acid (75%, 8.34 g, 36.2 mmol) in methylene chloride (120 mL) over 40 min. The mixture was warmed to rt and allowed to stir over night (16 h). The solution was washed twice with a half-saturated aqueous solution of sodium bisulfite to destroy excess oxidant. The mixture was then twice washed with half-saturated aqueous potassium carbonate, and brine. The extracts were dried over magnesium sulfate, filtered and concentrated to afford a crude oil which was purified by silica gel chromatography (100% hexanes—80% hexanes/20% ethyl acetate gradient) to afford pure 6-(4-Chloro-phenyl)-7-oxa-3-aza-bicyclo[4.1.0]heptane-3-carboxylic acid tert-butyl ester (5.34 g, 71%) as a clear, colorless oil which solidified on standing.

$^1$H-NMR (CDCl$_3$, 300 MHz) δ: 1.48 (s, 9 H), 2.06–2.22 (m, 1 H), 2.42 (ddd, 1 H), 3.08–3.23 (m, 2 H), 3.57–4.19 (m, 3 H), 7.26–7.36 (m, 4 H).

Step 3

To a solution of 6-(4-Chloro-phenyl)-7-oxa-3-aza-bicyclo[4.1.0]heptane-3-carboxylic acid tert-butyl ester (2.4 g, 7.8 mmol) in methanol (100 mL) was added a catalytic amount of p-toluenesulfonic acid (ca. 50 mg). The resulting solution was heated at reflux 24 h, cooled and concentrated. The crude residue was purified by silica gel chromatography (100% hexanes—80% hexanes/20% ethyl acetate gradient) to afford 4-(4-chloro-phenyl)-3-hydroxy-4-methoxy-piperidine-1-carboxylic acid tert-butyl ester (2.05 g, 77%); note the diol moiety has the trans-orientation.

$^1$H-NMR (CDCl$_3$, 300 MHz) δ: 1.47 (s, 9 H), 1.95 (d, 1 H), 2.37 (ddd, 1 H), 2.97 (s, 3 H), 3.47 (d, 1 H), 3.67 (br s, 1 H), 3.98–4.17 (m, 3 H), 7.29–7.42 (m, 4 H).

Step 4

A solution of 4-(4-chloro-phenyl)-3-hydroxy-4-methoxy-piperidine-1-carboxylic acid tert-butyl ester (2.05 g, 6.0 mmol) in methylene chloride (75 mL) was cooled to 0° C. Dess-Martin periodinane (3.30 g, 7.8 mmol) was added, followed by water (200 uL) and the reaction allowed to stir at rt 2 h. The reaction was quenched by the addition of a solution consisting of equal parts saturated aqueous sodium thiosulfate and saturated aqueous sodium bicarbonate; the resulting reaction was stirred until the mixture formed two homogenous phases. The phases were separated and the aqueous phase was extracted with ethyl acetate. The combined organic phases were washed with brine and dried over magnesium sulfate, filtered and concentrated. The crude mixture was purified by silica gel chromatography to afford recovered starting material (1.17 g, 57%) and 4-(4-chloro-phenyl)-4-methoxy-3-oxo-piperidine-1-carboxylic acid tert-butyl ester (540 mg, 27% (62% brsm)).

$^1$H-NMR (CDCl$_3$, 300 MHz) δ: 1.43 (s, 9 H), 2.16–2.40 (m, 2 H), 3.12 (s, 3 H), 3.55 (ddd, 1 H), 3.80 (br s, 1 H), 3.96 (d, 1 H), 4.34 (br s, 1 H), 7.23–7.40 (m, 4 H).

Step 5

To a solution of 4-(4-chloro-phenyl)-4-methoxy-3-oxo-piperidine-1-carboxylic acid tert-butyl ester (470 mg, 1.38 mmol) in anhydrous tetrahydrofuran (10 mL) at 0° C. was added methylmagnesium bromide (1.4 M in diethyl ether, 2.96 mL, 4.15 mmol) and the resulting mixture was stirred at that temperature for 3 h. Excess organomagnesium was quenched by the addition of saturated aqueous ammonium chloride and the reaction was allowed to warm to rt. To the biphasic mixture was added water and ethyl acetate. The phases were separated and the organic phase washed with brine, dried over magnesium sulfate, filtered, dried and concentrated to afford a crude residue which was purified by silica gel chromatography (100% methylene chloride—97.5% methylene chloride/2.5% methanol gradient) to afford pure 4-(4-chloro-phenyl)-3-hydroxy-4-methoxy-3-methyl-piperidine-1-carboxylic acid tert-butyl ester (269 mg, 58%).

$^1$H-NMR (CDCl$_3$, 300 MHz) δ: 0.97 (s, 3 H), 1.50 (s, 9 H), 1.81 (d, 1 H), 2.59 (ddd, 1 H), 2.96 (br t, 1 H), 3.11 (s, 3 H), 3.31 (s, 3 H), 3.72–3.88 (m, 1 H), 7.27–7.37 (m, 4 H).

Step 6

4-(4-Chloro-phenyl)-3-hydroxy-4-methoxy-3-methyl-piperidine-1-carboxylic acid tert-butyl ester (260 mg, 0.74 mmol) was dissolved in methylene chloride (5 mL) and the resulting solution was cooled to 0° C. Trifluoroacetic acid (1 mL) was added and the mixture was stirred 2 h. Solvents were then removed under reduced pressure and the residue dissolved in ethyl acetate. Water and 6 N aqueous sodium hydroxide were added until the pH=10. The organic phase was washed with brine and dried over magnesium sulfate, filtered and concentrated to afford 4-(4-chloro-phenyl)-4-methoxy-3-methyl-piperidin-3-ol.

$^1$H-NMR (CDCl$_3$, 300 MHz) δ: 0.94 (s, 3 H), 1.91 (d, 1 H), 2.65–2.81 (m, 2 H), 2.94 (ddd, 1 H), 3.13 (s, 3 H), 3.25 (d, 1 H), 3.30 (m, 1 H), 7.37 (s, 4 H). MS m/z: 256 (M+1).

Step 7

To a solution of 4-(4-chloro-phenyl)-4-methoxy-3-methyl-piperidin-3-ol (206 mg, 1.24 mmol) in acetonitrile/water (4:1, 20 mL) was added potassium carbonate (171 mg, 1.24 mmol) followed by 2-[5-(3-bromo-propylidene)-5,11- dihydro-10-oxa-1-aza-dibenzo[a,d]cyclohepten-7-yl]-propan-2-ol (417 mg, 1.12 mmol). The mixture was stirred at rt 40 h and concentrated. The product residue was partitioned between ethyl acetate and water and the organic phase was washed with brine, dried over magnesium sulfate, filtered and concentrated. The crude product was purified by silica gel chromatography (100% methylene chloride–90% methylene chloride/10% methanol gradient) to afford the titled compound (232 mg, 35%) as an off-white solid.

$^1$H-NMR (CDCl$_3$, 300 MHz) δ: 0.83 (s, 3 H), 1.57 (s, 6 H), 1.76–1.94 (m, 2 H), 2.20 (t, 1 H), 2.29–2.72 (m, 7 H), 3.06 (s, 3 H), 3.39 (br s, 1 H), 5.19–5.54 (br s, 2 H), 6.12 (t, 1 H), 6.82 (d, 1 H), 7.21–7.34 (m, 6 H), 7.46 (d, 1 H), 7.58 (d, 1 H), 8.51 (d, 1 H). MS m/z: 549 (M+1).

Example 474

4-(4-Chloro-phenyl)-1-{3-[7-(1-hydroxy-1-methyl-ethyl)-11H-10-oxa-1-aza-dibenzo[a,d]cyclohepten-5-ylidene]-propyl}-4-methoxy-piperidin-3-ol Step 1

4-(4-Chloro-phenyl)-4-methoxy-piperidin-3-ol was prepared following the procedure in Step 6 of Example 473, replacing 4-(4-chloro-phenyl)-3-hydroxy-4-methoxy-3-methyl-piperidine-1-carboxylic acid tert-butyl ester with 4-(4-chloro-phenyl)-3-hydroxy-4-methoxy-piperidine-1-carboxylic acid tert-butyl ester.

MS m/z: 242 (M+1).

Step 2

The titled compound was prepared following the procedure of Step 7 in Example 473, replacing 4-(4-chloro-phenyl)-4-methoxy-3-methyl-piperidin-3-ol with the product of Step 1 in Example 474.

$^1$H-NMR (CDCl$_3$, 300 MHz) δ: 1.58 (s, 6 H), 1.63–1.82 (m, 3 H), 1.95 (d, 1 H), 2.21–2.78 (m, 8 H), 2.91 (s, 3 H), 3.63 (br s, 1 H), 5.32 (br s, 2 H), 6.11 (t, 1 H), 6.81 (d, 1 H), 7.21–7.37 (m, 6 H), 7.44 (d, 1 H), 7.57 (dd, 1 H), 8.51 (dd, 1 H). MS m/z: 535 (M+1).

Example 475

2-(5-{3-[4-(4-Chloro-phenyl)-3,4-dimethoxy-piperidin-1-yl]-propylidene}-5,11-dihydro-10-oxa-1-aza-dibenzo[a,d]cyclohepten-7-yl)-propan-2-ol Step 1

The product of Step 3 in Example 473 (259 mg, 0.76 mmol) was dissolved in tetrahydrofuran (5 mL) and cooled to 0° C. Sodium hydride (60% dispersion in mineral oil, 46 mg, 1.15 mmol) was added in a single portion and the mixture stirred 5 min. Methyl iodide was added and the mixture was warmed to rt and stirred 48 h. Excess base was quenched by the addition of saturated aq. NH$_4$Cl and water. The biphasic mixture was extracted twice with ethyl acetate. The extracts were combined, washed with brine and dried over sodium sulfate, filtered and concentrated. The crude residue was purified by silica gel chromatography (hexanes—80 hexanes/20 ethyl acetate gradient) to afford 4-(4-chloro-phenyl)-3,4-dimethoxy-piperidine-1-carboxylic acid tert-butyl ester (191 mg, 71%).

$^1$H-NMR (CDCl$_3$, 300 MHz) δ: 1.47 (s, 9 H), 1.90 (d, 1 H), 2.31 (ddd, 1 H), 2.91–3.38 (m, 9 H), 3.93–4.37 (br m, 2 H), 7.24–7.37 (m, 4 H).

Step 2

4-(4-Chloro-phenyl)-3,4-dimethoxy-piperidine was prepared following the procedure in Step 6 of Example 473, substituting the product of Step 1 for 4-(4-Chloro-phenyl)-3-hydroxy-4-methoxy-3-methyl-piperidine-1-carboxylic acid tert-butyl ester.

$^1$H-NMR (CD$_3$OD, 300 MHz) δ: 1.96 (d, 1 H), 2.27 (dddd, 1 H), 2.71–3.03 (m, 9 H), 3.04–3.15 (m, 2 H), 7.30–7.41 (m, 4 H). MS m/z: 256 (M+1).

Step 3

The titled compound was prepared following the procedure in Step 7 of Example 473, substituting the product of Step 2 for 4-(4-chloro-phenyl)-4-methoxy-3-methyl-piperidin-3-ol.

$^1$H-NMR (CDCl$_3$, 300 MHz) δ: 1.58 (s, 6 H), 1.67 (br s, 2 H), 1.77 (s, 1 H), 1.91 (d, 1 H), 2.18–2.31 (m, 1 H), 2.33–2.47 (m, 2 H), 2.48–2.62 (m, 2 H), 2.65–2.75 (m, 1 H), 2.83–2.90 (m, 4 H), 2.92 (s, 3 H), 3.07 (br s, 1 H), 5.06–5.57 (br s, 2 H), 6.10 (t, 1 H), 6.82 (d, 1 H), 7.22–7.35 (m, 6 H), 7.44 (d, 1 H), 7.59 (d, 1 H), 8.50 (d, 1 H). MS m/z: 549 (M+1).

Example 476

3-Azido-4-(4-chloro-phenyl)-1-{3-[7-(1-hydroxy-1-methyl-ethyl)-11H-10-oxa-1-aza-dibenzo[a,d]cyclo-hepten-5-ylidene}-propyl}-piperidin-4-ol Step 1: 4-(4-Chloro-phenyl)-3,6-dihydro-2H-pyridine-1-carboxylic acid tert-butyl ester To a solution of di-tert-butyl-dicarbonate (9.96 g, 45.6 mmol) in CH$_2$Cl$_2$ (500 mL) was added 4-(4-chlorophenyl)-1,2,3,6-tetrahydropyridine hydrochloride (10.00 g, 43.5 mmol) and triethylamine (12.42 mL, 89 mmol). The solution was stirred at rt for 4 h. Gas evolution was observed. The reaction was quenched with 1N HCl and extracted with CH$_2$Cl$_2$ (3×), and the organic layers were collected together, dried over MgSO$_4$ and evaporated in vacuo. The residue was purified to yield the title compound as a colorless oil.
$^1$H-NMR (CDCl$_3$) δ: 1.50 (9H, s), 2.46 (2H, br s), 3.62 (2H, br s), 4.05 (2H, br s), 6.01 (1H, br s), 7.25 (4H, s).

Step 2: 6-(4-Chloro-phenyl)-7-oxa-3-aza-bicyclo[4.1.0]heptane-3-carboxylic acid tert-butyl ester To a solution of 4-(4-chloro-phenyl)-3,6-dihydro-2H-pyridine-1-carboxylic acid tert-butyl ester (4.0 g, 13.6 mmol) in CH$_2$Cl$_2$ (136 mL) cooled to 0° C. 3-Chloroperbenzoic acid (4.07 g, 20.4 mmol) was dissolved in CH$_2$Cl$_2$ and added portion wise over 45 min. A white precipitate was observed. The solution was allowed to stir at room temperature for 14 h. The reaction was washed with 1×10% NaSO$_3$, 1×10% Na$_2$CO$_3$, 1× brine and dried over Mg$_2$SO$_4$, filtered and evaporated in vacuo. The residue was purified by Biotage flash system (90% hexane/10% ethyl acetate to 80% hexane/20% ethyl acetate to yield the title compound as a colorless oil (2.75 g, 65%). $^1$H-NMR (CDCl$_3$) δ: 1.50 (9H, s), 2.15 (1H, m), 3.15 (2H, m), 3.6–4.2 (4H, m), 7.31 (4H, s).

Step 3: 4-Azido-4-(4-chloro-phenyl)-3-hydroxy-piperidine-1-carboxylic acid tert-butyl ester and 3-azido-4-(4-chlorophenyl)-4-hydroxy-piperidine-1-carboxylic acid tert-butyl ester To a solution of 6-(4-chloro-phenyl)-7-oxa-3-aza-bicyclo[4.1.0]heptane-3-carboxylic acid tert-butyl ester (0.960 g, 3.1 mmol) in 31 mL of DMSO was added sodium azide (0.970 g, 14.9 mmol). The solution was allowed to heat at 100° C. for 24 h and cooled to room temperature. The reaction was washed with water, dried over Mg$_2$SO$_4$, filtered and evaporated in vacuo. The residue was purified by Biotage flash system (90% hexane/10% ethyl acetate to 80% hexane/20% ethyl acetate to 70% hexane/30% ethyl acetate to yield two compounds. The faster eluting isomer 4-azido-4-(4-chloro-phenyl)-3-hydroxy-piperidine-1-carboxylic acid tert-butyl ester (0.010 g, 9%) $^1$H-NMR (CDCl$_3$) δ: 1.46(s, 9H), 1.93(d, 1H), 2.51(dt, 1H), 3.10(bt, 1H), 3.34(d, 1H), 3.80(bs, 1H), 4.08(m, 2H), 7.41 (s, 4H). The slower eluting isomer 3-azido-4-(4-chloro-phenyl)-4-hydroxy-piperidine-1-carboxylic acid tert-butyl ester (0.361 g, 33%) $^1$H-NMR (CDCl$_3$) δ: 1.43(s, 9H), 1.57(m, 1H), 2.40(t, 1H), 2.93(m, 1H), 3.11(t, 1H), 3.50(s, 1H), 3.56(d, 1H), 4.07(m, 2H), 7.33(d, 2H), 7.40 (d, 2H).

Step 4

The Boc-protected azido-alcohol (0.184 g, 0.5 mmol) was dissolved in CH$_2$Cl$_2$ (2 mL) and cooled to 0° C. and TFA (0.790 mL) was added. The solution was allowed to stir at 0° C. for 1 h. The solvent was evaporated in vacuo and the residue was partitioned between NaHCO$_3$ and CH$_2$Cl$_2$ The aqueous solution was extracted (3×) and then washed with brine and dried over Na$_2$SO$_4$. The residue was carried onto the next step without further purification.

Step 5

To a solution of the azido piperidine (0.142 g, 0.56 mmol) in isopropanol (5.6 mL) was added 2,6-lutidine (0.066 mL, 0.8 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.025 g, 0.067 mmol), added in portions over 2 h. The solution was then stirred at 80° C. for an additional 14 h. The reaction was concentrated in vacuo, then purified by Biotage flash chromatography (75% EtOAc/25% Hexane to 100% ethyl acetate) to yield the title compound (0.135 g, 66%). $^1$H-NMR (CDCl$_3$): δ 1.56(6H, s), 1.65(d, 1H), 1.85(s, 1H), 2.13(s, 1H), 2.36–2.94(m, 8H), 3.51(s, 1H), 5.24(bs, 2H), 6.16(t, 1H), 6.80(d, 1H), 7.21–7.45(m, 7H), 7.58(d, 1H), 8.44(d, 1H). ESI-MS m/z: 546(M+1), retention time 1.55.

Example 477

4-Azido-4-(4-chloro-phenyl)-1-{3-[7-(1-hydroxy-1-methyl-ethyl)-11H-10-oxa-1-aza-dibenzo[a,d]cyclohepten-5-ylidene}-propyl}-piperidin-3-ol Step 1

The Boc-protected azido-alcohol (Example 476, step 3) (0.050 g, 0.2 mmol) was dissolved in CH$_2$Cl$_2$ (2 mL) and cooled to 0° C. and TFA (0.2 mL) was added. The solution was allowed to stir at 0° C. for 1 h. The solvent was evaporated in vacuo and the residue was partitioned between NaHCO$_3$ and CH$_2$Cl$_2$ The aqueous solution was extracted (3×) and then washed with brine and dried over Na$_2$SO$_4$. The residue was carried onto the next step without further purification.

Step 2

To a solution of the azido piperidine (0.025 g, 0.1 mmol) in isopropanol (1.0 mL) was added 2,6-lutidine (0.012 mL, 0.1 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.025 g, 0.067 mmol), added in portions over 2 h. The solution was then stirred at 80° C. for an additional 14 h. The reaction was concentrated in vacuo, then purified by Biotage flash chromatography (100% ethyl acetate) to yield the title compound (0.013 g, 36%). $^1$H-NMR (CDCl$_3$): δ 1.56 (s, 6H), 1.65 (d, 1H), 1.85 (s, 1H), 2.13 (s, 1H), 2.36–2.94 (m, 8H), 3.51 (s, 1H), 5.24 (bs, 2H), 6.16 (t, 1H), 6.80 (d, 1H), 6.93 (d, 1H), 7.21–7.46 (m, 8H), 7.58 (d, 1H), 8.42 (d, 1H). ESI-MS m/z: 546(M+1), retention time 1.71.

Example 478

N-[4-(4-Chloro-phenyl)-4-hydroxy-1-{3-[7-(hydroxyl-1-methyl-ethyl)-11H-10-oxa-1-aza-dibenzo[a,d]cyclohepten-5-ylidene]-propyl}-piperidin-3-yl)-propionamide Step 1: 3-Amino-4-(4-chloro-phenyl)-4-hydroxy-piperidine-1-carboxylic acid tert-butyl ester 3-azido-4-(4-chloro-phenyl)-4-hydroxy-piperidine-1-carboxylic acid tert-butyl ester (0.67 g, 0.2 mmol) was dissolved in Et$_2$O (2 mL) and cooled to 0° C. and LiAlH$_4$ (0.280 mL, 0.23 mmol) was added. The solution was allowed to warm to room temperature and stir for 2 h. A white precipitate formed. The reaction mixture was quenched with water and extracted with Et$_2$O (3×). The organic layers were collected together, dried over MgSO$_4$ and evaporated in vacuo to give the amino alcohol which was used directly in the next reaction.

Step 2: 4-(4-Chloro-phenyl)-4-hydroxy 3-propionylamino-piperidine-1-carboxylic acid tert-butyl ester 3-Amino-4-(4-chloro-phenyl)-4-hydroxy-piperidine-1-carboxylic acid tert-butyl ester (0.116 g, 0.35 mmol) was dissolved in CH$_2$Cl$_2$. Propionyl chloride (0.034 mL, 0.39 mmol) and triethylamine (0.109 mL, 0.78 mmol) were added and the solution was stirred for 24 h at room temperature. The reaction was concentrated in vacuo, then purified by Biotage flash chromatography (30% ethyl acetate/70% hexane to 50% ethyl acetate/50% hexane) to yield the title compound (0.133 g, 97%). $^1$H-NMR (CDCl$_3$): δ 0.87 (t, 3H), 1.44 (s, 9H), 1.78–1.95 (m, 3H), 2.20 (dt, 1H), 3.24 (t, 1H), 3.50 (d, 1H), 3.90 (t, 1H), 4.08 (q, 2H), 4.28 (d, 1H), 5.48 (bd, 1H), 7.26 (d, 2H), 7.37 (d, 2H). ESI-MS m/z: 383 (M+1), retention time 2.21.

Step 3

The Boc-protected 3-N-acyl-alcohol (0.180 g, 0.47 mmol) was dissolved in CH$_2$Cl$_2$ (5 mL) and cooled to 0° C. and TFA (2 mL) was added. The solution was allowed to stir at 0° C. for 1 h. The solvent was evaporated in vacuo and the residue was partitioned between NaHCO$_3$ and CH$_2$Cl$_2$ The aqueous solution was extracted (3×) and then washed with brine and dried over Na$_2$SO$_4$. The residue was carried onto the next step without further purification.

Step 4

To a solution of the N-[4-(4-chloro-phenyl)-4-hydroxy-piperidin-3-yl]-propionamide (0.133 g, 0.47 mmol) in isopropanol (5.0 mL) was added 2,6-lutidine (0.055 mL, 0.47 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.176 g, 0.35 mmol), added in portions over 2 h. The solution was then stirred at 80° C. for an additional 14 h. The reaction was concentrated in vacuo, then purified by HPLC (acetonitrile/H$_2$O/Formic acid) to yield the title compound as a white formate salt (0.085 g, 27%). $^1$H-NMR (CDCl$_3$): δ 0.780 (t, 3H), 1.55 (s, 6H), 1.90 (m, 3H), 2.60 (m, 2H), 2.92–3.28 (m, 6H), 4.50 (d, 1H), 5.26 (bs, 2H), 6.00 (t, 1H), 6.82 (d, 1H), 7.22–7.37 (m, 6H), 7.44 (s, 1H), 7.56 (d, 1H), 8.20 (d, 1H), 8.34 (s, 1H), 8.47 (d, 1H). ESI-MS m/z: 576(M+1), retention time 1.43.

Example 479

Trans-4-(4-Chloro-phenyl)-4-hydroxy 1-{3-[7-(1-hydroxyl-1-methyl-ethyl)-11H-10-oxa-1-aza-dibenzo[a,d]cyclohepten-5-ylidene]-propyl}-piperidin-3-carbonitrile Step 1: Cis and trans-4-(4-chloro-phenyl)-3-cyano-4-hydroxy-piperidine-1-carboxylic acid tert-butyl ester Acetone cyanohydrin (0.917 mL, 10 mmol) was added to THF (22 mL) and cooled to 0° C. To the solution was added lithium hydride (0.077 g, 9.7 mmol) in several portions over 20 min. and then stirred at room temperature for 1 h. 6-(4-Chloro-phenyl)-7-oxa-3-aza-bicyclo[4.1.0]heptane-3-carboxylic acid tert-butyl ester (1.00 g, 3.2 mmol) dissolved in THF (10 mL) was added to the above solution and heated to reflux for 7½ h. The reaction was diluted with H$_2$O and extracted (3x). The reaction was washed with water, dried over Mg$_2$SO$_4$, filtered and evaporated in vacuo. The residue was purified by Biotage flash system (90% hexane/10% ethyl acetate to 80% hexane/20% ethyl acetate to 70% hexane/30% ethyl acetate to yield two compounds. The faster eluting isomer cis-4-(4-chloro-phenyl)-3-cyano-4-hydroxy-piperidine-1-carboxylic acid tert-butyl ester (0.210 g, 19%) $^1$H-NMR (CDCl$_3$): δ 1.35 (s, 9H), 1.59–1.86 (m, 2H), 2.83–3.30 (m, 3H), 3.88 (bs, 2H), 4.16 (m, 1H), 7.23 (d, 2H), 7.33 (d, 2H).

The second eluting isomer was the trans-4-(4-chloro-phenyl)-3-cyano-4-hydroxy-piperidine-1-carboxylic acid tert-butyl ester (0.560 g, 51%). $^1$H-NMR (CDCl$_3$): δ 1.43 (s, 9H), 1.70 (d, 1H), 2.47 (dt, 1H), 2.76 (bs, 2H), 3.10–3.54 (m, 2H), 4.18 (m, 2H), 7.31 (d, 2H), 7.44 (d, 2H).

Step 2

Trans-4-(4-chloro-phenyl)-3-cyano-4-hydroxy-piperidine-1-carboxylic acid tert-butyl ester (0.210 g, 0.62 mmol) was dissolved in CH$_2$Cl$_2$(5 mL) and cooled to 0° C. and TFA (1.0 mL) was added. The solution was allowed to stir at 0° C. for 1 h. The solvent was evaporated in vacuo and the residue was partitioned between NaHCO$_3$ and CH$_2$Cl$_2$ The aqueous solution was extracted (3x) and then washed with brine and dried over Na$_2$SO$_4$. The residue was carried onto the next step without further purification.

Step 3

To a solution of the trans-3-cyano-4-hydroxypiperidine (0.137 g, 0.58 mmol) in isopropanol (5.7 mL) was added 2,6-lutidene (0.067 mL, 0.58 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.108 g, 0.29 mmol), added in portions over 2 h. The solution was then stirred at 80° C. for an additional 14 h. The reaction was concentrated in vacuo, then purified by Biotage flash chromatography (50% ethyl acetate/50% hexane to 75% ethyl acetate/25% hexane to 100% ethyl acetate) to yield the title compound (0.040 g, 26%). $^1$H-NMR (CDCl$_3$): δ 1.50 (d, 6H), 1.63 (s, 1H), 1.78 (d, 1H), 2.08 (s, 1H), 2.35 (m, 2H), 2.51–3.03 (m, 6H), 3.48 (s, 1H), 5.29 (bs, 2H), 6.42 (t, 1H), 6.79 (d, 1H), 7.15 (d, 1H), 7.28 (m, 1H), 7.37 (d, 2H), 7.50 (d, 2H), 7.55 (s, 1H), 7.58 (d, 1H), 8.46 (d, 1H). ESI-MS m/z: 530.2(M+1), retention time 1.50.

Example 480

Cis-4-(4-Chloro-phenyl)-4-hydroxy-1-{3-[7-(1-hydroxyl-1-methyl-ethyl)-11H-10-oxa-1-aza-dibenzo [a,d]cyclohepten-5-ylidene]-propyl}-piperidin-3-carbonitrile Step 1

Cis-4-(4-chloro-phenyl)-3-cyano-4-hydroxy-piperidine-1-carboxylic acid tert-butyl ester (0.210 g, 0.62 mmol) was dissolved in CH$_2$Cl$_2$ (3 mL) and cooled to 0° C. and TFA (1 mL) was added. The solution was allowed to stir at 0° C. for 1 h. The solvent was evaporated in vacuo and the residue was partitioned between NaHCO$_3$ and CH$_2$Cl$_2$ The aqueous solution was extracted (3x) and then washed with brine and dried over Na$_2$SO$_4$. The residue was carried onto the next step without further purification.

Step 2

To a solution of the cis-3-cyano-4-hydroxypiperidine (0.125 g, 0.53 mmol) in isopropanol (5.8 mL) was added 2,6-lutidene (0.061 mL, 0.53 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.100 g, 0.26 mmol), added in portions over 2 h. The solution was then stirred at 80° C. for an additional 14 h. The reaction was concentrated in vacuo, then purified by Biotage flash chromatography (50% ethyl acetate/50% hexane to 75% ethyl acetate/25% hexane to 100% ethyl acetate) to yield the title compound (0.050 g, 35%). $^1$H-NMR (CDCl$_3$): δ 1.53 (d, 1H), 1.57(s, 6H), 1.74 (d, 1H), 1.89 (s, 1H), 2.35–2.68(m, 7H), 2.88 (d, 1H), 3.11 (d, 1H), 5.30 (bs, 2H), 6.11 (t, 1H), 6.82 (d, 1H), 7.23–7.45 (m, 7H), 7.57 (d, 1H), 8.48 (d, 1H). ESI-MS m/z: 530.2(M+1), retention time 1.58.

Example 481

4-(4-Chloro-phenyl)-4-hydroxy-1-{3-[7-(hydroxyl-1-methyl-ethyl)-11H-10-oxa-1-aza-dibenzo[a,d]cyclohepten-5-ylidene]-propyl}-3-methyl-piperidine-3-carboxylic acid methyl ester Step 1: 4-Oxo-piperidine-1,3-dicarboxylic acid 1-tert-butyl Ester 3-methyl Ester To a solution of di-tert-butyl-dicarbonate (3.08 g, 14.1 mmol) in CH$_2$Cl$_2$ (134 mL) was added methyl-4-oxo-3-piperidine carboxylate HCl (2.6 g, 13.4 mmol) and triethylamine (3.84 mL, 27.5 mmol). The solution was stirred at rt for 12 h. Gas evolution was observed. The reaction was quenched with 1N HCl and extracted with CH$_2$Cl$_2$ (3x), and the organic layers were collected together, dried over MgSO$_4$ and evaporated in vacuo. The residue was purified to yield the title compound as a colorless oil. $^1$H-NMR (CDCl$_3$) δ: 1.46 (s, 9H), 2.36 (t, 2H), 3.55 (t, 2H), 3.77 (s, 4H), 4.04 (s, 2H).

Step 2: 3-Methyl-4-oxo-piperidine-1,3-dicarboxylic acid-1-tert-butyl ester 3-methyl ester 4-Oxo-piperidine-1,3-dicarboxylic acid 1-tert-butyl ester 3-methyl ester (2.00 g, 6.8 mmol) was dissolved in tetrahydrofuran and cooled to 0° C. To the solution was added NaH (0.300 g, 12.5 mmol) portionwise over 1 h. H$_{2(g)}$ was evolved during the addition. The reaction was allowed to stir for 30 minutes at 0° C. and then methyl iodide (0.422 mL, 6.8 mmol) was added and allowed to stir at room temperature for 13 h. The reaction was quenched with ice water and concentrated down. The residue was partitioned between water and ethyl acetate. The aqueous layer was extracted with EtOAc (3×), the organics were collected together dried over Mg$_2$SO$_4$, filtered and evaporated in vacuo, then purified by Biotage flash chromatography (10% ethyl acetate/90% hexane to yield the title compound (1.1 g, 52%). $^1$H-NMR (CDCl$_3$): δ 1.29 (s, 3H), 1.47 (s, 9H), 2.47 (dt, 1H), 2.76 (m, 1H), 3.07 (d, 1H), 3.33 (dt, 1H), 3.71 (s, 3H), 4.11 (m, 1H), 4.50 (d, 1H).

Step 3: 4-(4-Chloro-phenyl)-4-hydroxy-3-methyl-piperidine-1,3-dicarboxylic acid 1-tert-butyl ester 3-methyl ester 3-Methyl-4-oxo-piperidine-1,3-dicarboxylic acid-1-tert-butyl ester 3-methyl ester (1.1 g, 4.07 mmol) was dissolved in tetrahydrofuran and cooled to 0° C. To the solution was added 4-chlorophenyl magnesium bromide (12.2 mL, 12.2 mmol) dropwise over ~½ h and then stirred at 0° C. for 1 h. The reaction was quenched with saturated solution of NH$_4$Cl and extracted with ethyl acetate (3×). The organics were collected, dried over Mg$_2$SO$_4$, filtered and evaporated in vacuo, then purified by Biotage flash chromatography (10% ethyl acetate/90% hexane to 20% ethyl acetate/80% hexane) to yield the title compound (1.1 g, 70%). $^1$H-NMR (CDCl$_3$): δ 1.17 (s, 3H), 1.44 (s, 9H), 1.55 (m, 1H), 1.96 (d, 1H) 3.00 (m, 1H), 3.37 (m, 2H), 3.53 (s, 3H), 3.91 (m, 2H), 4.07 (d, 1H), 7.27 (d, 2H), 7.43 (d, 2H). ESI-MS m/z: 384.1 (M+1), retention time 2.95.

Step 4

4-(4-Chloro-phenyl)-4-hydroxy-3-methyl-piperidine-1,3-dicarboxylic acid 1-tert-butyl, ester 3-methyl ester (1.1 g, 2.87 mmol) was dissolved in CH$_2$Cl$_2$ (35 mL) and cooled to 0° C. and TFA (8 mL) was added dropwise. The solution was allowed to stir at 0° C. for 1 h. The solvent was evaporated in vacuo and the residue was partitioned between 1N NaOH and CH$_2$Cl$_2$ The aqueous solution was extracted (3×) and then washed with brine and dried over Na$_2$SO$_4$. The residue was carried onto the next step without further purification.

Step 5

To a solution of 4-(4-chloro-phenyl)-4-hydroxy-3-methyl-piperidine-3-carboxylic acid methyl ester (0.71 g, 2.5 mmol) in acetonitrile/water (8:2) (25 mL) was added K$_2$CO$_3$ (1.40 g, 10.0 mmol) and 2-[5-(3-bromo-propylidene)-5,11-dihydro-10-oxa-1-aza-dibenzo[a,d]cyclohepten-7-yl]-propan-2-ol (0.937 g, 2.5 mmol). The solution was allowed to stir at room temperature for 48 h. The reaction was concentrated and partitioned between EtOAc/H$_2$O, extracted with EtOAc (3×). The organics were collected together dried over Mg$_2$SO$_4$, filtered and evaporated in vacuo, then purified by Biotage flash chromatography (50% ethyl acetate/50% hexane to 75% ethyl acetate/25% hexane to 100% ethyl acetate) to yield the title compound (0.835 g, 58%). $^1$H-NMR (CDCl$_3$): 1.30 (s, 3H), 1.57 (s, 6H), 1.76 (d, 1H), 2.24–2.53 (m, 7H), 2.65 (d, 1H), 2.86 (d, 2H), 3.44 (s, 3H), 5.30 (bs, 2H), 6.16 (d, 1H), 6.82 (d, 1H), 7.26 (m, 4H), 7.45 (s, 1H), 7.53 (d, 1H), 7.58 (d, 1H), 8.49 (d, 1H). ESI-MS m/z: 577 (M+1), retention time 1.50.

Example 482

4-(4-Chloro-phenyl)-3-hydroxymethyl-1-{3-[7-(hydroxyl-1-methyl-ethyl)-11H-10-oxa-1-aza-dibenzo[a,d]cyclohepten-5-ylidene]-propyl}-3-methyl-piperidine-4-ol 4-(4-Chloro-phenyl)-4-hydroxy-1-{3-[7-(hydroxyl-1-methyl-ethyl)-11H-10-oxa-1-aza-dibenzo[a,d]cyclohepten-5-ylidene]-propyl}-3-methyl-piperidine-3-carboxylic acid methyl ester (0.250 g, 0.43 mmol) was dissolved in tetrahydrofuran and cooled to 0° C. To the solution was added LiAlH$_4$ (1.3 mL, 1.3 mmol) dropwise and the reaction was allowed to stir at 0° C. for 3 h. The reaction was quenched with ice water slowly and diluted with ethyl acetate. The reaction mixture was allowed to stir at room temperature for 45 min. to break up any aluminum complexes. The organics were separated and the aqueous layer was extracted (2×) more. All of the organics were collected, dried over Mg$_2$SO$_4$, filtered and evaporated in vacuo, then purified by Biotage flash chromatography (50% ethyl acetate/50% hexane to 75% ethyl acetate/25% hexane) to yield the title compound (0.103 g, 43%). $^1$H-NMR (CDCl$_3$): δ 0.53 (s, 3H), 1.55 (d, 6H), 1.62 (m, 1H), 2.40 (q, 2H), 2.55 (q, 3H), 2.72–2.86 (m, 4H), 3.19 (dd, 1H), 3.24 (d, 1H), 3.41 (d, 1H), 5.33 (bs, 2H), 6.17 (t, 1H), 6.44 (bs, 1H), 6.79 (d, 1H), 7.17 (d, 1H), 7.26–7.59 (m, 7H), 8.50 (d, 1H). ESI-MS m/z: 549 (M+1), retention time 1.39.

Example 483-1, Example 483-2

Racemic 4-(4-Chloro-phenyl)-3-hydroxymethyl-1-{3-[7-(hydroxyl-1-methyl-ethyl)-11H-10-oxa-1-aza-dibenzo[a,d]cyclohepten-5-ylidene]-propyl}-3-methyl-piperidine-4-ol was resolved using a ChiralPak AD column eluting with May 5, 1990 methanol/ethanol/hexane. Peak One is the more active enantiomer, Example 483-1. Peak Two is the less active enantiomer, Example 483-2.

Example 484

4-(4-Chloro-phenyl)-3-ethoxymethyl]-{3[7-(-hydroxy-1-methyl-ethyl)-11H-10-oxa-1-aza-dibenzo[a,d]cyclohepten-5-ylidene]-propyl}-3-methyl-piperidin-4-ol Step 1

To a solution of 4-(4-chloro-phenyl)-4-hydroxy-3-hydroxymethyl-3-methyl-piperidine-1-carboxylic acid-tert-butyl ester (0.270 g, 0.76 mmol) in THF (4.8 mL) was added NaH (0.075 g, 1.9 mmol) and stirred for 20 min at room temperature. Ethyl iodide (0.066 mL, 0.83 mmol) was added and the solution was heated to 50° C. for 1 h. The reaction was quenched with water and extracted with ethyl acetate (3×). The organics were collected together dried over Mg$_2$SO$_4$, filtered and evaporated in vacuo, then purified by Biotage flash chromatography (10% ethyl acetate/90% hexane to 20% ethyl acetate/80% hexane to 30% ethyl acetate/70% hexane) to yield the title compound (0.110 g, 37%). $^1$H-NMR (CDCl$_3$): 0.79 (s, 3H), 1.10 (t, 3H), 1.26 (s, 1H), 1.45 (s, 9H), 1.84 (s, 1H), 2.74 (m, 2H), 2.98 (d, 1H), 3.18 (m, 1H), 3.28 (q, 2H), 3.97 (d, 2H), 7.26–7.39 (m, 4H).

Step 2

4-(4-Chloro-phenyl)-3-ethoxymethyl-4-hydroxy-3-methyl-piperidine-1-carboxylic acid-tert-butyl ester (0.052 g, 0.14 mmol) was dissolved in CH$_2$Cl$_2$ (3 mL) and cooled to 0° C. and TFA (1 mL) was added. The solution was allowed to stir at 0° C. for 1 h. The solvent was evaporated in vacuo and used directly in the next reaction.

Step 3

To a solution of 4-(4-chloro-phenyl)-3-ethoxymethyl-3-methyl-piperidin-4-ol (0.038 g, 0.13 mmol) in acetonitrile/water (8:2) (1.3 mL) was added K$_2$CO$_3$ (0.075 g, 0.53 mmol) and 2-[5-(3-bromo-propylidene)-5,11-dihydro-10-oxa-1- aza-dibenzo[a,d]cyclohepten-7-yl]-propan-2-ol (0.050 g, 0.13 mmol). The solution was allowed to stir at room temperature for 48 h. The reaction was concentrated and partitioned between EtOAc/H₂O, extracted with EtOAc (3×). The organics were collected, dried over MgSO₄, filtered and evaporated in vacuo, then purified by Biotage flash chromatography (75% ethyl acetate/25% hexane) to yield the title compound in 65% yield. ¹H-NMR (CDCl₃): δ 0.81 (s, 3H), 0.98 (t, 3H), 1.58 (s, 6H), 1.84 (s, 1H), 2.31–2.49 (m, 5H), 2.58 (d, 1H), 2.67 (s, 1H), 2.77 (d, 2H), 3.26 (q, 2H), 3.65 (d, 2H), 5.33 (bs, 2H), 6.16 (t, 1H), 6.82 (d, 1H), 7.22–7.36 (m, 7H), 7.45 (d, 1H), 7.60 (d, 1H). ESI-MS m/z: 577 (M+1), retention time 1.58.

Example 485

(4-(4-Chloro-phenyl)-4-hydroxy-1-{3 [7-(1-hydroxy-1-methyl-ethyl)-11H-10-oxa-1-aza-dibenzo[a,d]cyclohepten-5-ylidene]-propyl}-3-methyl-piperidin-3-ylmethoxy)-acetic acid ethyl ester Step 1

To a solution of 4-(4-chloro-phenyl)-4-hydroxy-3-hydroxymethyl-3-methyl-piperidine-1-carboxylic acid-tert-butyl ester (0.080 g, 0.22 mmol) in THF (2.2 mL) was added NaH (0.031 g, 0.78 mmol) and stirred for 20 min at room temperature. Ethyl bromoacetate (0.027 mL, 0.30 mmol) was added and the solution was heated to 50° C. for 1 h. The reaction was quenched with water and extracted with ethyl acetate (3×). The organics were collected together dried over Mg₂SO₄, filtered and evaporated in vacuo, then purified by Biotage flash chromatography (10% ethyl acetate/90% hexane to 20% ethyl acetate/80% hexane) to yield the ethyl ester (0.050 g, 50%). ¹H-NMR (CDCl₃): 0.85 (bs, 3H), 1.22 (t, 3H), 1.45 (s, 9H), 1.66 (s, 1 h), 2.64–3.39 (m, 6H), 3.96 (d, 2H), 4.12 (q, 2H), 7.26–7.38 (m, 4H).

Step 2

4-(4-Chloro-phenyl)-3-ethoxycarbonylmethoxymethyl-4-hydroxy-3-methyl-piperidine-1-carboxylic acid-tert-butyl ester (0.060 g, 0.14 mmol) was dissolved in CH₂Cl₂ (3 mL) and cooled to 0° C. and TFA (1 mL) was added. The solution was allowed to stir at 0° C. for 1 h. The solvent was evaporated in vacuo and used directly in the next reaction.

Step 3

To a solution of 4-(4-chloro-phenyl)-4-hydroxy-3-methyl-piperidin-3-ylmethoxy]-acetic acid ethyl ester (0.046 g, 0.13 mmol) in acetonitrile/water (8:2) (1.3 mL) was added K₂CO₃ (0.075 g, 0.53 mmol) and 2-[5-(3-bromo-propylidene)-5,11-dihydro-10-oxa-1-aza-dibenzo[a,d]cyclohepten-7-yl]-propan-2-ol (0.051 g, 0.13 mmol). The solution was allowed to stir at room temperature for 48 h. The reaction was concentrated down and partitioned between EtOAc/H₂O, extracted with EtOAc (3×). The organics were collected together dried over Mg₂SO₄, filtered and evaporated in vacuo, then purified by Biotage flash chromatography (75% ethyl acetate/25% hexane) to yield the title compound in 54% yield. ¹H-NMR (CDCl₃): δ 0.86 (s, 3H), 11.16 (t, 3H), 1.57 (s, 6H), 1.78 (s, 1H), 2.37 (t, 1H), 2.46–2.71 (m, 5H), 2.81 (t, 1H), 3.80 (d, 2H), 3.97 (d, 2H), 4.06 (q, 2H), 5.30 (bs, 2H), 6.18 (t, 1H), 6,82 (d, 1H), 7.22 (dd, 1H), 7.26–7.36 (m, 7H), 7.47 (d, 1H), 7.60 (d, 1H). ESI-MS m/z: 635 (M+1), retention time 1.62.

Example 486

4-(4-Chloro-phenyl)-3-(2-diethylamino-ethoxymethyl)-4-hydroxy-3-methyl-piperidine-1-carboxylic acid-tert-butyl ester Step 1

To a solution of 4-(4-chloro-phenyl)-4-hydroxy-3-hydroxymethyl-3-methyl-piperidine-1-carboxylic acid-tert-butyl ester (0.071 g, 0.15 mmol) in THF (1.5 mL) was added NaH (0.016 g, 0.39 mmol) and stirred for 20 min at room temperature. 2-Bromo-N,N-diethylethylamine HBr (0.044 mL, 0.17 mmol) was added and the solution was heated to 50° C. for 1 h. The reaction was quenched with water and extracted with ethyl acetate (3×). The organics were collected, dried over MgSO₄, filtered and evaporated in vacuo, then purified by Biotage flash chromatography (10% ethyl acetate/90% hexane to 20% ethyl acetate/80% hexane) to yield the diethylamine (0.035 g).

Step 2

4-(4-Chloro-phenyl)-3-(2-diethylamino-ethoxymethyl)-4-hydroxy-3-methyl-piperidine-1-carboxylic acid-tert-butyl ester (0.035 g, 0.62 mmol) was dissolved in CH₂Cl₂ (3 mL) and cooled to 0° C. and TFA (1 mL) was added. The solution was allowed to stir at 0° C. for 1 h. The solvent was evaporated in vacuo and used directly in the next reaction.

Step 3

To a solution of 4-(4-chloro-phenyl)-3-(2-diethylaminoethoxymethyl)-3-methyl-piperidin-4-ol in acetonitrile/water (8:2) (3.2 mL) was added K₂CO₃ and 2-[5-(3-bromo-propylidene)-5,11-dihydro-10-oxa-1 aza-dibenzo[a,d]cyclohepten-7-yl]-propan-2-ol. The solution was allowed to stir at room temperature for 48 h. The reaction was concentrated down and partitioned between EtOAc/H₂O, extracted with EtOAc (3×). The organics were collected, dried over MgSO₄, filtered and evaporated in vacuo, then purified by Biotage flash chromatography (5% methanol/95% methylene chloride to 10% methanol/90% methylene chloride to 15% methanol/85% methylene chloride) to yield the title compound. ¹H-NMR (CDCl₃): 0.50 (s, 3H), 0.97 (t, 6H), 1.52 (s, 6H), 2.40–2.66 (m, 12H), 3.16–3.30 (m, 6H), 5.32 (bs, 2H), 6.06 (t, 1H), 6.80 (t, 1H), 7.20 (dd, if H), 7.29 (dd, 1H), 7.29–7.31 (m, 6H), 7.58 (d, 2H), 8.51 (d, 1H). δ ESI-MS m/z: 648 (M+1), retention time 1.19.

Example 487

2-[5-(3-{4-[(4-Chloro-benzyl)ethyl-amino]-piperidin-1-yl}-propylidene)-5,11-dihydro-10-oxa-1-aza-dibenzo[a,d]cyclohepten-7-yl]-propan-2-ol Step 1: 4-(4-Chloro-benzylamino)-piperidine-1-carboxylic acid tert-butyl ester 4-Amino-1-N-Boc piperidine (1.80 g, 8.9 mmol) was dissolved in CH₂Cl₂ and 4-chlorobenzylbromide (1.84 g, 8.9 mmol) and triethylamine (1.25 mL, 8.9 mmol) were added. The solution was allowed to stir for 14 h at room temperature and evaporated in vacuo and partitioned between ether/1N NaOH. The aqueous layer was removed and the ether was washed with brine and dried over MgSO₄, filtered and evaporated in vacuo, then purified by Biotage flash chromatography (5% methanol/95% methylene chloride) to yield the title compound (0.800 g, 27%). ¹H-NMR (CDCl₃): δ 1.26 (m, 1H), 1.44 (s, 9H), 1.83 (d, 2H), 2.63 (t, 1H), 2.78

(t, 2H), 3.46 (s, 2H), 3.78 (s, 2H), 4.00 (bs, 2H), 7.26 (bs, 4H). ESI-MS m/z: 325.1 (M+1), retention time 1.86.

Step 2

(4-Chloro-benzyl)-ethyl-amino]-piperidine-1-carboxylic acid tert-butyl ester (0.500 g, 1.4 mmol) dissolved in 4M HCl/Dioxane (100 mL). The solution was stirred at rt for 1 h. The solvent was removed in vacuo and the mixture was carried on to the next step without further purification as the hydrochloride salt.

Step 3: (4-Chloro-benzyl)-ethyl-piperidin-4-yl-amine 4-(4-Chloro-benzylamino)-piperidine-1-carboxylic acid tert-butyl ester was dissolved in $CH_2Cl_2$ and acetaldehyde (0.678 g, 3.2 mmol), $Na(OAc)_3BH$ (0.163 g, 3.7 mmol) and 1 drop of AcOH was added. The solution was stirred in a sealed vessel for 10 h. The reaction mixture was washed with 1N NaOH, brine and dried over $Mg_2SO_4$, filtered and evaporated in vacuo, then purified by Biotage flash chromatography (15% ethyl acetate/85% hexane) to yield the title compound (0.350 g, 40%).

Step 4

To a solution of (4-chloro-benzyl)-ethyl-piperidin-4-yl-amine hydrochloride (0.200 g, 0.83 mmol) in acetonitrile/water (8:2) (8 mL) was added $K_2CO_3$ (0.476 g, 3.4 mmol) and 2-[5-(3-bromo-propylidene)-5,11-dihydro-10-oxa-1-aza-dibenzo[a,d]cyclohepten-7-yl]-propan-2-ol (0.282 g, 7.5 mmol). The solution was allowed to stir at room temperature for 48 h. The reaction was concentrated and partitioned between $EtOAc/H_2O$, extracted with EtOAc (3×). The organics were collected, dried over $MgSO_4$, filtered and evaporated in vacuo, then purified by Biotage flash chromatography (5% methanol/95% methylene chloride to 10% methanol/90% methylene chloride) to yield the title compound (0.240 g, 60%). $^1$H-NMR (CDCl$_3$): δ 0.988 (t, 3H), 1.57 (s, 6H), 1.67 (d, 2H), 1.85 (t, 2H), 2.32–2.46 (m, 5H), 2.51 (q, 2H), 2.84 (d, 2H), 3.47 (s, 2H), 3.56 (s, 2H), 5.29 (bs, 2H), 6.07 (t, 1H), 6.80 (d, 1H), 7.21–7.28 (m, 6H), 7.42 (s, 1H), 7.56 (d, 1H), 8.48 (d, 1H). ESI-MS m/z: 546 (M+1), retention time 1.87.

Example 488

1-{3-[7-(1-Hydroxy-1-methyl-ethyl)-11H-10-oxa-1-aza-dibenzo[a,d]cyclohepten-5-ylidene]-propyl}-4-phenyl-piperidin-4-ol To a solution of the 4-phenyl-piperidin-4-ol (0.212 g, 1.2 mmol) in isopropanol was added 2,6-lutidine (0.240 mL, 2.1 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.224 g, 0.6 mmol), added in portions over 1 h. The solution was then stirred at 80° C. for an additional 14 h. The reaction was concentrated in vacuo, then purified by Isco flash chromatography (15% methanol/85% methylene chloride) to yield the title compound (0.140 g, 50%). $^1$H-NMR (CDCl$_3$): δ 1.12 (t, 3H), 1.57(s, 6H), 2.67–2.80 (m, 4H), 1.95–2.11 (m, 2H), 2.34–2.41 (m, 2H), 2.43–2.54 (m, 2H), 2.88 (d, 2H), 3.22 (q, 2H), 3.43 (m, 1H), 5.28 (bs, 2H), 6.12 (t, 1H), 6.60 (d, 2H), 6.80 (d, 1H), 7.13 (d, 2H), 7.21–7.30 (m, 2H), 7.45 (s, 1H), 7.56 (d, 1H), 8.48 (dd, 1H). ESI-MS m/z: 534 (M+1), retention time 2.47.

Example 489

4-(2-Chloro-phenyl)-1-{3-[7-(1-hydroxy-1-methyl-ethyl)-11H-10-oxa-1-aza dibenzo[a,d]cyclohepten-5-ylidene]-propyl}-piperidin-4-ol Step 1

To a 1-bromo-2-chloro-benzene (0.97 mL, 8.3 mmol) in ether was added magnesium (0.238 g, 9.8 mmol) and catalytic iodide at room temperature for 2 h. This mixture was cooled to 0° C., and treated with 4-oxo-piperidine-1-carboxylic acid tert-butyl ester (1.5 g, 7.5 mmol) dissolved in ether (8 mL) and added to the reaction mixture slowly. The reaction was heated to reflux for 1 h. The reaction was quenched with ammonium chloride and the aqueous phase extracted with ethyl acetate. The organics were combined and dried over $MgSO_4$, filtered and evaporated in vacuo. The residue was purified by Isco flash system (75% hexane/25% ethyl acetate) to yield the alcohol (0.600 g, 38%).

Step 2

4-(2-Chloro-phenyl)-4-hydroxy-piperidine-1-carboxylic acid tert-butyl ester (0.600 g, 1.9 mmol) was dissolved in $CH_2Cl_2$ (19 mL) and cooled to 0° C. and TFA (4 mL) was added. The solution was allowed to stir at 0° C. for 1 h. The solvent was evaporated in vacuo and the residue was partitioned between $NaHCO_3$ and $CH_2Cl_2$ The aqueous solution was extracted (3×) and then washed with brine and dried over $Na_2SO_4$. The residue was carried onto the next step without further purification.

Step 3

To a solution of the 4-(2-chloro-phenyl)-piperidin-4-ol (0.210 g, 1.0 mmol) in isopropanol was added 2,6-lutidine (0.31 mL, 2.7 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.287 g, 0.77 mmol), added in portions over 1 h. The solution was then stirred at 80° C. for an additional 14 h. The reaction was concentrated in vacuo, then purified by Isco flash chromatography (15% methanol/85% methylene chloride) to yield the title compound (0.200 g, 52%). $^1$H-NMR (CDCl$_3$): δ 1.55 (s, 6H), 1.70 (d, 2H), 2.10–2.30 (m, 2H), 2.36–2.54 (m, 2H), 2.57–2.92 (m, 6H), 5.30 (bs, 2H), 6.16 (t, 1H), 6.77 (d, 1H), 7.16–7.36 (m, 5H), 7.48 (s, 2H), 7.58 (d, 1H), 8.37 (dd, 1H). ESI-MS m/z: 505 (M+1), retention time 1.48.

Example 490

4-(4-Chloro-2-methyl-phenyl)-1-{3-[7-(1-hydroxy-1-methyl-ethyl)-11H-10-oxa-1-aza-dibenzo[a,d]cyclohepten-5-ylidene]-propyl}-piperidin-4-ol Step 1

To 4-chloro-2-methylphenylmagnesium bromide (15 mL, 7.5 mmol) in ether cooled to 0° C. was added 4-oxo-piperidine-1-carboxylic acid tert-butyl ester (1.0 g, 5.0 mmol) over 30 min. The resulting solution was heated to reflux for 1 h. The reaction was quenched with ammonium chloride and the aqueous phase extracted with ethyl acetate. The organics were combined and dried over $MgSO_4$, filtered and evaporated in vacuo. The residue was purified by Isco flash system (75% hexane/25% ethyl acetate) to yield the alcohol (0.534 g, 33%).

Step 2

4-(4-Chloro-2-methyl-phenyl)-4-hydroxy-piperidine-1-carboxylic acid tert-butyl ester (0.534 g, 1.6 mmol) was dissolved in $CH_2Cl_2$ (16 mL) and cooled to 0° C. and TFA (3 mL) was added. The solution was allowed to stir at 0° C. for 1 h. The solvent was evaporated in vacuo and the residue was partitioned between $NaHCO_3$ and $CH_2Cl_2$ The aqueous solution was extracted (3×) and then washed with brine and dried over $Na_2SO_4$. The residue was carried onto the next step without further purification.

Step 3

To a solution of the 4-(4-chloro-2-methyl-phenyl)-piperidin-4-ol (0.160 g, 0.71 mmol) in isopropanol was added 2,6-lutidine (0.24 mL, 2.1 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.221 g, 0.59 mmol), added in portions over 1 h. The solution was then stirred at 80° C. for an additional 14 h. The reaction was concentrated in vacuo, then purified by Isco flash chromatography (15% methanol/85% methylene chloride) to yield the title compound (0.130 g, 36%). $^1$H-NMR ($CDCl_3$): δ 1.57 (s, 6H), 1.92 (d, 2H), 2.30 (t, 2H), 2.49 (s, 3H), 2.48–2.63 (m, 2H), 2.74–3.11 (m, 6H), 3.40 (s, 1H), 5.21 (bs, 2H), 6.09 (t, 1H), 6.75 (d, 1H), 7.06 (d, 1H), 7.08 (s, 1H), 7.20(d, 2H), 7.22–7.36 (m, 1H), 7.57 (d, 1H), 8.36 (dd, 1H). ESI-MS m/z: 519 (M+1), retention time 1.61.

Example 491

4-(3,4-Dichloro-phenyl)-1-{3-[7-(1-hydroxy-1-methyl-ethyl)-11H-10-oxa-1-aza-dibenzo[a,d]cyclohepten-5-ylidene]-propyl}-piperidin-4-ol Step 1

To 3,4-dichlorophenylmagnesium bromide (7.5 mL, 7.5 mmol) in ether cooled to 0° C. was added 4-oxo-piperidine-1-carboxylic acid tert-butyl ester (1.0 g, 5.0 mmol) over 30 min. The resulting solution was heated to reflux for 1 h. The reaction was quenched with ammonium chloride and the aqueous phase extracted with ethyl acetate. The organics were combined and dried over $MgSO_4$, filtered and evaporated in vacuo. The residue was purified by Isco flash system (75% hexane/25% ethyl acetate) to yield the alcohol (0.630 g, 36%).

Step 2

4-(3,4-Dichloro-phenyl)-4-hydroxy-piperidine-1-carboxylic acid tert-butyl ester (0.630 g, 1.8 mmol) was dissolved in $CH_2Cl_2$ and cooled to 0° C. and TFA (3 mL) was added. The solution was allowed to stir at 0° C. for 1 h. The solvent was evaporated in vacuo and the residue was partitioned between $NaHCO_3$ and $CH_2Cl_2$ The aqueous solution was extracted (3×) and then washed with brine and dried over $Na_2SO_4$. The residue was carried onto the next step without further purification.

Step 3

To a solution of the 4-(4-chloro-2-methyl-phenyl)-piperidin-4-ol (0.140 g, 0.57 mmol) in isopropanol was added 2,6-lutidine (0.23 mL, 2.0 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.213 g, 0.57 mmol), added in portions over 1 h. The solution was then stirred at 80° C. for an additional 14 h. The reaction was concentrated in vacuo, then purified by Isco flash chromatography (15% methanol/85% methylene chloride) to yield the title compound (0.110 g, 36%). $^1$H-NMR ($CDCl_3$): δ 1.55 (s, 6H), 1.70 (d, 2H), 2.10–2.30 (m, 2H), 2.45 (m, 2H), 2.57–2.92 (m, 6H), 5.30 (bs, 2H), 6.16 (t, 1H), 6.77 (d, 1H), 7.16–7.40 (m, 4H), 7.08 (s, 1H), 7.57 (s, 2H), 8.36 (dd, 1H). ESI-MS m/z: 539 (M+1), retention time 1.72.

Example 492

4-(4-Chloro-3-nitro-phenyl)-1-{3-[7-(1-hydroxy-1-methyl-ethyl)-11H-10-oxa-1-aza-dibenzo[a,d]cyclohepten-5-ylidene]-propyl}-piperidin-4-ol Step 1

To fuming nitric acid (20 mL) was added 4-(4-chlorophenyl)-piperidin-4-ol at 0° C. and stirred for 5 min. The solution was carefully neutralized with $Na_2CO_3$ and filtered. The resulting solid was trituated with water and then filtered to give a yellow solid. The solid was dissolved in sat $NaHCO_3$ and extrated with ethyl acetate (3×). The organics were collected together dried over $Mg_2SO_4$, filtered and evaporated in vacuo to give the 4-chloro-3-nitro compound (1.1 g, 18%).

Step 2

To a solution of the 4-(4-Chloro-3-nitro-phenyl)-piperidin-4-ol (0.295 g, 1.2 mmol) in isopropanol was added 2,6-lutidine (0.225 mL, 2.1 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.224 g, 0.6 mmol), added in portions over 1 h. The solution was then stirred at 80° C. for an additional 14 h. The reaction was concentrated in vacuo, then purified by Isco flash chromatography (15% methanol/85% methylene chloride) to yield the title compound (0.100 g, 30%). $^1$H-NMR ($CDCl_3$): δ 1.53 (s, 6H), 1.70 (d, 2H), 1.81–2.18 (m, 4H), 2.3–2.44 (m, 4H), 2.56 (t, 2H), 2.69 (d, 2H), 5.32 (bs, 2H), 6.16 (t, 1H), 6.81 (d, 1H), 7.28 (t, 2H), 7.48 (t, 2H), 7.58 (t, 2H), 8.06 (s, 1H). ESI-MS m/z: 550 (M+1), retention time 1.51.

Example 493

2-[5-(3-{4-[(4-Chloro-phenyl)-ethyl-amino]-piperidin-1-yl}-propylidene)-5,11-dihydro-10-oxa-1-aza-dibenzo[a,d]cyclohepten-7-yl]-propan-2-ol Step 1

4-Amino-piperidine-1-carboxylic acid tert-butyl ester (1.58 g, 7.9 mmol) and acetaldehyde (0.417 g, 9.48 mmol) were mixed with sodium triacetoxy borohydride (3.35, 15.8 mmol) in dichloroethane containing acetic acid (1%) and the resulting mixture was stirred at room temperature overnight. The reaction mixture was diluted with $CH_2Cl_2$ and washed with saturated aqueous sodium bicarbonate solution and brine and dried over sodium sulfate. The reaction was concentrated in vacuo, then purified by Isco flash chromatography (10% methanol/90% methylene chloride/ammonium hydroxide) to yield the tert-butyl ester (0.71 g, 39%).

Step 2

4-Ethylamino-piperidine-1-carboxylic acid tert-butyl ester (0.694 g, 3.04 mmol) and 1-Bromo-4-chloro-benzene (0.582, 3.04 mmol) was dissolved in toluene along with sodium t-butoxide (0.41, 4.26 mmol), $Pd_2(dba)_3$ (0.055 g, 0.061 mmol) and BINAP (0.037 g, 0.061 mmol). The solution was heated to 70° C. for 2 days and then filtered and the reaction was concentrated in vacuo, then purified by Isco flash chromatography (50% ethyl acetate/50% hexane) to yield the tert-butyl ester (0.25 g, 24%).

Step 3

4-(Ethyl-phenyl-amino)-piperidine-1-carboxylic acid tert-butyl ester (0.251 g, 1.0 mmol) was dissolved in 4M HCl/Dioxane (10 mL). The solution was stirred at rt for 1 h. The solvent was removed in vacuo and the mixture was carried on to the next step without further purification as the hydrochloride salt.

Step 4

To a solution of the (4-chloro-phenyl)-ethyl-piperidin-4-yl-amine (0.150 g, 0.63 mmol) in isopropanol was added 2,6-lutidine (0.24 mL, 2.1 mmol) and catalytic potassium iodide. This mixture was heated to 80° C., and treated with 2-[5-(3-Bromo-propylidene)-5,11-dihydro-10-oxa-1-aza-dibenzo[a, d]cyclohepten-7-yl]-propan-2-ol (0.221 g, 0.6 mmol), added in portions over 1 h. The solution was then stirred at 80° C. for an additional 14 h. The reaction was concentrated in vacuo, then purified by Isco flash chromatography (15% methanol/85% methylene chloride) to yield the title compound (0.108 g, 34%). $^1$H-NMR (CDCl$_3$): δ 1.12 (t, 3H), 1.57 (s, 6H), 2.67–2.80 (m, 4H), 2.00 (m, 2H), 2.34–2.41 (m, 2H), 2.43–2.54 (m, 2H), 2.88 (d, 2H), 3.22 (q, 2H), 3.37–3.51 (m, 1H), 5.28 (bs, 2H), 6.12 (t, 1H), 6.60 (d, 2H), 6.80 (d, 1H), 7.13 (d, 2H), 7.21–7.30 (m, 2H), 7.45 (s, 1H), 7.56 (d, 1H), 8.48 (dd, 1H). ESI-MS m/z: 532 (M+1), retention time 2.47.

Example 494

2-(5-{3-[4-(4-Chloro-phenyl)-4-methoxy-piperidin-1-yl]-propylidene}-5,11-dihydro-10-oxa-1-aza-dibenzo[a,d]cyclohepten-7-yl)-propan-2-ol Step 1

4-(4-Chloro-phenyl)-4-hydroxy-piperidine-1-carboxylic acid tert-butyl ester (200 mg, 0.641 mmol) was added portionwise as a solid to a suspension of sodium hydride (0.018 g, 0.770 mmol) in dimethylformamide (6 mL) at room temperature. After 30 minutes, methyl iodide (0.109 g, 60 uL, 0.770 mmol) was added and the mixture was stirred overnight. The mixture was poured into an equal volume of water and extracted with ethyl acetate (2×10 mL). The ethyl acetate extracts were dried over magnesium sulfate, filtered, and concentrated in vacuo to give a tan oil. The crude oil was purified by silica gel chromatography (hexane to 60:40 hexane/ethyl acetate gradient) to afford 4-(4-Chloro-phenyl)-4-methoxy-piperidine-1-carboxylic acid tert-butyl ester as a clear oil (108 mg, 52%).

$^1$H-NMR (CDCl$_3$, 300 MHz) δ: 1.45 (s, 9H), 1.80(td, 2H), 1.97 (bd, 2H), 2.96 (s, 3H), 3.16 (td, 2H), 3.90 (bd, 2H), 7.36 (s, 4H) MS m/z: 326 (M+1)

Step 2

4-(4-Chloro-phenyl)-4-methoxy-piperidine-1-carboxylic acid tert-butyl ester (0.108 g, 0.331 mmol) was dissolved in methylene chloride (6 mL) and cooled in an ice bath. Trifluoroacetic acid (2 mL) was added slowly dropwise. The mixture was stirred for 2 hr as it warmed to room temperature. The reaction mixture was concentrated in vacuo and then redissolved in methylene chloride and washed with saturated sodium bicarbonate (2×10 mL). The pooled aqueous layers were extracted with methylene chloride (2×10 mL). The methylene chloride extracts were pooled, dried over magnesium sulfate, filtered and concentrated in vacuo to give 4-(4-Chloro-phenyl)-4-methoxy-piperidine as a clear oil (72 mg, 97%).

$^1$H-NMR (CDCl$_3$, 300 MHz) δ: 1.92 (m, 4H), 2.98 (s, 3H), 3.07 (m, 4H), 4.50 (bs, 1H), 7.30 (s, 4H) MS m/z: 226 (M+1)

Step 3

4-(4-Chloro-phenyl)-4-methoxy-piperidine (0.072 g, 0.319 mmol) was dissolved in isopropanol (5 mL) and 2,6-lutidine (0.034 g, 37 uL, 0.319 mmol) was added. Catalytic iodine was also added. The resulting suspension was warmed to 80° C. Solid 2-[5-(3-Bromo-propylidene)-5,11-dihydro-10-oxa-1-aza-dibenzo[a,d]cyclohepten-7-yl]-propan-2-ol (0.060 g, 0.160 mmol) was added in approximately equal portions over 2 h. Stirring was continued an additional 20 h at 80° C. The mixture was concentrated and the resulting residue purified by silica gel chromatography (ethyl acetate to 87/10/3 ethyl acetate/methanol/triethylamine gradient) to afford the title compound (70 mg, 42%).

$^1$H-NMR (CDCl$_3$, 300 MHz) δ: 1.67 (s, 6H), 1.99–2.86 (m, 12H), 2.98 (s, 3H), 5.32 (brs, 2H), 6.16 (t, 1H), 6.81 (d, 1H), 7.25–7.40 (m, 6H), 7.50 (s, 1H), 7.66 (d, 1H), 7.59 (d, 1H) MS m/z: 519 (M+1)

Example 495

2-(5-{3-[4-(2-Chloro-phenoxy)-piperidin-1-yl]-propylidene}-5,11-dihydro-10-oxa-1-aza-dibenzo[a,d]cyclohepten-7-yl)-propan-2-ol 4-(2-Chloro-phenoxy)-piperidine hydrochloride (0.067 g, 0.268 mmol) was dissolved in a mixture of acetonitrile (1.32 mL) and water (0.17 mL). To this mixture was added 2-[5-(3-Bromo-propylidene)-5,11-dihydro-10-oxa-1-aza-dibenzo[a,d]cyclohepten-7-yl]-propan-2-ol (0.050 g, 0.134 mmol) and potassium carbonate (0.074 g, 0.536 mmol). The mixture was stirred at room temperature for 24 hrs and then concentrated in vacuo. The resulting white solid was suspended in ethyl acetate (5 mL) and an equal volume of water was added. The product was extracted into ethyl acetate (2×5 mL). The pooled organic layers were dried over magnesium sulfate, filtered and concentrated in vacuo to afford an oil. The residue was purified by silica gel chromatography (ethyl acetate to 87/10/3 ethyl acetate/methanol/triethylamine gradient) to afford the title compound (46 mg, 68%).

$^1$H-NMR (CDCl$_3$, 300 MHz) δ: 1.58 (s, 6H), 1.7–2.9 (m, 12H), 4.42 (br s, 1H), 5.34 (br s, 2H), 6.1 (t, 1H), 6.75 (d, 1H), 6.88 (d, 2H), 6.9–7.3 (m, 4H), 7.32 (s, 1H), 7.58 (d, 1H), 8.55 (d, 1H); MS m/z: 506 (M+1)

Example 496

(4-Chloro-phenyl)-(1-{3-[7-(1-hydroxy-1-methyl-ethyl)-11H-10-oxa-1-aza-dibenzo[a,d]cyclohepten-5-ylidene]-propyl}-piperidin-4-yl)-methanone The title compound was prepared by following the procedure of Example 494, Step 3, but replacing 4-(4-Chloro-phenyl)-4-methoxy-piperidine with (4-Chloro-phenyl)-piperidin-4-yl-methanone.

$^1$H-NMR (CDCl$_3$, 300 MHz) δ: 1.45 (s, 6H), 2.05 (m, 2H), 2.55 (m, 2H), 2.71(m, 2H), 3.05 (m, 2H), 3.20 (m, 2H), 3.61 (m, 2H), 5.20 (m, 2H), 6.05 (t, 1H), 6.77 (d, 1H), 7.35–7.60 (m, 6H), 7.82 (d, 1H), 8.35 (br s, 1H), 8.52 (d, 1H); MS m/z: 517 (M+1)

Example 497

2-(5-{3-[4-(4-trifluoromethyl-phenoxy)-piperidin-1-yl]-propylidene}-5,11-dihydro-10-oxa-1-aza-dibenzo[a,d]cyclohepten-7-yl)-propan-2-ol The title compound was prepared by following the procedure of Example 495, but replacing 4-(2-Chloro-phenoxy)-piperidine hydrochloride with 4-(4-Trifluoromethyl-phenoxy)-piperidine.

$^1$H-NMR (CDCl$_3$, 300 MHz) δ: 1.62 (s, 6H), 2.15 (br d, 2H), 2.60–3.15 (m, 8H), 3.3 (br d, 2H), 4.74 (s, 1H), 6.07 (t, 1H), 6.84 (d, 1H), 6.91 (d, 2H), 7.10–7.24 (m, 5H), 7.40 (s, 1H), 7.55 (m, 3H), 8.52 (d, 1H); MS m/z: 539 (M+1)

Example 498

4-(4-Chloro-benzyl)-3-(1-{3-[7-(1-hydroxy-1-methyl-ethyl)-11H-10-oxa-1-aza-dibenzo[a,d]cyclohepten-5-ylidene]-propyl}-piperidin-4-yl)-oxazolidin-2-one Step 1

2-Amino-3-(4-chloro-phenyl)-propan-1-ol and 4-oxo-piperidine-1-carboxylic acid tert-butyl ester were dissolved in 12 ml of methylene chloride. Sodium triacetoxyborohydride (1.03 g, 0.00487 mole) was added as a solid followed by catalytic acetic acid. The reaction was stirred overnight at room temperature. The reaction was quenched by adding 12 ml of 1N sodium hydroxide. The intermediate alcohol was extracted into methylene chloride (3×12 mL), the organics were dried over magnesium sulfate, filtered and concentrated in vacuo to give the intermediate alcohol as a clear yellow oil (1.1 g, 86%). This oil was carried on without additional characterization.

4-[1-(4-Chloro-benzyl)-2-hydroxy-ehtylamino]-piperidine-1-carboxylic acid tert-butyl ester, the intermediate alcohol was dissolved in 15 mL of methylene chloride. Triethylamine (0.423 g, 0.00418 mol, 583 uL 1.2 equiv) was added followed by portionwise addition of carbonyl diimidazole (0.68 g, 0.00418 mol, 1.2 equiv). The mixture was stirred at room temperature and then quenched with water (15 mL). The organic layers were separated and the remaining aqueous layer was extracted with methylene chloride (3×15 mL). The combined organics were dried over magnesium sulfate, filtered and concentrated in vacuo to afford a yellow solid. The crude oil was purified by silica gel chromatography (methylene chloride to 10% methanol in methylene chloride gradient) to afford 4-[4-(4-chloro-benzyl)-2-oxo-oxazolidin-3-yl]-piperidine-1-carboxylic acid tert-butyl ester as a white solid (1.1 g, 80%).

$^1$H-NMR (CDCl$_3$, 300 MHz) δ: 1.40 (s, 9H), 1.70–2.10 (m, 4H), 2.75 (m, 2H), 2.72 (td, 1H), 4.11 (m 3H), 4.15 (br t, 2H), 7.05 (d, 2H), 7.45 (d, 2H); MS m/z: 395 (M+1)

Step 2

4-[4-(4-chloro-benzyl)-2-oxo-oxazolidin-3-yl]-piperidine-1-carboxylic acid tert-butyl ester (0.9 g, 0.002279 mole) was dissolved in methylene chloride (41 mL). The solution was cooled to ice bath temperature and trifluoroacetic acid (14 mL) was added and the reaction mixture was stirred for 2.5 hours. The reaction mixture was concentrated in vacuo to give the trifluoroacetate salt of the product as an oil. The salt was free based by adding saturated sodium bicarbonate (50 mL) and extracting with methylene chloride (2×50 mL). The organic layers were pooled, dried over magnesium sulfate, filtered and concentrated in vacuo to give 4-(4-chloro-benzyl)-3-piperidin-4-yl-oxazolidin-2-one as an off-white foam (560 mg, 84%).

$^1$H-NMR (CDCl$_3$, 300 MHz) δ: 1.70–2.15 (m, 4H), 2.60–2.80 (m, 4H), 3.05–3.30 (m, 2H), 3.55 (br s, 1H), 3.71 (m, 1H), 3.87 (m, 2H), 7.01 (d, 2H), 7.23 (d, 2H); MS m/z: 295 (M+1)

Step 3

The title compound was prepared by following the procedure of Example 495, but replacing 4-(2-Chloro-phenoxy)-piperidine hydrochloride with 4-(4-chloro-benzyl)-3-piperidin-4-yl-oxazolidin-2-one.

$^1$H-NMR (CDCl$_3$, 300 MHz) δ: 1.60 (s, 6H), 1.97–3.10 (m, 14H), 3.75 (br s, 2H), 4.10 (br s, 2H), 5.98 (t, 1H), 6.80 (d, 1H), 7.00–7.20 (m, 8H), 7.40 (s, 1H), 7.62 (d, 1H), 8.60 (d, 1H); MS m/z: 590 (M+1).

Example 499

1-{4-(4-Chloro-phenyl)-1-[3-(7-isopropenyl-11H-10-oxa-1-aza-dibenzo[a,d]cyclohepten-5-ylidene)-propyl]-piperidin-4-yl}-ethanol The product of Example 457 (64 mg, 0.12 mmol) was dissolved in anhydrous methanol (2.5 mL) and the resulting solution cooled to 0° C. Sodium borohydride (37 mg, 1 mmol,) was added portionwise over 5 h. The reaction was quenched with water and concentrated. The crude product residue was purified by reverse phase HPLC (water, acetonitrile, formic acid gradient) to afford the titled compound (note elimination of tertiary benzylic alcohol). MS m/z: 515 (m+1).

Example 500

[(4-Chloro-benzyl)-(1-{3-[7-(1-hydroxy-1-methyl-ethyl)-11H-10-oxa-1-aza-dibenzo[a,d]cyclohepten-5-ylidene]-propyl}-piperidin-4-yl)-amino]-acetic acid methyl ester Step 1.

To a solution of 4-chlorobenzylamine (859 mg, 6.07 mmol) in 1,2-dichloroethane (20 mL) was added t-butyl-4-oxo-piperidine-1-carboxylate (1.451 g, 7.282 mmol), acetic acid (400 uL), and sodium triacetoxyborohydride (1.800 g, 8.497 mmol). The mixture was stirred at rt under nitrogen for 2 h, diluted with ethyl acetate, washed thrice with saturated sodium bicarbonate solution and dried over magnesium sulfate. The extracts were filtered and concentrated to afford 4-(4-chloro-benzylamino)-piperidine-1-carboxylic acid tert-butyl ester (2.49 g, >100%) as a yellow oil, which was of sufficient purity by H-NMR to use without further purification.

$^1$H-NMR (CDCl$_3$, 300 MHz) δ: 1.44 (s, 9 H), 1.56–1.70 (br s, 2 H), 1.81–1.90 (br d, 2 H), 2.63 (dddd, 1 H), 2.78 (dd, 2 H), 3.72 (s, 1 H), 3.78 (s, 1 H), 4.00 (br s, 2 H), 7.16–7.25 (m, 4 H). MS m/z: 325 (M+1).

Step 2

To a solution of the product from step 1 (620 mg, 1.91 mmol) in tetrahydrofuran (20 mL) was added triethylamine (0.386 g, 532 uL, 3.82 mmol) followed by methyl bromoacetate (0.584 g, 361 uL, 3.82 mmol). The resulting mixture was heated at 55° C. for 2 d then rt for 3 days. The reaction was diluted with ethyl acetate, washed twice with water and once with brine, dried over magnesium sulfate, filtered and concentrated. The resulting crude 4-[(4-chloro-benzyl)- methoxycarbonylmethyl-amino]-piperidine-1-carboxylic acid tert-butyl ester (0.697 g, 92%) was of sufficient purity to use without further purification.

$^1$H-NMR (CDCl$_3$, 300 MHz) δ: 1.44 (s, 9 H), 1.78–1.95 (m, 2 H), 2.60–2.83 (m, 2 H), 3.3–4.2 (m, 12 H), 7.24–7.36 (m, 4 H). MS m/z: 397 (M+1).

Step 3

To a solution of the product of step 2 (0.270 g, 0.681 mmol) in methanol (6 mL) was added hydrogen chloride in dioxane (4.0 M, 340 uL, 1.36 mmol). After stirring at rt 3 h, an additional 1 mL aliquot of the HCl in dioxane solution was added and the mixture was allowed to stir at rt overnight. The mixture was concentrated under reduced pressure to afford [(4-chloro-benzyl)-piperidin-4-yl-amino]-acetic acid methyl ester which was used without further purification.

MS m/z: 297 (M+1).

Step 4

To a solution of the product of step 3 (0.251 g, 0.680 mmol) in acetonitrile (4 mL) was added potassium carbonate (0.310 g, 2.24 mmol) in water (2 mL), followed by 2-[5-(3-bromo-propylidene)-5,11-dihydro-10-oxa-1-aza-dibenzo[a,d]cyclohepten-7-yl]-propan-2-ol (170 mg, 448 mmol). The resulting orange solution was stirred at rt 13 days. The mixture was diluted with ethyl acetate and washed with water and brine. The washed extracts were dried over magnesium sulfate, filtered and concentrated. Pure titled compound was afforded by silica gel chromatography of the crude material (methylene chloride—98/2 methylene chloride/methanol gradient); 107 mg, 41%.

$^1$H-NMR (CDCl$_3$, 300 MHz) δ: 1.56 (s, 6H), 1.74–1.92 (m, 6H), 2.28–2.48 (m, 4 H), 2.53–2.66 (m, 2 H), 2.82 (br d, 2 H), 3.30 (s, 2 H), 3.63 (s, 3 H), 3.77 (s, 2 H), 5.21–5.39 (br s, 2 H), 6.07 (t, 1 H), 6.80 (d, 1 H), 7.21–7.32 (m, 6 H), 7.42 (d, 1 H), 7.55 (dd, 1 H), 8.50 (dd, 1 H). MS m/z: 590.

Example 501

[(4-Chloro-benzyl)-(1-{3-[7-(1-hydroxy-1-methyl-ethyl)-11H-10-oxa-1-aza-dibenzo[a,d]cyclohepten-5-ylidene]-propyl}-piperidin-4-yl)-amino]-acetic acid To a solution of the product of step 4 in Example 500 (209 mg, 0.353 mmol) in dioxane (5 mL) and water (2.5 mL) was added lithium hydroxide (59 mg, 1.41 mmol). The reaction was allowed to stir at rt 24 h, was concentrated and purified by reverse-phase HPLC (water, acetonitrile, formic acid gradient) to afford the titled compound (44 mg, 22%) as a white solid.

$^1$H-NMR (CDCl$_3$, 300 MHz) δ: 1.49 (s, 6 H), 1.69 (d, 2 H), 2.05 (d, 2 H), 2.28–2.53 (m, 5 H), 2.82 (m, 3 H), 3.14–3.20(4 H), 4.06 (s, 2 H), 5.18–5.36 (brd, 2 H), 6.12 (t, 1 H), 6.76 (d, 1 H), 7.25 (dd, 1 H), 7.32–7.40 (m, 2 H), 7.45–7.51 (m, 4 H), 7.78 (dd, 1 H), 8.49 (dd, 1 H). MS m/z: 576 (M+1).

Example 502

S-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol Step 1

To a dry, 2 L 2-neck, round-bottom flask equipped with a magnetic stirrer, a condenser, and a large 10° C. water bath was added 4-oxo-piperidine-1-carboxylic acid tert-butyl ester (125 g, 628 mmol) and anhydrous tetrahydrofuran (1 L). To the resulting yellow solution was added methyl iodide (85 mL, 1365 mmol). Sodium t-butoxide (150 g, 1560 mmol) was then added portionwise over 30 minutes. An exotherm was detected, especially at the beginning of the addition. The reaction mixture did warm to a gentle reflux, the rate was controlled by the speed of addition of base. The mixture was stirred an additional 30 minutes. The solvent was removed in vacuo. The oily residue was treated with NH$_4$Cl/water (500 mL), and extracted with ether (3×200 mL). The combined organics were washed with brine, dried over Na$_2$SO$_4$, and filtered through a short plug of silica gel. The solvent was removed in vacuo, and the resulting yellow oil had started to crystallize. It was left under high vacuum overnight. The mixture was slurried in hexane (50–100 mL) and sonicated for one minute. The yellow solid was collected by filtration and washed with hexane (100 mL). The first crop of 3,3-dimethyl-4-oxo-piperidine-1-carboxylic acid tert-butyl ester yielded a yellow solid. (See, preparation of (37) in Vice, S. et al., *J. Org. Chem.*, 66:2487–2492 (2001).)

$^1$H-NMR (CDCl$_3$, 300 MHz) δ: 1.13 (s, 6 H), 1.49 (s, 9 H), 2.49 (t, 2 H), 3.43 (br s, 2 H), 3.73 (t, 2 H).

Step 2

A 2-neck, 2-L round bottom flask was fitted with 2 125 mL dropping funnels and a stir bar. The assembly was flame-dried under dry nitrogen. The flask was charged with THF (700 mL) and 4-bromo-chlorobenzene (33.7 g, 176 mmol, 2.5 eq.). The resulting solution was cooled to −78° C. in a dry ice/acetone bath. To one of the dropping funnels was added butyllithium (2.5 M in hexanes, 70 mL, 175 mmol, 2.5 eq) via canula. The butyllithium solution was slowly added to the cold THF solution over 1 h. Stirring continued for an additional 0.5 h affording a white suspension. A solution of 3,3-dimethyl-4-oxo-piperidine-1-carboxylic acid tert-butyl ester (16.0 g, 70.5 mmol, 1 eq.) in THF (100 mL) was prepared and added to the reaction mixture via the second dropping funnel over 1.75 h. The resulting mixture was stirred at −78° C. for 2 h, at which time reaction appears to be essentially complete by TLC analysis. Saturated aqueous NH$_4$Cl (150 mL) was added and the reaction was allowed to warm to rt. Water (150 mL) was added and the mixture extracted with ethyl acetate (2+1 L). The combined extracts were washed with water and brine, dried over magnesium sulfate, filtered and concentrated. The solid residue was triturated with ethyl acetate and filtered. The supernatant was concentrated and triturated with ether. The resulting supernatant was then triturated with ether/petroleum ether. The resulting solids were combined to afford 4-(4-Chloro-phenyl)-4-hydroxy-3,3-dimethyl-piperidine-1-carboxylic acid tert-butyl ester (17.52 g, 51.6 mmol, 73%) as an off-white solid.

$^1$H-NMR (CDCl$_3$, 300 MHz) δ: 0.82 (s, 6 H), 1.34–1.44 (m, 2 H), 1.49 (s, 9 H), 2.67 (ddd, 1 H), 3.10–3.70 (m, 3 H), 4.00–4.30 (m, 1 H), 7.31 (d, 2 H), 7.39 (d, 2 H).

Step 3

To a cooled (0° C.) solution of the compound prepared in step 2 (10.42 g, 30.7 mmol) in methylene chloride (300 mL) was slowly added trifluoroacetic acid (60 mL) over 1.25 h. The resulting yellow solution was stirred at 0° C. for an additional 1.5 h. The mixture was concentrated under reduced pressure and the residue dissolved in ethyl acetate (1.2 L), washed with aqueous sodium hydroxide (1 N, 150 mL). The aqueous layer was extracted with additional ethyl acetate (200 mL) and the combined extracts were washed with brine, dried over sodium sulfate, filtered and concentrated. The resulting solid residue was triturated with ether to afford 4-(4-chloro-phenyl)-3,3-dimethyl-piperidin-4-ol (6.94 g, 29.0 mmol, 94%) as an off-white solid.

$^1$H-NMR (CD$_3$OD, 300 MHz) δ: 0.73 (s, 3 H), 0.85 (s, 3 H), 1.42 (ddd, 1 H), 2.36 (d, 1 H), 2.61 (ddd, 1 H), 2.91 (br dd, 1 H), 3.08–3.19 (m, 2 H), 7.26–7.32 (m, 2 H), 7.44–7.50 (m, 2 H). MS m/z: 240 (M+1).

Step 4

A visibly clean 5 L, 3-neck flask was fitted with an overhead stirrer and flushed with nitrogen for 20 min. 4-(4-Chloro-phenyl)-3,3-dimethyl-piperidin-4-ol (202 g, 843 mmol), L-(+)-tartaric acid (114 g, 759 mmol) and 4040 mL of a 9:1 butanone:water mixture were added to the flask. The mixture was heated to reflux. Water (202 mL) was added portionwise over 45 min (ratio of butanone to water: 6:1) to fully dissolve the solid mixture. Reflux was continued an additional 45 min, the heat source was then turned off and the flask allowed to cool slowly to rt overnight. Solids were removed under suction filtration and dried 3 d in vacuo to afford S-enantiomer (134.4 g, 41%) as the L-(+) tartrate salt.

The above salt was partitioned between 1 M NaOH and methylene chloride (brine washed and sodium sulfate-dried) to afford the free base.

$^1$H-NMR (CD$_3$OD, 300 MHz) δ: 0.73 (s, 3 H), 0.85 (s, 3 H), 1.42 (ddd, 1 H), 2.36 (d, 1 H), 2.61 (ddd, 1 H), 2.91 (br dd, 1 H), 3.08–3.19 (m, 2 H), 7.26–7.32 (m, 2 H), 7.44–7.50 (m, 2 H). MS m/z: 240 (M+1).

Step 5

To a solution of the homochiral product of step 4 (2.40 g, 10 mmol) in acetonitrile (80 mL) and water (20 mL) was added potassium carbonate (1.39 g, 10 mmol) followed by 2-[5-(3-bromo-propylidene)-5,11-dihydro-10-oxa-1-aza-dibenzo[a,d]cyclohepten-7-yl]-propan-2-ol (2.49 g, 6.67 mmol). The biphasic mixture was stirred at rt 48 h. Acetonitrile was removed by rotary evaporation and the resulting slurry was partitioned between ethyl acetate and brine. The organic phase was dried over magnesium sulfate, filtered and concentrated to afford an oily solid which was purified by silica gel chromatography (methylene chloride—90/10 methylene chloride/methanol gradient) to afford the title compound as an off-white powder (2.63 g, 74%).

$^1$H-NMR (CD$_3$OD, 300 MHZ) δ: 0.71 (s, 3 H), 0.84 (s, 3 H), 1.4–1.55 (m, 9 H), 2.18–2.81 (m, 9 H), 5.15–5.40 (br s, 2 H), 6.23 (t, 1 H), 6.74 (d, 1 H), 7.23–7.31 (m, 3 H), 7.42–7.50 (m, 4 H), 7.80 (dd, 1 H), 8.47 (dd, 1 H). MS m/z: 533 (M+1).

Example 503

R-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol Step 1

Racemic 4-(4-chloro-phenyl)-3,3-dimethyl-piperidin-4-ol (0.500 g, 2.086 mmol) was dissolved in minimal hot isopropyl alcohol (ca. 5 mL). The hot solution was filtered through a plug of cotton and transferred to a solution of (1S)-(+)-10-camphorsulfonic acid (0.484 g, 2.086 mmol) in isopropyl alcohol (ca. 3 mL). The mixture was stirred vigorously for several minutes, during which a thick precipitate forms, and allowed to cool to rt over 0.25 h. The solids were removed by suction filtration and dried in vacuo.

The dried salt was dissolved in hot isopropyl alcohol (ca. 50 mL), filtered thorugh a cotton plug, and allowed to slowly cool to rt, undisturbed, overnight. The solids that formed on cooling (95 mg, 19% of theoretical) were removed by suction filtration and shown by analytical HPLC to be enantiomerically pure. The salt was suspended in ethyl acetate and neutralized with sodium hydroxide (1 N). The homogenous organic phase was washed with water and brine, dried over sodium sulfate, filtered and dried to afford R-4-(4-chloro-phenyl)-3,3-dimethyl-piperidin-4-ol.

$^1$H-NMR (CD$_3$OD, 300 MHz) δ: 0.73 (s, 3 H), 0.85 (s, 3 H), 1.42 (ddd, 1 H), 2.36 (d, 1 H), 2.61 (ddd, 1 H), 2.91 (br dd, 1 H), 3.08–3.19 (m, 2 H), 7.26–7.32 (m, 2 H), 7.44–7.50 (m, 2 H). MS m/z: 240 (M+1).

Step 2

The titled compound was prepared following the procedure in step 5 of Example 502, substituting S-4-(4-chloro-phenyl)-3,3-dimethyl-piperidin-4-ol for R-4-(4-chloro-phenyl)-3,3-dimethyl-piperidin-4-ol.

$^1$H-NMR (CD$_3$OD, 300 MHz) δ: 0.71 (s, 3 H), 0.84 (s, 3 H), 1.4–1.55 (m, 9 H), 2.18–2.81 (m, 9 H), 5.15–5.40 (br s, 2 H), 6.23 (t, 1 H), 6.74 (d, 1 H), 7.23–7.31 (m, 3 H), 7.42–7.50 (m, 4 H), 7.80 (dd, 1 H), 8.47 (dd, 1 H). MS m/z: 533 (M+1).

Example 504

S-1-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yl)-ethanone To a solution of S-4-(4-chloro-phenyl)-3,3-dimethyl-piperidin-4-ol (180 mg, 0.75 mmol) in acetonitrile/water (4/1) was added potassium carbonate (120 mg, 0.86 mmol), followed by 1-[5-(3-bromo-propylidene)-5,11-dihydro-10-oxa-1-aza-dibenzo[a,d]cyclohepten-7-yl]-ethanone (214 mg, 0.6 mmol). The reaction mixture was stirred at 50° C. for 8 hours and then concentrated in vacuo. The resulting residue was treated with water and extracted with ethyl acetate. Solvent was evaporated from the combined dried (MgSO$_4$) organic extracts, and the residue was purified by column chromatography on silica gel using methylene chloride-methanol (96:4) to afford the title compound (217 mg, 70%).

$^1$H-NMR (CDCl$_3$) δ: 0.6–0.9 (6H, d), 1.2–1.6 (4H, m), 2.2–2.4 (4H, m), 2.55 (3H, s), 2.8 (2H, d), 5.3 (2H, brs), 6.25 (1H, t), 6.85 (1H, d), 7.27–7.4 (6H, m), 7.6–7.8 (2H, m), 8.0 (1H,d), 8.5 (1H, d). MS m/z: 517 (M+1).

Example 505

R-1-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yl)-ethanone To a solution of R-4-(4-chloro-phenyl)-3,3-dimethyl-piperidin-4-ol (100 mg, 0.417 mmol) in acetonitrile/water (4/1) was added potassium carbonate (57 mg, 0.413 mmol), followed by 1-[5-(3-bromo-propylidene)-5,11-dihydro-10-oxa-1-aza-dibenzo[a,d]cyclohepten-7-yl]-ethanone (100 mg, 0.279 mmol). The reaction mixture was stirred at 50° C. for 8 hours and then concentrated in vacuo. The resulting residue was treated with water and extracted with ethyl acetate. Solvent was evaporated from the combined dried (MgSO$_4$) organic extracts, and the residue was purified by column chromatography on silica gel using methylene chloride-methanol (96:4) to afford the titled compound (102 mg, 71%).

$^1$H-NMR (CDCl$_3$) δ: 0.6–0.9 (6H, d), 1.2–1.6 (4H, m), 2.2–2.4 (4H, m), 2.55 (3H, s), 2.8 (2H, d), 5.3 (2H, brs), 6.25 (1H, t), 6.85 (1H, d), 7.27–7.4 (6H, m), 7.6–7.8 (2H, m), 8.0 (1H,d), 8.5 (1H, d). MS m/z: 517 (M+1).

Example 506

Acetic acid 2-(5-{3-[4-(4-chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-ethyl ester To a solution of 5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-ol (64.5 mg, 0.131 mmol) in N,N-dimethylformamide (2.5 ml) was added sodium hydride (6 mg, 0.158 mmol), 60% dispersion in mineral oil, then acetic acid 2-bromo-ethyl ester (17 µl, 0.158 mmol). The reaction stirred at room temperature overnight under a nitrogen atmosphere. The reaction was quenched the following day with water and diluted with ethyl acetate. The organic layer was washed twice with water, then brine. After the organic layer was dried over magnesium sulfate the solvent was distilled off under reduced pressure to give the title compound, 132 mg (100%).

$^1$H-NMR(CDCl$_3$) δ:1.73–1.90(4H,m), 2.07–2.90(4H,s), 2.29–2.79(6H,m), 4.11–4.14(2H,bt), 4.36–4.40(2H,bt), 5.23–5.30(2H,bs), 6.10–6.15(1H,t), 6.73–6.84(3H,m), 7.24–7.39(10H,m), 7.56–7.59(1H,dd), 8.47–8.50(1H,dd). MS m/z: 577 (M).

Example 507

4-(4-Chloro-phenyl)-1-{3-[7-(2-hydroxy-ethoxy)-11H-10-oxa-1-aza-dibenzo[a,d]cyclohepten-5-ylidene]-propyl}-3,3-dimethyl-piperidin-4-ol To a solution of 75.8 mg (0.1314 mmol) Acetic acid 2-(5-{3-[4-(4-chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-ethyl ester (example 10) in ethanol (5 ml) was added a 15% sodium hydroxide in water (2 ml) solution. The reaction was heated to reflux for 30 minutes, at which time the LC/MS showed it to be complete. After cooling to room temperature the reaction was worked up by diluting with ethyl acetate and washing with water and brine. The combined aqueous layers were back extracted with ethyl acetate. The combined organics were dried over magnesium sulfate and the solvent was distilled under reduced pressure. The residue was purified by reverse phase HPLC to give the title compound (42 mg, 60%).

$^1$H-NMR(CDCl$_3$) δ: 0.821(3H.s), 0.975(3H,s), 2.56–5.64 (2H,bq), 2.68–2.74(1H,bd), 2.80–3.08(5H,m), 3.30–3.38(1H,bd), 3.62–3.67(2H,t), 4.04–4.08(2H, t), 5.19–5.32(2H,bs), 5.94–6.00(1H,t), 6.79–6.87(4H,m), 7.26–7.40(4H,m) 7.56–7.60(1H,bd), 8.35–8.37(1H,s), 8.50–8.53(1H,dd) MS m/z: 535 (M)

Example 508

4-(4-Chloro-phenyl)-1-{3-[7-(2-methoxy-ethoxy)-11H-10-oxa-1-aza-dibenzo[a,d]cyclohepten-5-ylidene]-propyl}-3,3-dimethyl-piperidin-4-ol The titled compound was prepared by following the procedure of Example 506, but replacing acetic acid 2-bromo-ethyl ester with 1-Bromo-2-methoxy-ethane. The residue was purified by reverse phase HPLC to give the title compound (27 mg, 39%).

$^1$H-NMR(CDCl$_3$) δ: 0.79–0.085(3H,s), 0.95–1.03(3H,s), 2.55–3.12(8H,m), 3.28–3.45(2H,m), 3.48(3H,bs), 3.70–3.78 (2H,bs), 4.06–4.13(2H,bs), 5.18–5.28(2H, bs), 5.92–6.01 (1H,bt), 6.75–6.88(3H,m), 7.25–7.43(4H,m), 7.55–7.63(1H, bd), 8.48–8.55(2H, bd) MS m/z: 549 (M)

Example 509

5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-ol The titled compound was prepared following the procedure in step 5 of Example 502, substituting 5-(3-bromo-propylidene)-5,11-dihydro-10-oxa-1-aza-dibenzo[a,d]cyclo-hepten-7-ol for 2-[5-(3-bromo-propylidene)-5,11-dihydro-10-oxa-1-aza-dibenzo[a,d]-cyclohepten-7-yl]-propan-2-ol and racemic piperidine for the S-piperidine.

$^1$H-NMR (CDCl$_3$, 300 MHz) δ: 0.74 (s, 3 H), 0.88 (s, 3 H), 1.45 (m, 1 H), 2.20–2.54 (m, 7 H), 2.66–2.77 (m, 2 H), 5.27 (br s, 2 H), 6.11 (t, 1 H), 6.67 (dd, 1 H), 6.74–6.79 (m, 2 H), 7.25–7.31 (m, 3 H), 7.36–7.42 (m, 2 H), 7.59 (d, 1 H), 8.50 (dd, 1 H). MS m/z: 491 (M+1).

Example 510

2-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-2-methyl-propionic acid ethyl ester To a cooled (0° C.) solution of 5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-ol (250 mg, 0.51 mmol) in dimethylformamide (7 mL) was added sodium hydride (60% dispersion in oil, 31 mg, 0.76 mmol). The resulting mixture was stirred at 0° C. for 10 min. Ethyl 2-bromo-2-methyl propionate (149 mg, 0.76 mmol) was added. Stirring at 0° C. was continued 10 min before the mixture was warmed to rt and stirred 4 h. The reaction was then partitioned between ethyl acetate and water; the aqueous phase was back-extracted with additional ethyl acetate. The combined organic phases were washed thrice with water, brine and dried over magnesium sulfate, filtered and concentrated. The crude residue was purified by silica gel chromatography (methylene chloride—95:5 methylene chloride:methanol gradient) to afford the titled compound (233 mg, 76%).

$^1$H-NMR (CDCl$_3$, 300 MHz) δ: 0.74 (s, 3 H), 0.87 (s, 3 H), 1.27 (t, 3 H), 1.41 (d, 1 H), 1.50 (br s, 1 H), 1.55 (s, 6 H), 2.18–2.56 (m, 7 H), 2.64–2.78 (m, 2 H), 4.24 (q, 2 H), 5.27 (br s, 1 H), 6.09 (t, 1 H), 6.67–6.76 (m, 2 H), 6.87 (d, 1 H), 7.25–7.31 (m, 2 H), 7.37–7.42 (m, 2 H), 7.57 (d, 2 H), 8.01 (s, 1 H), 8.50 (d, 1 H). MS m/z: 605 (M+1).

Example 511

4-(4-Chloro-phenyl)-1-{3-[7-(2-hydroxy-1,1-dimethyl-ethoxy)-11H-10-oxa-1-aza-dibenzo[a,d]cyclohepten-5-ylidene]-propyl}-3,3-dimethyl-piperidin-4-ol To a cooled (0° C.) solution of 2-(5-{3-[4-(4-Chlorophenyl)-4-hydroxy-3,3-dimethyl-piperidin-1-yl]-propylidene}-5,11-dihydro-10-oxa-1-aza-dibenzo[a,d]cyclohepten-7-yloxy)-2-methyl-propionic acid ethyl ester (117 mg, 0.193 mmol) in tetrahydrofuran (5 mL) was added lithium aluminum hydride (1.0 M solution in tetrahydrofuran, 0.39 mL, 0.39 mmol). The reaction was allowed to stir at 0° C. for 2 h. Excess hydride was quenched by the addition of a saturated aqueous potassium/sodium tartrate solution. The mixture was stirred at rt until two clear phases formed. The mixture was diluted with ethyl acetate and shaken. The extracts were dried over magnesium sulfate, filtered and concentrated. The crude residue was purified by silica gel chromatography (methylene chloride—90:10 methylene chloride/methanol gradient) to afford the titled compound (102 mg, 94%).

$^1$H-NMR (CDCl$_3$, 300 MHz) δ: 0.74 (s, 3 H), 0.87 (s, 3 H), 1.25 (s, 6 H), 1.41 (d, 1 H), 2.18–2.55 (m, 9 H), 2.65–2.79 (m, 2 H), 3.58 (d, 2 H), 5.20–5.40 (br s, 2 H), 6.12 (t, 1 H), 6.74–6.84 (m, 2 H), 6.92 (d, 1 H), 7.25–7.32 (m, 3 H), 7.36–7.42 (m, 2 H), 7.60 (dd, 1 H), 8.51 (dd, 1 H). MS m/z: 563(M+1).

Example 512

2-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-2-methyl-propionic acid To a solution of 2-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-2-methyl-propionic acid ethyl ester (158 mg, 0.261 mmol) in methanol (3 mL) was added sodium hydroxide (1 N in water, 1 mL). Following a slight exotherm, the mixture clarified. An additional aliquot of sodium hydroxide (1 N, 1 mL) was added after 1 h and the mixture was allowed to stir an additional 1 h at rt. The solvents were evaporated under reduced pressure and the residue dissolved in water (2.5 mL). The basic solution was neutralized (pH=7) with hydrochloric acid (1 N) and the titled compound was precipitated and collected by suction filtration (86 mg, 57%).

$^1$H-NMR (CD$_3$OD, 300 MHz) δ: 0.80 (s, 3 H), 0.91 (s, 3 H), 1.47 (s, 6 H), 1.72 (d, 1 H), 2.56–2.72 (m, 2 H), 2.83–3.00 (m, 2 H), 3.15–3.24 (m, 3 H), 3.32–3.48 (m, 2 H), 5.18 (br s, 2 H), 6.04 (t, 1 H), 6.69–6.84 (m, 2 H), 6.97 (d, 1 H), 7.28–7.37 (m, 3 H), 7.40–7.47 (m, 2 H), 7.67 (dd, 1 H), 8.42 (dd, 1 h). MS m/z: 577 (M+1).

Example 513

2-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-2-methyl-propionamide To a solution of 2-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-2-methyl-propionic acid (72 mg, 0.125 mmol) in dimethyl formamide (3 mL) was added 1-(3-dimethylaminopropyl)-3-ethylcarbodiimide hydrochloride (48 mg, 0.25 mmol), 1-hydroxybenzotriazole (34 mg, 0.25 mmol), and ammonium hydroxide (170 μL, 0.50 mmol) and triethylamine (100 μL). Stir at rt 48 h. The mixture was poured into chloroform and washed with water. The organic phase was washed with additional water and brine; dried over magnesium sulfate, filtered and concentrated. The crude residue was purified by silica gel chromatography (methylene chloride—90:10 methylene chloride/methanol gradient) to yield the titled compound (22 mg, 31%).

$^1$H-NMR (CDCl$_3$, 300 MHz) δ: 0.74 (s, 3 H), 0.87 (s, 3 H), 1.42 (br d, 1 H), 1.49 (s, 6 H), 2.16–2.61 (m, 7 H), 2.63–2.78 (m, 2 H), 5.20–5.40 (br s, 2 H), 5.50 (br s, 1 H), 6.11 (t, 1 h), 6.68–6.82 (m, 3 H), 6.91 (dd, 1 H), 7.26–7.33 (m, 4 H), 7.36–7.43 (m, 2 H), 7.60 (dd, 1 H), 8.51 (dd, 1 H). MS m/z: 576 (M+1).

Example 514

(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-acetic acid methyl ester 5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-ol (0.4 g, 0.814 mmol) was dissolved in dimethyl formamide (10 mL). Sodium hydride (0.029 g, 1.22 mmol, 1.5 equiv, 48 mg of a 60% suspension in mineral oil) was added at room temperature and gas evolution was visible. Methyl bromoacetate (0.187 g, 1.22 mmol, 116 uL) was added and the mixture was stirred at room temperature. After stirring overnight at room temperature, the reaction was quenched with water (10 mL). The resulting suspension was extracted with ethyl acetate (3×10 mL). The combined ethyl acetate extracts were dried over magnesium sulfate, filtered and concentrated in vacuo to give an oil. The crude oil was purified by silica gel chromatography (methylene chloride to 10% methanol in methylene chloride gradient) to afford the title compound as a white solid (222 mg, 48%).

$^1$H-NMR (CDCl$_3$, 300 MHz) δ: 0.7 (s, 3H), 1.2 (s, 3H), 1.30–1.70 (m, 3H), 2.62–3.51 (m, 9 H), 3.82 (s, 3H), 4.55 (s, 2H), 5.22 (br s, 1H), 5.88 (t, 1H), 6.85 (m, 2H), 7.15–7.33 (m, 6H), 7.62 (d, 1H), 8.43 (d, 1H); MS m/z: 564 (M+1).

Example 515

(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-acetic acid (5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-acetic acid methyl ester (0.060 g, 0.107 mmol) was dissolved in methanol (1.5 mL). Sodium hydroxide (150 uL, 1N stock solution) was added and the resulting mixture was stirred at room temperature. After stirring overnight at room temperature, the reaction mixture was concentrated in vacuo to give a yellow oil. The oil was suspended in water (2 mL) and then washed with ethyl acetate (3×3 mL). The aqueous layer was then acidified to pH=2 and extracted with ethyl acetate (3×5 mL). The pooled organic layers were dried over magnesium sulfate, filtered and concentrated in vacuo to afford a white solid (55 mg, 94%).

¹H-NMR (CDCl₃, 300 MHz) δ: 0.8 (s, 3H), 0.92 (s, 3H), 1.12–1.31 (m, 6H), 2.68 (br d, 2H), 3.89 (m, 1H), 2.95 (d, 1H), 3.10–3.36 (m, 2H), 4.45 (s, 1H), 5.20 (br s, 2H), 5.98 (t, 1H), 6.81 (m, 2H), 6.96 (d, 1H), 7.40 (d, 2H), 7.40 (m, 3H), 7.83 (d, 1H), 8.44 (d, 1H); MS m/z: 550 (M+1).

Example 516

2-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-acetamide The title compound was prepared by following the procedure of Example 514, but replacing methyl bromoacetate with bromoacetamide. This yielded 58 mg of the title compound after chromatography (52%).

¹H-NMR (CDCl₃, 300 MHz) δ: 0.5 (br s, 6H), 0.78–2.90 (m, 10 H), 4.35 (s, 1H), 5.22 (br s, 2H), 5.74 (br s, 1H), 6.11 (br s, 1H), 6.55 (br s, 1H), 6.82 (m, 3H), 7.33 (d, 3 H), 7.25 (d, 2H), 7.65, (d, 1H), 8.55 (d, 1H); MS m/z: 549 (M+1)

Example 517

4-(4-Chloro-phenyl)-1-{3-[7-(2-hydroxy-2-methyl-propoxy)-11H-10-oxa-1-aza-dibenzo[a,d]cyclohepten-5-ylidene]-propyl}-3,3-dimethyl-piperidin-4-ol (5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yloxy)-acetic acid methyl ester (52 mg, 0.0923 mmole) was dissolved in tetrahydrofuran (2 mL). The resulting solution was cooled to ice bath temperatures and methylmagnesium bromide (0.369 mmol, 264 uL of 1.4 M solution in toluene/tetrahydrofuran) was added dropwise. The reaction was stirred for 4 hrs at ice bath temperature and then warmed to room temperature overnight. Tetrahydrofuran was removed by concentration in vacuo. The resulting solid was dissolved in ethyl acetate (10 mL) and washed with saturated ammonium chloride (10 mL). The ethyl acetate extracts were dried over magnesium sulfate, filtered and concentrated in vacuo to give an oil. The crude oil was purified by silica gel chromatography (methylene chloride to 10% methanol in methylene chloride gradient) to afford the title compound as a white solid (40 mg, 77%).

¹H-NMR (CDCl₃, 300 MHz) δ: 0.92 (d, 6H), 1.34 (s, 6H), 1.62, (br s, 2H), 2.24 (m, 9H), 3.78 (s, 2H), 6.82 (m, 3H), 7.22–7.41 (m, 7H), 7.62 (d, 11H), 8.52 (d, 1H); MS m/z: 564 (M+1)

Example 518

3-(5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-yl)propane-1,2-diol 1-[3-(Allyl-11H-10-oxa-1-aza-dibenzo[a,d]cyclohepten-5-ylidene)-propyl]-4-(4-chloro-phenyl)-3,3-dimethyl-piperidin-4-ol (0.044 g, 0.08 mmol) was dissolved THF (2 mL)/H₂O (0.5 mL) and cooled to 0° C. To the solution was added OsO₄ (1.07 mL-2.5% OsO₄ in t-butanol) and stirred at room temperature for 4 h. The reaction was diluted with sat. sodium bisulfite, the organics were removed dried over Mg₂SO₄, filtered and evaporated in vacuo, then purified by Biotage flash chromatography (5% methanol/95% methylene chloride to 7.5% methanol/92.5% methylene chloride to 15% methanol/85% methylene chloride) to yield the title compound (0.025 g, 53%). ¹H-NMR (CDCl₃): δ 0.74 (ss 3H), 0.87 (s, 3H), 1.22 (d, 1H), 1.41 (s, 1H), 1.44 (d, 1H), 2.26–2.77 (m, 9H), 3.53 (d, 1H), 3.70 (dd, 1H), 3.93 (s, 1H), 5.30 (bs, 2H), 6.14 (t, 1H), 6.79 (d, 1H), 7.02 (d, 1H), 7.16 (s, 1H), 7.27 (d, 3H), 7.37 (d, 2H), 7.58 (d, 1H), 8.48 (dd, 1H). ESI-MS m/z: 515 (M+1), retention time 1.72.

Example 519

2-(5-{3-[4-(4-Chloro-phenyl)-3-methyl-piperazin-1-yl]-propylidene}-5,11-dihydro-10-oxa-1-aza-dibenzo[a,d]cyclohepten-7-yl)-propan-2-ol Step 1: 4-(4-Chloro-phenyl)-3-methyl-piperazine-1-carboxylic acid tert-butyl ester To a solution of 3-Methyl-piperazine-1-carboxylic acid tert-butyl ester (1.0 g, 5 mmol) and 4-bromochlorobenzene (0.77 g, 4 mmol) was added sodium tert-butoxide (0.96 g, 10 mmol), palladium(1H) dibenzylideneacetone (Pd₂DBA₃, 0.09 g, 0.1 mmol), and BINAP (0.19 g, 0.3 mmol). The suspension was stirred at 120° C. for 10 hours. The reaction was filtered through celite and evaporated in vacuo. The residue was purified by silica gel chromatography (hexane→ethyl acetate) to yield 0.84 g (68%) of the title compound. ¹H-NMR (CDCl₃): δ 1.00 (3H, m), 1.74 (9H, s), 3.10 (3H, m), 3.30 (1H, m), 3.80 (2H, m), 4.10 (1H, brs), 6.85 (2H, d), 7.20 (2H, d).

Step 2: 1-(4-Chloro-phenyl)-2-methyl-piperazine 4-(4-Chloro-phenyl)-3-methyl-piperazine-1-carboxylic acid tert-butyl ester (0.83 g, 0.68 mmol) was dissolved in HCl/dioxane (4M, 8 mL) and stirred for 2 hr at rt. The mixture was then evaporated in vacuo, basified with aqueous sodium hydroxide (1M, 50 mL), and extracted with ethyl acetate (3×100 mL). The organic layers were evaporated and the crude residue used in the next step, (0.56 g, brown oil).

Step 3: 2-(5-{3-[4-(4-Chloro-phenyl)-3-methyl-piperazin-1-yl]-propylidene}-5,11-dihydro-10-oxa-1-aza-dibenzo[a,d]cyclohepten-7-yl)-propan-2-ol A solution of 2-[5-(3-Bromo-propylidene)-5,11-dihydro-10-oxa-1-aza-dibenzo[a,d]cyclohepten-7-yl]-propan-2-ol (0.24 g, 0.64 mmol) in isopropanol (5 mL) was treated with 1-(4-Chloro-phenyl)-2-methyl-piperazine (0.25 g, 1.2 mmol) and catalytic potassium iodide. The solution was stirred at 80° C. for 5 hr, and evaporated in vacuo. The residue was purified by silica gel chromatography (ethyl acetate→87:10:3 ethyl acetate/methanol/triethylamine) to yield 0.22 g (69%) of the title compound, ¹H-NMR (CDCl₃) δ: 1.00 (3H, m), 1.60 (6H, s), 2.20–2.70 (8H, m), 3.10 (2H, m), 3.75 (1H, m), 5.30 (2H, brs), 6.12 (1H, t), 6.87(4H, d), 7.18–7.32 (3H, m), 7.45 (1H, s), 7.70 (1H, d), 8.55 (1H, d). ESI-MS m/z: 504 [M+1].

The freebase was converted to the formate salt with formic acid/methanol. CHN passed, 0.4 formic acid.

Example 520

2-(5-{3-[6-chloro-1,2-dihydro-2-oxo-spiro[4H-3,1-benzoxazin-4,4'-piperidin]-1-yl]-propylidene}-5,11-dihydro-10-oxa-1-aza-dibenzo[a,d]cyclohepten-7-yl)-propan-2-ol A solution of 6-chloro-1,2-dihydro-2-oxo-spiro[4H-3,1-benzoxazin-4,4'-piperidine] (Made by the procedure of Bock, et al. GB2,355,465, 0.25 g, 0.7 mmol) in isopropanol (5 mL) was treated with 2-[5-(3-Bromo-propylidene)-5,11-dihydro-10-oxa-1-aza-dibenzo[a,d]cyclohepten-7-yl]-propan-2-ol (0.19 g, 0.50 mmol) and catalytic potassium iodide. The solution was stirred at 80° C. for 5 hr, and evaporated in vacuo. The residue was purified by reverse-phase preparative HPLC to yield 0.029 g (10%) of the title compound, $^1$H-NMR (CD$_3$OD) δ: 1.50 (3H, s), 2.18 (2H, brs), 2.95–3.2 (6H, m), 5.30 (2H, brs), 6.18 (1H, t), 6.79(1H, m), 6.92 (1H, m), 7.12 (1H, m), 7.38 (2H, m), 7.48 (2H, m), 7.81 (2H, m), 8.31 (1H, m), 8.55 (1H, d).

ESI-MS m/z: 546 [M+1].

Example 521

2-(5-{3-[4-(2-Chloro-phenyl)-4-methyl-piperidin-1-yl]-propylidene}-5,11-dihydro-10-oxa-1-aza-dibenzo[a,d]cyclohepten-7-yl)-propan-2-ol Step 1: 1-Benzyl-4-methyl-piperidin-4-ol A solution of 1-benzyl-4-piperidone (4.9 mL, 26.5 mmol) in anhydrous diethyl ether (50 mL) was cooled to −78° C. and treated with methyllithium (1.4 M, 21 mL, 29 mmol). This mixture was stirred for 2.5 hr at −78° C., then quenched with aqueous brine, and extracted with ethyl acetate (3×100 mL). The combined organics were dried over sodium sulfate and evaporated in vacuo. The residue was purified by silica gel chromatography (CH$_2$Cl$_2$→90:10:1 CH$_2$Cl$_2$/methanol/NH$_4$OH) to yield 4.5 g (83%) of the title compound, ESI-MS m/z: 206 [M+1].

Step 2: 1-Benzyl-4-(2-chloro-phenyl)-4-methyl-piperidine

A solution of 1-Benzyl-4-methyl-piperidin-4-ol (4.5 g, 22 mmol) in chlorobenzene (60 mL) was treated with anhydrous AlCl$_3$ (15 g, 110 mmol). This mixture was stirred for 3 hr at reflux, then quenched into ice (250 g), basified with sodium hydroxide, and extracted with ethyl acetate (3×100 mL). The combined organics were dried over sodium sulfate and evaporated in vacuo. The residue was purified by silica gel chromatography (CH$_2$Cl$_2$→90:10 CH$_2$Cl$_2$/methanol) to yield 0.59 g (10%) of the title compound, ESI-MS m/z: 300 [M+1].

Step 3: 4-(2-Chloro-phenyl)-4-methyl-piperidine

A solution of 1-benzyl-4-(2-chloro-phenyl)-4-methyl-piperidine (0.59 g, 1.95 mmol) in 1,2-dichloroethane (10 mL) was treated with 1-chloroethyl chloroformate (0.28 mL, 2.6 mmol). This mixture was stirred for 12 hr at reflux, then evaporated in vacuo. The residue was redissolved in methanol (10 mL) and heated to reflux for 1 hr, then evaporated in vacuo. The resulting brown solid (the hydrochlorie salt) was washed with ethyl acetate, then freebased with ethyl acetate/sodium hydroxide to yield 0.30 g (72%) of the title compound, ESI-MS m/z: 246 [M+1].

Step 4: 2-(5-{3-[4-(2-Chloro-phenyl)-4-methyl-piperidin-1-yl]-propylidene}-5,11-dihydro-10-oxa-1-aza-dibenzo[a,d]cyclohepten-7-yl)-propan-2-ol A solution of 4-(2-Chloro-phenyl)-4-methyl-piperidine (0.29 g, 1.38 mmol) in isopropanol (5 mL) was treated with 2-[5-(3-Bromo-propylidene)-5,11-dihydro-10-oxa-1-aza-dibenzo[a,d]cyclohepten-7-yl]-propan-2-ol (0.19 g, 0.50 mmol) and catalytic potassium iodide. The solution was stirred at 80° C. for 12 hr, and evaporated in vacuo. The residue was purified by silica gel chromatography (ethyl acetate→87:10:3 ethyl acetate/methanol/triethylamine) to yield 0.062 g (25%) of the title compound, $^1$H-NMR (CDCl$_3$) ∂: 1.10 (3H, s), 1.58 (6H, s), 1.78 (2H, m), 1.90 (1H, m), 2.10 (2H, m), 2.40 (8H, m), 5.30 (2H, brs), 6.18 (1H, t), 6.79(1H, m), 6.92 (1H, m), 7.19–7.39 (6H, m), 7.42 (1H, m), 7.55 (1H, m), 8.55 (1H, d).

ESI-MS m/z: 503 [M+1].

Example 522

4-(4-Chloro-phenyl)-1-{3-[7-(2-hydroxy-2-methyl-propoxy)-11H-10-oxa-1-aza-dibenzo[a,d]cyclohepten-5-ylidene]-propyl}-3-methyl-piperidin-4-ol Step 1: (5-{3-[4-(4-Chloro-phenyl)-4-hydroxy-3-methyl-piperidin-1-yl]-propylidene}-5,11-dihydro-10-oxa-1-aza-dibenzo[a,d]cyclohepten-7-yloxy)-acetic acid methyl ester A solution of 5-{3-[4-(4-Chloro-phenyl)-4-hydroxy-3-methyl-piperidin-1-yl]-propylidene}-5,11-dihydro-10-oxa-1-aza-dibenzo[a,d]cyclohepten-7-ol (0.14 g, 0.28 mmol) in dimethylformamide (3 mL) was treated with sodium hydride (60% in mineral oil, 0.016 g, 0.4 mmol) and methyl bromoacetate (0.038 mL, 0.4 mmol). The mixture was allowed to stir at rt for 2 hr, then quenched with aqueous brine, and extracted with ethyl acetate (3×10 mL). The combined organics were washed several time with water, dried over sodium sulfate, and evaporated in vacuo. The residue was purified by silica gel chromatography (ethyl acetate→487:10:3 ethyl acetate/methanol/triethylamine) to yield 0.07 g (50%) of the title compound, ESI-MS m/z: 549 [M+1].

Step 2: 4-(4-Chloro-phenyl)-1-{3-[7-(2-hydroxy-2-methyl-propoxy)-11H-10-oxa-1-aza-dibenzo[a,d]cyclohepten-5-ylidene]-propyl}-3-methyl-piperidin-4-ol A solution of (5-{3-[4-(4-Chloro-phenyl)-4-hydroxy-3-methyl-piperidin-1-yl]-propylidene}-5,11-dihydro-10-oxa-1-aza-dibenzo[a,d]cyclohepten-7-yloxy)-acetic acid methyl ester (0.07 g, 0.13 mmol) in THF (3 mL) was treated with methylmagnesium bromide (3M, 0.15 mL, 0.45 mmol). The solution was stirred at rt for 2 hr, and quenched with brine. The aqueous residue was extracted with ethyl acetate (3×10 mL), and the combined organics were evaporated in vacuo. The residue was purified by silica gel chromatography (ethyl acetate→87:10:3 ethyl acetate/methanol/triethylamine) to yield 0.038 g (50%) of the title compound, $^1$H-NMR (CDCl$_3$) ∂: 0.6 (3H, s), 1.37 (6H, s), 1.66 (2H, m), 1.99–2.80 (9H, m), 3.78 (2H, s), 5.30 (2H, brs), 6.18 (1H, t), 6.79–6.89 (3H, m), 6.92 (1H, m), 7.25–7.45 (6H, m), 7.55 (1H, m), 8.55 (1H, d).

ESI-MS m/z: 549 [M+1].

Example 523

4-(4-Chloro-phenyl)1-{3-[7-(1-hydroxy-1-methyl-ethyl)-1-oxy-11H-10-oxa-1-aza-dibenzo[a,d]cyclohepten-5-ylidene]-propyl}-3,3-dimethyl-piperidin-4-ol Step 1: 1-[5-(3-Bromo-propylidene)-1-oxy-5,11-dihydro-10-oxa-1-aza-dibenzo[a,d]cyclohepten-7-yl]-ethanone A solution of 1-[5-(3-Bromo-propylidene)-5,11-dihydro-10-oxa-1-aza-dibenzo[a,d]cyclohepten-7-yl]-ethanone (1.5 g, 4.2 mmol) in CH$_2$Cl$_2$ (10 mL) was treated with m-chloroperbenzoic acid (77%, 1.2 g, 5.0 mmol). The mixture was allowed to stir at rt for 12 hr, then quenched with aqueous brine and extracted with CH$_2$Cl$_2$ (3×30 mL). The combined organics were dried over sodium sulfate and evaporated in vacuo. The resulting brown foam, 1.5 g (95%), was carried on to the next step crude. ESI-MS m/z: 374 [M+1].

Step 2: 1-(5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cyclohepten-7-yl)-ethanone A solution of 1-[5-(3-Bromo-propylidene)-1-oxy-5,11-dihydro-10-oxa-1-aza-dibenzo[a,d]cyclohepten-7-yl]-ethanone (1.4 g, 3.8 mmol) in acetonitrile/water (12 mL/3 mL) was treated with 4-(4-Chloro-phenyl)-3,3-dimethyl-piperidin-4-ol (1.0 g, 4.2 mmol) and potassium carbonate (1.1 g, 7.6 mmol). The suspension was stirred at rt for 72 hr, and evaporated in vacuo. The residue was purified by silica gel chromatography (ethyl acetate→87:10:3 ethyl acetate/methanol/triethylamine) to yield 1.2 g (58%) of the title compound, ESI-MS m/z: 533 [M+1].

Step 3: 4-(4-Chloro-phenyl)-1-{3-[7-(1-hydroxy-1-methyl-ethyl)-1-oxy-11H-10-oxa-1-aza-dibenzo[a,d]cyclohepten-5-ylidene]-propyl}-3,3-dimethyl-piperidin-4-ol A solution of 1-(5-{3-[4-(4-Chloro-phenyl)-4-hydroxy-3,3-dimethyl-piperidin-1-yl]-propylidene}-1-oxy-5,11-dihydro-10-oxa-1-aza-dibenzo[a,d]cyclohepten-7-yl)-ethanone (0.43 g, 0.81 mmol) in THF (3 mL) was treated with methylmagnesium bromide (1.4M, 0.74 mL, 1.0 mmol). The solution was stirred at rt for 48 hr, and quenched with brine. The aqueous residue was extracted with ethyl acetate (3×10 mL), and the combined organics were evaporated in vacuo. The residue was purified by silica gel chromatography (ethyl acetate→87:10:3 ethyl acetate/methanol/triethylamine) to yield 0.10 g (25%) of the title compound, $^1$H-NMR (CDCl$_3$) a: 0.6 (3H, s), 0.9 (3H, s), 1.55 (6H, s), 1.99–2.80 (10H, m), 5.30 (2H, brs), 6.18 (1H, br), 6.89 (1H, m), 7.25–7.45 (7H, m); 7.50 (1H, m), 8.55 (1H, d).

ESI-MS m/z: 549 [M+1].

Example 524

(R)-2-[5-(3-{3-[(4-Chloro-benzyl)-ethyl-amino]-pyrrolidin-1-yl}-propylidene)-5,11-dihydro-10-oxa-1-aza-dibenzo[a,d]cyclohepten-7-yl]-propan-2-ol (R)-Pyrrolidin-3-yl-carbamic acid tert-butyl ester (7.85 g, 42.1 mmol) was dissolved in methylene chloride at 0° C. and triethylamine (11.72 mL, 84.3 mmol) and ethyl chloroformate (8.06 mL, 84.3 mmol) were added. The solution was warmed to room temperature and stirred for 30 min, the reaction was washed with NaHCO$_3$. The organics were combined and dried over MgSO$_4$, filtered and evaporated in vacuo. The residue was purified by Isco flash system (70% hexane/30% ethyl acetate) to yield the ester (7.73 g, 71%).

Part 2:
(R)-3-tert-Butoxycarbonylamino-pyrrolidine-1-carboxylic acid ethyl ester (7.73 g, 29.9 mmol) was dissolved in 4M HCl/dioxane. The solution was stirred at rt for 1 h. The solvent was removed in vacuo and the mixture was carried on to the next step without further purification as the hydrochloride salt.

Part 3:
(R)-3-Amino-pyrrolidine-1-carboxylic acid ethyl ester and acetaldehyde (1.76 mL, 31.43 mmol) were mixed with sodium triacetoxyborohydride (9.54 g, 45 mmol) in dichloroethane (200 mL) containing acetic acid (1%) and the resulting mixture was stirred at room temperature overnight. The reaction mixture was diluted with CH$_2$Cl$_2$ and washed with 1 N NaOH solution and brine and dried over magnesium sulfate. The reaction was concentrated in vacuo. The residue was used directly in the next reaction (4.0 g, 72%).

Part 4:
(R)-3-Ethylamino-pyrrolidine-1-carboxylic acid ethyl ester (1.00 g, 5.4 mmol) was dissolved in acetonitrile (100 mL) and potassium carbonate (3.7 g, 27 mmol), KI (0.050 mg) and 1-bromomethyl-4-chloro-benzene (1.1 g, 5.4 mmol) were added. The solution was heated at 60° C. for 20 h. The reaction mixture was filtered and concentrated in vacuo. The residue was purified by Isco flash system (75% hexane/25% ethyl acetate) to yield coupled product (0.410 g, 25%).

Part 5:
(R)-3-[(4-Chloro-benzyl)-ethyl-amino]-pyrrolidine-1-carboxylic acid ethyl ester (4.00 g, 1.29 mmol) was dissolved in 15 mL of ethanol and potassium hydroxide (1.5 g, 26.7 mmol) in water (8 mL) was added. The solution was heated to reflux for 14 h and the ethanol was removed in vacuo. The residue was partitioned between water and methylene chloride. The organics were removed and washed with sat'd solution of NaHCO$_3$ and brine, then dried over magnesium sulfate. The reaction was concentrated in vacuo (0.253 g, 82%).

Part 6:
To a solution of the (R)-(4-chloro-benzyl)-ethyl-pyrrolidin-3-yl-amine (0.253 g, 1.06 mmol) in isopropanol was added 2,6-lutidine (0.225 g, 2.1 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.224 g, 0.6 mmol), added in portions over 1 h. The solution was then stirred at 80° C. for an additional 14 h. The reaction was concentrated in vacuo, then purified by Isco flash chromatography (15% methanol/85% methylene chloride) to yield the title compound (0.100 g, 31%). $^1$H-NMR (MeOD): δ 0.94 (t, 3H), 1.40 (s, 6H), 1.88–2.01 (m, 1H), 2.02–2.18 (m, 1H), 2.42–2.67 (m, 4H), 3.03–3.36 (m, 7H), 3.56 (d, 1H), 3.72 (d, 1H), 5.16 (bs, 2H), 6.03 (t, 1H), 6.77 (d, 1H), 7.22–7.37 (m, 4H), 7.38–7.47 (m, 2H), 7.69 (d, 1H), 8.30 (s, 1H), 8.37 (dd, 1H). ESI-MS m/z: 534 (M+1), retention time 1.22.

Example 525

(R)-2-[5-(3-{3-[(4-Chloro-phenyl)-ethyl-amino]-pyrrolidin-1-yl}-propylidene)-5,11-dihydro-10-oxa-1-aza-dibenzo[a,d]cyclohepten-7-yl]-propan-2-ol Part 1:
(R)-3-Ethylamino-pyrrolidine-1-carboxylic acid ethyl ester (2.0 g, 10.8 mmol) and 1-bromo-4-chloro-benzene (2.06 g, 10.8 mmol) was dissolved in toluene along with sodium t-butoxide (1.45 g, 15.12 mmol), Pd$_2$(dba)$_3$ (0.195 g, 0.21 mmol) and BINAP (0.13 g, 0.21 mmol). The solution was heated to 100° C. for 2 days, then filtered, and the reaction was concentrated in vacuo, and then purified by Isco flash chromatography (50% ethyl acetate/50% hexane) to yield the product (0.536 g, 17%).

Part 2:
(R)-3-[(4-Chloro-phenyl)-ethyl-amino]-pyrrolidine-1-carboxylic acid ethyl ester (0.536 g, 1.8 mmol) was dissolved in 15 mL of ethanol and potassium hydroxide (2.05 g, 36.2 mmol) in water (8 mL) was added. The solution was heated to reflux for 14 h and the ethanol was removed in vacuo. The residue was partitioned between water and methylene chloride. The organics were removed and washed with sat'd solution of NaHCO$_3$ and brine, then dried over magnesium sulfate. The reaction was concentrated in vacuo (0.273 g, 67%).

Part 3:

To a solution of the (R)-(4-Chloro-phenyl)-ethyl-pyrrolidin-3-yl-amine (0.270 g, 1.2 mmol) in isopropanol was added 2,6-lutidine (0.20 g, 1.7 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.180 g, 0.48 mmol), added in portions over 1 h. The solution was then stirred at 80° C. for an additional 14 h. The reaction was concentrated in vacuo, then purified by Isco flash chromatography (15% methanol/85% methylene chloride) to yield the title compound (0.180 g, 72%). $^1$H-NMR (CDCl$_3$): δ 1.08 (t, 3H), 1.54 (s, 6H), 1.68–1.92 (m, 2H), 2.08–2.25 (m, 1H), 2.36–2.92 (m, 7H), 3.26 (q, 2H), 42.8 (t, 1H), 5.29 (bs, 2H), 6.12 (t, 1H), 6.74 (d, 2H), 6.82 (d, 1H), 7.08 (d, 2H), 71.3–7.31 (m, 2H), 7.44 (s, 1H), 7.52 (d, 1H), 8.48 (dd, 1H). ESI-MS m/z: 520 (M+1), retention time 2.01.

Example 526

(R)-2-{5-[3-(3-{[(4-Chloro-benzyl)-ethyl-amino]-methyl}-pyrrolidin-1-yl)-propylidene]5,11-dihydro-10-oxa-1-aza-dibenzo[a,d]cyclohepten-7-yl}-propan-2-ol Part 1:

(R)-3-Aminomethyl-pyrrolidine-1-carboxylic acid tert-butyl ester (0.385 g, 1.92 mmol) and 1-bromomethyl-4-chloro-benzene (0.395 g, 1.92 mmol) were dissolved in acetonitrile at 0° C. (10 mL) and triethyl amine (0.793 mL, 5.76 mmol) was added. The solution was allowed to warm to room temperature and stir overnight. The reaction was concentrated down and partitioned between 1N NaOH and extracted with CH$_2$Cl$_2$ (3×). The organics were collected together and dried over MgSO$_4$, filtered and evaporated in vacuo. The residue was purified by Isco flash system (20% hexane/80% ethyl acetate) to yield the product (0.35 g, 57%).

Part 2:

(R)-3-[(4-Chloro-benzylamino)-methyl]-pyrrolidine-1-carboxylic acid tert-butyl ester (0.35 g, 0.1 mmol) and acetaldehyde (0.15 mL, 0.15 mmol) were mixed with sodium triacetoxyborohydride (0.35 g, 0.15 mmol) in dichloroethane (15 mL) containing acetic acid (1%) and the resulting mixture was stirred at room temperature overnight. The reaction mixture was diluted with CH$_2$Cl$_2$ and washed with 1 N NaOH solution and brine and dried over magnesium sulfate. The reaction was concentrated in vacuo. The residue was used directly in the next reaction (0.34 g, 100%).

Part 3:

3-{[(4-Chloro-benzyl)-ethyl-amino]-methyl}-pyrrolidine-1-carboxylic acid tert-butyl ester (0.34 g, 0.98 mmol) was dissolved in 4M HCl/dioxane. The solution was stirred at rt for 1 h. The solvent was removed in vacuo and the mixture was carried on to the next step without further purification as the hydrochloride salt.

Part 4:

To a solution of (R)-(4-Chloro-benzyl)-ethyl-pyrrolidin-3-ylmethyl-amine in acetonitrile/water (8:2) (10 mL) was added K$_2$CO$_3$ (0.54 g, 3.9 mmol) and 2-[5-(3-bromo-propylidene)-5,11-dihydro-10-oxa-1-aza-dibenzo[a,d]cyclohepten-7-yl]-propan-2-ol (0.368 g, 0.98 mmol). The solution was allowed to stir at room temperature for 48 h. The reaction was concentrated down and partitioned between EtOAc/H$_2$O, extracted with EtOAc (3×). The organics were collected together dried over Mg$_2$SO$_4$, filtered and evaporated in vacuo, then purified by Isco flash chromatography (5% methanol/95% methylene chloride/ammonium hydroxide) to yield the title compound (0.110 g, 33%). $^1$H-NMR (CDCl$_3$): δ0.94 (t, 3H), 1.37 (m, 1H), 1.48 (s, 6H), 1.76–2.15 (m, 4H), 2.22–2.68 (m, 10H), 3.41 (d, 1H), 3.52 (d, 1H), 5.28 (bs, 2H), 6.11 (t, 1H), 6.82 (d, 1H), 7.14–7.32 (m, 6H), 7.48 (s, 1H), 7.54 (d, 1H), 8.51 (dd, 1H). ESI-MS m/z: 548 (M+1), retention time 1.02.

Example 527

(R)-5-(3-{3-[(4-Chloro-benzyl)-ethyl-amino]-pyrrolidin-1-yl}-propylidene)-5,11-dihydro-10-oxa-1-aza-dibenzo[a,d]cycloheptene-7-carboxylic acid Part 1:

To a solution of (R)-(4-Chloro-benzyl)-ethyl-pyrrolidin-3-yl-amine (0.43 g, 1.8 mmol) in acetonitrile/water (8:2) was added K$_2$CO$_3$ (0.99 g, 7.2 mmol) and 1-[5-(3-Bromo-propylidene)-5,11-dihydro-10-oxa-1-aza-dibenzo[a,d]cyclohepten-7-yl]-ethanone (0.65 g, 1.8 mmol). The solution was allowed to stir at room temperature for 48 h. The reaction was concentrated down and partitioned between EtOAc/H$_2$O, extracted with EtOAc (3×). The organics were collected together dried over Mg$_2$SO$_4$, filtered and evaporated in vacuo, then purified by Isco flash chromatography (5% methanol/95% methylene chloride/ammonium hydroxide) to yield the ketone tricycle (0.683 g, 73%). $^1$H-NMR (MeOD): δ 0.96 (t. 3H), 1.39 (dd, 1H), 1.48 (dd, 1H), 1.84 (s, 1H), 1.81 (m, 1H), 1.94 (m, 1H), 2.33–2.47 (m, 2H), 2.53 (s, 3H), 2.58–2.66 (m, 2H), 2.68–2.86 (m, 4H), 5.42 (bs, 2H), 6.24 (t, 1H), 6.81 (d, 1H), 7.17–7.32 (m, 4H), 7.46 (dd, 1H), 7.77 (t, 2H), 7.96 (s, 1H), 8.48 (d, 1H). ESI-MS m/z: 517 (M+1), retention time 2.61.

Part 2:

Bromine (0.13 mL, 2.5 mmol) was added dropwise to a solution of NaOH (0.332 g, 8.3 mmol) in water (3 mL) at 10° C. The solution was cooled to 0° C. and (R)-1-[5-(3-{3-[(4-Chloro-benzyl)-ethyl-amino]-pyrrolidin-1-yl}-propylidene)-5,11-dihydro-10-oxa-1-aza-dibenzo[a,d]cyclohepten-7-yl]-ethanone (0.43 g, 0.83 mmol) dissolved in dioxane (8 mL) was added to the solution dropwise. The reaction was allowed to warm to room temperature and stirred for 3 h. The reaction was evaporated in vacuo and purified by HPLC. $^1$H-NMR (MeOD): δ 0.96 (t. 3H), 1.37 (m, 1H), 1.48 (m, 1H), 1.95 (s, 1H), 1.94 (m, 1H), 2.10 (m, 1H), 2.42–2.63 (m, 3H), 2.90 (t, 1H), 2.97–3.23 (m, 3H), 5.82 (bs, 2H), 6.26 (t, 1H), 6.65 (d, 1H), 7.13–7.31 (m, 4H), 7.39 (t, 1H), 7.61 (d, 1H), 7.67 (d, 1H), 7.86 (s, 1H), 8.37 (d, 1H). ESI-MS m/z: 519 (M+1), retention time 1.91.

Example 528

2-{5-[3-(3-{[2-(4-Chloro-phenyl)-ethyl]-ethyl-amino}-pyrrolidin-1-yl)-propylidene]-5,11-dihydro-10-oxa-1-aza-dibenzo[a,d]cyclohepten-7-yl}-propan-2-ol Part 1:

To a solution of 3-amino-pyrrolidine-1-carboxylic acid tert-butyl ester (0.300 g, 1.37 mmol) dissolved in dimethylformamide was added K$_2$CO$_3$ (0.567 g, 4.11 mmol) and 1-(2-bromo-ethyl)-4-chloro-benzene (0.30 g, 1.37 mmol).

The solution was heated to 60° C. for 2 d and then concentrated down and partitioned between EtOAc/H₂O, extracted with EtOAc (3×). The organics were collected together dried over Mg₂SO₄, filtered and evaporated in vacuo, then purified by Isco flash chromatography (60% ethyl acetate/40% hexane) to yield the intermediate compound (0.263 g, 59%).

Part 2:

(R)-3-[2-(4-Chloro-phenyl)-ethylamino]-pyrrolidine-1-carboxylic acid tert-butyl ester (0.263 g, 0.81 mmol) and acetaldehyde (0.068 mL, 1.2 mmol) were mixed with sodium triacetoxyborohydride (0.25 g, 1.2 mmol) in dichloroethane containing acetic acid (1%) and the resulting mixture was stirred at room temperature overnight. The reaction mixture was diluted with CH₂Cl₂ and washed with 1 N NaOH solution and brine and dried over magnesium sulfate. The reaction was concentrated in vacuo. The residue was used directly in the next reaction (0.24 g, 85%).

Part 3:

(R)-3-{[2-(4-Chloro-phenyl)-ethyl]-ethyl-amino}-pyrrolidine-1-carboxylic acid tert-butyl ester (0.242 g) was dissolved in 4M HCl/dioxane. The solution was stirred at rt for 1 h. The solvent was removed in vacuo and the mixture was carried on to the next step without further purification as the hydrochloride salt.

Part 4:

To a solution of (R)-[2-(4-Chloro-phenyl)-ethyl]-ethyl-pyrrolidin-3-yl-amine (0.100 g, 0.39 mmol) in acetonitrile/water (8:2) (10 mL) was added K₂CO₃(0.837 g, 6.06 mmol) and 2-[5-(3-Bromo-propylidene)-5,11-dihydro-10-oxa-1-aza-dibenzo[a,d]cyclohepten-7-yl]-propan-2-ol (0.100 g, 0.26 mmol). The solution was allowed to stir at room temperature for 48 h. The reaction was concentrated down and partitioned between EtOAc/H₂O, extracted with EtOAc (3×). The organics were collected together dried over Mg₂SO₄, filtered and evaporated in vacuo, then purified by Isco flash chromatography (5% methanol/95% methylene chloride/ammonium hydroxide) to yield the title compound (0.048 g, 33%). ¹H-NMR (CDCl₃): δ 1.06 (t, 3H), 1.52 (s, 6H), 1.58 (m, 1H), 2.10 (m, 1H), 2.20–2.78 (m, 13H), 3.30(m, 1H), 5.28 (bs, 2H), 6.12 (t, 1H), 6.80 (d, 1H), 7.06 (d, 2H), 7.14–7.30 (m, 4H), 7.46 (s, 1H), 7.52 (d, 1H), 8.52 (dd, 1H). ESI-MS m/z: 548 (M+1), retention time 1.35.

Example 529

(S)-2-(5-{3-[3-(4-Chloro-benzyloxy)-pyrrolidin-1-yl]-propylidene}-5,11-dihydro-10-oxa-1-aza-dibenzo[a,d]cyclohepten-7-yl)-propan-2-ol To a solution of (S)-3-hydroxy-pyrrolidine-1-carboxylic acid tert-butyl ester (0.5 g, 2.67 mmol) in THF (10 mL) was added NaH (0.128 g, 3.2 mmol) (60% dispersion in oil). The resulting solution was stirred for 5 min. and 1-bromomethyl-4-chloro-benzene (0.658 g, 3.2 mmol) dissolved in THF (5 mL) was added. The reaction mixture was stirred overnight. The reaction was quenched with water and extracted with ethyl acetate (3×). The organics were collected together dried over Mg₂SO₄, filtered and evaporated in vacuo, then purified by Isco flash chromatography (15% ethyl acetate/85% hexane) to yield the intermediate compound (0.48 g, 58%).

Part 2:

(S)-3-(4-Chloro-benzyloxy)-pyrrolidine-1-carboxylic acid tert-butyl ester (0.48 g) was dissolved in 4M HCl/dioxane was stirred at rt for 1 h. The solvent was removed in vacuo and the mixture was carried on to the next step without further purification as the hydrochloride salt.

Part 3:

To a solution of (S)-3-(4-chloro-benzyloxy)-pyrrolidine (0.38 g, 1.54 mmol) in acetonitrile/water (8:2) (10 mL) was added K₂CO₃ (0.85 g, 6.15 mmol) and 2-[5-(3-bromo-propylidene)-5,11-dihydro-10-oxa-1-aza-dibenzo[a,d]cyclohepten-7-yl]-propan-2-ol (0.575 g, 1.54 mmol). The solution was allowed to stir at room temperature for 48 h. The reaction was concentrated down and partitioned between EtOAc/H₂O, extracted with EtOAc (3×). The organics were collected together dried over Mg₂SO₄, filtered and evaporated in vacuo, then purified by Isco flash chromatography (5% methanol/95% methylene chloride/ammonium hydroxide) to yield the title compound (0.112 g, 14%). ¹H-NMR (CDCl₃): δ 1.54 (s, 6H), 1.81 (m, 1H), 1.94–2.12 (m, 2H), 2.31 (t, 3H), 2.48–2.72 (m, 4H), 4.10 (m, 1H), 4.38 (q, 2H), 5.28 (bs, 2H), 6.12 (t, 1H), 6.84 (d, 1H), 7.16–7.30 (m, 6H), 7.48 (s, 1H), 7.56 (d, 1H), 8.52 (dd, 1H). ESI-MS m/z: 507 (M+1), retention time 1.56.

Example 530

1-{3-[7-(1-Hydroxy-1-methyl-ethyl-11 H-10-oxa-1-aza-dibenzo[a,d]cyclohepten-5-ylidene]-propyl}-pyrrolidine-3-carboxylic acid4-chloro-benzylamide 3-(4-Chloro-benzylcarbamoyl)-pyrrolidine-1-carboxylic acid tert-butyl ester To a solution of di-tert-butyl-dicarbonate (1.86 g, 8.5 mmol) in dioxane (100 mL) was added 3-pyrrolidine carboxylic acid (1.0 g, 8.5 mmol) and 1 N NaOH (5 mL). The solution was stirred at rt for 12 h. The reaction was concentrated down and partitioned between EtOAc/1N HCl. The reaction was quenched with 1N HCl and extracted with EtOAc (3×), and the organic layers were collected together, dried over MgSO₄ and evaporated in vacuo. The residue was used directly in the next reaction.

Step 2:

Pyrrolidine-1,3-dicarboxylic acid (1.59 g, 7.3 mmol) was dissolved in CH₂Cl₂ and EDCI (2.53 g, 13.2 mmol), HOBt (1.48 g, 10.9 mmol) and 4-chlorobenzylamine (0.97 mL, 8.05 mmol) was added. The solution was allowed to stir at room temperature for 10 h and then washed 1N NaOH (1×), 1N HCl (1×) and brine (1×). The organic layers was dried over MgSO₄ and evaporated in vacuo, then purified by Biotage flash chromatography (50% ethyl acetate/50% hexane) to yield the title compound (1.50 g, 62%). ¹H-NMR (CDCl₃): δ 1.43 (s, 9H), 2.07 (m, 2H), 2.85 (pentet, 1H), 3.30 (q, 1H), 3.49 (q, 1H), 3.55 (q, 2H), 4.38 (d, 2H), 6.16 (bs, 1H), 7.17 (d, 2H), 7.27 (d, 2H).

3-(4-Chloro-benzylcarbamoyl)-pyrrolidine-1-carboxylic acid tert-butyl ester (0.707 g, 2.07 mmol) was dissolved in 4M HCl/Dioxane (5 mL). The solution was stirred at rt for 1 h. The solvent was removed in vacuo and the mixture was carried on to the next step without further purification as the hydrochloride salt.

To a solution of pyrrolidine-3-carboxylic acid 4-chloro-benzylamide hydrochloride (0.2 g, 0.83 mmol) in acetonitrile/water (8:2) (8 mL) was added K₂CO₃ (0.476 g, 3.4 mmol) and 2-[5-(3-bromo-propylidene)-5,11-dihydro-10-oxa-1-aza-dibenzo[a,d]cyclohepten-7-yl]-propan-2-ol (0.282 g, 0.83 mmol). The solution was allowed to stir at room temperature for 48 h. The reaction was concentrated down and partitioned between EtOAc/H₂O, extracted with EtOAc (3×). The organics were collected together dried over Mg₂SO₄, filtered and evaporated in vacuo, then purified by Biotage flash chromatography (5% methanol/95% methylene chloride to 10% methanol/90% methylene chloride) to yield the title compound (0.240 g, 60%). ¹H-NMR (CDCl₃): 1.54 (s, 6H), 1.93 (m, 1H), 2.12 (m, 2H), 2.29–2.82 (m, 10H), 4.26 (bs, 2H), 5.26(BS, 1 h), 6.05 (t, 1H), 6.79 (d, 1H), 7.03 (d, 2H), 7.19–7.26 (m, 4H), 7.42 (s, 1H), 7.51 (d, 1H), 8.46 (d, 1H). ESI-MS m/z: 532.05 (M+1), retention time 1.68.

Example 531

1-{3-[7-(1-Hydroxy-1-methyl-ethyl)-11H-10-oxa-1-aza-dibenzo[a,d]cyclohepten-5-ylidene]-propyl}-pyrrolidine-3-carboxylic acid (4-chloro-phenyl)-ethyl-amide 3-[(4-Chloro-phenyl)-ethyl-carbamoyl)]-pyrrolidine-1-carboxylic acid tert-butyl ester To a solution of di-tert-butyl-dicarbonate (1.86 g, 8.5 mmol) in dioxane (100 mL) was added 3-pyrrolidine carboxylic acid (1.0 g, 8.5 mmol) and 1 N NaOH (5 mL). The solution was stirred at rt for 12 h. The reaction was concentrated down and partitioned between EtOAc/1N HCl. The reaction was quenched with 1N HCl and extracted with EtOAc (3×), and the organic layers were collected together, dried over MgSO₄ and evaporated in vacuo. The residue was used directly in the next reaction.

Step 2:
Pyrrolidine-1,3-dicarboxylic acid (0.300 g, 1.4 mmol) was dissolved in CH₂Cl₂ and EDCI (0.477 g, 2.4 mmol), HOBt (0.280 g, 2.1 mmol) and N-ethyl-4-chloro aniline (0.236 g, 1.5 mmol) was added. The solution was allowed to stir at room temperature for 24 h and then washed 1N NaOH (1×), 1N HCl (1×) and brine (1×). The organic layers was dried over MgSO₄ and evaporated in vacuo, then purified by Biotage flash chromatography (30% ethyl acetate/70% hexane to 40% ethyl acetate/60% hexane) to yield the title compound 0.040 g, 8%). ¹H-NMR (CDCl₃): δ 1.08 (t, 3H), 1.41 (s, 9H), 1.78 (m, 1H), 2.13 (m, 1H), 2.76 (pentet, 1H), 3.10 (q, 1H), 3.36 (pentet, 2H), 3.50 (t, 1H), 3.73 (m, 2H), 7.09 (d, 2H), 7.42 (d, 2H).

3-[(4-Chloro-phenyl)-ethyl-carbamoyl)]-pyrrolidine-1-carboxylic acid tert-butyl ester (0.040 g, 0.1 mmol) was dissolved in 4M HCl/Dioxane (2 mL). The solution was stirred at rt for 1 h. The solvent was removed in vacuo and the mixture was carried on to the next step without further purification as the hydrochloride salt.

To a solution of pyrrolidine-3-carboxylic acid (4-chloro-phenyl)-ethyl-amide hydrochloride (0.033 g, 0.11 mmol) in acetonitrile/water (8:2) (2 mL) was added K₂CO₃ (0.125 g, 0.89 mmol) and 2-[5-(3-bromo-propylidene)-5,11-dihydro-10-oxa-1-aza-dibenzo[a,d]cyclohepten-7-yl]-propan-2-ol (0.042 g, 0.111 mmol). The solution was allowed to stir at room temperature for 48 h. The reaction was concentrated down and partitioned between EtOAc/H₂O, extracted with EtOAc (3×). The organics were collected together dried over Mg₂SO₄, filtered and evaporated in vacuo, then purified by Biotage flash chromatography (2½% methanol/97½% methylene chloride to 5% methanol/95% methylene chloride) to yield the title compound (0.028 g, 46%). ¹H-NMR (CDCl₃): δ 1.07 (t, 3H), 1.55 (6H, s), 1.62 (m, 1H), 1.99 (m, 3H), 2.30 (pentet, 3H), 2.47–2.77 (m, 5H), 3.68 (m, 2H), 5.26 (bs, 2H), 6.09 (t, 1H), 6.79 (d, 1H), 7.03 (d, 2H), 7.24 (m, 2H), 7.37 (d, 2H), 7.42 (s, 1H), 7.52 (d, 1H), 8.47 (d, 1H). ESI-MS m/z: 546.04 (M+1), retention time 1.44.

Example 532

(R)-2-(5-{3-[3-(5-Chloro-1,3-dihydro-isoindol-2-yl)-pyrrolin-1-y;]-propylidene-5,11-dihydro-10-oxa-1-aza-dibenzo[a,d]cyclohepten-7-yl-propan-2-ol (R)-3-(5-Chloro-1,3-dioxo-1,3-dihydro-isoindol-2-yl)-pyrrolidine-1-carboxylic acid tert-butyl ester 4-Chlorophthalic acid monosodium (2.00 g, 8.9 mmol) and PCl₅ (5.61 g, 26.9 mmol) were added neat to a flask and heated to 180° C. (caution the initial mixture of the acid and PCl₅ was very exothermic). The mixture was heated for 3 h and then the suspension was diluted with toluene and filtered. The reaction was concentrated down and used without further purification.

Part 2:
(R)-4-Chloro-phthaloyl dichloride (0.556 g, 2.3 mmol) and (R)-3-amino-1-N-Boc-pyrrolidine (0.400 g, 2.1 mmol) were dissolved in 21 mL of pyridine and heated to 80° C. for 2½ h. The solution was diluted with water and extracted with EtOAc. The organic were collected together and washed with 1N HCl, 1N NaOH, brine and dried over Mg₂SO₄, filtered and evaporated in vacuo, then purified by Biotage flash chromatography (5% methanol/95% methylene chloride to 10% ethyl acetate/90% hexane to 20% ethyl acetate/80% hexane) to yield the title compound (0.200 g, 26%). ¹H-NMR (CDCl₃): δ 1.46 (s, 9H), 2.12 (m, 1H), 2.59 (pentet, 1H), 3.38 (quartet, 1H), 3.71 (m, 3H), 4.83 (pentet, 1H), 7.69 (d, 1H), 7.77 (d, 1H), 7.80 (s, 1H). ESI-MS m/z: 351 (M+1), retention time 2.73.

(R)-3-(5-Chloro-1,3-dihydro-isoindol-2-yl)-pyrrolidine-1-carboxylic acid tert-butyl ester (R)-3-(5-Chloro-1,3-dioxo-1,3-dihydro-isoindol-2-yl)-pyrrolidine-1-carboxylic acid tert-butyl ester (0.200 g, 0.57 mmol) was dissolved in ether and cooled to 0° C. and LiAlH₄ (2.85 mL, 2.8 mmol) was added dropwise, followed by AlCl₃ (0.380 g, 2.8 mmol). The solution was allowed to stir at 0° C. for 1½ h and then slowly quenched with water and extracted with ethyl acetate (3×). The organic were collected together and dried over Mg₂SO₄, filtered and evaporated in vacuo, to yield the title compound (0.076 g, 41%) without further purification. ESI-MS m/z: 323 (M+1), retention time 1.27.

(R)-3-(5-Chloro-1,3-dihydro-isoindol-2-yl)-pyrrolidine-1-carboxylic acid tert-butyl ester (0.076 g, 0.23 mmol) was dissolved in 4M HCl/Dioxane (2 mL). The solution was stirred at rt for 1 h. The solvent was removed in vacuo and the mixture was carried on to the next step without further purification as the hydrochloride salt.

Step 2:
To a solution of (R)-5-chloro-2-pyrrolin-3-yl-2,3-dihydro-1H-isoindole hydrochloride (0.052 g, 0.23 mmol) in acetonitrile/water (8:2) (2 mL) was added K₂CO₃ (0.215 g, 1.5 mmol) and 2-[5-(3-bromo-propylidene)-5,11-dihydro-10-oxa-1-aza-dibenzo[a,d]cyclohepten-7-yl]-propan-2-ol (0.079 g, 0.21 mmol). The solution was allowed to stir at room temperature for 48 h. The reaction was concentrated down and partitioned between EtOAc/H₂O, extracted with EtOAc (3×). The organics were collected together dried over $Mg_2SO_4$, filtered and evaporated in vacuo, then purified by Biotage flash chromatography (5% methanol/95% methylene chloride to 10% methanol/90% methylene chloride to 15% methanol/85% methylene chloride) to yield the title compound (0.055 g, 55%). $^1$H-NMR ($CDCl_3$): δ 1.55(s, 9H), 1.77 (m, 1H), 2.02 (m, 2H), 2.37(pentet, 3H), 2.42–2.64 (m, 4H), 2.81 (t, 1H), 3.17 (pentet, 1H), 3.43 (s, 3H), 3.84 (s, 4H), 5.26 (bs, 2H), 6.11 (t, 1H), 6.79 (d, 1H), 7.08–7.28 (m, 5H), 7.43 (s, 1H), 7.56 (d, 1H), 8.46 (d, 1H). ESI-MS m/z: 516.02 (M+1), retention time 1.26.

Example 533

(R)-1-(4-Chloro-benzyl)-1-(1-{3-[7-(1-hydroxy-1-methyl-ethyl)-11H-10-oxa-1-aza-dibenzo[a, d]cyclohepten-5-ylidene]-propyl}-pyrrolidin-3-yl)urea (R)-1-(4-Chloro-benzyl)-1-pyrrolidin-3-yl-urea (R)-3-(4-Chloro-benzylamino)-pyrrolidine-1-carboxylic acid tert-butylester (0.690 g, 2.2 mmol) was dissolved in $CH_2Cl_2$ with a few drops of isopropanol and trimethylsilyl-isocyanate (0.365 mL, 2.6 mmol) were added. The solution was allowed to stir at room temperature for 12 h, the reaction was concentrated down and used directly in the next reaction. ESI-MS m/z: 354 (M+1), retention time 2.15.

Part 2:
(R)-3-[1 (4-Chloro-benzyl)-ureido]-pyrrolidine-1-carboxylic acid tert-butyl ester (0.300 g, 0.84 mmol) was dissolved in 4M HCl/Dioxane (2 mL). The solution was stirred at rt for 1 h. The solvent was removed in vacuo and the mixture was carried on to the next step without further purification as the hydrochloride salt.

To a solution of (R)-1-(4-Chloro-benzyl)-1-pyrrolidin-3-yl-urea (0.200 g, 0.78 mmol) in acetonitrile/water (8:2) (8 mL) was added $K_2CO_3$ (0.449 g, 3.2 mmol) and 2-[5-(3-bromo-propylidene)-5,11-dihydro-10-oxa-1-aza-dibenzo[a, d]cyclohepten-7-yl]-propan-2-ol (0.267 g, 0.71 mmol). The solution was allowed to stir at room temperature for 48 h. The reaction was concentrated down and partitioned between $EtOAc/H_2O$, extracted with EtOAc (3×). The organics were collected together dried over $Mg_2SO_4$, filtered and evaporated in vacuo, then purified by Biotage flash chromatography (5% methanol/95% methylene chloride to 10% methanol/90% methylene chloride) to yield the title compound (0.231 g, 60%). $^1$H-NM ($CDCl_3$): δ 1.55 (s, 6H), 1.88 (pentet, 1H), 2.01–2.28 (m, 5H), 2.53 (pentet, 6H), 3.12 (t, 1H), 3.14 (t, 1H), 3.83 (q, 1H), 4.37 (s, 1H), 4.53 (s, 2H), 5.28 (bs, 2H), 6.18 (t, 1H), 6.78 (d, 1H), 7.11 (dd, 1H), 7.16 (s, 1H), 7.18–7.27 (m, 4H), 7.49 (d, 1H), 7.51 (s, 1H), 8.47 (dd, 1H). ESI-MS m/z: 547.06 (M+1), retention time 1.65.

Example 534

(R)-8-Chloro-4-(1-{3[7-(-hydroxy-1-methyl-ethyl)-11H-10-oxa-1-aza-dibenzo[a,d]cyclohepten-5-ylidene]-propyl}-pyrrolidine-3-yl)-1,3,4,5-tetrahydro-benzo[e][1,4]diazepin-2-one Step 1: 3-(4-Chloro-2-nitro-benzylamino)-pyrrolidine-1-carboxylic acid tert-butyl ester To a solution of 3-Amino-pyrrolidine-1-carboxylic acid tert-butyl ester (2 g, 10.7 mmol) in methanol (20 mL) was added 4-Chloro-2-nitro-benzaldehyde (1.98 g, 10.7 mmol). The resultant solution was heated at 60° C. overnight. The reaction mixture was cooled to 0° C. and to it was added NaBH4 (629 mg, 10 mmol). After 1 h, the reaction solution was quenched with saturated NaHCO3 solution and extracted with ethyl acetate. The organic extract was dried over MgSO4, filtered and concentrated to provide the crude product as an oil. The crude product was used in the subsequent reaction without further purification. LCMS (retention time=10.28, ES+; 356).

Step 2: 3-[(4-Chloro-benzyl)-methoxycarbonylmethyl-amino]-pyrrolidine-1-carboxylic acid tert-butyl ester To a solution of 3-(4-Chloro-2-nitro-benzylamino)-pyrrolidine-1-carboxylic acid tert-butyl ester (3.8 g, 10.7 mmol) in DMF (40 mL) was added Bromo-acetic acid methyl ester (1.01 mL, 10.7 mmol) and $K_2CO_3$ (1.48 g, 10.7 mmol). The resultant suspension was stirred at 70° C. overnight. The reaction mixture was diluted with water and ethyl ether. The organic extract was dried over $MgSO_4$, filtered and concentrated to provide the desired product as an oil. The crude product was purified on $SiO_2$ and concentrated to provide the desired product as an oil (2 g, 44%). LCMS (retention time=3.03, ES+428).

Step 3: 3-(8-Chloro-2-oxo-1,2,3,5-tetrahydro-benzo[e][1,4]diazepin-4-yl)-pyrrolidine-1-carboxylic acid tert-butyl ester To a solution of 3-[(4-Chloro-2-nitro-benzyl)-methoxycarbonylmethyl-amino]-pyrrolidine-1-carboxylic acid tert-butyl ester (1.04 g, 2.4 mmol) in ethyl acetate (20 mL) was added 10% Pd/C. Hydrogenolysis of the reaction solution at rt under atmospheric pressure provided the desired product after 1.5 h. The reaction mixture was filtered through a pad of celite and concentrated. The crude product (662 mg, 1.7 mmol) was dissolved in DMF (5 mL) and to it was added 60% NaH (100 mg, 2.5 mmol). The resultant solution was stirred at rt overnight. The reaction was quenched with water and extracted with ethyl ether. The organic extract was dried over $MgSO_4$, filtered and concentrated to get the crude product. Purification on $SiO_2$ provided the desired product. LCMS (retention time=1.89, ES+; 310)

(R)-3-(8-Chloro-2-oxo-1,2,3,5-tetrahydro-benzo[e] [1,4]diazepin-4-yl)pyrrolidine-1-carboxylic acid tert-butyl ester (0.210 g, 0.57 mmol) was dissolved in 4M HCl/Dioxane (5.7 mL). The solution was stirred at rt for 1 h. The solvent was removed in vacuo and the mixture was carried on to the next step without further purification as the hydrochloride salt.

Step 2:
To a solution of (R)-8-chloro-4-pyrrolidin-3-yl-1,3,4,5-tetrahydro-benzo[e][1,4]diazepin-2-one (0.198 g, 0.58 mmol) in acetonitrile/water (8:2) (5.8 mL) was added $K_2CO_3$ (0.655 g, 4.6 mmol) and 2-[5-(3-bromo-propylidene)-5,11-dihydro-10-oxa-1-aza-dibenzo[a,d]cyclohepten-7-yl]-propan-2-ol (0.183 g, 0.48 mmol). The solution was allowed to stir at room temperature for 48 h. The reaction was concentrated down and partitioned between $EtOAc/H_2O$, extracted with EtOAc (3×). The organics were collected together dried over $Mg_2SO_4$, filtered and evaporated in vacuo, then purified by Biotage flash chromatography (5% methanol/95% methylene chloride to 10% methanol/90% methylene chloride to 15% methanol/85% methylene chloride) to yield the title compound (0.077 g, 28%). $^1$H-NMR ($CDCl_3$): δ 1.55 (s, 6H), 1.74 (septet, 1H), 2.01 (sextet, 1H), 2.32–2.60 (m, 6H), 2.76 (t, 1H), 3.26 (pentet, 1H), 3.43 (d, 1H), 3.46 (s, 2H), 3.74 (s, 2H), 5.27 (bs, 2H), 6.12 (t, 1H), 6.78 (d, 1H), 6.96 (s, 1H), 7.06 (dd, 1H), 7.13 (d, 1H), 7.19–7.27 (m, 2H), 7.44 (d, 1H), 7.55 (dd, 1H), 8.47 (dd, 1H), 8.49 (s, 1H). ESI-MS m/z: 559 (M+1), retention time 1.24.

Example 535

(R)-8-Chloro-1-ethyl-4-(1-{3[7-(-hydroxy-1-methyl-ethyl)-11H-10-oxa-1-aza-dibenzo[a,d]cyclohepten-5-ylidene]-propyl}-pyrolidine-3-yl)-1,3,4,5-tetrahydro-benzo[e][1,4]diazepin-2-one (R)-3-(8-Chloro-1-ethyl-2-oxo-1,2,3,5-tetrahydro-benzo[e] [1,4]diazepin-4-yl)pyrrolidine-1-carboxylic acid tert-butyl ester (R)-3-(8-Chloro-2-oxo-1,2,3,5-tetrahydro-benzo[e][1,4] diazepin-4-yl)pyrrolidine-1-carboxylic acid tert-butyl ester (0.258 g, 0.70 mmol) was dissolved in THF (7 mL) and cooled to 0° C. To the solution was added NaH (0.042 g, 1.0 mmol) and stirred for 15 min, followed by ethyl iodide (0.085 mL, 1.0 mmol). The solution was allowed to warm to room temperature slowly and stir at room temperature for 14 h. The reaction was quenched with water and extracted with EtOAc (3×). The organics were collected together dried over $Mg_2SO_4$, filtered and evaporated in vacuo, then purified by Biotage flash chromatography (75% ethyl acetate/25% ethyl acetate to 100% ethyl acetate) to yield the title compound (0.130 g, 47%). $^1$H-NMR ($CDCl_3$): δ 1.16 (t, 3H), 1.43 (s, 9H), 1.75 (sextet, 1H), 2.18 (pentet, 1H), 3.05–3.9 (m, 1H), 7.20 (m, 3H). ESI-MS m/z: 394 (M+1), retention time 2.25.

(R)-3-(8-Chloro-1-ethyl-2-oxo-1,2,3,5-tetrahydro-benzo[e][1,4]diazepin-4-yl)pyrrolidine-1-carboxylic acid tert-butyl ester (0.130 g, 0.32 mmol) was dissolved in 4M HCl/Dioxane (3.2 mL). The solution was stirred at rt for 1 h. The solvent was removed in vacuo and the mixture was carried on to the next step without further purification as the hydrochloride salt.

Step 2:

To a solution of (R)-8-chloro-1-ethyl-4-pyrrolidin-3-yl-1,3,4,5-tetrahydro-benzo[e][1,4]diazepin-2-one (0.121 g, 0.32 mmol) in acetonitrile/water (8:2) (3.2 mL) was added $K_2CO_3$ (0.368 g, 2.6 mmol) and 2-[5-(3-bromo-propylidene)-5,11-dihydro-10-oxa-1-aza-dibenzo[a,d]cyclohepten-7-yl]-propan-2-ol (0.102 g, 0.27 mmol). The solution was allowed to stir at room temperature for 48 h. The reaction was concentrated down and partitioned between EtOAc/$H_2O$, extracted with EtOAc (3×). The organics were collected together dried over $Mg_2SO_4$, filtered and evaporated in vacuo, then purified by Biotage flash chromatography (5% methanol/95% methylene chloride to 10% methanol/90% methylene chloride to 15% methanol/85% methylene chloride) to yield the title compound (0.033 g, 21%). $^1$H-NMR ($CDCl_3$): 1.17 (t, 3H), 1.55 (s, 6H), 1.73 (septet, 1H), 2.08 (m, 1H), 2.34(pentet, 2H), 2.43–2.61 (m, 4H), 2.85 (t, 1H), 2.92 (d, 1H), 3.10 (q, 1H), 3.22 (m, 1H), 3.52 (q, 2H), 3.91 (septet, 2H), 5.29 (bs, 2H), 6.12 (t, 1H), 6.79 (dd, 1H), 7.15–7.28 (m, 5H), 7.44 (s, 1H), 7.56 (d, 1H), 8.47 (d, 1H). ESI-MS m/z: 587 (M+1), retention time 1.37.

Example 536

[(4-Chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amino]-acetic acid methyl ester Step 1: 3-(4-Chloro-benzylamino)-pyrrolidine-1-carboxylic acid tert-butyl ester To a solution of 3-Amino-pyrrolidine-1-carboxylic acid tert-butyl ester (2 g, 10.7 mmol) in methanol (20 mL) was added 4-Chloro-benzaldehyde (1.5 g, 10.7 mmol). The resultant solution was heated at 60° C. overnight. The reaction mixture was cooled to 0° C. and to it was added NaBH4 (629 mg, 10 mmol). After 1 h, the reaction solution was quenched with saturated NaHCO3 solution and extracted with ethyl acetate. The organic extract was dried over MgSO4, filtered and concentrated to provide the crude product as an oil. The crude product was used in the subsequent reaction without further purification. LCMS (retention time=1.27, ES+311).

Step 2: 3-[(4-Chloro-benzyl)-methoxycarbonylmethyl-amino]-pyrrolidine-1-carboxylic acid tert-butyl ester To a solution of 3-(4-Chloro-benzylamino)-pyrrolidine-1-carboxylic acid tert-butyl ester (3.3 g, 10.7 mmol) in DMF (40 mL) was added Bromo-acetic acid methyl ester (1.01 mL, 10.7 mmol) and $K_2CO_3$ (1.48 g, 10.7 mmol). The resultant suspension was stirred at 70° C. overnight. The reaction mixture was diluted with water and ethyl ether. The organic extract was dried over $MgSO_4$, filtered and concentrated to provide the desired product as an oil. The crude product was purified on $SiO_2$ and concentrated to provide the desired product as an oil (3.5 g, 87%). LCMS (retention time=2.96, ES+383).

Step 3: [(4-Chloro-benzyl)-pyrrolidin-3-yl-amino]-acetic acid methyl ester

3-[(4-Chloro-benzyl)-methoxycarbonylmethyl-amino]-pyrrolidine-1-carboxylic acid tert-butyl ester (3.5 g, 9.1 mmol) was dissolved in 4N HCl in dioxane (60 mL). The resultant solution was stirred for 2 h at rt then concentrated to provide the desired product as a white solid. LCMS (retention time=1.26, ES+283).

Step 4: [(4-Chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amino]-acetic acid methyl ester To a solution of [(4-Chloro-benzyl)-pyrrolidin-3-yl-amino]-acetic acid methyl ester (188 mg, 0.67 mmol) in isopropanol (5 mL) was added 2,6-lutidine (186 uL, 1.6 mmol), and a catalytic amount of potassium iodide. The resultant solution was heated at 80° C. and to it was added 2-[5-(3-Bromo-propylidene)-5,11-dihydro-10-oxa-1-aza-dibenzo[a,d]cyclohepten-7-yl]-propan-2-ol (149 mg, 0.4 mmol) portionwise over 0.5 h. The reaction solution was heated overnight then partitioned between water and ethyl acetate. The product was purified on $SiO_2$ (ethyl acetate:Methanol:triethylamine 95:4.5:0.4) and isolated as a film. LCMS (retention time=1.84, ES+; 576); $^1$H NMR ($CD_3OD$): δ 8.46 (1H,d), 7.76 (1H, d), 7.45 (2H, m), 7.23 (5H, m), 6.74 (1H, d), 6.15 (1H, m), 3.72 (2H, m), 3.60 (4H, s), 3.30 (6H, m), 2.78 (4H, m), 2.42 (2H, m), 2.05 (1H, m), 1.82 (1H, m), 1.50 (6H, s).

Example 537

[(4-Chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amino]-acetic acid Step 1: [(4-Chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amino]-acetic acid To a solution of [(4-Chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amino]-acetic acid methyl ester (116 mg, 0.2 mmol) in THF:$H_2O$ (4:1, 10 mL total volume) was added lithium hydroxide monohydrate (17 mg, 0.4 mmol). The resultant solution was stirred at rt for 3 h. The reaction solution was quenched with 1N HCl and extracted with ethyl ether, dried over $MgSO_4$, filtered and concentrated. The final product was filtered through filter paper and re-concentrated. This product was submitted without further purification. LCMS (retention time=1.72, ES+562); $^1$H NMR ($CD_3OD$): δ 8.48 (1H, d), 7.78 (1H, d), 7.48 (2H, m), 7.31 (5H, m), 6.76 (1H, d), 6.15 (1H, t), 3.85 (2H, dd), 3.60 (2H, m), 3.30 (7H, m), 3.24 (1H, s), 3.18 (1H, m), 3.06 (1H, m), 2.58 (1H, m), 2.48 (1H, t), 2.06 (2H, m), 1.50 (6H, s).

Example 538

2-(5-{3-[4-(3,4-Dichloro-phenyl)-piperazin-1-yl]-propylidene}-5,11-dihydro-10-oxa-1-aza-dibenzo[a,d]cyclohepten-7-yl)-propan-2-ol To a solution of 1-(3,4-dichloro-phenyl)-piperazine (0.14 g, 0.601 mmol) in isopropanol (6.0 mL) was added 2,6-lutidine (95 uL, 0.802 mmol) and catalytic potassium iodide. This mixture was heated to 80° C. and treated with 2-[5-(3-bromo-propylidene)-5,11-dihydro-10-oxa-1-aza-dibenzo[a,d]cyclohepten-7-yl]-propan-2-ol (0.37 g, 1.0 mmol), added in three portions over 2 h. The reaction was then stirred at 80° C. for 18 hours. The reaction was concentrated in vacuum, then purified by flash chromatography on silica gel (gradient elution from 95% ethyl acetate/5% methanol to 90% ethyl acetate/10% methanol) to yield the title compound as a white solid (0.15 g, 69%). $^1$H-NMR (MeOD) δ: 1.55 (6H, s), 2.35–2.65 (8H, m), 3.15–3.25 (4H, m), 5.30 (2H, br s), 6.20 (1H, t), 6.82 (1H, dd), 7.23–7.55 (5H, m), 7.59 (1H, d), 8.50 (1H, dd). ESI-MS m/z: 524 (M+1), UV retention time: 1.66 min.

Example 539

2-(5-{3-[4-(4-Chloro-2-methyl-phenyl)-piperazin-1-yl]-propylidene}-5,11-dihydro-10-oxa-1-aza-dibenzo[a,d]cyclohepten-7-yl)-propan-2-ol Step 1: 4-(4-Chloro-2-methyl-phenyl)-piperazine-1-carboxylic acid tert-butyl ester 2-Bromo-5-chlorotoluene (0.82 g, 4 mmol) and tert-Butyl 1-piperazine carboxylate (0.89 g, 2.32 mmol) were added to a solution of tri-t-butyl phosphine (0.033 g, 4 mmol %), tris(dibenzylideneacetone)dipalladium(0) (0.075 g, 2.0 mmol %) and cesium carbonate (1.95 g, 6.0 mmol) in toluene and heated to 80° C. overnight. The reaction mixture was filtered through celite and concentrated in vacuo. The crude product was purified on silica gel (gradient elution from 20% ethyl acetate/hexane to 50% ethyl acetate/hexane) to give the title compound in 20% yield. ESI-MS m/z: 311 (M+1), UV retention time: 3.49 min.

Step 2: 1-(4-Chloro-2-methyl-phenyl)-piperazine

A solution of 4-(4-chloro-2-methyl-phenyl)-piperazine-1-carboxylic acid tert-butyl ester (0.26 g, 0.837 mmol) in dichloromethane cooled at 0° C. was treated with trifluoroacetic acid (20%) and warmed to room temperature and stirred for 2 hours. The reaction mixture was concentrated in vacuo, diluted with ethyl acetate and free based with 10% aqueous sodium bicarbonate. The organics were separated and dried over sodium sulfate and concentrated. The product was used without further purification ESI-MS m/z: 211 (M+1), UV retention time: 1.25 min.

Step 3. 2-(5-{3-[4-(4-Chloro-2-methyl-phenyl)-piperazin-1-yl]-propylidene}-5,11-dihydro-10-oxa-1-aza-dibenzo[a,d]cyclohepten-7-yl)-propan-2-ol To a solution of 1-(4-chloro-2-methyl-phenyl)-piperazine (0.13 g, 0.6 mmol) in isopropanol (6.0 mL) was added 2,6-lutidine (95 uL, 0.802 mmol) and catalytic potassium iodide. This mixture was heated to 80° C., and treated with 2-[5-(3-Bromo-propylidene)-5,11-dihydro-10-oxa-1-aza-dibenzo[a,d]cyclohepten-7-yl]-propan-2-ol (0.15 g, 0.4 mmol), added in portions over 2 h. The solution was then stirred at 80° C. for an additional 12 h. The reaction mixture was concentrated in vacuo, then purified by flash chromatography on silica gel (gradient elution from 95% ethyl acetate/5% methanol to 90% ethyl acetate/10% methanol) to yield the title compound (0.11 g, 54%). $^1$H-NMR (DMSO) δ: 1.45 (6H, s), 2.30–2.65 (8H, m), 2.75–2.85 (4H, m), 3.30 (3H, d), 5.30 (2H, br s), 6.20 (1H, t), 6.75 (1H, d), 7.00–7.47 (6H, m), 7.80 (1H, dd), 8.50 (1H, dd). ESI-MS m/z: 504 (M+1), UV retention time: 1.65 min.

Example 540

5-Chloro-2-(4-{3-[7-(1-hydroxy-1-methyl-ethyl)-11H-10-oxa-1-aza-dibenzo[a,d]cyclohepten-5-ylidene]-propyl}-piperazin-1-yl)-benzonitrile Step 1: 4-(2-Cyano-phenyl)-piperazine-1-carboxylic acid tert-butyl ester To a solution of 2-piperazin-1-yl-benzonitrile (1.1 g, 5.87 mmol) in dichloromethane (10 mL) was added diisopropylethylamine (3.1 mL, 17.62 mmol) followed by di-tert-butyl-dicarbonate (1.28 g, 5.87 mmol) and reaction mixture was stirred at room temperature for 20 hours. The reaction mixture was concentrated in vacuo, dissolved in ethyl acetate and washed with saturated aqueous sodium bicarbonate solution. The aqueous layer was back extracted twice with ethyl acetate. The organic layers were combined, dried over sodium sulfate and concentrated in vacuo. The crude product was purified using a short plug of silica gel using hexane/ethyl acetate (50%) $^1$H-NMR ($CDCL_3$) δ: 1.47 (9H, s), 3.12–3.16 (4H, m), 3.61–3.65 (4H, m), 6.90–7.05 (2H, m), 7.47–7.70 (2H, m). ESI-MS m/z: 288 (M+1), UV retention time: 2.75 min.

Step 2 4-(4-Chloro-2-cyano-phenyl)-piperazine-1-carboxylic acid tert-butyl ester To a solution of 4-(2-cyano-phenyl)-piperazine-1-carboxylic acid tert-butyl ester (7.1 g, 24.72 mmol) in acetonitrile (120 ml) was added N-chlorosuccinimide (3.96 g, 29.66 mmol) and the resulting mixture was slowly heated to 80° C. and stirred for 1.5 h. The reaction mixture was cooled to room temperature, concentrated in vacuo diluted with dichloromethane and extracted with saturated aqueous sodium bicarbonate solution. The aqueous layer was back extracted twice with dichloromethane. The organic layers were combined, dried over sodium sulfate and concentrated in vacuo. The crude product was purified using a short plug of silica gel using gradient elution from hexane/ether (10%) to hexane/ether (40%) to give the p-chloro isomer in 50% yield. $^1$H-NMR ($CDCL_3$) δ: 1.48 (9H, s), 3.10–3.38 (4H, m), 3.60–3.70 (4H, m), 6.85–7.18 (1H, m), 7.40–7.60 (2H, m). ESI-MS m/z: 322 (M+1), UV retention time: 3.07 min.

Step 3: 5-Chloro-2-piperazin-1-yl-benzonitrile

A solution of 4-(4-chloro-2-cyano-phenyl)-piperazine-1-carboxylic acid tert-butyl ester (0.32 g, 1 mmol) in dichloromethane cooled at 0° C. was treated with trifluoroacetic acid (20%) and warmed to room temperature and stirred for 2 h. The reaction mixture was concentrated in vacuo, diluted with ethyl acetate and free based with 10% aqueous sodium bicarbonate. The organic layers were separated and dried over sodium sulfate and concentrated in vacuo. The product used without further purification.

ESI-MS m/z: 222 (M+1), UV retention time: 1.05 min.

Step 4  5-Chloro-2-(4-{3-[7-(1-hydroxy-1-methyl-ethyl)-11H-10-oxa-1-azadibenzo[a,d]cyclohepten-5-ylidene]-propyl}-piperazin-1-yl)-benzonitrile To a solution of 5-chloro-2-piperazin-1-yl-benzonitrile (0.22 g, 1 mmol) in isopropanol (8 mL) was added 2,6-lutidine (0.16 mL, 1.33 mmol) and catalytic potassium iodide. This mixture was heated to 80° C. and treated with 2-[5-(3-bromo-propylidene)-5,11-dihydro-10-oxa-1-aza-dibenzo[a,d]cyclohepten-7-yl]-propan-2-ol (0.26 g, 0.67 mmol) in portions over 2 h. The solution was then stirred at 80° C. for an additional 18 h. The reaction mixture was concentrated in vacuo, then purified by flash chromatography on silica gel (gradient elution from 95% ethyl acetate/5% methanol to 90% ethyl acetate/10% methanol) to yield the title compound (0.11 g, 54%). $^1$H-NMR (MeOD) δ: 1.40 (6H, s), 2.30–2.58 (8H, m), 3.00–3.15 (4H, m), 5.20 (1H, br s), 6.18 (1H, t), 6.70 (1H, dd), 7.18–7.84 (7H, m), 8.50 (1H, dd). ESI-MS m/z: 515 (M+1), UV retention time: 1.75 min.

Example 541

5-Chloro-2-(4-{3-[7-(1-hydroxy-1-methyl-ethyl)-11H-10-oxa-1-aza-dibenzo[a,d]cyclohepten-5-ylidene]-propyl}-piperazin-1-yl)-benzoic acid methyl ester Step 1:  4-(2-Carboxy-4-chloro-phenyl)-piperazine-1-carboxylic acid tert-butyl ester To a solution of 4-(4-chloro-2-cyano-phenyl)-piperazine-1-carboxylic acid tert-butyl ester (0.6 g, 1.86 mmol) in methanol (4.0 mL) was added 1.0 N NaOH (4.0 mL, 4.0 mmol) and the resulting mixture was heated to reflux at 80° C. for 36 h. Additional 1.0 N NaOH (2.0 ml, 2.0 mmol) was added to the reaction mixture and refluxed further for 18 hrs. The reaction mixture was concentrated and acidified to pH 4.0–5.0 using 1.0 N HCl and extracted with chloroform (5×). The combined organics were dried over sodium sulfate, concentrated and dried in vacuo overnight. The product contained approximately 20% amide and was separated after esterification in the next step. ESI-MS m/z: 341(M+1), UV retention time: 2.33 min.

Step 2:  4-(4-Chloro-2-methoxycarbonyl-phenyl)-piperazine-1-carboxylic acid tert-butyl ester To a solution of 4-(2-Carboxy-4-chloro-phenyl)-piperazine-1-carboxylic acid tert-butyl ester (0.64 g, 1.88 mmol) in toluene: methanol (9:1) was added a trimethylsilyldiazomethane (2.0 M in hexanes) (1.05 mL, 2.07 mmol) and the resulting mixture was stirred at room temperature for 1 h. The reaction mixture was concentrated in vacuo and purified using gradient elution from hexane/ethyl acetate (10%) to hexane/ethyl acetate (50%). $^1$H-NMR (CDCL$_3$) δ: 1.45 (9H, s), 2.90–3.00 (4H, m), 3.50–3.60 (4H, m), 3.90 (3H, s), 6.90–7.00 (1H, d), 7.35–7.45 (1H, dd), 7.80 (1H, d). ESI-MS m/z: 355 (M+1), UV retention time: 3.11 min.

Step 3: 5-Chloro-2-piperazin-1-yl-benzoic acid methyl ester

A solution of 4-(4-chloro-2-methoxycarbonyl-phenyl)-piperazine-1-carboxylic acid tert-butyl ester (0.32 g, 0.92 mmol) in dichloromethane (5.0 mL) cooled at 0° C. was treated with trifluoroacetic acid (20%) and warmed to room temperature and stirred for 2 h. The reaction mixture was concentrated in vacuo, diluted with ethyl acetate and free based with 10% aqueous sodium bicarbonate. The organics were separated and dried over sodium sulfate and concentrated in vacuo. The product used without any further purification. ESI-MS m/z: 255 (M+1), UV retention time: 1.14 min.

Step 4: 5-Chloro-2-(4-{3-[7-(1-hydroxy-1-methyl-ethyl)-11H-10-oxa-1-aza-dibenzo[a,d]cyclohepten-5-ylidene]-propyl}-piperazin-1-yl)-benzoic acid methyl ester To a solution of 5-chloro-2-piperazin-1-yl-benzoic acid methyl ester (0.23 g, 0.916 mmol) in isopropanol (8.0 mL) was added 2,6-lutidine (0.16 mL, 1.33 mmol) and catalytic potassium iodide. This mixture was heated to 80° C. and treated with 2-[5-(3-bromo-propylidene)-5,11-dihydro-10-oxa-1-aza-dibenzo[a,d]cyclohepten-7-yl]-propan-2-ol (0.26 g, 0.67 mmol) in portions over 2 h. The solution was then stirred at 80° C. for an additional 18 h. The reaction mixture was concentrated in vacuo, then purified by flash chromatography on silica gel (gradient elution from 95% ethyl acetate/5% methanol to 90% ethyl acetate/10% Methanol) to yield the title compound. $^1$H-NMR (DMSO) δ: 1.40 (6H, s), 2.15–2.55 (8H, m), 2.75–2.95 (4H, m), 3.75 (3H, s), 5.20 (2H, br s), 6.10 (1H, t), 6.65 (1H, dd), 7.00–7.60 (6H, m), 7.70 (1H, dd), 8.50 (1H, dd). ESI-MS m/z: 548 (M+1), UV retention time: 1.56 min.

Example 542

2-(4-Chloro-phenyl)-N-(1-{3-[7-(1-hydroxy-1-methyl-ethyl)-11H-10-oxa-1-aza dibenzo[a,d]cyclohepten-5-ylidene]-propyl}-piperidin-4-yl)-acetamide Step 1: 4-[2-(4-Chloro-phenyl)-acetylamino]-piperidine-1-carboxylic acid tert-butyl ester To a solution of 4-amino-piperidine 1-carboxylic acid tert-butyl ester (0.44 g, 2.2 mmol) and 4-chlorophenyl acetic acid (0.34 g, 2 mmol) in dichloromethane (10 mL) were added EDCI (0.55 g, 2.8 mmol), HOBT (0.42 g, 2.8 mmol) and N-methylmorpholine (0.6 g, 6 mmol) and the resulting mixture was stirred at room temperature overnight. The reaction mixture was concentrated in vacuo, diluted with dichloromethane and extracted with saturated aqueous sodium bicarbonate solution. The aqueous layer was back extracted twice with dichloromethane. The combined organics were dried over sodium sulfate and concentrated in vacuo. Crude product was purified using a short plug of silica gel using ethyl acetate to give the desired product $^1$H-NMR (CDCL$_3$) δ: 1.15–1.25 (2H, m), 1.40 (9H, s), 1.80–1.90 (2H, m), 2.85 (2H, dd), 3.5 (2H, s), 4.00 (1H, br s), 5.20 (1H, d), 7.15–7.35 (4H, m). ESI-MS m/z: 353 (M+1), UV retention time: 2.47 min.

Step 2: 2-(4-Chloro-phenyl)-N-piperidin-4-yl-acetamide

A solution of 4-[2-(4-chloro-phenyl)-acetylamino]-piperidine-1-carboxylic acid tert-butyl ester (0.55 g, 1.54 mmol) in dichloromethane (8.0 mL) cooled at 0° C. was treated with trifluoroacetic acid (20%) and warmed to room temperature and stirred for 2 h. The reaction mixture was concentrated in vacuo, diluted with ethyl acetate and free based with 10% aqueous sodium bicarbonate. The combined organic layers were dried over sodium sulfate and concentrated in vacuo. The crude product was purified on silica using gradient elution from ethyl acetate/methanol (2%) to ethyl acetate/methanol (20%). $^1$H-NMR (CDCL$_3$) δ:

1.15–1.25 (2H, m), 1.80–1.90 (2H, m), 2.60–2.75 (2H, m), 2.90–3.10 (2H, m), 3.5 (2H, s), 3.85 (1H, m), 5.20 (1H, d), 7.15–7.35 (4H, m). ESI-MS m/z: 253 (M+1), UV retention time: 0.87 min.

Step 3: 2-(4-Chloro-phenyl)-N-(1-{3-[7-(1-hydroxy-1-methyl-ethyl)-11H-10-oxa-1-aza-dibenzo[a,d]cyclohepten-5-ylidene]-propyl}-piperidin-4-yl)-acetamide To a solution of 2-(4-chloro-phenyl)-N-piperidin-4-yl-acetamide (0.2 g, 0.8 mmol) in isopropanol (6.0 mL) was added 2,6-lutidine (0.095 mL, 0.8 mmol) and catalytic potassium iodide. This mixture was heated to 80° C. and treated with 2-[5-(3-bromo-propylidene)-5,11-dihydro-10-oxa-1-aza-dibenzo[a,d]cyclohepten-7-yl]-propan-2-ol (0.15 g, 0.4 mmol) in portions over 2 h. The solution was then stirred at 80° C. for an additional 18 h. The reaction mixture was concentrated in vacuo, then purified by flash chromatography on silica gel (gradient elution from 95% ethyl acetate/5% methanol to 90% ethyl acetate/20% methanol) to yield the title compound. $^{1}$H-NMR (CDCL$_{3}$) δ: 1.15–1.50 (4H, m), 1.60 (6H,s), 1.80–2.85 (8H, m), 3.50 (2H, s), 3.70–3.90 (1H, m), 5.20 (2H, br s), 6.05(1H, t), 6.80 (1H, d), 7.20–7.40 (7H, m) 7.60 (1H,dd), 8.50 (1H,dd). ESI-MS m/z: 546 (M+1), UV retention time: 1.24 min.

Example 543

2-{5-[3-({2-[(4-Chloro-phenyl)-ethyl-amino]-ethyl}-ethyl-amino)-propylidene]-5,11-dihydro-10-oxa-1-aza-dibenzo[a,d]cyclohepten-7-yl}-propan-2-ol Step 1: 2-(5-{3-[2-(4-Chloro-phenylamino)-ethylamino]-propylidene}-5,11-dihydro-10-oxa-1-aza-dibenzo[a,d]cyclohepten-7-yl)-propan-2-ol To a solution of N-(4-chloro-phenyl)-ethane-1,2-diamine (0.68 g, 3.96 mmol) in isopropanol (8.0 mL) was added 2,6-lutidine (0.31 mL, 2.64 mmol) and catalytic potassium iodide. This mixture was heated to 80° C. and then treated with 2-[5-(3-bromo-propylidene)-5,11-dihydro-10-oxa-1-aza-dibenzo[a,d]cyclohepten-7-yl]-propan-2-ol (0.15 g, 0.4 mmol) in portions over 2 h. The solution was then stirred at 80° C. for an additional 18 h. The reaction mixture was concentrated in vacuo, then purified by flash chromatography on silica gel (gradient elution from 95% ethyl acetate/5% methanol to 90% ethyl acetate/20% methanol) to yield the title compound. $^{1}$H-NMR (DMSO) δ: 1.40 (6H, s), 2.20–2.40 (2H, m), 2.70–2.90(3H, m), 3.10–3.30 (3H,m), 5.20 (2H, br, s), 5.80 (1H, m), 6.15 (1H, t), 6.60–6.70 (1H, m), 7.10–7.30 (4H, m) 7.50 (2H, m), 7.80 (1H, dd), 8.50 (1H, dd). ESI-MS m/z: 464 (M+1), UV retention time: 1.40 min.

Step 2: 2-{5-[3-({2-[(4-Chloro-phenyl)-ethyl-amino]-ethyl}-ethyl-amino)-propylidene]-5,11-dihydro-10-oxa-1-aza-dibenzo[a,d]cyclohepten-7-yl}-propan-2-ol To a solution of 2-(5-{3-[2-(4-chloro-phenylamino)-ethylamino]-propylidene}-5,11-dihydro-10-oxa-1-aza-dibenzo[a,d]cyclohepten-7-yl)-propan-2-ol (0.13 g, 0.27 mmol) in dichloroethane (5.0 mL) was added acetaldehyde (0.045 mL, 0.81 mmol), sodium triacetoxy borohydride (0.17 g, 0.81 mmol) and catalytic acetic acid and stirred at room temperature overnight. The reaction mixture was concentrated and the residue was dissolved in dichloromethane and washed with saturated aqueous sodium bicarbonate. The combined organics were washed with brine, dried over sodium sulfate and concentrated in vacuo. The crude product was purified on silica using gradient elution from ethyl acetate (100%) to ethyl acetate/methanol (5%). $^{1}$H-NMR (CDCL$_{3}$) δ: 0.90–1.20 (6H, 2×t), 1.60 (6H,s), 2.20–2.40 (2H, m), 2.45–2.65 (6H, m), 3.20–3.40 (4H, 2×q), 5.30 (2H, br, s), 6.10 (1H, t), 6.50 (2H, dd), 6.80 (1H, d), 7.10 (2H, dd) 7.20–7.35 (2H, m), 7.45 (1H, dd),7.55 (1H, dd), 8.50 (1H, dd). ESI-MS m/z: 520 (M+1), UV retention time: 1.51 min.

Example 544

1-(4-Chloro-phenyl)-4-{3-[7-(1-hydroxy-1-methyl-ethyl)-11H-10-oxa-1-aza-dibenzo[a,d]cyclo hepten-5-ylidene]-propyl}-piperazine-2-carboxylic acid amide Step 1:1-(4-Chloro-phenyl)-4-{3-[7-(1-hydroxy-1-methyl-ethyl)-11H-10-oxa-1-aza-dibenzo[a,d]cyclo hepten-5-ylidene]-propyl}-piperazine-2-carbonitrile To a solution of 2-(5-{3-[2-(4-chloro-phenylamino)-ethylamino]-propylidene}-5,11-dihydro-10-oxa-1-aza-dibenzo[a,d]cyclohepten-7-yl)-propan-2-ol (0.4 g, 0.86 mmol) in toluene (6 mL) was added triethylamine (0.48 mL, 3.44 mmol) and 2,3-dibromopropionitrile (0.19 mL, 1.72 mmol) and reaction mixture was heated to 110° C. (reflux) and stirred overnight for 18 h. The reaction mixture was concentrated in vacuo and the residue was diluted with ethyl acetate and extracted with 1.0N NaOH solution. The aqueous layer was back extracted twice with ethyl acetate. The combined organics were dried over sodium sulfate and concentrated. The crude product was purified using a short plug of silica gel using ethyl acetate to give the title compound. $^{1}$H-NMR (CDCl$_{3}$) δ: 1.05 (6H, s), 2.20–2.70 (8H, 2×m), 3.00 (1H, m), 3.10–3.40 (3H, 2×m), 4.50 (1H, br, s), 5.30 (2H, br, s), 6.20 (1H, t), 6.70–6.90 (3H, 2×d), 7.10–7.35 (4H, m), 7.50 (2H, d), 8.50 (1H, dd). ESI-MS m/z: 515 (M+1), UV retention time: 2.36 min.

Step 2: 1-(4-Chloro-phenyl)-4-{3-[7-(1-hydroxy-1-methyl-ethyl)-11H-10-oxa-1-aza-dibenzo[a,d]cyclohepten-5-ylidene]-propyl}-piperazine-2-carboxylic acid amide To a solution of 1-(4-chloro-phenyl)-4-{3-[7-(1-hydroxy-1-methyl-ethyl)-11H-10-oxa-1-aza-dibenzo[a,d]cyclohepten-5-ylidene]-propyl}-piperazine-2-carbonitrile (0.12 g, 0.23 mmol) in methanol (0.5 mL) and THF (0.5 mL) was added 1.0 N NaOH (0.5 mL, 0.5 mmol) and the resulting mixture was heated to reflux at 80° C. for 18 h. Additional 2.0 N NaOH (0.5 mL, 0.5 mmol) was added to the reaction mixture and refluxed further for 18 h. The reaction mixture was concentrated, acidified to pH 5.0 using 1.0 N HCl and extracted with ethyl acetate (3×). The combined organics were dried over sodium sulfate and concentrated. The crude product was purified on a short plug of silica gel using gradient elution from ethyl acetate/methanol (2–10%) to give the title compound.

$^{1}$H-NMR (CDCl$_{3}$) δ: 1.05 (6H, s), 2.20–2.70 (8H, 2×m), 3.00 (1H, m), 3.10–3.40 (3H, 2×m), 4.50 (1H, br, s), 5.30 (2H, br, s), 6.00(1H, br, s), 6.20 (1H, t), 6.40 (1H, br,s), 6.70–6.90 (3H, 2×d), 7.10–7.35 (4H, m), 7.50 (2H, d), 8.50 (1H, dd). ESI-MS m/z: 515 (M+1), UV retention time: 1.32 min.

Example 545

1-(4-Chloro-phenyl)-4-{3-[7-(1-hydroxy-1-methyl-ethyl)-11H-10-oxa-1-aza-dibenzo[a,d]cyclo hepten-5-ylidene]-propyl}-piperazine-2-carbonitrile To a solution of 2-(5-{3-[2-(4-chloro-phenylamino)-ethylamino]-propylidene}-5,11-dihydro-10-oxa-1-aza-dibenzo[a,d]cyclohepten-7-yl)-propan-2-ol (0.4 g, 0.87 mmol) in toluene (6 mL) was added triethylamine (0.48 mL, 3.44 mmol) and 2,3-dibromopropionitrile (0.19 mL, 1.72 mmol) and reaction mixture was heated to 110° C. (reflux) and stirred overnight for 18 h. The reaction mixture was concentrated in vacuo and the residue was diluted with ethyl acetate and extracted with 1.0N NaOH solution. The aqueous layer was back extracted twice with ethyl acetate. The combined organics were dried over sodium sulfate and concentrated. The crude product was purified using a short plug of silica gel using ethyl acetate to give the desired product. $^1$H-NMR (CDCl$_3$) δ: 1.05 (6H, s), 2.20–2.70 (8H, 2×m), 3.00 (1H, m), 3.10–3.40 (3H, 2×m), 4.50 (1H, br, s), 5.30 (2H, br, s), 6.20 (1H, t), 6.70–6.90 (3H, 2×d), 7.10–7.35 (4H, m), 7.50 (2H, d), 8.50 (1H, dd). ESI-MS m/z: 515 (M+1), UV retention time: 2.36 min.

Example 546

1-(4-Chloro-phenyl)-4-{3-[7-(1-hydroxy-1-methyl-ethyl)-11H-10-oxa-1-aza-dibenzo[a,d]cyclohepten-5-ylidene]-propyl}-piperazine-2-carboxylic acid methyl ester Step 1: Piperazine-1,2,4-tricarboxylic acid 1-tert-butyl ester 4-(9H-fluoren-9-ylmethyl) ester 2-methyl ester To a solution of piperazine-1,2,4-tricarboxylic acid 1-tert-butyl ester 4-(9H-fluoren-9-ylmethyl)ester (2.21 mmol) in toluene: methanol (9:1) was added equimolar trimethylsilyldiazomethane (2.0 M in hexanes) and the resulting mixture was stirred overnight at room temperature. The reaction mixture was concentrated in vacuo and purified using gradient elution from hexane/ethyl acetate (5%) to hexane/ethyl acetate (30%). ESI-MS m/z: 467 (M+1), UV retention time: 3.04 min.

Step 2: Piperazine-1,2-dicarboxylic acid 1-tert-butyl ester 2-methyl ester

To a solution of piperazine-1,2,4-tricarboxylic acid 1-tert-butyl ester 4-(9H-fluoren-9-ylmethyl)ester 2-methyl ester (2.03 mmol) in DMF (4.0 mL) was added diethylamine (5%) and the resulting solution was stirred at room temperature overnight. The reaction mixture was concentrated in vacuo and purified using ethyl acetate/methanol (10%). ESI-MS m/z: 245(M+1), UV retention time: 0.78 min.

Step 3: 4-(4-Chloro-phenyl)-piperazine-1,3-dicarboxylic acid1-tert-butyl ester 3-methyl ester 4-Chloro phenyl boronic acid (2.0 equiv, 3.68 mmol) and piperazine-1,2-dicarboxylic acid 1-tert-butyl ester 2-methyl ester (1.0 equiv, 1.84 mmol) were dissolved in dichloromethane followed by the addition of copper acetate (1.0 equiv), 4 Å molecular sieves and pyridine (2.0 equiv). The reaction mixture was stirred at room temperature for 72 h. The reaction mixture was concentrated in vacuo, dissolved in ethyl acetate, filtered through celite and concentrated. The crude product was purified using gradient elution from hexane/ethyl acetate (5%) to hexane/ethyl acetate (20%). ESI-MS m/z: 354 (M+1), UV retention time: 2.88 min. Reference: *Tetrahedron Letters*, 2001, 42, 3415–3418.

Step 4: 1-(4-Chloro-phenyl)-piperazine-2-carboxylic acid methyl ester

A solution of 4-(4-chloro-phenyl)-piperazine-1,3-dicarboxylic acid 1-tert-butyl ester 3-methyl ester (0.4 g, 1.13 mmol) in dichloromethane (5.0 mL) cooled at 0° C. was treated with trifluoroacetic acid (20%) and warmed to room temperature and stirred for 2 h. The reaction mixture was concentrated in vacuo, diluted with ethyl acetate and free based with 10% aqueous sodium bicarbonate. The combined organics were dried over sodium sulfate and concentrated. The product was used without any further purification. ESI-MS m/z: 254 (M+1), UV retention time: 1.01 min.

Step 5: 1-(4-Chloro-phenyl)-4-{3-[7-(1-hydroxy-1-methyl-ethyl)-11H-10-oxa-1-aza-dibenzo[a,d]cyclohepten-5-ylidene]-propyl}-piperazine-2-carboxylic acid methyl ester To a solution of 1-(4-chloro-phenyl)-piperazine-2-carboxylic acid methyl ester (0.14 g, 0.53 mmol) in acetonitrile: water (4:1) was added potassium carbonate (0.083 g, 0.6 mmol) and (E)-2-[5-(3-bromo-propylidene)-5,11-dihydro-10-oxa-1-aza-dibenzo[a,d]cyclohepten-7-yl]-propan-2-ol (150 mg, 0.4 mmol) and the resulting mixture was stirred at 50° C. for 5 hours. The reaction mixture was concentrated in vacuo, diluted with ethyl acetate, and dried over sodium sulfate. The crude product was purified by flash chromatography on silica using gradient elution from ethyl acetate (100%) to ethyl acetate/methanol (5%). $^1$H-NMR (CDCl$_3$) δ: 1.05 (6H, s), 2.20–2.70 (8H, 2×m), 3.00 (1H, m), 3.10–3.40 (3H, 2×m), 3.55 (3H, s), 4.50 (1H, br,s), 5.30 (2H, br,s), 6.20 (1H, t), 6.70–6.90 (3H, 2×d), 7.10–7.35 (4H, m), 7.50 (2H, d), 8.50 (1H, dd). ESI-MS m/z: 548 (M+1), UV retention time: 1.62 min.

Example 547

Isopropyl-carbamic acid 5-{3-[4-(4-chloro-phenyl)-4-hydroxy-3,3-dimethyl-piperidin-1-yl]-propylidene}-5,11-dihydro-10-oxa-1-aza-dibenzo[a,d]cyclohepten-7-yl ester 5-{3-[4-(4-Chloro-phenyl)-4-hydroxy-3,3-dimethyl-piperidin-1-yl]-propylidene}-5,11-dihydro-10-oxa-1-aza-dibenzo[a,d]cyclohepten-7-ol (0.27 mmol, 1.0 equiv) was dissolved in tetrahydrofuran and treated with triethylamine (1.50 equiv) and isopropyl isocyanate (0.4 mmol, 1.50 equiv). The resulting mixture was heated to 50° C. for 18 h. The reaction mixture was concentrated and crude product was purified on silica using gradient elution from ethyl acetate (100%) and ethyl acetate/methanol (5%). $^1$H-NMR (CDCl$_3$) δ: 0.70 (3H, s), 0.90 (3H, s), 1.1 (3H, d), 1.25 (3H, d), 1.4 (1H, m), 1.6 (1H, m), 2.30–2.50 (8H, m), 2.70 (2H, m), 3.80–4.00 (3H, m), 3.55 (3H, s), 4.85 (1H, m), 5.30 (2H, br, s), 6.20 (1H, t), 6.80–7.00 (2H, dd), 7.20–7.45 (6H, m), 7.60 (1H, dd), 8.50 (1H, dd). ESI-MS m/z: 576 (M+1), UV retention time: 1.58 min.

Example 548

3-(4-Chloro-phenyl)-1-ethyl-1-(1-{3-[7-(1-hydroxy-1-methyl-ethyl)-11H-10-oxa-1-aza-dibenzo[a,d]cyclohepten-5-ylidene]-propyl}-pyrrolidin-3-yl)-urea Step 1: 3-Ethylamino-pyrrolidine-1-carboxylic acid tert-butyl ester To a solution of (R)-3-amino-1-N-Boc pyrrolidine (1 eq, 5.37 mmol) in methanol (20 mL) was added acetaldehyde (0.95 eq) and the resulting mixture was heated to 80° C. and stirred for 2 h., then stirred at room temperature overnight. Sodium borohydride (0.95 eq, 5.1 mmol) was added and reaction mixture was stirred for an additional 2 h. The reaction mixture was concentrated, dissolved in ethyl acetate and washed with saturated aqueous sodium bicarbonate. The combined organics were washed with brine and dried over sodium sulfate. The crude product was purified on silica using hexane/ethyl acetate (10%) to hexane/ethyl acetate (50%). $^1$H-NMR (CDCL$_3$) δ: 1.05 (3H, t), 1.45 (9H, s), 1.60–1.75 (1H, m), 2.00–2.10 (1H, m), 2.68 (4H, q), 2.90–3.15 (1H, m), 3.25–3.65 (4H, m).

ESI-MS m/z: 215 (M+1), UV retention time: 0.75 min.

Step 2: 3-[3-(4-Chloro-phenyl)-1-ethyl-ureido]-pyrrolidine-1-carboxylic acid tert-butyl ester To a solution of 3-ethylamino-pyrrolidine-1-carboxylic acid tert-butyl ester (0.33 g, 1.5 mmol) in DMF (5.0 mL) was added drop wise a solution of 4-chlorophenyl isocyanate (0.23 g, 1.51 mmol) in DMF (2.5 mL) at room temperature and the resulting mixture was stirred for 3 h. The reaction mixture was concentrated in vacuo and the crude product was purified on silica using hexane/ethyl acetate (50%) followed by ethyl acetate (100%) to give the desired product as white foamy solid.

ESI-MS m/z: 368 (M+1), UV retention time: 2.61 min.

Step 3: 3-(4-Chloro-phenyl)-1-ethyl-1-pyrrolidin-3-yl-urea

A solution of 3-[3-(4-chloro-phenyl)-1-ethylureido]-pyrrolidine-1-carboxylic acid tert-butyl ester (0.4 g, 1.08 mmol) in dichloromethane (5.0 ml) cooled at 0° C. was treated with trifluoroacetic acid (20%) and warmed to room temperature and stirred for 2 h. The reaction was concentrated in vacuo, diluted with ethyl acetate and free based with 10% aqueous sodium bicarbonate. The combined organics were dried over sodium sulfate. The product was used without any further purification. ESI-MS m/z: 268 (M+1), UV retention time: 1.02 min.

Step 4: 3-(4-Chloro-phenyl)-1-ethyl-1-(1-{3-[7-(1-hydroxy-1-methyl-ethyl)-11H-10-oxa-1-aza-dibenzo[a,d]cyclohepten-5-ylidene]-propyl}-pyrrolidin-3-yl)-urea To a solution of 3-(4-chloro-phenyl)-1-ethyl-1-pyrrolidin-3-yl-urea (0.21 g, 0.8 mmol) in acetonitrile:water (4:1) was added potassium carbonate (0.16 g, 0.8 mmol) and (E)-2-[5-(3-bromo-propylidene)-5,11-dihydro-10-oxa-1-aza-dibenzo[a,d]cyclohepten-7-yl]-propan-2-ol (0.15 g, 0.4 mmol) and the resulting mixture was stirred at 50° C. for 24 h. The reaction mixture was concentrated in vacuo, diluted with ethyl acetate, and dried over sodium sulfate. The crude product was purified by flash chromatography on silica using gradient elution from ethyl acetate/methanol (5%) to ethyl acetate/methanol (10%) to give the desired product as yellow solid. $^1$H-NMR (CDCl$_3$) δ: 1.05 (3H, t), 1.40 (6H, s), 1.80 (1H, m), 2.20–2.40 (3H, m), 2.50–3.00 (8H, m), 3.40 (4H, q and m), 4.20 (1H, m), 5.20 (2H, br, s), 6.20 (1H, t), 6.65(1H, d), 7.00 (2H, dd), 7.20–7.40 (5H, m), 7.70 (1H, dd), 8.50 (1H, dd) 9.80 (1H, br s). ESI-MS m/z: 561 (M+1), UV retention time: 1.45 min.

Example 549

2-(5-{3-[3-(4-Chloro-benzyloxy)-pyrrolidin-1-yl]-propylidene}-5,11-dihydro-10-oxa-1-aza-dibenzo[a,d]cyclohepten-7-yl)-propan-2-ol Step 1: (R)-3-(4-Chloro-benzyloxy)-pyrrolidine-1-carboxylic acid tert-butyl ester A solution of (R)-3-hydroxy-pyrrolidine-1-carboxylic acid tert-butyl ester (1.14 mmol, 1.0 eq) in THF (2.5 mL) was added to a suspension of sodium hydride (1.15 eq) in THF (2.5 mL) cooled at 0° C. and the resulting mixture was stirred for 45 min. A solution of 4-chlorobenzyl bromide (1.31 mmol, 1.15 eq) in THF (2.0 mL) was then added drop wise and reaction mixture was slowly warmed to room temperature and stirred for 18 h. The reaction mixture was quenched with water (1.0 ml) and diluted with ethyl acetate. The combined organics were dried over sodium sulfate. The crude product was purified on silica using gradient elution from hexane/ethyl acetate (10%) to hexane/ethyl acetate (30%). $^1$H-NMR (CDCL$_3$) δ: 1.45 (9H, s), 1.80–2.05 (2H, m), 3.30–3.55 (4H, m), 4.05 (1H, m), 4.45 (2H, s), 7.15–7.30 (4H, m). ESI-MS m/z:311 (M+1), UV retention time: 2.94 min.

Step 2: (R)-3-(4-Chloro-benzyloxy)-pyrrolidine

A solution of (R)-3-(4-chlorobenzyloxy)-pyrrolidine-1-carboxylic acid tert-butyl ester (0.88 mmol) in dichloromethane cooled at 0° C. was treated with trifluoroacetic acid (20%) and warmed to room temperature and stirred for 2 h. The reaction mixture was concentrated in vacuo, diluted with ethyl acetate and free based with 10% aqueous sodium bicarbonate. The combined organics were dried over sodium sulfate. The product was used without any further purification. ESI-MS m/z: 211(M+1), WV retention time: 0.97 min.

Step 3: 2-(5-{3-[3-(4-Chloro-benzyloxy)-pyrrolidin-1-yl]-propylidene}-5,11-dihydro-10-oxa-1-aza-dibenzo[a,d]cyclohepten-7-yl)-propan-2-ol To a solution of (R)-3-(4-chloro-benzyloxy)-pyrrolidine (0.88 mmol, 2.0 eq) in acetonitrile:water (4:1) was added potassium carbonate (0.88 mmol, 2.0 eqv) and (E)-2-[5-(3-bromo-propylidene)-5,11-dihydro-10-oxa-1-aza-dibenzo[a,d]cyclohepten-7-yl]-propan-2-ol and the resulting mixture was stirred at room temperature for 24 h. The reaction mixture was concentrated in vacuo, diluted with ethyl acetate, and dried over sodium sulfate. The crude product was purified by Reverse Phase HPLC. $^1$H-NMR (CDCl$_3$) δ: 1.40 (6H, s), 1.15–1.35 (1H, m), 1.85–2.05 (1H, m), 2.20–2.40 (1H, m), 2.35–2.65 (8H, m), 3.90–4.10 (1H, m), 4.30–4.50 (2H, d), 5.10–5.30 (2H, br, s), 6.05 (1H, t), 6.50 (1H, dd), 7.10–7.50 (4H, m), 7.70 (1H, dd), 8.50 (1H, dd). ESI-MS m/z: 505 (M+1), UV retention time: 1.52 min.

Example 550

2-[5-(3-{3-[(4-Chloro-benzyl)-isobutyl-amino]-pyrrolidin-1-yl}-propylidene)-5,11-dihydro-10-oxa-1-aza-dibenzo[a,d]cyclohepten-7-yl]-propan-2-ol Step 1: 3-(4-Chloro-benzylamino)-pyrrolidine-1-carboxylic acid tert-butyl ester (R)-3-amino-1-N-Boc pyrrolidine (1.0 eq, 2.68 mmol), 4-chlorobenzyl bromide (1.0 eq, 2.68 mmol), and potassium carbonate (1.75 eq) were mixed in ethanol (10 mL) and the resulting mixture was stirred at room temperature overnight. The reaction mixture was concentrated in vacuo, taken up in ethyl acetate, filtered and concentrated. The crude product was purified by flash chromatography on silica using ethyl acetate. ESI-MS m/z: 311 (M+1), WV retention time: 1.18 min.

Step 2: 3-[(4-Chloro-benzyl)-isobutyl-amino]-pyrrolidine-1-carboxylic acid tert-butyl ester To a solution of 3-(4-chloro-benzylamino)-pyrrolidine-1-carboxylic acid tert-butyl ester (0.4 g, 1.28 mmol) and isobutyraldehyde (0.14 g, 1.92 mmol) in dichloroethane was added sodium triacetoxy borohydride (0.81 g, 3.85 mmol) and catalytic acetic acid. The resulting reaction mixture was stirred at room temperature overnight. The reaction mixture was concentrated, dissolved in dichloromethane and washed with saturated aqueous sodium bicarbonate. The combined organics were washed with brine and dried over sodium sulfate. The crude product was purified on silica using gradient elution from hexane/ethyl acetate (10%) to hexane/ethyl acetate (50%). ¹H-NMR (CDCl₃) δ: 0.80 (6H, 2×d), 1.45 (9H, s), 1.60–1.90 (2H, m), 2.20 (2H, d), 3.00–3.70 (7H, m), 7.20 (4H,s). ESI-MS m/z: 367 (M+1), UV retention time: 1.89 min.

Step 3: (4-Chloro-benzyl)-isobutyl-pyrrolidin-3-yl-amine

To a solution of 3-[(4-chloro-benzyl)-isobutyl-amino]-pyrrolidine-1-carboxylic acid tert-butyl ester in dichloromethane cooled at 0° C. was added trifluoroacetic acid (20%) and warmed to room temperature and stirred for 2 h. The reaction mixture was concentrated in vacuo, diluted with ethyl acetate and free based with 10% aqueous sodium bicarbonate. The combined organics were dried over sodium sulfate and concentrated. The product was used without any further purification.

ESI-MS m/z: 267(M+1), UV retention time: 0.93 min.

Step 4: 2-[5-(3-{3-[(4-Chloro-benzyl)-isobutyl-amino]-pyrrolidin-1-yl}-propylidene)-5,11-dihydro-10-oxa-1-aza-dibenzo[a,d]cyclohepten-7-yl]-propan-2-ol To a solution of (4-chloro-benzyl)-isobutyl-pyrrolidin-3-yl-amine (0.16 g, 0.6 mmol) in acetonitrile:water (4:1) was added potassium carbonate (0.8 mmol) and (E)-2-[5-(3-bromo-propylidene)-5,11-dihydro-10-oxa-1-aza-dibenzo[a,d]cyclohepten-7-yl]-propan-2-ol (0.15 g, 0.4 mmol) and the resulting mixture was stirred at 50° C. for 24 h. The reaction was concentrated, diluted with ethyl acetate, and dried over sodium sulfate. The crude product was purified by flash chromatography using ethyl acetate/methanol (5%). ¹H-NMR (CDCl₃) δ: 0.80 (6H, d), 1.55(6H, s), 1.60–1.90 (4H, m), 2.15 (1H, d), 2.20–2.60 (6H, m), 3.25–3.60 (2H, m), 5.30 (2H, br, s), 6.10 (1H, t), 6.80 (1H, dd), 7.15–7.30 (6H, m), 7.40 (1H, d), 7.55 (1H, dd), 8.45 (1H, dd). ESI-MS m/z: 560 (M+1), UV retention time: 1.66 min.

Example 551

2-[5-(3-{3-[(4-Chloro-benzyl)-isopropyl-amino]-pyrrolidin-1-yl}-propylidene)-5,11-dihydro-10-oxa-1-aza-dibenzo[a,d]cyclohepten-7-yl]-propan-2-ol Step 1: 3-Isopropylamino-pyrrolidine-1-carboxylic acid tert-butyl ester To a solution of (R)-3-amino-1-N-Boc pyrrolidine (1.0 eq, 2.68 mmol) in methanol (15 mL) was added acetone (1.07 eq), sodium cyano borohydride (2.0 eq) and few drops of acetic acid and the resulting mixture was stirred at room temperature overnight. The reaction mixture was concentrated dissolved in dichloromethane and washed with saturated aqueous sodium bicarbonate. The combined organics were washed with brine and dried over sodium sulfate. The crude product was purified on silica using gradient elution from hexane/ethyl acetate (5%) to hexane/ethyl acetate (30%). ¹H-NMR (CDCl₃) δ: 1.05 (6H, d), 1.45 (9H, s), 1.60 (1H, m), 2.80–3.00 (2H, m), 3.20–3.70 (4H, m). ESI-MS m/z: 229 (M+1), UV retention time: 0.77 min.

Step 2: 3-[(4-Chloro-benzyl)-isopropyl-amino]-pyrrolidine-1-carboxylic acid tert-butyl ester To a solution of isopropyl-pyrrolidin-3-yl-amine (0.3 g, 1.31 mmol) in dichloroethane (5.0 ml) was added 4-chlorobenzaldehyde (0.22 g, 1.57 mmol), sodium triacetoxy borohydride (0.83 g, 3.93 mmol) and catalytic acetic acid and the resulting reaction mixture was stirred at room temperature overnight. The reaction mixture was concentrated, dissolved in dichloromethane and washed with 10% aqueous sodium bicarbonate. The combined organics were washed with brine and dried over sodium sulfate. The crude product was purified on silica using hexane/ethyl acetate (50%). ¹H-NMR (CDCl₃) δ: 1.05 (6H, d), 1.45 (9H, s), 1.60 (1H, m), 2.80–3.00 (2H, m), 3.20–3.70 (4H, m), 7.20 (4H, m). ESI-MS m/z: 353(M+1), UV retention time: 1.49 min.

Step 3: (4-Chloro-benzyl)-isopropyl-pyrrolidin-3-yl-amine

A solution of 3-[(4-chloro-benzyl)-isopropyl-amino]-pyrrolidine-1-carboxylic acid tert-butyl ester in dichloromethane cooled at 0° C. was treated with trifluoroacetic acid (20%) and warmed to room temperature and stirred for 2 hours. The reaction mixture was concentrated in vacuo, diluted with ethyl acetate and free based with 10% aqueous sodium bicarbonate. The combined organics were dried over sodium sulfate. The product was used without any further purification. ESI-MS m/z: 253 (M+1, UV retention time: 0.59 min.

Step 4: 2-[5-(3-{3-[(4-Chloro-benzyl)-isopropyl-amino]-pyrrolidin-1-yl}-propylidene)-5,11-dihydro-10-oxa-1-aza-dibenzo[a,d]cyclohepten-7-yl]-propan-2-ol To a solution of (4-chloro-benzyl)-isopropyl-pyrrolidin-3-yl-amine (0.68 mmol, 1.7 eq) in acetonitrile:water (4:1) was added potassium carbonate (0.8 mmol, 2 eq) and (E)-2-[5-(3-bromo-propylidene)-5,11-dihydro-10-oxa-1-aza-dibenzo[a,d]cyclohepten-7-yl]-propan-2-ol (0.4 mmol, 1.0 eq) and the resulting mixture was stirred at 50° C. for 24 h. The reaction mixture was concentrated in vacuo, diluted with ethyl acetate, and dried over sodium sulfate. The crude product was purified by flash chromatography using ethyl acetate/methanol (5%). ¹H-NMR (CDCl₃) δ: 0.85 (6H, d), 1.50–1.90 (10H, m), 2.10–2.60 (8H, m), 3.50 (3H, m), 5.30 (2H, br, s), 6.10 (1H, t), 6.80 (1H, dd), 7.10–7.40 (8H, m), 7.50 (1H, d), 8.50 (1H, dd). ESI-MS m/z: 546 (M+1), UV retention time: 1.40 min.

Example 552

2-[(4-Chloro-benzyl)-(1-{3-[7-(1-hydroxy-1-methyl-ethyl)-11H-10-oxa-1-aza dibenzo[a,d]cyclo hepten-5-ylidene]-propyl}-pyrrolidin-3-yl)-amino]-acetamide Step 1: 3-(Carbamoylmethyl-amino)-pyrrolidine-1-carboxylic acid tert-butyl ester To a solution of (R)-3-amino-1-N-Boc pyrrolidine (0.5 g, 2.68 mmol) and 2-bromo acetamide (0.44 g, 3.21 mmol) in DMF (6.0 mL) was added potassium carbonate (1.11 g, 8.04 mmol) and the reaction mixture was stirred at room temperature overnight. The reaction mixture was concentrated and re-dissolved in dichloromethane. Potassium carbonate was filtered off and filtrate was concentrated and purified using ethyl acetate/methanol (5%). ¹H-NMR (CDCl₃) δ: 1.50 (9H, s), 1.60–1.80 (2H, m), 2.10 (1H, m), 3.10–3.60 (6H, m), 5.65 (1H, br, s), 6.90 (1H, br, s). ESI-MS m/z: 367(M+1), UV retention time: 0.61 min.

Step 2: 3-[Carbamoylmethyl-(4-chloro-benzyl)-amino]-pyrrolidine-1-carboxylic acid tert-butyl ester To a solution of 3-(carbamoylmethyl-amino)-pyrrolidine-1-carboxylic acid tert-butyl ester (0.49 g, 2.03 mmol) in dichloroethane (5.0 mL) was added 4-chlorobenzaldehyde 0.34 g, 2.44 mmol), sodium triacetoxy borohydride (0.86 g, 4.06 mmol) and catalytic acetic acid and the resulting mixture was stirred at room temperature overnight. The reaction mixture was concentrated, dissolved in dichloromethane and washed with 10% aqueous sodium bicarbonate. The combined organics were washed with brine and dried over sodium sulfate. The crude product was purified on silica using ethyl acetate. ¹H-NMR (CDCl₃) δ: 1.50 (9H, s), 1.60–1.80 (2H, m), 2.10 (1H, m), 3.10–3.60 (8H, m), 5.65 (1H, br, s), 6.90 (1H, br, s) 7.20–7.40 (4H, m). ESI-MS m/z: 367(M+1), UV retention time: 1.94 min.

Step 3: 2-[(4-Chloro-benzyl)-pyrrolidin-3-yl-amino]-acetamide

A solution of 3-[carbamoylmethyl-(4-chloro-benzyl)-amino]-pyrrolidine-1-carboxylic acid tert-butyl ester (0.49 g, 1.32 mmol) in dichloromethane cooled at 0° C. was treated with trifluoroacetic acid (20%). The resulting mixture was warmed to room temperature and stirred for 2 h. The reaction mixture was concentrated in vacuo, diluted with ethyl acetate and free based with 10% aqueous sodium bicarbonate. The combined organics were dried over sodium sulfate. The product was used without any further purification ESI-MS m/z: 267 (M+1), UV retention time: 0.82 min.

Step 4: 2-[(4-Chloro-benzyl)-(1-{3-[7-(1-hydroxy-1-methyl-ethyl)-11H-10-oxa-1-aza dibenzo[a,d]cyclohepten-5-ylidene]-propyl}-pyrrolidin-3-yl)-amino]-acetamide To a solution of 2-[(4-chloro-benzyl)-pyrrolidin-3-yl-amino]-acetamide (0.21 g, 0.8 mmol) in acetonitrile:water (4:1) was added potassium carbonate (0.6 mmol) and (E)-2-[5-(3-bromo-propylidene)-5,11-dihydro-10-oxa-1-aza-dibenzo[a,d]cyclohepten-7-yl]-propan-2-ol (0.15 g, 0.4 mmol) and the resulting mixture was stirred at 50° C. for 24 h. The reaction mixture was concentrated in vacuo, diluted with ethyl acetate, and dried over sodium sulfate. The crude product was purified by HPLC. ¹H-NMR (CDCl₃) δ: 1.35 (6H, s), 1.55–1.75 (1H, m), 1.80–2.00 (1H, m), 2.20–2.85 (8H, m), 2.90–3.10 (2H, d), 3.30–3.50 (1H, m), 3.60 (1H, d), 4.80–5.30 (2H, br, s), 6.10 (1H, t), 6.70 (1H, dd), 7.00–7.45 (7H, m), 7.70 (1H, dd), 8.50 (1H, dd). ESI-MS m/z: 562 (M+1), UV retention time: 1.31 min.

Example 553

2-[(4-Chloro-benzyl)-(1-{3-[7-(1-hydroxy-1-methyl-ethyl)-1H-10-oxa-1-aza-dibenzo[a,d]cyclohepten-5-ylidene]-propyl}-pyrrolidin-3-yl)-amino]-N-ethyl-acetamide Step 1: 3-(Methoxycarbonylmethyl-amino)-pyrrolidine-1-carboxylic acid tert-butyl ester To a solution of (R)-3-amino-1-N-Boc pyrrolidine (0.5 g, 2.68 mmol) and methyl bromo acetate (0.49 g, 2.95 mmol) in DMF (6.0 mL) was added potassium carbonate (1.11 g, 8.04 mmol) and the reaction mixture was stirred at room temperature overnight. The reaction mixture was concentrated and re-dissolved in dichloromethane. Potassium carbonate was filtered off and filtrate was concentrated and purified using gradient elution from hexane/ethyl acetate (10%) to hexane/ethyl acetate (50%).

¹H-NMR (CDCl₃) δ: 1.40 (9H, s), 1.70 (2H, m), 2.00 (1H, m), 3.20–3.60 (5H, m), 3.79 (3H, br s). ESI-MS m/z: 258(M+1), UV retention time: 0.74 min.

Step 2: 3-[(4-Chloro-benzyl)-methoxycarbonylmethyl-amino]-pyrrolidine-1-carboxylic acid tert-butyl ester To a solution of 3-(methoxycarbonylmethyl-amino)-pyrrolidine-1-carboxylic acid tert-butyl ester (0.5 g, 2.03 mmol) in dichloroethane (5.0 mL) was added 4-chlorobenzaldehyde (0.34 g, 2.44 mmol), sodium triacetoxy borohydride (0.86 g, 4.06 mmol) and catalytic acetic acid and the resulting mixture was stirred at room temperature overnight. The reaction mixture was concentrated, dissolved in dichloromethane and washed with 10% aqueous sodium bicarbonate. The combined organics were washed with brine and dried over sodium sulfate. The crude product was purified on silica using ethyl acetate. ¹H-NMR (CDCl₃) δ: 1.40 (9H, s), 1.80 (1H, m), 2.10 (1H, m), 3.00–3.80 (7H, m), 4.70(1H, br,s), 7.20 (4H,m). ESI-MS m/z: 383(M+1), UV retention time: 2.91 min.

Step 3: 3-[Carboxymethyl-(4-chloro-benzyl)-amino]-pyrrolidine-1-carboxylic acid tert-butyl ester A solution of 3-[(4-chloro-benzyl)-methoxycarbonylmethyl-amino]-pyrrolidine-1-carboxylic acid tert-butyl ester (0.5 g, 1.31 mmol) in methanol (4.00 mL) and 1.0 N NaOH (aqueous) (4.00 mL) was heated to reflux at 80° C. for 2.5 h. The reaction mixture was concentrated, acidified to pH 5.0 using 1.0 N HCl and extracted with dichloromethane (3×). The product was used for the next step without further purification. ESI-MS m/z: 369(M+1), UV retention time: 1.85 min.

Step 4: 3-[(4-Chloro-benzyl)-ethylcarbamoylmethyl-amino]-pyrrolidine-1-carboxylic acid tert-butyl ester To a solution of 3-[carboxymethyl-(4-chloro-benzyl)-amino]-pyrrolidine-1-carboxylic acid tert-butyl ester (0.48 g, 1.30 mmol) in tetrahydrofuran (10 mL) was added EDCI (0.39 g, 1.95 mmol), HOBT (0.26 g, 1.95 mmol), and stirred for 30 min., followed by the addition of N-methyl morpholine (0.43 mL, 3.90 mmol) and N-ethyl amine (0.1 mL, 1.95 mmol). The reaction mixture was stirred at room temperature for 18 h. Upon concentration, the residue was dissolved in ethyl acetate and washed with saturated aqueous sodium bicarbonate. The combined organics were washed with brine and dried over sodium sulfate. The crude product was purified on silica using gradient elution from hexane/ethyl acetate (50%) to ethyl acetate (100%).

ESI-MS m/z: 396 (M+1), UV retention time: 2.18 min.

Step 5: 2-[(4-Chloro-benzyl)-pyrrolidin-3-yl-amino]-N-ethyl-acetamide

A solution of 3-[(4-chloro-benzyl)-ethylcarbamoylmethyl-amino]-pyrrolidine-1-carboxylic acid tert-butyl ester (0.12 g, 0.31 mmol) in dichloromethane cooled at 0° C. was treated with trifluoroacetic acid (20%) The resulting mixture was warmed to room temperature and stirred for 2 hours. The reaction mixture was concentrated in vacuo, diluted with ethyl acetate and free based with 10% aqueous sodium bicarbonate. The combined organics were dried over sodium sulfate. The product was used without any further purification. ESI-MS m/z: 296 (M+1), UV retention time: 1.02 min.

Step 6: 2-[(4-Chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amino]-N-ethyl-acetamide To a solution of 2-[(4-chloro-benzyl)-pyrrolidin-3-yl-amino]-N-ethyl-acetamide (0.09 g, 0.31 mmol) in acetonitrile:water (4:1) was added potassium carbonate (0.07 g, 0.51 mmol) and (E)-2-[5-(3-bromo-propylidene)-5,11-dihydro-10-oxa-1-aza-dibenzo[a,d]cyclohepten-7-yl]-propan-2-ol (0.095 g, 0.25 mmol) and the resulting mixture was stirred at 50° C. for 24 h. The reaction mixture was concentrated in vacuo, diluted with ethyl acetate, and dried over sodium sulfate.

The crude product was purified on silica using ethyl acetate. ¹H-NMR (CDCl₃) δ: 0.90 (3H, t), 1.40(6H, s), 1.60 (1H, m), 1.85 (1H, m), 2.10–2.55 (8H, m), 2.90–3.10 (4H, m), 3.25–3.40 (4H, m), 3.55 (2H, d), 4.95 (2H, s), 5.10 (2H, br, s), 6.10 (1H, t), 6.70 (1H, dd), 7.15–7.25 (1H, dd), 7.25–7.45 (4H, m), 7.55–7.75 (2H, m), 8.50 (1H, dd). ESI-MS m/z: 589 (M+1), UV retention time: 1.42 min.

Example 554

2-[5-(3-{3-[(4-Chloro-benzyl)-(2-hydroxy-ethyl)-amino]-pyrrolidin-1-yl}-propylidene)-5,11-dihydro-10-oxa-1-aza-dibenzo[a,d]cyclohepten-7-yl]-propan-2-ol Step 1: 3-[(4-Chloro-benzyl)-(2-hydroxy-ethyl)-amino]-pyrrolidine-1-carboxylic acid tert-butyl ester To a solution of 3-[(4-chloro-benzyl)-methoxycarbonyl-methyl-amino]-pyrrolidine-1-carboxylic acid tert-butyl ester (0.44 g, 1.15 mmol) in methanol cooled to 0° C. was added sodium borohydride (0.13 g, 3.45 mmol) and the resulting mixture was heated to 65° C. for 16 h. Additional sodium borohydride (0.26 g, 6.90 mmol) was added to the reaction mixture and stirred further at 65° C. for 18 h. The reaction mixture was concentrated, dissolved in ethyl acetate and washed with saturated aqueous sodium bicarbonate. The aqueous layer was extracted with ethyl acetate. The combined organics were dried over sodium sulfate. The crude product was purified on silica using gradient elution from hexane/ethyl acetate (50%) to ethyl acetate (100%). ESI-MS m/z: 355 (M+1), UV retention time: 1.27 min.

Step 2: 2-[(4-Chloro-benzyl)-pyrrolidin-3-yl-amino]-ethanol

A solution of 3-[(4-chloro-benzyl)-(2-hydroxy-ethyl)-amino]-pyrrolidine-1-carboxylic acid tert-butyl ester (0.22 g, 0.6 mmol) in dichloromethane cooled at 0° C. was treated with trifluoroacetic acid (20%). The resulting mixture was warmed to room temperature and stirred for 2 h. The reaction mixture was concentrated in vacuo, diluted with ethyl acetate and free based with 10% aqueous sodium bicarbonate. The combined organics were dried over sodium sulfate. The product was used without any further purification. ESI-MS m/z: 255 (M+1), UV retention time: 0.34 min.

Step 3: 2-[5-(3-{3-[(4-Chloro-benzyl)-(2-hydroxy-ethyl)-amino]-pyrrolidin-1-yl}-propylidene)-5,11-dihydro-10-oxa-1-aza-dibenzo[a,d]cyclohepten-7-yl]-propan-2-ol To a solution of 2-[(4-chloro-benzyl)-pyrrolidin-3-yl-amino]-ethanol (0.15 g, 0.6 mmol) in acetonitrile:water (4:1) was added potassium carbonate (0.11 g, 0.8 mmol) and (E)-2-[5-(3-bromo-propylidene)-5,11-dihydro-10-oxa-1-aza-dibenzo[a,d]cyclohepten-7-yl]-propan-2-ol (0.15 g, 0.4 mmol) and the resulting mixture was stirred at 50° C. for 24 h. The reaction mixture was concentrated in vacuo, diluted with ethyl acetate and dried over sodium sulfate. The crude product was purified on silica. $^1$H-NMR (CDCl$_3$) δ:1.40 (6H, s), 1.60 (1H, m), 1.80 (1H, m), 2.10–2.60 (8H, m), 3.20–3.40 (6H, m), 3.50 (2H, m), 5.20 (2H, br, s), 6.15 (1H, t), 6.70 (1H, t), 7.18–7.42 (7H, m), 7.70 (1H, dd), 8.50 (1H, dd). ESI-MS m/z: 548 (M+1), UV retention time: 1.26 min.

Example 555

3-[(4-Chloro-benzyl)-(1-{3-[7-(1-hydroxy-1-methyl-ethyl)-11H-10-oxa-1-aza-dibenzo[a,d]cyclo hepten-5-ylidene]-propyl}-pyrrolidin-3-yl)-amino]-propionic acid methyl ester Step 1: 3-(2-Methoxycarbonyl-ethylamino)-pyrrolidine-1-carboxylic acid tert-butyl ester To a solution of (R)-3-amino-1-N-Boc pyrrolidine (0.5 g, 2.68 mmol) and 3-bromo propionate (0.49 g, 2.95 mmol) in DMF (6.0 mL) was added potassium carbonate (1.11 g, 8.04 mmol) and the resulting mixture was stirred at room temperature overnight. The reaction mixture was concentrated and re-dissolved in dichloromethane. Potassium carbonate was filtered off and filtrate was concentrated and crude product was used further in the next step. ESI-MS m/z: 272 (M+1), UV retention time: 1.28 min.

Step 2: 3-[(4-Chloro-benzyl)-(2-methoxycarbonyl-ethyl)-amino]-pyrrolidine-1-carboxylic acid tert-butyl ester To a solution of 3-(2-methoxycarbonyl-ethylamino)-pyrrolidine-1-carboxylic acid tert-butyl ester (0.73 g, 2.68 mmol) in dichloroethane (10.0 mL) was added 4-chlorobenzaldehyde (0.42 g, 2.95 mmol), sodium triacetoxy borohydride (1.71 g, 8.04 mmol) and catalytic acetic acid and the resulting mixture was stirred at room temperature overnight. The reaction mixture was concentrated, dissolved in dichloromethane and washed with saturated aqueous sodium bicarbonate. The combined organics were washed with brine and dried over sodium sulfate. The crude product was purified on silica using gradient elution from hexane/ethyl acetate (15%) to hexane/ethyl acetate (50%). $^1$H-NMR (CDCl$_3$) δ: 1.35 (9H, s), 1.80 (1H, m), 1.90 (1H, m), 2.40 (2H, t), 2.85 (2H, t), 3.00–3.80 (7H, m), 4.70(1H, d), 7.20 (4H, m). ESI-MS m/z: 397 (M+1), UV retention time: 1.99 min.

Step 3: 3-[(4-Chloro-benzyl)-pyrrolidin-3-yl-amino]-propionic acid methyl ester

A solution of 3-[(4-chloro-benzyl)-(2-methoxycarbonyl-ethyl)-amino]-pyrrolidine-1-carboxylic acid tert-butyl ester (0.08 g, 0.2 mmol) in dichloromethane cooled at 0° C. was treated with trifluoroacetic acid (20%). The resulting mixture was warmed to room temperature and stirred for 2 h. The reaction mixture was concentrated in vacuo, diluted with ethyl acetate and free based with 10% aqueous sodium bicarbonate. The combined organics were dried over sodium sulfate. The product was used without any further purification. ESI-MS m/z: 297 (M+1), UV retention time: 1.05 min.

Step 4: 3-[(4-Chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amino]-propionic acid methyl ester To a solution of 3-[(4-chloro-benzyl)-pyrrolidin-3-yl-amino]-propionic acid methyl ester (0.06 g, 0.2 mmol) in acetonitrile:water (3:1) was added potassium carbonate (0.056 g, 0.4 mmol) and (E)-2-[5-(3-bromo-propylidene)-5,11-dihydro-10-oxa-1-aza-dibenzo[a,d]cyclohepten-7-yl]-propan-2-ol (0.065 g, 0.17 mmol) and reaction stirred at 50° C. for 24 h. The reaction mixture was concentrated in vacuo, diluted with ethyl acetate and dried over sodium sulfate. The crude product was purified by flash chromatography on silica using ethyl acetate/methanol (5%). $^1$H-NMR (CDCl$_3$) δ: 1.40 (6H, s), 1.60 (1H, m), 1.80 (1H, m), 2.10–2.60 (8H, m), 3.20–3.40 (6H, m), 3.50 (2H, m; 2H, s), 5.20 (2H, br s), 6.15 (1H, t), 6.70 (1H, t), 7.18–7.42 (7H, m), 7.70 (1H, dd), 8.50 (1H, dd). ESI-MS m/z: 590 (M+1), UV retention time: 1.51 min.

Example 556

2-(5-{3-[4-(4-Chloro-phenyl)-3-(S)-methyl-piperazin-1-yl]-propylidene}-5,11-dihydro-10-oxa-1-aza-dibenzo[a,d]cyclohepten-7-yl)-propan-2-ol Step 1: 3-(S)-Methyl-piperazine-1-carboxylic acid tert-butyl ester Triethylamine (3 g, 4.2 mL, 30 mmol) was added to a solution of 2-(S)-methyl piperazine (2 g, 20 mmol) in dichloromethane (40 mL) followed by di-tert-butyl-dicarbonate (4.8 g, 22 mmol). The reaction mixture was stirred at room temperature for 20 h. The mixture was diluted with dichloromethane and washed with saturated aqueous sodium bicarbonate and brine and dried over sodium sulfate. The crude product was purified using a short plug of silica gel using hexane/ethyl acetate (1:1). ¹H-NMR (CDCl₃) δ: 1.03 (3H, d), 1.45 (9H, s), 1.65 (1H, s), 2.35–2.42 (1H, m), 2.66–2.80 (3H, m), 2.92–2.95 (1H, m), 3.92 (2H, br s). ESI-MS m/z: 201(M+1).

Step 2: 4-(4-Chloro-phenyl)-3-(S)-methyl-piperazine-1-carboxylic acid tert-butyl ester To a mixture of 4-chlorobromobenzene (1.05 g, 5.5 mmol) and 3-(S)-Methyl-piperazine-1-carboxylic acid tert-butyl ester (1 g, 5 mmol) in toluene (30 mL) was added tris(dibenzylideneacetone)dipalladium(0) (0.057 g, 0.063 mmol), BINAP (0.12 g, 0.19 mmol) and sodium-t-butoxide (2.02 g, 21 mmol). The resulting mixture was heated 110° C. for 20 h. The solvent was evaporated and the residue was taken up in ethyl acetate and washed with saturated aqueous sodium bicarbonate and brine and dried over magnesium sulfate. Column chromatography (10% ethyl acetate/hexane) provided 0.79 g (51%) of the title compound.

¹H-NMR (CDCl₃) δ: 0.97 (3H, d), 1.48 (9H, s), 3.00–3.24 (3H, m), 3.32–3.38 (1H, m), 3.72–3.79 (2H, m), 3.88–4.05 (1H, m), 6.81 (2H, d), 7.21 (2H, d). ESI-MS m/z: 311(M), UV retention time: 3.2 min.

Step 3: 2-(5-{3-[4-(4-Chloro-phenyl)-3-(S)-methyl-piperazin-1-yl]-propylidene}-5,11-dihydro-10-oxa-1-aza-dibenzo[a,d]cyclohepten-7-yl)-propan-2-ol 4-(4-Chloro-phenyl)-3-(S)-methyl-piperazine-1-carboxylic acid tert-butyl ester (0.79 g, 2.6 mmol) was treated with 4M HCl/Dioxane (20 mL) at room temperature for 3 h. The solvent was evaporated and the residue was taken up in dichoromethane and washed several times with saturated sodium bicarbonate. The combined organic phases were dried over sodium sulfate. The residue was carried to the next step without further purification.

To a solution of 4-(4-chloro-phenyl)-3-(S)-methyl-piperazine (0.56 g, 2.6 mmol) in isopropanol (20 mL) was added 2,6-lutidine (0.305 mL, 2.6 mmol) and catalytic potassium iodide. This mixture was heated to 80° C., and then treated with 2-[5-(3-bromo-propylidene)-5,11-dihydro-10-oxa-1-aza-dibenzo[a,d]cyclohepten-7-yl]-propan-2-ol (0.64 g, 1.7 mmol), added in portions over 2 h. The solution was then stirred at 80° C. for an additional 20 h. The reaction was concentrated in vacuo and purified by flash chromatography (100% dichloromethane to 2% methanol/dichloromethane) to yield the title compound (0.151 g, 18%). ¹H-NMR (CDCl₃) δ: 1.0 (3H, d), 1.57 (6H, s), 1.79 (s, 1H), 2.25–2.52 (7H, m), 2.66–2.69 (1H, m), 2.98–3.12 (2H, m), 3.68–3.73 (1H, m), 5.32 (2H, br s), 6.17 (1H, t), 6.82 (3H, d), 7.18–7.31 (4H, m), 7.44 (1H, d), 7.56–7.60 (1H, m), 8.50 (1H, dd). ESI-MS m/z: 504 (M), UV retention time: 1.49 min.

Example 557

2-(5-{3-[4-(4-Chloro-phenyl)-3-(R)-methyl-piperazin-1-yl]-propylidene}-5,11-dihydro-10-oxa-1-aza-dibenzo[a,d]cyclohepten-7-yl)-propan-2-ol Step 1: 3-(R)-Methyl-piperazine-1-carboxylic acid tert-butyl ester Triethylamine (3 g, 4.2 mL, 30 mmol) was added to a solution of (R)-2-methyl piperazine (2 g, 20 mmol) in dichloromethane (40 mL) followed by di-tert-butyl-dicarbonate (4.8 g, 22 mmol). The reaction mixture was stirred at room temperature for 20 h. The mixture was diluted with dichloromethane and washed with saturated aqueous sodium bicarbonate and brine and dried over sodium sulfate. The crude product was purified using a short plug of silica gel using hexane/ethyl acetate (1:1). ¹H-NMR (CDCl₃) δ: 1.05 (3H, d), 1.45 (9H, s), 2.11 (1H, s), 2.37–2.44 (1H, m), 2.66–2.79 (3H, m), 2.93–2.96 (1H, m), 3.93 (2H, br s). ESI-MS m/z: 201(M+1).

Step 2: 4-(4-Chloro-phenyl)-3-(R)-methyl-piperazine-1-carboxylic acid tert-butyl ester To a mixture of 4-chlorobromobenzene (0.53 g, 2.75 mmol) and 3-(R)-Methyl-piperazine-1-carboxylic acid tert-butyl ester (0.5 g, 2.5 mmol) in toluene (20 mL) was added tris(dibenzylideneacetone)dipalladium(0) (0.029 g, 0.032 mmol), BINAP (0.058 g, 0.093 mmol) and sodium-t-butoxide (1.01 g, 10.5 mmol). The resulting mixture was heated 110° C. for 20 h. The solvent was evaporated and the residue was taken up in ethyl acetate and washed with saturated aqueous sodium bicarbonate and brine and dried over magnesium sulfate. Column chromatography (10% ethyl acetate/hexane) provided the title compound.

¹H-NMR (CDCL₃) δ: 0.98 (3H, d), 1.48 (9H, s), 3.04–3.21 (3H, m), 3.34–3.38 (1H, m), 3.72–3.76 (2H, m), 3.80–4.05 (1H, m), 6.81 (2H, d), 7.21 (2H, d). ESI-MS m/z: 311(M), UV retention time: 3.21 min.

Step 3: 2-(5-{3-[4-(4-Chloro-phenyl)-3-(R)-methyl-piperazin-1-yl]-propylidene}-5,11-dihydro-10-oxa-1-aza-dibenzo[a,d]cyclohepten-7-yl)-propan-2-ol 4-(4-Chloro-phenyl)-3-(R)-methyl-piperazine-1-carboxylic acid tert-butyl ester (0.36 g, 2.6 mmol) was treated with 4M HCl/Dioxane (10 mL) at room temperature for 3 h. The solvent was evaporated and the residue was taken up in dichloromethane and washed several times with saturated sodium bicarbonate. The combined organic phases were dried over sodium sulfate. The residue was taken to the next step without further purification.

To a solution of 4-(4-chloro-phenyl)-3-(R)-methyl-piperazine (0.2 g, 0.95 mmol) in isopropanol (20 mL) was added 2,6-lutidine (0.11 mL, 0.94 mmol) and catalytic potassium iodide. This mixture was heated to 80° C. and then treated with 2-[5-(3-bromo-propylidene)-5,11-dihydro-10-oxa-1-aza-dibenzo[a,d]cyclohepten-7-yl]-propan-2-ol (0.24 g, 0.63 mmol), added in portions over 2 h. The solution was then stirred at 80° C. for an additional 20 h. The reaction was concentrated in vacuo and purified by flash chromatography (100% dichloromethane to 2% methanol/dichloromethane) to yield the title compound.

¹H-NMR (CDCl₃) δ: 1.0 (3H, d), 1.57 (6H, s), 1.72 (s, 1H), 2.25–2.55 (7H, m), 2.61–2.73 (1H, m), 2.96–3.17 (2H, m), 3.66–3.77 (1H, m), 5.3 (2H, br s), 6.16 (1H, t), 6.77–6.87 (3H, m), 7.17–7.31 (4H, m), 7.45 (1H, d), 7.59 (1H, dd), 8.51 (1H, dd). ESI-MS m/z: 504 (M), UV retention time: 1.50 min.

Example 558

(1-(4-Chloro-phenyl)-4-{3-[7-(1-hydroxy-1-methyl-ethyl)-11H-10-oxa-1-aza-dibenzo[a,d]cyclohepten-5-ylidene]-propyl}-piperazin-2-yl)-acetic acid methyl ester Step 1: 4-(4-Chloro-phenyl)-3-methoxycarbonylmethyl-piperazine-1-carboxylic acid tert-butyl ester 4-Chlorophenyl boronic acid (1.08 g, 6.97 mmol) and 3-methoxycarbonylmethyl-piperazine-1-carboxylic acid tert-butyl ester (0.9 g, 3.48 mmol) were dissolved in dichloromethane. To this mixture was added copper acetate (0.63 g, 3.48 mmol), 4 Å molecular sieves and pyridine (0.56 mL, 6.97 mmol) and the reaction mixture was stirred at room temperature for 72 h. The reaction mixture was concentrated in vacuo and dissolved in ethyl acetate, filtered through celite and concentrated. The crude product was purified using gradient elution from hexane/ethyl acetate (5%) to hexane/ethyl acetate (20%). ESI-MS m/z: 369 (M+1), UV retention time: 2.97 min.

Step 2: (1-(4-Chloro-phenyl)-4-{3-[7-(1-hydroxy-1-methyl-ethyl)-11H-10-oxa-1-aza-dibenzo[a,d]cyclohepten-5-ylidene]-propyl}-piperazin-2-yl)-acetic acid methyl ester 4-(4-Chloro-phenyl)-3-methoxycarbonylmethyl-piperazine-1-carboxylic acid tert-butyl ester (0.19 g, 0.5 mmol) was treated with 4M HCl/Dioxane (10 mL) at room temperature for 3 h. The solvent was evaporated and the residue was taken up in dichloromethane and washed several times with saturated sodium bicarbonate. The combined organic phases were dried over sodium sulfate. The residue was taken to the next step without further purification.

To a solution of 4-(4-Chloro-phenyl)-3-methoxycarbonylmethyl-piperazine (0.13 g, 0.5 mmol) in acetonitrile/water (8:2) (10 mL) was added $K_2CO_3$ (0.2 g, 0.42 mmol) and 2-[5-(3-bromo-propylidene)-5,11-dihydro-10-oxa-1-aza-dibenzo[a,d]cyclohepten-7-yl]-propan-2-ol (0.16 g, 0.42 mmol). The solution was allowed to stir at room temperature for 48 h. The reaction was concentrated, partitioned between EtOAc/$H_2O$, and extracted with EtOAc (3×). The organics were combined, dried over $Mg_2SO_4$, filtered and evaporated in vacuo, then purified by Biotage flash chromatography (50% ethyl acetate/50% hexane to 75% ethyl acetate/25% hexane to 100% ethyl acetate) to yield the title compound.
$^1$H-NMR (CDCl$_3$) δ: 1.57 (6H, s), 2.16–2.49 (8H, m), 2.78–3.01 (4H, m), 3.22 (1H, d), 3.54 (3H, s), 4.21–4.24 (1H, m), 5.29 (2H, br s), 6.19 (1H, t), 6.77–6.82 (3H, m), 7.17–7.30 (4H, m), 7.48 (1H, d), 7.58 (1H, dd), 8.51 (1H, dd). ESI-MS m/z: 562 (M), UV retention time: 1.63 min.

Example 559

4-(4-Chloro-phenyl)-3,3-dimethyl 1-{3-[7-(2-morpholin-4-yl-ethoxy)-11H-10-oxa-1-aza-dibenzo[a,d]cyclohepten-5-ylidene]-propyl}-piperidin-4-ol To a solution of 5-{3-[4-(4-chloro-phenyl)-4-hydroxy-3,3-dimethyl-piperidin-1-yl]-propylidene}-5,11-dihydro-10-oxa-1-aza-dibenzo[a,d]cyclohepten-7-ol (0.15 g, 0.28 mmol) in DMF (1.5 mL) was added NaH (0.034 g, 0.84 mmol) and stirred for 20 min. at room temperature. 4-(2-Chloro-ethyl)-morpholine HCl (0.063 g, 0.34 mmol) was added and the solution was heated to 50° C. for 16 h. The reaction was quenched with water and extracted with ethyl acetate (3×). The organics were combined, dried over $Mg_2SO_4$, filtered and concentrated, then purified by Biotage flash chromatography (5–10% methanol/dichloromethane) to yield the title compound (0.050 g). $^1$H-NMR (MeOD) δ: 0.73 (3H, s), 0.85 (3H, s), 2.39–2.90 (11H, m), 3.29–3.31 (3H, m), 3.69–3.72 (4H, m), 4.1 (2H, t), 5.20 (2H, br s), 6.18 (1H, t), 6.74–6.79 (2H, m), 6.89 (1H, d), 7.27–7.30 (2H, m), 7.43–7.47 (3H, m), 7.79 (1H, dd), 8.46 (1H, dd). ESI-MS m/z: 604 (M), UV retention time: 1.20 min.

Examples 560–571

General Procedures:

The N-BOC protected amine (0.0565–0.6911 mmol) was subjected to 1N NaOH, extracted with dichloromethane, washed with brine, dried over magnesium sulfate and filtered. The solution was evaporated via steady $N_2$ airflow. To the residue was added the corresponding bromide (0.8 eq), potassium carbonate (1.0 eq), 11 mLs of acetonitrile and 2.75 mLs water. The resulting solution was agitated via and orbital shaker for 48 hours. The vials were transferred to a heating plate and stirred at 50° C. for 48 hours. The solutions were quenched with a 1:1 brine/water mixture, washed with 1N NaOH, dried over magnesium sulfate, filtered and concentrated via steady $N_2$ airflow. The residue was dissolved in dichloromethane and subjected to column chromatography ($SiO_2$, Biotage 12M column, 95% dichloromethane/5% methanol with 0.1% triethyl amine) to afford the desired product.

Example 560

N-(4-Chloro-benzyl)-N-(1-{3-[7-(1-hydroxy-1-methyl-ethyl)-11H-10-oxa-1-aza-dibenzo[a,d]cyclohepten-5-ylidene]-propyl}-pyrrolidin-3-yl)-2-methyl-butyramide To a heated (77° C.) stirring solution of 1-(4-chloro-phenyl)-2-imidazolidin-1-yl-4-methyl-hexan-3-one (110 mg, 0.374 mmol), 2,6-lutidiene (130 μL, 11.229 mmol) and 5 mL isopropanol was added 2-[5-(3-bromo-propylidene)-5,11-dihydro-10-oxa-1-aza-dibenzo[a,d]cyclohepten-7-yl]-propan-2-ol (70 mg, 0.187 mmol) portion-wise over a 30 minute period. The resulting solution was monitored using thin layer chromatography and allowed to stir at 77° C. for 16 hours. The solution was concentrated in vacuo at 35° C. The residue was dissolved in ethyl acetate and subjected to column chromatography ($SiO_2$, Biotage 12M column, gradient elution 100% ethyl acetate→92% ethyl acetate/8% methanol with 1% triethyl amine) to afford 54 mg of 1-(4-chloro-phenyl)-2-(3-{3-[7-(1-hydroxy-1-methyl-ethyl)-11H-10-oxa-1-aza-dibenzo[a,d]cyclohepten-5-ylidene]-propyl}-imidazolidin-1-yl)-4-methyl-hexan-3-one as a tan foam. LC/MS: $t_{UV}$=1.68 min, M/Z=588 amu.

Example 561

N-(4-Chloro-benzyl)-N-(1-{3-[7-(1-hydroxy-1-methyl-ethyl)-11H-10-oxa-1-aza-dibenzo[a,d]cyclohepten-5-ylidene]-propyl}-pyrrolidin-3-yl)-acetamide LC/MS: $t_{UV}$=1.66 min, M/Z=546 amu. $^1$H NMR ((CD$_3$)$_2$SO): δ 8.54 (1H,d), 7.70 (1H,m), 7.44(3H,m), 7.28 (3H,m), 7.13 (1H,m), 6.76(1H,d), 6.12 (1H,d), 5.21 (3H,m), 5.00 (1H,s), 4.63 (2H,m), 4.50 (2H,m), 3.12 (2H,d), 2.39 (4H,m), 2.27 (2H,m), 2.18 (3H,s), 1.90 (5H,m), 1.60 (2H, m), 1.43 (6H,s), 1.21 (2H,t), 0.92 (1H,m).

Example 562

N-(4-Chloro-benzyl)-N-(1-{3-[7-(1-hydroxy-1-methyl-ethyl)-11H-10-oxa-1-aza-dibenzo[a,d]cyclohepten-5-ylidene]-propyl}-pyrrolidin-3-yl)-isobutyramide LC/MS: $t_{UV}$=1.56 min, M/Z=574 amu. $^1$H NMR ((CD$_3$)$_2$SO): δ 8.51 (1H,d), 7.66 (1H,d), 7.42 (3H,m), 7.25 (2H,t), 7.12 (1H,m), 7.04 (1H,d), 6.74 (1H,d), 6.11 (1H,m), 5.18 (2H,m), 4.98 (2H,s), 4.91 (2H,m), 4.48 (1H,s), 3.04 (1H,m), 2.40 (5H,m), 2.14 (4H,m), 1.40 (6H,s), 1.04 (3H,d), 0.90 (3H,m).

Example 563

N-(4-Chloro-benzyl)-N-(1-{3-[7-(1-hydroxy-1-methyl-ethyl)-11H-10-oxa-1-aza-dibenzo[a,d]cyclohepten-5-ylidene]-propyl}-pyrrolidin-3-yl)-propionamide LC/MS: $t_{UV}$=1.49 min, M/Z=560 amu. $^1$H NMR ((CD$_3$)$_2$SO): δ 8.48 (1H,d), 7.64 (1H,d), 7.40 (3H,m), 7.27 (2H,t), 7.07 (2H,m), 6.72 (1H,d), 6.10 (1H,m), 5.17 (3H,m), 4.96 (2H,s), 4.52 (4H,m), 2.35 (3H,m), 2.12 (5H,m), 1.52 (1H,m), 1.34 (6H,s), 1.00 (2H,t), 0.89 (1H,m).

Example 564

Cyclopentanecarboxylic acid(4-chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amide LC/MS: $t_{UV}$=1.73 min, M/Z=600 amu. $^1$H NMR ((CD$_3$)$_2$SO): δ 8.50 (1H,d), 7.65 (1H,d), 7.40 (3H,m), 7.24 (2H,t), 7.11 (1H,m), 7.02 (1H,d), 6.72 (1H,d), 6.11 (1H,m), 5.14 (3H,m), 4.96 (1H,s), 4.82 (1H,m), 4.64 (2H,m), 4.46 (1H,s), 3.13 (1H,m), 2.34 (3H,t), 2.19 (2H,m), 2.06 (2H,m), 1.71 (2H,m), 1.57 (7H,m), 1.39 (6H,s).

Example 565

Cyclohexanecarboxylic acid(4-chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amide LC/MS: $t_{UV}$=1.79 min, M/Z=614 amu. $^1$H NMR ((CD$_3$)$_2$SO): δ 8.48 (1H,d), 7.64 (1H,d), 7.39 (3H,m), 7.23 (2H,t), 7.10 (1H,m), 7.00 (1H,d), 6.69 (1H,d), 6.08 (1H,m), 5.13 (2H,m), 4.95 (1H,s), 4.58 (2H,m), 4.43 (1H,s), 2.73 (1H,m), 2.34 (3H,m), 2.12 (4H,m), 1.67 (7H,m), 1.38 (6H,s), 1.29 (3H,m), 1.03 (3H,m).

Example 566

2-Ethyl-hexanoic acid(4-chloro-benzyl)-(1-{3-[7-(1-hydroxy-1-methyl-ethyl)-11H-10-oxa-1-aza-dibenzo[a,d]cyclohepten-5-ylidene]-propyl}-pyrrolidin-3-yl)-amide LC/MS: $t_{UV}$=1.92 min, M/Z=630 amu. $^1$H NMR ((CD$_3$)$_2$SO): δ 8.44 (1H,m), 7.61 (1H,m), 7.35 (3H,m), 7.20 (2H,m), 7.11 (1H,m), 7.02 (1H,d), 6.68 (1H,d), 6.05 (1H,m), 5.10 (3H,m), 4.91 (1H,s), 4.61 (2H,m), 4.44 (1H,s), 2.66 (3H,m), 2.32 (3H,m), 2.07 (4H,m), 1.46 (3H,m), 1.34 (6H,s), 1.17 (4H,m), 0.94 (2H,m), 0.75 (4H,m), 0.60 (1H,m).

Example 567

1-(4-Chloro-benzyl)-1-(1-{3-[7-(1-hydroxy-1-methyl-ethyl)-11H-10-oxa-1-aza-dibenzo[a,d]cyclohepten-5-ylidene]-propyl}-pyrrolidin-3-yl)-3-isopropyl-urea LC/MS: $t_{UV}$=1.53 min, M/Z=589 amu. $^1$H NMR ((CD$_3$)$_2$SO): δ 8.50 (1H,m), 7.69 (1H,d), 7.40 (2H,m), 7.32 (2H,d), 7.19 (3H,m), 6.71 (1H,d), 6.09 (1H,m), 5.17 (2H,m), 4.95 (1H,s), 4.41 (2H,s), 4.12 (1H,m), 3.69 (1H,m), 3.05 (2H,m), 2.78 (2H,m), 2.58 (1H,m), 2.26 (2H,m), 1.91 (2H,m), 1.61 (1H,m), 1.38 (6H,s), 1.16 (1H,m), 0.92 (6H,m).

Example 568

1-(4-Chloro-benzyl)-3-cyclohexyl-1-(1-{3-[7-(1-hydroxy-1-methyl-ethyl)-11H-10-oxa-1-aza-dibenzo[a,d]cyclohepten-5-ylidene]-propyl}-pyrrolidin-3-yl)-urea LC/MS: $t_{UV}$=1.70 min, M/Z=629 amu. $^1$H NMR ((CD$_3$)$_2$SO): δ 8.50 (1H,d), 7.69 (1H,d), 7.40 (2H,m), 7.32 (4H,m), 7.18 (3H,m), 6.70 (1H,d), 6.10 (1H,m), 5.16 (2H,m), 4.95 (1H,s), 4.43 (2H,m), 4.02 (1H,m), 3.14 (1H,m), 2.71 (3H,m), 2.22 (3H,m), 1.87 (2H,m), 1.62 (5H,m), 1.38 (6H,s), 0.98 (8H,m).

Example 569

1-(4-Chloro-benzyl)-3-ethyl-1-(1-{3-[7-(1-hydroxy-1-methyl-ethyl)-11H-10-oxa-1-aza-dibenzo[a,d]cyclohepten-5-ylidene]-propyl}-pyrrolidin-3-yl)-urea LC/MS: $t_{UV}$=1.46 min, M/Z=5.75 amu. $^1$H NMR ((CD$_3$)$_2$SO): δ 8.52 (1H,d), 7.70 (1H,d), 7.43 (2H,m), 7.33 (2H,d), 7.23 (1H,dd), 7.17 (2H,d), 6.73 (1H,d), 6.13 (1H,t), 5.19 (2H,m), 4.98 (1H,s), 4.43 (2H,s), 4.20 (1H,m), 2.96 (4H,m), 2.71 (2H,m), 2.26 (3H,m), 1.95 (2H,m), 1.61 (1H,m), 1.41 (6H,s), 1.19 (1H,m), 1.01 (1H,m), 0.85 (2H,m).

Example 570

1-(4-Chloro-benzyl)-1-(1-{3-[7-(1-hydroxy-1-methyl-ethyl)-11H-10-oxa-1-aza-dibenzo[a,d]cyclohepten-5-ylidene]-propyl}-pyrrolidin-3-yl)-3-(1,1,3,3-tetramethyl-butyl)-urea LC/MS: $t_{UV}$=2.05 min, M/z=659 amu

Example 571

N-(4-Chloro-benzyl)-N-(1-{3-[7-(1-hydroxy-1-methyl-ethyl)-11H-10-oxa-1-aza-dibenzo [a,d]cyclohepten-5-ylidene]-propyl}-pyrrolidin-3-yl)-methanesulfonamide LC/MS: $t_{UV}$=1.49 min, M/Z=582 amu.

Additional compounds of the invention can be prepared by the schemes set forth in FIGS. 1–5, 7, 8A–8C, 9A–9E, 10A–10d and 12–19 and by the procedures described herein.

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A compound having the formula:

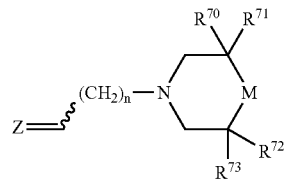

or physiologically acceptable salt thereof, wherein:

n is one to four;

M is >$CR^1R^2$;

$R^1$ is —H, —OH, —$N_3$, a halogen, an aliphatic group, a substituted aliphatic group, an aminoalkyl group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —C(O)O-(aliphatic group), —C(O)O-(substituted aliphatic group), —COOH, —CN, —CO—$NR^3R^4$, or —$NR^3R^4$;

$R^2$ is —OH, a halogen, an acyl group, a substituted acyl group, —$NR^5R^6$, an aliphatic group, a substituted aliphatic group, an aromatic group, a substituted aromatic group, a benzyl group, a substituted benzyl group, a non-aromatic heterocyclic group, a substituted non-aromatic heterocyclic group, —O-(substituted or unsubstituted aromatic group), —O-(substituted or unsubstituted aliphatic group), —C(O)-(substituted or unsubstituted aromatic group) or —C(O)-substituted or substituted aliphatic group);

$R^3$, $R^4$, $R^5$ and $R^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group; or $R^1$ and $R^2$, $R^3$ and $R^4$, or $R^5$ and $R^6$ taken together with the atom to which they are bonded, form a substituted or unsubstituted non-aromatic carbocyclic or heterocyclic ring;

$R^{70}$ and $R^{71}$ are independently —H, —OH, —$N_3$, a halogen, an aliphatic group, a substituted aliphatic group, an aminoalkyl group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —C(O)O-(aliphatic group), —C(O)O-(substituted aliphatic group), —COOH, —CN, —CO—$NR^3R^4$, —$NR^3R^4$, an acyl group, a substituted acyl group, a benzyl group, a substituted benzyl group, a non-aromatic heterocyclic group, a substituted non-aromatic heterocyclic group, or —O-(substituted or unsubstituted aromatic group);

$R^{72}$ and $R^{73}$ are independently —O, —$N_3$, a halogen, an aliphatic group, a substituted aliphatic group, an aminoalkyl group, —O-(aliphatic group), —O-(substituted aliphatic group), —SH, —S-(aliphatic group), —S-(substituted aliphatic group), —O—C(O)-(aliphatic group), —O—C(O)-(substituted aliphatic group), —C(O)O-(aliphatic group), —C(O)O-(substituted aliphatic group), —COOH, —CN, —CO—$NR^3R^4$, —$NR^3R^4$, an acyl group, a substituted acyl group, a benzyl group, a substituted benzyl group, a non-aromatic heterocyclic group, a substituted non-aromatic heterocyclic group, or —O-(substituted or unsubstituted aromatic group);

Z is

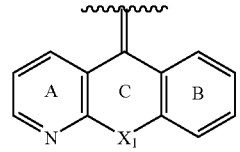

$X_1$ is —$CH_2$—O—, —O—$CH_2$—, —S—, —$CH_2$—, —$CH_2$—$CH_2$—, —$CH_2$—S—, —S—$CH_2$—, —$NR_c$—$CH_2$—, —$CH_2$—$NR_c$—, —SO—$CH_2$—, —$CH_2$—SO—, —$S(O)_2$—$CH_2$—, —$CH_2$—$S(O)_2$—, —CH=CH—, —$NR_c$—CO—, a bond, —O—, or —CO—$NR_c$—, $R_c$ is —H, an aliphatic group, a substituted aliphatic group, an aromatic group, a substituted aromatic group, a benzyl group or a substituted benzyl group;

Rings A and B are independently unsubstituted or substituted;

said acyl group is an aliphatic carbonyl aromatic carbonyl, aliphatic sulfonyl or aromatic sulfonyl;

said aliphatic group is a $C_1$–$C_6$ alkenyl or alkynyl;

said aromatic group is selected from the group consisting of phenyl, 1-naphthyl, 2-naphthyl, 1-anthracyl, 2-anthracyl, N-imidazolyl, 2-imidazolyl, 4-imidazolyl, 5-imidazolyl, 2-thienyl, 3-thienyl, 2-furanyl, 3-furanyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 4-pyridazinyl, 3-pyrazolyl, 4-pyrazolyl, 5-pyrazolyl, 2-pyrazinyl, 2-thiazolyl, 4-thiazolyl, 5-thiazolyl, 5-tetrazolyl, 2-oxazolyl, 4-oxazolyl, 5-oxazolyl, tetrahydronaphthyl, 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzooxazolyl, 2-benzimidazolyl, 1-isoquinolinyl, 3-quinolinyl, 1-isoindolyl, 3-isoindolyl, acridinyl, 3-benzisoxazolyl, benzocyclopentyl, and benzocyclohexyl;

said non-aromatic heterocyclic group is a five to eight-membered non-aromatic ring which contains one or more heteroatoms independently selected from the group consisting of nitrogen, oxygen and sulfur;

said substituted aliphatic group is substituted with one or more substituents selected form the group consisting of oxo group, epoxy group, non-aromatic heterocyclic ring, benzyl group, substituted benzyl group, aromatic group, substituted aromatic group, electron withdrawing group, halo, azido, —CN, —$CONR^{24}R^{25}$, —$NR^{24}R^{25}$, —$OS(O)_2NR^{24}R^{25}$, —$S(O)_2NR^{24}R^{25}$, —$SO_3H$, guanidino, oxalo, —C(=$NR^{60}$)$NR^{21}R^{22}$, =$NR^{60}$, —$(O)_u$—$(CH_2)_t$—$C(O)OR^{20}$, —$(O)_u$—$(CH_2)_t$—$OC(O)R^{20}$, —$(O)_u$—$(CH_2)_t$—$C(O)$—$NR^{21}R^{22}$, —$(O)_u$—$(CH_2)_t$—$NHC(O)O$—$R^{20}$, -Q-H, -Q-(aliphatic group), -Q-(substituted aliphatic group), -Q(aryl), -Q(aromatic group), -Q-(substituted aromatic group), -Q-$(CH_2)_p$-(substituted or unsubstituted aromatic group), -Q-(non-aromatic heterocyclic group) and -Q-$(CH_2)_p$-(non-aromatic heterocyclic group);

said substituted non-aromatic heterocyclic ring is substituted with one or more substituents selected from the group consisting of =O, =S, electron withdrawing group, halo, azido, —CN, —$CONR^{24}R^{25}$, —$NR^{24}R^{25}$, —$OS(O)_2NR^{24}R^{25}$, —$S(O)_2NR^{24}R^{25}$, —$SO_3H$, guanidino, oxalo, —C(=$NR^{60}$)$NR^{21}R^{22}$, =$NR^{60}$, —$(O)_u$—$(CH_2)_t$—$C(O)OR^{20}$, —$(O)_u$—$(CH_2)_t$—$OC(O)R^{20}$, —$(O)_u$—$(CH_2)_t$—$C(O)$—$NR^{21}R^{22}$, —$(O)_u$—$(CH_2)_t$—$NHC(O)O$—$R^{20}$, -Q-H, -Q-(aliphatic group), -Q-(substituted aliphatic group), -Q-(aryl), -Q-(aromatic group), -Q-(substituted aromatic group), -Q-$(CH_2)_p$-(substituted or unsubstituted aromatic group), -Q-(non-aromatic heterocyclic group) and -Q-$(CH_2)_p$-(non-aromatic heterocyclic group);

said substituted aromatic group, substituted benzyl group, Ring A when substituted and Ring B when substituted, are substituted with one or more substituents selected from the group consisting of electron withdrawing group, aliphatic group, substituted aliphatic group, aromatic group, substituted aromatic group, halo, azido, —CN, —CONR$^{24}$R$^{25}$, —NR$^{24}$R$^{25}$, —OS(O)$_2$NR$^{24}$R$^{25}$, —S(O)$_2$NR$^{24}$R$^{25}$, —SO$_3$H, guanidino, oxalo, —C(=NR$^{60}$)NR$^{21}$R$^{22}$, =NR$^{60}$, —(O)$_u$—(CH$_2$)$_t$—C(O)OR$^{20}$, —(O)$_u$—(CH$_2$)$_t$—OC(O)R$^{20}$, —(O)$_u$—(CH$_2$)$_t$—C(O)—NR$^{21}$R$^{22}$, —(O)$_u$—(CH$_2$)$_t$—NHC(O)O—R$^{20}$, -Q-H, -Q-(aliphatic group), -Q-(substituted aliphatic group), -Q-(aryl), Q-(aromatic group), -Q-(substituted aromatic group), -Q-(CH$_2$)$_p$-(substituted or unsubstituted aromatic group), -Q-(non-aromatic heterocyclic group) and -Q-(CH$_2$)$_p$-(non-aromatic heterocyclic group);

Q is —O—, —S—, —S(O)—, —S(O)$_2$—, —OS(O)$_2$—, —C(O)—, —OC(O)—, —C(O)O—, —C(O)C(O)—O—, —O—C(O)C(O)—, —NHC(O)—, —OC(O)NH—, —NH—C(O)—NH—, —S(O)$_2$NH—, —NHS(O)$_2$—, —C(NR$^{23}$)NHNH—, —NHNHC(NR$^{23}$)—, —NR$^{24}$C(O)— or —NR$^{24}$S(O)$_2$—;

R$^{20}$, R$^{21}$ and R$^{22}$ are independently —H, an aliphatic group, an aromatic group, a non-aromatic heterocyclic group, —NHC(O)—O-(aliphatic group), —NHC(O)—O-(aromatic group) or —NHC(O)—O-(non-aromatic heterocyclic group) or R$^{21}$ and R$^{22}$, taken together with the nitrogen atom to which they are bonded, can form a substituted or unsubstituted non-aromatic heterocyclic ring;

R$^{23}$ is —H, an aliphatic group, a benzyl group, an aryl group or non-aromatic heterocyclic group;

R$^{24}$ and R$^{25}$ are independently —H, an aliphatic group, a substituted aliphatic group, a benzyl group, an aryl group, non-aromatic heterocyclic group or R$^{24}$ and R$^{25}$ taken together with the nitrogen atom to which they are bonded can form a substituted or unsubstituted non-aromatic heterocyclic ring;

R$^{60}$ is a —H, —OH, —NH$_2$, an aromatic group or a substituted aromatic group;

t is zero to three;

u is zero or one; and p is one to five.

2. The compound of claim 1 wherein Ring A is unsubstituted and B is substituted para to the carbon atom of ring B that is bonded to X$_1$ in ring C, and Z is represented by the structural formula:

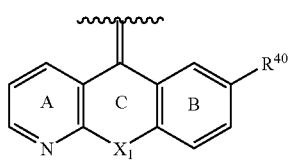

wherein R$^{40}$ is —OH, —COOH, —NO$_2$, halogen, aliphatic group, substituted aliphatic group, an aromatic group, a substituted aromatic group, —NR$^{24}$R$^{25}$, —CONR$^{24}$R$^{25}$, —NR$^{24}$C(O)-(aliphatic group), —NR$^{24}$C(O)-(substituted aliphatic group), —NR$^{24}$S(O)$_2$-(aliphatic group), —NR$^{24}$S(O)$_2$-(substituted aliphatic group), —C(O)O-(aliphatic group), —C(O)O-(substituted aliphatic group), —C(O)-(aliphatic group), —C(O)-(substituted aliphatic group), —O-(aliphatic group), —O-(substituted aliphatic group), —O-(aromatic group), —O-(substituted aromatic group), an electron withdrawing group, —(O)$_u$—(CH$_2$)$_t$—C(O)OR$^{20}$, —(O)$_u$—(CH$_2$)$_t$—OC(O)R$^{20}$, —(O)$_u$—(CH$_2$)$_t$—C(O)—NR$^{21}$R$^{22}$ or —(O)$_u$—(CH$_2$)$_t$—NHC(O)O—R$^{20}$;

R$^{20}$, R$^{21}$ or R$^{22}$ are independently —H, an aliphatic group, a substituted aliphatic group, an aromatic group, a substituted aromatic group or a non-aromatic heterocyclic group; or R$^{21}$ and R$^{22}$, taken together with the nitrogen atom to which they are bonded, form a non-aromatic heterocyclic ring;

R$^{24}$ and R$^{25}$ are independently —H, an aliphatic group or a substituted aliphatic group;

u is zero or one; and t is an integer from zero to 3.

3. The compound of claim 2 wherein
R$^1$ is —H or —OH; and
R$^2$ is substituted aromatic group, wherein said substituted aromatic group is 4-halophenyl.

4. The compound of claim 3 wherein said 4-halophenyl is selected from the group consisting of 4-chlorophenyl, 4-bromophenyl and 4-fluorophenyl.

5. The compound of claim 4 wherein said 4-halophenyl is 4-chlorophenyl.

6. The compound of claim 3 wherein X$_1$ is —CH$_2$—O—.

7. The compound of claim 2 wherein at least one of R$^{70}$, R$^{71}$, R$^{72}$ and R$^{73}$ is an aliphatic group or a substituted aliphatic group; wherein said aliphatic group is a C$_1$–C$_6$ alkyl and said substituted aliphatic group is a C$_1$–C$_6$ alkyl substituted with a substitutent selected from the group consisting of —OH, —(O)$_u$—(CH$_2$)$_t$—C(O)OR$_{20}$ and —O-(aliphatic group);

t is zero to three;

u is zero or one; and

R$^{20}$ is C$_1$–C$_6$ alkyl.

8. The compound of claim 7 wherein
R$^{70}$ and R$^{71}$ are both —H;
R$^{72}$ and R$^{73}$ are independently selected from the group consisting of C$_1$–C$_6$ alkyl and substituted C$_1$–C$_6$ alkyl.

9. The compound of claim 8 wherein R$^{72}$ is —CH$_3$.

10. A pharmaceutical composition comprising a therapeutically effective amount of a compound according to claim 1 and a physiologically acceptable carrier.

11. A compound having the formula:

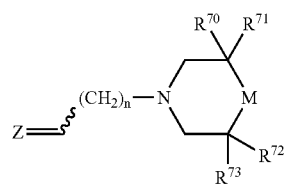

or physiologically acceptable salt thereof, wherein:
n is one to four;
M is >CR$^1$R$^2$;
R$^1$ is —OH;
R$^2$ is 4-halophenyl;

$R^{70}$ and $R^{71}$ are —H, and $R^{72}$ and $R^{73}$ are —CH$_3$; or $R^{70}$ and $^{71}$ are —CH$_3$, and $R^{72}$ and $R^{73}$ are —H;

Z is

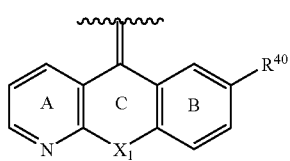

$X_1$ is —CH$_2$—O—; and
$R^{40}$ is selected from the group consisting of:

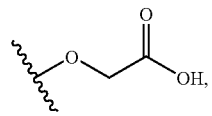 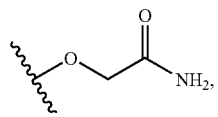

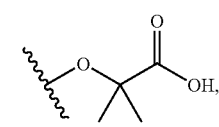 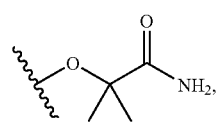

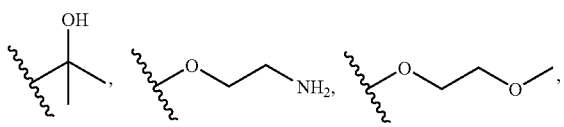

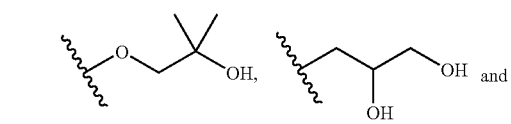

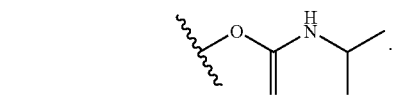

12. The compound of claim 11 wherein $R^{40}$ is

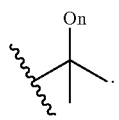

13. The compound of claim 11 wherein said 4-halophenyl is selected from the group consisting of 4-chlorophenyl, 4-bromophenyl and 4-fluorophenyl.

14. The compound of claim 13 wherein said 4-halophenyl is 4-chlorophenyl.

15. The compound of claim 14 wherein $R^{70}$ and $R^{71}$ are —H, $R^{72}$ and $R^{73}$ are —CH$_3$, n is two, and the compound has the structure:

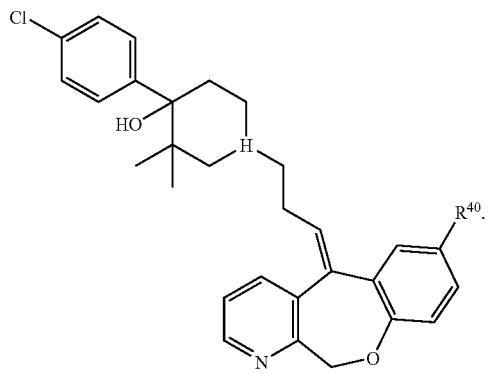

16. The compound of claim 15 wherein $R^{40}$ is

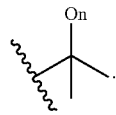

17. A pharmaceutical composition comprising a therapeutically effective amount of a compound of claim 11 and a physiologically acceptable carrier.

18. A compound having the structure:

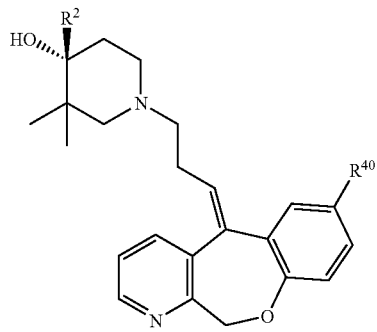

or a physiologically acceptable salt thereof, wherein
$R^2$ is 4-halophenyl; and
$R^{40}$ is selected from the group consisting of:

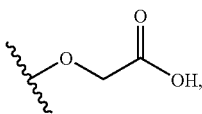 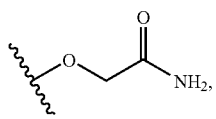

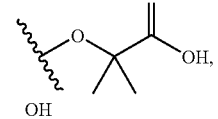 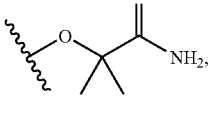

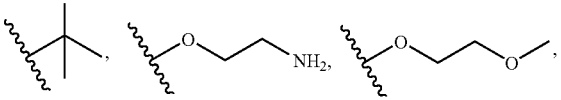

-continued

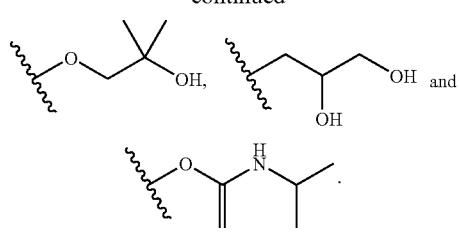

19. The compound of claim 18 wherein $R^{40}$ is

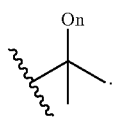

20. The compound of claim 18 wherein $R^2$ is selected from the group consisting of 4-chlorophenyl, 4-bromophenyl and 4-fluorophenyl.

21. The compound of claim 20 wherein $R^2$ is 4-chlorophenyl.

22. The compound of claim 19 wherein $R^2$ is 4-chlorophenyl.

23. A pharmaceutical composition comprising a therapeutically effective amount of the compound of claim 18 and a physiologically acceptable carrier.

24. A pharmaceutical composition comprising a therapeutically effective amount of a compound of claim 16 and a physiologically acceptable carrier.

25. A pharmaceutical composition comprising a therapeutically effective amount of a compound of claim 22 and a physiologically acceptable carrier.

* * * * *

UNITED STATES PATENT AND TRADEMARK OFFICE
CERTIFICATE OF CORRECTION

PATENT NO. : 7,271,176 B2  Page 1 of 3
APPLICATION NO. : 10/487168
DATED : September 18, 2007
INVENTOR(S) : Jay R. Luly et al.

It is certified that error appears in the above-identified patent and that said Letters Patent is hereby corrected as shown below:

Claim 1

Column 207, line 21, delete "substituted" and insert --unsubstituted--

Column 207, line 44, delete "O," and insert --OH,--

Column 208, line 3, delete "," and insert --;--

Column 208, line 12, delete "alkenyl or alkynyl;" and insert --alkyl, alkenyl or alkynyl;--

Column 208, line 36, delete "form" and insert --from--

Column 208, line 48, delete "-Q(aryl), -Q(aromatic group)" and insert -- -Q-(aryl), -Q-(aromatic group)--

Column 209, line 13, delete "Q-(aromatic group)" and insert -- -Q-(aromatic group)--

Claim 12

Column 211, line 55, delete " 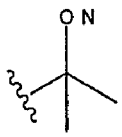 " and insert

-- 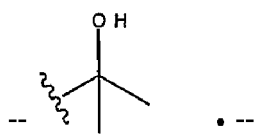 --

UNITED STATES PATENT AND TRADEMARK OFFICE
CERTIFICATE OF CORRECTION

PATENT NO. : 7,271,176 B2  Page 2 of 3
APPLICATION NO. : 10/487168
DATED : September 18, 2007
INVENTOR(S) : Jay R. Luly et al.

It is certified that error appears in the above-identified patent and that said Letters Patent is hereby corrected as shown below:

Claim 15

Column 212, lines 1 through 16, delete
"
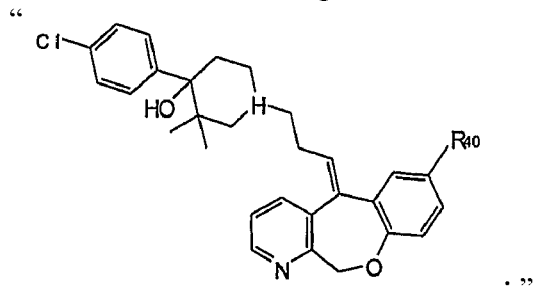
."

and insert

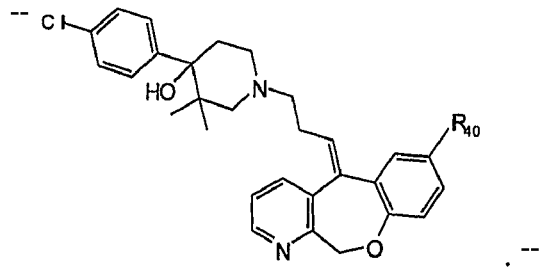
--

Claim 16

Column 212, line 22, delete " 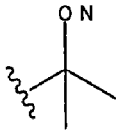 • " and insert

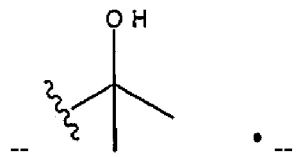
-- • --

Claim 18

Column 213, line 10, delete " 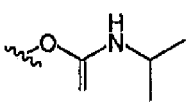 " and insert

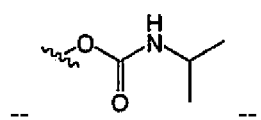
-- --

UNITED STATES PATENT AND TRADEMARK OFFICE
CERTIFICATE OF CORRECTION

PATENT NO. : 7,271,176 B2
APPLICATION NO. : 10/487168
DATED : September 18, 2007
INVENTOR(S) : Jay R. Luly et al.

It is certified that error appears in the above-identified patent and that said Letters Patent is hereby corrected as shown below:

Claim 19

Column 213, line 15, delete " 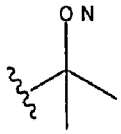 " and insert

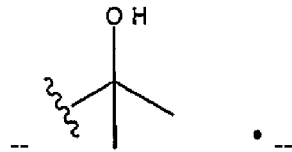

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,271,176 B2 | |
| APPLICATION NO. | : 10/487168 | |
| DATED | : September 18, 2007 | |
| INVENTOR(S) | : Jay R. Luly et al. | |

It is certified that error appears in the above-identified patent and that said Letters Patent is hereby corrected as shown below:

ON THE TITLE PAGE, ITEM 56:

Page 2, under Foreign Patent Documents, delete "WO 96/31496 10/1996" and insert --WO 96/31469 10/1996--.

Signed and Sealed this

Nineteenth Day of May, 2009

JOHN DOLL
*Acting Director of the United States Patent and Trademark Office*